United States Patent
Jeong

(10) Patent No.: US 9,624,202 B2
(45) Date of Patent: Apr. 18, 2017

(54) HETEROCYCLIC AMIDES AS KINASE INHIBITORS

(71) Applicant: GlaxoSmithKline Intellectual Property Development Limited, Brentford, Middlesex (GB)

(72) Inventor: Jae U. Jeong, Collegeville, PA (US)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 15/271,581

(22) Filed: Sep. 21, 2016

(65) Prior Publication Data

US 2017/0008878 A1    Jan. 12, 2017

Related U.S. Application Data

(63) Continuation of application No. 14/763,183, filed as application No. PCT/IB2014/059004 on Feb. 14, 2014.

(Continued)

(51) Int. Cl.
*A61K 31/55* (2006.01)
*C07D 223/08* (2006.01)
(Continued)

(52) U.S. Cl.
CPC ............ *C07D 403/12* (2013.01); *A61K 31/55* (2013.01); *A61K 31/553* (2013.01);
(Continued)

(58) Field of Classification Search
CPC ..... C07D 223/08; C07D 403/12; A61K 31/55
(Continued)

(56) References Cited

U.S. PATENT DOCUMENTS

| 4,692,522 A | 9/1987 | Parsons et al. |
| 5,206,234 A | 4/1993 | Bock et al. |

(Continued)

FOREIGN PATENT DOCUMENTS

| CN | 102343102 A | 2/2012 |
| ES | 2446494 A1 | 3/2014 |

(Continued)

OTHER PUBLICATIONS

Pierdomenico, et al. The American Journal of Gastroenterology, 109: 279-287 (2014).

(Continued)

*Primary Examiner* — Kamal Saeed
*Assistant Examiner* — Janet L Coppins
(74) *Attorney, Agent, or Firm* — Kathryn A. Lutomski; Edward R. Gimmi; William R. Majarian

(57) ABSTRACT

Disclosed are compounds having the formula:

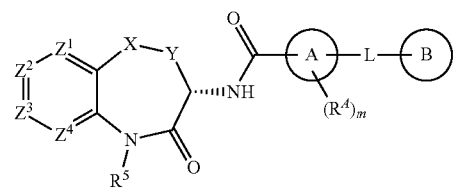

wherein X, Y, $Z^1$, $Z^2$, $Z^3$, $Z^4$, $R^5$, $R^4$, m, A, L, and B are as defined herein, and methods of making and using the same.

26 Claims, 7 Drawing Sheets

Related U.S. Application Data

(60) Provisional application No. 61/790,044, filed on Mar. 15, 2013, provisional application No. 61/765,664, filed on Feb. 15, 2013.

(51) Int. Cl.

| | | |
|---|---|---|
| *C07D 403/12* | (2006.01) | |
| *A61K 31/553* | (2006.01) | |
| *C07D 413/14* | (2006.01) | |
| *C07D 403/14* | (2006.01) | |
| *C07D 409/12* | (2006.01) | |
| *C07D 413/12* | (2006.01) | |
| *C07D 417/12* | (2006.01) | |
| *C07D 487/04* | (2006.01) | |
| *C07D 267/14* | (2006.01) | |
| *C07D 498/04* | (2006.01) | |
| *C07D 281/10* | (2006.01) | |

(52) U.S. Cl.
CPC ......... *C07D 223/08* (2013.01); *C07D 267/14* (2013.01); *C07D 281/10* (2013.01); *C07D 403/14* (2013.01); *C07D 409/12* (2013.01); *C07D 413/12* (2013.01); *C07D 413/14* (2013.01); *C07D 417/12* (2013.01); *C07D 487/04* (2013.01); *C07D 498/04* (2013.01)

(58) Field of Classification Search
USPC ..................................... 514/211.05; 540/552
See application file for complete search history.

(56) References Cited

U.S. PATENT DOCUMENTS

| | | | |
|---|---|---|---|
| 5,691,332 | A | 11/1997 | Claremon et al. |
| 6,228,854 | B1 | 5/2001 | Scarborough et al. |
| 6,514,965 | B1 | 2/2003 | Tomazic et al. |
| 7,622,106 | B1 | 11/2009 | Wang et al. |
| 8,257,921 | B1 | 9/2012 | Yao et al. |
| 2002/0061874 | A1 | 5/2002 | Yang et al. |
| 2002/0103184 | A1 | 8/2002 | Olson et al. |
| 2002/0107239 | A1 | 8/2002 | Lauffer et al. |
| 2002/0137737 | A1 | 9/2002 | Olson |
| 2005/0234041 | A1 | 10/2005 | Tomazic et al. |
| 2006/0067942 | A1 | 3/2006 | Salama |
| 2006/0135762 | A1 | 6/2006 | Olson et al. |
| 2008/0019909 | A1 | 1/2008 | Chan et al. |
| 2008/0220083 | A1 | 9/2008 | Salama |
| 2008/0226645 | A1 | 9/2008 | O'Toole et al. |
| 2008/0269123 | A1 | 10/2008 | Li et al. |
| 2009/0099242 | A1 | 4/2009 | Cuny et al. |
| 2009/0186863 | A1 | 7/2009 | Pruss et al. |
| 2009/0203662 | A1 | 8/2009 | Drouot et al. |
| 2011/0201048 | A1 | 8/2011 | Yoo et al. |
| 2011/0224180 | A1 | 9/2011 | Pruss et al. |
| 2011/0275680 | A1 | 11/2011 | Drouot et al. |
| 2012/0022116 | A1 | 1/2012 | Deng et al. |
| 2012/0122889 | A1 | 5/2012 | Yuan et al. |
| 2013/0005726 | A1 | 1/2013 | Abbott et al. |
| 2013/0137642 | A1 | 5/2013 | Vavvas et al. |
| 2013/0184222 | A1 | 7/2013 | Popovici-Muller et al. |
| 2013/0195884 | A1 | 8/2013 | Boutros et al. |
| 2014/0024598 | A1 | 1/2014 | Vavvas et al. |
| 2014/0066466 | A1 | 3/2014 | Yuan |
| 2014/0251917 | A1 | 9/2014 | Felder |
| 2014/0323489 | A1 | 10/2014 | Yuan et al. |
| 2015/0209389 | A1 | 7/2015 | Gothelf et al. |
| 2015/0347672 | A1 | 12/2015 | Van Ooijen et al. |
| 2015/0361396 | A1 | 12/2015 | Regev et al. |
| 2016/0024098 | A1 | 1/2016 | Yuan et al. |

FOREIGN PATENT DOCUMENTS

| | | | | |
|---|---|---|---|---|
| JP | 5239065 | A2 | 7/2013 | |
| KR | 20130099727 | A | 9/2013 | |
| WO | WO 98/41510 | A1 | 9/1998 | |
| WO | WO 02/36148 | A2 | 5/2002 | |
| WO | WO 2004/092410 | A2 | 10/2004 | |
| WO | WO 2004/098589 | A1 | 11/2004 | |
| WO | WO 2007/075772 | A2 | 7/2007 | |
| WO | WO 2007075772 | A2 * | 7/2007 | ......... A61K 31/4178 |
| WO | WO 2008/056059 | A2 | 5/2008 | |
| WO | WO 2008/086043 | A2 | 7/2008 | |
| WO | WO 2009/045397 | A1 | 4/2009 | |
| WO | WO 2010/075290 | A1 | 7/2010 | |
| WO | WO 2013/013826 | A1 | 1/2013 | |
| WO | WO 2013/059791 | A2 | 4/2013 | |
| WO | WO 2014/022102 | A1 | 2/2014 | |
| WO | WO 2014/125444 | A1 | 8/2014 | |
| WO | WO 2014/126127 | A1 | 8/2014 | |

OTHER PUBLICATIONS

Berger, et al. Journal of Immunology, 192: 5476-5480 (2014).
Hayashi, et al. Cell Communication and Signaling, 11: 84 (2013).
Ofengeim, et al. Cell Reports, 10: 1836-1849 (2015).
Prajzlerova, et al. Autoimmunity Reviews, 15: 501-509 (2016).
Temkin, et al. Immunological Reviews, 220: 8-21 (2007).
Lee, et al. Osteoarthritis and Cartilage, 23: 2269-2278 (2015).
Zhou, et al. Seminars in Cell & Developmental Biology, 35: 14-23 (2014).
Rodriguez, et al. RMD Open, 1(Supp.1): (e000054) 1-7 (2015).
Yu, et al. Cytokine Growth Factor Rev., 22(2): 63-72 (2011).
Rosauer, et al. Bioorganic & Medicinal Chemistry Letters, 13: 4385-4388 (2003).
Uchikawa, et al. Chemical & Pharmaceutical Bulletin, 44(11): 2070-2077 (1996).
Nie, et al. Bioorganic & Medicinal Chemistry Letters, 23: 3662-3666 (2013).

* cited by examiner

HETEROCYCLIC AMIDES AS KINASE INHIBITORS

FIELD OF THE INVENTION

The present invention relates to heterocyclic amides that inhibit RIP1 kinase and methods of making and using the same.

BACKGROUND OF THE INVENTION

Receptor-interacting protein-1 (RIP1) kinase, originally referred to as RIP, is a TKL family serine/threonine protein kinase involved in innate immune signaling. RIP1 kinase is a RHIM domain containing protein, with an N-terminal kinase domain and a C-terminal death domain ((2005) Trends Biochem. Sci. 30, 151-159). The death domain of RIP1 mediates interaction with other death domain containing proteins including Fas and TNFR-1 ((1995) Cell 81 513-523), TRAIL-R[1] and TRAIL-R[2] ((1997) Immunity 7, 821-830) and TRADD ((1996) Immunity 4, 387-396), while the RHIM domain is crucial for binding other RHIM domain containing proteins such as TRIF ((2004) Nat Immunol. 5, 503-507), DAI ((2009) EMBO Rep. 10, 916-922) and RIP3 ((1999) J. Biol. Chem. 274, 16871-16875); (1999) Curr. Biol. 9, 539-542) and exerts many of its effects through these interactions. RIP1 is a central regulator of cell signaling, and is involved in mediating both pro-survival and programmed cell death pathways which will be discussed below.

The role for RIP1 in cell signaling has been assessed under various conditions [including TLR3 ((2004) Nat Immunol. 5, 503-507), TLR4 ((2005) J. Biol. Chem. 280, 36560-36566), TRAIL ((2012) J. Virol. Epub, ahead of print), FAS ((2004) J. Biol. Chem. 279, 7925-7933)], but is best understood in the context of mediating signals downstream of the death receptor TNFR1 ((2003) Cell 114, 181-190). Engagement of the TNFR by TNF leads to its oligomerization, and the recruitment of multiple proteins, including linear K63-linked polyubiquitinated RIP1 ((2006) Mol. Cell 22, 245-257), TRAF2/5 ((2010) J. Mol. Biol. 396, 528-539), TRADD ((2008) Nat. Immunol. 9, 1037-1046) and cIAPs ((2008) Proc. Natl. Acad. Sci. USA. 105, 11778-11783), to the cytoplasmic tail of the receptor. This complex which is dependent on RIP1 as a scaffolding protein (i.e. kinase independent), termed complex I, provides a platform for pro-survival signaling through the activation of the NFκB and MAP kinases pathways ((2010) Sci. Signal. 115, re4). Alternatively, binding of TNF to its receptor under conditions promoting the deubiquitination of RIP1 (by proteins such as A20 and CYLD or inhibition of the cIAPs) results in receptor internalization and the formation of complex II or DISC (death-inducing signaling complex) ((2011) Cell Death Dis. 2, e230). Formation of the DISC, which contains RIP1, TRADD, FADD and caspase 8, results in the activation of caspase 8 and the onset of programmed apoptotic cell death also in a RIP1 kinase independent fashion ((2012) FEBS J 278, 877-887). Apoptosis is largely a quiescent form of cell death, and is involved in routine processes such as development and cellular homeostasis.

Under conditions where the DISC forms and RIP3 is expressed, but apoptosis is inhibited (such as FADD/caspase 8 deletion, caspase inhibition or viral infection), a third RIP1 kinase-dependent possibility exists. RIP3 can now enter this complex, become phosphorylated by RIP1 and initiate a caspase-independent programmed necrotic cell death through the activation of MLKL and PGAM5 ((2012) Cell 148, 213-227); ((2012) Cell 148, 228-243); ((2012) Proc. Natl. Acad. Sci. USA. 109, 5322-5327). As opposed to apoptosis, programmed necrosis (not to be confused with passive necrosis which is not programmed) results in the release of danger associated molecular patterns (DAMPs) from the cell. These DAMPs are capable of providing a "danger signal" to surrounding cells and tissues, eliciting proinflammatory responses including inflammasome activation, cytokine production and cellular recruitment ((2008 Nat. Rev. Immunol 8, 279-289).

Dysregulation of RIP1 kinase-mediated programmed cell death has been linked to various inflammatory diseases, as demonstrated by use of the RIP3 knockout mouse (where RIP1-mediated programmed necrosis is completely blocked) and by Necrostatin-1 (a tool inhibitor of RIP1 kinase activity with poor oral bioavailability). The RIP3 knockout mouse has been shown to be protective in inflammatory bowel disease (including Ulcerative colitis and Crohn's disease) ((2011) Nature 477, 330-334), Psoriasis ((2011) Immunity 35, 572-582), retinal-detachment-induced photoreceptor necrosis ((2010) PNAS 107, 21695-21700), retinitis pigmentosa ((2012) Proc. Natl. Acad. Sci., 109:36, 14598-14603), cerulein-induced acute pancreatits ((2009) Cell 137, 1100-1111) and Sepsis/systemic inflammatory response syndrome (SIRS) ((2011) Immunity 35, 908-918). Necrostatin-1 has been shown to be effective in alleviating ischemic brain injury ((2005) Nat. Chem. Biol. 1, 112-119), retinal ischemia/reperfusion injury ((2010) J. Neurosci. Res. 88, 1569-1576), Huntington's disease ((2011) Cell Death Dis. 2 e115), renal ischemia reperfusion injury ((2012) Kidney Int. 81, 751-761), cisplatin induced kidney injury ((2012) Ren. Fail. 34, 373-377) and traumatic brain injury ((2012) Neurochem. Res. 37, 1849-1858). Other diseases or disorders regulated at least in part by RIP1-dependent apoptosis, necrosis or cytokine production include hematological and solid organ malignancies ((2013) Genes Dev. 27: 1640-1649), bacterial infections and viral infections ((2014) Cell Host & Microbe 15, 23-35) (including, but not limited to, tuberculosis and influenza ((2013) Cell 153, 1-14)) and Lysosomal storage diseases (particularly, Gaucher Disease, Nature Medicine Advance Online Publication, 19 Jan. 2014, doi:10.1038/nm.3449).

A potent, selective, small molecule inhibitor of RIP1 kinase activity would block RIP1-dependent cellular necrosis and thereby provide a therapeutic benefit in diseases or events associated with DAMPs, cell death, and/or inflammation.

SUMMARY OF THE INVENTION

The invention is directed to compounds according to Formula (I):

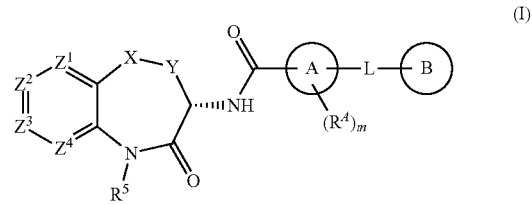

wherein:
X is O, S, SO, SO$_2$, NH, CO, CH$_2$, CF$_2$, CH(CH$_3$), CH(OH), or N(CH$_3$);
Y is CH$_2$ or CH$_2$CH$_2$;
Z$^1$ is N, CH or CR$^1$;

$Z^2$ is CH or $CR^2$;
$Z^3$ is N, CH or $CR^3$;
$Z^4$ is CH or $CR^4$;
$R^1$ is fluoro or methyl;
one of $R^2$ and $R^3$ is halogen, cyano, $(C_1-C_6)$alkyl, halo $(C_1-C_4)$alkyl, $(C_1-C_6)$alkoxy, halo$(C_1-C_4)$alkoxy, hydroxyl, $B(OH)_2$, —COOH, halo$(C_1-C_4)$alkylC(OH)$_2$—, $(C_1-C_4)$ alkoxy$(C_1-C_4)$alkoxy, $(C_1-C_4)$alkylSO$_2$—, $(C_1-C_4)$ alkylSO$_2$NHC(O)—, $(C_1-C_4)$alkylC(O)NH—, $((C_1-C_4)$ alkyl)$((C_1-C_4)$alkyl)NC(O)—, $(C_1-C_4)$alkylOC(O)—, $(C_1-C_4)$alkylC(O)N$(C_1-C_4)$alkyl)-, $(C_1-C_4)$alkylNHC(O)—, $(C_1-C_4)$alkoxy$(C_2-C_4)$alkylNHC(O)—, $(C_1-C_4)$alkoxy$(C_2-C_4)$alkylC(O)NH—, $(C_1-C_4)$alkoxy$(C_2-C_4)$alkylNHC(O)NH—, $(C_1-C_4)$alkyl SO$_2$$(C_2-C_4)$alkylNHC(O)—, $(C_1-C_4)$ alkylNHC(O)NH—, $(C_1-C_4)$alkylOC(O)NH—, hydroxy $(C_1-C_4)$alkylOC(O)NH—, 5-6 membered heterocycloalkyl-C(O)—, 5-6 membered heterocycloalkyl-$(C_1-C_4)$alkyl-NHC(O)—, 5-6 membered heterocycloalkyl-$(C_1-C_4)$ alkoxy-, 3-6 membered cycloalkyl, 5-6 membered heteroaryl, or 5-6 membered heteroaryl-C(O)NH, wherein said 3-6 membered cycloalkyl, 5-6 membered heterocycloalkyl and 5-6 membered heteroaryl are optionally substituted by 1 or 2 substituents each independently selected from the group consisting of $(C_1-C_4)$alkyl and —$(C_1-C_4)$alkyl-CN;

and the other of $R^2$ and $R^3$ is halogen or $(C_1-C_6)$alkyl;
$R^4$ is fluoro, chloro, or methyl;
$R^5$ is H or methyl;

A is phenyl, 5-6 membered heteroaryl, or 5-6 membered heterocycloalkyl, wherein the carbonyl moiety and L are substituted 1,3 on ring A;

m is 0 or m is 1 and $R^A$ is $(C_1-C_4)$alkyl; and

L is O, S, NH, N(CH$_3$), CH$_2$, CH$_2$CH$_2$, CH(CH$_3$), CHF, CF$_2$, CH$_2$O, CH$_2$N(CH$_3$), CH$_2$NH, or CH(OH);

B is an optionally substituted $(C_3-C_6)$cycloalkyl, phenyl, 5-6 membered heteroaryl, or 5-6 membered heterocycloalkyl;

wherein said $(C_3-C_6)$cycloalkyl, phenyl, 5-6 membered heteroaryl, or 5-6 membered heterocycloalkyl is unsubstituted or is substituted by one or two substituents each independently selected from halogen, $(C_1-C_4)$alkyl, halo $(C_1-C_4)$alkyl, $(C_1-C_4)$alkoxy, halo$(C_1-C_4)$alkoxy, nitro, and $(C_1-C_4)$alkylC(O)—;

or the moiety -L-B is $(C_3-C_6)$alkyl, $(C_3-C_6)$alkoxy, halo $(C_3-C_6)$alkoxy, $(C_3-C_6)$alkenyl, or $(C_3-C_6)$alkenyloxy;

or a salt, particularly a pharmaceutically acceptable salt, thereof.

The compounds according to Formula (I), or salts, particularly pharmaceutically acceptable salts, thereof, are inhibitors of RIP1 kinase.

Accordingly, the present invention is also directed to a method of inhibiting RIP1 kinase which method comprises contacting a cell with a compound according to Formula (I), or a salt, particularly a pharmaceutically acceptable salt, thereof.

The invention is further directed to a method of treating a RIP1 kinase-mediated disease or disorder which comprises administering a therapeutically effective amount of a compound according to Formula (I), or a salt, particularly a pharmaceutically acceptable salt thereof, to a patient (a human or other mammal, particularly, a human) in need thereof. Such RIP1 kinase-mediated diseases or disorders include inflammatory bowel disease (including Crohn's disease and ulcerative colitis), psoriasis, retinal detachment, retinitis pigmentosa, arthritis (including rheumatoid arthritis, spondyloarthritis, gout, and SoJIA), transplant rejection, ischemia reperfusion injury of solid organs, multiple sclerosis, and tumor necrosis factor receptor-associated periodic syndrome.

The present invention is further directed to a pharmaceutical composition comprising a compound according to Formula (I), or a salt, particularly a pharmaceutically acceptable salt, thereof and a pharmaceutically acceptable excipient. Particularly, this invention is directed to a pharmaceutical composition for the treatment of a RIP1 kinase-mediated disease or disorder, where the composition comprises a compound according to Formula (I), or a salt, particularly a pharmaceutically acceptable salt, thereof and a pharmaceutically acceptable excipient.

DETAILED DESCRIPTION OF THE INVENTION

Figure 1A:
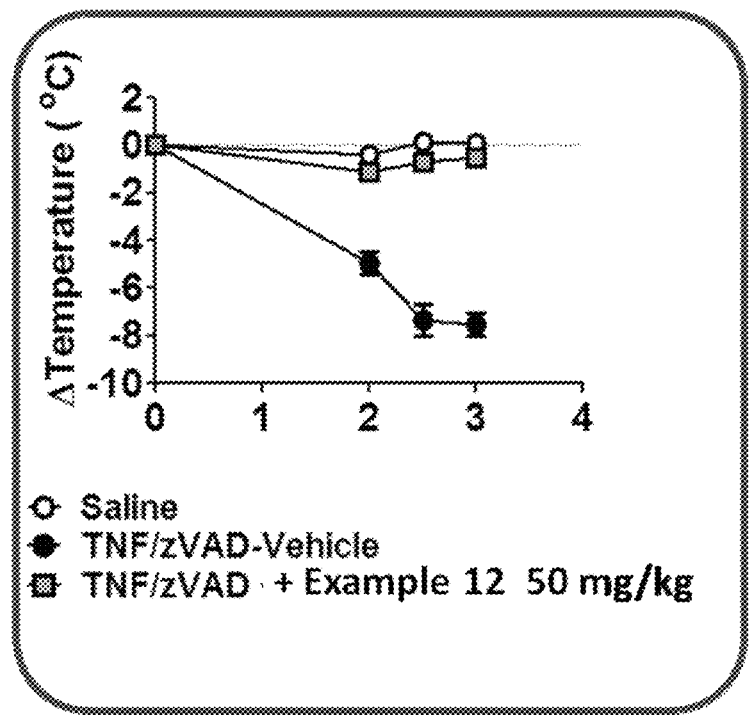
FIG. 1A shows the temperature loss over time in mice after oral pre-dosing with the compound of Example 12 or vehicle followed by simultaneous i.v. administration of mouse TNF and zVAD.
Figure 1B:
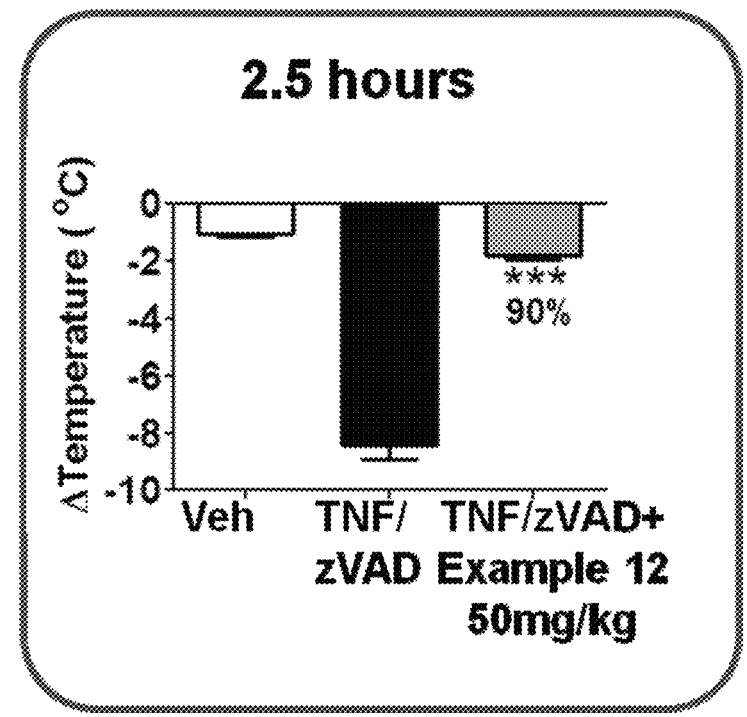
FIG. 1B shows the temperature loss in mice 2.5 hours after oral pre-dosing with the compound of Example 12 or vehicle followed by simultaneous i.v. administration of mouse TNF and zVAD.
Figure 2A:
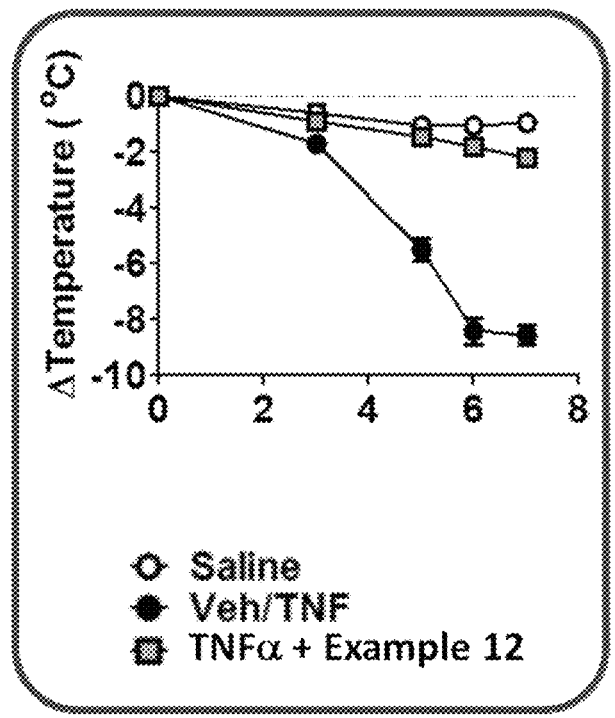
FIG. 2A shows the temperature loss over time in mice after oral pre-dosing with the compound of Example 12 or vehicle followed by i.v. administration of mouse TNF.
Figure 2B:
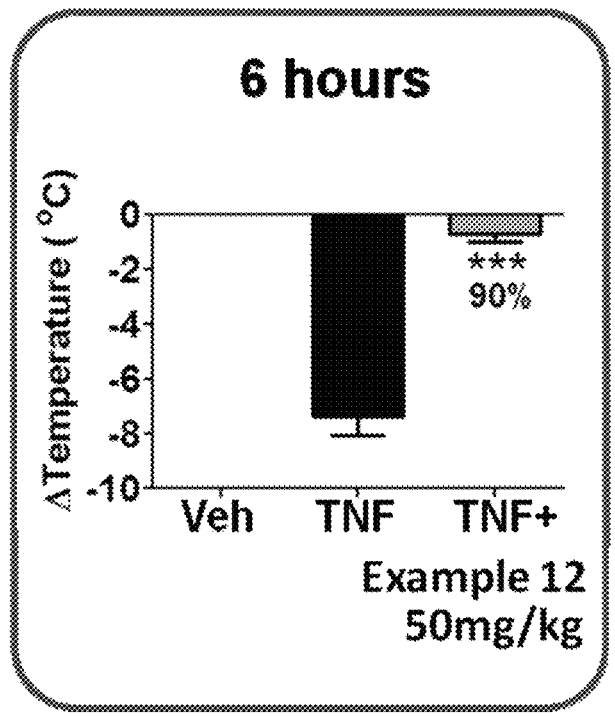
FIG. 2B shows the temperature loss in mice 6 hours after oral pre-dosing with the compound of Example 12 or vehicle followed by i.v. administration of mouse TNF.

This invention is also directed to a compound of Formula (I) wherein:

X is O, S, SO, $SO_2$, NH, CO, $CH_2$, $CF_2$, $CH(CH_3)$, CH(OH), or $N(CH_3)$;

Y is $CH_2$ or $CH_2CH_2$;

$Z^1$ is N, CH or $CR^1$;

$Z^2$ is CH or $CR^2$;

$Z^3$ is N, CH or $CR^3$;

$Z^4$ is CH or $CR^4$;

$R^1$ is fluoro or methyl;

one of $R^2$ and $R^3$ is halogen, cyano, $(C_1-C_6)$alkyl, halo$(C_1-C_4)$alkyl, $(C_1-C_6)$alkoxy, hydroxyl, $B(OH)_2$, —COOH, halo$(C_1-C_4)$alkylC(OH)_2—, $(C_1-C_4)$alkoxy$(C_1-C_4)$alkoxy, $(C_1-C_4)$alkylSO_2—, $(C_1-C_4)$alkylSO_2NHC(O)—, $(C_1-C_4)$alkylC(O)NH—, $((C_1-C_4)$alkyl)($(C_1-C_4)$alkyl)NC(O)—, $(C_1-C_4)$alkylOC(O)—, $(C_1-C_4)$alkylC(O)N($C_1-C_4$alkyl)-, $(C_1-C_4)$alkylNHC(O)—, $(C_1-C_4)$alkoxy$(C_2-C_4)$alkylNHC(O)—, $(C_1-C_4)$alkoxy$(C_2-C_4)$alkylC(O)NH—, $(C_1-C_4)$alkoxy$(C_2-C_4)$alkylNHC(O)NH—, $(C_1-C_4)$alkyl $SO_2(C_2-C_4)$alkylNHC(O)—, $(C_1-C_4)$alkylNHC(O)NH—, $(C_1-C_4)$alkylOC(O)NH—, hydroxy$(C_1-C_4)$alkylOC(O)NH—, 5-6 membered heterocycloalkyl-C(O)—, 5-6 membered heterocycloalkyl-$(C_1-C_4)$alkyl-NHC(O)—, 5-6 membered heterocycloalkyl-$(C_1-C_4)$alkoxy-, 5-6 membered heteroaryl, or 5-6 membered heteroaryl-C(O)NH, wherein said 5-6 membered heterocycloalkyl and 5-6 membered heteroaryl are optionally substituted by 1 or 2 substituents each independently selected from the group consisting of $(C_1-C_4)$alkyl and —$(C_1-C_4)$alkyl-CN;

and the other of $R^2$ and $R^3$ is halogen or $(C_1-C_6)$alkyl;

$R^4$ is fluoro, chloro, or methyl;

$R^5$ is H or methyl;

A is phenyl, 5-6 membered heteroaryl, or 5-6 membered heterocycloalkyl, wherein the carbonyl moiety and L are substituted 1,3 on ring A;

m is 0 or m is 1 and $R^A$ is $(C_1-C_4)$alkyl; and

L is O, S, NH, $N(CH_3)$, $CH_2$, $CH_2CH_2$, $CH(CH_3)$, CHF, $CF_2$, $CH_2O$, $CH_2N(CH_3)$, $CH_2NH$, or CH(OH);

B is an optionally substituted $(C_3-C_6)$cycloalkyl, phenyl, 5-6 membered heteroaryl, or 5-6 membered heterocycloalkyl;

wherein said $(C_3-C_6)$cycloalkyl, phenyl, 5-6 membered heteroaryl, or 5-6 membered heterocycloalkyl is unsubstituted or is substituted by one or two substituents each independently selected from halogen, $(C_1-C_4)$alkyl, halo$(C_1-C_4)$alkyl, $(C_1-C_4)$alkoxy, halo$(C_1-C_4)$alkoxy, nitro, and $(C_1-C_4)$alkylC(O)—;

or the moiety -L-B is $(C_3-C_6)$alkyl, $(C_3-C_6)$alkoxy, halo$(C_3-C_6)$alkoxy, $(C_3-C_6)$alkenyl, or $(C_3-C_6)$alkenyloxy;

or a salt, particularly a pharmaceutically acceptable salt, thereof.

The alternative definitions for the various groups and substituent groups of Formula (I) provided throughout the specification are intended to particularly describe each compound species disclosed herein, individually, as well as groups of one or more compound species. The scope of this invention includes any combination of these group and substituent group definitions. The compounds of the invention are only those which are contemplated to be "chemically stable" as will be appreciated by those skilled in the art.

As used herein, the term "alkyl" represents a saturated, straight or branched hydrocarbon group having the specified number of carbon atoms. The term "$(C_1-C_4)$alkyl" refers to an alkyl moiety containing from 1 to 4 carbon atoms. Exemplary alkyls include, but are not limited to methyl, ethyl, n-propyl, isopropyl, n-butyl, isobutyl, s-butyl, and t-butyl.

When a substituent term such as "alkyl" is used in combination with another substituent term, for example as in "hydroxy$(C_1-C_4)$alkyl" or "aryl$(C_1-C_4)$alkyl", the linking substituent term (e.g., alkyl) is intended to encompass a divalent moiety, wherein the point of attachment is through that linking substituent. Examples of "aryl$(C_1-C_4)$alkyl" groups include, but are not limited to, benzyl (phenylmethyl), 1-methylbenzyl (1-phenylethyl), and phenethyl (2-phenylethyl). Examples of "hydroxy$(C_1-C_4)$alkyl" groups include, but are not limited to, hydroxymethyl, hydroxyethyl, and hydroxyisopropyl.

The term "halo$(C_1-C_4)$alkyl" represents a group having one or more halogen atoms, which may be the same or different, at one or more carbon atoms of an alkyl moiety containing from 1 to 4 carbon atoms. Examples of "halo$(C_1-C_4)$alkyl" groups include, but are not limited to, —$CF_3$ (trifluoromethyl), —$CCl_3$ (trichloromethyl), 1,1-difluoroethyl, 2,2,2-trifluoroethyl, and hexafluoroisopropyl.

"Alkenyl" refers to straight or branched hydrocarbon group having at least 1 and up to 3 carbon-carbon double bonds. Examples include ethenyl and propenyl.

"Alkoxy" refers to an "alkyl-oxy-" group, containing an alkyl moiety attached through an oxygen linking atom. For example, the term "$(C_1-C_4)$alkoxy" represents a saturated, straight or branched hydrocarbon moiety having at least 1 and up to 4 carbon atoms attached through an oxygen linking atom. Exemplary "$(C_1-C_4)$alkoxy" groups include, but are not limited to, methoxy, ethoxy, n-propoxy, isopropoxy, n-butoxy, s-butoxy, and t-butoxy.

The term "halo$(C_1-C_4)$alkoxy" refers to a "haloalkyl-oxy-" group, containing a "halo$(C_1-C_4)$alkyl" moiety attached through an oxygen linking atom, which "halo$(C_1-C_4)$alkyl" refers to a moiety having one or more halogen atoms, which may be the same or different, at one or more carbon atoms of an alkyl moiety containing from 1 to 4 carbon atoms. Exemplary "halo$(C_1-C_4)$alkoxy" groups include, but are not limited to, —$OCHF_2$ (difluoromethoxy), —$OCF_3$ (trifluoromethoxy), —$OCH_2CF_3$ (trifluoroethoxy), and —$OCH(CF_3)_2$ (hexafluoroisopropoxy).

A carbocyclic group is a cyclic group in which all of the ring members are carbon atoms, which may be saturated, partially unsaturated (non-aromatic) or fully unsaturated (aromatic). The term "carbocyclic" includes cycloalkyl and aryl groups.

"Cycloalkyl" refers to a non-aromatic, saturated, cyclic hydrocarbon group containing the specified number of carbon atoms. For example, the term "$(C_3-C_6)$cycloalkyl" refers to a non-aromatic cyclic hydrocarbon ring having from three to six ring carbon atoms. Exemplary "$(C_3-C_6)$cycloalkyl" groups include cyclopropyl, cyclobutyl, cyclopentyl, and cyclohexyl.

The terms "cycloalkyloxy" or "cycloalkoxy" refer to a group containing a cycloalkyl moiety, defined hereinabove, attached through an oxygen linking atom. Exemplary "$(C_3-C_6)$cycloalkyloxy" groups include cyclopropyloxy, cyclobutyloxy, cyclopentyloxy, and cyclohexyloxy.

"Aryl" refers to a group or moiety comprising an aromatic, monocyclic or bicyclic hydrocarbon radical containing from 6 to 10 carbon ring atoms and having at least one aromatic ring. Examples of "aryl" groups are phenyl, naphthyl, indenyl, and dihydroindenyl (indanyl). Generally, in the compounds of this invention, aryl is phenyl.

A heterocyclic group is a cyclic group having, as ring members, atoms of at least two different elements, which cyclic group may be saturated, partially unsaturated (non-aromatic) or fully unsaturated (aromatic). The terms "heterocyclic" or "heterocyclyl" includes heterocycloalkyl and heteroaryl groups. It is to be understood that the terms heterocyclic, heterocyclyl, heteroaryl, and heterocycloalkyl, are intended to encompass stable groups where a ring nitrogen heteroatom is optionally oxidized (e.g., heteroaryl groups containing an N-oxide, such as oxo-pyridyl (pyridyl-N-oxide) and oxo-oxadiazolyl (oxo-4,5-dihydro-1,3,4-oxadiazolyl) or where a ring sulfur heteroatom is optionally oxidized (e.g., heterocycloalkyl groups containing sulfones or sulfoxide moieties, such as tetrahydrothienyl-1-oxide (tetrahydrothienyl sulfoxide, tetrahydrothiophenyl sulfoxide) and tetrahydrothienyl-1,1-dioxide (tetrahydrothienyl sulfone)).

"Heterocycloalkyl" refers to a non-aromatic, monocyclic or bicyclic group containing 3-10 ring atoms, being saturated or having one or more degrees of unsaturation and containing one or more (generally one or two) heteroatom substitutions independently selected from oxygen, sulfur, and nitrogen. Examples of "heterocycloalkyl" groups include, but are not limited to, aziridinyl, thiiranyl, oxiranyl, azetidinyl, oxetanyl, thietanyl, pyrrolidinyl, pyrrolinyl, pyrazolidinyl, pyrazolinyl, imidazolidinyl, imidazolinyl, oxazolinyl, thiazolinyl, tetrahydrofuranyl, dihydrofuranyl, tetrahydrothienyl, 1,3-dioxolanyl, piperidinyl, piperazinyl, tetrahydropyranyl, dihydropyranyl, tetrahydrothiopyranyl, 1,3-dioxanyl, 1,4-dioxanyl, 1,3-oxathiolanyl, 1,3-oxathianyl, 1,3-dithianyl, 1,4-oxathiolanyl, 1,4-oxathianyl, 1,4-dithianyl, morpholinyl, thiomorpholinyl, hexahydro-1H-1,4-diazepinyl, azabicylo[3.2.1]octyl, azabicylo[3.3.1]nonyl, azabicylo[4.3.0]nonyl, oxabicylo[2.2.1]heptyl, 1,1-dioxido-tetrahydro-2H-thiopyranyl, and 1,5,9-triazacyclododecyl.

Examples of "4-membered heterocycloalkyl" groups include oxetanyl, thietanyl and azetidinyl.

The term "5-6-membered heterocycloalkyl" represents a non aromatic, monocyclic group, which is saturated or partially unsaturated, containing 5 or 6 ring atoms, which includes one or two heteroatoms selected independently from oxygen, sulfur, and nitrogen. Illustrative examples of 5 to 6-membered heterocycloalkyl groups include, but are not limited to pyrrolidinyl, piperidinyl, piperazinyl, tetrahydrofuranyl, tetrahydrothienyl, tetrahydropyranyl, tetrahydrothiopyranyl, morpholinyl, and thiomorpholinyl.

"Heteroaryl" represents a group or moiety comprising an aromatic monocyclic or bicyclic radical, containing 5 to 10 ring atoms, including 1 to 4 heteroatoms independently selected from nitrogen, oxygen and sulfur. This term also encompasses bicyclic heterocyclic-aryl groups containing either an aryl ring moiety fused to a heterocycloalkyl ring moiety or a heteroaryl ring moiety fused to a cycloalkyl ring moiety.

Illustrative examples of heteroaryls include, but are not limited to, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl (pyridyl), oxo-pyridyl (pyridyl-N-oxide), pyridazinyl, pyrazinyl, pyrimidinyl, triazinyl, benzofuranyl, isobenzofuryl, 2,3-dihydrobenzofuryl, 1,3-benzodioxolyl, dihydrobenzodioxinyl, benzothienyl, indolizinyl, indolyl, isoindolyl, dihydroindolyl, benzimidazolyl, dihydrobenzimidazolyl, benzoxazolyl, dihydrobenzoxazolyl, benzothiazolyl, benzoisothiazolyl, dihydrobenzoisothiazolyl, indazolyl, imidazopyridinyl, pyrazolopyridinyl, benzotriazolyl, triazolopyridinyl, purinyl, quinolinyl, tetrahydroquinolinyl, isoquinolinyl, tetrahydroisoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl.

As used herein, "5-6-membered heteroaryl" represents an aromatic monocyclic group containing 5 or 6 ring atoms, including at least one carbon atom and 1 to 4 heteroatoms independently selected from nitrogen, oxygen and sulfur. Selected 5-membered heteroaryl groups contain one nitrogen, oxygen, or sulfur ring heteroatom, and optionally contain 1, 2, or 3 additional nitrogen ring atoms. Selected 6-membered heteroaryl groups contain 1, 2, or 3 nitrogen ring heteroatoms. Examples of 5-membered heteroaryl groups include furyl (furanyl), thienyl, pyrrolyl, imidazolyl, pyrazolyl, triazolyl, tetrazolyl, thiazolyl, isothiazolyl, thiadiazolyl, oxazolyl, isoxazolyl, oxadiazolyl and oxo-oxadiazolyl. Selected 6-membered heteroaryl groups include pyridinyl, oxo-pyridyl, pyrazinyl, pyrimidinyl, pyridazinyl and triazinyl.

Bicyclic heteroaryl groups include 6,5-fused heteroaryl (9-membered heteroaryl) and 6,6-fused heteroaryl (10-membered heteroaryl) groups. Examples of 6,5-fused heteroaryl (9-membered heteroaryl) groups include benzothienyl, benzofuranyl, indolyl, indolinyl, isoindolyl, isoindolinyl, indazolyl, indolizinyl, isobenzofuryl, 2,3-dihydrobenzofuryl, benzoxazolyl, benzthiazolyl, benzimidazolyl, benzoxadiazolyl, benzthiadiazolyl, benzotriazolyl, 1,3-benzoxathiol-2-on-yl (2-oxo-1,3-benzoxathiolyl), purinyl and imidazopyridinyl.

Examples of 6,6-fused heteroaryl (10-membered heteroaryl) groups include quinolyl, isoquinolyl, phthalazinyl, naphthridinyl (1,5-naphthyridinyl, 1,6-naphthyridinyl, 1,7-naphthyridinyl, 1,8-naphthyridinyl), quinazolinyl, quinoxalinyl, 4H-quinolizinyl, tetrahydroquinolinyl, cinnolinyl, and pteridinyl.

Unless otherwise specified, all bicyclic ring systems may be attached at any suitable position on either ring.

The terms "halogen" and "halo" represent chloro, fluoro, bromo, or iodo substituents. "Oxo" represents a double-bonded oxygen moiety; for example, if attached directly to a carbon atom forms a carbonyl moiety (C=O). "Hydroxy" or "hydroxyl" is intended to mean the radical —OH. As used herein, the term "cyano" refers to the group —CN.

As used herein, the term "optionally substituted" indicates that a group (such as an alkyl, cycloalkyl, alkoxy, heterocycloalkyl, aryl, or heteroaryl group) or ring or moiety (such as a carbocyclic or heterocyclic ring or moiety) may be unsubstituted, or the group, ring or moiety may be substituted with one or more substituent(s) as defined. In the case where groups may be selected from a number of alternative groups, the selected groups may be the same or different.

The term "independently" means that where more than one substituent is selected from a number of possible substituents, those substituents may be the same or different.

The term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein, the terms "compound(s) of the invention" or "compound(s) of this invention" mean a compound of Formula (I), particularly a compound of any one of Formulas (I-IV), as defined herein, in any form, i.e., any salt or non-salt form (e.g., as a free acid or base form, or as a salt, particularly a pharmaceutically acceptable salt thereof) and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di- and hemi-hydrates)), and mixtures of various forms.

Accordingly, included within the present invention are the compounds of Formula (I), particularly, compounds of any one of Formulas (I-IV), as defined herein, in any salt or non-salt form and any physical form thereof, and mixtures of various forms. While such are included within the present invention, it will be understood that the compounds of Formula (I), particularly compounds of any one of Formulas (I-IV), as defined herein, in any salt or non-salt form, and in any physical form thereof, may have varying levels of activity, different bioavailabilities and different handling properties for formulation purposes.

In one embodiment of the compounds of this invention, X is O, S, SO, $SO_2$, NH, CO, $CH_2$, $CF_2$, $CH(CH_3)$, $N(CH_3)$, or CH(OH). In a specific embodiment, X is O, S, SO, $SO_2$, NH, CO, $CH_2$, or $N(CH_3)$. In another embodiment, X is S, SO, $SO_2$, or CO. In yet another embodiment, X is $CF_2$, $CH(CH_3)$, or CH(OH). In a further embodiment, X is O, $CH_2$, NH or $N(CH_3)$. In selected embodiments, X is O or $CH_2$.

In one embodiment of the compounds of this invention, Y is $CH_2$ or $CH_2CH_2$. In another embodiment, Y is $CH_2CH_2$. In selected embodiments, Y is $CH_2$.

In one embodiment of the compounds this invention, $Z^1$, $Z^2$, $Z^3$, and $Z^4$ are each CH. In another embodiment, $Z^1$ is $CR^1$ and $Z^2$, $Z^3$ and $Z^4$ are each CH. In a further embodiment, $Z^1$, $Z^2$, $Z^3$, and $Z^4$ are each CH and $Z^3$ is $CR^3$. In a further embodiment, $Z^1$, $Z^3$, and $Z^4$ are each CH and $Z^2$ is $CR^2$. In a still further embodiment, $Z^1$, $Z^2$, and $Z^3$ are each CH and $Z^4$ is $CR^4$. In another embodiment, $Z^1$ and $Z^2$ are CH, $Z^3$ is $CR^3$, and $Z^4$ is $CR^4$. In another embodiment, $Z^1$ and $Z^4$ are CH, $Z^2$ is $CR^2$, and $Z^3$ is $CR^3$. In another embodiment, $Z^1$ and $Z^3$ are CH, $Z^2$ is $CR^2$, and $Z^4$ is $CR^4$. In another embodiment, $Z^1$ is CH, $Z^2$ is $CR^2$, $Z^3$ is $CR^3$, and $Z^4$ is $CR^4$.

In yet another embodiment of the compounds of this invention $Z^1$ and $Z^3$ are both N, $Z^2$ is CH and $Z^4$ is CH or $CR^4$. In yet another embodiment of the compounds of this invention $Z^1$ and $Z^3$ are both N, $Z^2$ is CH or $CR^2$ and $Z^4$ is CH. In still other embodiments, $Z^1$ is N, $Z^2$ is $CR^2$ and $Z^3$ and $Z^4$ are CH. In yet other embodiments, $Z^3$ is N, and $Z^2$, $Z^3$ and $Z^4$ are CH.

In one embodiment of the compounds of this invention, $R^1$ is fluoro. In another embodiment, $R^1$ is methyl.

In one embodiment, one of $R^2$ and $R^3$ is halogen, cyano, $(C_1-C_6)$alkyl, halo$(C_1-C_4)$alkyl, $(C_1-C_6)$alkoxy, halo$(C_1-C_4)$alkoxy, hydroxyl, $B(OH)_2$, —COOH, halo$(C_1-C_4)$alkylC(OH)$_2$—, $(C_1-C_4)$alkoxy$(C_1-C_4)$alkoxy, $(C_1-C_4)$alkylSO$_2$—, $(C_1-C_4)$alkylSO$_2$NHC(O)—, $(C_1-C_4)$alkylC(O)NH—, $((C_1-C_4)$alkyl)$((C_1-C_4)$alkyl)NC(O)—, $(C_1-C_4)$alkylOC(O)—, $(C_1-C_4)$alkylC(O)N$(C_1-C_4)$alkyl)-, $(C_1-C_4)$alkylNHC(O)—, $(C_1-C_4)$alkoxy$(C_2-C_4)$alkylNHC(O)—, $(C_1-C_4)$alkoxy$(C_2-C_4)$alkylC(O)NH—, $(C_1-C_4)$alkoxy$(C_2-C_4)$alkylNHC(O)NH—, $(C_1-C_4)$alkyl SO$_2$$(C_2-C_4)$alkylNHC(O)—, $(C_1-C_4)$alkylNHC(O)NH—, $(C_1-C_4)$alkylOC(O)NH—, hydroxy$(C_1-C_4)$alkylOC(O)NH—, 5-6 membered heterocycloalkyl-C(O)—, 5-6 membered heterocycloalkyl-$(C_1-C_4)$alkyl-NHC(O)—, 5-6 membered heterocycloalkyl-$(C_1-C_4)$alkoxy-, 3-6 membered cycloalkyl, 5-6 membered heteroaryl, or 5-6 membered heteroaryl-C(O)NH, wherein said 3-6 membered cycloalkyl, 5-6 membered heterocycloalkyl and 5-6 membered heteroaryl are optionally substituted by 1 or 2 substituents each independently selected from the group consisting of $(C_1-C_4)$alkyl and —$(C_1-C_4)$alkyl-CN;

and the other of $R^2$ and $R^3$ is halogen, cyano or $(C_1-C_6)$alkyl.

In one embodiment of the compounds of this invention, one of $R^2$ and $R^3$ is halogen, cyano, $(C_1-C_6)$alkyl, halo$(C_1-C_4)$alkyl, $(C_1-C_6)$alkoxy, hydroxyl, $B(OH)_2$, —COOH, halo$(C_1-C_4)$alkylC(OH)$_2$—, $(C_1-C_4)$alkoxy$(C_1-C_4)$alkoxy, $(C_1-C_4)$alkylSO$_2$—, $(C_1-C_4)$alkylSO$_2$NHC(O)—, $(C_1-C_4)$alkylC(O)NH—, $((C_1-C_4)$alkyl)$((C_1-C_4)$alkyl)NC(O)—, $(C_1-C_4)$alkylOC(O)—, $(C_1-C_4)$alkylC(O)N$(C_1-C_4)$alkyl)-, $(C_1-C_4)$alkylNHC(O)—, $(C_1-C_4)$alkoxy$(C_2-C_4)$alkylNHC(O)—, $(C_1-C_4)$alkoxy$(C_2-C_4)$alkylC(O)NH—, $(C_1-C_4)$alkoxy$(C_2-C_4)$alkylNHC(O)NH—, $(C_1-C_4)$alkylSO$_2$$(C_2-C_4)$alkylNHC(O)—, $(C_1-C_4)$alkylNHC(O)NH—, $(C_1-C_4)$alkylOC(O)NH—, hydroxy$(C_1-C_4)$alkylOC(O)NH—, 5-6 membered heterocycloalkyl-C(O)—, 5-6 membered heterocycloalkyl-$(C_1-C_4)$alkyl-NHC(O)—, 5-6 membered heterocycloalkyl-$(C_1-C_4)$alkoxy-, 5-6 membered heteroaryl, or 5-6 membered heteroaryl-C(O)NH, wherein said 5-6 membered heterocycloalkyl and 5-6 membered heteroaryl are optionally substituted by 1 or 2 substituents each independently selected from the group consisting of $(C_1-C_4)$alkyl and —$(C_1-C_4)$alkyl-CN;

and the other of $R^2$ and $R^3$ is halogen or $(C_1-C_6)$alkyl.

In another embodiment, $R^2$ is halogen, cyano, $(C_1-C_6)$alkyl, $(C_1-C_6)$alkoxy, halo$(C_1-C_4)$alkoxy, hydroxyl, $B(OH)_2$, —COOH, halo$(C_1-C_4)$alkylC(OH)$_2$—, $(C_1-C_4)$alkoxy$(C_1-C_4)$alkoxy, 3-5 membered cycloalkyl, or 5-6 membered heteroaryl, wherein said 3-5 membered cycloalkyl or 5-6 membered heteroaryl is optionally substituted by a $(C_1-C_3)$alkyl substituent; and $Z^3$ is CH or $CR^3$ and $R^3$ is cyano, $(C_1-C_6)$alkyl, or a 5-6 membered heteroaryl, optionally substituted by a $(C_1-C_3)$alkyl substituent. In another embodiment, $R^2$ is halogen, cyano, $(C_1-C_6)$alkyl, hydroxyl, $B(OH)_2$, —COOH, halo$(C_1-C_4)$alkylC(OH)$_2$—, $(C_1-C_4)$alkoxy$(C_1-C_4)$alkoxy, or 5-6 membered heteroaryl, wherein said 5-6 membered heteroaryl is optionally substituted by a $(C_1-C_3)$alkyl substituent; and $Z^3$ is CH.

In another embodiment, $R^3$ is halogen, $(C_1-C_6)$alkyl, halo$(C_1-C_4)$alkyl, $(C_1-C_6)$alkoxy, halo$(C_1-C_6)$alkoxy, $B(OH)_2$, —COOH, $(C_1-C_4)$alkylSO$_2$—, $(C_1-C_4)$alkylSO$_2$NHC(O)—, $(C_1-C_4)$alkylC(O)NH—, $((C_1-C_4)$alkyl)$((C_1-C_4)$alkyl)NC(O)—, $(C_1-C_4)$alkylOC(O)—, $(C_1-C_4)$alkylC(O)N$(C_1-C_4)$alkyl)-, $(C_1-C_4)$alkoxy$(C_2-C_4)$alkylNHC(O)NH—, $(C_1-C_4)$alkyl SO$_2$$(C_2-C_4)$alkylNHC(O)—, $(C_1-C_4)$alkylNHC(O)NH—, $(C_1-C_4)$alkylOC(O)NH—, hydroxy$(C_1-C_4)$alkylOC(O)NH—, 5-6 membered heterocycloalkyl-C(O)—, 5-6 membered heterocycloalkyl-$(C_1-C_4)$alkyl-NHC(O)—, 5-6 membered heterocycloalkyl-$(C_1-C_4)$alkoxy-, 5-6 membered heteroaryl, or 5-6 membered heteroaryl-C(O)NH, herein said 5-6 membered heterocycloalkyl and 5-6 membered heteroaryl are optionally substituted by $(C_1-C_3)$alkyl or —$(C_1-C_3)$alkyl-CN; and $Z^2$ is CH.

In another embodiment, $R^3$ is halogen, $(C_1-C_6)$alkyl, halo$(C_1-C_4)$alkyl, $(C_1-C_6)$alkoxy, $B(OH)_2$, —COOH, $(C_1-C_4)$alkylSO$_2$—, $(C_1-C_4)$alkylSO$_2$NHC(O)—, $(C_1-C_4)$alkylC(O)NH—, $((C_1-C_4)$alkyl)$((C_1-C_4)$alkyl)NC(O)—, $(C_1-C_4)$alkylOC(O)—, $(C_1-C_4)$alkylC(O)N$(C_1-C_4)$alkyl)-, $(C_1-C_4)$alkoxy$(C_2-C_4)$alkylNHC(O)NH—, $(C_1-C_4)$alkyl SO$_2$$(C_2-C_4)$alkylNHC(O)—, $(C_1-C_4)$alkylNHC(O)NH—, $(C_1-C_4)$alkylOC(O)NH—, hydroxy$(C_1-C_4)$alkylOC(O)NH—, 5-6 membered heterocycloalkyl-C(O)—, 5-6 membered heterocycloalkyl-$(C_1-C_4)$alkyl-NHC(O)—, 5-6 membered heterocycloalkyl-$(C_1-C_4)$alkoxy-, 5-6 membered heteroaryl, or 5-6 membered heteroaryl-C(O)NH, herein said 5-6 membered heterocycloalkyl and 5-6 membered heteroaryl are optionally substituted by $(C_1-C_3)$alkyl or —$(C_1-C_3)$alkyl-CN; and $Z^2$ is CH.

In specific embodiments, $R^2$ is fluoro, chloro, bromo, —CN, —$CH_3$, —$OCH_3$, —$OCHF_2$, —OH, $B(OH)_2$, $CF_3C(OH)_2$—, $CH_3OCH_2CH_2O$—, cyclopropyl, 5H-tetrazol-5-yl, pyrazol-3-yl, or 5-methyl-1,3,4-oxadiazol-2-yl.

In other specific embodiments, $R^2$ is fluoro, chloro, bromo, —CN, —CH$_3$, —OH, B(OH)$_2$, CF$_3$C(OH)$_2$—, CH$_3$OCH$_2$CH$_2$O—, 5H-tetrazol-5-yl, pyrazol-3-yl, or 5-methyl-1,3,4-oxadiazol-2-yl.

In another specific embodiment, $R^2$ is chloro, bromo, —CN, —CH$_3$, —OH, B(OH)$_2$, CF$_3$C(OH)$_2$—, CH$_3$OCH$_2$CH$_2$O—, 5H-tetrazol-5-yl, pyrazol-3-yl, or 5-methyl-1,3,4-oxadiazol-2-yl.

In specific embodiments, $R^3$ is fluoro, chloro, bromo, —CN, —OCH$_3$, —OCHF$_2$, B(OH)$_2$, —COOH, CH$_3$SO$_2$—, CH$_3$SO$_2$NHC(O)—, CH$_3$C(O)NH—, (CH$_3$)$_2$NC(O)—, CH$_3$OC(O)—, (CH$_3$)C(O)N(CH$_3$)—, HOCH$_2$CH$_2$C(O)NH—, CH$_3$OCH$_2$CH$_2$NHC(O)NH—, CH$_3$SO$_2$CH$_2$CH$_2$NHC(O)—, CH$_3$CH$_2$NHC(O)NH—, CH$_3$OC(O)NH—, morpholin-4-yl-CO—, pyrrolidin-1-yl-CH$_2$CH$_2$NHC(O)—, pyridin-2-yl, tetrahydrofuran-2-yl-CH$_2$O—, pyrrolidin-1-yl-CH$_2$CH$_2$O—, tetrazol-5-yl, 1-(2-cyanoethyl)-tetrazol-5-yl, pyrazol-1-yl, pyrazol-3-yl, pyrazol-4-yl, 1-methyl-pyrazol-3-yl, 1-methyl-pyrrol-4-yl-C(O)NH—, 5-methyl-1,3,4-oxadiazol-2-yl, or 5-oxo-4,5-dihydro-1,3,4-oxadiazol-2-yl.

In other specific embodiments, $R^3$ is fluoro, chloro, bromo, —OCH$_3$, B(OH)$_2$, —COOH, CH$_3$SO$_2$—, CH$_3$SO$_2$NHC(O)—, CH$_3$C(O)NH—, (CH$_3$)$_2$NC(O)—, CH$_3$OC(O)—, (CH$_3$)C(O)N(CH$_3$)—, HOCH$_2$CH$_2$C(O)NH—, CH$_3$OCH$_2$CH$_2$NHC(O)NH—, CH$_3$SO$_2$CH$_2$CH$_2$NHC(O)—, CH$_3$CH$_2$NHC(O)NH—, CH$_3$OC(O)NH—, morpholin-4-yl-CO—, pyrrolidin-1-yl-CH$_2$CH$_2$NHC(O)—, tetrahydrofuran-2-yl-CH$_2$O—, pyrrolidin-1-yl-CH$_2$CH$_2$O—, tetrazol-5-yl, 1-(2-cyanoethyl)-tetrazol-5-yl, pyrazol-1-yl, pyrazol-3-yl, 1-methyl-pyrazol-3-yl, 1-methyl-pyrrol-4-yl-C(O)NH—, 5-methyl-1,3,4-oxadiazol-2-yl, or 5-oxo-4,5-dihydro-1,3,4-oxadiazol-2-yl.

In still other embodiments, $R^3$ is fluoro, chloro, bromo, —OCH$_3$, B(OH)$_2$, —COOH, CH$_3$SO$_2$—, CH$_3$SO$_2$NHC(O)—, CH$_3$C(O)NH—, (CH$_3$)$_2$NC(O)—, CH$_3$OC(O)—, (CH$_3$)C(O)N(CH$_3$)—, HOCH$_2$CH$_2$C(O)NH—, CH$_3$OCH$_2$CH$_2$NHC(O)NH—, CH$_3$SO$_2$CH$_2$CH$_2$NHC(O)—, CH$_3$CH$_2$NHC(O)NH—, CH$_3$OC(O)NH—, morpholin-4-yl-CO—, pyrrolidin-1-yl-CH$_2$CH$_2$NHC(O)—, tetrahydrofuran-2-yl-CH$_2$O—, pyrrolidin-1-yl-CH$_2$CH$_2$O—, tetrazol-5-yl, 1-(2-cyanoethyl)-tetrazol-5-yl, pyrazol-1-yl, pyrazol-3-yl, 1-methyl-pyrazol-3-yl, 1-methyl-pyrrol-4-yl-C(O)NH—, or 5-oxo-4,5-dihydro-1,3,4-oxadiazol-2-yl.

In one embodiment of the compounds of this invention, $R^4$ is fluoro, chloro, methyl, or trifluoromethyl. In another embodiment, $R^4$ is fluoro. In yet another embodiment, $R^4$ is methyl.

In one embodiment of the compounds of this invention, $R^5$ is H. In another embodiment, $R^5$ is methyl.

In one embodiment of the compounds of this invention, A is phenyl, 5-6 membered heteroaryl, or 5-6 membered heterocycloalkyl, wherein the carbonyl moiety and L are substituted 1,3 on ring A.

In another embodiment, A is a 5 membered heteroaryl containing one oxygen or sulfur atom and optionally containing one or two nitrogen atoms; specifically A is furyl, thienyl, oxazolyl, isoxazolyl, thiazolyl, or oxadiazolyl (more specifically, 1, 2, 4-oxadiazolyl or 1, 3, 4-oxadiazolyl). In another embodiment, A is a 5 membered heteroaryl containing one nitrogen atom and optionally containing one, two or three additional nitrogen atoms, specifically; A is pyrrolyl, pyrazolyl, imidazolyl, triazolyl (more specifically, 1, 2, 3-triazolyl or 1, 2, 4-triazolyl) or tetrazolyl. In selected embodiments, A is triazolyl. In yet embodiment of this invention, A is a 5 or 6 membered heterocycloalkyl specifically, A is piperidinyl or pyrrolidinyl. In a further embodiment of this invention, A is a 6 membered aromatic group selected from phenyl and pyridyl.

Another embodiment of this invention is directed to a compound according to Formula (II):

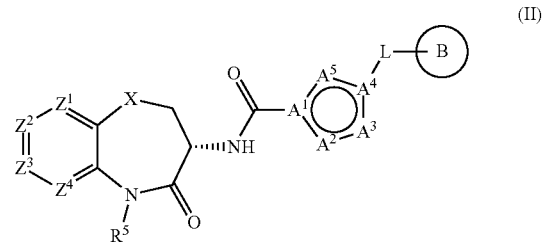

(II)

wherein:

$A^1$ is C, $A^4$ is C or N, and $A^2$, $A^3$, and $A^5$ are each independently selected from CH, CR$^4$, O, S, N, NH and NR$^4$ to form a furyl, thienyl, oxazolyl, isoxazolyl, thiazolyl, oxadiazolyl, pyrrolyl, pyrazolyl, imidazolyl, triazolyl or tetrazolyl ring moiety, wherein said ring moiety contains 0 or 1 of CR$^4$ and NR$^4$; and wherein X, $Z^1$, $Z^2$, $Z^3$, $Z^4$, $R^5$, L, and B are as defined herein, or a salt, particularly a pharmaceutically acceptable salt, thereof.

In selected embodiments, $A^1$ is C, $A^4$ is C or N, and $A^2$, $A^3$, and $A^5$ are each independently selected from CH, O, N, and NH to form an oxazolyl, isoxazolyl, oxadiazolyl, pyrrolyl, pyrazolyl, imidazolyl, triazolyl or tetrazolyl ring moiety.

In other selected embodiments, $A^1$ and $A^4$ are each C, and $A^2$, $A^3$ and $A^5$ are each independently selected from N and NH to form a triazolyl ring moiety.

Another embodiment of this invention, wherein A is piperidinyl or pyrrolidinyl, may be represented by Formula (III):

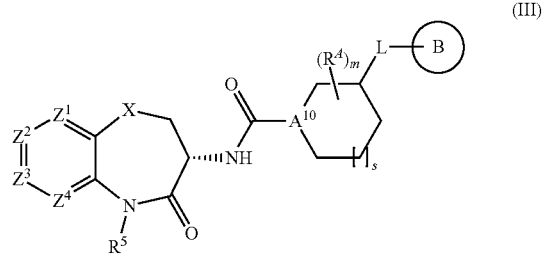

(III)

wherein s is 0 or 1, $A^{10}$ is N and X, $Z^1$, $Z^2$, $Z^3$, $Z^4$, $R^5$ $R^4$, m, L, and B are as defined herein. In specific embodiments, m is 0 and A is an unsubstituted piperidinyl or pyrrolidinyl moiety.

In one embodiment of the compounds of this invention, m is 0. In another embodiment, m is 1 and $R^4$ is (C$_1$-C$_4$)alkyl, specifically $R^4$ is (C$_1$-C$_2$)alkyl. In selected embodiments, $R^4$ is methyl.

A further embodiment of this invention, wherein A is phenyl, pyridinyl, or pyridinyl-N-oxide, may be represented by Formula (IV):

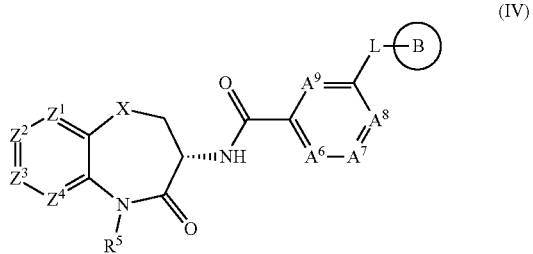

(IV)

wherein:

$A^6$, $A^7$, $A^8$, and $A^9$ are each CH;

one of $A^6$, $A^7$, $A^8$, and $A^9$ is $CR^A$ and the others of $A^6$, $A^7$, $A^8$, and $A^9$ are CH;

one of $A^6$, $A^7$, $A^8$, and $A^9$ is N and the others of $A^6$, $A^7$, $A^8$, and $A^9$ are CH;

one of $A^6$, $A^7$, $A^8$, and $A^9$ is N—O and the other of $A^6$, $A^7$, $A^8$, and $A^9$ are CH;

and X, $Z^1$, $Z^2$, $Z^3$, $Z^4$, $R^5$, L, and B are as defined herein.

In one embodiment of the compounds of this invention, L is O, S, NH, N(CH$_3$), CH$_2$, CH$_2$CH$_2$, CH(CH$_3$), CHF, CF$_2$, CH$_2$O, CH$_2$N(CH$_3$), CH$_2$NH, or CH(OH). In another embodiment, L is O, S, N(CH$_3$), CH$_2$, CH$_2$CH$_2$, CH(CH$_3$), CF$_2$, CH$_2$O, CH$_2$N(CH$_3$), or CH(OH). In another embodiment, L is CH$_2$O, CH$_2$CH$_2$, CH$_2$NH, or CH$_2$N(CH$_3$). In a further embodiment, L is N(CH$_3$), CH(CH$_3$), or CH(OH). In another further embodiment, L is —(R)CH(CH$_3$). In a still further embodiment, L is O, CH$_2$, or NH. In one selected embodiment, L is O. In another selected embodiment, L is CH$_2$.

In one embodiment of the compounds of this invention, B is an optionally substituted (C$_3$-C$_6$)cycloalkyl, phenyl, 5-6 membered heteroaryl, or 5-6 membered heterocycloalkyl; wherein said (C$_3$-C$_6$)cycloalkyl, phenyl, 5-6 membered heteroaryl, or 5-6 membered heterocycloalkyl is unsubstituted or is substituted by one or two substituents each independently selected from halogen, (C$_1$-C$_4$)alkyl, halo(C$_1$-C$_4$)alkyl, (C$_1$-C$_4$)alkoxy, halo(C$_1$-C$_4$)alkoxy, nitro, and (C$_1$-C$_4$)alkylC(O)—. In one embodiment of this invention, B is an optionally substituted 5-6 membered heteroaryl or 5-6 membered heterocycloalkyl. In one embodiment, B is an optionally substituted pyrazolyl, thienyl, pyridinyl (pyridyl), oxo-pyridyl, pyrimidinyl, isoxazolyl, morpholinyl, tetrahydropyranyl or tetrahydrofuranyl, wherein the pyrazolyl, thienyl, pyridinyl (pyridyl), oxo-pyridyl, pyrimidinyl, isoxazolyl, morpholinyl, tetrahydropyranyl or tetrahydrofuranyl is optionally substituted by one or two independently selected (C$_1$-C$_4$)alkyl substituents. In another embodiment, B is an optionally substituted pyrazolyl, thienyl, pyridinyl (pyridyl), oxo-pyridyl, pyrimidinyl, isoxazolyl, morpholinyl, or tetrahydrofuranyl, wherein the pyrazolyl, thienyl, pyridinyl (pyridyl), oxo-pyridyl, pyrimidinyl, isoxazolyl, morpholinyl, or tetrahydrofuranyl is optionally substituted by one or two independently selected (C$_1$-C$_4$)alkyl substituents. In specific embodiments, B is thien-2-yl (thiophen-2-yl), 5-methyl-thien-2-yl (5-methyl-thiophen-2-yl), pyrazol-1-yl, 3,5-dimethylpyrazol-1-yl, 4-methylpyrazol-1-yl, 3,5-dimethylisoxazol-4-yl, tetrahydropyran-3-yl, tetrahydrofuran-2-yl, morpholin-4-yl, pyridin-2-yl, 2-oxo-pyridin-1-yl, 6-methylpyridin-3-yl, or 2-methylpyrimidin-5-yl.

In other specific embodiments, B is thien-2-yl (thiophen-2-yl), 5-methyl-thien-2-yl (5-methyl-thiophen-2-yl), pyrazol-1-yl, 3,5-dimethylpyrazol-1-yl, 4-methylpyrazol-1-yl, 3,5-dimethylisoxazol-4-yl, tetrahydrofuran-2-yl, morpholin-4-yl, pyridin-2-yl, 2-oxo-pyridin-1-yl, 6-methylpyridin-3-yl, and 2-methylpyrimidin-5-yl.

In specific embodiments, B is thien-2-yl, pyrazol-1-yl, 3,5-dimethylpyrazol-1-yl, 4-methylpyrazol-1-yl, 3,5-dimethylisoxazol-4-yl, tetrahydrofuran-2-yl, morpholin-4-yl, pyridin-2-yl, 2-oxo-pyridin-1-yl, 6-methylpyridin-3-yl, and 2-methylpyrimidin-5-yl.

In another embodiment of the compounds of this invention, B is unsubstituted (C$_3$-C$_6$)cycloalkyl or phenyl. In a selected embodiment of this invention, B is unsubstituted cyclopropyl, cyclobutyl, cyclopentyl or cyclohexyl. In a specific embodiment, B is unsubstituted cyclopentyl or cyclohexyl. In another selected embodiment of the compounds of this invention, B is unsubstituted phenyl.

In another selected embodiment, B is substituted phenyl. In one embodiment, B is phenyl, substituted by 1 or 2 substituents independently selected from halogen, (C$_1$-C$_4$)alkyl, halo(C$_1$-C$_4$)alkyl, (C$_1$-C$_4$)alkoxy, halo(C$_1$-C$_4$)alkoxy, nitro, and (C$_1$-C$_4$)alkylC(O)—. In other embodiments, B is phenyl, substituted by 1 or 2 substituents independently selected from halogen, (C$_1$-C$_3$)alkyl and (C$_1$-C$_3$)alkoxy. In specific embodiments, B is phenyl, substituted by a substituent selected from fluoro, chloro, bromo, iodo, nitro, methyl, ethyl, isopropyl, trifluoromethyl, methoxy, and —COCH$_3$. In specific embodiments, B is phenyl, substituted by 1 or 2 substituents independently selected from iodo, fluoro, chloro, bromo, methyl and methoxy.

In one selected embodiment, B is phenyl, substituted by 1 or 2 substituents independently selected from fluoro, chloro, bromo, and methyl, specifically B is phenyl, substituted by 1 or 2 fluoro substituents. In specific embodiments, B is cyclopentyl, cyclohexyl, 2-methylphenyl, 4-methylphenyl, 2-trifluoromethylphenyl, 2-fluorophenyl, 3-fluorophenyl, 4-fluorophenyl, 2-iodophenyl, 3-bromophenyl, 4-bromophenyl, 4-chlorophenyl, 2,5-difluorophenyl, 2,4-difluorophenyl, 3,4-difluorophenyl, 3,5-difluorophenyl, or 4-methoxyphenyl. In other embodiments, B is 2,3-difluorophenyl or 2,6-difluorophenyl.

In one embodiment of the compounds of this invention, the moiety -L-B is (C$_3$-C$_6$)alkyl, (C$_3$-C$_6$)alkoxy, halo(C$_3$-C$_6$)alkoxy, (C$_3$-C$_6$)alkenyl, or (C$_3$-C$_6$)alkenyloxy. In another embodiment, the moiety -L-B is (C$_3$-C$_6$)alkyl, (C$_3$-C$_6$)alkoxy, or (C$_3$-C$_5$)alkenyloxy. In specific embodiments, -L-B is —OCH$_2$CH=CH$_2$, —CH$_2$CH$_2$CH$_2$CH$_2$CH$_3$, —OCH$_2$CH$_2$CH$_2$CH$_3$, —CH$_2$CH$_2$CH$_3$, —CH$_2$CH(CH$_3$)$_2$ or —CH$_2$CH$_2$CH(CH$_3$)$_2$. In other specific embodiments, -L-B is —OCH$_2$CH=CH$_2$, —CH$_2$CH$_2$CH$_2$CH$_3$, —OCH$_2$CH$_2$CH$_2$CH$_3$, —CH$_2$CH$_2$CH$_3$, or —CH$_2$CH(CH$_3$)$_2$.

Representative compounds of this invention include the compounds of the Examples. It will be appreciated that the present invention encompasses compounds of Formula (I) as the free base and as salts thereof, for example as a pharmaceutically acceptable salt thereof. In one embodiment the invention relates to compounds of Formula (I) in the form of a free base. In another embodiment the invention relates to compounds of Formula (I) in the form of a salt, particularly, a pharmaceutically acceptable salt. It will be further appreciated that, in one embodiment, the invention relates to compounds of the Examples in the form of a free base. In another embodiment the invention relates to compounds of the Examples in the form of a salt, particularly, a pharmaceutically acceptable salt.

Specifically, this invention is directed to (S)-5-benzyl-N-(5-methyl-4-oxo-2,3,4,5-tetrahydrobenzo[b][1,4]oxazepin-3-yl)-4H-1,2,4-triazole-3-carboxamide; (S)-5-benzyl-N-(6- fluoro-5-methyl-4-oxo-2,3,4,5-tetrahydrobenzo[b][1,4]
oxazepin-3-yl)-4H-1,2,4-triazole-3-carboxamide; and
5-benzyl-N-(7-bromo-2-oxo-2,3,4,5-tetrahydro-1H-benzo
[b]azepin-3-yl)-4H-1,2,4-triazole-3-carboxamide, or a salt
thereof, particularly a pharmaceutically acceptable salt,
thereof. Specifically, this invention is directed to (S)-5-
benzyl-N-(5-methyl-4-oxo-2,3,4,5-tetrahydrobenzo [1,4]
oxazepin-3-yl)-4H-1,2,4-triazole-3-carboxamide; (S)-5-
benzyl-N-(6-fluoro-5-methyl-4-oxo-2,3,4,5-
tetrahydrobenzo[b][1,4]oxazepin-3-yl)-4H-1,2,4-triazole-3-
carboxamide; or 5-benzyl-N-(7-bromo-2-oxo-2,3,4,5-
tetrahydro-1H-benzo[b]azepin-3-yl)-4H-1,2,4-triazole-3-
carboxamide, or a pharmaceutically acceptable salt, thereof.

More specifically, this invention is directed to (S)-5-
benzyl-N-(5-methyl-4-oxo-2,3,4,5-tetrahydrobenzo[b][1,4]
oxazepin-3-yl)-4H-1,2,4-triazole-3-carboxamide and (S)-5-
benzyl-N-(7-chloro-2-oxo-2,3,4,5-tetrahydro-1H-benzo[b]
azepin-3-yl)-4H-1,2,4-triazole-3-carboxamide, or a
pharmaceutically acceptable salt thereof.

This invention is directed to (S)-5-benzyl-N-(5-methyl-
4-oxo-2,3,4,5-tetrahydrobenzo[b][1,4]oxazepin-3-yl)-4H-1,
2,4-triazole-3-carboxamide or a salt, particularly a pharmaceutically acceptable salt, thereof. Accordingly, one particular compound of the invention is (S)-5-benzyl-N-(5-methyl-4-oxo-2,3,4,5-tetrahydrobenzo[b][1,4]oxazepin-3-yl)-4H-1,2,4-triazole-3-carboxamide (free base). In another embodiment, the compound of the invention is a salt of (S)-5-benzyl-N-(5-methyl-4-oxo-2,3,4, 5-tetrahydrobenzo[b][1,4]oxazepin-3-yl)-4H-1,2,4-triazole-3-carboxamide. In another embodiment, the compound of the invention is a pharmaceutically acceptable salt of (S)-5-benzyl-N-(5-methyl-4-oxo-2,3,4,5-tetrahydrobenzo[b][1,4]oxazepin-3-yl)-4H-1,2,4-triazole-3-carboxamide. In another embodiment, the compound of the invention is a base-addition salt of (S)-5-benzyl-N-(5-methyl-4-oxo-2,3,4,5-tetrahydrobenzo[b][1,4]oxazepin-3-yl)-4H-1,2,4-triazole-3-carboxamide. In still another embodiment, the compound of the invention is a crystalline form of anhydrous (S)-5-benzyl-N-(5-methyl-4-oxo-2,3,4,5-tetrahydrobenzo [1,4]oxazepin-3-yl)-4H-1,2,4-triazole-3-carboxamide (free base) characterized by the PXRD pattern of FIG. 7. In yet another embodiment, a particular compound of the invention is a crystalline form of anhydrous (S)-5-benzyl-N-(5-methyl-4-oxo-2,3,4,5-tetrahydrobenzo[b][1,4]oxazepin-3-yl)-4H-1,2,4-triazole-3-carboxamide (free base) characterized by the diffraction data in Table 1.

This invention is directed (S)-5-benzyl-N-(7-chloro-2-oxo-2,3,4,5-tetrahydro-1H-benzo[b]azepin-3-yl)-4H-1,2,4-triazole-3-carboxamide, or a salt, particularly a pharmaceutically acceptable salt, thereof. Accordingly, one particular compound of the invention is (S)-5-benzyl-N-(7-chloro-2-oxo-2,3,4,5-tetrahydro-1H-benzo[b]azepin-3-yl)-4H-1,2,4-triazole-3-carboxamide (free base). In another embodiment, the compound of the invention is a salt of (S)-5-benzyl-N-(7-chloro-2-oxo-2,3,4,5-tetrahydro-1H-benzo[b]azepin-3-yl)-4H-1,2,4-triazole-3-carboxamide. In another embodiment, the compound of the invention is a pharmaceutically acceptable salt of (S)-5-benzyl-N-(7-chloro-2-oxo-2,3,4,5-tetrahydro-1H-benzo[b]azepin-3-yl)-4H-1,2,4-triazole-3-carboxamide. In another embodiment, the compound of the invention is a base-addition salt of (S)-5-benzyl-N-(7-chloro-2-oxo-2,3,4, 5-tetrahydro-1H-benzo[b]azepin-3-yl)-4H-1,2,4-triazole-3-carboxamide.

In a specific embodiment, this invention is directed to a compound of Formula (I) wherein:
X is O, S, SO, $SO_2$, NH, CO, $CH_2$, or $N(CH_3)$;
Y is $CH_2$ or $CH_2CH_2$;
$Z^1$, $Z^2$, $Z^3$, and $Z^4$ are each CH; or $Z^1$ is $CR^1$ and $Z^2$, $Z^3$ and $Z^4$ are each CH; or $Z^1$, $Z^2$, and $Z^4$ are each CH and $Z^3$ is $CR^3$; or $Z^1$, $Z^3$, and $Z^4$ are each CH and $Z^2$ is $CR^2$; or $Z^1$, $Z^2$, and $Z^3$ are each CH and $Z^4$ is $CR^4$; or $Z^1$ and $Z^2$ are CH, $Z^3$ is $CR^3$, and $Z^4$ is $CR^4$; or $Z^1$ and $Z^4$ are CH, $Z^2$ is $CR^2$, and $Z^3$ is $CR^3$; or $Z^1$ and $Z^3$ are CH, $Z^2$ is $CR^2$, and $Z^4$ is $CR^4$; or $Z^1$ is CH, $Z^2$ is $CR^2$, $Z^3$ is $CR^3$, and $Z^4$ is $CR^4$; or $Z^1$ and $Z^3$ are both N, $Z^2$ is CH and $Z^4$ is CH or $CR^4$; or $Z^1$ and $Z^3$ are both N, $Z^2$ is CH or $CR^2$ and $Z^4$ is CH; or $Z^1$ is N, $Z^2$ is $CR^4$ and $Z^3$ and $Z^4$ are CH; or $Z^3$ is N, and $Z^2$, $Z^3$ and $Z^4$ are CH;

$R^1$ is methyl,
$R^2$ is fluoro, chloro, bromo, —CN, —$CH_3$, —$OCH_3$, —$OCHF_2$, —OH, $B(OH)_2$, $CF_3C(OH)_2$—, $CH_3OCH_2CH_2O$—, cyclopropyl, 5H-tetrazol-5-yl, pyrazol-3-yl, or 5-methyl-1,3,4-oxadiazol-2-yl;
$R^3$ is fluoro, chloro, bromo, —CN, —$OCH_3$, —$OCHF_2$, $B(OH)_2$, —COOH, $CH_3SO_2$—, $CH_3SO_2NHC(O)$—, $CH_3C(O)NH$—, $(CH_3)_2NC(O)$—, $CH_3OC(O)$—, $(CH_3)C(O)N(CH_3)$—, $HOCH_2CH_2C(O)NH$—, $CH_3OCH_2CH_2NHC(O)NH$—, $CH_3SO_2CH_2CH_2NHC(O)$—, $CH_3CH_2NHC(O)NH$—, $CH_3OC(O)NH$—, morpholin-4-yl-CO—, pyrrolidin-1-yl-$CH_2CH_2NHC(O)$—, pyridin-2-yl, tetrahydrofuran-2-yl-$CH_2O$—, pyrrolidin-1-yl-$CH_2CH_2O$—, tetrazol-5-yl, 1-(2-cyanoethyl)-tetrazol-5-yl, pyrazol-1-yl, pyrazol-3-yl, pyrazol-4-yl, 1-methyl-pyrazol-3-yl, 1-methyl-pyrrol-4-yl-C(O)NH—, 5-methyl-1,3,4-oxadiazol-2-yl, or 5-oxo-4,5-dihydro-1,3,4-oxadiazol-2-yl;
$R^4$ is fluoro, chloro, methyl, or trifluoromethyl;
$R^5$ is H or methyl;
A is furyl, thienyl, oxazolyl, isoxazolyl, thiazolyl, 1, 2, 4-oxadiazolyl, 1, 3, 4-oxadiazolyl, pyrrolyl, pyrazolyl, imidazolyl, 1, 2, 3-triazolyl, 1, 2, 4-triazolyl, tetrazolyl, piperidinyl, pyrrolidinyl, phenyl or pyridyl;
m is 0 or m is 1 and $R^A$ is methyl;
L is O, S, $N(CH_3)$, $CH_2$, $CH_2CH_2$, $CH(CH_3)$, —(R)CH$(CH_3)$, $CF_2$, $CH_2O$, $CH_2N(CH_3)$, or $CH(OH)$; and
B is thien-2-yl, 5-methyl-thien-2-yl, pyrazol-1-yl, 3,5-dimethylpyrazol-1-yl, 4-methylpyrazol-1-yl, 3,5-dimethylisoxazol-4-yl, tetrahydropyran-3-yl, tetrahydrofuran-2-yl, morpholin-4-yl, pyridin-2-yl, 2-oxo-pyridin-1-yl, 6-methylpyridin-3-yl, 2-methylpyrimidin-5-yl, cyclopentyl, cyclohexyl, phenyl, 2-methylphenyl, 4-methylphenyl, 2-trifluoromethylphenyl, 2-fluorophenyl, 3-fluorophenyl, 4-fluorophenyl, 2-iodophenyl, 3-bromophenyl, 4-bromophenyl, 4-chlorophenyl, 2,5-difluorophenyl, 2,4-difluorophenyl, 3,4-difluorophenyl, 3,5-difluorophenyl, 4-methoxyphenyl, 2,3-difluorophenyl or 2,6-difluorophenyl;
or -L-B—$R^B$ is —$OCH_2CH=CH_2$, —$CH_2CH_2CH_2CH_2CH_3$, —$OCH_2CH_2CH_2CH_3$, —$CH_2CH_2CH_3$, —$CH_2CH(CH_3)_2$ or —$CH_2CH_2CH(CH_3)_2$;
or a salt, particularly, a pharmaceutically acceptable salt thereof.

In another specific embodiment, this invention is directed to a compound of Formula (I) wherein:
X is O, S, SO, $SO_2$, NH, CO, $CH_2$, or $N(CH_3)$;
Y is $CH_2$ or $CH_2CH_2$;
$Z^1$, $Z^2$, $Z^3$, and $Z^4$ are each CH; or $Z^1$ is $CR^1$ and $Z^2$, $Z^3$ and $Z^4$ are each CH; or $Z^1$, $Z^2$, and $Z^4$ are each CH and $Z^3$ is $CR^3$; or $Z^1$, $Z^3$, and $Z^4$ are each CH and $Z^2$ is $CR^2$; or $Z^1$, $Z^2$, and $Z^3$ are each CH and $Z^4$ is $CR^4$; or $Z^1$ and $Z^3$ are CH, $Z^2$ is $CR^2$, and $Z^4$ is $CR^4$; or $Z^1$ and $Z^3$ are both N, $Z^2$ is CH and $Z^4$ is CH or $CR^4$; or $Z^1$ is N, $Z^2$ is $CR^4$ and $Z^3$ and $Z^4$ are CH; or $Z^3$ is N, and $Z^2$, $Z^3$ and $Z^4$ are CH;
$R^1$ is methyl, $R^2$ is fluoro, chloro, bromo, —CN, —CH$_3$, —OH, B(OH)$_2$, CF$_3$C(OH)$_2$—, CH$_3$OCH$_2$CH$_2$O—, 5H-tetrazol-5-yl, pyrazol-3-yl, or 5-methyl-1,3,4-oxadiazol-2-yl;

$R^3$ is fluoro, chloro, bromo, —OCH$_3$, B(OH)$_2$, —COOH, CH$_3$SO$_2$—, CH$_3$SO$_2$NHC(O)—, CH$_3$C(O)NH—, (CH$_3$)$_2$NC(O)—, CH$_3$OC(O)—, (CH$_3$)C(O)N(CH$_3$)—, HOCH$_2$CH$_2$C(O)NH—, CH$_3$OCH$_2$CH$_2$NHC(O)NH—, CH$_3$SO$_2$CH$_2$CH$_2$NHC(O)—, CH$_3$CH$_2$NHC(O)NH—, CH$_3$OC(O)NH—, morpholin-4-yl-CO—, pyrrolidin-1-yl-CH$_2$CH$_2$NHC(O)—, tetrahydrofuran-2-yl-CH$_2$O—, pyrrolidin-1-yl-CH$_2$CH$_2$O—, tetrazol-5-yl, 1-(2-cyanoethyl)-tetrazol-5-yl, pyrazol-1-yl, pyrazol-3-yl, 1-methyl-pyrazol-3-yl, 1-methyl-pyrrol-4-yl-C(O)NH—, 5-methyl-1,3,4-oxadiazol-2-yl, or 5-oxo-4,5-dihydro-1,3,4-oxadiazol-2-yl;

$R^4$ is fluoro, chloro, methyl, or trifluoromethyl;

$R^5$ is H or methyl;

A is furyl, thienyl, oxazolyl, isoxazolyl, thiazolyl, 1, 2, 4-oxadiazolyl, 1, 3, 4-oxadiazolyl, pyrrolyl, pyrazolyl, imidazolyl, 1, 2, 3-triazolyl, 1, 2, 4-triazolyl, tetrazolyl, piperidinyl, pyrrolidinyl, phenyl or pyridyl;

m is 0 or m is 1 and $R^4$ is methyl;

L is O, S, N(CH$_3$), CH$_2$, CH$_2$CH$_2$, CH(CH$_3$), CF$_2$, CH$_2$O, CH$_2$N(CH$_3$), or CH(OH); and B is thien-2-yl, 5-methyl-thien-2-yl, pyrazol-1-yl, 3,5-dimethylpyrazol-1-yl, 4-methylpyrazol-1-yl, 3,5-dimethylisoxazol-4-yl, tetrahydrofuran-2-yl, morpholin-4-yl, pyridin-2-yl, 2-oxo-pyridin-1-yl, 6-methylpyridin-3-yl, 2-methylpyrimidin-5-yl, cyclopentyl, cyclohexyl, phenyl, 2-methylphenyl, 4-methylphenyl, 2-trifluoromethylphenyl, 2-fluorophenyl, 3-fluorophenyl, 4-fluorophenyl, 2-iodophenyl, 3-bromophenyl, 4-bromophenyl, 4-chlorophenyl, 2,5-difluorophenyl, 2,4-difluorophenyl, 3,4-difluorophenyl, 3,5-difluorophenyl, or 4-methoxyphenyl;

or -L-B—$R^B$ is —OCH$_2$CH=CH$_2$, —CH$_2$CH$_2$CH$_2$CH$_3$, —OCH$_2$CH$_2$CH$_2$CH$_3$, —CH$_2$CH$_2$CH$_3$, —CH$_2$CH(CH$_3$)$_2$ or —CH$_2$CH$_2$CH(CH$_3$)$_2$;

or a salt, particularly, a pharmaceutically acceptable salt thereof.

In another specific embodiment, this invention is directed to a compound of Formula (I) wherein:

X is O, CH$_2$, NH or N(CH$_3$);

Y is CH$_2$ or CH$_2$CH$_2$;

$Z^1$, $Z^2$, $Z^3$, and $Z^4$ are each CH; or $Z^1$ is CR$^1$ and $Z^2$, $Z^3$ and $Z^4$ are each CH; or $Z^1$, $Z^2$, and $Z^4$ are each CH and $Z^3$ is CR$^3$; or $Z^1$, $Z^3$, and $Z^4$ are each CH and $Z^2$ is CR$^2$; or $Z^1$, $Z^2$, and $Z^3$ are each CH and $Z^4$ is CR$^4$; or $Z^1$ and $Z^3$ are CH, $Z^2$ is CR$^2$, and $Z^4$ is CR$^4$; or $Z^1$ and $Z^3$ are both N, $Z^2$ is CH and $Z^4$ is CH or CR$^4$; or $Z^1$ is N, $Z^2$ is CR$^4$ and $Z^3$ and $Z^4$ are CH; or $Z^3$ is N, and $Z^2$, $Z^3$ and $Z^4$ are CH;

$R^1$ is methyl, $R^2$ is chloro, bromo, —CN, —CH$_3$, —OH, B(OH)$_2$, CF$_3$C(OH)$_2$—, CH$_3$OCH$_2$CH$_2$O—, 5H-tetrazol-5-yl, pyrazol-3-yl, or 5-methyl-1,3,4-oxadiazol-2-yl;

$R^3$ is fluoro, chloro, bromo, —OCH$_3$, B(OH)$_2$, —COOH, CH$_3$SO$_2$—, CH$_3$SO$_2$NHC(O)—, CH$_3$C(O)NH—, (CH$_3$)$_2$NC(O)—, CH$_3$OC(O)—, (CH$_3$)C(O)N(CH$_3$)—, HOCH$_2$CH$_2$C(O)NH—, CH$_3$OCH$_2$CH$_2$NHC(O)NH—, CH$_3$SO$_2$CH$_2$CH$_2$NHC(O)—, CH$_3$CH$_2$NHC(O)NH—, CH$_3$OC(O)NH—, morpholin-4-yl-CO—, pyrrolidin-1-yl-CH$_2$CH$_2$NHC(O)—, tetrahydrofuran-2-yl-CH$_2$O—, pyrrolidin-1-yl-CH$_2$CH$_2$O—, tetrazol-5-yl, 1-(2-cyanoethyl)-tetrazol-5-yl, pyrazol-1-yl, pyrazol-3-yl, 1-methyl-pyrazol-3-yl, 1-methyl-pyrrol-4-yl-C(O)NH—, or 5-oxo-4,5-dihydro-1,3, 4-oxadiazol-2-yl;

$R^4$ is fluoro or methyl;

A is furyl, thienyl, oxazolyl, isoxazolyl, thiazolyl, 1, 2, 4-oxadiazolyl, 1, 3, 4-oxadiazolyl, pyrrolyl, pyrazolyl, imidazolyl, 1, 2, 3-triazolyl, 1, 2, 4-triazolyl, tetrazolyl, piperidinyl, pyrrolidinyl, phenyl or pyridyl;

m is 0 or m is 1 and $R^4$ is methyl;

L is O, S, N(CH$_3$), CH$_2$, CH$_2$CH$_2$, CH(CH$_3$), CF$_2$, CH$_2$O, CH$_2$N(CH$_3$), or CH(OH); and B is thien-2-yl, pyrazol-1-yl, 3,5-dimethylpyrazol-1-yl, 4-methylpyrazol-1-yl, 3,5-dimethylisoxazol-4-yl, tetrahydrofuran-2-yl, morpholin-4-yl, pyridin-2-yl, 2-oxo-pyridin-1-yl, 6-methylpyridin-3-yl, 2-methylpyrimidin-5-yl, cyclopentyl, cyclohexyl, phenyl, 2-methylphenyl, 4-methylphenyl, 2-trifluoromethylphenyl, 2-fluorophenyl, 3-fluorophenyl, 4-fluorophenyl, 2-iodophenyl, 3-bromophenyl, 4-bromophenyl, 4-chlorophenyl, 2,5-difluorophenyl, 2,4-difluorophenyl, 3,4-difluorophenyl, 3,5-difluorophenyl, or 4-methoxyphenyl;

or -L-B is —OCH$_2$CH=CH$_2$, —CH$_2$CH$_2$CH$_2$CH$_3$, —OCH$_2$CH$_2$CH$_2$CH$_3$, —CH$_2$CH$_2$CH$_3$, or —CH$_2$CH(CH$_3$)$_2$;

or a pharmaceutically acceptable salt thereof.

In another specific embodiment, this invention is directed to a compound of Formula (I) wherein X is O or CH$_2$; Y is CH$_2$; $Z^1$, $Z^2$, and $Z^4$ are each CH and $Z^3$ is CR$^3$; or $Z^1$, $Z^3$, and $Z^4$ are each CH and $Z^2$ is CR$^2$; or $Z^1$, $Z^2$, and $Z^3$ are each CH and $Z^4$ is CR$^4$; or $Z^1$ and $Z^3$ are CH, $Z^2$ is CR$^2$, and $Z^4$ is CR$^4$; $R^2$ is fluoro, chloro, bromo, or —CH$_3$; $R^3$ is 5-methyl-1,3,4-oxadiazol-2-yl; $R^4$ is fluoro; $R^5$ is H or methyl; A is triazolyl; m is 0; L is CH$_2$; and B is cyclopentyl or phenyl; or a salt, particularly a pharmaceutically acceptable salt thereof.

The compounds of this invention contain one or more asymmetric centers (also referred to as a chiral center), such as a chiral carbon, or a chiral —SO— moiety. The stereochemistry of the chiral carbon center present in compounds of this invention is generally represented in the compound names and/or in the chemical structures illustrated herein. Compounds of this invention containing one or more chiral centers may be present as racemic mixtures, diastereomeric mixtures, enantiomerically enriched mixtures, diastereomerically enriched mixtures, or as enantiomerically or diastereomerically pure individual stereoisomers.

Individual stereoisomers of a compound of this invention may be resolved (or mixtures of stereoisomers may be enriched) using methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The invention also includes various deuterated forms of the compounds of this invention, a specific example of which is N-[(3S)-7-deuterio-1-methyl-2-oxo-2,3,4,5-tetrahydro-1H-1-benzazepin-3-yl]-5-(phenylmethyl)-1H-pyrazole-3-carboxamide. Each available hydrogen atom attached to a carbon atom may be independently replaced with a deuterium atom. A person of ordinary skill in the art will know how to synthesize deuterated forms of the compounds of this invention. For example, α-deuterated α-amino acids are commercially available or may be prepared by conventional techniques (see for example: Elemes, Y. and Ragnarsson, U. *J. Chem. Soc., Perkin Trans.* 1, 1996, 6, 537-40). Employing such compounds may allow for the preparation of compounds in which the hydrogen atom at a chiral center is replaced with a deuterium atom. Other commercially available deuterated starting materials may be employed in the preparation of deuterated analogs of the compounds of this invention (see for example: methyl-$d_3$-amine available from Aldrich Chemical Co., Milwaukee, Wis.), or they may be synthesized using conventional techniques employing deuterated reagents (e.g. by reduction using lithium aluminum deuteride or sodium borodeuteride or by metal-halogen exchange followed by quenching with $D_2O$ or methanol-$d_3$).

The skilled artisan will appreciate that solvates (particularly, hydrates) of a compound of Formula (I), particularly a compound of any one of Formulas (I-IV), including solvates of salts of a compound of Formula (I), particularly a compound of any one of Formulas (I-IV), may be formed when solvent molecules are incorporated into the crystalline lattice during crystallization. The present invention includes within its scope all possible stoichiometric and non-stoichiometric salt and/or hydrate forms.

When a disclosed compound or its salt is named or depicted by structure, it is to be understood that the compound or salt, including solvates (particularly, hydrates) thereof, may exist in crystalline forms, non-crystalline forms or a mixture thereof. The compound or salt, or solvates (particularly, hydrates) thereof, may also exhibit polymorphism (i.e. the capacity to occur in different crystalline forms). These different crystalline forms are typically known as "polymorphs." It is to be understood that when named or depicted by structure, the disclosed compound, or solvates (particularly, hydrates) thereof, also include all polymorphs thereof. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in crystallizing/recrystallizing the compound. It is well known and understood to those skilled in the art that the apparatus employed, humidity, temperature, orientation of the powder crystals, and other parameters involved in obtaining a powder X-ray diffraction (PXRD) pattern may cause some variability in the appearance, intensities, and positions of the lines in the diffraction pattern. A powder X-ray diffraction pattern that is "substantially in accordance" with that of the Figure provided herein is a PXRD pattern that would be considered by one skilled in the art to represent a compound possessing the same crystal form as the compound that provided the PXRD pattern of the Figure. For example, the PXRD pattern may be identical to that of FIG. 7, or more likely it may be somewhat different. Such a PXRD pattern may not necessarily show each of the lines of the diffraction patterns presented herein, and/or may show a slight change in appearance, intensity, or a shift in position of said lines resulting from differences in the conditions involved in obtaining the data. A person skilled in the art is capable of determining if a sample of a crystalline compound has the same form as, or a different form from, a form disclosed herein by comparison of their PXRD patterns. For example, one skilled in the art can overlay a PXRD pattern of a sample of a crystalline form of anhydrous (S)-5-benzyl-N-(5-methyl-4-oxo-2,3,4,5-tetrahydrobenzo[b][1,4]oxazepin-3-yl)-4H-1,2,4-triazole-3-carboxamide (free base) with the PXRD pattern of FIG. 7, and using expertise and knowledge in the art, readily determine whether the PXRD pattern of the sample is substantially in accordance with the PXRD pattern of FIG. 7. If the PXRD pattern is substantially in accordance with FIG. 7, the sample form can be readily and accurately identified as having the same form as the crystalline form of anhydrous (S)-5-benzyl-N-(5-methyl-4-oxo-2,3,4,5-tetrahydrobenzo[b][1,4]oxazepin-3-yl)-4H-1,2,4-triazole-3-carboxamide (free base) described herein. Similarly, a person skilled in the art is capable of determining if a given diffraction angle (expressed in ° 2θ) obtained from a PXRD pattern is at about the same position as a recited value.

Because of their potential use in medicine, the salts of the compounds of Formula (I), particularly a compound of any one of Formulas (I-IV), are preferably pharmaceutically acceptable. Suitable pharmaceutically acceptable salts can include acid or base addition salts.

As used herein, the term "pharmaceutically acceptable" means a compound which is suitable for pharmaceutical use. Salts and solvates (e.g. hydrates and hydrates of salts) of the compounds of the invention which are suitable for use in medicine are those wherein the counterion or associated solvent is pharmaceutically acceptable. Salts and solvates having non-pharmaceutically acceptable counterions or associated solvents are within the scope of the present invention, for example, for use as intermediates in the preparation of other compounds of the invention and their salts and solvates.

Salts may be prepared in situ during the final isolation and purification of a compound of Formula (I), particularly a compound of any one of Formulas (I-IV). If a basic compound of Formula (I-IV) is isolated as a salt, the corresponding free base form of that compound may be prepared by any suitable method known to the art, including treatment of the salt with an inorganic or organic base, suitably an inorganic or organic base having a higher $pK_a$ than the free base form of the compound. Similarly, if a disclosed compound containing a carboxylic acid or other acidic functional group is isolated as a salt, the corresponding free acid form of that compound may be prepared by any suitable method known to the art, including treatment of the salt with an inorganic or organic acid, suitably an inorganic or organic acid having a lower $pK_a$ than the free acid form of the compound. This invention also provides for the conversion of one salt of a compound of this invention, e.g., a hydrochloride salt, into another salt of a compound of this invention, e.g., a sulfate salt.

Salts of the compounds of Formula (I), particularly compounds of Formulas (I-IV), containing a basic amine or other basic functional group may be prepared by any suitable method known in the art, such as treatment of the free base with an acid. Examples of pharmaceutically acceptable salts so formed include acetate, adipate, ascorbate, aspartate, benzenesulfonate, benzoate, camphorate, camphor-sulfonate (camsylate), caprate (decanoate), caproate (hexanoate), caprylate (octanoate), carbonate, bicarbonate, cinnamate, citrate, cyclamate, dodecylsulfate (estolate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hippurate, hydrobromide, hydrochloride, hydroiodide, isobutyrate, lactate, lactobionate, laurate, maleate, malate, malonate, mandelate, methanesulfonate (mesylate), naphthalene-1,5-disulfonate (napadisylate), naphthalene-sulfonate (napsylate), nicotinate, nitrate, oleate, oxalate, palmitate, pamoate, phosphate, diphosphate, proprionate, pyroglutamate, salicylate, sebacate, stearate, succinate, sulfate, tartrate, thiocyanate, p-toluenesulfonate (tosylate), undecylenate, 1-hydroxy-2-naphthoate, 2,2-dichloroacetate, 2-hydroxyethanesulfonate (isethionate), 2-oxoglutarate, 4-acetamidobenzoate, and 4-aminosalicylate.

Salts of the disclosed compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, choline, quinine, quinoline, and basic amino acids such as lysine and arginine. In one embodiment, the pharmaceutically acceptable base-addition salt of a compound of Formula (I) is a sodium salt or a potassium salt thereof.

Because the compounds of this invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

General Synthetic Methods

The compounds of this invention may be prepared using synthetic procedures illustrated in the Schemes below or by drawing on the knowledge of a skilled organic chemist. The synthesis provided in these Schemes are applicable for producing compounds of the invention having a variety of different R groups employing appropriate precursors, which are suitably protected if needed, to achieve compatibility with the reactions outlined herein. Subsequent deprotection, where needed, affords compounds of the nature generally disclosed. While the Schemes are shown with compounds only of Formulas (I-IV), they are illustrative of processes that may be used to make the compounds of the invention.

Intermediates (compounds used in the preparation of the compounds of the invention) may also be present as salts. Thus, in reference to intermediates, the phrase "compound(s) of formula (number)" means a compound having that structural formula or a pharmaceutically acceptable salt thereof.

(S)—N-(4-Oxo-2,3,4,5-tetrahydrobenzo[b][1,4]oxazepin-3-yl)carboxamides may be prepared via the general method outlined in Scheme 1. Boc-L-serine can be condensed with an appropriate substituted 1-fluoro-2-nitrobenzene with a base, followed by reduction of the nitro group to the amine and cyclisation to the Boc protected (S)-3-amino-2,3-dihydrobenzo[b][1,4]oxazepin-4(5H)-one using an amide coupling agent. The Boc protecting group can be removed using acidic conditions and the resulting free amine can be coupled to the appropriate acid using an amide coupling agent. The Boc protected (S)-3-amino-2,3-dihydrobenzo[b][1,4]oxazepin-4(5H)-one can also be methylated to give the Boc protected (S)-3-amino-5-methyl-2,3-dihydrobenzo[b][1,4]oxazepin-4(5H)-one, which can then be deprotected using acidic conditions, and the resulting free amine can be coupled to an appropriate acid using an amide coupling agent.

Scheme 1

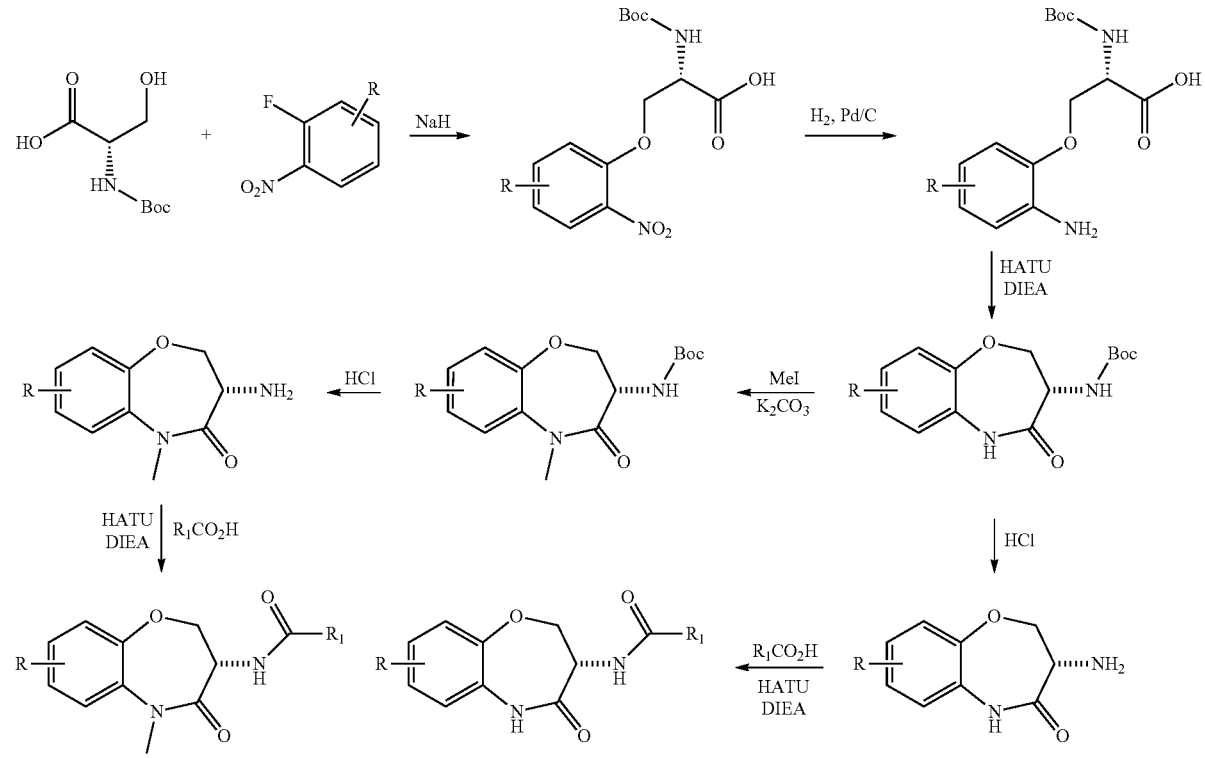

(R)—N-(4-Oxo-2,3,4,5-tetrahydrobenzo[b][1,4]thiazepin-3-yl)carboxamides may be prepared via the general method outlined in Scheme 2. Boc-L-cysteine can be condensed with an appropriate substituted 1-fluoro-2-nitrobenzene with a base, followed by reduction of the nitro group to the amine and cyclisation to the Boc protected (R)-3-amino-2,3-dihydrobenzo[b][1,4]thiazepin-4(5H)-one using an amide coupling agent. The Boc protecting group can be removed using acidic conditions and the resulting free amine can be coupled to an appropriate acid using an amide coupling agent. The Boc protected (R)-3-amino-2,3-dihydrobenzo[b][1,4]thiazepin-4(5H)-one can also be methylated to give the Boc protected (R)-3-amino-5-methyl-2,3-dihydrobenzo[b][1,4]thiazepin-4(5H)-one, which can then be deprotected using acidic conditions, and the resulting free amine can be coupled to an appropriate acid using an amide coupling agent.

zene with a base, followed by reduction of the nitro group to the amine and cyclisation to the Boc protected (S)-3-amino-4,5-dihydro-1H-benzo[b][1,4]diazepin-2(3H)-one using an amide coupling agent. The Boc protecting group can be removed using acidic conditions and the resulting free amine can be coupled to the appropriate acid using an amide coupling agent. The Boc protected (S)-3-amino-4,5-dihydro-1H-benzo[b][1,4]diazepin-2(3H)-one can also be methylated with methyl iodide using sodium hydride as base to give the Boc protected (S)-3-amino-1-methyl-4,5-dihydro-1H-benzo[b][1,4]diazepin-2(3H)-one, which can then be deprotected using acidic conditions, and the resulting free amine can be coupled to the appropriate acid using an amide coupling agent. Alternatively, the Boc protected (S)-3-amino-4,5-dihydro-1H-benzo[b][1,4]diazepin-2(3H)-one can also be methylated with methyl iodide using potassium carbonate as base in ethanol to give the Boc protected

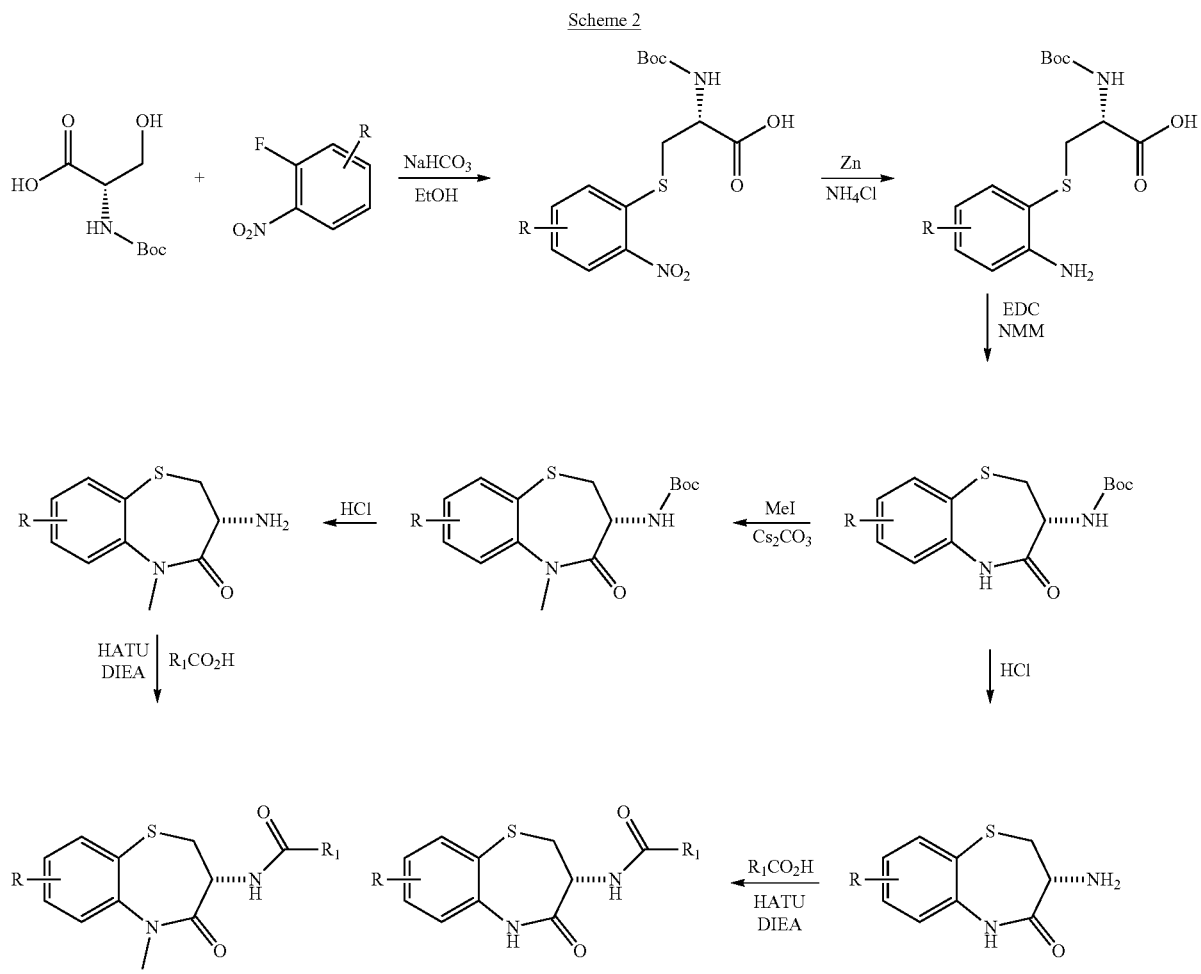

Scheme 2

(S)—N-(2-Oxo-2,3,4, 5-tetrahydro-1H-benzo[b][1,4]diazepin-3-yl)carboxamides may be prepared via the general method outlined in Scheme 3. 3-Aminoalanine can be condensed with the appropriate substituted 1-fluoro-2-nitroben- (S)-3-amino-5-methyl-4,5-dihydro-1H-benzo[b][1,4]diazepin-2(3H)-one, which can then be deprotected using acidic conditions, and the resulting free amine can be coupled to the appropriate acid using an amide coupling agent.

Scheme 3

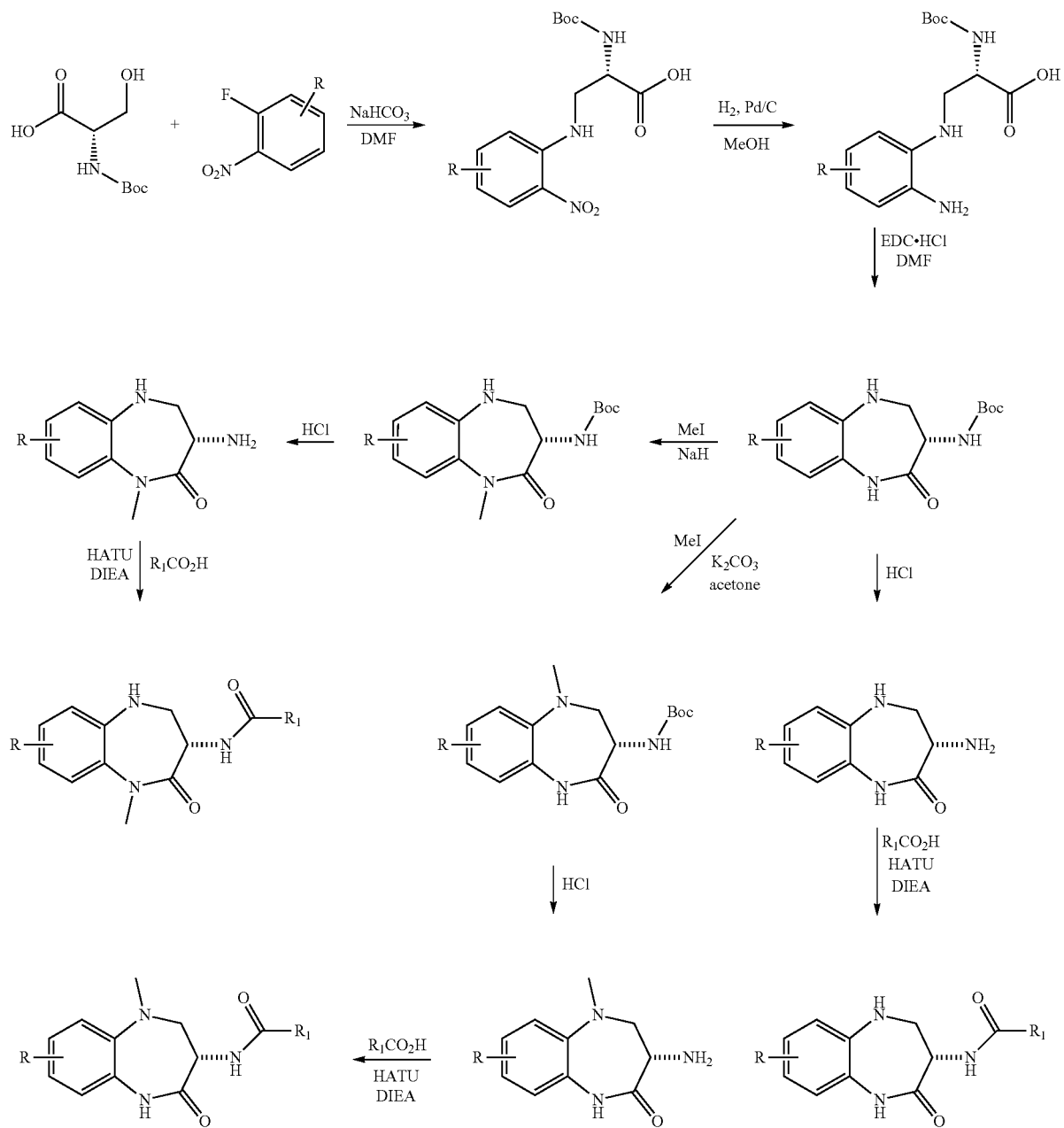

(S)—N-(6-Oxo-6,7,8,9-tetrahydro-5H-pyrimido[4,5-b][1,4]diazepin-7-yl)carboxamides may be prepared via the general method outlined in Scheme 4. Boc-L-serine can be condensed with 4,6-dichloropyrimidin-5-amine in the presence of a base such as triethylamine, followed by cyclisation to the Boc protected (S)-7-amino-4-chloro-8,9-dihydro-5H-pyrimido[4,5-b][1,4]diazepin-6(7H)-one using an amide coupling agent. The chloride can be removed by reduction using hydrogenation with a palladium/carbon catalyst. The Boc protecting group can then be removed using acidic conditions and the resulting free amine can be coupled to the appropriate acid using an amide coupling agent. Alternatively, the Boc protected (S)-7-amino-8,9-dihydro-5H-pyrimido[4,5-b][1,4]diazepin-6(7H)-one can be methylated in the presence of a base, deprotected using acidic conditions, and the resulting free amine can be coupled to the appropriate acid using an amide coupling agent to yield (S)—N-(5-methyl-6-oxo-6,7,8,9-tetrahydro-5H-pyrimido[4,5-b][1,4]diazepin-7-yl)carboxamides (Scheme 4, R=H). If the chloride is not removed, then this sequence can be repeated to yield the corresponding (S)—N-(4-chloro-5-methyl-6-oxo-6,7,8,9-tetrahydro-5H-pyrimido[4,5-b][1,4]diazepin-7-yl)carboxamides (Scheme 4, R=Cl).

Scheme 4

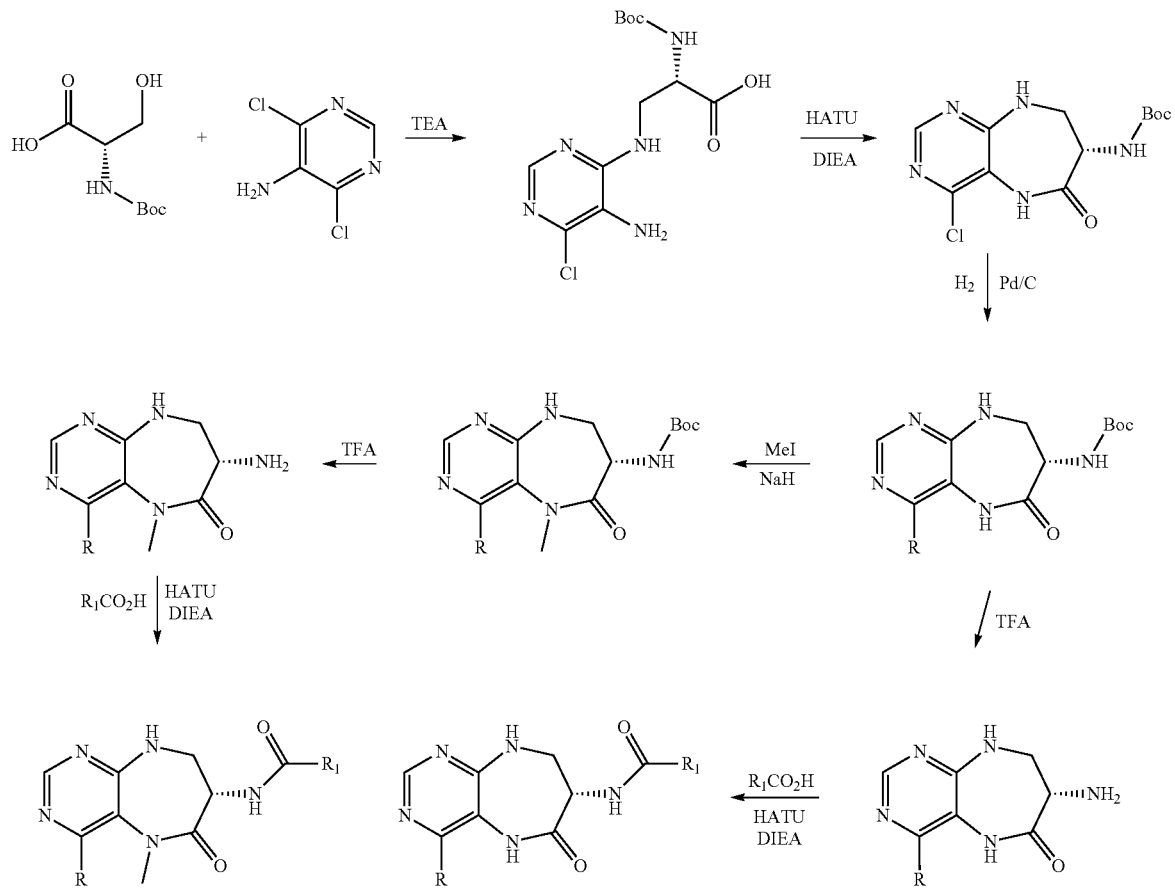

R = H or Cl (S)—N-(2-oxo-2,3,4,5-tetrahydro-1H-benzo[b]azepin-3-yl) carboxamides may be prepared via the general method outlined in Scheme 5. The appropriately substituted tetralone can be converted to the 1,3,4,5-tetrahydro-1-benzazepin-2-one via either an acid-mediated Schmidt reaction with sodium azide, or Beckmann rearrangement of the corresponding ketoximes formed from reaction with hydroxylamine. The 1,3,4,5-tetrahydro-1-benzazepin-2-one can then be converted to the α-iodobenzlactam by iodotrimethylsilane-mediate iodination, subsequently converted to the α-azido-benzlactam with sodium azide, and following a Staudinger reduction with triphenylphosphine yields the α-aminobenzlactam. A racemization/resolution of the α-aminobenzlactam can be accomplished using L-pyroglutamic acid and 5-nirosalicylaldehyde to yield the (S)-3-amino-4,5-dihydro-1H-benzo[b]azepin-2(3H)-one as described by Armstrong et. al. in Tetrahedron Letters 1994, pages 3239-42. This amine can then be coupled to the appropriate acid using an amide coupling agent. Alternatively the amine can protected with a Boc protecting group, then methylated at the lactam nitrogen with methyl iodide, followed by deprotected using acidic conditions. The resulting free amine can be coupled to the appropriate acid using an amide coupling agent.

Scheme 5

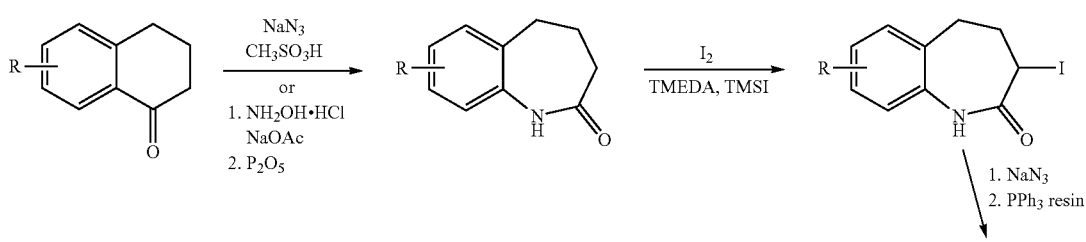

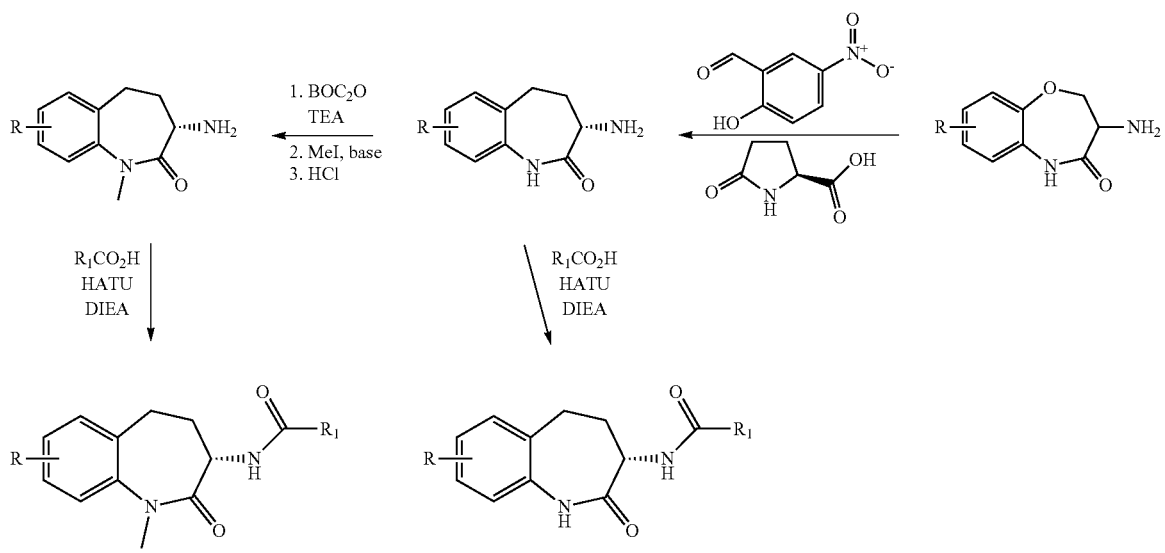

5-Substituted-4H-1,2,4-triazole-3-carboxylic acids may be prepared via the general method outlined in Scheme 6. The appropriately substituted acetohydrazide is condensed with ethyl 2-ethoxy-2-iminoacetate in ethanol. The resulting ethyl 2-amino-2-(2-substituted hydrazono)acetate is then heated neat or in a high boiling solvent such as xylenes resulting in cyclization to the 5-substituted-4H-1,2,4-triazole-3-carboxylic ethyl ester. This can then by hydrolyzed using aqueous base, for example lithium hydroxide in THF and water.

Scheme 6

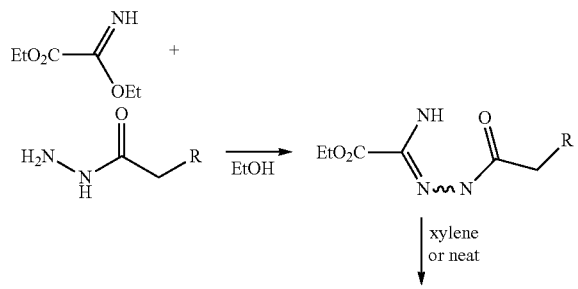

-continued

5-Benzyl-1H-pyrazole-3-carboxylic acids can be prepared following the route shown in Scheme 7. The appropriately substituted benzyl methyl ketone is condensed with diethyl oxalate in the presence of a base such as potassium tert-butoxide in ethanol. The resulting ethyl 5-(substituted-phenyl)-2,4-dioxopentanoate is then condensed with hydrazine in ethanol resulting in cyclization to the ethyl 5-substituted benzyl-1H-pyrazole-3-carboxylate. This can then by hydrolyzed using aqueous base, for example lithium hydroxide in THF and water.

Scheme 7

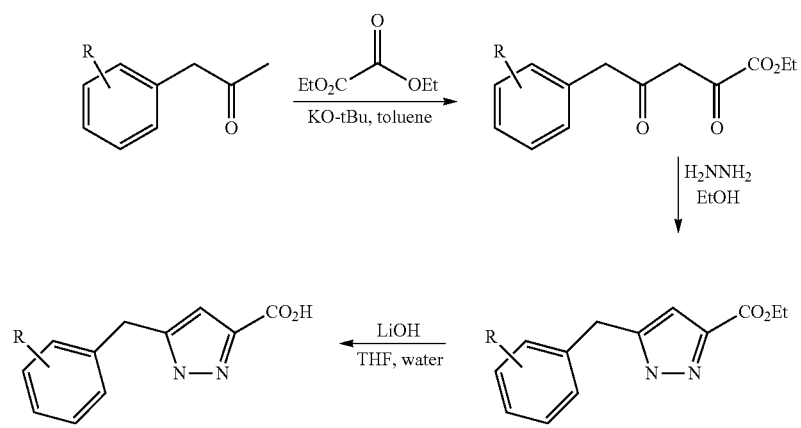

5-Methyl-1-substituted-1H-pyrazole-3-carboxylic acids can be prepared following the route shown in Scheme 8. Ethyl 3-methyl-1H-pyrazole-5-carboxylate is alkylated in the presence of a base such as potassium hydroxide with the appropriate alkylating agent, such as an alkyl or arylbromide, to give a mixture of desired ethyl 5-methyl-1-propyl-1H-pyrazole-3-carboxylate and undesired regioisomer ethyl 3-methyl-1-substituted-1H-pyrazole-5-carboxylate ethyl oxalate. The ethyl 5-methyl-1-substituted-1H-pyrazole-3-carboxylates can be isolated using chromatography and then hydrolyzed using aqueous base, for example lithium hydroxide in THF and water to yield 5-methyl-1-propyl-1H-pyrazole-3-carboxylic acids.

Scheme 8

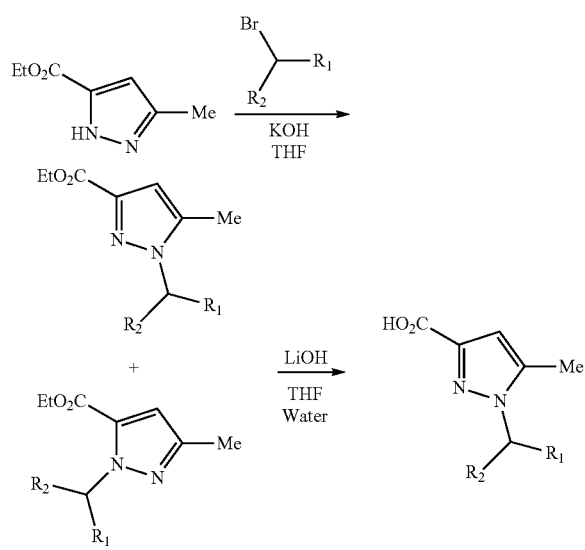

The compounds of this invention may be particularly useful for the treatment of RIP1 kinase-mediated diseases or disorders. Such RIP1 kinase-mediated diseases or disorders are diseases or disorders that are mediated by activation of RIP1 kinase, and as such, are diseases or disorders where inhibition of RIP1 kinase would provide benefit. The compounds of this invention may be particularly useful for the treatment of diseases/disorders which are likely to be regulated at least in part by programmed necrosis, particularly inflammatory bowel disease (including Crohn's disease and ulcerative colitis), psoriasis, retinal detachment, retinitis pigmentosa, macular degeneration, pancreatitis, atopic dermatitis, arthritis (including rheumatoid arthritis, spondyloarthritis, gout, SoJIA), systemic lupus erythematosus (SLE), Sjogren's syndrome, systemic scleroderma, anti-phospholipid syndrome (APS), vasculitis, osteoarthritis, liver damage/diseases (non-alcohol steatohepatitis, alcohol steatohepatitis, autoimmune hepatitis autoimmune hepatobiliary diseases, primary sclerosing cholangitis (PSC)), nephritis, Celiac disease, autoimmune ITP, transplant rejection, ischemia reperfusion injury of solid organs, sepsis, systemic inflammatory response syndrome (SIRS), cerebrovascular accident (CVA), myocardial infarction (MI), Huntington's disease, Alzheimer's disease, Parkinson's disease, allergic diseases (including asthma and atopic dermatitis), multiple sclerosis, type I diabetes, Wegener's granulomatosis, pulmonary sarcoidosis, Behcet's disease, interleukin-1 converting enzyme (ICE, also known as caspase-1) associated fever syndrome, chronic obstructive pulmonary disease (COPD), tumor necrosis factor receptor-associated periodic syndrome (TRAPS) and peridontitis.

The compounds of this invention may be particularly useful for the treatment of diseases/disorders which are likely to be regulated at least in part by programmed necrosis, apoptosis or the production of inflammatory cytokines, particularly inflammatory bowel disease (including Crohn's disease and ulcerative colitis), psoriasis, retinal detachment, retinitis pigmentosa, macular degeneration, pancreatitis, atopic dermatitis, arthritis (including rheumatoid arthritis, spondyloarthritis, gout, systemic onset juvenile idiopathic arthritis (SoJIA), psoriatic arthritis), systemic lupus erythematosus (SLE), Sjogren's syndrome, systemic scleroderma, anti-phospholipid syndrome (APS), vasculitis, osteoarthritis, liver damage/diseases (non-alcohol steatohepatitis, alcohol steatohepatitis, autoimmune hepatitis, autoimmune hepatobiliary diseases, primary sclerosing cholangitis (PSC), acetaminophen toxicity, hepatotoxicity), kidney damage/injury (nephritis, renal transplant, surgery, administration of nephrotoxic drugs e.g. cisplatin, acute kidney injury (AKI)) Celiac disease, autoimmune idiopathic thrombocytopenic purpura (autoimmune ITP), transplant rejection, ischemia reperfusion injury of solid organs, sepsis, systemic inflammatory response syndrome (SIRS), cerebrovascular accident (CVA, stroke), myocardial infarction (MI), atherosclerosis, Huntington's disease, Alzheimer's disease, Parkinson's disease, Amyotrophic lateral sclerosis (ALS), allergic diseases (including asthma and atopic dermatitis), multiple sclerosis, type I diabetes, Wegener's granulomatosis, pulmonary sarcoidosis, Behcet's disease, interleukin-1 converting enzyme (ICE, also known as caspase-1) associated fever syndrome, chronic obstructive pulmonary disease (COPD), tumor necrosis factor receptor-associated periodic syndrome (TRAPS), peridontitis, NEMO-deficiency syndrome (NF-kappa-B essential modulator gene (also known as IKK gamma or IKKG) deficiency syndrome), HOIL-1 deficiency ((also known as RBCK1) heme-oxidized IRP2 ubiquitin ligase-1 deficiency), linear ubiquitin chain assembly complex (LUBAC) deficiency syndrome, hematological and solid organ malignancies, bacterial infections and viral infections (such as tuberculosis and influenza), and Lysosomal storage diseases (particularly, Gaucher Disease, and including GM2 Gangliosidosis, Alpha-mannosidosis, Aspartylglucosaminuria, Cholesteryl Ester storage disease, Chronic Hexosaminidase A Deficiency, Cystinosis, Danon disease, Fabry disease, Farber disease, Fucosidosis, Galactosialidosis, GM1 gangliosidosis, Mucolipidosis, Infantile Free Sialic Acid Storage Disease, Juvenile Hexosaminidase A Deficiency, Krabbe disease, Lysosomal acid lipase deficiency, Metachromatic Leukodystrophy, Mucopolysaccharidoses disorders, Multiple sulfatase deficiency, Niemann-Pick Disease, Neuronal Ceroid Lipofuscinoses, Pompe disease, Pycnodysostosis, Sandhoff disease, Schindler disease, Sialic Acid Storage Disease, Tay-Sachs and Wolman disease).

The treatment of the above-noted diseases/disorders may concern, more specifically, the amelioration of organ injury or damage sustained as a result of the noted diseases. For example, the compounds of this invention may be particularly useful for amelioration of brain tissue injury or damage following ischemic brain injury or traumatic brain injury, or for amelioration of heart tissue injury or damage following myocardial infarction, or for amelioration of brain tissue injury or damage associated with Huntington's disease, Alzheimer's disease or Parkinson's disease, or for amelioration of liver tissue injury or damage associated with non-alcohol steatohepatitis, alcohol steatohepatitis, autoimmune hepatitis autoimmune hepatobiliary diseases, or primary sclerosing cholangitis. In addition, the treatment of diseases/disorders selected from those described herein may concern, more specifically, the amelioration of liver tissue injury or damage associated with overdose of acetaminophen, or for amelioration of kidney tissue injury or damage following renal transplant or the administration of nephrotoxic drugs or substances e.g. cisplatin.

The compounds of this invention may be particularly useful for the treatment of inflammatory bowel disease (including Crohn's disease and ulcerative colitis), psoriasis, retinal detachment, retinitis pigmentosa, arthritis (including rheumatoid arthritis, spondyloarthritis, gout, and SoJIA), transplant rejection, ischemia reperfusion injury of solid organs, multiple sclerosis, and/or tumor necrosis factor receptor-associated periodic syndrome. More specifically, the compounds of this invention may be particularly useful for the treatment of inflammatory bowel disease (including Crohn's disease and ulcerative colitis), psoriasis, retinal detachment, retinitis pigmentosa, arthritis (including rheumatoid arthritis, spondyloarthritis, gout, and systemic onset juvenile idiopathic arthritis (SoJIA)), transplant rejection, and/or ischemia reperfusion injury of solid organs.

Treatment of RIP1-mediated disease conditions, or more broadly, treatment of immune mediated disease, such as, but not limited to, allergic diseases, autoimmune diseases, prevention of transplant rejection and the like, may be achieved using a compound of this invention as a monotherapy, or in dual or multiple combination therapy, particularly for the treatment of refractory cases, such as in combination with other anti-inflammatory and/or anti-TNF agents, which may be administered in therapeutically effective amounts as is known in the art.

The compounds of any one of Formulas (I-IV) and pharmaceutically acceptable salts thereof may be employed alone or in combination with other therapeutic agents. Combination therapies according to the present invention thus comprise the administration of at least one compound of any one of Formulas (I-IV) or a pharmaceutically acceptable salt thereof, and at least one other therapeutically active agent. Preferably, combination therapies according to the present invention comprise the administration of at least one compound of any one of Formulas (I-IV) or a pharmaceutically acceptable salt thereof, and at least one other therapeutically active agent. The compound(s) of any one of Formulas (I-IV) and pharmaceutically acceptable salts thereof, and the other therapeutically active agent(s) may be administered together in a single pharmaceutical composition or separately and, when administered separately this may occur simultaneously or sequentially in any order. The amounts of the compound(s) of any one of Formulas (I-IV) and pharmaceutically acceptable salts thereof, and the other therapeutically active agent(s) and the relative timings of administration will be selected in order to achieve the desired combined therapeutic effect. Thus in a further aspect, there is provided a combination comprising a compound of any one of Formulas (I-IV) or a pharmaceutically acceptable salt thereof, together with one or more other therapeutically active agents. In one aspect, there is provided a combination comprising (S)-5-benzyl-N-(5-methyl-4-oxo-2,3,4,5-tetrahydrobenzo[b][1,4]oxazepin-3-yl)-4H-1,2,4-triazole-3-carboxamide, or a pharmaceutically acceptable salt thereof, together with one or more other therapeutically active agents. In another aspect, there is provided a combination comprising (S)-5-benzyl-N-(7-chloro-2-oxo-2,3,4,5-tetrahydro-1H-benzo[b]azepin-3-yl)-4H-1,2,4-triazole-3-carboxamide, or a pharmaceutically acceptable salt thereof, together with one or more other therapeutically active agents. Thus in one aspect of this invention, a compound of any one of Formulas (I-IV) or a pharmaceutically acceptable salt thereof, and a pharmaceutical composition comprising a compound of any one of Formulas (I-IV) or a pharmaceutically acceptable salt thereof, may be used in combination with or include one or more other therapeutic agents, for example an anti-inflammatory agent and/or an anti-TNF agent.

For example, the compounds of this invention may be administered in combination with other anti-inflammatory agents for any of the indications above, including oral or topical corticosteroids (such as prednisone (Deltasone®) and bundesonide), anti-TNF agents (including anti-TNF biologic agents), 5-aminosalicyclic acid and mesalamine preparations, hydroxycloroquine, thiopurines (azathioprin, mercaptopurin), methotrexate, cyclophosphamide, cyclosporine, JAK inhibitors (tofacitinib), anti-IL6 biologics, anti-IL1 or IL12 or IL23 biologics (ustekinumab (Stelara®)), anti-integrin agents (natalizumab (Tysabri®)), anti-CD20 or CD4 biologics and other cytokine inhibitors or biologics to T-cell or B-cell receptors or interleukins.

The compounds of this invention may be administered in combination with other anti-inflammatory agents for any of the indications above, including oral or topical corticosteroids (such as prednisone (Deltasone®) and bundesonide), anti-TNF agents (including anti-TNF biologic agents), 5-aminosalicyclic acid and mesalamine preparations, hydroxycloroquine, thiopurines (azathioprin, mercaptopurin), methotrexate, cyclophosphamide, cyclosporine, calcineurin inhibitors (cyclosporine, pimecrolimus, tacrolimus), mycophenolic acid (CellCept®), mTOR inhibitors (temsirolimus, everolimus), JAK inhibitors (tofacitinib), (Xeljan®)), Syk inhibitors (fostamatinib), anti-IL6 biologics, anti-LI (anakinra (Kineret®), canakinumab (Ilaris®), rilonacept (Arcalyst®)), anti-IL12 and IL23 biologics (ustekinumab (Stelara®)), anti-IL17 biologics (secukinumab), anti-CD22 (epratuzumab), anti-integrin agents (natalizumab (Tysabri®)), vedolizumab (Entyvio®)), anti-IFNa (sifalimumab), anti-CD20 or CD4 biologics and other cytokine inhibitors or biologics to T-cell or B-cell receptors or interleukins.

Examples of suitable anti-inflammatory biologic agents include Actemra® (anti-IL6R mAb), anti-CD20 mAbs (rituximab (Rituxan®) and ofatumumab (Arzerra®)), abatacept (Orencia®), anakinra (Kineret®), ustekinumab (Stelara®), and belimumab (Benlysta®). Examples of other suitable anti-inflammatory biologic agents include Actemra® (tocilizumab, anti-IL6R mAb), anti-CD20 mAbs (rituximab (Rituxan®) and ofatumumab (Arzerra®)), abatacept (Orencia®), anakinra (Kineret®), Canakinumab (Ilaris®), rilonacept (Arcalyst®), secukinumab, epratuzumab, sifalimumab, ustekinumab (Stelara®), and belimumab (Benlysta®). Examples of suitable anti-TNF agents biologic agents include etanecerpt (Enbrel®), adalimumab (Humira®), infliximab (Remicade®), certolizumab (Cimzia®), and golimumab (Simponi®).

Accordingly, one embodiment of this invention is directed to a method of inhibiting RIP1 kinase comprising contacting a cell with a compound of the invention. In another embodiment, the invention is directed to a method of treating a RIP1 kinase-mediated disease or disorder (specifically, a disease or disorder recited herein) comprising administering a therapeutically effective amount of a compound of Formula (I), particularly a compound of any one of Formulas (I-IV), or a salt, particularly a pharmaceutically acceptable salt thereof, to a human in need thereof.

In one specific embodiment, the invention is directed to a method of treating a RIP1 kinase-mediated disease or disorder (specifically, a disease or disorder recited herein) comprising administering a therapeutically effective amount of (S)-5-benzyl-N-(5-methyl-4-oxo-2,3,4, 5-tetrahydrobenzo[b][1,4]oxazepin-3-yl)-4H-1,2,4-triazole-3-carboxamide, or a pharmaceutically acceptable salt thereof, to a human in need thereof. In another specific embodiment, the invention is directed to a method of treating a RIP1 kinase-mediated disease or disorder (specifically, a disease or disorder recited herein) comprising administering a therapeutically effective amount of (S)-5-benzyl-N-(7-chloro-2-oxo-2,3,4, 5-tetrahydro-1H-benzo[b]azepin-3-yl)-4H-1,2,4-triazole-3-carboxamide, or a pharmaceutically acceptable salt thereof, to a human in need thereof.

Specifically, this invention provides a compound of the invention for use in therapy. This invention also provides a compound of Formula (I), particularly a compound of any one of Formulas (I-IV), or a pharmaceutically acceptable salt thereof, for use in therapy. This invention particularly provides a compound of Formula (I), particularly a compound of any one of Formulas (I-IV), or a pharmaceutically acceptable salt thereof, for use in the treatment of a RIP1 kinase-mediated disease or disorder (for example, a disease or disorder recited herein).

Specifically, this invention provides a compound described herein, or a pharmaceutically acceptable salt thereof, for use in therapy. More specifically, this invention provides (S)-5-benzyl-N-(5-methyl-4-oxo-2,3,4,5-tetrahydrobenzo[b][1,4]oxazepin-3-yl)-4H-1,2,4-triazole-3-carboxamide, or a pharmaceutically acceptable salt thereof, for use in therapy. This invention further provides (S)-5-benzyl-N-(7-chloro-2-oxo-2,3,4, 5-tetrahydro-1H-benzo[b]azepin-3-yl)-4H-1,2,4-triazole-3-carboxamide, or a pharmaceutically acceptable salt thereof, for use in therapy.

In another embodiment, this invention provides a compound of the invention for use in the treatment of a RIP1 kinase-mediated disease or disorder. Specifically, this invention provides a compound described herein, or a pharmaceutically acceptable salt thereof, for use in the treatment of a RIP1 kinase-mediated disease or disorder. In another embodiment, this invention provides a compound of Formula (I), particularly a compound of any one of Formulas (I-IV), or a pharmaceutically acceptable salt thereof, for use in the treatment of diseases/disorders which are likely to be regulated at least in part by programmed necrosis, apoptosis or the production of inflammatory cytokines, particularly inflammatory bowel disease (including Crohn's disease and ulcerative colitis), psoriasis, retinal detachment, retinitis pigmentosa, macular degeneration, pancreatitis, atopic dermatitis, arthritis (including rheumatoid arthritis, spondyloarthritis, gout, systemic onset juvenile idiopathic arthritis (SoJIA)), systemic lupus erythematosus (SLE), Sjogren's syndrome, systemic scleroderma, anti-phospholipid syndrome (APS), vasculitis, osteoarthritis, liver damage/diseases (non-alcohol steatohepatitis, alcohol steatohepatitis, autoimmune hepatitis, autoimmune hepatobiliary diseases, primary sclerosing cholangitis (PSC)), nephritis, Celiac disease, autoimmune idiopathic thrombocytopenic purpura (autoimmune ITP), transplant rejection, ischemia reperfusion injury of solid organs, sepsis, systemic inflammatory response syndrome (SIRS), cerebrovascular accident (CVA, stroke), myocardial infarction (MI), atherosclerosis, Huntington's disease, Alzheimer's disease, Parkinson's disease, Amyotrophic lateral sclerosis (ALS), allergic diseases (including asthma and atopic dermatitis), multiple sclerosis, type I diabetes, Wegener's granulomatosis, pulmonary sarcoidosis, Behcet's disease, interleukin-1 converting enzyme (ICE, also known as caspase-1) associated fever syndrome, chronic obstructive pulmonary disease (COPD), tumor necrosis factor receptor-associated periodic syndrome (TRAPS), peridontitis, NEMO-deficiency syndrome (NF-kappa-B essential modulator gene (also known as IKK gamma or IKKG) deficiency syndrome), HOIL-1 deficiency ((also known as RBCK1) heme-oxidized IRP2 ubiquitin ligase-1 deficiency), linear ubiquitin chain assembly complex (LUBAC) deficiency syndrome, hematological and solid organ malignancies, bacterial infections and viral infections (such as tuberculosis and influenza), and Lysosomal storage diseases (particularly, Gaucher Disease, and including GM2 Gangliosidosis, Alpha-mannosidosis, Aspartylglucosaminuria, Cholesteryl Ester storage disease, Chronic Hexosaminidase A Deficiency, Cystinosis, Danon disease, Fabry disease, Farber disease, Fucosidosis, Galactosialidosis, GM1 gangliosidosis, Mucolipidosis, Infantile Free Sialic Acid Storage Disease, Juvenile Hexosaminidase A Deficiency, Krabbe disease, Lysosomal acid lipase deficiency, Metachromatic Leukodystrophy, Mucopolysaccharidoses disorders, Multiple sulfatase deficiency, Niemann-Pick Disease, Neuronal Ceroid Lipofuscinoses, Pompe disease, Pycnodysostosis, Sandhoff disease, Schindler disease, Sialic Acid Storage Disease, Tay-Sachs and Wolman disease), wherein treatment of the above-noted diseases/disorders may concern, more specifically, the amelioration of organ injury or damage sustained as a result of the noted diseases.

In another embodiment, this invention provides a compound of Formula (I), or a pharmaceutically acceptable salt thereof, for use in the treatment of inflammatory bowel disease. In another embodiment, this invention provides a compound of Formula (I), or a pharmaceutically acceptable salt thereof, for use in the treatment of Crohn's disease. In another embodiment, this invention provides a compound of Formula (I), or a pharmaceutically acceptable salt thereof, for use in the treatment of ulcerative colitis. In another embodiment, this invention provides a compound of Formula (I), or a pharmaceutically acceptable salt thereof, for use in the treatment of psoriasis. In another embodiment, this invention provides a compound of Formula (I), or a pharmaceutically acceptable salt thereof, for use in the treatment of retinal detachment. In another embodiment, this invention provides a compound of Formula (I), or a pharmaceutically acceptable salt thereof, for use in the treatment of retinitis pigmentosa. In another embodiment, this invention provides a compound of Formula (I), or a pharmaceutically acceptable salt thereof, for use in the treatment of arthritis. In another embodiment, this invention provides a compound of Formula (I), or a pharmaceutically acceptable salt thereof, for use in the treatment of rheumatoid arthritis. In another embodiment, this invention provides a compound of Formula (I), or a pharmaceutically acceptable salt thereof, for use in the treatment of spondyloarthritis. In another embodiment, this invention provides a compound of Formula (I), or a pharmaceutically acceptable salt thereof, for use in the treatment of gout. In another embodiment, this invention provides a compound of Formula (I), or a pharmaceutically acceptable salt thereof, for use in the treatment of systemic onset juvenile idiopathic arthritis. In another embodiment, this invention provides a compound of Formula (I), or a pharmaceutically acceptable salt thereof, for use in the treatment of transplant rejection. In another embodiment, this invention provides a compound of Formula (I), or a pharmaceutically acceptable salt thereof, for use in the treatment of ischemia reperfusion injury of solid organs.

This invention specifically provides for the use of a compound of Formula (I), particularly a compound of any one of Formulas (I-IV), or a pharmaceutically acceptable salt thereof, as an active therapeutic substance. More specifically, this provides for the use of the compounds described herein for the treatment of a RIP1 kinase-mediated disease or disorder. Accordingly, the invention provides for the use of a compound of Formula (I), particularly a compound of any one of Formulas (I-IV), or a pharmaceutically acceptable salt thereof, as an active therapeutic substance in the treatment of a human in need thereof with a RIP1 kinase-mediated disease or disorder.

The invention further provides for the use of a compound of Formula (I), particularly a compound of any one of Formulas (I-IV), or a salt thereof, particularly a pharmaceutically acceptable salt thereof, in the manufacture of a medicament for use in the treatment of a RIP1 kinase-mediated disease or disorder, for example the diseases and disorders recited herein. Specifically, the invention also provides for the use of a compound described herein, or a pharmaceutically acceptable salt thereof, in the manufacture of a medicament for use in the treatment of a RIP1 kinase-mediated disease or disorder, for example the diseases and disorders recited herein. More specifically, the invention also provides for the use of (S)-5-benzyl-N-(5-methyl-4-oxo-2,3,4,5-tetrahydrobenzo[b][1,4]oxazepin-3-yl)-4H-1,2,4-triazole-3-carboxamide, or a pharmaceutically acceptable salt thereof, in the manufacture of a medicament for use in the treatment of a RIP1 kinase-mediated disease or disorder, for example the diseases and disorders recited herein. The invention further provides for the use of (S)-5-benzyl-N-(7-chloro-2-oxo-2,3,4,5-tetrahydro-1H-benzo[b]azepin-3-yl)-4H-1,2,4-triazole-3-carboxamide, or a pharmaceutically acceptable salt thereof, in the manufacture of a medicament for use in the treatment of a RIP1 kinase-mediated disease or disorder, for example the diseases and disorders recited herein. Accordingly, the invention provides for the use of a compound of Formula (I), particularly a compound of any one of Formulas (I-IV), or a pharmaceutically acceptable salt thereof, in the manufacture of a medicament for use in the treatment of a human in need thereof with a RIP1 kinase-mediated disease or disorder.

In one embodiment, this invention provides for the use of a compound of Formula (I), particularly a compound of any one of Formulas (I-IV), or a pharmaceutically acceptable salt thereof, in the manufacture of a medicament for use in the treatment of diseases/disorders which are likely to be regulated at least in part by programmed necrosis, apoptosis or the production of inflammatory cytokines, particularly inflammatory bowel disease (including Crohn's disease and ulcerative colitis), psoriasis, retinal detachment, retinitis pigmentosa, macular degeneration, pancreatitis, atopic dermatitis, arthritis (including rheumatoid arthritis, spondyloarthritis, gout, systemic onset juvenile idiopathic arthritis (SoJIA)), systemic lupus erythematosus (SLE), Sjogren's syndrome, systemic scleroderma, anti-phospholipid syndrome (APS), vasculitis, osteoarthritis, liver damage/diseases (non-alcohol steatohepatitis, alcohol steatohepatitis, autoimmune hepatitis, autoimmune hepatobiliary diseases, primary sclerosing cholangitis (PSC)), nephritis, Celiac disease, autoimmune idiopathic thrombocytopenic purpura (autoimmune ITP), transplant rejection, ischemia reperfusion injury of solid organs, sepsis, systemic inflammatory response syndrome (SIRS), cerebrovascular accident (CVA, stroke), myocardial infarction (MI), atherosclerosis, Huntington's disease, Alzheimer's disease, Parkinson's disease, Amyotrophic lateral sclerosis (ALS), allergic diseases (including asthma and atopic dermatitis), multiple sclerosis, type I diabetes, Wegener's granulomatosis, pulmonary sarcoidosis, Behcet's disease, interleukin-1 converting enzyme (ICE, also known as caspase-1) associated fever syndrome, chronic obstructive pulmonary disease (COPD), tumor necrosis factor receptor-associated periodic syndrome (TRAPS), peridontitis, NEMO-deficiency syndrome (NF-kappa-B essential modulator gene (also known as IKK gamma or IKKG) deficiency syndrome), HOIL-1 deficiency ((also known as RBCK1) heme-oxidized IRP2 ubiquitin ligase-1 deficiency), linear ubiquitin chain assembly complex (LUBAC) deficiency syndrome, hematological and solid organ malignancies, bacterial infections and viral infections (such as tuberculosis and influenza), and Lysosomal storage diseases (particularly, Gaucher Disease, and including GM2 Gangliosidosis, Alpha-mannosidosis, Aspartylglucosaminuria, Cholesteryl Ester storage disease, Chronic Hexosaminidase A Deficiency, Cystinosis, Danon disease, Fabry disease, Farber disease, Fucosidosis, Galactosialidosis, GM1 gangliosidosis, Mucolipidosis, Infantile Free Sialic Acid Storage Disease, Juvenile Hexosaminidase A Deficiency, Krabbe disease, Lysosomal acid lipase deficiency, Metachromatic Leukodystrophy, Mucopolysaccharidoses disorders, Multiple sulfatase deficiency, Niemann-Pick Disease, Neuronal Ceroid Lipofuscinoses, Pompe disease, Pycnodysostosis, Sandhoff disease, Schindler disease, Sialic Acid Storage Disease, Tay-Sachs and Wolman disease), wherein treatment of the above-noted diseases/disorders may concern, more specifically, the amelioration of organ injury or damage sustained as a result of the noted diseases.

In another embodiment, this invention provides for the use of a compound of Formula (I), or a pharmaceutically acceptable salt thereof, in the manufacture of a medicament for use in the treatment of inflammatory bowel disease. In another embodiment, this invention provides for the use of a compound of Formula (I), or a pharmaceutically acceptable salt thereof, in the manufacture of a medicament for use in the treatment of Crohn's disease. In another embodiment, this invention provides for the use of a compound of Formula (I), or a pharmaceutically acceptable salt thereof, in the manufacture of a medicament for use in the treatment of ulcerative colitis. In another embodiment, this invention provides for the use of a compound of Formula (I), or a pharmaceutically acceptable salt thereof, in the manufacture of a medicament for use in the treatment of psoriasis. In another embodiment, this invention provides for the use of a compound of Formula (I), or a pharmaceutically acceptable salt thereof, in the manufacture of a medicament for use in the treatment of retinal detachment. In another embodiment, this invention provides for the use of a compound of Formula (I), or a pharmaceutically acceptable salt thereof, in the manufacture of a medicament for use in the treatment of retinitis pigmentosa. In another embodiment, this invention provides for the use of a compound of Formula (I), or a pharmaceutically acceptable salt thereof, in the manufacture of a medicament for use in the treatment of arthritis. In another embodiment, this invention provides for the use of a compound of Formula (I), or a pharmaceutically acceptable salt thereof, in the manufacture of a medicament for use in the treatment of rheumatoid arthritis. In another embodiment, this invention provides for the use of a compound of Formula (I), or a pharmaceutically acceptable salt thereof, in the manufacture of a medicament for use in the treatment of spondyloarthritis. In another embodiment, this invention provides for the use of a compound of Formula (I), or a pharmaceutically acceptable salt thereof, in the manufacture of a medicament for use in the treatment of gout. In another embodiment, this invention provides for the use of a compound of Formula (I), or a pharmaceutically acceptable salt thereof, in the manufacture of a medicament for use in the treatment of systemic onset juvenile idiopathic arthritis. In another embodiment, this invention provides for the use of a compound of Formula (I), or a pharmaceutically acceptable salt thereof, in the manufacture of a medicament for use in the treatment of transplant rejection. In another embodiment, this invention provides for the use of a compound of Formula (I), or a pharmaceutically acceptable salt thereof, in the manufacture of a medicament for use in the treatment of ischemia reperfusion injury of solid organs.

A therapeutically "effective amount" is intended to mean that amount of a compound that, when administered to a patient in need of such treatment, is sufficient to effect treatment, as defined herein. Thus, e.g., a therapeutically effective amount of a compound of Formula (I), particularly a compound of any one of Formulas (I-IV), or a pharmaceutically acceptable salt thereof, is a quantity of an inventive agent that, when administered to a human in need thereof, is sufficient to modulate and/or inhibit the activity of RIP1 kinase such that a disease condition which is mediated by that activity is reduced, alleviated or prevented. The amount of a given compound that will correspond to such an amount will vary depending upon factors such as the particular compound (e.g., the potency ($pIC_{50}$), efficacy ($EC_{50}$), and the biological half-life of the particular compound), disease condition and its severity, the identity (e.g., age, size and weight) of the patient in need of treatment, but can nevertheless be routinely determined by one skilled in the art. Likewise, the duration of treatment and the time period of administration (time period between dosages and the timing of the dosages, e.g., before/with/after meals) of the compound will vary according to the identity of the mammal in need of treatment (e.g., weight), the particular compound and its properties (e.g., pharmacokinetic properties), disease or disorder and its severity and the specific composition and method being used, but can nevertheless be determined by one of skill in the art.

"Treating" or "treatment" is intended to mean at least the mitigation of a disease or disorder in a patient. The methods of treatment for mitigation of a disease or disorder include the use of the compounds in this invention in any conventionally acceptable manner, for example for prevention, retardation, prophylaxis, therapy or cure of a RIP1 kinase-mediated disease or disorder, as described hereinabove.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the disease or disorder being treated, the severity of the disease or disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change. Total daily dosages range from 1 mg to 2000 mg, preferably, total daily dosages range from 1 mg to 250 mg.

For use in therapy, the compounds of the invention will be normally, but not necessarily, formulated into a pharmaceutical composition prior to administration to a patient. Accordingly, the invention also is directed to pharmaceutical compositions comprising a compound of the invention and one or more pharmaceutically acceptable excipients.

In one embodiment, there is provided a pharmaceutical composition comprising (S)-5-benzyl-N-(5-methyl-4-oxo-2,3,4,5-tetrahydrobenzo [1,4]oxazepin-3-yl)-4H-1,2,4-triazole-3-carboxamide (free base), and one or more pharmaceutically acceptable excipients. In another embodiment, there is provided a pharmaceutical composition comprising (S)-5-benzyl-N-(5-methyl-4-oxo-2,3,4,5-tetrahydrobenzo[b][1,4]oxazepin-3-yl)-4H-1,2,4-triazole-3-carboxamide, or a pharmaceutically acceptable salt thereof, and one or more pharmaceutically acceptable excipients. In another embodiment, there is provided a pharmaceutical composition comprising crystalline (S)-5-benzyl-N-(5-methyl-4-oxo-2,3,4,5-tetrahydrobenzo[b][1,4]oxazepin-3-yl)-4H-1,2,4-triazole-3-carboxamide (free base) having the PXRD pattern of FIG. 7 and one or more pharmaceutically acceptable excipients. In another embodiment, there is provided a pharmaceutical composition comprising crystalline (S)-5-benzyl-N-(5-methyl-4-oxo-2,3,4,5-tetrahydrobenzo[b][1,4]oxazepin-3-yl)-4H-1,2,4-triazole-3-carboxamide (free base) characterized by the diffraction data in Table 1, and one or more pharmaceutically acceptable excipients. In one embodiment, there is provided a pharmaceutical composition comprising (S)-5-benzyl-N-(7-chloro-2-oxo-2,3,4,5-tetrahydro-1H-benzo[b]azepin-3-yl)-4H-1,2,4-triazole-3-carboxamide (free base) and one or more pharmaceutically acceptable excipients. In another embodiment, there is provided a pharmaceutical composition comprising (S)-5-benzyl-N-(7-chloro-2-oxo-2,3,4,5-tetrahydro-1H-benzo[b]azepin-3-yl)-4H-1,2,4-triazole-3-carboxamide, or a pharmaceutically acceptable salt thereof, and one or more pharmaceutically acceptable excipients.

The pharmaceutical compositions of the invention may be prepared and packaged in bulk form wherein an effective amount of a compound of the invention can be extracted and then given to the patient such as with powders, syrups, and solutions for injection. Alternatively, the pharmaceutical compositions of the invention may be prepared and packaged in unit dosage form. For oral application, for example, one or more tablets or capsules may be administered. A dose of the pharmaceutical composition contains at least a therapeutically effective amount of a compound of this invention (i.e., a compound of Formula (I), particularly a compound of any one of Formulas (I-IV), or a salt, particularly a pharmaceutically acceptable salt, thereof). When prepared in unit dosage form, the pharmaceutical compositions may contain from 1 mg to 1000 mg of a compound of this invention.

As provided herein, unit dosage forms (pharmaceutical compositions) containing from 1 mg to 1000 mg of a compound of the invention may be administered one, two, three, or four times per day, preferably one, two, or three times per day, and more preferably, one or two times per day, to effect treatment of a RIP1 kinase-mediated disease or disorder.

The pharmaceutical compositions of the invention typically contain one compound of the invention. However, in certain embodiments, the pharmaceutical compositions of the invention contain more than one compound of the invention. In addition, the pharmaceutical compositions of the invention may optionally further comprise one or more additional pharmaceutically active compounds.

As used herein, "pharmaceutically acceptable excipient" means a material, composition or vehicle involved in giving form or consistency to the composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically acceptable.

The compounds of the invention and the pharmaceutically acceptable excipient or excipients will typically be formulated into a dosage form adapted for administration to the patient by the desired route of administration. Conventional dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound or compounds of the invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company). Accordingly, another embodiment of this invention is a method of preparing a pharmaceutical composition comprising the step of admixing crystalline (S)-5-benzyl-N-(5-methyl-4-oxo-2,3,4,5-tetrahydrobenzo[b][1,4]oxazepin-3-yl)-4H-1,2,4-triazole-3-carboxamide (free base) having the PXRD pattern of FIG. 7 with one or more pharmaceutically acceptable excipients. In another embodiment, there is provided a method of preparing a pharmaceutical composition comprising the step of admixing crystalline (S)-5-benzyl-N-(5-methyl-4-oxo-2,3,4,5-tetrahydrobenzo[b][1,4]oxazepin-3-yl)-4H-1,2,4-triazole-3-carboxamide (free base) characterized by the diffraction data in Table 1, with one or more pharmaceutically acceptable excipients.

In one aspect, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmellose, alginic acid, and sodium carboxymethyl cellulose. The oral solid dosage form may further comprise a lubricant. Suitable lubricants include stearic acid, magnesium stearate, calcium stearate, and talc.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

The reactions described herein are applicable for producing compounds of the invention having a variety of different substituent groups (e.g., $R^1$, $R^2$, etc.), as defined herein. The skilled artisan will appreciate that if a particular substituent is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999).

Names for the intermediate and final compounds described herein were generated using the software naming program ACD/Name Pro V6.02 available from Advanced Chemistry Development, Inc., 110 Yonge Street, 14th Floor, Toronto, Ontario, Canada, M5C 1T4 (http://www.acdlabs.com/) or the naming program in ChemDraw, Struct=Name Pro 12.0, as part of ChemBioDraw Ultra, available from CambridgeSoft. 100 CambridgePark Drive, Cambridge, Mass. 02140 USA (www.cambridgesoft.com).

It will be appreciated by those skilled in the art that in certain instances these programs may name a structurally depicted compound as a tautomer of that compound. It is to be understood that any reference to a named compound or a structurally depicted compound is intended to encompass all tautomers of such compounds and any mixtures of tautomers thereof.

EXAMPLES

In the following experimental descriptions, the following abbreviations may be used:

| Abbreviation | Meaning |
| --- | --- |
| AcOH | acetic acid |
| aq | aqueous |
| BOC, tBOC | tert-butoxycarbonyl |
| brine | saturated aqueous sodium chloride |
| BuOH | butanol |
| CDCl$_3$ | deuterated chloroform |
| CDI | 1,1'-carbonyldiimidazole |
| CH$_2$Cl$_2$ or DCM | methylene chloride or dichloromethane |
| CH$_3$CN or MeCN | acetonitrile |
| CH$_3$NH$_2$ | methylamine |
| d | day |
| DAST | diethylaminosulfur trifluoride |
| DCE | 1,2-dichloroethane |
| DCM | 1,2-dichloromethane |
| DIEA or DIPEA | diisopropyl ethylamine |
| DMA | dimethylacetamide |
| DMAP | 4-Dimethylaminopyridine |
| DMF | N,N-dimethylformamide |
| DMSO | dimethylsulfoxide |
| EDC | 1-ethyl-3-(3-dimethylaminopropyl) carbodiimide |
| equiv | equivalents |
| Et | ethyl |
| Et$_3$N or TEA | triethylamine |
| Et$_2$O | diethyl ether |
| EtOAc | ethyl acetate |
| FCC | flash column chromatography |
| h, hr | hour(s) |
| HATU | O-(7-Azabenzotriazol-1yl)-N,N,N',N'-tetramethylyronium hexafluorophosphate |
| HCl | hydrochloric acid |
| HPLC | high-performance liquid chromatography |
| ICl | iodine monochloride |
| i-Pr$_2$NEt | N',N'-diisopropylethylamine |
| KOt-Bu | potassium tert-butoxide |
| KOH | potassium hydroxide |
| LCMS | liquid chromatography-mass spectroscopy |
| LiHDMS | lithium hexamethyldisilazide |
| LiOH | lithium hydroxide |
| Me | methyl |
| MeOH or CH$_3$OH | methanol |
| MgSO$_4$ | magnesium sulfate |
| min | minute(s) |
| MS | mass spectrum |
| μw | microwave |
| NaBH$_4$ | sodium borohydride |
| Na$_2$CO$_3$ | sodium carbonate |
| NaHCO$_3$ | sodium bicarbonate |
| NaOH | sodium hydroxide |
| Na$_2$SO$_4$ | sodium sulfate |
| NBS | N-Bromosuccinimide |
| N$_2$H$_2$ | hydrazine |
| NH$_4$Cl | ammonium chloride |
| NH$_4$OH | ammonium hydroxide |
| NiCl$_2$•6H$_2$O | nickel (II) chloride hexahydrate |
| NMP | N-methyl-2-pyrrolidone |
| NMR | nuclear magnetic resonance |
| Pd/C | palladium on carbon |
| Ph | phenyl |
| POCl$_3$ | phosphoryl chloride |
| PSI | pound-force per square inch |
| rm or rxn mixture | reaction mixture |
| rt | room temperature |
| satd. | saturated |
| sm | starting material |
| TEA | thiethylamine |
| TFA | trifluoroacetic acid |
| THF | tetrahydrofuran |
| TMEDA | tetramethylethylenediamine |
| TMSI | trimethylsilyl iodide |
| TMSN$_3$ | trimethylsilyl azide |
| T3P | 2,4,6-tripropyl-1,3,5,2,4,6-trioxatriphosphorinane-2,4,6-trioxide |
| t$_R$ or Rf | retention time |

Preparation 1

(S)-2-((tert-butoxycarbonyl)amino)-3-(2-nitrophenoxy)propanoic Acid

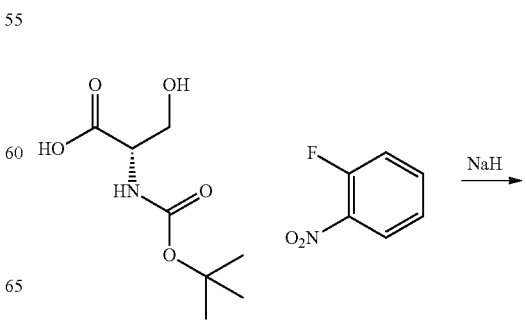

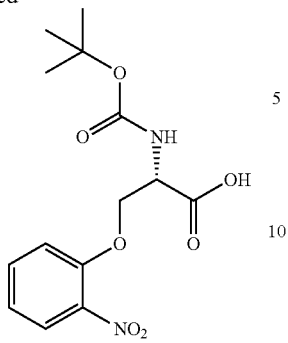

To a suspension of sodium hydride (9.75 g, 244 mmol) in DMF (250 mL) was added a solution of (S)-2-((tert-butoxycarbonyl)amino)-3-hydroxypropanoic acid (25 g, 122 mmol) in 50 mL of DMF dropwise over 10 min at 0° C. Vigorous gas evolution was observed. Once gas evolution had ceased, 1-fluoro-2-nitrobenzene (12.85 mL, 122 mmol) was added dropwise neat at 0° C. The reaction mixture was allowed to stir at room temperature for 16 hr. The reaction mixture was partitioned between ethyl acetate (1000 mL) and 0.5 M HCl solution (1000 mL). The layers were separated, the organic layer was washed with water (3×400 ml), brine (400 mL), and concentrated under reduced pressure to provide the crude product. The crude compound was purified by silica gel column using 0-10% MeOH in DCM to afford (S)-2-((tert-butoxycarbonyl)amino)-3-(2-nitrophenoxy)propanoic acid (32 g, 76 mmol, 62.3% yield) as reddish yellow semi solid. 1H NMR (400 MHz, CDCl$_3$) δ ppm 7.88 (dd, J=8.46, 1.64 Hz, 1H), 7.52-7.61 (m, 1H), 7.06-7.15 (m, 2H), 5.68 (br. d., 1H), 4.75 (br. s., 1H), 4.60-4.72 (m, 1H), 2.07 (s, 2H), 1.48 (s, 9H). MS (m/z) 325.13 (M−H$^+$).

The following intermediates used for the preparation of titled example compounds were synthesized using methods analogous to the ones described above.

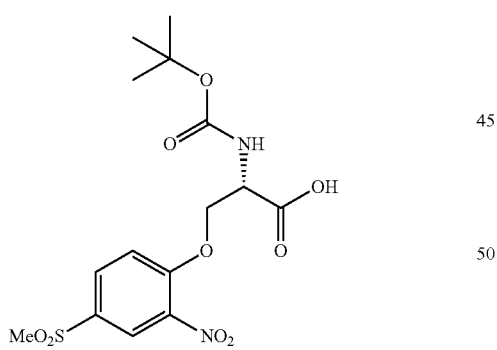

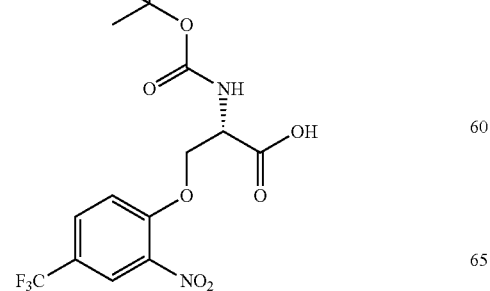

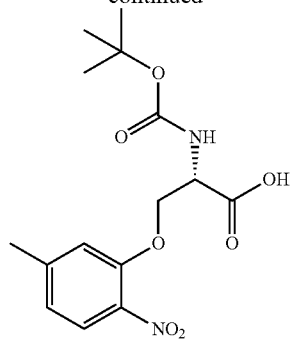

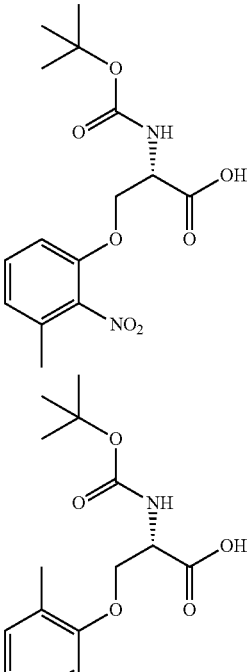

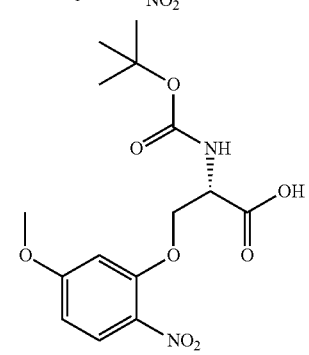

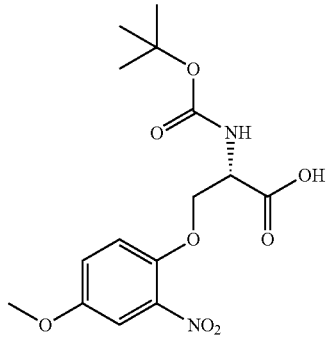

-continued
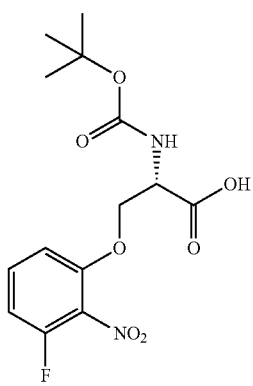
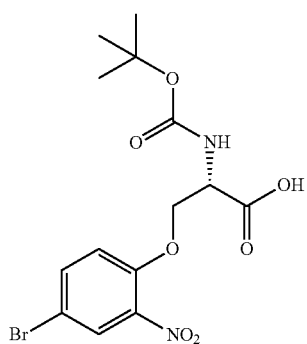
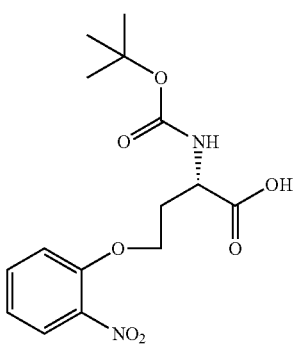
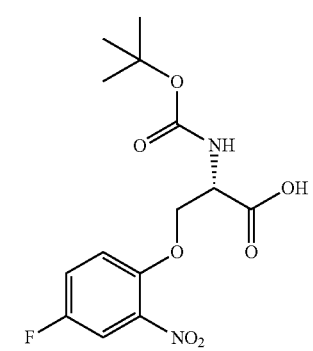
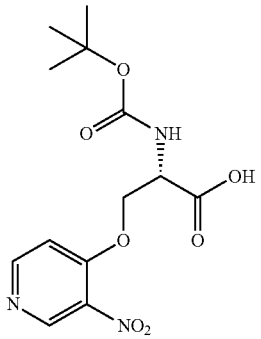

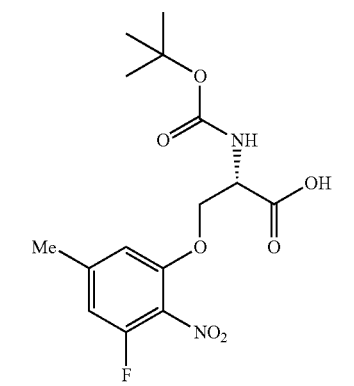
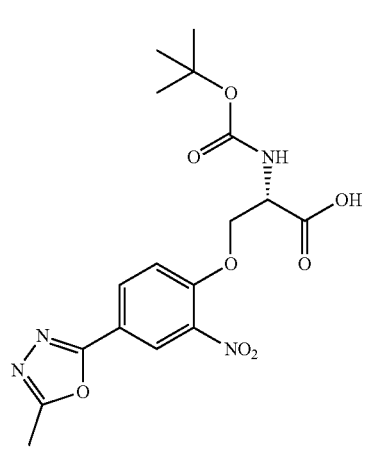
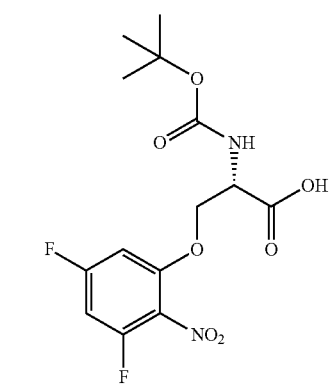
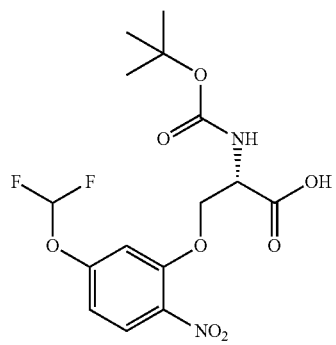
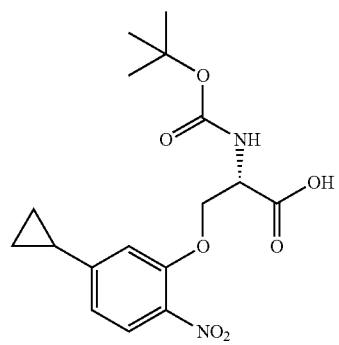
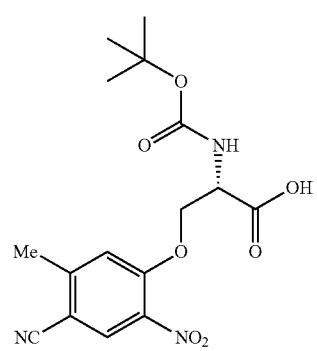
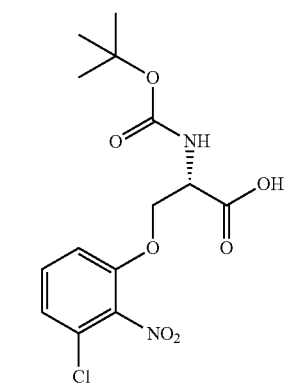
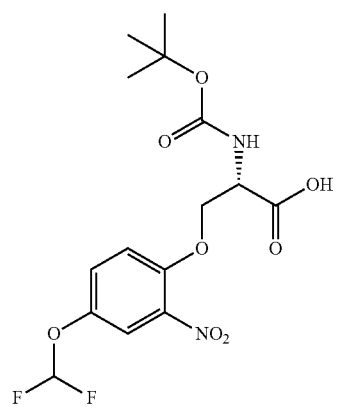

The following intermediates used for the preparation of titled example compounds were synthesized using (S)-3-amino-2-((tert-butoxycarbonyl)amino)-propanoic acid as described by Scott B. Hoyt et. al. in patent application WO 2008/106077.

Preparation 2

(S)-3-(2-aminophenoxy)-2-((tert-butoxycarbonyl)amino)propanoic Acid

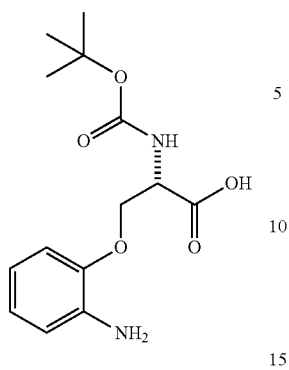

A solution of (S)-2-((tert-butoxycarbonyl)amino)-3-(2-nitrophenoxy)propanoic acid (32 g, 98 mmol) and Pd/C (2.82 g, 2.65 mmol) in methanol (500 mL) using Parr apparatus was hydrogenated with 60 PSI at rt for 2 hr. The TLC (10% MeOH in DCM; Rf: 0.4) shows complete conversion of all of the starting material and the reaction mixture was filtered through a celite bed. The celite bed was washed with methanol (130 mL, 3 times) and the combined filtrate was concentrated to afford (S)-3-(2-aminophenoxy)-2-((tert-butoxycarbonyl)amino)propanoic acid (32 g, 95 mmol, 97% yield) as pale brown semi solid. The residue was used in the next step without further purification. $^1$H NMR (DMSO-$d_6$) δ: 7.42 (br. s., 1H), 6.74 (d, J=7.1 Hz, 1H), 6.64-6.70 (m, 1H), 6.57-6.62 (m, 1H), 6.47 (td, J=7.6, 1.6 Hz, 1H), 4.40 (d, J=4.3 Hz, 1H), 4.24 (dd, J=9.5, 4.9 Hz, 1H), 4.00 (dd, J=9.6, 3.5 Hz, 1H), 1.41 (s, 9H). MS (m/z) 295.19 (M–H$^+$), 222.15 (-tBuO group).

The following intermediates used for the preparation of titled example compounds were synthesized using methods analogous to the ones described above.

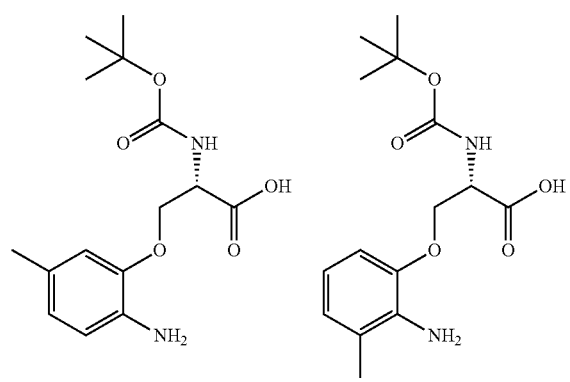

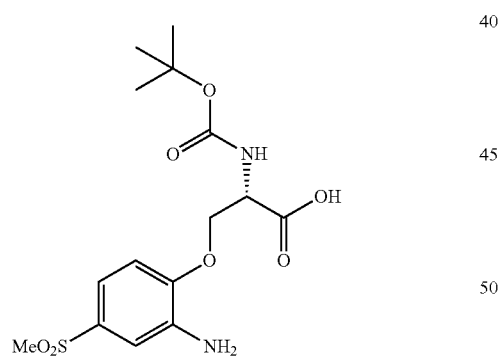

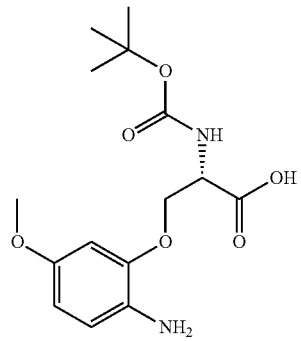

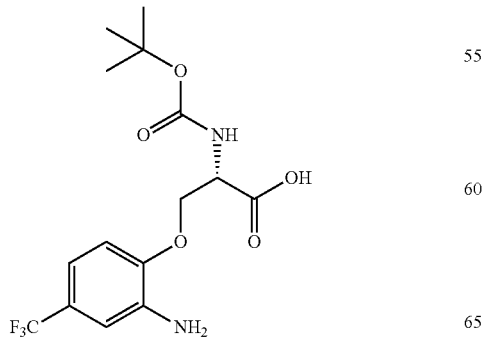

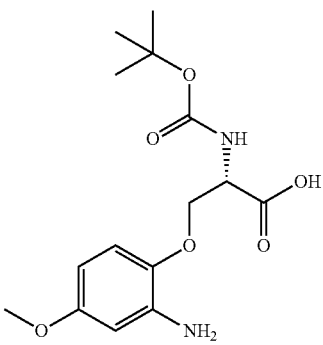

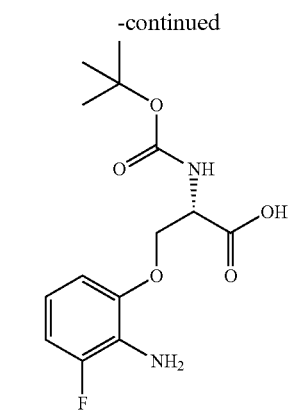
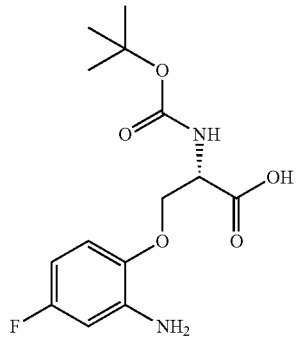
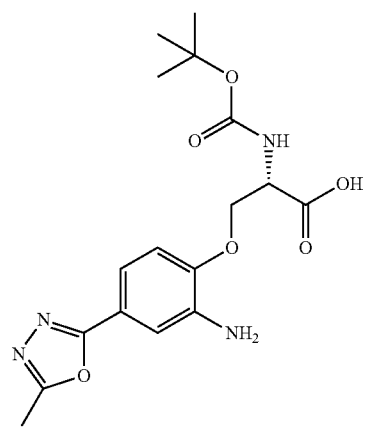
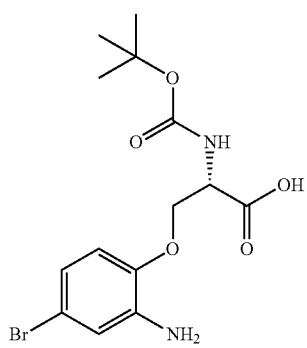
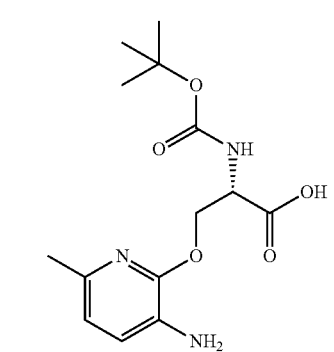
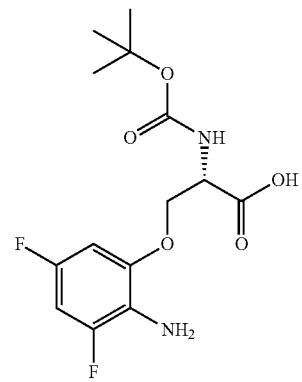
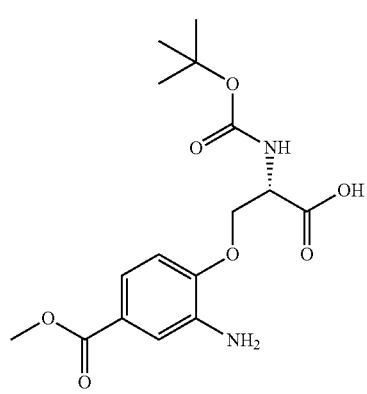
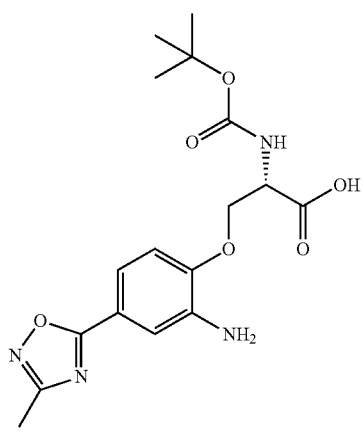

57
-continued
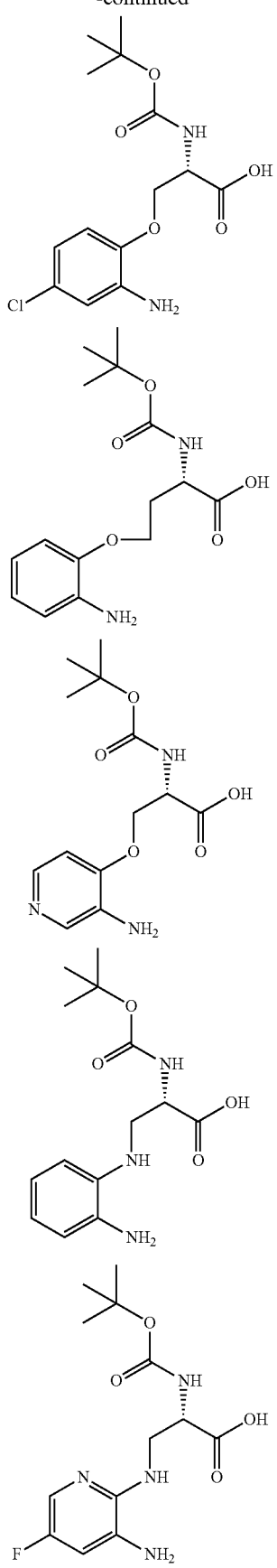
58
-continued
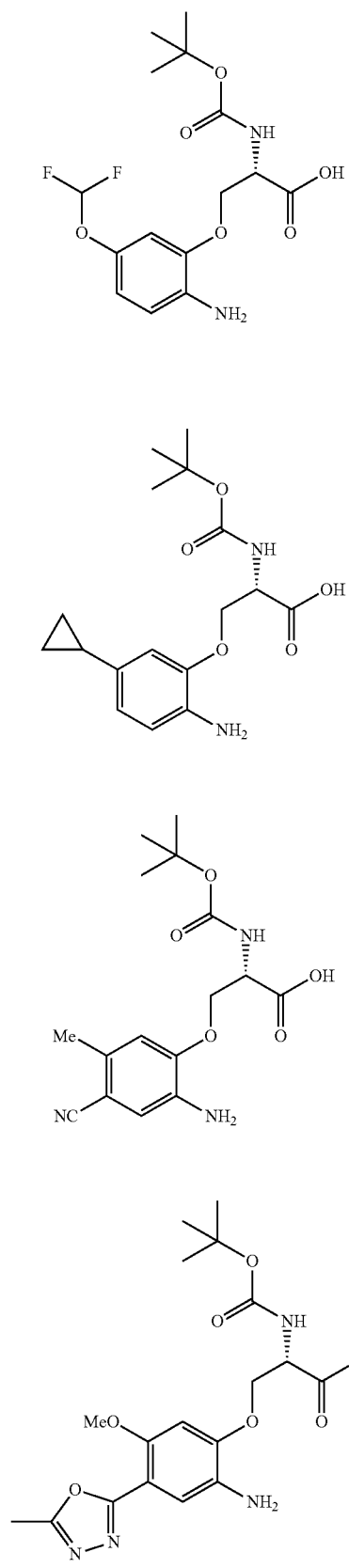

59
-continued
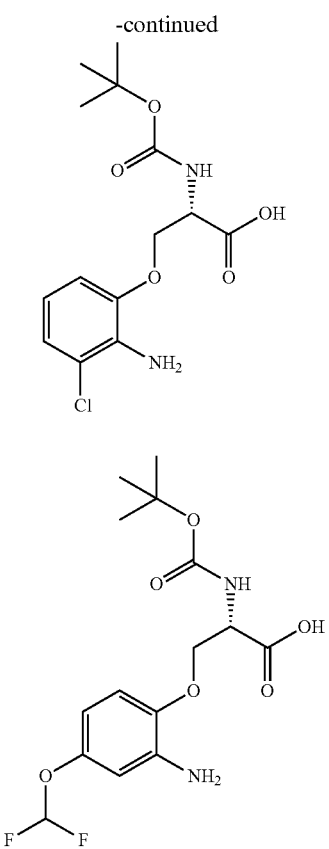
60
-continued
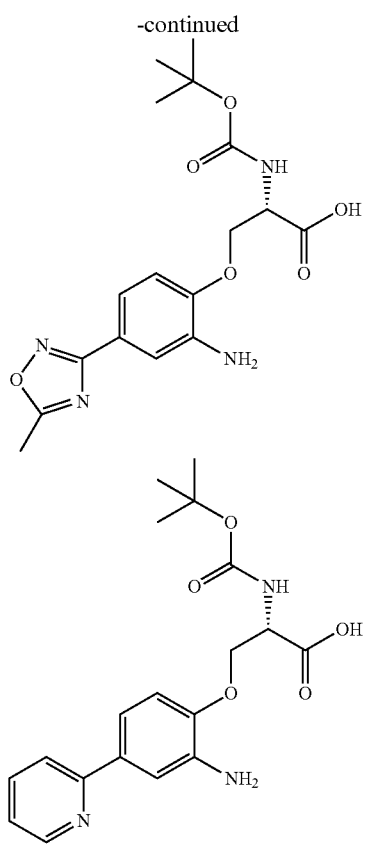
Preparation 3
(S)-tert-butyl (4-oxo-2,3,4,5-tetrahydrobenzo[b][1,4]oxazepin-3-yl)carbamate
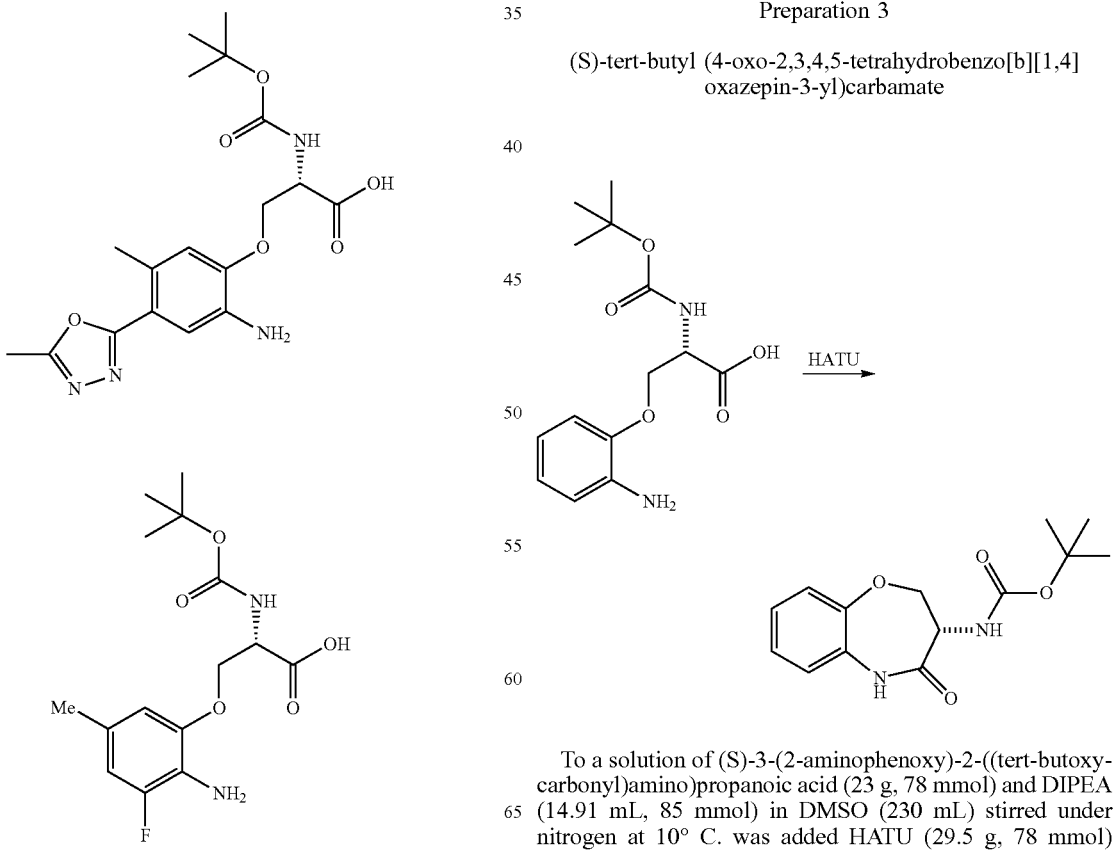
To a solution of (S)-3-(2-aminophenoxy)-2-((tert-butoxycarbonyl)amino)propanoic acid (23 g, 78 mmol) and DIPEA (14.91 mL, 85 mmol) in DMSO (230 mL) stirred under nitrogen at 10° C. was added HATU (29.5 g, 78 mmol) portionwise during 15 min. The reaction mixture was stirred at room temperature for 16 hr. Reaction was quenched with water (900 mL) (resulting in formation of a solid) and was stirred at 18° C. for 20 min. The resultant solid was filtered, washed with excess water (3 times) and dried in vacuo (high vacuum) to afford (S)-tert-butyl (4-oxo-2,3,4,5-tetrahydrobenzo[b][1,4]oxazepin-3-yl)carbamate (18 g, 61.6 mmol, 79% yield) as a pale brown solid. TLC: 50% EtOAc in Hexane; Rf: 0.55. 1H NMR (400 MHz, DMSO-d6) d ppm 9.92 (s, 1H), 6.99-7.21 (m, 5H), 4.17-4.45 (m, 3H), 1.36 (s, 9H). MS (m/z): 179.16 ([M-BOC]+H$^+$).

The following intermediates used for the preparation of titled example compounds were synthesized using methods analogous to the ones described above.

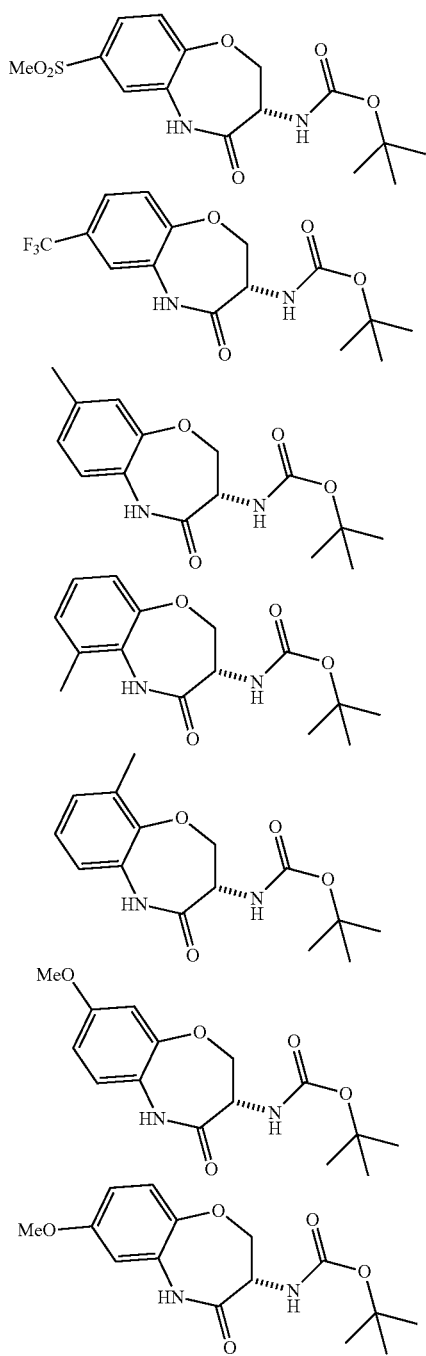

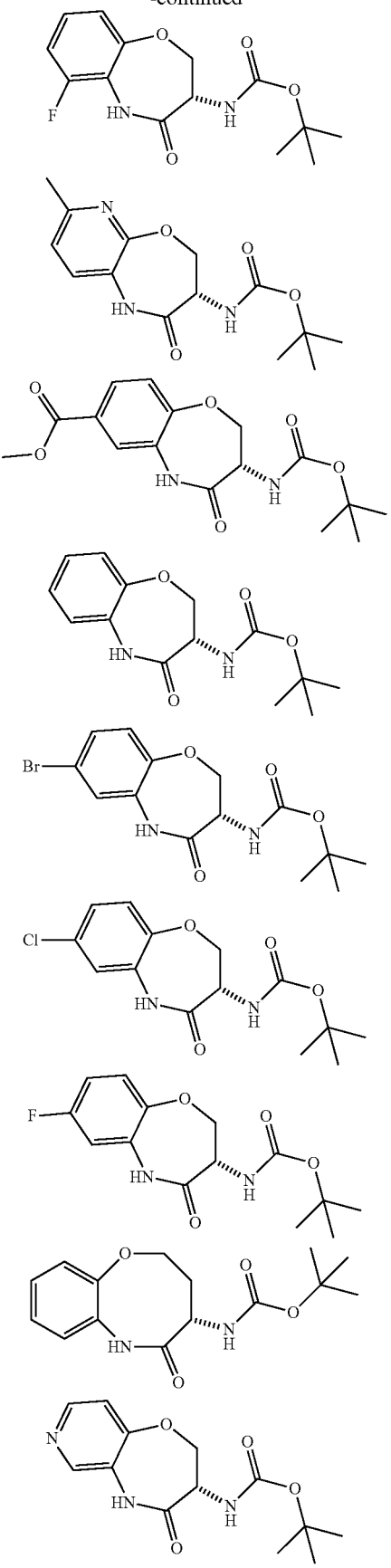

-continued
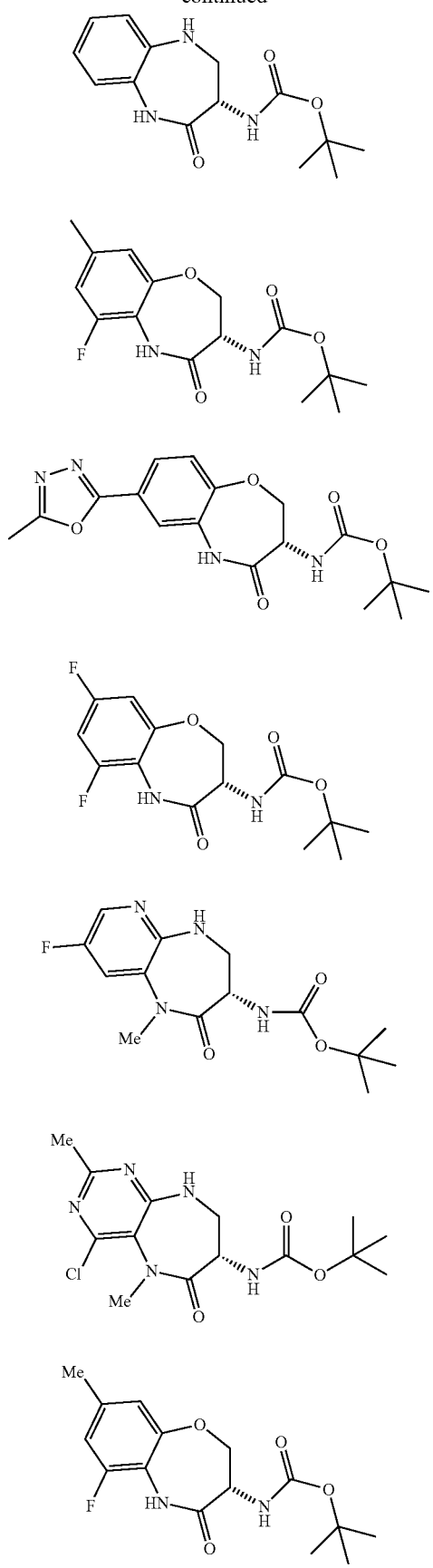
-continued
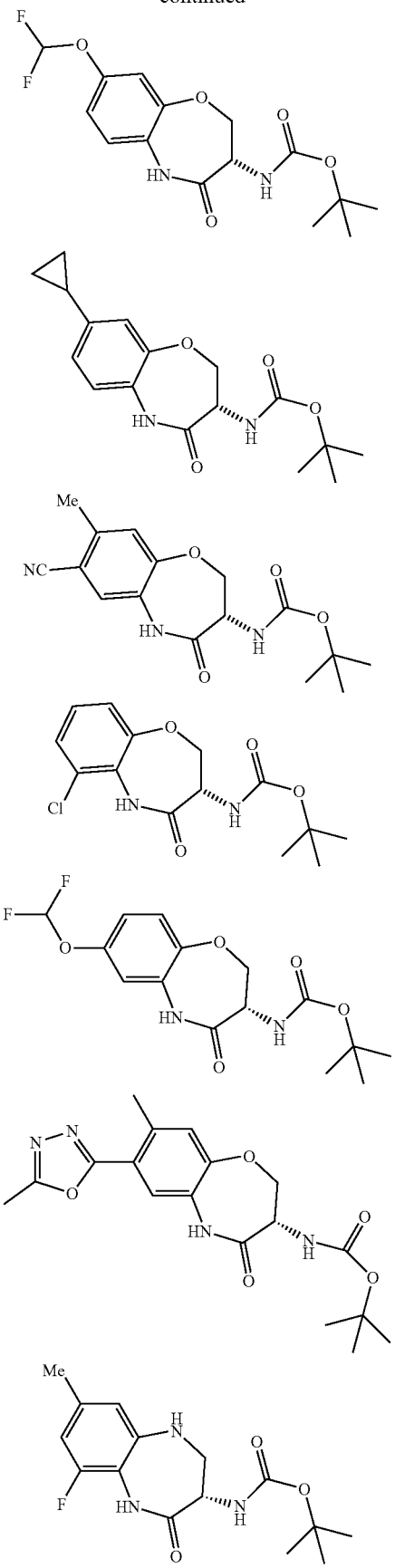

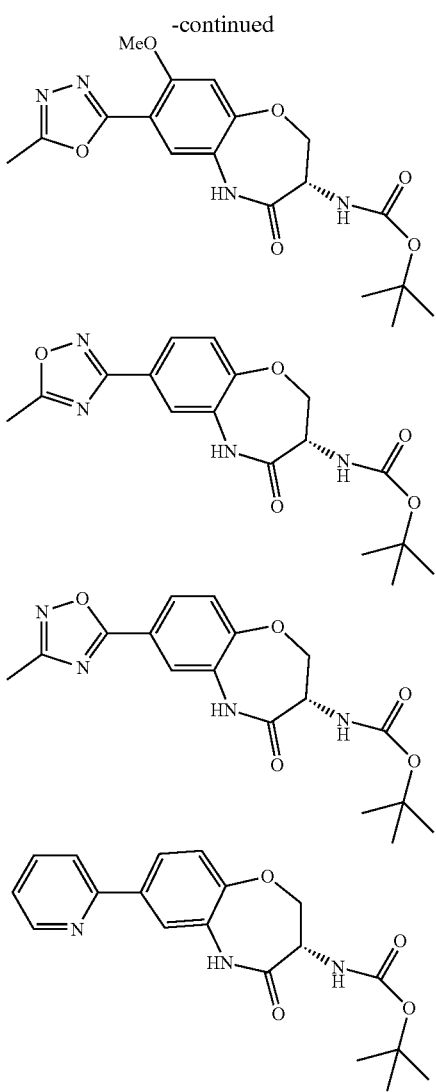

Preparation 4

(S)-tert-butyl (7-fluoro-5-methyl-4-oxo-2,3,4,5-tetrahydrobenzo[b][1,4]oxazepin-3-yl)carbamate

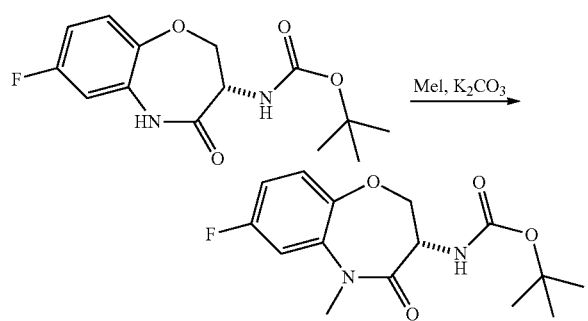

To a suspension of (S)-tert-butyl (7-fluoro-5-methyl-4-oxo-2,3,4,5-tetrahydrobenzo[b][1,4]oxazepin-3-yl)carbamate (0.89 g, 2.70 mmol) and K$_2$CO$_3$ (0.392 g, 2.84 mmol) in DMF (10.0 mL) at rt was added a solution of MeI (0.161 mL, 2.57 mmol) in DMF. The reaction mixture was stirred at rt overnight, then additional 0.74 eq of MeI and K$_2$CO$_3$ were added and the reaction was monitored by LCMS. The reaction mixture was diluted with EtOAc then washed with water (2×), sat. aq. NH$_4$Cl and brine. The organic phase was concentrated in vacuo then purified by FCC [EtOAc/Hex: 15-50%] to yield the desired product (640 mg, 76%). $^1$H NMR (DMSO-d$_6$) δ: 7.44 (dd, J=9.9, 3.0 Hz, 1H), 7.17-7.25 (m, 2H), 7.10 (td, J=8.5, 3.0 Hz, 1H), 4.23-4.42 (m, 3H), 3.28 (s, 3H), 1.35 (s, 9H). MS (m/z) 211.1 ([M-BOC]+H$^+$).

The following intermediates used for the preparation of titled example compounds were synthesized using methods analogous to the one described above.

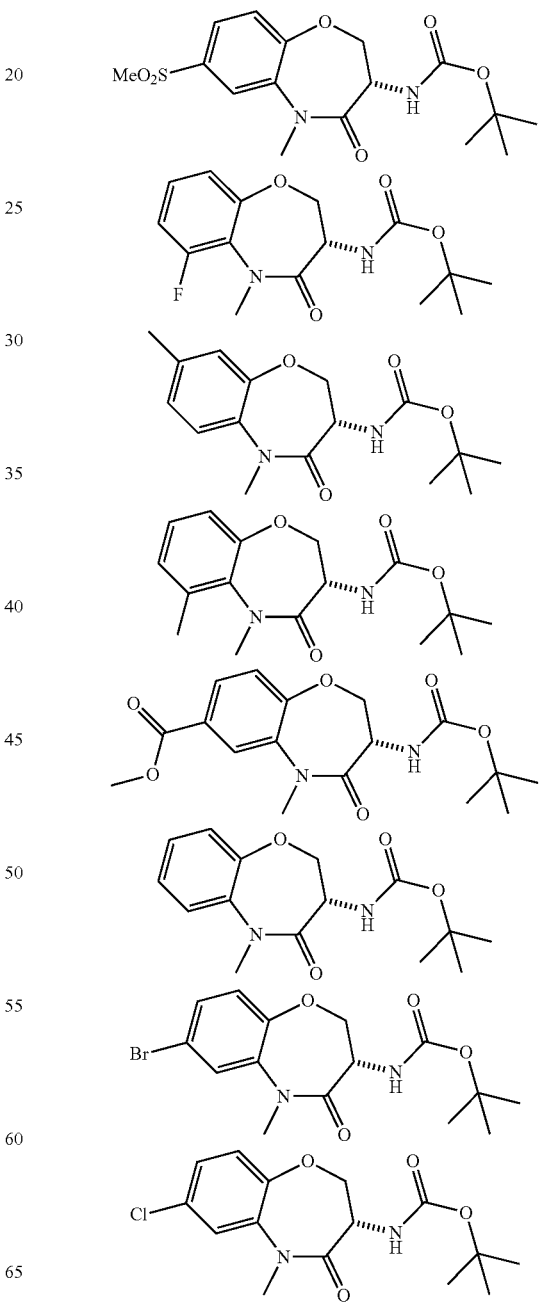

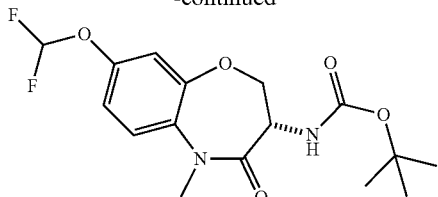

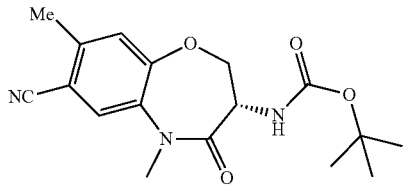 [SMILES: Cc1cc2c(cc1C#N)N(C)C(=O)[C@@H](NC(=O)OC(C)(C)C)CO2]

Preparation 5

(S)-tert-butyl (5-methyl-4-oxo-2,3,4,5-tetrahydrobenzo[b][1,4]oxazepin-3-yl)carbamate

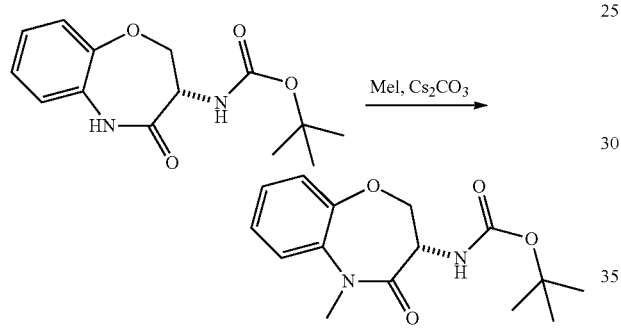

To a solution of (S)-tert-butyl (4-oxo-2,3,4,5-tetrahydrobenzo[b][1,4]oxazepin-3-yl)carbamate (30 g, 108 mmol) and Cs$_2$CO$_3$ (49.2 g, 151 mmol) in DMF (300 mL) stirred under nitrogen at room temp was added methyl iodide (8.09 mL, 129 mmol) dropwise during 15 min. The reaction mixture was stirred at rt for 16 hr. TLC (30% EtOAc in Hexane; Rf: 0.4) shows reaction was complete. The reaction was poured into cold water (1500 mL) which formed a solid, the resultant solid was filtered, the filter cake was washed with water (two times) and dried in vacuo to afford the crude compound. This was triturated with 5% Et$_2$O in hexane (300 mL) to afford (S)-tert-butyl (5-methyl-4-oxo-2,3,4,5-tetrahydrobenzo[b][1,4]oxazepin-3-yl)carbamate (19 g, 62.7 mmol, 58.1% yield) as a brown solid. $^1$H NMR (DMSO-d$_6$) δ: 7.47 (dd, J=7.7, 1.6 Hz, 1H), 7.23-7.33 (m, 2H), 7.14-7.21 (m, 2H), 4.25-4.41 (m, 3H), 3.28 (s, 3H), 1.34 (s, 9H). MS (m/z) 193.33 ([M-BOC]+H$^+$).

The following intermediates used for the preparation of titled example compounds were synthesized using methods analogous to the one described above.

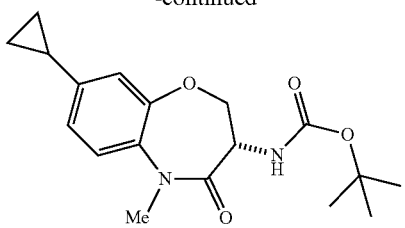

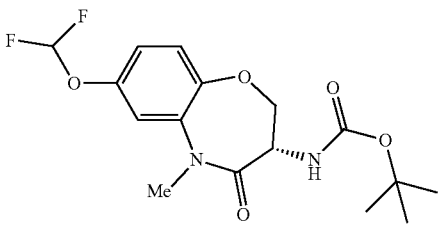

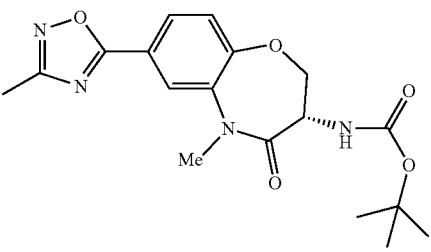

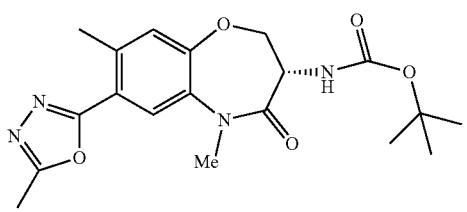

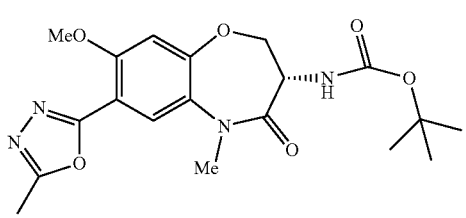

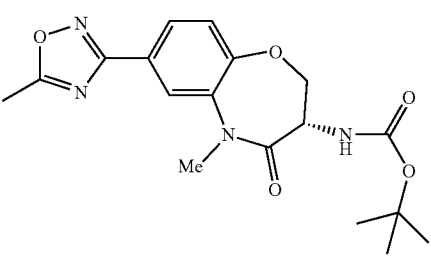

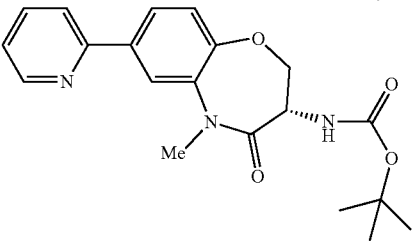

Preparation 6

(S)-3-amino-7-fluoro-2,3-dihydrobenzo[b][1,4]ox-azepin-4(5H)-one trifluoroacetate

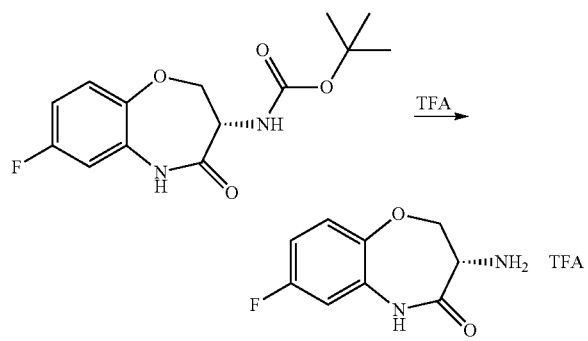

To a suspension of (S)-tert-butyl (7-fluoro-4-oxo-2,3,4,5-tetrahydrobenzo[b][1,4]oxazepin-3-yl)carbamate (105.0 mg, 0.354 mmol) in DCM (1.5 mL) was added TFA (0.191 mL, 2.481 mmol). The reaction became homogeneous almost immediately and was allowed to stir at rt and monitored by LCMS. (about 2 h). The reaction was diluted with ethyl ether then concentrated under reduced pressure (repeated 3 times) to give the desired product as a TFA salt. The sample was once azeotroped with toluene. Quantitative recovery was assumed.

The following intermediates used for the preparation of titled example compounds were synthesized using methods analogous to the one described above.

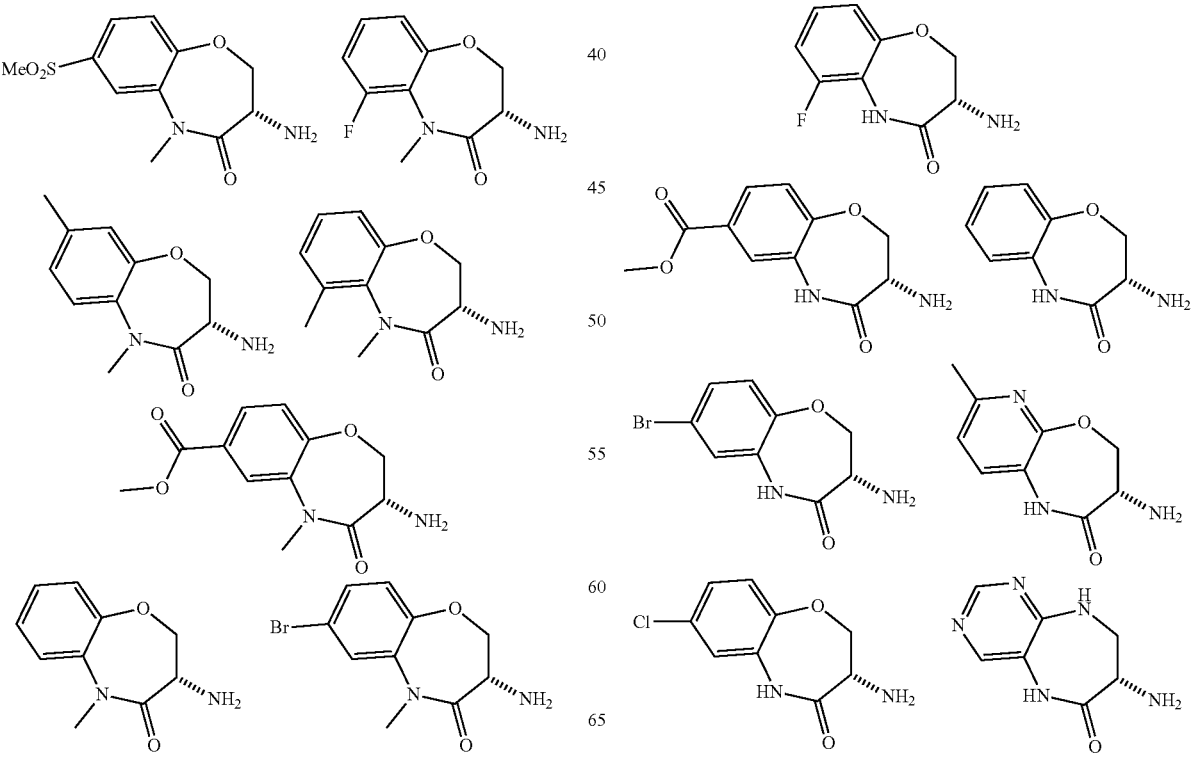

-continued

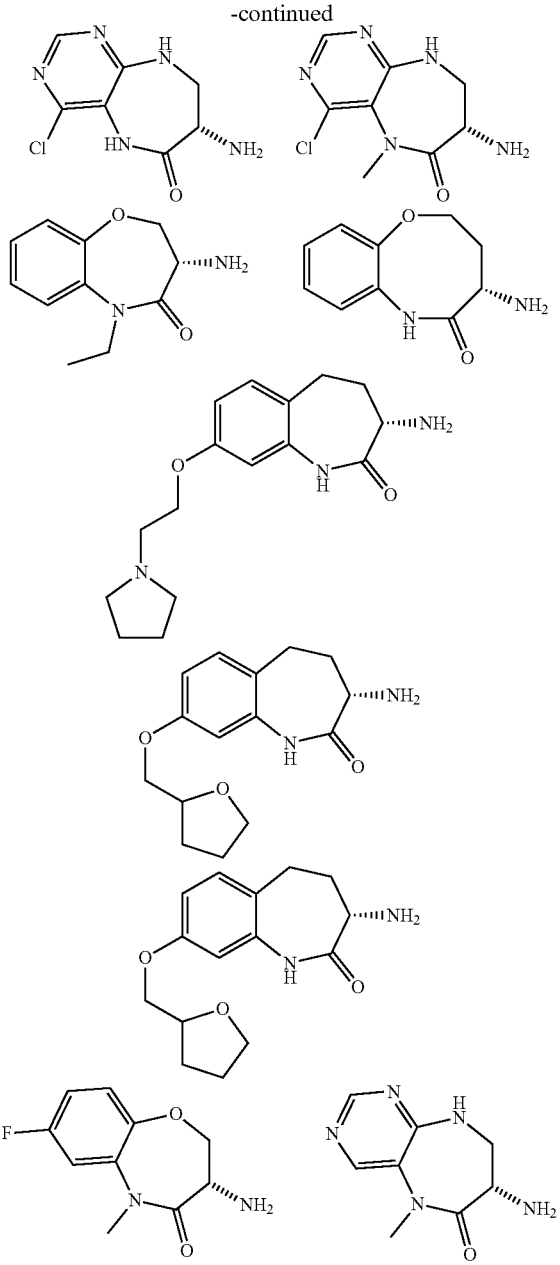

Mixture was stirred cooled for 15 minutes, then at rt for 30 minutes. Reaction was poured over ice and stirred for 10 minutes. The resulting solid was filtered, rinsed with water and hexanes, and dried to give 6.10 g tan solid. $^1$H NMR (DMSO-$d_6$) δ: 9.51 (br. s., 1H), 7.16-7.29 (m, 2H), 7.04-7.12 (m, 1H), 6.96 (d, J=7.6 Hz, 1H), 2.68 (t, J=6.8 Hz, 2H), 2.04-2.19 (m, 4H); MS (m/z) 162.0 (M+H$^+$).

The following intermediates used for the preparation of titled example compounds were synthesized using methods analogous to the ones described above.

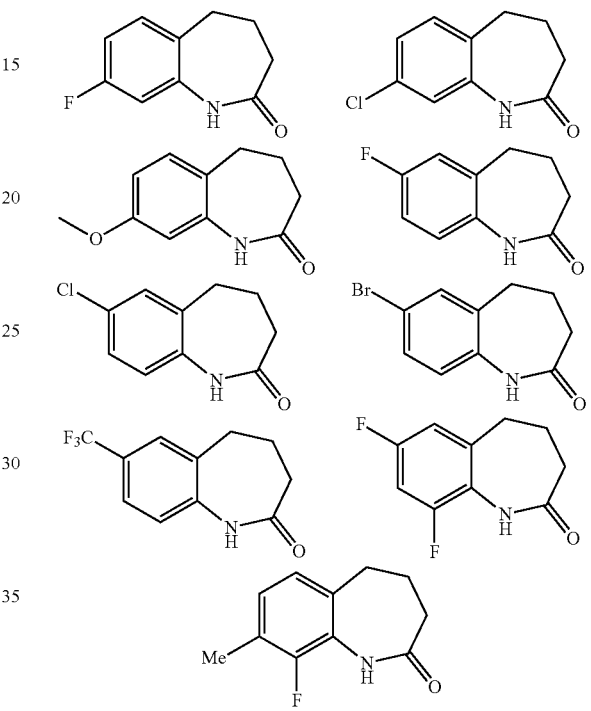

Preparation 8

3-iodo-4,5-dihydro-1H-benzo[b]azepin-2(3H)-one

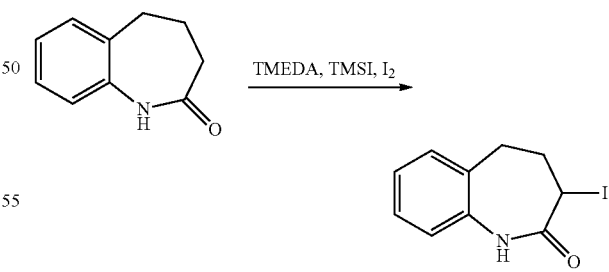

To a mixture of 4,5-dihydro-1H-benzo[b]azepin-2(3H)-one (10.6 g, 65.8 mmol) in DCM (150 mL) cooled in an ice/water bath was added TMEDA (29.8 mL, 197 mmol), then dropwise over 20 minutes was added TMSI (26.9 mL, 197 mmol). The mixture was stirred cooled for 60 minutes, iodine (25.03 g, 99 mmol) was added and the mixture was stirred cooled for another 60 minutes. The reaction was quenched with 5% Na$_2$S$_2$O$_3$ and stirred 15 minutes. The Preparation 7

4,5-dihydro-1H-benzo[b]azepin-2(3H)-one

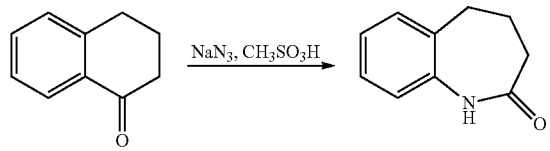 [SMILES: O=C1CCCc2ccccc21 ; O=C1CCCc2ccccc2N1]

To a solution of 3,4-dihydronaphthalen-1(2H)-one (4.55 mL, 34.2 mmol) in methanesulfonic acid (40 mL) cooled in an ice/brine bath was added sodium azide (2.5 g, 38.5 mmol) in 5 portions over 15 minutes. Moderate gas evolution.

resulting solid was filtered and dried to give 11.3 g tan solid. Layers of filtrate were separated. Organics were concentrated to a solid, triturated in diethyl ether and solid was filtered and dried to give 5.52 g light brown solid (87% yield, both batches). $^1$H NMR (DMSO-$d_6$) δ: 9.93 (s, 1H), 7.22-7.30 (m, 2H), 7.09-7.17 (m, 1H), 6.99 (d, J=7.3 Hz, 1H), 4.63 (dd, J=9.1, 6.8 Hz, 1H), 2.52-2.81 (m, 4H); MS (m/z) 288.0 (M+H$^+$).

The following intermediates used for the preparation of titled example compounds were synthesized using methods analogous to the ones described above.

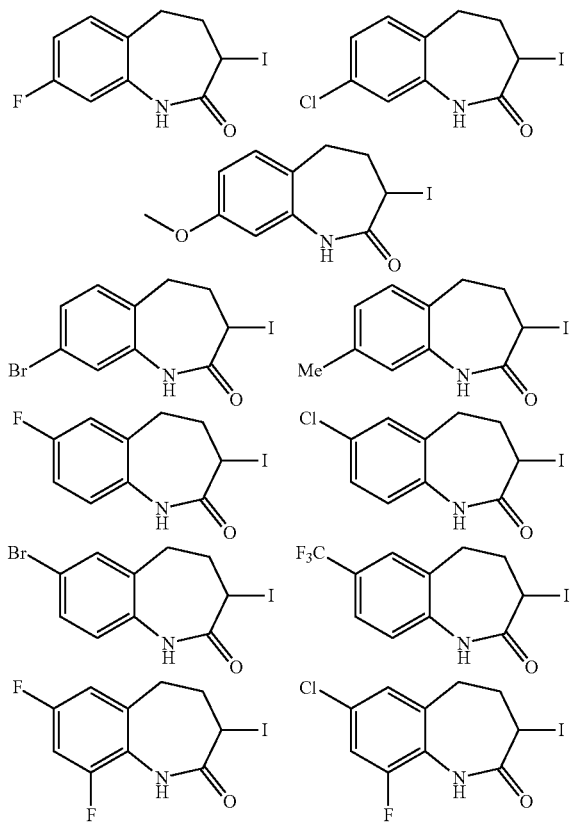

Preparation 9

3-amino-4,5-dihydro-1H-benzo[b]azepin-2(3H)-one

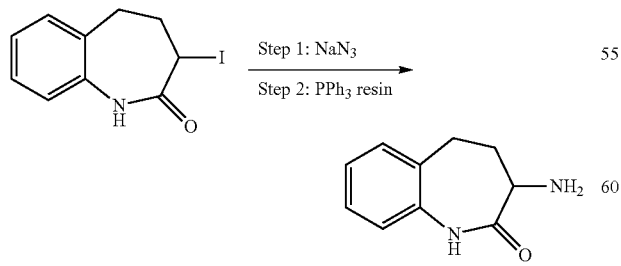

Step 1: To a solution of 3-iodo-4,5-dihydro-1H-benzo[b] azepin-2(3H)-one (16.8 g, 58.5 mmol) in N,N-Dimethylformamide (DMF) (100 mL) was added sodium azide (4.57 g, 70.2 mmol) (mild exotherm) and mixture was stirred at rt for 1 hour. A precipitate formed after 30 minutes. Ice was added to the reaction and it was then diluted with 300 mL water. More solid precipitated out and the mixture was stirred for 10 minutes. Filtered tan solid, rinsed with water and used as-is in next step (was not dried because next step contained water). Small amount dried for HNMR analysis. $^1$H NMR (DMSO-$d_6$) δ: 10.05 (s, 1H), 7.20-7.33 (m, 2H), 7.06-7.17 (m, 1H), 7.00 (d, J=7.8 Hz, 1H), 3.89 (dd, J=11.6, 8.1 Hz, 1H), 2.65-2.81 (m, 2H), 2.41 (tt, J=12.7, 7.8 Hz, 1H), 2.04-2.17 (m, 1H); MS (m/z) 203.0 (M+H$^+$).

Step 2: To a solution of 3-azido-4,5-dihydro-1H-benzo[b]azepin-2(3H)-one in THF (120 mL) was added 1.0 mL water and PPh$_3$ resin (21.5 g, 3 mmol/g loading, 1.1 eq, 64.4 mmol, Aldrich). Stirred at rt for 20 hours. Reaction was filtered to remove resin, rinsed with THF and filtrate was concentrated. Triturated solid in 10% DCM/diethyl ether, filtered and dried to give a tan solid (9.13 g, 85% yield over 2 steps). $^1$H NMR (DMSO-$d_6$) δ: 9.68 (br. s., 1H), 7.18-7.29 (m, 2H), 7.04-7.13 (m, 1H), 6.96 (d, J=7.8 Hz, 1H), 3.13 (dd, J=11.4, 7.8 Hz, 1H), 2.55-2.70 (m, 2H), 2.27 (tt, J=12.9, 7.7 Hz, 1H), 1.70-1.83 (m, 1H), 1.62 (br. s., 2H); MS (m/z) 177.0 (M+H$^+$).

The following intermediates used for the preparation of titled example compounds were synthesized using methods analogous to the ones described above.

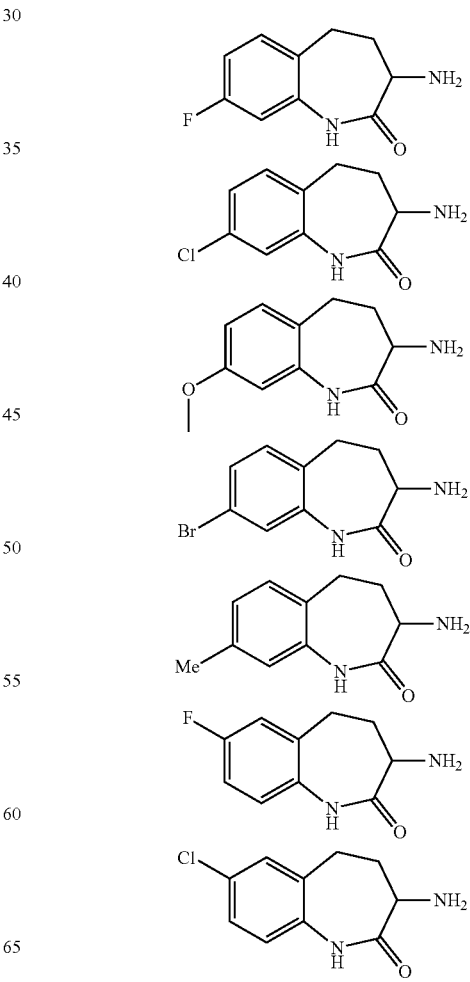

-continued

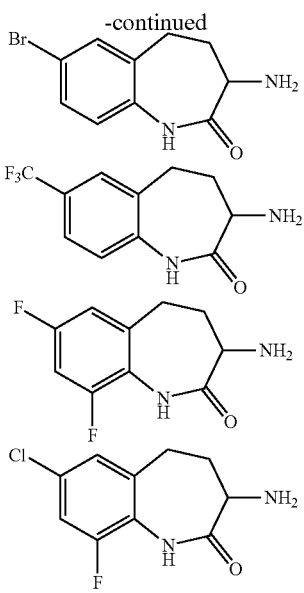

Preparation 10

(S)-3-amino-4,5-dihydro-1H-benzo[b]azepin-2(3H)-one

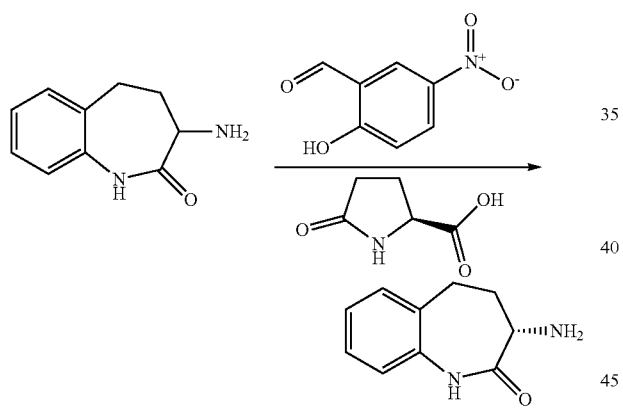

To a solution of 3-amino-4,5-dihydro-1H-benzo[b]azepin-2(3H)-one (24.1 g, 127 mmol) in isopropanol (300 mL) at 70° C. was added L-pyroglutamic acid (16.42 g, 127 mmol). Stirred for 30 minutes. Added 400 mL more isopropanol to facilitate stirring. Then 2-hydroxy-5-nitrobenzaldehyde (0.638 g, 3.82 mmol) was added and mixture was stirred at 70° C. for 3.5 days. Mixture was cooled to rt, solid was filtered, rinsing with isopropanol and hexanes. Solid was dried to give a tan solid as the pyroglutamic acid salt (33 g, 84%). The % ee=97.4% @ 220 nm and 97.8% @ 254 nm. MS (m/z) 177.0 (M+H$^+$).

(S)-3-amino-4,5-dihydro-1H-benzo[b]azepin-2(3H)-one, pyroglutamic acid salt (33 g) was basified with minimum amount of concentrated NH$_4$OH and extracted with DCM four times. The combined organics were concentrated to a solid which was triturated in diethyl ether, filtered and dried to give a light orange/tan solid as free base (19.01 g, 81%). $^1$H NMR (DMSO-d$_6$) δ: 9.70 (br. s., 1H), 7.17-7.30 (m, 2H), 7.05-7.13 (m, 1H), 6.96 (d, J=7.8 Hz, 1H), 3.15 (dd, J=11.5, 8.0 Hz, 1H), 2.56-2.73 (m, 2H), 2.28 (tt, J=12.9, 7.6 Hz, 1H), 2.04 (br. s., 2H), 1.69-1.83 (m, 1H); MS (m/z) 177.0 (M+H$^+$).

The following intermediates used for the preparation of titled example compounds were synthesized using methods analogous to the ones described above.

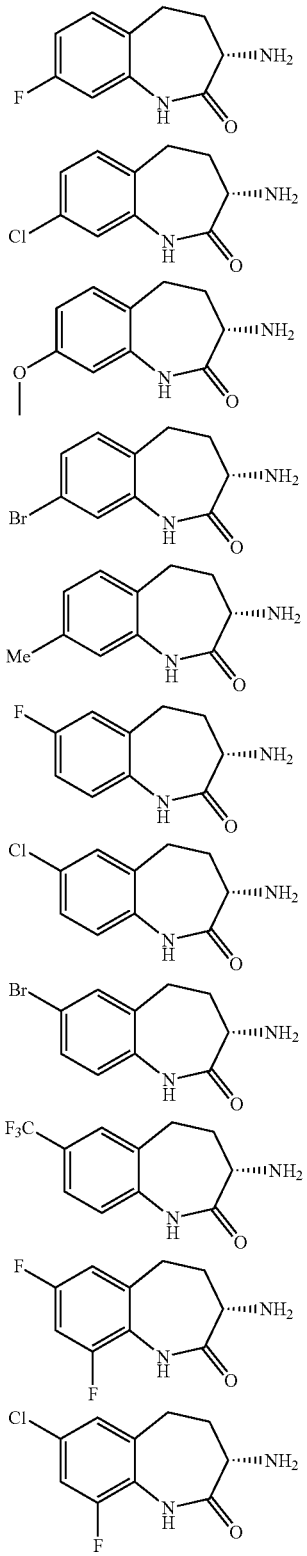

Preparation 11

(S)-3-amino-1-methyl-4,5-dihydro-1H-benzo[b]azepin-2(3H)-one, HCl salt

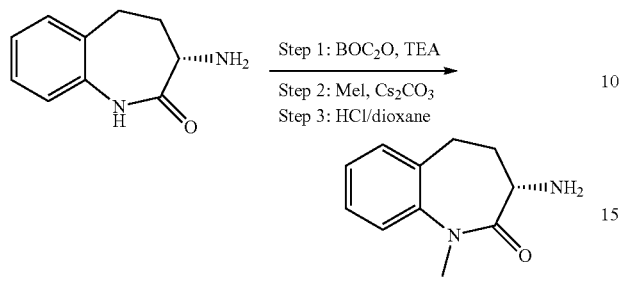

Step 1: To a mixture of (S)-3-amino-4,5-dihydro-1H-benzo[b]azepin-2(3H)-one (0.615 g, 3.49 mmol) in DCM (20 mL) was added TEA (0.730 mL, 5.24 mmol) and BOC$_2$O (0.851 mL, 3.66 mmol). The reaction was stirred at rt for 1 hour, diluted with water and layers were separated. The organics were concentrated and dried to give 950 mg of (S)-tert-butyl (2-oxo-2,3,4,5-tetrahydro-1H-benzo[b]azepin-3-yl)carbamate as an off-white solid. $^1$H NMR (DMSO-d$_6$) δ: 9.71 (s, 1H), 7.22-7.30 (m, 2H), 7.08-7.15 (m, 1H), 6.95-7.03 (m, 2H), 3.87 (dt, J=12.1, 8.2 Hz, 1H), 2.61-2.70 (m, 2H), 2.19 (ddd, J=12.0, 8.0, 4.0 Hz, 1H), 2.01-2.12 (m, 1H), 1.34 (s, 9H); MS (m/z) 277 (M+H$^+$).

Step 2: To a mixture of cesium carbonate (1.592 g, 4.89 mmol) and (S)-tert-butyl (2-oxo-2,3,4,5-tetrahydro-1H-benzo[b]azepin-3-yl)carbamate (950 mg, 3.40 mmol) in N,N-Dimethylformamide (DMF) (10 mL) was added iodomethane (0.262 mL, 4.19 mmol). The reaction was stirred at rt for 20 hours, then water (30 mL) was added and mixture was stirred vigorously for 15 minutes. The resulting solid was filtered, rinsed with water and hexanes and dried to give 800 mg of (S)-tert-butyl (1-methyl-2-oxo-2,3,4,5-tetrahydro-1H-benzo[b]azepin-3-yl)carbamate as an off-white solid. $^1$H NMR (DMSO-d$_6$) δ: 7.34-7.39 (m, 2H), 7.29 (d, J=7.3 Hz, 1H), 7.18-7.24 (m, 1H), 7.03 (d, J=8.6 Hz, 1H), 3.86 (dt, J=11.6, 8.3 Hz, 1H), 3.27 (s, 3H), 2.60-2.66 (m, 2H), 2.01-2.13 (m, 2H), 1.33 (s, 9H); MS (m/z) 291 (M+H$^+$).

Step 3: To a solution of (S)-tert-butyl (1-methyl-2-oxo-2,3,4,5-tetrahydro-1H-benzo[b]azepin-3-yl)carbamate (800 mg, 2.73 mmol) in DCM (20 mL) was added HCl (4.0 M in dioxane) (4.0 mL, 16.00 mmol). The mixture was stirred at rt for 1.5 hours, then concentrated and dried to give 670 mg of (S)-3-amino-1-methyl-4,5-dihydro-1H-benzo[b]azepin-2(3H)-one, HCl salt as a tan solid. $^1$H NMR (DMSO-d$_6$) δ: 8.33 (br. s., 3H), 7.39-7.43 (m, 2H), 7.36 (d, J=7.1 Hz, 1H), 7.24-7.30 (m, 1H), 3.62 (dd, J=11.4, 8.1 Hz, 1H), 3.57 (s, 3H), 2.70-2.77 (m, 2H), 2.44 (ddd, J=12.1, 8.0, 4.2 Hz, 1H), 2.07-2.17 (m, 1H); MS (m/z) 191 (M+H$^+$).

The following intermediates used for the preparation of titled example compounds were synthesized using methods analogous to the ones described above.

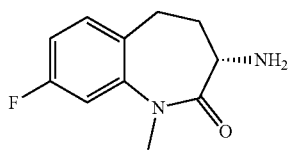

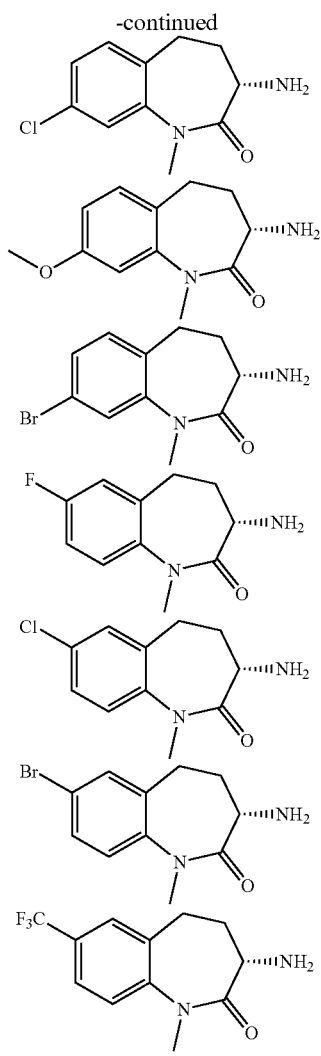

Preparation 12

8-bromo-4,5-dihydro-1H-benzo[b]azepin-2(3H)-one

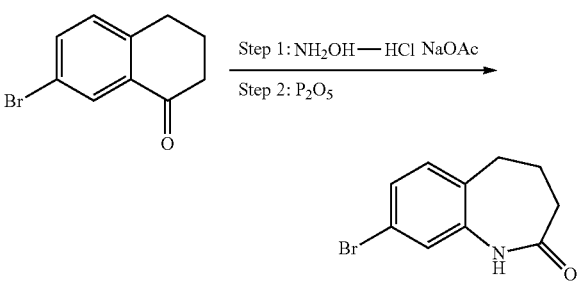

Step 1: To a solution of sodium acetate (7.47 g, 91 mmol) in Water (13.33 mL) was added hydroxylamine hydrochloride (6.33 g, 91 mmol), then Ethanol (40 mL) and 7-bromo-3,4-dihydronaphthalen-1(2H)-one (10.25 g, 45.5 mmol). The white slurry was heated at 80° C. for 45 minutes. Reaction was removed from heat, stirred for 10 minutes, then poured over ice and stirred until all ice melted. Filtered resulting solid, rinsed with water and dried to give a white solid (10.58 g, 95%). $^1$H NMR (DMSO-$d_6$) δ: 11.29 (s, 1H), 7.94 (d, J=2.0 Hz, 1H), 7.42 (dd, J=8.2, 2.1 Hz, 1H), 7.17 (d, J=8.3 Hz, 1H), 2.66 (dt, J=16.9, 6.3 Hz, 4H), 1.74 (quin, J=6.4 Hz, 2H); MS (m/z) 240/242 (M+H$^+$), bromine splitting pattern.

Step 2: To methanesulfonic acid (100 mL) was added phosphorus pentoxide (9.70 g, 68.3 mmol) and mixture was heated at 90° C. for 1.5 hours. Removed from heat and added 7-bromo-3,4-dihydronaphthalen-1(2H)-one oxime (10.58 g, 43.2 mmol) in portions over 10 minutes. Mixture was heated at 80° C. for 20 hours. Reaction was removed from heat and poured over ice, then 50% w/w NaOH was added slowly along with ice to control temperature. Resulting precipitate was stirred for 10 minutes, filtered, rinsed with water and dried to give a pink powder that was 80% pure (9.81 g, 74%). $^1$H NMR (DMSO-$d_6$) δ: 9.61 (s, 1H), 7.19-7.32 (m, 2H), 7.13 (d, J=2.0 Hz, 1H), 2.66 (t, J=6.9 Hz, 2H), 2.04-2.21 (m, 4H); MS (m/z) 240/242 (M+H$^+$), bromine splitting pattern.

Preparation 13

(R)-2-((tert-butoxycarbonyl)amino)-3-((2-nitrophenyl)thio)propanoic acid

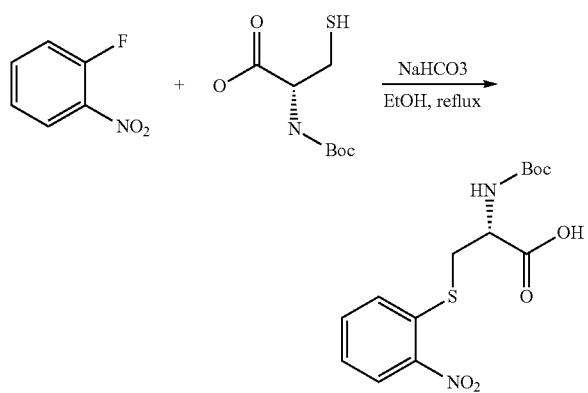

To a solution of (R)-2-((tert-butoxycarbonyl)amino)-3-mercaptopropanoic acid (5.02 g, 22.69 mmol) in Water (32 mL) was added NaHCO$_3$ (5.72 g, 68.1 mmol) stirred at 25° C. was slowly added a solution of 1-fluoro-2-nitrobenzene (3.20 g, 22.69 mmol) in Ethanol (40 mL). The reaction mixture was stirred at reflux for 4 h and cooled to rt. LCMS indicated the reaction was completed. The ethanol was removed under vacuum and the resulting aqueous phase was diluted with water (50 ml), washed with ether (2×100 ml), (discarded the ether phase LCMS showed minor product). The aqueous was acidified to pH 4 with 1N aqueous HCl and extracted with DCM (2×300 mL). The organic layers were combined, washed with brine, dried over Na$_2$SO$_4$ and concentrated in vacuo to afford the title compound as yellow solid (R)-2-((tert-butoxycarbonyl)amino)-3-((2-nitrophenyl)thio)propanoic acid (7 g, 20.4 mmol, 90% yield). MS (m/z) 343 (M+H$^+$).

Preparation 14

(R)-3-((2-aminophenyl)thio)-2-((tert-butoxycarbonyl)amino)propanoic acid

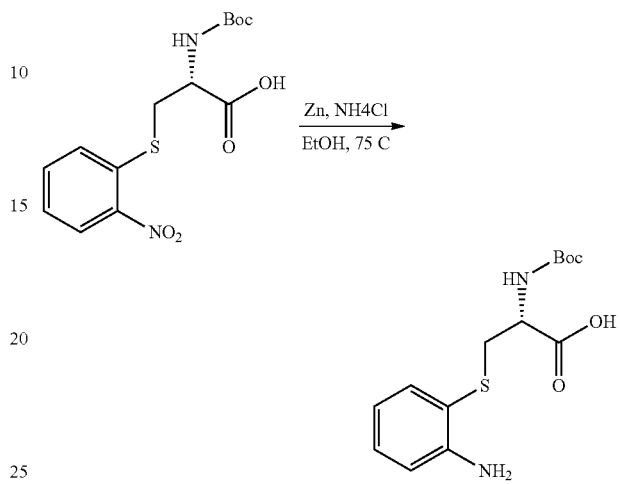

To a solution of (R)-2-((tert-butoxycarbonyl)amino)-3-((2-nitrophenyl)thio)propanoic acid (0.8 g, 2.337 mmol) in MeOH (100 mL) was added ammonium chloride (0.250 g, 4.67 mmol) and zinc (1.528 g, 23.37 mmol) at 25° C. After stirring at rt for 1 h, the mixture was heated to 75 C for 2 h. The resulting mixture was then directly filtered through celite and celite was washed with boiling MeOH (2×100 ml). The combined organic were partially concentrated under vacuum (25 ml) and the residue was allowed to stand overnight at rt. Solid salts were eliminated by filtration, then DCM (100 ml) and water (100 ml) was added to the filtrate, the resulting organic phase was washed with water (3×100 ml), dried over Na$_2$SO$_4$ and concentrated in vacuo to afford the title compound as solid (R)-3-((2-aminophenyl)thio)-2-((tert-butoxycarbonyl)amino)propanoic acid (700 mg, 2.241 mmol, 96% yield). MS (m/z) 313 (M+H$^+$).

Preparation 15

(R)-tert-butyl (4-oxo-2,3,4,5-tetrahydrobenzo[b][1,4]thiazepin-3-yl)carbamate

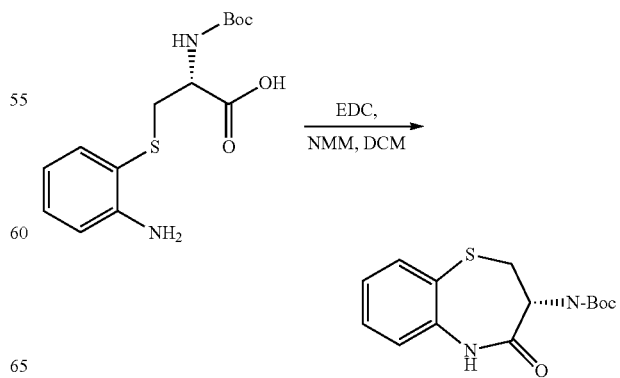

To a solution of (R)-3-((2-aminophenyl)thio)-2-((tert-butoxycarbonyl)amino)propanoic acid (3.3 g, 10.56 mmol) in DCM (100 mL) was added N1-((ethylimino)methylene)-N3,N3-dimethylpropane-1,3-diamine hydrochloride (2.228 g, 11.62 mmol). Stirred at rt for 5 min, then added 4-methylmorpholine (1.742 mL, 15.85 mmol). The reaction mixture was stirred at 25° C. for 5 h. LCMS showed product and the reaction was completed. Removed all the DCM and added 200 ml of EtOAc and the mixture was washed with water, 0.1N HCl(aq), NaHCO$_{3(aq)}$ and brine. The organic phase was dried over Na$_2$SO$_4$ and concentrated under reduced pressure to afford crude product. ISCO purification (eluting with 0-70% of EtOAc in hexane) to afford the pure title compound as (R)-tert-butyl (4-oxo-2,3,4,5-tetrahydrobenzo[b][1,4]thiazepin-3-yl)carbamate (1.5 g, 5.10 mmol, 48.2% yield). 1H NMR (400 MHz, CDCl$_3$) δ=7.73-7.57 (m, 1H), 7.39 (td, J=1.4, 7.6 Hz, 2H), 7.27-7.03 (m, 2H), 5.58 (br. s., 1H), 4.49 (dt, J=7.2, 11.8 Hz, 1H), 3.85 (dd, J=6.7, 11.0 Hz, 1H), 2.95 (t, J=11.4 Hz, 1H), 1.42 (s, 9H). MS (m/z) 295 (M+H$^+$).

Preparation 16

(R)-3-amino-2,3-dihydrobenzo[b][1,4]thiazepin-4(5H)-one, Hydrochloride

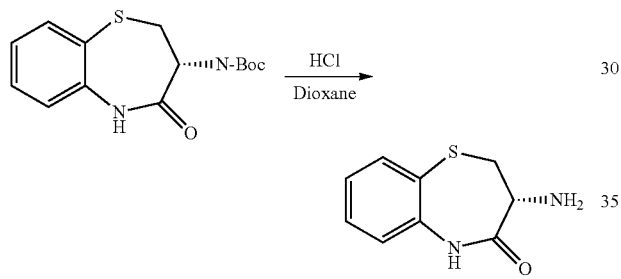

To a solution of (R)-tert-butyl (4-oxo-2,3,4,5-tetrahydrobenzo[b][1,4]thiazepin-3-yl)carbamate (100 mg, 0.340 mmol) in dioxane (3 mL) was added HCl (0.425 mL, 1.699 mmol, 4M in dioxane). The reaction mixture was stirred at 25° C. for 18 h. LCMS indicated the product w/o starting material. Removed all the solvents and washed the solid with ether and the solid was used without further purification. MS (m/z) 195 (M+H$^+$).

The following intermediates used for the preparation of titled example compounds was synthesized using methods analogous to the ones described above.

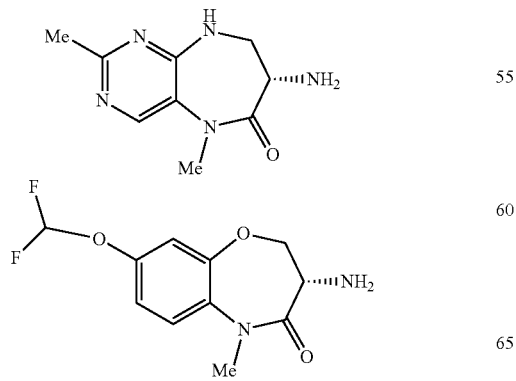

-continued

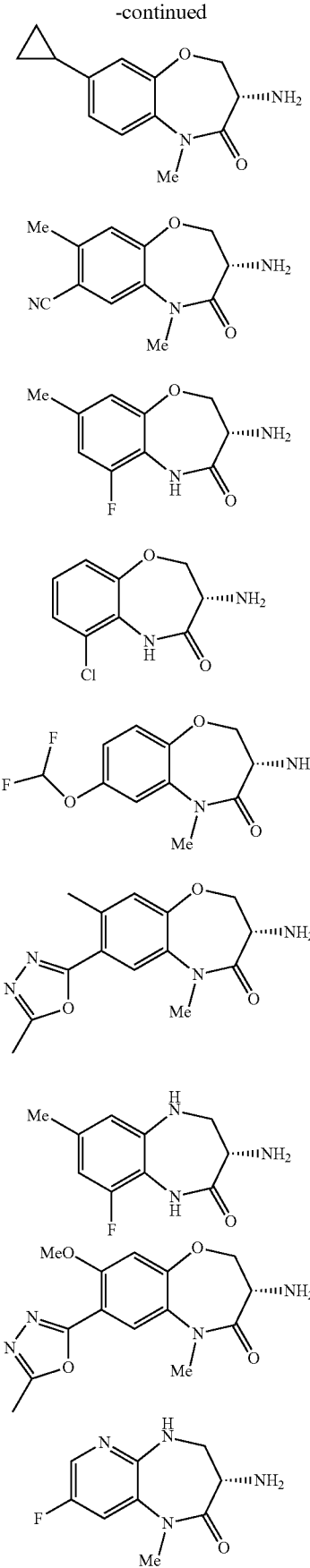

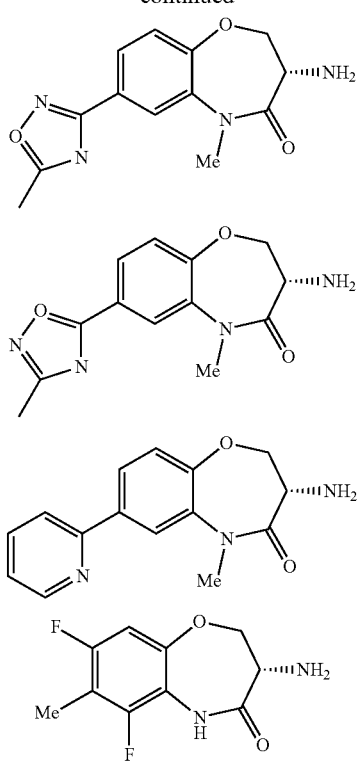

Preparation 17

(R)-tert-butyl (5-methyl-4-oxo-2,3,4,5-tetrahydrobenzo[b][1,4]thiazepin-3-yl)carbamate

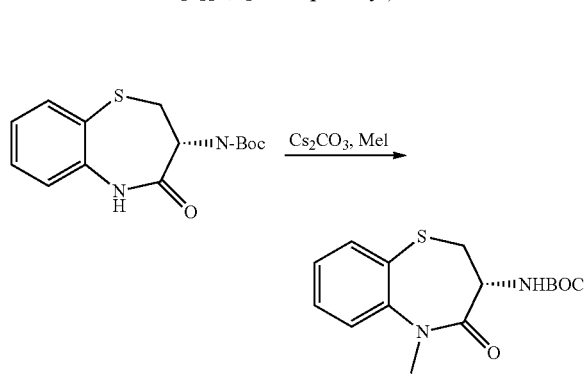

To a solution of (R)-tert-butyl (4-oxo-2,3,4,5-tetrahydrobenzo[b][1,4]thiazepin-3-yl)carbamate (200 mg, 0.679 mmol) in N,N-Dimethylformamide (DMF) (5 mL) was added Cs2CO3 (332 mg, 1.019 mmol) The reaction mixture was stirred at rt for 5 min, then MeI (0.051 mL, 0.815 mmol) was added. The reaction mixture was stirred at rt for 3 h and LCMS showed the reaction was completed. Added EtOAc and washed with water, brine and dried over Na$_2$SO$_4$. Removed all the solvent to afford the title compound as (R)-tert-butyl (5-methyl-4-oxo-2,3,4,5-tetrahydrobenzo[b][1,4]thiazepin-3-yl)carbamate (200 mg, 0.649 mmol, 95% yield). MS (m/z) 309 (M+H$^+$).

Preparation 18

(R)-3-amino-5-methyl-2,3-dihydrobenzo[b][1,4]thiazepin-4(5H)-one hydrochloride

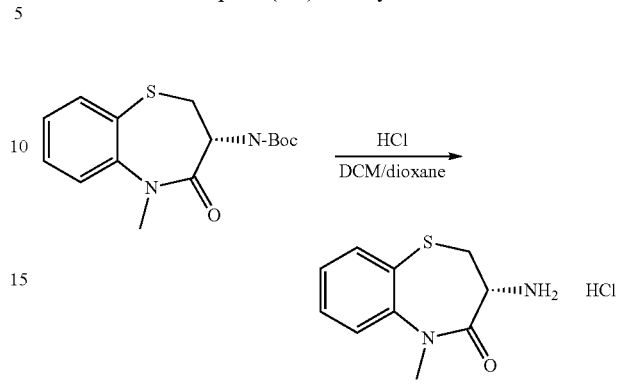

To a solution of (R)-tert-butyl (5-methyl-4-oxo-2,3,4,5-tetrahydrobenzo[b][1,4]thiazepin-3-yl)carbamate (290 mg, 0.940 mmol) in DCM (3 mL) was added HCl (7.05 mL, 28.2 mmol, 4M in dioxane). The reaction mixture was stirred at 25° C. for 3 h. LCMS indicated the product w/o starting material. Removed all the solvents and the solid (200 mg, 87%) was washed with ether and hexane and used without further purification. MS (m/z) 209 (M+H$^+$).

Preparation 19

(S)-3-((tert-butoxycarbonyl)amino)-5-methyl-4-oxo-2,3,4,5-tetrahydrobenzo[b][1,4]oxazepine-7-carboxylic acid

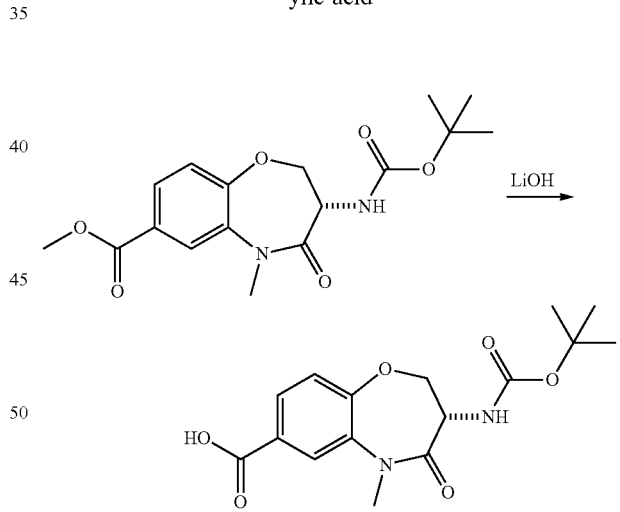

To a solution of ester (500.0 mg, 1.427 mmol) in THF (16 mL)/Water (5 mL) was added LiOH (2.141 mL, 2.141 mmol) as a solution in water (1.0 mL). After 3 h, the reaction mixture was poured into cold water (70 mL) then extracted twice with EtOAc. The aqueous phase was acidified to pH-3 then extracted with EtOAc twice to extract the desired product. The organic phase was dried over Na$_2$SO$_4$, filtered, then concentrated in vacuo. The solid was azeotroped twice with toluene then concentrated to a final solid that was sufficiently pure to use in the next step. No further purification appeared necessary. Yield: 456 mg (90%) white solid. MS (m/z) 337.3 (M+H$^+$).

Preparation 20

(S)-tert-butyl (7-(hydrazinecarbonyl)-5-methyl-4-oxo-2,3,4,5-tetrahydro benzo[b][1,4]xazepin-3-yl)carbamate

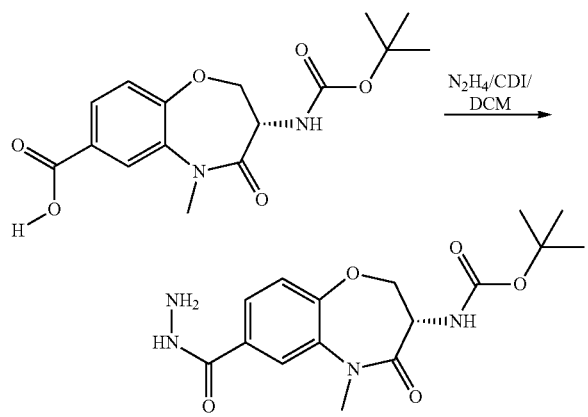

To a suspension of (S)-3-((tert-butoxycarbonyl)amino)-5-methyl-4-oxo-2,3,4,5-tetrahydrobenzo[b][1,4]oxazepine-7-carboxylic acid (228 mg, 0.678 mmol) in dry DCM (5.5 ml) was added CDI (115 mg, 0.712 mmol) as a solid. The reaction mixture was stirred at rt for 1 h 30 min then this mixture was added slowly dropwise to a separate stirring solution of anhydrous hydrazine (217 mg, 6.78 mmol) in 3.0 mL of dry DCM at rt. After 1 h, the reaction mixture was diluted with DCM then washed with water and brine. After drying the sample over Na$_2$SO$_4$ and concentration, the solid product had sufficient purity to carry to the next step, (164 mg, 69%). $^1$H NMR (DMSO-d$_6$) δ: 9.84 (s, 1H), 7.88 (d, J=2.0 Hz, 1H), 7.71 (dd, J=8.3, 2.0 Hz, 1H), 7.26 (d, J=8.3 Hz, 1H), 7.21 (d, J=7.8 Hz, 1H), 4.55 (br. s., 1H), 4.30-4.41 (m, 4H), 3.31 (s, 3H), 1.34 (s, 9H). MS (m/z) 351.3 (M+H$^+$).

Preparation 21

(S)-tert-butyl (5-methyl-4-oxo-7-(5-oxo-4,5-dihydro-1,3,4-oxadiazol-2-yl)-2,3,4,5-tetrahydrobenzo[b][1,4]oxazepin-3-yl)carbamate

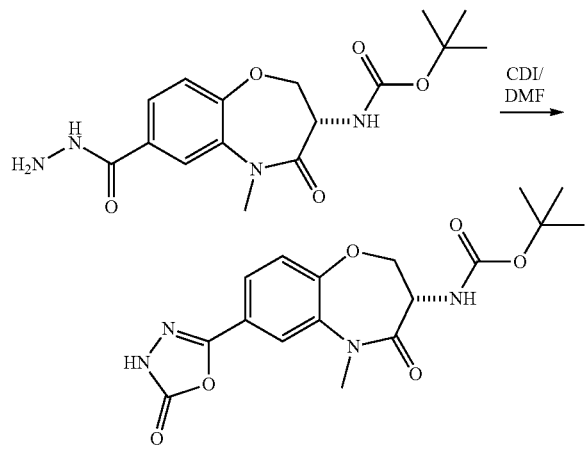

To a solution of (S)-tert-butyl (7-(hydrazinecarbonyl)-5-methyl-4-oxo-2,3,4,5-tetrahydro benzo[b][1,4]xazepin-3-yl)carbamate (191.0 mg, 0.545 mmol) in N,N-Dimethylformamide (DMF) (3.0 mL) was added TEA (0.114 mL, 0.818 mmol) followed by CDI (97 mg, 0.600 mmol). The mixture was stirred at rt. The reaction mixture was diluted with EtOAc then washed with cold dilute HCl, water (2×), and brine. The organic phase was dried over Na$_2$SO$_4$, filtered, then concentrated in vacuo. The residue was washed with small amount of DCM then filtered and collected as a white powder then used in the next step without further purification (150.0 mg, 80%). $^1$H NMR (DMSO-d$_6$) δ: 12.67 (br. s., 1H), 7.83 (d, J=2.0 Hz, 1H), 7.68 (dd, J=8.3, 2.0 Hz, 1H), 7.35 (d, J=8.3 Hz, 1H), 7.23 (d, J=7.8 Hz, 1H), 4.32-4.45 (m, 3H), 1.35 (s, 9H). MS (m/z) 377.3 (M+H$^+$).

Preparation 22

(S)-3-amino-5-methyl-7-(5-oxo-4,5-dihydro-1,3,4-oxadiazol-2-yl)-2,3-dihydrobenzo[b][1,4]oxazepin-4(5H)-one, Hydrochloride

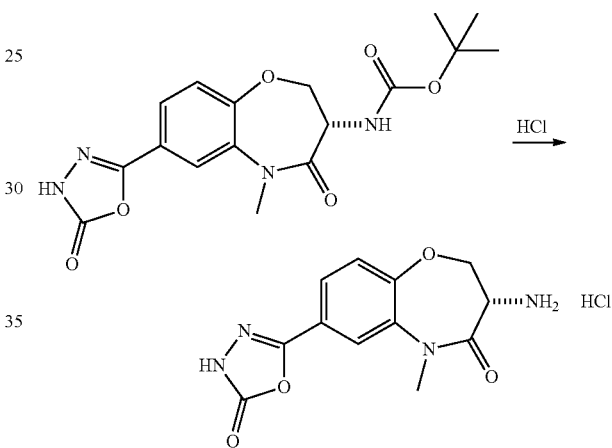

To a solution of (S)-tert-butyl (5-methyl-4-oxo-7-(5-oxo-4,5-dihydro-1,3,4-oxadiazol-2-yl)-2,3,4,5-tetrahydrobenzo[b][1,4]oxazepin-3-yl)carbamate (40.0 mg, 0.106 mmol) in DCM (1.0 mL) was added a solution of 4M HCl in 1,4 dioxane (0.531 mL, 2.126 mmol). The mixture was stirred at rt for 1 h. The reaction mixture was concentrated in vacuo, then it was azeotroped twice with toluene to yield the desired product. MS (m/z) 277.1 (M+H$^+$).

Preparation 23

(S)-3-(5-benzylisoxazole-3-carboxamido)-5-methyl-4-oxo-2,3,4,5-tetrahydro benzo[b][1,4]oxazepine-7-carboxylic acid

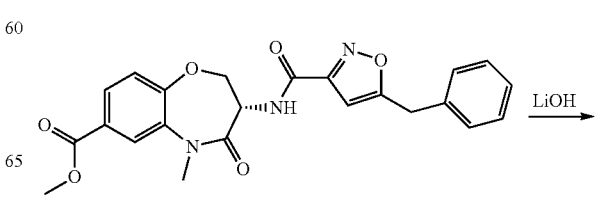

-continued

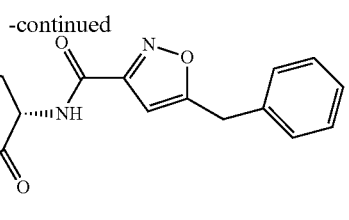

To a solution of (S)-methyl 3-(5-benzylisoxazole-3-carboxamido)-5-methyl-4-oxo-2,3,4,5-tetrahydrobenzo[b][1,4]oxazepine-7-carboxylate (332 mg, 0.762 mmol) in THF (6 mL)/Water (2.0 mL) was added LiOH (1.144 mL, 1.144 mmol) as a solution in water. Reaction was stirred at rt for about 2 h. The reaction mixture was diluted with water then extracted with EtOAc twice. The aqueous phase was acidified to pH-3.0 then it was extracted with EtOAc. The latter organic phase was dried over $Na_2SO_4$ then filtered and concentrated in vacuo to yield the desired product as a solid. The solid was warmed in toluene then decanted to give the final solid product that was used directly in the next step. $^1$H NMR (DMSO-$d_6$) δ: 13.18 (br. s., 1H), 8.87 (d, J=8.1 Hz, 1H), 7.98 (d, J=2.0 Hz, 1H), 7.85 (dd, J=8.3, 2.0 Hz, 1H), 7.25-7.38 (m, 6H), 6.55 (s, 1H), 4.87 (dt, J=11.8, 7.7 Hz, 1H), 4.64 (dd, J=11.6, 10.1 Hz, 1H), 4.46 (dd, J=9.9, 7.6 Hz, 1H), 4.22 (s, 2H). MS (m/z) 422.3 (M+H$^+$).

Preparation 24

(S)-5-benzyl-N-(7-(hydrazinecarbonyl)-5-methyl-4-oxo-2,3,4,5-tetrahydrobenzo [b][1,4]oxazepin-3-yl) isoxazole-3-carboxamide

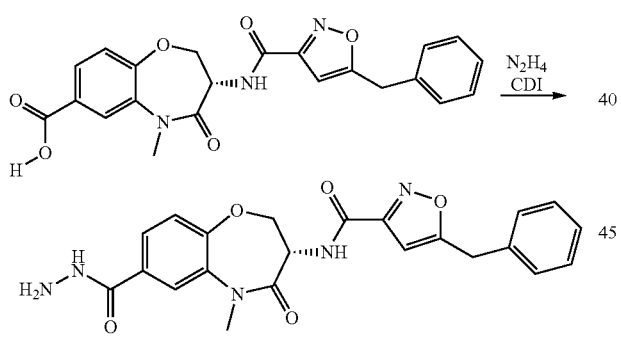

To a suspension of (S)-3-(5-benzylisoxazole-3-carboxamido)-5-methyl-4-oxo-2,3,4,5-tetrahydro benzo[b][1,4]oxazepine-7-carboxylic acid (178.0 mg, 0.422 mmol) in DCM (6.0 mL) was added CDI (75 mg, 0.465 mmol). The reaction mixture was stirred at rt for 1 h 30 min. The mixture was then added slowly dropwise to a solution of hydrazine (0.199 mL, 6.34 mmol) in 0.50 mL DCM. After 1 h LCMS indicated about 79% conversion to the desired product. The reaction mixture was diluted with DCM then washed with water and brine. After drying the sample over $Na_2SO_4$ and concentration, the solid product had sufficient purity to carry to next step. $^1$H NMR (DMSO-$d_6$) δ: 9.86 (s, 1H), 8.90 (d, J=8.1 Hz, 1H), 7.91 (d, J=2.3 Hz, 1H), 7.73 (dd, J=8.3, 2.0 Hz, 1H), 7.27-7.38 (m, 6H), 6.55 (s, 1H), 4.85 (dt, J=11.8, 7.9 Hz, 1H), 4.62 (dd, J=11.6, 10.1 Hz, 1H), 4.54 (br. s., 2H), 4.44 (dd, J=9.9, 7.8 Hz, 1H), 4.22 (s, 2H), 3.33 (s, 3H). MS (m/z) 436.2 (M+H$^+$).

Preparation 25

(S)-5-benzyl-N-(7-(hydrazinecarbonyl)-5-methyl-4-oxo-2,3,4, 5-tetrahydrobenzo[b][1,4]oxazepin-3-yl)-1H-pyrazole-3-carboxamide To a solution of (S)-methyl 3-(5-benzyl-1H-pyrazole-3-carboxamido)-5-methyl-4-oxo-2,3,4,5-tetrahydrobenzo[b][1,4]oxazepine-7-carboxylate (191.0 mg, 0.440 mmol) in MeOH (5.0 mL) was added hydrazine monohydrate (0.058 mL, 1.199 mmol) as a solution in MeOH (1.0 mL). The reaction mixture was refluxed overnight then it was diluted with EtOAc and partitioned with water. The organic phase was dried over $Na_2SO_4$, filtered, then concentrated in vacuo. The residue was purified by FCC (MeOH-DCM: 0-7.0%]) to yield the desired the product (119.0 mg, 62.3%). $^1$H NMR (DMSO-$d_6$) δ: 13.22 (s, 1H), 9.85 (s, 1H), 8.09 (d, J=8.1 Hz, 1H), 7.90 (d, J=2.0 Hz, 1H), 7.73 (dd, J=8.3, 2.0 Hz, 1H), 7.18-7.34 (m, 6H), 6.37 (d, J=1.5 Hz, 1H), 4.84 (dt, J=11.6, 7.8 Hz, 1H), 4.48-4.62 (m, 3H), 4.36-4.47 (m, 1H), 3.99 (s, 2H). MS (m/z) 435.2 (M+H$^+$).

Preparation 26

(S)-tert-butyl (7-((2-cyanoethyl)carbamoyl)-5-methyl-4-oxo-2,3,4,5-tetra hydro benzo[b][1,4]oxazepin-3-yl)carbamate

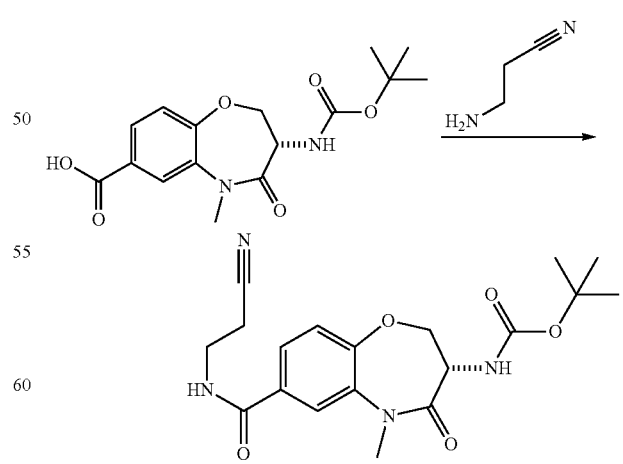

To a suspension of (S)-3-((tert-butoxycarbonyl)amino)-5-methyl-4-oxo-2,3,4,5-tetra-hydrobenzo[b][1,4]oxazepine-7-carboxylic acid (185.0 mg, 0.550 mmol) in DCM (5.0 mL)

was added 1-chloro-N,N,2-trimethylprop-1-en-1-amine (88 mg, 0.660 mmol) as a solution in DCM (0.10 ml) dropwise over 1 min. The reaction mixture was stirred at rt for 1 h and became a homogeneous solution. The reaction mixture was cooled in an ice-bath then 3-aminopropanenitrile (154 mg, 2.200 mmol) was added dropwise as a solution in DCM (0.25 mL). After 10 min, the ice-bath was removed then 10% aq citric acid solution was added and the mixture was stirred vigorously for 15 min. The organic phase was separated, washed with sat. aq sodium bicarbonate, brine then dried over $Na_2SO_4$ and concentrated in vacuo. The residue was purified by FCC [EtOAc-Hex: 45-80%] to yield the desired product (190.0 mg, 89%). MS (m/z) 389.3 (M+H$^+$).

Preparation 27

(S)-tert-butyl (7-(1-(2-cyanoethyl)-1H-tetrazol-5-yl)-5-methyl-4-oxo-2,3,4,5-tetrahydrobenzo[b][1,4]oxazepin-3-yl)carbamate

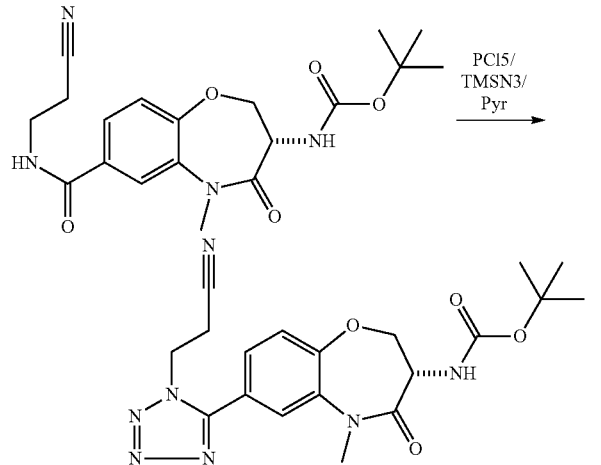

To a solution of (S)-tert-butyl (7-((2-cyanoethyl)carbamoyl)-5-methyl-4-oxo-2,3,4,5-tetra hydro benzo[b][1,4]oxazepin-3-yl)carbamate (188.0 mg, 0.484 mmol) and pyridine (0.243 mL, 3.00 mmol) in DCM (2.0 mL) was added phosphorus pentachloride (161 mg, 0.774 mmol). The reaction mixture was heated to reflux for 3.0 h. The reaction mixture was cooled to rt then TMSN$_3$ (0.257 mL, 1.936 mmol) was added and the reaction mixture was stirred overnight. At 20 h, 5.0 eq of TMS-N$_3$ followed by 3.0 eq pyridine was added. The reaction mixture was warmed in an oil bath at 45 deg C. for ~4 h. The reaction mixture was carefully quenched with a few drops of sat. aq. NaHCO$_3$ initially, then after 5 min excess NaHCO$_3$ was added and the mixture was stirred for 15 min. The organic phase was separated and washed with 10% aq citric acid and brine. The organic solution was dried over $Na_2SO_4$, filtered and concentrated in vacuo. The residue was purified by FCC (EtOAc-Hex: 50-70%) to yield the desired product (152.0 mg, 72%). $^1$H NMR (DMSO-d$_6$) δ: 7.87 (d, J=2.0 Hz, 1H), 7.68 (dd, J=8.2, 2.1 Hz, 1H), 7.44 (d, J=8.3 Hz, 1H), 7.21 (d, J=8.6 Hz, 1H), 4.73-4.87 (m, 2H), 4.35-4.54 (m, 3H), 3.24 (t, J=6.3 Hz, 2H), 1.36 (s, 9H). MS (m/z) 414.3 (M+H$^+$).

Preparation 28

(S)-3-(5-(3-amino-5-methyl-4-oxo-2,3,4,5-tetrahydrobenzo[b][1,4]oxazepin-7-yl)-1H-tetrazol-1-yl)propanenitrile, Trifluoroacetic acid salt

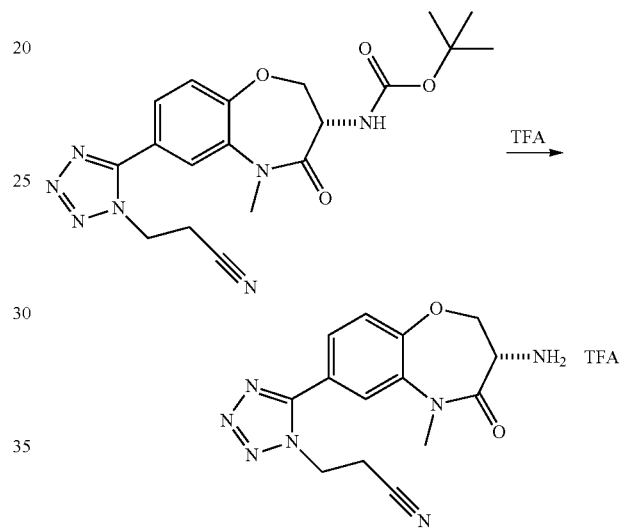

To a solution of (S)-tert-butyl (7-(1-(2-cyanoethyl)-1H-tetrazol-5-yl)-5-methyl-4-oxo-2,3,4,5-tetrahydrobenzo[b][1,4]oxazepin-3-yl)carbamate (152 mg, 0.368 mmol) in DCM (1.0 mL) was added TFA (0.50 mL, 6.49 mmol). The mixture was stirred at rt for 1 h then the reaction mixture was concentrated in vacuo to a residue that was azeotroped with toluene to yield solid product that was used directly in the next step (149.0 mg, 95%). MS (m/z) 314.2 (M+H$^+$).

Preparation 29

(S)-3-(5-benzylisoxazole-3-carboxamido)-N-(2-cyanoethyl)-5-methyl-4-oxo-2,3,4,5-tetrahydrobenzo[b][1,4]oxazepine-7-carboxamide

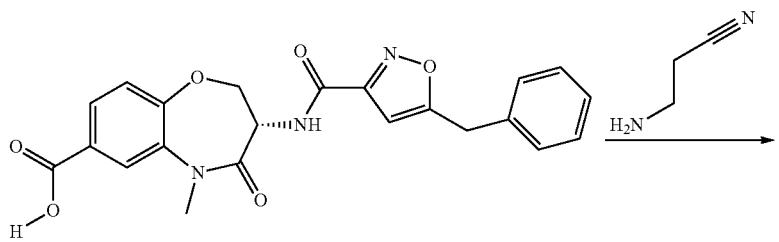

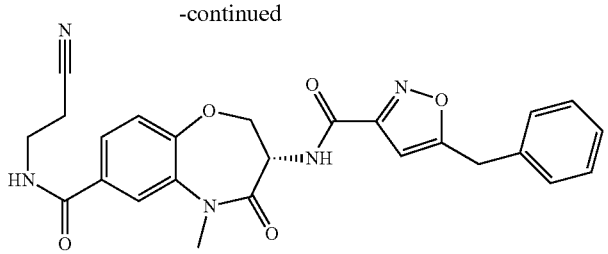

To a suspension of (S)-3-(5-benzylisoxazole-3-carboxamido)-5-methyl-4-oxo-2,3,4,5-tetrahydrobenzo[b][1,4]oxazepine-7-carboxylic acid (87.0 mg, 0.206 mmol) in DCM (2.0 mL) was added 1-chloro-N,N,2-trimethylprop-1-en-1-amine (33.1 mg, 0.248 mmol) as a solution in DCM (0.10 ml) dropwise over 1 min. The reaction mixture was stirred at rt for 1 h and became a homogeneous solution. The reaction mixture was cooled in an ice-bath then 3-aminopropanenitrile (57.9 mg, 0.826 mmol) was added dropwise as a solution in DCM (0.25 mL). The ice-bath was removed then 10% aq citric acid solution was added and the mixture was stirred vigorously for 15 min. The organic phase was separated, washed with sat. aq sodium bicarbonate and brine then dried over sodium sulfate and concentrated in vacuo. The residue was purified by FCC (EtOAc-Hex: 60-80%) to yield the desired product (67.0 mg, 68.5%). MS (m/z) 474.4 (M+H$^+$).

Preparation 30

(S)-tert-butyl (5-methyl-7-(N,N-dimethylcarbamoyl)-4-oxo-2,3,4,5-tetrahydrobenzo[b][1,4]oxazepin-3-yl)carbamate

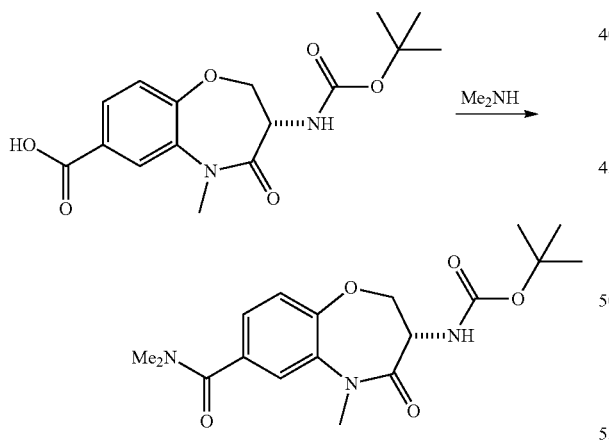

To a solution of (S)-3-((tert-butoxycarbonyl)amino)-5-methyl-4-oxo-2,3,4,5-tetrahydrobenzo[b][1,4]oxazepine-7-carboxylic acid (100.0 mg, 0.297 mmol DMSO (2.0 mL) was added DIEA (0.109 mL, 0.624 mmol) then HATU (113 mg, 0.297 mmol). After 5 min dimethylamine (0.156 mL, 0.312 mmol was added and the reaction mixture was stirred at rt. The reaction mixture was diluted with EtOAc then washed with sat. aq. NH4Cl, water and brine. The organic phase was dried over Na$_2$SO$_4$, filtered and concentrated in vacuo, The residue was purified by FCC [EtOAc-Hex: 15-50%] to yield the desired product (44.0 mg, 40.7%). $^1$H NMR (DMSO-d$_6$) δ: 7.53 (d, J=1.8 Hz, 1H), 7.27-7.31 (m, 1H), 7.21-7.25 (m, 1H), 7.18 (d, J=8.1 Hz, 1H), 4.27-4.44 (m, 3H), 3.29 (s, 3H), 2.99 (br. s, 6H), 1.35 (s, 9H). MS (m/z) 364.0 (M+H$^+$).

The following intermediates used for the preparation of titled example compounds were synthesized using methods analogous to the ones described above.

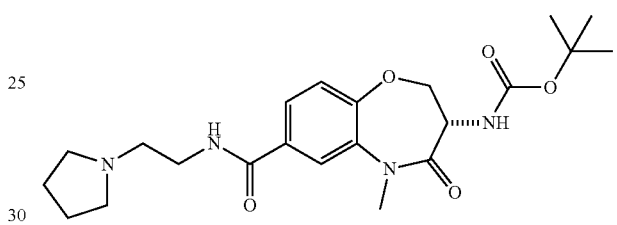

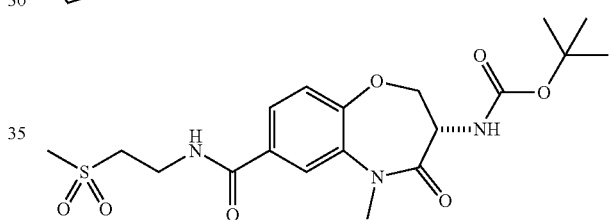

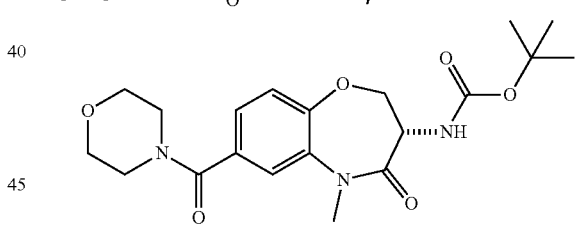

Preparation 31

(S)-3-amino-N,N, 5-trimethyl-4-oxo-2,3,4,5-tetrahydrobenzo[b][1,4]oxazepine-7-carboxamide trifluoroacetate

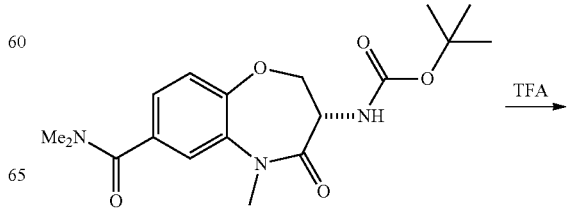

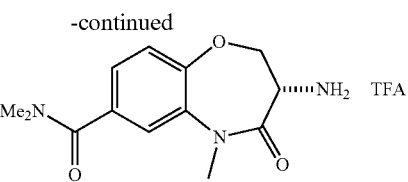

To a suspension of (S)-tert-butyl (5-methyl-7-(N,N-dimethylcarbamoyl)-4-oxo-2,3,4,5-tetrahydrobenzo[b][1,4]oxazepin-3-yl)carbamate (46.0 mg, 0.113 mmol) in DCM (1.5 mL) was added TFA (0.175 mL, 2.269 mmol). The reaction mixture was stirred for 4 h at rt and found to be complete by LC/MS. The reaction mixture was concentrated in vacuo then azeotroped with toluene twice. The residue was used without further purification and used directly in the next step. MS (m/z) 264.0 (M+H$^+$).

The following intermediates used for the preparation of titled example compounds were synthesized using methods analogous to the ones described above.

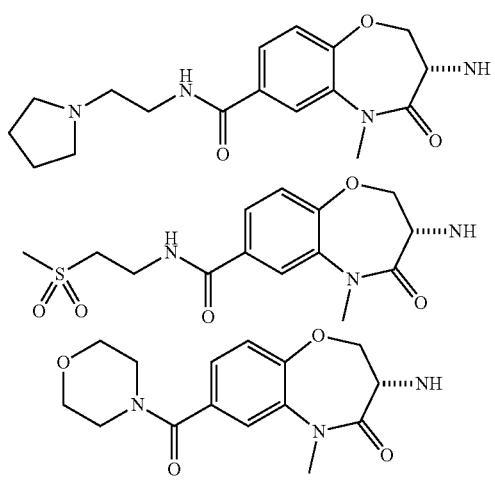

Preparation 32

(S)-di-tert-butyl (5-methyl-4-oxo-2,3,4,5-tetrahydrobenzo[b][1,4]oxazepine-3,7-diyl)dicarbamate

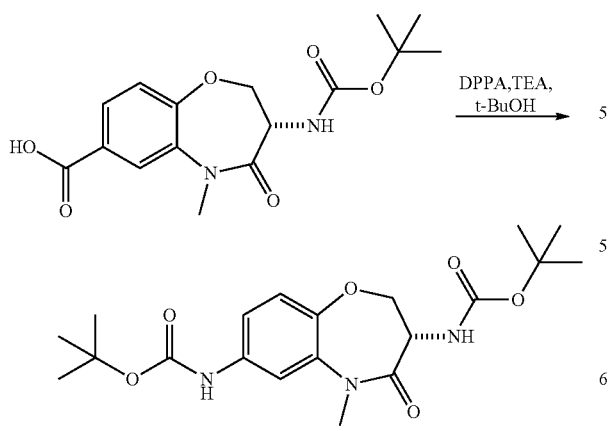

A mixture of (S)-3-((tert-butoxycarbonyl)amino)-5-methyl-4-oxo-2,3,4,5-tetrahydro benzo[b][1,4]oxazepine-7-carboxylic acid (78.0 mg, 0.232 mmol), diphenylphosphorylazide (DPPA) (0.070 mL, 0.325 mmol), TEA (0.091 mL, 0.649 mmol), and tBuOH (0.439 mL, 4.59 mmol) in toluene were first heated to 70 deg C. for 30 min then to 100 deg C. for overnight. After 20 min some desired product was observed; the reaction mixture was left overnight and appeared to be complete. The solvent was removed in vacuo then the residue was purified by FCC [E/H 25%]. (No work-up was needed and the sample was well purified by column.); $^1$H NMR (DMSO-d$_6$) δ: 9.47 (br. s., 1H), 7.54 (d, J=1.5 Hz, 1H), 7.25 (dd, J=8.5, 1.9 Hz, 1H), 7.15 (d, J=8.8 Hz, 1H), 7.07 (d, J=8.6 Hz, 1H), 4.30-4.39 (m, 1H), 4.20-4.26 (m, 2H), 3.23 (s, 3H), 1.48 (s, 9H), 1.35 (s, 9H). MS (m/z) 408.3 (M+H$^+$).

Preparation 33

(S)-3,7-diamino-5-methyl-2,3-dihydrobenzo[b][1,4]oxazepin-4(5H)-one

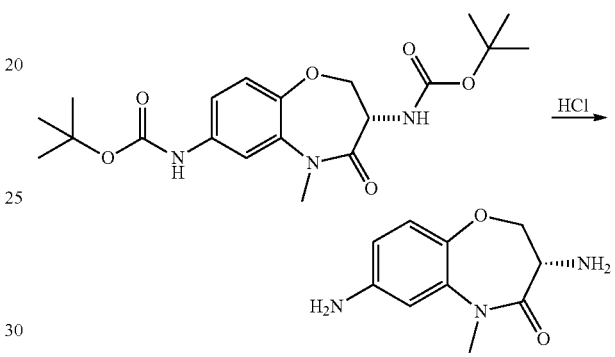

To a suspension of (S)-di-tert-butyl (5-methyl-4-oxo-2,3,4,5-tetrahydrobenzo[b][1,4]oxazepine-3,7-diyl)dicarbamate (75.0 mg, 0.184 mmol) in DCM (1.5 mL) was added HCl (0.782 mL, 3.13 mmol). The reaction mixture was stirred overnight at rt. The solvent was evaporated, then the residue was azeotroped with toluene to obtain a solid residue that was used in the next step without further purification; quantitative yield was assumed. MS (m/z) 208.1 (M+H$^+$).

Preparation 34

(S)—N-(7-amino-5-methyl-4-oxo-2,3,4,5-tetrahydrobenzo[b][1,4]oxazepin-3-yl)-5-benzylisoxazole-3-carboxamide

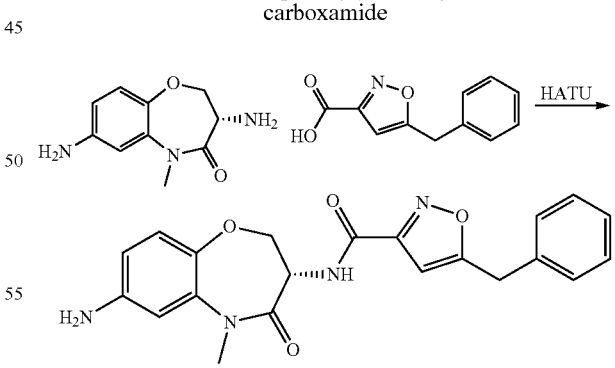

A solution of 5-benzylisoxazole-3-carboxylic acid (37.4 mg, 0.184 mmol) and HATU (77 mg, 0.202 mmol) in acetonitrile (2.5 mL) (1 mL) was stirred for 1 h. This mixture was added slowly to a second mixture of mixture of (9.0 eq)N-methylmorpholine (0.182 mL, 1.656 mmol) and (S)-3,7-diamino-5-methyl-2,3-dihydrobenzo[b][1,4]oxazepin-4 (5H)-one, 2 hydrochloride (51.5 mg, 0.184 mmol). LCMS showed predominantly one product 70% plus bis-coupled 23%. The reaction mixture was diluted with EtOAc then washed with water and brine. After drying over sodium sulfate, and filtering the sample was concentrated in vacuo and purified by FCC [EtOAc-Hex: 20-60%]. $^1$H NMR (DMSO-d$_6$) δ: 8.78 (d, J=8.3 Hz, 1H), 7.27-7.39 (m, 5H), 6.87 (d, J=8.3 Hz, 1H), 6.58 (d, J=2.8 Hz, 1H), 6.55 (s, 1H), 6.43 (dd, J=8.6, 2.5 Hz, 1H), 5.16 (s, 2H), 4.77-4.87 (m, 1H), 4.36-4.44 (m, 1H), 4.20-4.27 (m, 3H), 3.22 (s, 3H). MS (m/z) 393.2 (M+H$^+$).

Preparation 35

(S)-tert-butyl (3-((tert-butoxycarbonyl)amino)-5-methyl-4-oxo-2,3,4,5-tetrahydrobenzo[b][1,4]oxazepin-7-yl)(methyl)carbamate

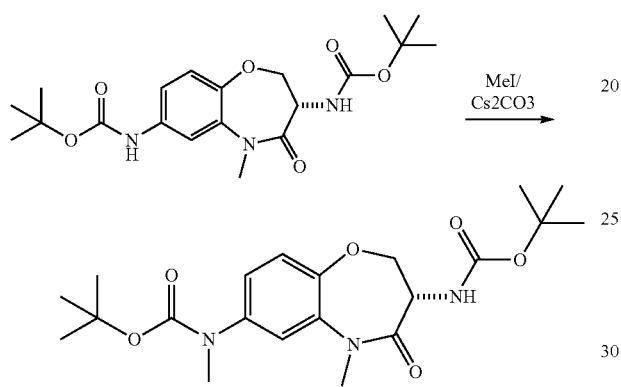

To a suspension of (S)-di-tert-butyl (5-methyl-4-oxo-2,3,4,5-tetrahydrobenzo[b][1,4]oxazepine-3,7-diyl)dicarbamate (60.0 mg, 0.147 mmol) DMF (1.0 mL) was added Cs$_2$CO$_3$ (48.0 mg, 0.147 mmol) then MeI (9.21 μL, 0.147 mmol). The reaction mixture was combined with a second batch reaction of 40 mg scale and both were processed together. The reaction mixture was diluted with EtOAc then washed successively with water and brine. The organic phase was dried over Na$_2$SO$_4$ and filtered. The concentrated residue was purified by FCC (EtOAc-Hex: 15-35%) to yield an 86.0 mg mixture of desired product with some starting material (7:3 by LC/MS) that was used in the next step. MS (m/z) 422.4 (M+H$^+$).

Preparation 36

(S)-3-amino-5-methyl-7-(methyl-amino)-2,3-dihydrobenzo[b][1,4]oxazepin-4(5H)-one

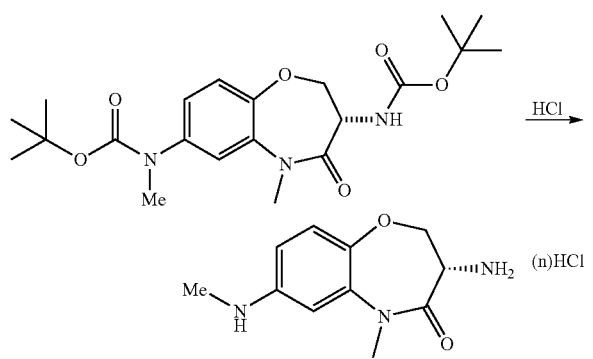

To a mixture of (S)-tert-butyl (3-((tert-butoxycarbonyl)amino)-5-methyl-4-oxo-2,3,4,5-tetrahydrobenzo[b][1,4]ox-azepin-7-yl)(methyl)carbamate from previous step (86.0 mg, 0.204 mmol) in DCM (3.0 ml) was added HCl (1.020 mL, 4.08 mmol) as a 4 M HCl solution in 1,4 dioxane. The reaction mixture was stirred at rt overnight then additional 0.5 mL of 4M HCl in 1,4 dioxane was added and stirring was continued 1 h. The reaction mixture was concentrated in vacuo, then azeotroped with toluene to yield residual solid having the desired product that was used directly in the next step. MS (m/z) 222.1 (M+H$^+$).

Preparation 37

(S)-3-((5-Amino-6-chloropyrimidin-4-yl)amino)-2-((tert-butoxycarbonyl)amino)propanoic Acid

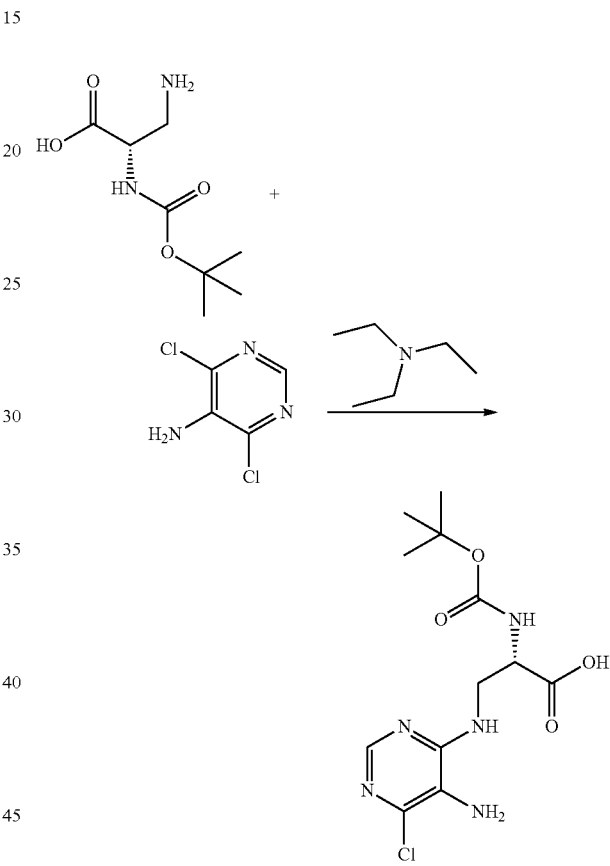

To a suspension of 4,6-dichloropyrimidin-5-amine (0.402 g, 2.448 mmol) and triethylamine (0.751 mL, 5.39 mmol) in BuOH (10 mL) was added (S)-3-amino-2-((tert-butoxycarbonyl)amino)propanoic acid (0.5 g, 2.448 mmol) at rt. The reaction mixture was heated at 90° C. After heating for 1 hr, another 10 mL of BuOH and EtOH (15 mL) were added to the reaction mixture. After heating for 2 days (Note: still some starting material remained), the reaction mixture was concentrated, then diluted with water and EtOAc.

After separation, the aqueous solution was extracted with EtOAc (×2), and then the aqueous solution was acidified with 1N HCl (pH around 3). After extraction with EtOAc (×3), the combined organic solution was washed with brine, dried over MgSO$_4$. After filtration and evaporation in vacuo, (S)-3-((5-amino-6-chloropyrimidin-4-yl)amino)-2-((tert-butoxycarbonyl)amino)propanoic acid (430 mg, 1.296 mmol, 52.9% yield) was obtained as pale brownish solids, which was used for the next reaction without further purification. MS (m/z) 332.2 (M+H$^+$). $^1$H NMR (DMSO-d$_6$) δ: 12.67 (br. s., 1H), 7.75 (s, 1H), 7.09 (d, J=8.3 Hz, 1H), 6.85-6.91 (m, 1H), 5.05 (s, 2H), 4.24 (td, J=8.0, 5.3 Hz, 1H), 3.71-3.82 (m, 1H), 3.55-3.68 (m, 1H), 1.35-1.41 (m, 9H).

The following intermediates used for the preparation of titled example compounds were synthesized using a method analogous to the ones described above using 4,6-dichloro-2-methylpyrimidin-5-amine and 2-chloro-5-fluoro-3-nitropyridine in DMSO as solvent at 70° C.

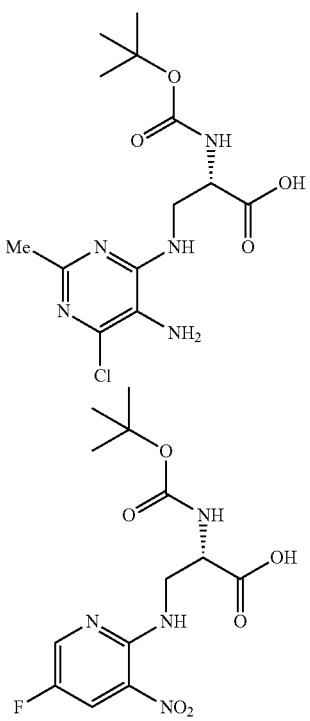

Preparation 38

(S)-tert-butyl (4-chloro-6-oxo-6,7,8,9-tetrahydro-5H-pyrimido[4,5-b][1,4]diazepin-7-yl)carbamate

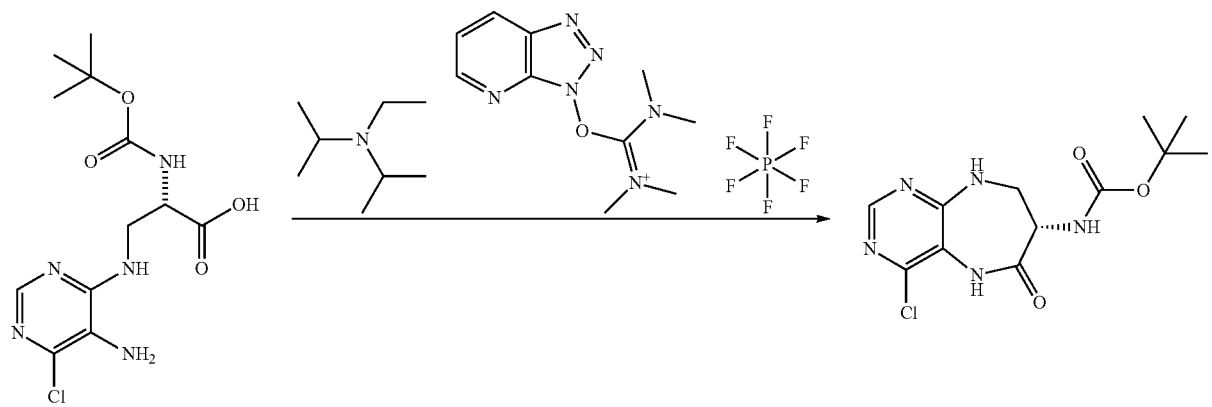

To a solution of (S)-3-((5-amino-6-chloropyrimidin-4-yl)amino)-2-((tert-butoxycarbonyl)amino)propanoic acid (300 mg, 0.904 mmol) and HATU (378 mg, 0.995 mmol) in DMSO (4.0 mL) was added DIEA (0.237 mL, 1.356 mmol) at rt. After 5 hr at rt, another 378 mg of HATU and 0.24 mL of DIEA were added. After stirring for overnight at rt, water was added, then extracted with EtOAc (×3). The combined organic solution was washed with brine, and dried over MgSO$_4$. After filtration and evaporation in vacuo, the crude material was purified by silica gel column chromatography (Biotage, 25 g cartridge, 10% to 60% EtOAc in hexane) to give (S)-tert-butyl (4-chloro-6-oxo-6,7,8,9-tetrahydro-5H-pyrimido[4,5-b][1,4]diazepin-7-yl)carbamate (125 mg, 0.394 mmol, 43.6% yield) as colorless solid. MS (m/z) 314.2 (M+H$^+$). $^1$H NMR (DMSO-d$_6$) δ: 9.49 (s, 1H), 8.14-8.22 (m, 1H), 8.07 (s, 1H), 6.95 (d, J=7.1 Hz, 1H), 4.23-4.34 (m, 1H), 3.41-3.51 (m, 2H), 1.39 (s, 9H).

Preparation 39

(S)-tert-butyl (6-oxo-6,7,8,9-tetrahydro-5H-pyrimido[4,5-b][1,4]diazepin-7-yl)carbamate

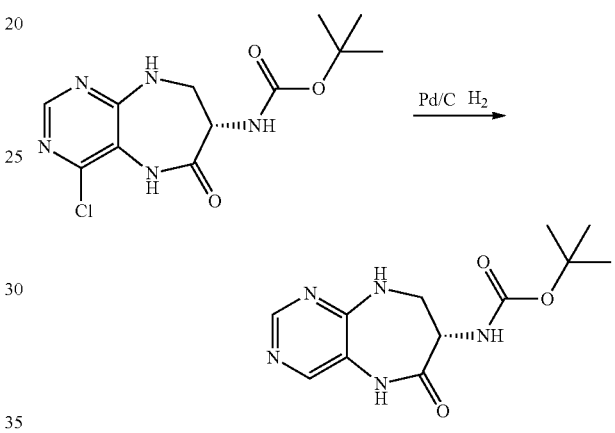

To a suspension of (S)-tert-butyl (4-chloro-6-oxo-6,7,8,9-tetrahydro-5H-pyrimido[4,5-b][1,4]diazepin-7-yl)carbamate (300 mg, 0.956 mmol) in EtOH (5 mL), EtOAc (5.00 mL), and MeOH (7.5 mL) was added Pd/C (153 mg, 0.143 mmol) at rt. The reaction mixture was stirred under H$_2$ balloon for 3 hr. The reaction mixture was filtered and washed with EtOAc and MeOH. The combined filtrate was evaporated in vacuo and the resultant solid (S)-tert-butyl (6-oxo-6,7,8,9-tetrahydro-5H-pyrimido[4,5-b][1,4]diazepin-7-yl)carbamate (260 mg, 0.912 mmol, 95% yield) was used for the next reaction without further purification. MS (m/z) 280.2 (M+H$^+$). $^1$H NMR (DMSO-d$_6$) δ: 10.32 (s, 1H), 9.41 (br. s., 1H), 8.50 (s, 1H), 8.01 (s, 1H), 7.06 (d, J=7.1 Hz, 1H), 4.36-4.50 (m, 1H), 3.53-3.63 (m, 1H), 3.40-3.52 (m, 1H), 1.40 (s, 9H).

The following intermediate used for the preparation of titled example compounds was synthesized from (S)-tert-butyl (4-chloro-2,5-dimethyl-6-oxo-6,7,8,9-tetrahydro-5H-pyrimido[4,5-b][1,4]diazepin-7-yl)carbamate using methods analogous to the ones described above.

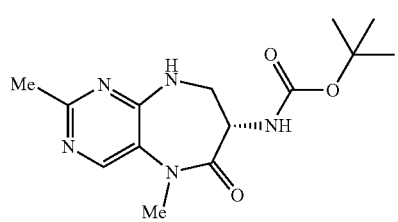 [SMILES: Cc1ncc2c(n1)NC[C@H](NC(=O)OC(C)(C)C)C(=O)N2C]

Preparation 40

(S)-tert-butyl (4-chloro-5-methyl-6-oxo-6,7,8,9-tetrahydro-5H-pyrimido[4,5-b][1,4]diazepin-7-yl)carbamate

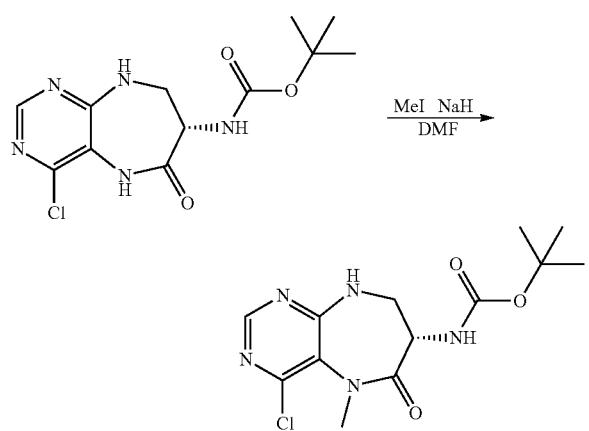

To a solution of (S)-tert-butyl (4-chloro-6-oxo-6,7,8,9-tetrahydro-5H-pyrimido[4,5-b][1,4]diazepin-7-yl)carbamate (0.7 g, 2.231 mmol) in DMF (10 ml) was added NaH (0.094 g, 2.343 mmol) at rt. After 30 min at rt, iodomethane (0.146 ml, 2.343 mmol) was added and stirred for 1 hr 20 min. The addition of water triggered a precipitation. The solid was filtered and washed with water and hexane. The wet solid was collected and dried at 50° C. in a vacuum oven to give (S)-tert-butyl (4-chloro-5-methyl-6-oxo-6,7,8,9-tetrahydro-5H-pyrimido[4,5-b][1,4]diazepin-7-yl)carbamate (620 mg, 1.797 mmol, 81% yield) as a colorless solid, which was used for the next reaction without further purification. MS (m/z) 328.2 (M+H+). 1H NMR (DMSO-d6) δ: 8.18 (s, 1H), 8.09 (br. d, 1H), 7.02 (d, J=7.6 Hz, 1H), 4.38-4.48 (m, 1H), 3.37-3.54 (m, 2H), 3.12 (s, 3H), 1.38 (s, 9H).

The following intermediates used for the preparation of titled example compounds were synthesized using methods analogous to the ones described above.

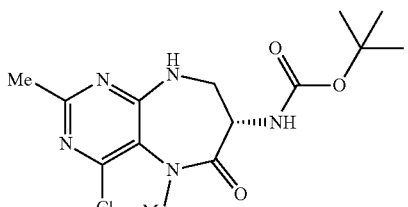

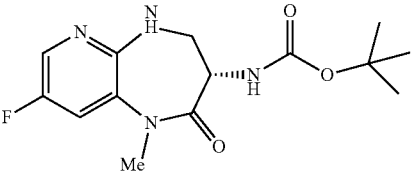

Preparation 41

(S)-tert-butyl (7-bromo-2-oxo-2,3,4,5-tetrahydro-1H-benzo[b]azepin-3-yl)carbamate

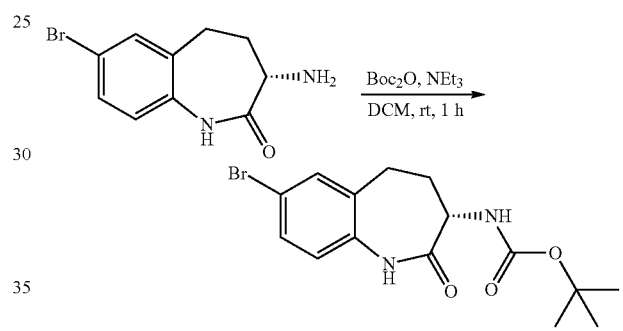

To a mixture of (S)-3-amino-7-bromo-4,5-dihydro-1H-benzo[b]azepin-2(3H)-one (800 mg, 3.14 mmol) in DCM (20 mL) was added NEt3 (0.656 mL, 4.70 mmol) and BOC$_2$O (0.764 mL, 3.29 mmol). The mixture was stirred at rt for 1 h, and then was diluted with H$_2$O (20 mL). The organic layer was separated and concentrated. The resulting residue was purified by Isco Combiflash (20%-80% EtOAc/Hexane; 40 g RediSep column). Collected fractions containing the product were combined and concentrated to give the desired product as a white solid (900 mg, 81% yield). 1H NMR (CDCl$_3$) δ ppm 9.21 (s, 1H), 7.32 (d, J=2.0 Hz, 1H), 7.24 (dd, J=8.3, 2.0 Hz, 1H), 6.83 (d, J=8.3 Hz, 4H), 5.68 (d, J=7.8 Hz, 1H), 4.17-4.31 (m, 1H), 2.76-2.95 (m, 1H), 2.52-2.68 (m, 2H), 1.94-2.01 (m, 1H), 1.39 (s, 9H); MS (m/z): 355 (M+H+).

Preparation 42

Tert-butyl (7-cyano-2-oxo-2,3,4,5-tetrahydro-1H-benzo[b]azepin-3-yl)carbamate

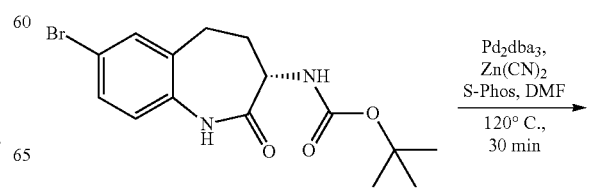

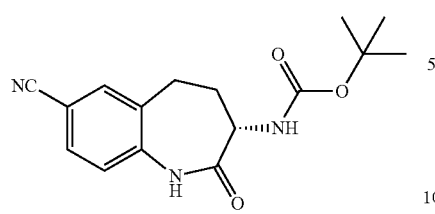

Tert-butyl (7-bromo-2-oxo-2,3,4,5-tetrahydro-1H-benzo[b]azepin-3-yl)carbamate (200 mg, 0.563 mmol), zinc cyanide (99 mg, 0.845 mmol), Pd$_2$dba$_3$ (258 mg, 0.282 mmol), and S-Phos (277 mg, 0.676 mmol) were mixed in a 5 ml microwave vial. The vial was flushed with N$_2$ 3 times, and then 2 ml of DMF was added. The reaction mixture was microwaved using an Emrys Optimizer (150 W, absorption normal, 120° C., 20 min). The mixture was then filtered and the filtrate was concentrated. The residue was purified by Isco Combiflash (20%-50% EtOAc/Hexane; 40 g RediSep column). Collected fractions containing the product were combined and concentrated to give the desired product as a brown oil. This oil was lyophilized to a pale yellow solid (146 mg, 86% yield). $^1$H NMR (CDCl$_3$) δ ppm 9.18 (s, 1H), 7.47-7.59 (m, 2H), 7.13 (d, J=8.1 Hz, 1H), 5.50 (d, J=7.8 Hz, 1H), 4.26 (dt, J=11.4, 7.7 Hz, 1H), 2.84-3.00 (m, 1H), 2.62-2.79 (m, 2H), 1.98-2.12 (m, 1H), 1.41 (s, 9H); MS (m/z): 302 (M+H$^+$).

Preparation 43

3-amino-2-oxo-2,3,4,5-tetrahydro-1H-benzo[b]azepine-7-carbonitrile

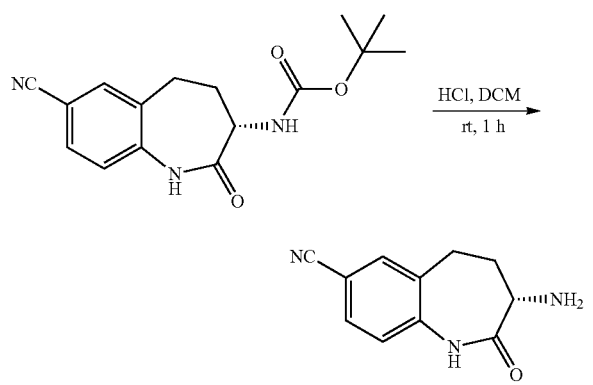

To a mixture of tert-butyl (7-cyano-2-oxo-2,3,4,5-tetrahydro-1H-benzo[b]azepin-3-yl)carbamate (70 mg, 0.234 mmol) in DCM (5 mL) was added HCl (4N in dioxane) (0.31 mL, 1.23 mmol). The reaction mixture was stirred at rt for 1 h. The mixture was then concentrated and dried. This crude material was taken to the next step without purification (47 mg, 100% yield). MS (m/z): 202 (M+H$^+$).

Preparation 44

(S)-tert-butyl (2-oxo-7-(1H-tetrazol-5-yl)-2,3,4,5-tetrahydro-1H-benzo[b]azepin-3-yl)carbamate

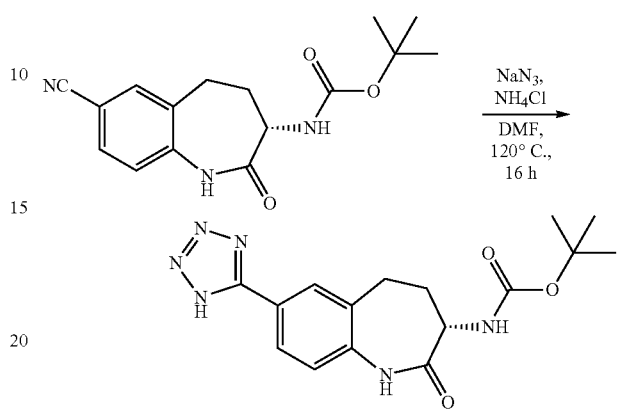

(S)-tert-butyl (7-cyano-2-oxo-2,3,4,5-tetrahydro-1H-benzo[b]azepin-3-yl)carbamate (100 mg, 0.332 mmol) was dissolved in DMF (2 mL), and then sodium azide (64.9 mg, 0.999 mmol) and ammonium chloride (53.8 mg, 1.006 mmol) were added. The mixture was maintained at 120° C. for 16 h. The mixture was filtered and the filtrate was then concentrated and the residue was purified by Isco Combiflash (2%-10% MeOH/CH$_2$Cl$_2$, 10% NEt$_3$ in MeOH; 12 g RediSep column). Collected fractions containing the product were combined and concentrated to give the desired product as a colorless oil (114 mg, 100% yield). MS (m/z): 345 (M+H$^+$).

Preparation 45

(S)-3-amino-7-(1H-tetrazol-5-yl)-4,5-dihydro-1H-benzo[b]azepin-2(3H)-one

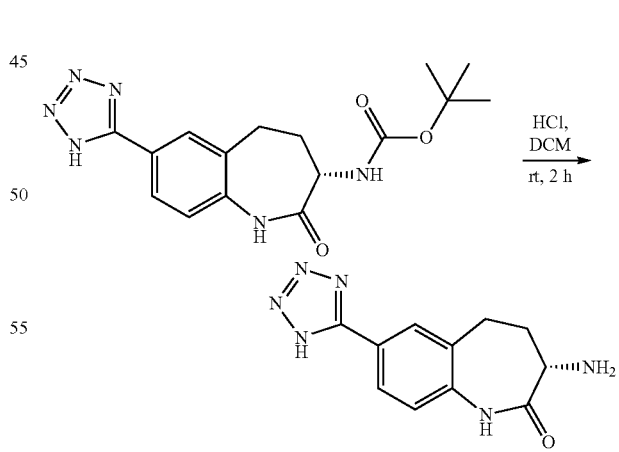

(S)-tert-butyl (2-oxo-7-(1H-tetrazol-5-yl)-2,3,4,5-tetrahydro-1H-benzo[b]azepin-3-yl)carbamate (114 mg, 0.332 mmol) was dissolved in DCM (2 mL), and then HCl (4 N in dioxane, 0.83 mL) was added. The mixture was maintained at rt for 2 h. The rxn mixture was concentrated to an off-white solid. MS (m/z): 245 (M+H$^+$).

Preparation 46 tert-butyl (7-bromo-2-oxo-2,3,4,5-tetrahydro-1H-benzo[b]azepin-3-yl)carbamate

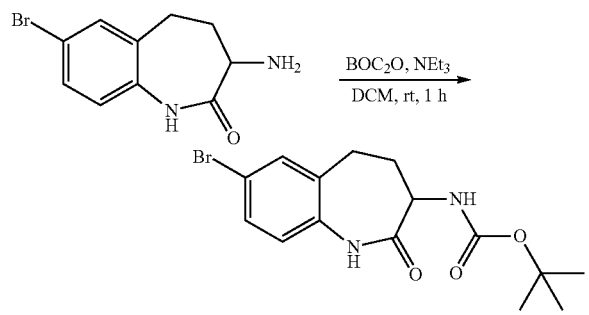

To a mixture of 3-amino-7-bromo-4,5-dihydro-1H-benzo[b]azepin-2(3H)-one (1.7 g, 6.66 mmol) in DCM (50 mL) was added NEt₃ (1.393 mL, 10.00 mmol) and BOC₂O (1.625 mL, 7.00 mmol). The mixture was maintained at rt for 1 h. The reaction mixture was then diluted with water and the organic layer was separated, concentrated and dried under high vacuum for 16 h. This crude material was taken to the next step without further purification (2.36 g, 100% yield). MS (m/z): 355 (M+H⁺).

Preparation 47 tert-butyl (7-bromo-1-methyl-2-oxo-2,3,4,5-tetrahydro-1H-benzo[b]azepin-3-yl)carbamate

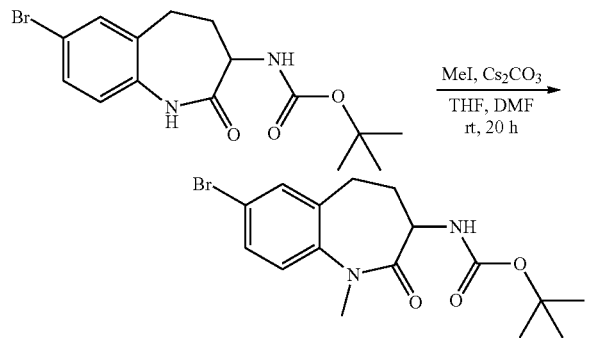

To a mixture of cesium carbonate (3.04 g, 9.33 mmol) and tert-butyl (7-bromo-2-oxo-2,3,4,5-tetrahydro-1H-benzo[b]azepin-3-yl)carbamate (2.36 g, 6.66 mmol) in 1 ml DMF and THF (50 mL) mixed solution was added iodomethane (0.500 mL, 8.00 mmol). The reaction mixture was maintained at rt for 20 h. The mixture was then filtered and the filtrate was concentrated. The residue was purified by Isco Combiflash (10%-50% EtOAc/Hexane; 330 g RediSep column). Collected fractions containing the product were combined and concentrated to give the desired product as a white solid (1.6 g, 65% yield). $^1$H NMR (CDCl₃) δ ppm 7.44 (dd, J=8.5, 2.1 Hz, 1H), 7.37 (d, J=2.3 Hz, 1H), 7.07 (d, J=8.6 Hz, 1H), 5.47 (d, J=7.6 Hz, 1H), 4.23 (dt, J=11.5, 7.5 Hz, 1H), 3.39 (s, 3H), 2.73-2.91 (m, 1H), 2.49-2.65 (m, 2H), 1.87-2.03 (m, 1H), 1.42 (s, 9H); MS (m/z): 369 (M+H⁺).

Preparation 48

1,1-dimethylethyl (1-methyl-2-oxo-2,3,4,5-tetrahydro-1H-1-benzazepin-3-yl)carbamate-d1

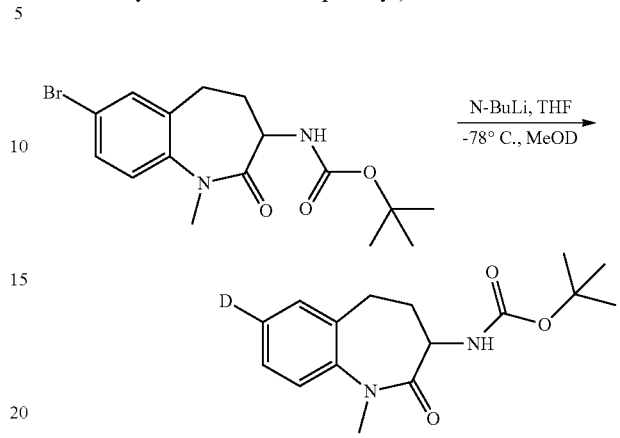

Tert-butyl (7-bromo-1-methyl-2-oxo-2,3,4,5-tetrahydro-1H-benzo[b]azepin-3-yl)carbamate (80 mg, 0.217 mmol) was dissolved in 50 ml THF and then cooled to −78° C. N-butyllithium (2.5M in Hexane) (0.217 mL, 0.542 mmol) was added dropwise at −78° C. The reaction mixture was maintained at −78° C. for 30 min, and then was quenched by MeOD. The mixture was washed by sat. NaHCO₃₍aq₎. The organic layer was separated and purified by Isco Combiflash (20%-80% EtOAc/Hexane; 12 g RediSep column). Collected fractions containing the product were combined and concentrated to give the desired product as a white solid (64 mg, 100% yield). $^1$H NMR (400 MHz, CDCl₃) δ ppm 1.41 (s, 9H) 1.95 (dd, J=7.45, 3.92 Hz, 1H) 2.51-2.68 (m, 2H) 2.73-2.98 (m, 1H) 3.41 (s, 3H) 4.19-4.34 (m, 1H) 5.37-5.64 (m, 1H) 7.11-7.24 (m, 2H) 7.23-7.38 (m, 1H); MS (m/z): 292 (M+H⁺).

Preparation 49

3-amino-1-methyl-1,3,4,5-tetrahydro-2H-1-benzazepin-2-one-d1

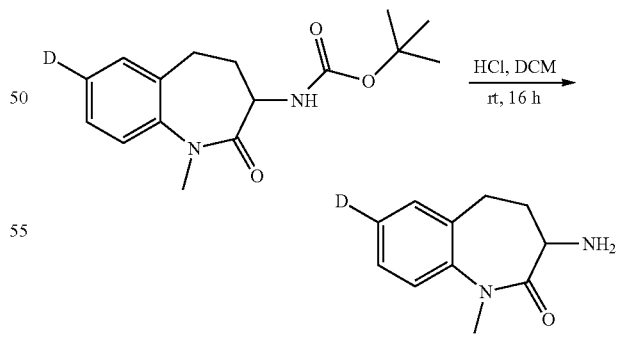

1,1-dimethylethyl (1-methyl-2-oxo-2,3,4,5-tetrahydro-1H-1-benzazepin-3-yl)carbamate-d1 (64 mg) was dissolved in 2 mL DCM, and then 0.54 mL HCl (4N in dioxane) was added dropwise. The reaction mixture was maintained at rt for 4 h. The mixture was then concentrated and the crude material was taken to the next step without further purification (35 mg, 84% yield). MS (m/z): 192 (M+H⁺).

Preparation 50

3-amino-1-methyl-7-(2,2,2-trifluoro-1,1-dihydroxyethyl)-1,3,4,5-tetrahydro-2H-1-benzazepin-2-one

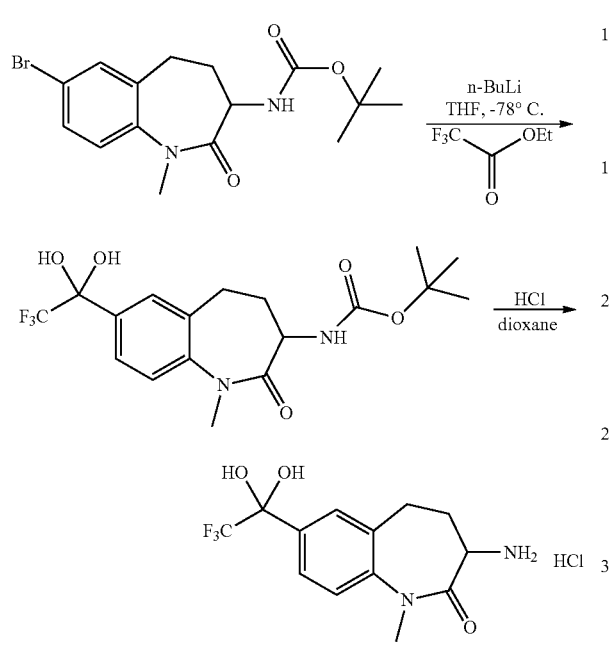

Tert-butyl (7-bromo-1-methyl-2-oxo-2,3,4,5-tetrahydro-1H-benzo[b]azepin-3-yl)carbamate (100 mg, 0.271 mmol) was dissolved in 50 ml THF and then cooled to −78° C. N-butyllithium (2.5M in Hexane, 0.271 mL, 0.677 mmol) was added dropwise at −78° C. This mixture was maintained at −78° C. for 30 min, and then ethyl 2,2,2-trifluoroacetate (0.129 mL, 1.083 mmol) was added dropwise at −78° C. The mixture turned into colorless solution after addition. This mixture was maintained at −78° C. for 1 h, and then was slowly warmed up to rt. The rxn mixture was quenched by MeOH, and then washed by sat.NH$_4$Cl(aq). The organic layer was separated and concentrated. The residue was purified by Isco CombiFlash (20%-80% EtOAc/Hexane; 40 g RediSep column). Collected fractions containing the product were combined and concentrated to give the desired product as a yellow oil (24 mg, 23% yield). MS (m/z): 404 (M+H$^+$).

1,1-Dimethylethyl [1-methyl-2-oxo-7-(2,2,2-trifluoro-1,1-dihydroxyethyl)-2,3,4,5-tetrahydro-1H-1-benzazepin-3-yl]carbamate (125 mg, 0.324 mmol) was dissolved in DCM (2 mL), and then HCl (4N in dioxane) (0.809 mL, 3.24 mmol) was added. The yellow solution was maintained at room temperature for 16 hours. This solution was then concentrated to give the 3-amino-1-methyl-7-(2,2,2-trifluoro-1,1-dihydroxyethyl)-1,3,4,5-tetrahydro-2H-1-benzazepin-2-one as a yellow oil (92 mg, 100% yield). MS (m/z): 304 (M+H$^+$).

Preparation 51

(S)-tert-butyl (2-oxo-7-(4,4,5,5-tetramethyl-1,3,2-dioxaborolan-2-yl)-2,3,4,5-tetrahydro-1H-benzo[b]azepin-3-yl)carbamate

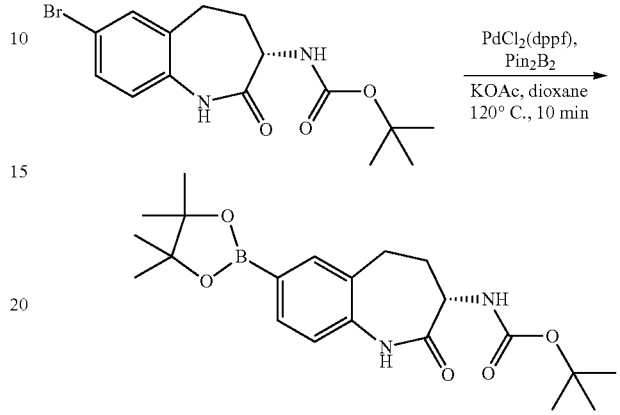

(S)-tert-butyl (7-bromo-2-oxo-2,3,4,5-tetrahydro-1H-benzo[b]azepin-3-yl)carbamate (200 mg, 0.563 mmol), bis(pinacolato)diboron (157 mg, 0.619 mmol), PdCl2(dppf)-CH$_2$Cl$_2$ adduct (46.0 mg, 0.056 mmol) and potassium acetate (182 mg, 1.858 mmol) were mixed in 1,4-Dioxane (2 mL). The reaction mixture was put in an Emrys Optimizer (150 W, absorption normal, 120° C., 10 min). The reaction mixture was then partitioned between H$_2$O and DCM. The organic layer was washed by brine, dried over MgSO$_4$ and concentrated to a brown residue. This residue was purified by Isco Combiflash (10%-80% EtOAc/Hexane; 40 g RediSep column). Collected fractions containing the product were combined and concentrated to give the desired product as a white solid (82 mg, 36% yield). MS (m/z): 402 (M+H$^+$).

Preparation 52

(S)-3-amino-7-(4,4,5,5-tetramethyl-1,3,2-dioxaborolan-2-yl)-4,5-dihydro-1H-benzo[b]azepin-2(3H)-one

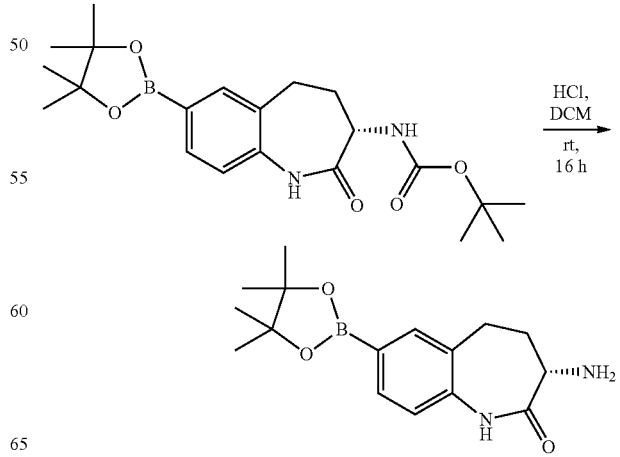

(S)-tert-butyl (2-oxo-7-(4,4,5,5-tetramethyl-1,3,2-dioxaborolan-2-yl)-2,3,4,5-tetrahydro-1H-benzo[b]azepin-3-yl)carbamate (82 mg, 0.205 mmol) was dissolved in 2 mL DCM, and then HCl (4N in dioxane, 1.408 mL, 5.63 mmol) was added dropwise. The reaction solution was maintained at rt for 16 h. The solution was then concentrated to a yellow oil (62 mg, 100% yield). MS (m/z): 302 (M+H$^+$).

Preparation 53

(S)-5-benzyl-N-(2-oxo-7-(4,4,5,5-tetramethyl-1,3,2-dioxaborolan-2-yl)-2,3,4,5-tetrahydro-1H-benzo[b]azepin-3-yl)-4H-1,2,4-triazole-3-carboxamide

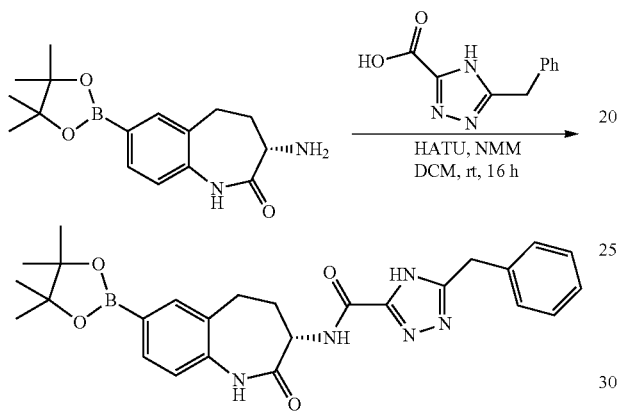

To a magnetically stirred solution of 5-benzyl-4H-1,2,4-triazole-3-carboxylic acid (41.7 mg, 0.205 mmol) in 5 mL DCM at rt was added 4-methylmorpholine (66.4 mg, 0.657 mmol) and HATU (94 mg, 0.246 mmol). A solution of (S)-3-amino-7-(4,4,5,5-tetramethyl-1,3,2-dioxaborolan-2-yl)-4,5-dihydro-1H-benzo[b]azepin-2(3H)-one (62 mg, 0.205 mmol) and in 2 mL DCM was add to this mixture. The reaction mixture was maintained at rt for 16 h. The crude mixture was then purified by Isco Combiflash (20%-50% EtOAc/Hexane; 40 g RediSep column). Collected fractions containing the product were combined and concentrated to give the desired product as a yellow solid (65 mg, 65% yield). MS (m/z): 488 (M+H$^+$).

Preparation 54

(S)-3-amino-8-hydroxy-2,3-dihydrobenzo[b][1,4]oxazepin-4(5H)-one

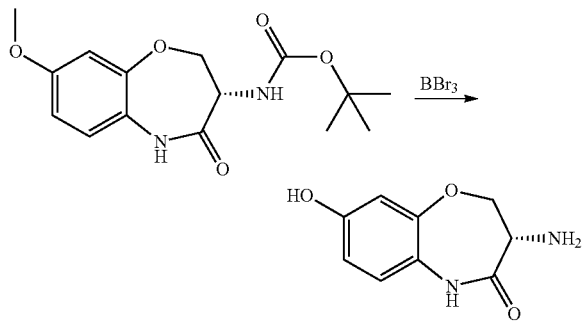

(S)-tert-butyl (8-methoxy-4-oxo-2,3,4,5-tetrahydrobenzo[b][1,4]oxazepin-3-yl)carbamate (300 mg, 0.973 mmol) was dissolved in DCM (15 mL) and cooled in an ice/brine bath. Then boron tribromide (2.92 mL, 2.92 mmol) was added and reaction was stirred cooled for 10 minutes. Removed ice bath and stirred at rt for 60 minutes. Added another 2.0 mL BBr$_3$ and stirred for 45 minutes, then added another 2 mL BBr$_3$ and stirred for another 20 minutes. Reaction was cooled in an ice bath, quenched with 5 mL satd. NaHCO$_3$ and stirred vigorously for 5 minutes. The pH of the aqueous was ~7-8. The layers were separated and aqueous was extracted with 10% MeOH/DCM: both organics contained impurities and aqueous contained majority product. Concentrated aqueous to give 2.4 g crude solid (contained inorganic salts). Used as is in next step. MS (m/z) 195.0 (M+H$^+$).

Preparation 55

(S)-3-amino-5-methyl-7-(1H-pyrazol-3-yl)-2,3-dihydrobenzo[b][1,4]oxazepin-4(5H)-one

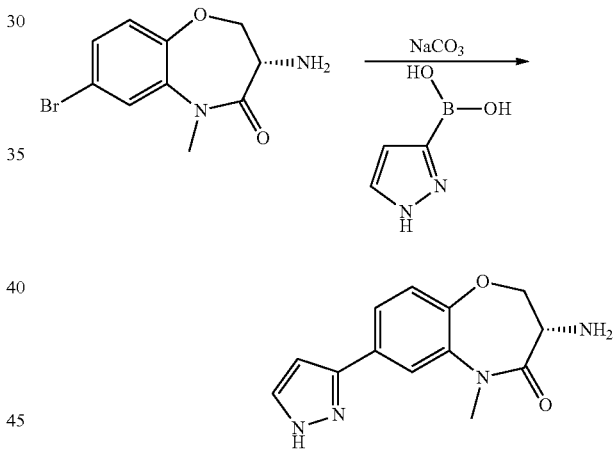

(S)-3-amino-7-bromo-5-methyl-2,3-dihydrobenzo[b][1,4]oxazepin-4(5H)-one (50.5 mg, 0.186 mmol), (1H-pyrazol-3-yl)boronic acid (31.3 mg, 0.279 mmol), sodium carbonate (59.2 mg, 0.559 mmol) and Pd(PPh$_3$)$_4$ (21.53 mg, 0.019 mmol) were combined in DME (2 mL) and Water (0.7 mL) and reaction was heated at 85° C. in oil bath for 3 hours. After 2 hours, more Pd(PPh$_3$)$_4$ (15 mg) and boronic acid (15 mg) were added. After 3 hours in oil bath, reaction was put in microwave at 120° C. for 15 min. Reaction was partitioned between 10% MeOH/DCM and water. Concentrated organics and purified by Biotage (4 g silica column; 0.5-5% MeOH/DCM (plus NH$_4$OH), 15 min.) to give 30 mg light yellow oil in 60% yield. $^1$H NMR (DMSO-d$_6$) δ: 7.79 (m, 2H), 7.66 (m, 1H), 7.19 (m, 1H), 6.76 (m, 1H), 4.27 (m, 1H), 4.00 (m, 1H), 3.65 (m, 1H), 3.35 (s, 3H), 1.72 (br. s., 2H); MS (m/z) 259.1 (M+H$^+$).

Preparation 56

(S)-3-amino-5-methyl-7-(1H-pyrazol-1-yl)-2,3-dihydrobenzo[b][1,4]oxazepin-4(5H)-one

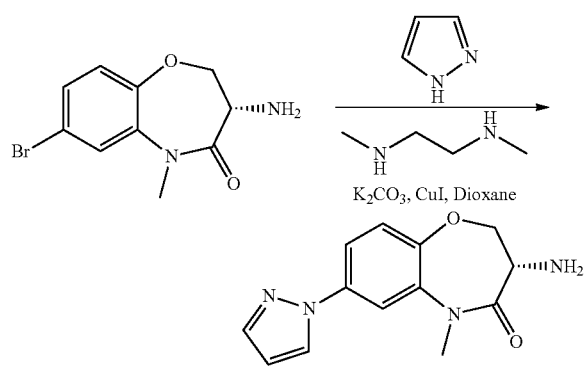

(S)-3-amino-7-bromo-5-methyl-2,3-dihydrobenzo[b][1,4]oxazepin-4(5H)-one (100 mg, 0.369 mmol), 1H-pyrazole (50.2 mg, 0.738 mmol) and potassium carbonate (153 mg, 1.107 mmol) were added to 1,4-Dioxane (2.0 mL) and mixture was degassed for 10 minutes under nitrogen. Then copper(I) iodide (35.1 mg, 0.184 mmol) and N1,N2-dimethylethane-1,2-diamine (0.020 mL, 0.184 mmol) were added and mixture was heated at 100° C. for 3 days. Cooled to rt, diluted with water and 10% MeOH/DCM and separated layers. Concentrated organics and purified by Biotage (12 g silica column; 0.5-3% MeOH/DCM (plus NH$_4$OH), 15 min.; 3-4.5%, 3 min; 4.5% 5 min.) to give 18 mg light brown solid in 19% yield. $^1$H NMR (DMSO-d$_6$) δ: 8.54 (d, J=2.5 Hz, 1H), 7.85 (d, J=2.5 Hz, 1H), 7.76 (d, J=1.5 Hz, 1H), 7.69 (dd, J=8.7, 2.7 Hz, 1H), 7.27 (d, J=8.8 Hz, 1H), 6.54-6.59 (m, 1H), 4.29 (dd, J=9.9, 7.6 Hz, 1H), 4.02 (t, J=10.7 Hz, 1H), 3.68 (br. s., 1H), 3.36 (s, 3H), 1.75 (br. s., 2H); MS (m/z) 259.1 (M+H$^+$).

Preparation 57

(S)-tert-butyl (2-oxo-8-(2-(pyrrolidin-1-yl)ethoxy)-2,3,4,5-tetrahydro-1H-benzo[b]azepin-3-yl)carbamate

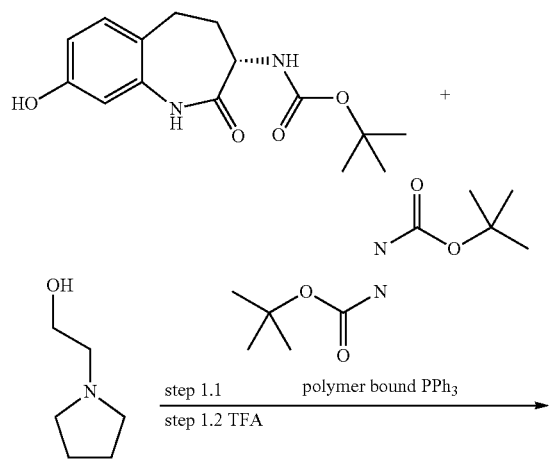

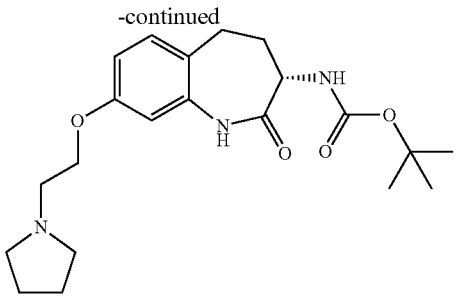

Polymer bound PPh$_3$ (3 mmol/g loading, 2.5 eq, 330 mg), (S)-tert-butyl (8-hydroxy-2-oxo-2,3,4,5-tetrahydro-1H-benzo[b]azepin-3-yl)carbamate (130 mg, 0.400 mmol) and 2-(pyrrolidin-1-yl)ethanol (0.094 mL, 0.800 mmol) were combined in THF (4 mL). Next added di-tert-butyl azodicarboxylate (184 mg, 0.800 mmol) and stirred mixture at rt for 3 days. Added 0.5 eq more of the following reagents: polymer bound PPh$_3$, di-tert-butyl azodicarboxylate and 2-(pyrrolidin-1-yl)ethanol and stirred for another 24 hours. Reaction was filtered through a small plug of Celite, rinsing with 10% MeOH/DCM. Filtrate was concentrated, partitioned between DCM and 6N NaOH and layers were separated. Crude was concentrated and purified by Biotage (4 g silica column; 1-5% MeOH/DCM (plus NH$_4$OH), 15 min.) to give 74 mg white foam in 46% yield. $^1$H NMR (DMSO-d$_6$) δ: 9.64 (s, 1H), 7.15 (d, J=8.3 Hz, 1H), 6.97 (d, J=8.3 Hz, 1H), 6.70 (dd, J=8.3, 2.5 Hz, 1H), 6.57 (d, J=2.5 Hz, 1H), 3.96-4.10 (m, 2H), 3.88 (dt, J=11.9, 8.3 Hz, 1H), 2.77 (t, J=5.9 Hz, 2H), 2.54-2.62 (m, 2H), 2.53 (m, 1H), 2.09-2.22 (m, 2H), 1.95-2.07 (m, 2H), 1.62-1.71 (m, 5H), 1.34 (s, 9H); MS (m/z) 390.3 (M+H$^+$).

Preparation 58

Butyl 4-butoxypicolinate

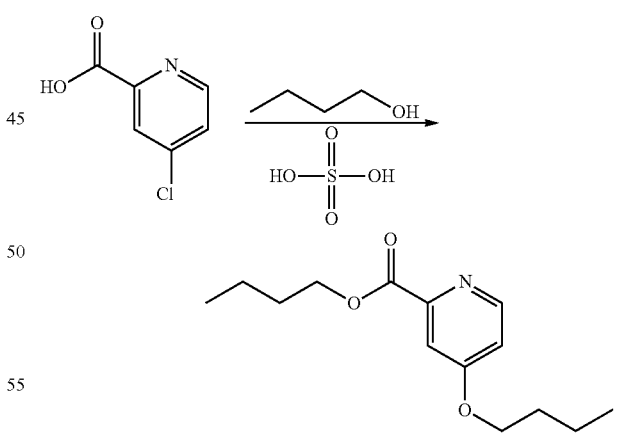

To a mixture of 4-chloropicolinic acid (1 g, 6.35 mmol) and butan-1-ol (5.80 ml, 63.5 mmol) was added sulfuric acid (0.101 ml, 1.904 mmol) and heated to 80° C. for 2 days. After cooling down to rt, the reaction mixture was diluted with water and neutralized with 1N NaOH solution to pH 5-6, then extracted with EtOAc (×3). After drying over MgSO$_4$, filtration, and evaporation in vacuo, the residue was purified by Biotage (50 g cartridge, 0% to 40% EtOAc in hexane) to give butyl 4-butoxypicolinate (765 mg, 3.04 mmol, 48.0% yield). MS (m/z) 252.1 (M+H⁺). ¹H NMR (CDCl₃) δ: 8.55 (d, J=6.1 Hz, 1H), 7.65 (d, J=2.3 Hz, 1H), 6.95 (dd, J=5.7, 2.7 Hz, 1H), 4.42 (t, J=6.8 Hz, 2H), 4.09 (t, J=6.4 Hz, 2H), 1.77-1.87 (m, 4H), 1.43-1.57 (m, 4H), 0.97-1.03 (m, 6H).

The following intermediates used for the preparation of titled example compounds were synthesized using methods analogous to the ones described above.

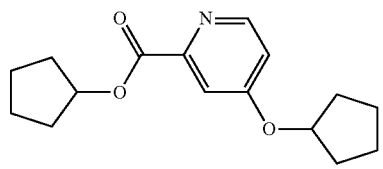 [SMILES: O=C(OC1CCCC1)c1cc(OC2CCCC2)ccn1]

Preparation 59

Ethyl 2-amino-2-(2-(2-(3-fluorophenyl)acetyl)hydrazono)acetate

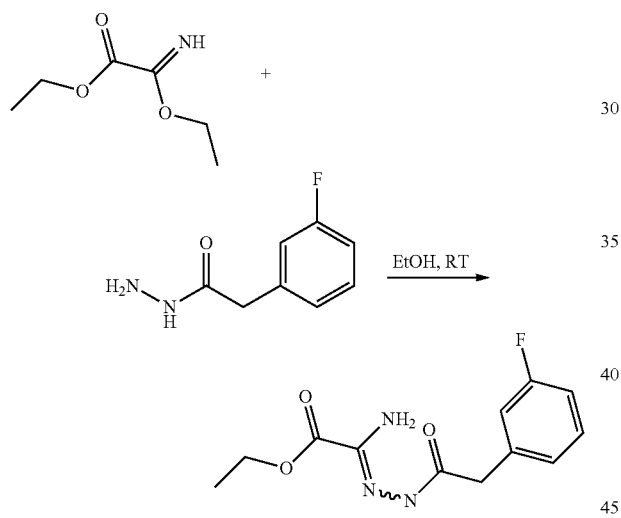

2-(3-Fluorophenyl)acetohydrazide (2.90 g, 17.22 mmol) and ethyl 2-ethoxy-2-iminoacetate (2.5 g, 17.22 mmol) in ethanol (30 mL) was stirred under nitrogen at rt for overnight, the resultant suspension was filtered. The white solid was washed with EtOH and dried under vacuum to give the title compound ethyl 2-amino-2-(2-(2-(3-fluorophenyl)acetyl)hydrazono)acetate (3 g, 11.23 mmol, 65.2% yield) which was used without further purification. MS (m/z) 268 (M+H⁺).

The following intermediates used for the preparation of titled example compounds were synthesized using methods analogous to the ones described above.

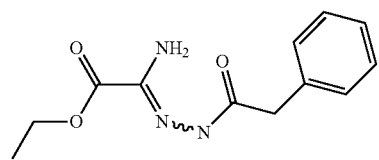

-continued

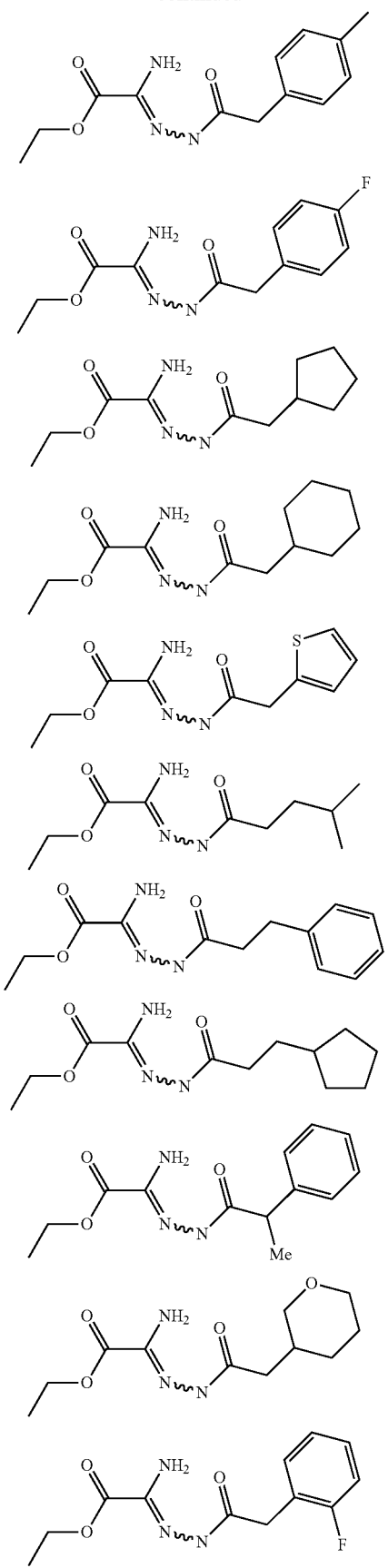

-continued

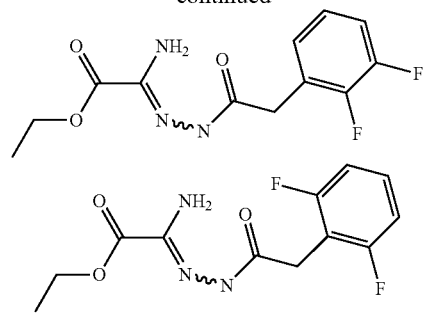

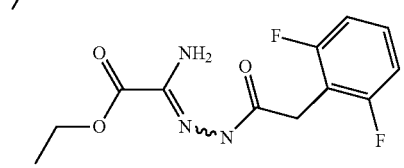

Preparation 60

Ethyl 5-(3-fluorobenzyl)-4H-1,2,4-triazole-3-carboxylate

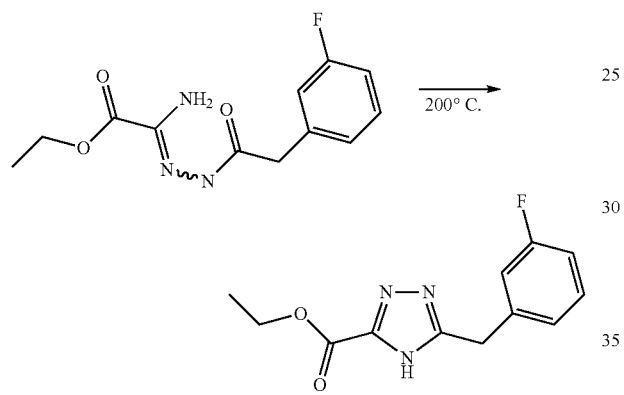

Ethyl 2-amino-2-(2-(2-(3-fluorophenyl)acetyl)hydrazono)acetate (3 g, 11.23 mmol) in a flask was placed in a pre-heated oil bath at 2000 C for 15 minutes. The melt was allowed to cool, the resultant solid taken up into MeOH (20 mL), and then the solvent was evaporated. The resultant white solid was suspended in ether (30 mL), stirred for 10 minutes, filtered off, washed with ether (40 mL), and dried under vacuum to give the title compound ethyl 5-(3-fluorobenzyl)-4H-1,2,4-triazole-3-carboxylate (0.2 g, 4.81 mmol, 42.9% yield), which was used without further purification. MS (m/z) 250 (M+H$^+$).

The following intermediates used for the preparation of titled example compounds were synthesized using methods analogous to the ones described above.

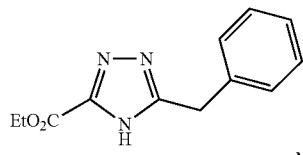

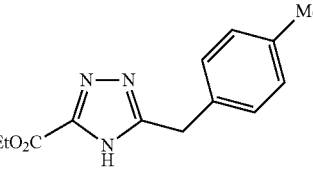

-continued

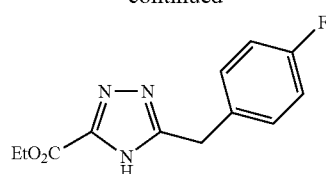

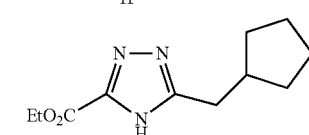

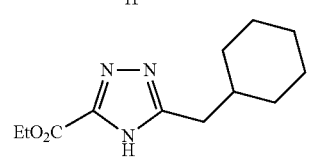

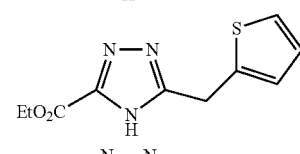

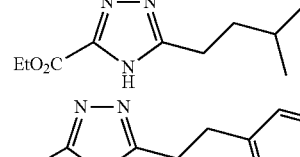

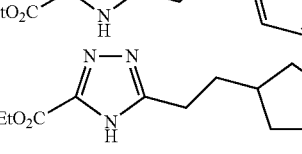

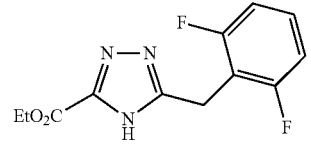

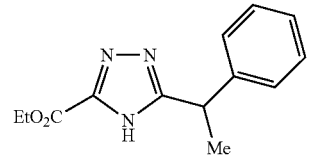

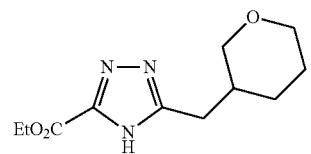

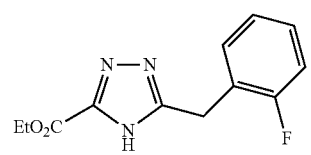

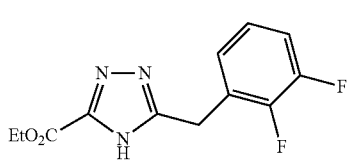

Preparation 61

5-Benzyl-4H-1,2,4-triazole-3-carboxylic acid

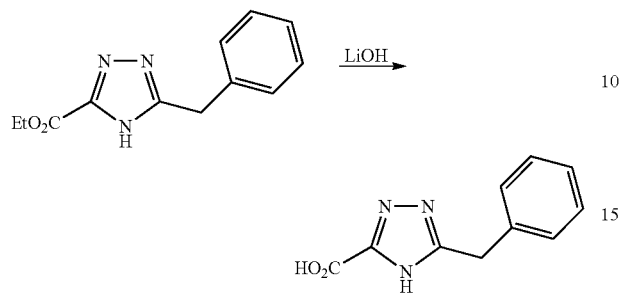

To a solution of ethyl 5-benzyl-4H-1,2,4-triazole-3-carboxylate (8.29 g, 35.85 mmol) in THF (100 mL) was added a solution of lithium hydroxide (2.00 g, 84 mmol) in water (20 mL). The mixture was stirred for 20 hours at room temperature. The reaction was concentrated to remove THF and conc. HCl was added until pH~2 at which point a solid precipitated out. The suspension was stirred for 15 minutes in an ice/water bath, filtered, rinsed with cold water and dried under vacuum to give 6.93 g (80% yield) of 5-benzyl-4H-1,2,4-triazole-3-carboxylic acid hydrochloride. MS (m/z) 204 (M+H$^+$).

The following intermediates used for the preparation of titled example compounds were synthesized using methods analogous to the ones described above.

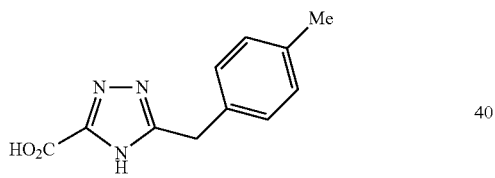


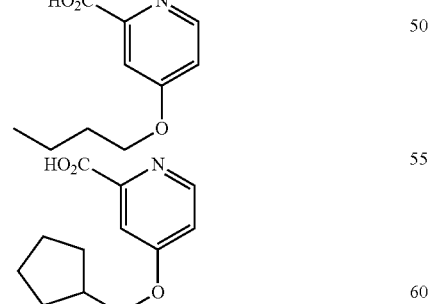

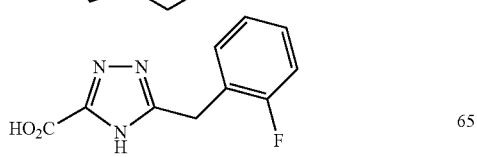

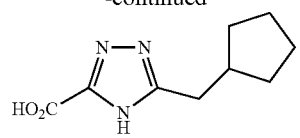

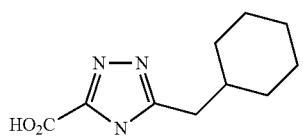

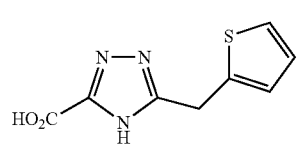

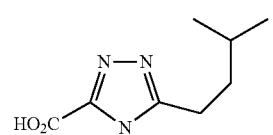

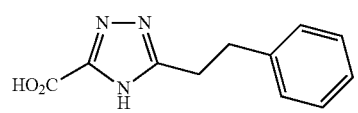

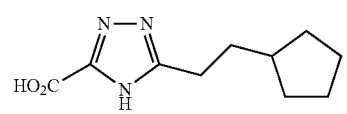

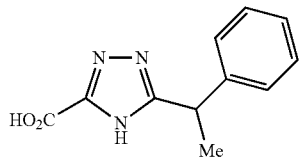

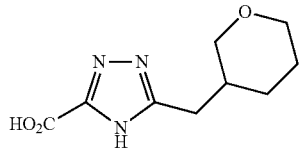

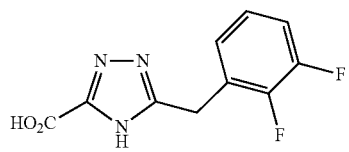

Preparation 62 ethyl 1-(3-fluorobenzyl)-1H-imidazole-4-carboxylate

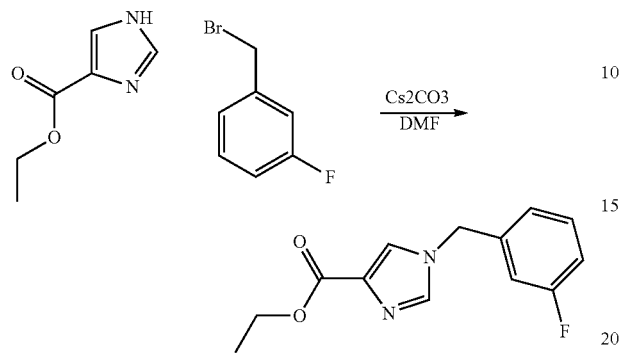

To a solution of ethyl 1H-imidazole-4-carboxylate (1 g, 7.14 mmol), Cs₂CO₃ (2.56 g, 7.85 mmol) and in N,N-Dimethylformamide (DMF) (5 mL) was 1-(bromomethyl)-3-fluorobenzene (1.349 g, 7.14 mmol). The reaction mixture was stirred at for 5 h. LCMS showed the reaction was completed with product. Added 150 ml of EtOAc and extracted with water, brine and dried over Na₂SO₄. Evaporated all the solvents to afford the crude product as ethyl 1-(3-fluorobenzyl)-1H-imidazole-4-carboxylate (1.7 g, 6.85 mmol, 96% yield). MS (m/z) 250 (M+H⁺).

The following intermediates used for the preparation of titled example compounds were synthesized using methods analogous to the ones described above.

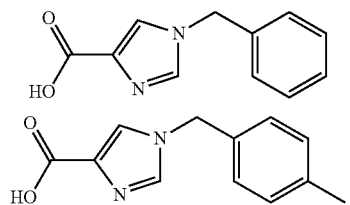

Preparation 63

1-(3-fluorobenzyl)-1H-imidazole-4-carboxylic acid

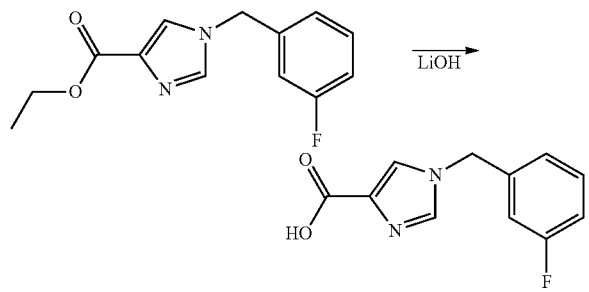

Freshly prepared lithium hydroxide (34.2 mL, 68.5 mmol) was added to a stirring, room temperature solution of ethyl 1-(3-fluorobenzyl)-1H-imidazole-4-carboxylate (1.7 g, 6.85 mmol) in THF (25 mL) under N₂. The reaction was then stirred at rt overnight and LCMS showed completed. The reaction was concentrated and then dissolved in H₂O (10 mL). 2N HCl was added dropwise until the pH=3. The white solid that precipitated from the reaction was filtered off and washed with cold H₂O. The solid was dried under vacuum overnight to obtain title product. 1-(3-fluorobenzyl)-1H-imidazole-4-carboxylic acid (1.2 g, 79.5%). MS (m/z) 221 (M+H⁺).

The following intermediates used for the preparation of titled example compounds were synthesized using methods analogous to the ones described above.

Preparation 64

Ethyl 5-(4-fluorophenyl)-2,4-dioxopentanoate

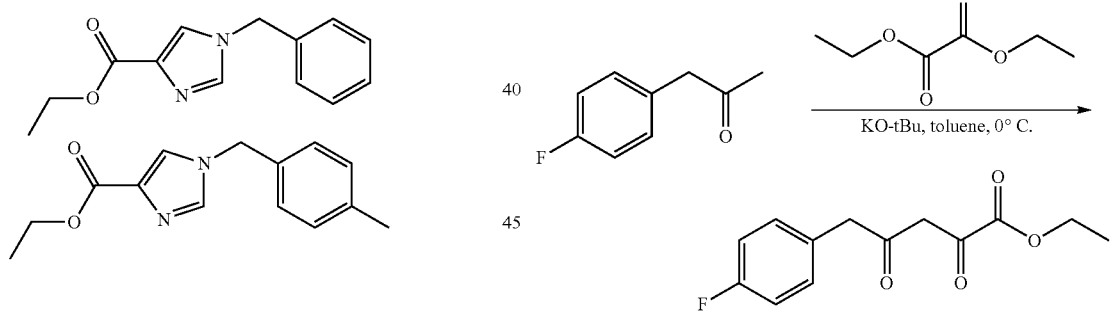

To a solution of 1-(4-fluorophenyl)propan-2-one (25 g, 164 mmol) diethyl oxalate (28.8 g, 197 mmol) in toluene (300 mL) stirred under nitrogen at 0° C. was added potassium tert-butoxide (23.97 g, 214 mmol) in toluene (300 mL). The reaction mixture was stirred at OC for 2 more hours and then at rt for over night. LCMS indicated the reaction was completed. Removed all the toluene and dissolved the residue in water and neutralized to pH=6 and extracted with EtOAc twice. The organic phase was combined and washed with brine, and dried over Na₂SO₄. Removed all the solvents to afford the title compound used without further purification (32 g, 77%). MS (m/z) 253 (M+H⁺).

The following intermediates used for the preparation of titled example compounds were synthesized using methods analogous to the ones described above.

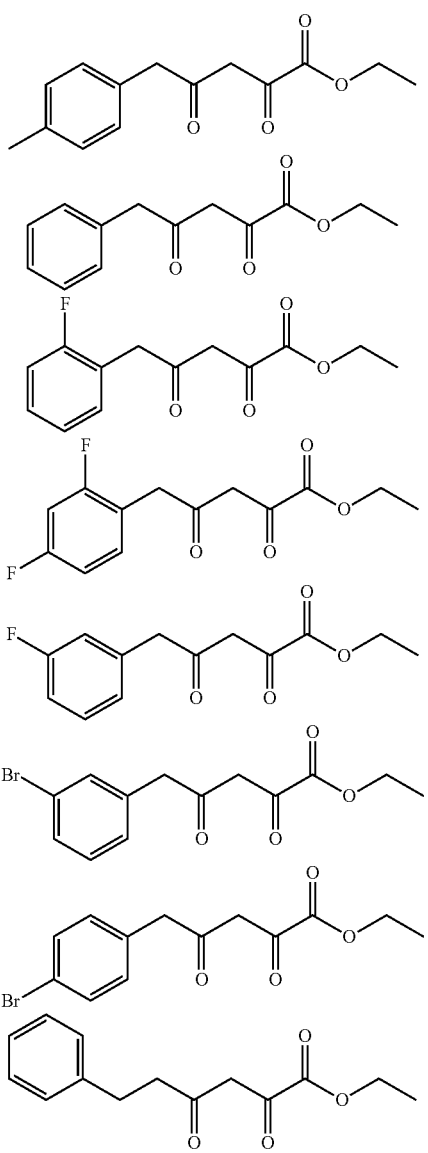

Preparation 65

Ethyl 5-(4-fluorobenzyl)-1H-pyrazole-3-carboxylate

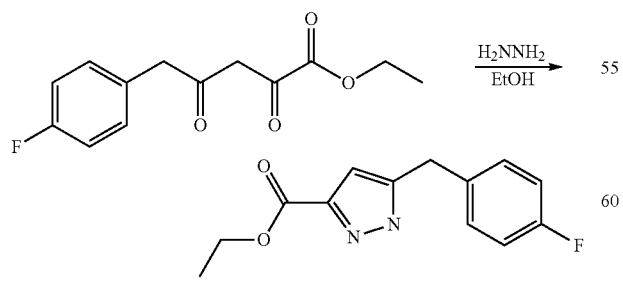

Hydrazine (1.095 mL, 34.9 mmol) was added to a stirring room temperature solution of ethyl 5-(4-fluorophenyl)-2,4-dioxopentanoate (8 g, 31.7 mmol) in ethanol (100 mL) under N$_2$. The reaction was then heated to reflux (95 C oil bath) until judged complete by HPLC (3 h). The reaction was concentrated and purified by silica gel chromatography (solid loading, Isco, 0-45% of EtOAc in hexane). Only pure fractions were combined and concentrated to obtain product as ethyl 5-(4-fluorobenzyl)-1H-pyrazole-3-carboxylate (4 g, 16.11 mmol, 50.8% yield). MS (m/z) 249 (M+H$^+$).

The following intermediates used for the preparation of titled example compounds were synthesized using methods analogous to the ones described above.

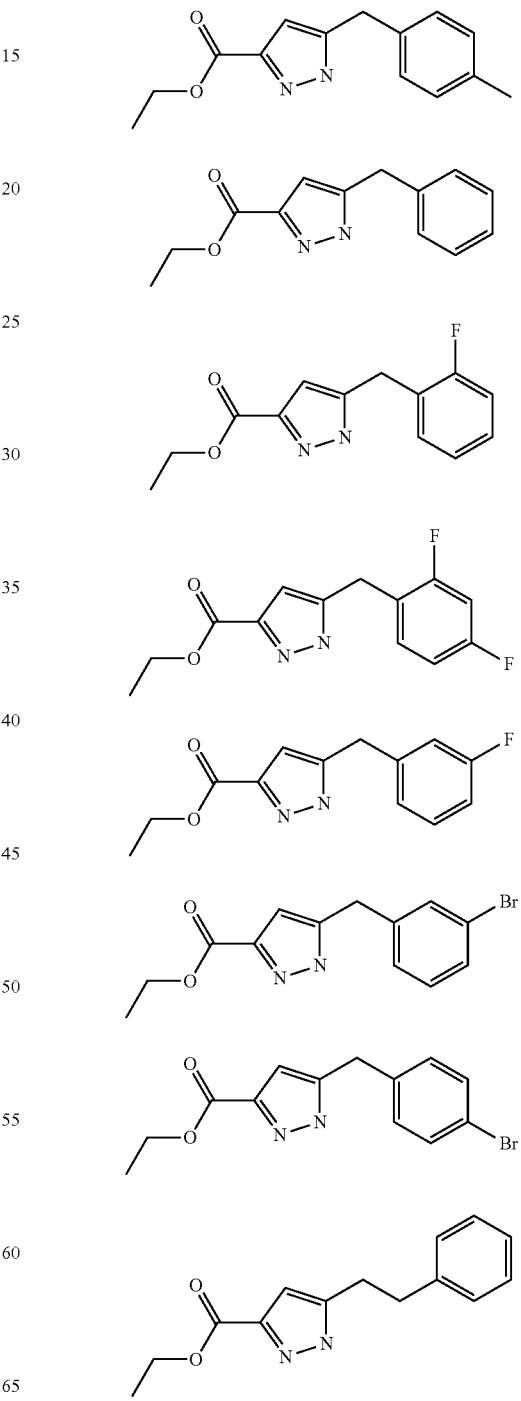

Preparation 66

5-(4-fluorobenzyl)-1H-pyrazole-3-carboxylic Acid

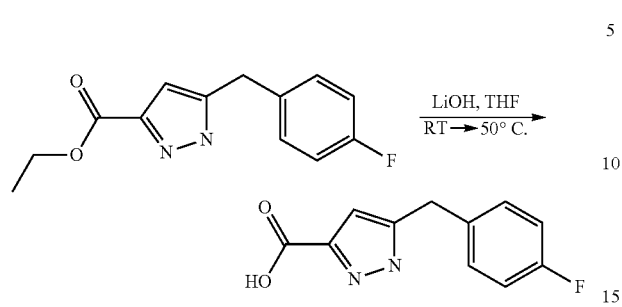

Freshly prepared 2M LiOH aqueous solution (64.5 mL, 129 mmol) was added to a stirring, room temperature solution of ethyl 5-(4-fluorobenzyl)-1H-pyrazole-3-carboxylate (4 g, 16.11 mmol) in THF (65 mL) under $N_2$. The reaction was then stirred at rt for 12 hours and LCMS showed 70% completed. Heated to 50 C for 2 h and reaction was completed. The reaction was concentrated and then dissolved in 20 mL $H_2O$. To a stirring aqueous solution, 2N HCl was added dropwise until the pH=4. The white solid that precipitated from the reaction was filtered off and washed with cold $H_2O$. The solid was dried under vacuum overnight (at 40° C.) to obtain title product as 5-(4-fluorobenzyl)-1H-pyrazole-3-carboxylic acid (3 g, 85%). MS (m/z) 221 (M+H$^+$). $^1$H NMR (DMSO-d$_6$) δ: 12.59-13.70 (m, 1H), 7.01-7.41 (m, 4H), 6.46 (s, 1H), 3.95 (s, 2H).

The following intermediates used for the preparation of titled example compounds were synthesized using methods analogous to the ones described above.

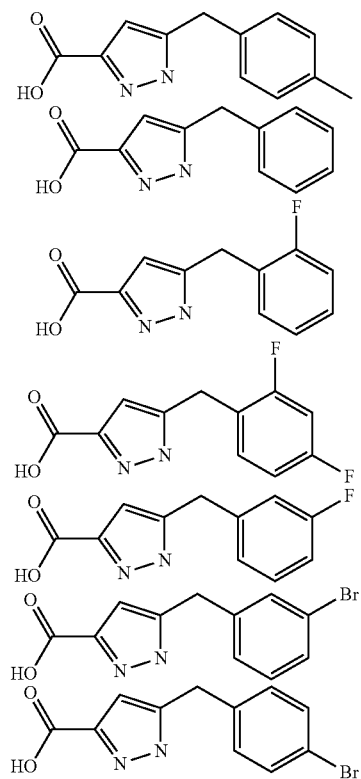

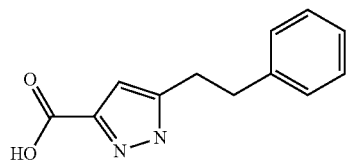

Preparation 67

Ethyl 5-methyl-1-(4-methylbenzyl)-1H-pyrazole-3-carboxylate

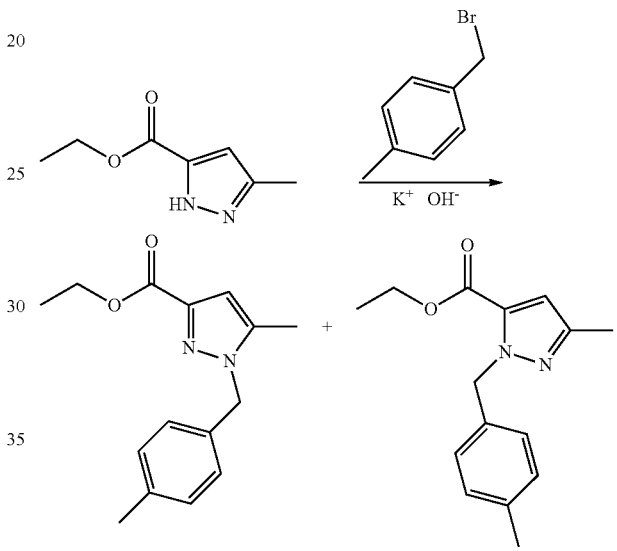

To a solution of ethyl 3-methyl-1H-pyrazole-5-carboxylate (607 mg, 3.94 mmol) in THF (20 mL) was added KOH (221 mg, 3.94 mmol). After stirring for 1 hr at rt, the reaction mixture turned to the suspension, then 1-(bromomethyl)-4-methylbenzene (729 mg, 3.94 mmol) was added and heated to reflux. After overnight, the reaction mixture was cooled down to rt and concentrated. The residue was subjected to Biotage (cartridge 50 g/pre-wet 5% EtOAc/Hex/eluent: 5% to 25% EtOAc, then maintained 25% EtOAc/Hex) to give ethyl 5-methyl-1-(4-methylbenzyl)-1H-pyrazole-3-carboxylate (833 mg, 3.16 mmol, 80% yield) as a desired product and the regioisomer ethyl 3-methyl-1-(4-methylbenzyl)-1H-pyrazole-5-carboxylate (58 mg, 0.220 mmol, 5.59% yield). Ethyl 5-methyl-1-(4-methylbenzyl)-1H-pyrazole-3-carboxylate: $^1$H NMR (CDCl$_3$) δ: 7.13 (d, J=7.1 Hz, 2H), 7.03 (d, 2H), 6.62 (br. s., 1H), 5.36 (br. s., 2H), 4.42 (dd, J=7.1, 1.3 Hz, 2H), 2.34 (br. s., 3H), 2.19 (s, 3H), 1.35-1.50 (m, 3H); MS (m/z) 259.1 (M+H$^+$). The regioisomer ethyl 3-methyl-1-(4-methylbenzyl)-1H-pyrazole-5-carboxylate: $^1$H NMR (CDCl$_3$) δ: 7.05-7.24 (m, 4H), 6.66 (br. s., 1H), 5.67 (br. s., 2H), 4.19-4.42 (m, 2H), 2.32 (d, J=3.0 Hz, 6H), 1.27-1.40 (m, 3H).

The following intermediates used for the preparation of titled example compounds were synthesized using methods analogous to the ones described above.

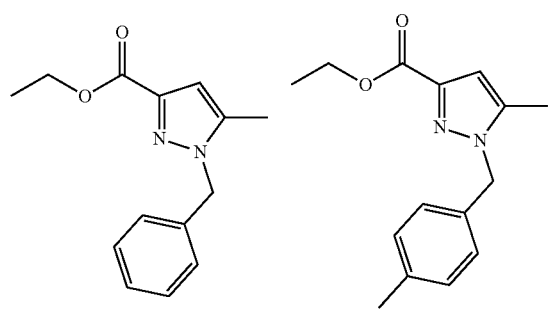
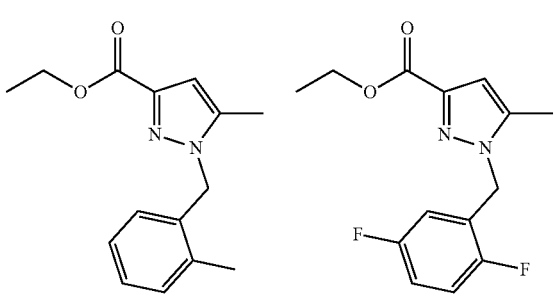
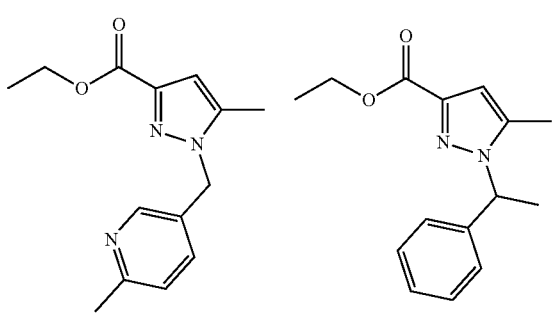
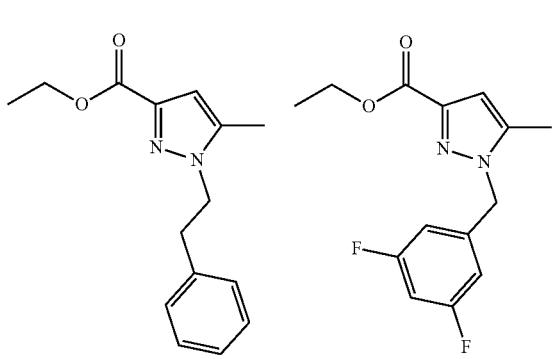
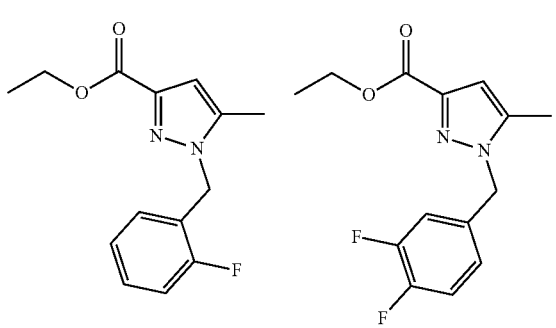
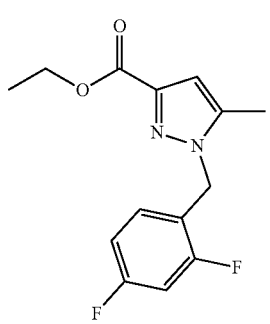
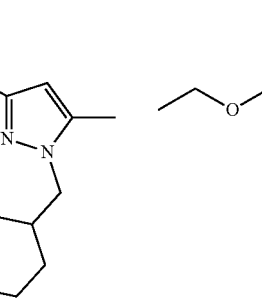
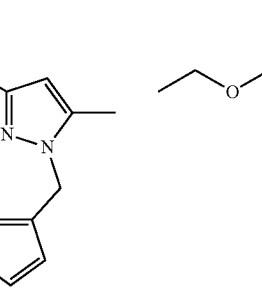
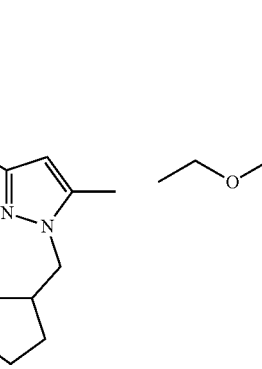

Preparation 68

5-methyl-1-(4-methylbenzyl)-1H-pyrazole-3-carboxylate Acid

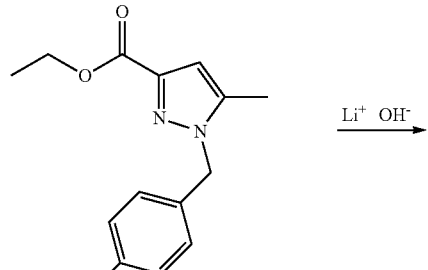
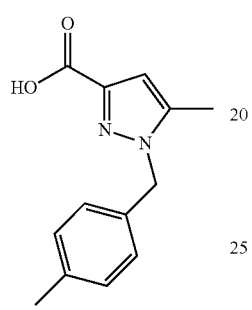
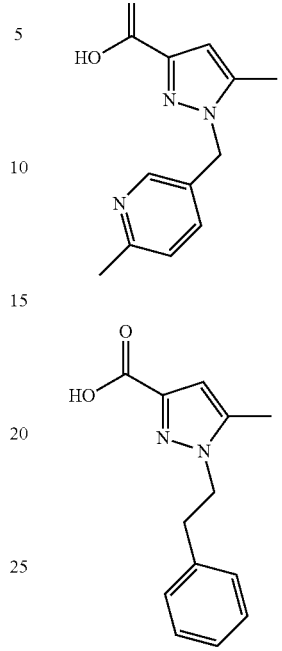

To a solution of ethyl 5-methyl-1-(4-methylbenzyl)-1H-pyrazole-3-carboxylate (830 mg, 3.21 mmol) in THF (3.0 mL) and water (3.0 mL) was added lithium hydroxide, $H_2O$ (539 mg, 12.85 mmol) at rt. After stirring for overnight at rt, the reaction mixture was concentrated in vacuo. The aqueous solution was diluted with water (5 mL) and acidified with 1N HCl (about 5.1 mL) to pH 3-4. The resultant white solid was collected and dried under a vacuum oven to give 5-methyl-1-(4-methylbenzyl)-1H-pyrazole-3-carboxylic acid (670 mg, 2.88 mmol, 90% yield) as white solids. MS (m/z) 231.1 (M+H$^+$). $^1$H NMR (DMSO-d$_6$) δ: 12.58 (br. s., 1H), 7.16 (d, J=7.8 Hz, 2H), 7.03 (d, J=7.8 Hz, 2H), 6.51 (s, 1H), 5.32 (s, 2H), 2.27 (s, 3H), 2.22 (s, 3H).

The following intermediates used for the preparation of titled example compounds were synthesized using methods analogous to the ones described above.

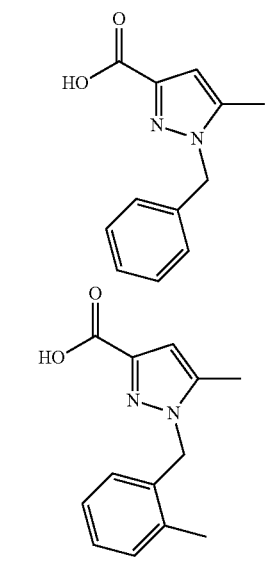
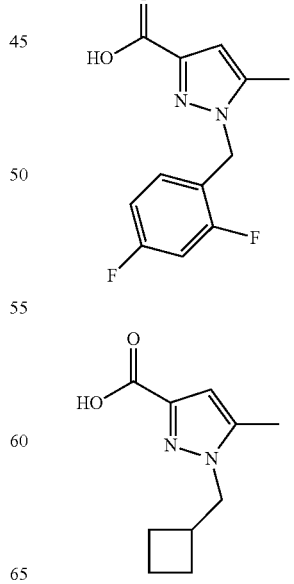
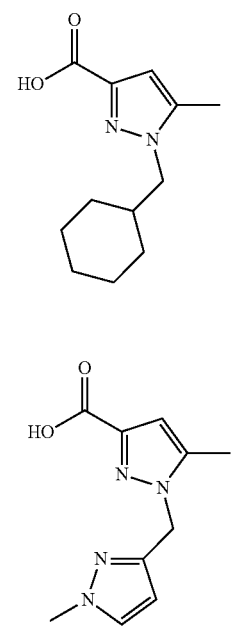

-continued

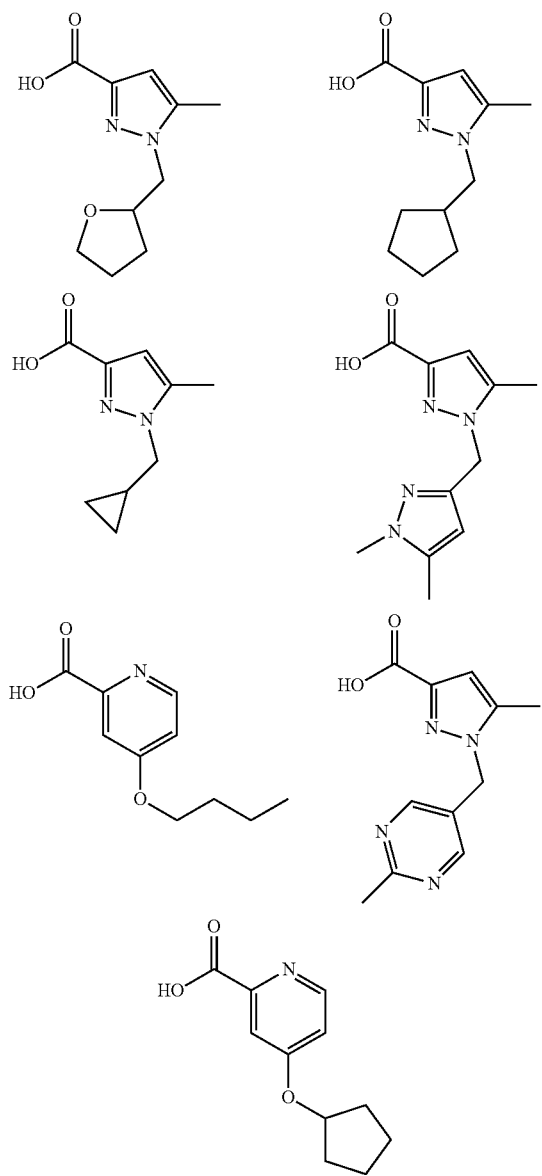

Preparation 69

Ethyl 2H-tetrazole-5-carboxylate

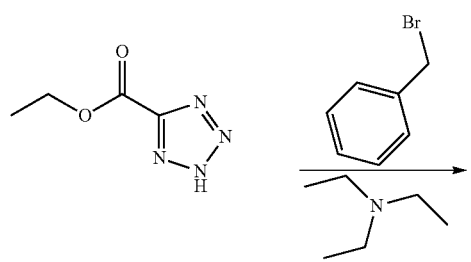

-continued

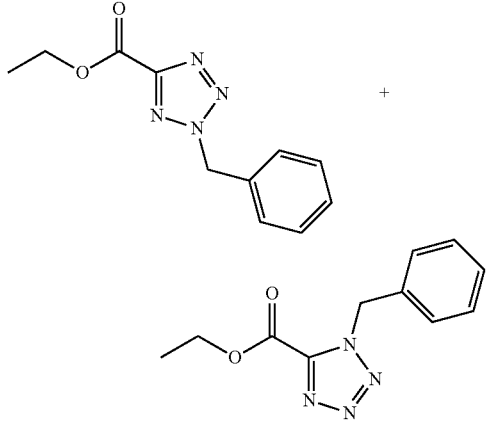

To a solution of ethyl 2H-tetrazole-5-carboxylate, sodium salt (800 mg, 4.85 mmol) in DMF (8 mL) was added (bromomethyl)benzene (1.151 mL, 9.69 mmol) at rt. After stirring for 48 hr at rt, Et₃N (1.013 mL, 7.27 mmol) was added to the reaction mixture, then stirred for overnight. After adding water, the reaction mixture was extracted with EtOAc. The combined organic solution was washed with water and brine, dried over MgSO₄. After filtration and concentration, the residue was subjected to Biotage (50 g of silica gel cartridge; eluent: 5% to 15% EtOAc, then maintained 15% EtOAc/Hex) to give ethyl 2-benzyl-2H-tetrazole-5-carboxylate (342 mg, 1.473 mmol, 30.4% yield, unoptimized) as a major product: MS (m/z) 233.1 (M+H⁺); ¹H NMR (DMSO-d₆) d: 7.36-7.46 (m, 5H), 6.05 (s, 2H), 4.40 (q, J=7.1 Hz, 2H), 1.33 (t, 3H). The regioisomer ethyl 1-benzyl-1H-tetrazole-5-carboxylate (87 mg, 0.375 mmol, 7.73% yield) was obtained as a minor product: ¹H NMR (DMSO-d₆) d: 7.29-7.43 (m, 5H), 5.92 (s, 2H), 4.44 (q, J=7.1 Hz, 2H), 1.33 (t, 3H) (Note: some mixture of both products was also obtained).

The following intermediate used for the preparation of titled example compounds was synthesized using methods analogous to the ones described above.

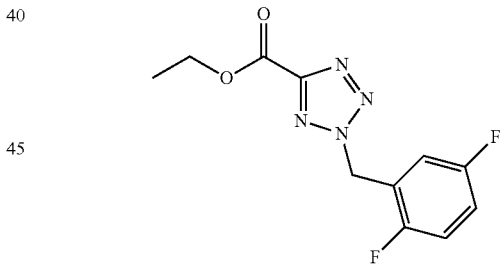

Preparation 70

2-Benzyl-2H-tetrazole-5-carboxylic acid

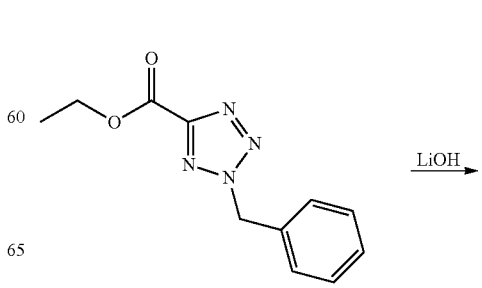

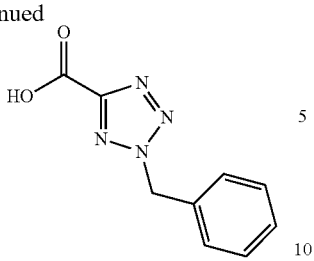

To a solution of ethyl 2-benzyl-2H-tetrazole-5-carboxylate (338 mg, 1.455 mmol) in THF (3 mL) and water (3.00 mL) was added LiOH (183 mg, 4.37 mmol). After stirring for 1 hr at rt, the reaction mixture was concentrated in vacuo and the residual aqueous solution was acidified with 1N HCl (around pH ~2-3). A small amount of white solids was precipitated out. After collecting solids, the aqueous solution was placed in a hood and allowed to slow evaporation of water. Another white solid was obtained (followed this step two more times. Note: some product was still detected in water). The combined solid was dried in a vacuum oven at 50° C. to give 2-benzyl-2H-tetrazole-5-carboxylic acid (167.4 mg, 0.820 mmol, 56.3% yield) as white solids. MS (m/z) 205.0 (M+H⁺). ¹H NMR (DMSO-d₆) δ: 14.30 (br. s., 1H), 7.33-7.49 (m, 5H), 6.03 (s, 2H).

The following intermediates used for the preparation of titled example compounds were synthesized using methods analogous to the ones described above.

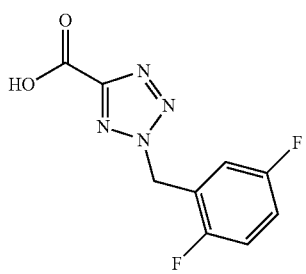 [SMILES: O=C(O)c1nnn(Cc2cc(F)ccc2F)n1]

Preparation 71

Ethyl 5-(difluoro(phenyl)methyl)isoxazole-3-carboxylate

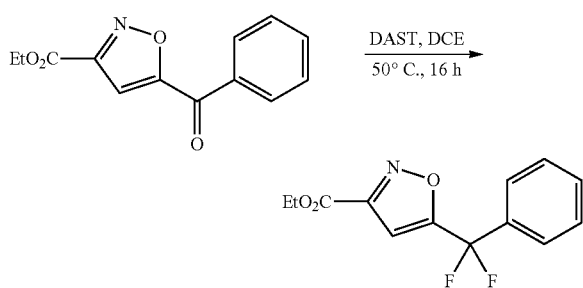

Ethyl 5-benzoylisoxazole-3-carboxylate (630 mg, 2.57 mmol) was dissolved in 2 mL of dichloroethane (DCE), and then a solution of DAST (0.944 mL, 7.71 mmol) in 2 mL of DCE was added dropwise at 0° C. The reaction mixture was maintained at 50° C. for 16 h, and then the mixture was concentrated. The resulting brown residue was purified by Isco Combiflash (10%-30% EtOAc/Hexane; 80 g Isco RediSep column). Collected fractions containing the product were combined and concentrated to give the desired product as a yellow oil (207 mg, 31% yield). ¹H NMR (CDCl₃) δ ppm 7.56-7.64 (m, 2H), 7.45-7.56 (m, 3H), 6.87 (s, 1H), 4.45 (q, J=7.2 Hz, 4H), 1.41 (t, J=7.1 Hz, 3H); MS (m/z): 268 (M+H⁺).

Preparation 72

5-(difluoro(phenyl)methyl)isoxazole-3-carboxylic Acid

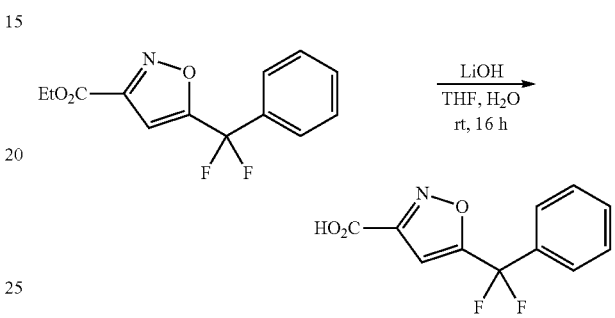

Ethyl 5-(difluoro(phenyl)methyl)isoxazole-3-carboxylate (207 mg, 0.775 mmol) was dissolved in 2 mL of THF, and then lithium hydroxide monohydrate (48.8 mg, 1.162 mmol) was added. The reaction mixture was maintained at rt for 16 h. The rxn mixture was neutralized by adding a solution of 4N HCl/dioxane dropwise. The mixture was then filtered and the filtrate was concentrated to a yellow oil (185 mg, 100% yield). MS (m/z): 240 (M+H⁺).

Preparation 73

5-(hydroxy(phenyl)methyl)isoxazole-3-carboxylic acid

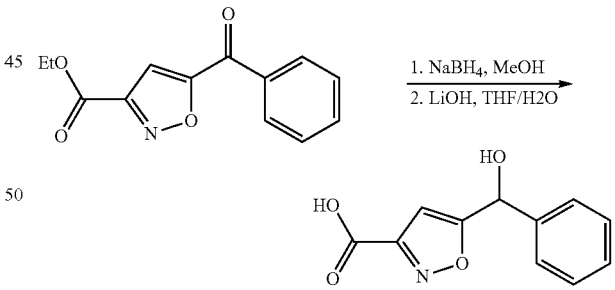

Ethyl 5-benzoylisoxazole-3-carboxylate (400 mg, 1.631 mmol) was dissolved in 5 mL MeOH, and then NaBH₄ (93 mg, 2.447 mmol) was added at 0° C. The reaction mixture was maintained at rt for 16 h. The mixture was concentrated, and then partitioned between sat. NaHCO₃₍ₐq₎ and DCM. The organic layer was concentrated and dissolved in 1 mL THF. An aqueous solution of LiOH (1.2 mL, 50 mg/ml solution) was added to this THF solution. The mixture was maintained at rt for 16 h. A solution of HCl (0.8 mL, 4N in dioxane) was added to the mixture. The organic layer was separated and concentrated to a yellow oil (190 mg, 53% yield). ¹H NMR (DMSO-d₆) δ ppm 7.26-7.54 (m, 6H), 6.50 (s, 2H), 5.91 (s, 1H); MS (m/z): 220 (M+H⁺).

Preparation 74

Ethyl 5-benzylisoxazole-3-carboxylate

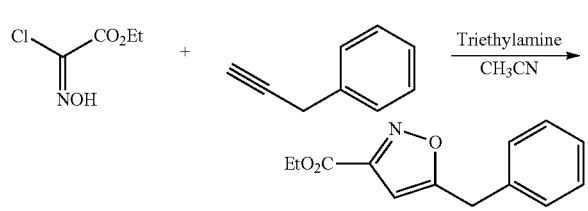

A solution of the ethyl 2-chloro-2-(hydroxyimino)acetate (39.1 g, 258 mmol) was dispensed into a solution of prop-2-yn-1-ylbenzene (10 g, 86 mmol) and triethylamine (29.4 mL, 430 mmol) in $CH_3CN$ (300 mL). After standing for overnight at 80° C. the solvent was removed in vacuum. The crude was dissolved in EtOAc (200 mL) and was washed with saturated sodium bicarbonate solution (50 mL), water (50 mL) and saturated brine (50 mL). The organic phase was separated and dried over sodium sulphate and evaporated in vacuo to give ethyl 5-benzylisoxazole-3-carboxylate (6 g, 25.9 mmol, 30% yield) as a yellow solid. Used directly in the next step without further purification. MS (m/z): 232 (M+H$^+$).

Preparation 75

5-Benzylisoxazole-3-carboxylic Acid

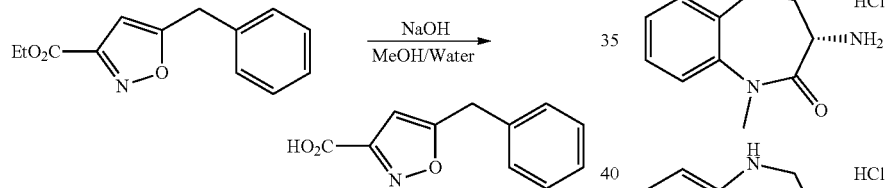

A solution of the ethyl 5-benzylisoxazole-3-carboxylate (6 g, 25.9 mmol) was dispensed into a solution of the sodium hydroxide (2.1 mL, 78 mmol) in methanol (100 mL) and water (10 mL). After standing for 2 h at 20° C., the solvent was removed in vacuum. The residue was acidified with dilute HCl (20 mL) and then extracted with EtOAc (50 mL). The organic phase was washed with water (20 mL) and saturated brine (20 mL), and dried over sodium sulphate. Evaporation in vacuo gave 5-benzylisoxazole-3-carboxylic acid (3.2 g, 15.31 mmol, 59.0% yield) as a yellow solid. $^1$H NMR (DMSO-d$_6$) δ ppm 14.0 (bs, 1H), 7.2-7.4 (m, 5H), 6.6 (s, 1H), 4.2 (s, 2H); MS (m/z): 204 (M+H$^+$).

Preparation 76

(S)-3-amino-5-methyl-2,3-dihydrobenzo[b][1,4]oxazepin-4(5H)-one hydrochloride

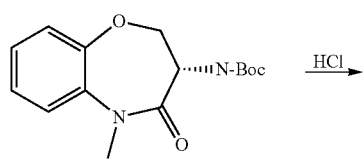

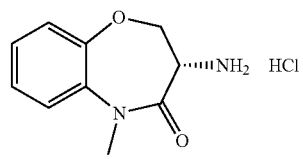

To a solution of (S)-tert-butyl (5-methyl-4-oxo-2,3,4,5-tetrahydrobenzo[b][1,4]oxazepin-3-yl)carbamate (28 g, 96 mmol)) in DCM (300 mL) was added 4M HCl (71.8 mL, 287 mmol) and reaction stirred under nitrogen at room temp for 3 hr. The solvents were evaporated to dryness to yield the crude compound which was triturated with diethyl ether (200 mL), filtered and dried in vacuo to afford (S)-3-amino-5-methyl-2,3-dihydrobenzo[b][1,4]oxazepin-4(5H)-one hydrochloride (22.2 g, 97 mmol, 101% yield) as brown solid. MS (m/z): 193.20 (M+H$^+$).

The following intermediates used for the preparation of titled example compounds were synthesized using methods analogous to the ones described above.

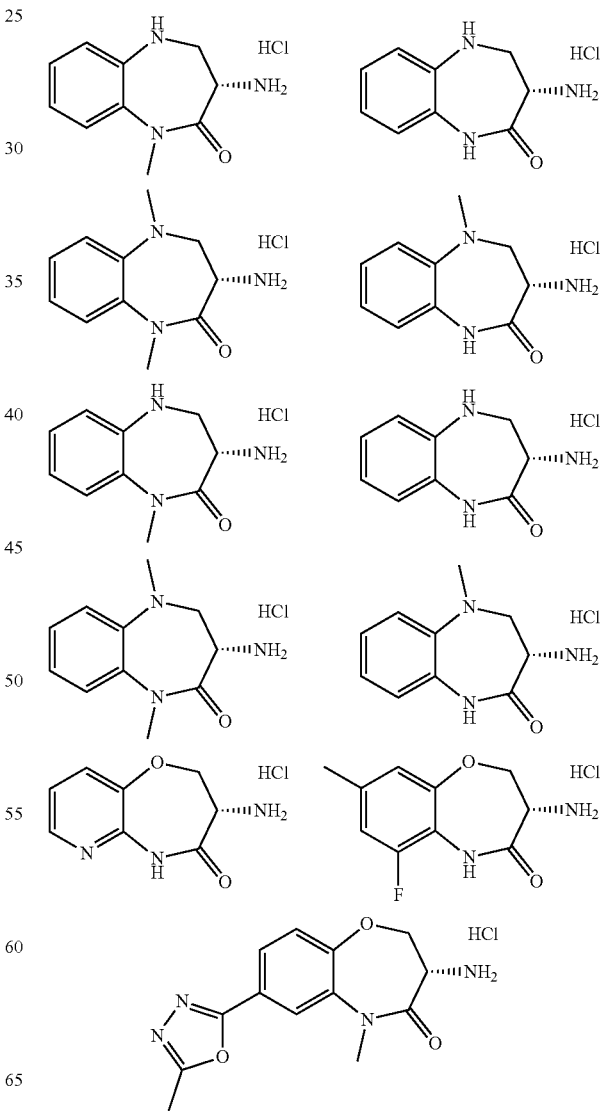

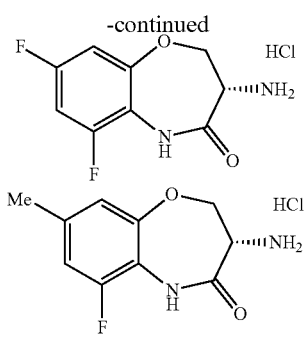

Preparation 77

5-(4-Chlorobenzyl)isoxazole-3-carboxylic Acid

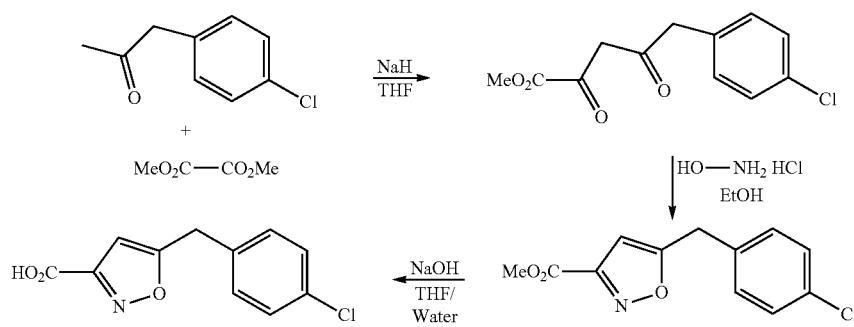

To a solution of 1-(4-chlorophenyl)propan-2-one (10 g, 59.3 mmol) in THF (150 mL) in an ice bath was added NaH (1.423 g, 59.3 mmol) portion wise over 30 min. Dimethyl oxalate (7.0 g, 59.3 mmol) was added at room temperature for 1 hour and the mixture was stirred at 25° C. for 2 hours. The solvent was removed in vacuo and the residue was dissolved in EtOAc which was washed with water. The aqueous phase was separated and extracted with EtOAc. The combined organic phases were dried over Na$_2$SO$_4$, filtered, and concentrated in vacuo to give methyl 5-(4-chlorophenyl)-2,4-dioxopentanoate (15 g, 50.1 mmol, 84% yield) as an oil which was used in next step without further purification. MS (m/z): 255/257 (M+H$^+$).

To a solution of methyl 5-(4-chlorophenyl)-2,4-dioxopentanoate (5 g, 19.63 mmol) in ethanol (80 mL) was added hydroxylamine hydrochloride (1.364 g, 19.63 mmol) and then the mixture was stirred at 78° C. for 2 hours monitored. The solvent was removed in vacuo and the residue was dissolved in EtOAc which was washed with water. The aqueous phase was separated and extracted with EtOAc. The combined organic phases were dried over Na$_2$SO$_4$, filtered, and concentrated in vacuo to give methyl 5-(4-chlorobenzyl) isoxazole-3-carboxylate (4.7 g, 16.81 mmol, 86% yield) as a solid, which was used in next step without further purification. MS (m/z): 252/254 (M+H$^+$).

To a solution of methyl 5-(4-chlorobenzyl)isoxazole-3-carboxylate (100 mg, 0.397 mmol) in THF (5 mL) in an ice bath was added a solution of NaOH (15.89 mg, 0.397 mmol) in water (5 mL). The mixture was stirred at room temperature for 2 hours. The solvent was removed in vacuo and the residue was dissolved in water. The aqueous solution was acidified by addition of 1N HCl to pH=2-3. The resulting solid which deposited was collected by filtration and dried in vacuo to give pure 5-(4-chlorobenzyl)isoxazole-3-carboxylic acid (90 mg, 0.360 mmol, 91% yield) as a white solid. MS (m/z): 238/240 (M+H$^+$).

Preparation 78

5-((Methyl(phenyl)amino)methyl)-1H-pyrazole-3-carboxylic acid

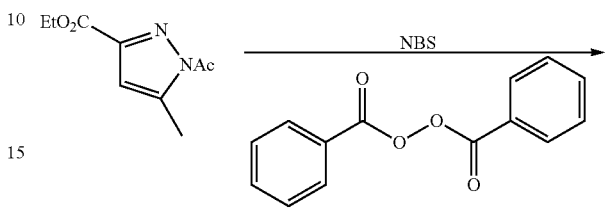

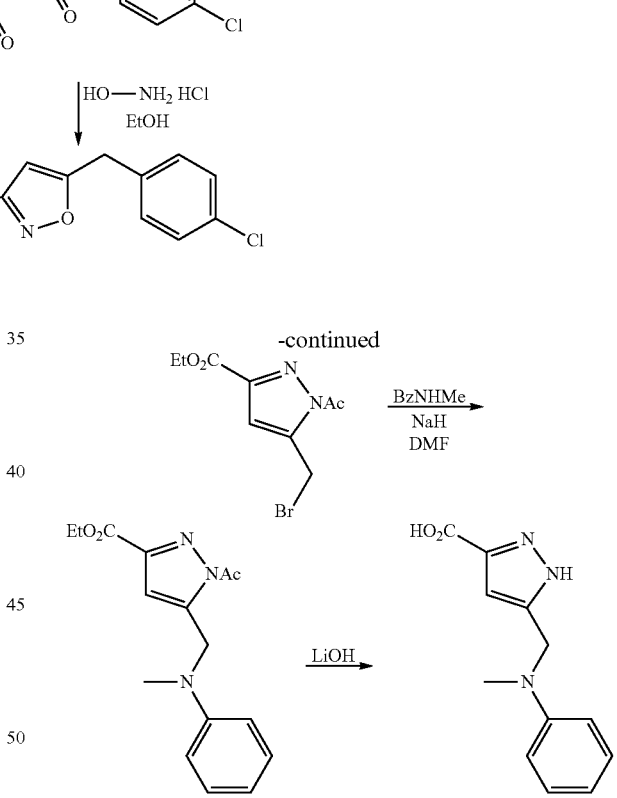

To a mixture of ethyl 1-acetyl-5-methyl-1H-pyrazole-3-carboxylate (2 g, 10.19 mmol) and NBS (1.996 g, 11.21 mmol) in CCl$_4$ (20 mL) was added benzoic peroxyanhydride (0.123 g, 0.51 mmol) at room temperature followed by reflux for 5 hours. LCMS showed product with some starting material left. Removed all the solvent and the residue was purified by flash chromatography by solid loading (eluting 0-30% of ethyl acetate in hexane) to afford the product. Combined the fractions and removed all the solvents to afford the crude product as ethyl 1-acetyl-5-(bromomethyl)-1H-pyrazole-3-carboxylate (1.6 g, 5.82 mmol, 57.1% yield) MS (m/z) 232/234 (M+H$^+$,-Acetyl)

To a solution of N-methylaniline (42.9 mg, 0.4 mmol) in DMF (2 mL) at 20° C. was added NaH (21.84 mg, 0.546 mmol). The reaction mixture was stirred for 5 min. Then ethyl 1-acetyl-5-(bromomethyl)-1H-pyrazole-3-carboxylate (100 mg, 0.364 mmol) was added and the mixture were stirred at room temperature for 3 more hours. LCMS indicated the reaction was completed. The reaction was quenched with drop of water and the solvents were removed to dryness. The crude ethyl 1-acetyl-5-((methyl(phenyl)amino)methyl)-1H-pyrazole-3-carboxylate (100 mg, 91%) was used for hydrolysis without further purification. MS (m/z) 260 (M+H$^+$-Acetyl).

To a solution of ethyl 1-acetyl-5-((methyl(phenyl)amino)methyl)-1H-pyrazole-3-carboxylate (110 mg, 0.365 mmol) in THF (2 mL) was added a solution of LiOH (1.825 mL, 3.65 mmol) in water (1.0 mL). The reaction mixture was stirred at room temperature for 16 hours and then heated to 50° C. for 4 h at which time LCMS showed hydrolysis was completed. Cooled to 0° C. and added 1N HCl until pH=2. The resulting solid was filtered and dried under vacuum. The 5-((methyl(phenyl)amino)methyl)-1H-pyrazole-3-carboxylic acid (80 mg, 95%) was used as such without further purification. MS (m/z)=231 (M+H$^+$)

Preparation 79

5-(3-fluorobenzyl)-4H-1,2,4-triazole-3-carboxylic acid

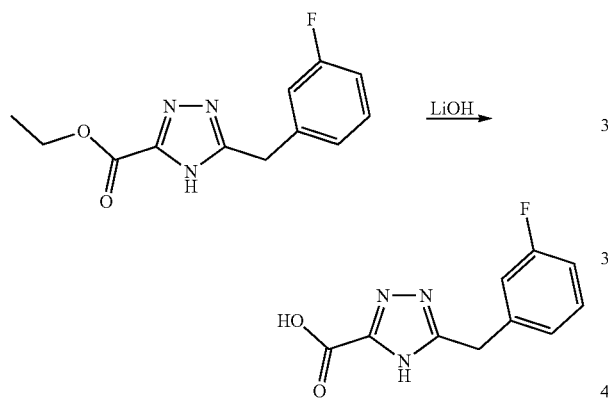

Freshly prepared LiOH (11.03 mL, 22.07 mmol) was added to a stirring, room temperature solution of ethyl 5-(3-fluorobenzyl)-4H-1,2,4-triazole-3-carboxylate (1.1 g, 4.41 mmol) in THF (10 mL) under N$_2$. The reaction was then stirred at rt for 5 h and LCMS showed the reaction was complete. The reaction was concentrated and then dissolved in 10.0 mL H$_2$O. 2N HCl was added dropwise until the pH=4. The white solid that precipitated from the reaction was filtered off and washed with cold H$_2$O. The solid was dried under vacuum overnight to obtain title product. 5-(3-fluorobenzyl)-4H-1,2,4-triazole-3-carboxylic acid (750 mg, 3.39 mmol, 77% yield). MS (m/z) 222 (M+H$^+$).

Preparation 80

(S)-tert-butyl (1-methyl-2-oxo-2,3,4,5-tetrahydro-1H-benzo[b][1,4]diazepin-3-yl)carbamate

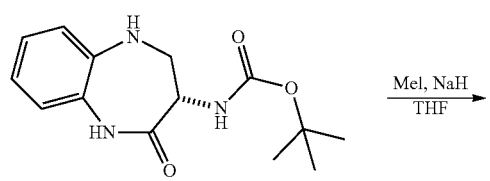

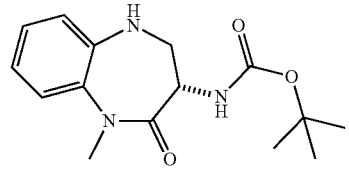

To a suspension of NaH (72.1 mg, 1.803 mmol) in THF (25 mL) stirred under nitrogen at room temp was added a solution of (S)-tert-butyl (2-oxo-2,3,4,5-tetrahydro-1H-benzo[b][1,4]diazepin-3-yl)carbamate (500 mg, 1.803 mmol) in THF (10 mL) dropwise during 5 min. The reaction mixture was stirred at room temperature for 1 hour and then iodomethane (0.114 mL, 1.821 mmol) was added dropwise during 2 min. The reaction mixture was stirred at room temperature for 36 hours. Reaction was quenched with water (40 mL) and extracted with EtOAc (3×75 mL). The organic layer was dried over anh. Na$_2$SO$_4$ and concentrated to provide the crude product (700 mg). This was purified by silica gel column using 25-50% EtOAc in Hexane to afford (S)-tert-butyl (1-methyl-2-oxo-2,3,4, 5-tetrahydro-1H-benzo[b][1,4]diazepin-3-yl)carbamate (340 mg, 1.162 mmol, 64% yield) as off-white solid. MS (m/z) 192.15 ([M-BOC]+H$^+$).

Preparation 81

(S)-Tert-butyl (1,5-dimethyl-2-oxo-2,3,4,5-tetrahydro-1H-benzo[b][1,4]diazepin-3-yl)carbamate

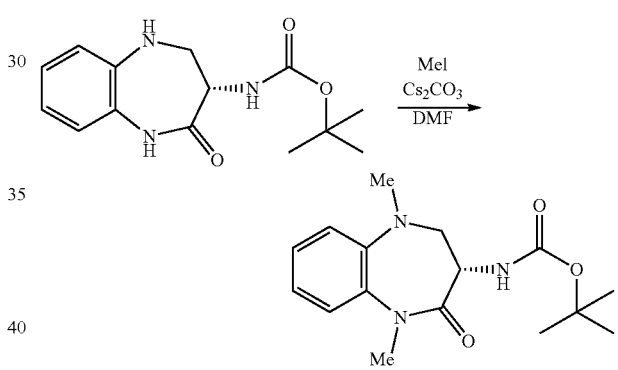

To a solution of (S)-tert-butyl (2-oxo-2,3,4,5-tetrahydro-1H-benzo[b][1,4]diazepin-3-yl)carbamate (167 mg, 0.602 mmol) in DMF (2 mL) was added Cs$_2$CO$_3$ (785 mg, 2.409 mmol) followed by MeI (0.113 mL, 1.807 mmol). The reaction mixture was stirred at room temperature overnight. The solution was diluted with EtOAc and washed with water and brine, dried over Na$_2$SO$_4$ and concentrated. The crude material was purified by biotage column (10 to 60% EA/Hexane) to provide (S)-tert-butyl (1,5-dimethyl-2-oxo-2,3,4,5-tetrahydro-1H-benzo[b][1,4]diazepin-3-yl)carbamate (123 mg, 0.403 mmol, 66.9% yield).

Preparation 82

(S)-tert-butyl (1-methyl-4-oxo-2,3,4,5-tetrahydro-1H-benzo[b][1,4]diazepin-3-yl)carbamate

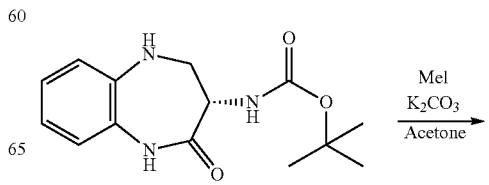

-continued

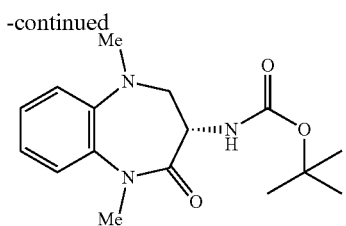

To a suspension (S)-tert-butyl (2-oxo-2,3,4,5-tetrahydro-1H-benzo[b][1,4]diazepin-3-yl)carbamate (500 mg, 1.803 mmol) and potassium carbonate (336 mg, 2.434 mmol) in acetone (10 mL) was added iodomethane (1.240 mL, 19.83 mmol). The reaction mixture was sealed and heated 80° C. using CEM Microwave operator for 40 min. After cooling, to the reaction mixture was filtered and concentrated under reduced pressure to afford the crude product (600 mg). The crude was purified by silica gel (100-200 mesh) flash chromatography using 20-40% ethyl acetate in hexane as an eluent to afford (S)-tert-butyl (1-methyl-4-oxo-2,3,4,5-tetrahydro-1H-benzo[b][1,4]diazepin-3-yl)carbamate (390 mg, 1.298 mmol, 72.0% yield). TLC: 30% EtOAc in Hexane; Rf: 0.35. MS (m/z) 290.21 (M+H$^+$).

Preparation 83

2-(4-Fluoro-3-nitrophenyl)-5-methyl-1,3,4-oxadiazole

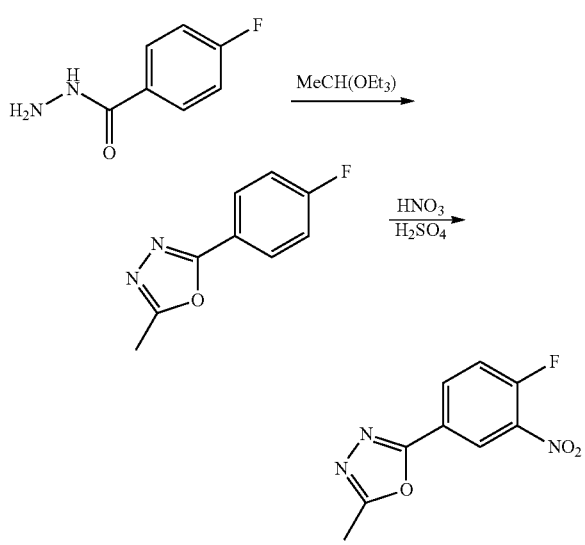

To a suspension of 4-fluorobenzohydrazide (18 g, 117 mmol) in 1,1,1-triethoxyethane (85 ml, 467 mmol) was heated at 150° C. After refluxing for 24 hr at 150° C., the reaction solution was cooled down to room temperature, then a solid precipitated out. After flushing with nitrogen for 2-3 minutes, the resultant solid was treated with 1-2% ethyl ether in hexane. After collecting and washing solid with hexane followed by drying in vacuo at 50° C., 2-(4-fluorophenyl)-5-methyl-1,3,4-oxadiazole (17.80 g, 99 mmol, 85% yield) was obtained as light brown solid: MS (m/z) 179.0 (M+H$^+$); $^1$H NMR (DMSO-d$_6$) δ: 7.97-8.10 (m, 2H), 7.38-7.51 (m, 2H), 2.58 (s, 3H).

To a suspension (a partial solution, close to dark red color) of 2-(4-fluorophenyl)-5-methyl-1,3,4-oxadiazole (2 g, 11.23 mmol) in concentrated (fuming) H$_2$SO$_4$ (8 ml) at 0° C. was added nitric acid (1.394 ml, 28.1 mmol) (the solution color was changed to orange yellow). After 30 min at 0° C., the reaction solution was poured into cold water (around 300 ml). The resultant solid was collected by filtration and washed with water. The light tan solid was dried over in a vacuum oven at 50° C. for overnight to give 2-(4-fluoro-3-nitrophenyl)-5-methyl-1,3,4-oxadiazole (2.28 g, 10.22 mmol, 91% yield); MS (m/z) 224.0 (M+H$^+$); $^1$H NMR (DMSO-d$_6$) δ: 8.61 (dd, J=7.1, 2.3 Hz, 1H), 8.38 (ddd, J=8.8, 4.3, 2.3 Hz, 1H), 7.84 (dd, J=11.1, 8.8 Hz, 1H), 2.62 (s, 3H).

The following intermediates used for the preparation of titled example compounds were synthesized using methods analogous to the ones described above.

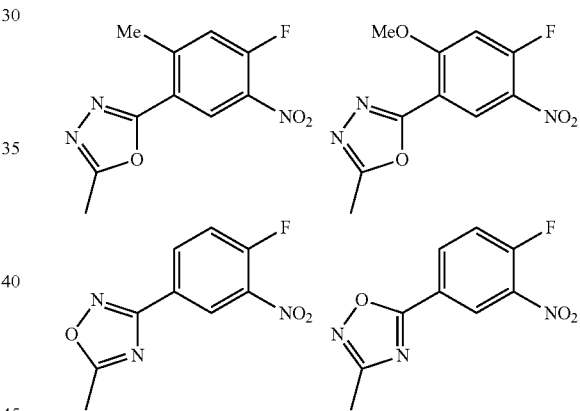

Preparation 84

(S)-3-amino-5-methyl-8-(5-methyl-1,3,4-oxadiazol-2-yl)-2,3-dihydrobenzo[b][1,4]oxazepin-4(5H)-one, bis hydrochloride-chloride

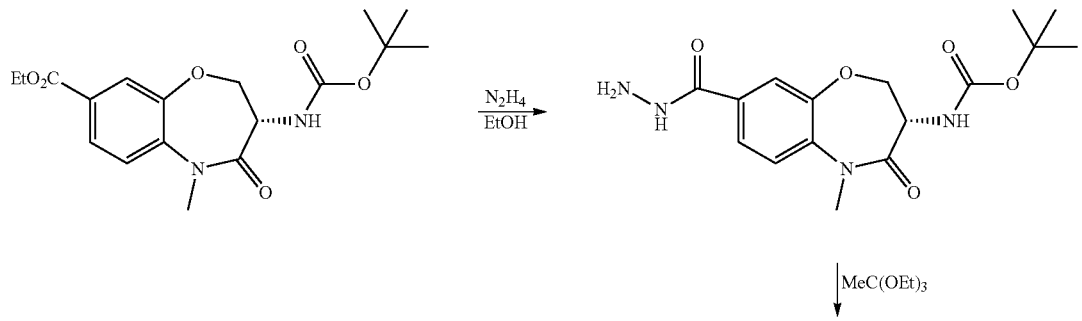

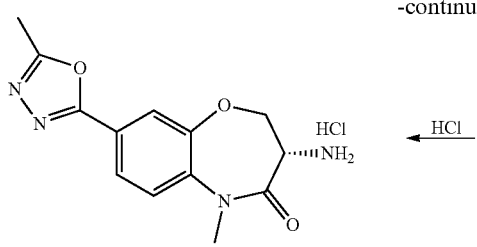 ← HCl 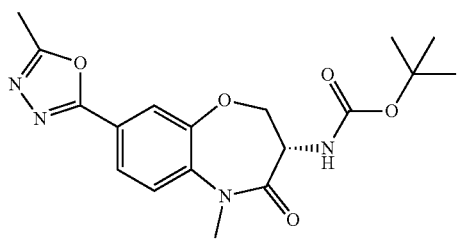

A mixture of (S)-ethyl 3-((tert-butoxycarbonyl)amino)-5-methyl-4-oxo-2,3,4,5-tetrahydro benzo[b][1,4]oxazepine-8-carboxylate (0.45 g, 1.235 mmol) and anhydrous hydrazine (0.465 mL, 14.82 mmol) in EtOH (5.0 mL) was heated to reflux overnight. The solvent was removed in vacuo then the resulting residue was suspended in ethyl ether, filtered and washed with ethyl ether having 5% ethanol to yield (S)-tert-butyl (8-(hydrazinecarbonyl)-5-methyl-4-oxo-2,3,4,5-tetrahydrobenzo[b][1,4]oxazepin-3-yl)carbamate (253.0 mg, 58.5%); MS (m/z): 351.3 (M+H$^+$).

A suspension of (S)-tert-butyl (8-(hydrazinecarbonyl)-5-methyl-4-oxo-2,3,4,5-tetrahydrobenzo[b][1,4]oxazepin-3-yl)carbamate (253.0 mg, 0.722 mmol) in 1,1,1-triethoxyethane (2896 μl, 15.89 mmol) was heated to 150° C. under nitrogen. After 2 h the reaction mixture was cooled to room temperature. On cooling, the solid product precipitated and was collected by filtration then washed with a small amount of ethyl ether to give (S)-tert-butyl (5-methyl-8-(5-methyl-1,3,4-oxadiazol-2-yl)-4-oxo-2,3,4,5-tetrahydrobenzo[b][1,4]oxazepin-3-yl)carbamate (165.0 mg, yield 61%). $^1$H NMR (DMSO-d$_6$) D: 7.89 (dd, J=8.5, 1.9 Hz, 1H), 7.66-7.78 (m, 2H), 7.25 (d, J=6.6 Hz, 1H), 4.42 (br. s., 3H), 3.33 (br. s., 3H), 2.60 (s, 3H), 1.35 (s, 9H); MS (m/z): 375.3 (M+H$^+$).

To a solution of (S)-tert-butyl (5-methyl-8-(5-methyl-1,3,4-oxadiazol-2-yl)-4-oxo-2,3,4,5-tetrahydrobenzo[b][1,4]oxazepin-3-yl)carbamate (165.0 mg, 0.441 mmol) in DCM (3.0 mL) was added a solution of 4M HCl in 1,4 dioxane (1.653 mL, 6.61 mmol). The mixture was stirred at room temperature for 1 h. The solid product precipitated from the reaction mixture and it was collected by filtration, then washed with ethyl ether, to yield (S)-3-amino-5-methyl-8-(5-methyl-1,3,4-oxadiazol-2-yl)-2,3-dihydrobenzo[b][1,4]oxazepin-4(5H)-one, bis hydrochloride-chloride salt (150.0 mg, 89%). MS (m/z): 275.1 (M+H$^+$).

Preparation 85

Ethyl 2-amino-2-(2-(2-phenylacetyl)hydrazono)acetate

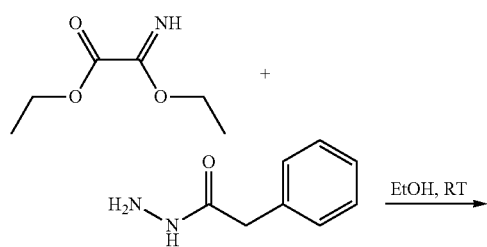 EtOH, RT →

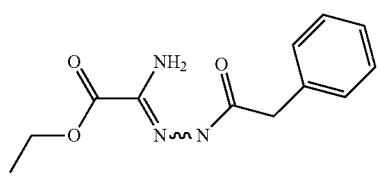

To a solution of 2-phenylacetohydrazide (20 g, 133 mmol) in ethanol (75 mL) and diethyl ether (250 mL) was added ethyl 2-ethoxy-2-iminoacetate (20 g, 138 mmol). Stirred at room temperature for 4 hours. A precipitate started to form after 10 minutes. The resulting solid was filtered off, rinsed with diethyl ether and dried to give ethyl 2-amino-2-(2-(2-phenylacetyl)hydrazono)acetate (27.85 g, yield 82%) as a white solid, which was used without further purification. MS (m/z) 250 (M+H$^+$).

Preparation 86

Ethyl 5-benzyl-4H-1,2,4-triazole-3-carboxylate

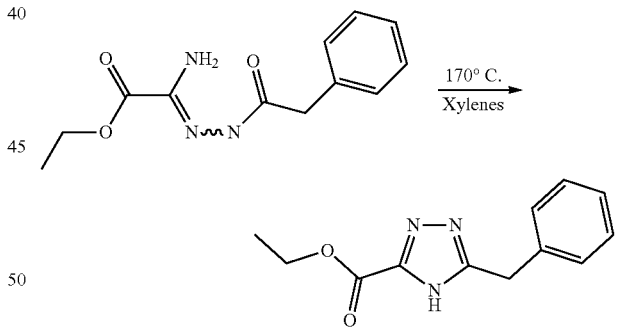

Ethyl 2-amino-2-(2-(2-phenylacetyl)hydrazono)acetate (27.85 g, 109 mmol) was suspended in xylenes (300 mL) and heated at 170° C. for 24 hours with a Dean-Stark trap.

Initially a very thick mixture formed which became light yellow and homogeneous as the reaction progressed. The reaction was cooled to room temperature and a solid precipitated out. Diethyl ether was added and the reaction mixture stirred for 15 minutes in an ice/water bath. The solid was filtered off, rinsing with diethyl ether and hexanes and dried to give ethyl 5-benzyl-4H-1,2,4-triazole-3-carboxylate (24.67 g, 95% yield) as a white solid, which was used without further purification. MS (m/z) 232 (M+H$^+$).

Preparation 87

(S)-tert-butyl (6,8-difluoro-7-methyl-4-oxo-2,3,4,5-tetrahydrobenzo[b][1,4]oxazepin-3-yl)carbamate

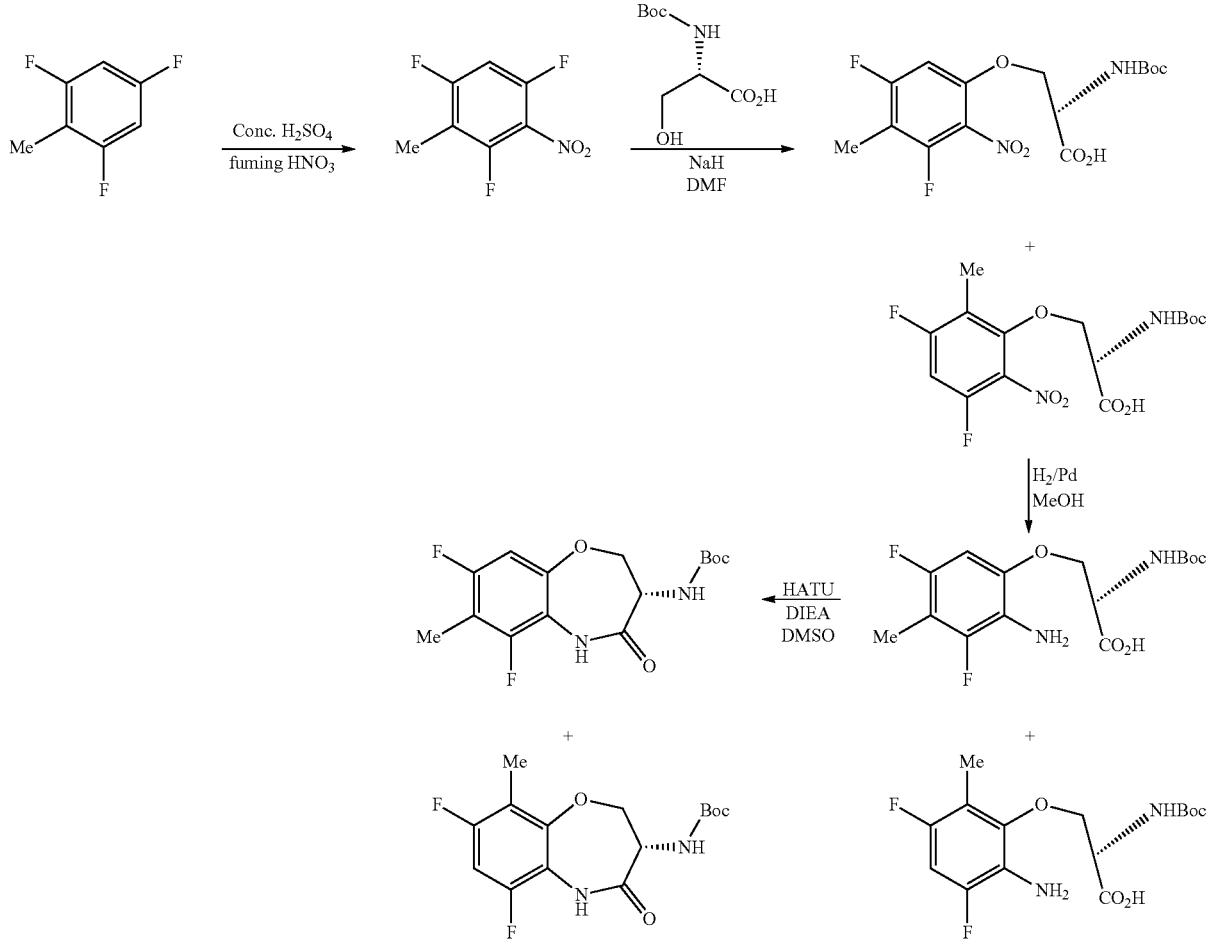

To a solution of 1,3,5-trifluoro-2-methylbenzene (6.0 g, 41.1 mmol) in sulfuric acid (46.0 ml, 862 mmol) stirred at −10° C. was added a mixture of nitric acid (1.835 ml, 41.1 mmol) in sulfuric acid (15.32 ml, 287 mmol) dropwise over 10 min. The reaction mixture was stirred at −10 to 15° C. for 1.5 hr, at which time TLC indicated starting material was consumed. The reaction mixture was poured on to ice-water (500 mL), extracted with DCM (250 mL), and the organic layer was washed with water (100 mL), dried over anh. $Na_2SO_4$ and concentrated to afford 1,3,5-trifluoro-2-methyl-4-nitrobenzene (6.9 g, 31.3 mmol, 76% yield) as yellow liquid. TLC: 20% EtOAc in hexane; Rf: 0.65. GCMS (m/z) 191 (M+).

To a solution of 1,3,5-trifluoro-2-methyl-4-nitrobenzene (6.9 g, 36.1 mmol) and NaH (2.89 g, 72.2 mmol) in DMF (70 mL) stirred under nitrogen at 0° C. was added a solution of (S)-2-((tert-butoxycarbonyl)amino)-3-hydroxypropanoic acid (7.41 g, 36.1 mmol) in DMF (70 mL) dropwise during 5 min. The reaction mixture was stirred at 0-25° C. for 3 hr at which time TLC indicated starting material was consumed. 0.5M HCl (250 mL) was then added, and the aqueous phase extracted with EtOAc (500 mL). The organic layer was washed with water (100 mL×2), followed by brine (100 mL). The organic layer was dried over anh. $Na_2SO_4$, filtered and concentrated to yield the crude (S)-2-((tert-butoxycarbonyl)amino)-3-(3,5-difluoro-2-methyl-6-nitrophenoxy)propanoic acid and (S)-2-((tert-butoxycarbonyl) amino)-3-(3,5-difluoro-4-methyl-2-nitrophenoxy)propanoic acid (1:1 mixture) (12 g, 32 mmol, 89% yield) as yellow gum. This crude compound was carried over to next step. TLC: 10% MeOH in DCM; Rf: 0.3. MS (m/z) 375 (M–H+).

To a solution of (S)-2-((tert-butoxycarbonyl)amino)-3-(3,5-difluoro-2-methyl-6-nitrophenoxy)propanoic acid compound and (S)-2-((tert-butoxycarbonyl)amino)-3-(3,5-difluoro-4-methyl-2-nitrophenoxy)propanoic acid (1:1) (12 g, 32 mmol) in methanol (250 mL) stirred under nitrogen at room temp was added palladium on carbon (2.55 g, 2.392 mmol) portionwise during 5 min. The contents were stirred under hydrogen at a pressure of 60 PSI at 25° C. for 3 hr, at which time TLC indicated starting material was consumed. The reaction mixture was filtered through a celite pad, washed with excess methanol (300 mL) and concentrated to provide the crude (S)-3-(2-amino-3,5-difluoro-4-methylphenoxy)-2-((tert-butoxycarbonyl)amino)propanoic acid compound and (S)-3-(2-amino-3,5-difluoro-6-methylphenoxy)-2-((tert-butoxycarbonyl)amino)propanoic acid (1:1 mixture) (9 g, 92% recovery). TLC: 10% MeOH in DCM; Rf: 0.4. This compound was used to next step without further purification.

To a solution of (S)-3-(2-amino-3,5-difluoro-4-methylphenoxy)-2-((tert-butoxycarbonyl)amino)propanoic acid compound and (S)-3-(2-amino-3,5-difluoro-6-methylphenoxy)-2-((tert-butoxycarbonyl)amino)propanoic acid (1:1) (9 g, 26.0 mmol) and DIEA (6.81 mL, 39.0 mmol) in DMSO (90 mL) stirred under nitrogen at 20° C. was added HATU (9.88 g, 26.0 mmol) portionwise during 5 min. The reaction mixture was stirred at 25° C. for 20 h, at which time TLC indicated starting material was consumed. Reaction was quenched with water (500 mL), extracted with EtOAc (300 mL) and the organic layer was dried over anh. Na$_2$SO$_4$, filtered and concentrated to yield the crude product. This was purified by prep. HPLC to afford a regioisomeric mixture of (S)-tert-butyl (6,8-difluoro-7-methyl-4-oxo-2,3,4,5-tetrahydrobenzo[b][1,4]oxazepin-3-yl)carbamate and (S)-tert-butyl (6,8-difluoro-9-methyl-4-oxo-2,3,4,5-tetrahydrobenzo[b][1,4]oxazepin-3-yl)carbamate (1.98 g, 23%) as a pale brown solid. The desired regioisomer was isolated by chiral HPLC (column: Chiralpak-IC (250*30*5.0μ), mobile phase: n-hexane:IPA (80:20), flow rate: 30 ml/min) of the regioisomeric mixture (2.57 g, 7.8 mmol) to afford (S)-tert-butyl (6,8-difluoro-7-methyl-4-oxo-2,3,4,5-tetrahydrobenzo[b][1,4]oxazepin-3-yl)carbamate (710 mg, 27% recovery) as an off-white solid. $^1$H NMR (DMSO-d$_6$) δ: 9.8 (s, 1H), 7.15 (m, 1H), 6.95 (m, 1H), 4.35 (m, 3H), 3.15 (s, 3H), 1.35 (s, 9H). MS (m/z) 329 (M+H$^+$).

Preparation 88

7-Chloro-9-fluoro-4,5-dihydro-1H-benzo[b]azepin-2(3H)-one

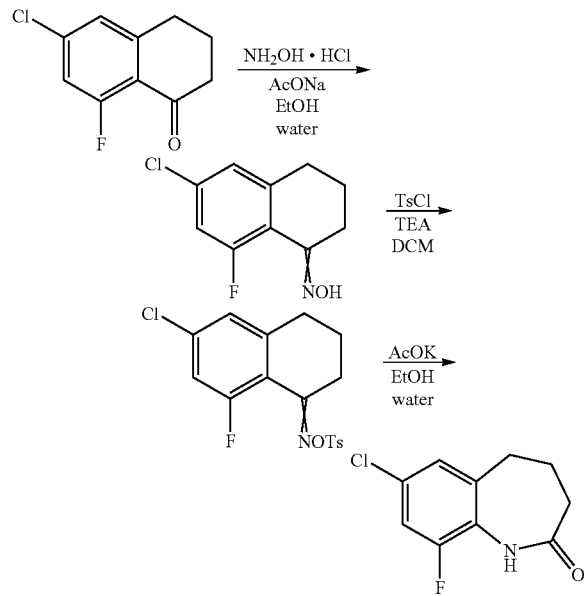

To a solution of 6-chloro-8-fluoro-3,4-dihydronaphthalen-1(2H)-one (3.2 g, 16.11 mmol) in ethanol (32 mL) and water (16 mL) stirred in air at room temp was added sodium acetate (2.64 g, 32.2 mmol) and hydroxylamine hydrochloride (2.239 g, 32.2 mmol) in one charge. The reaction mixture was stirred at 100° C. for 1 h. Reaction was monitored by TLC using 20% of ethyl acetate in hexane as mobile phase (twice elution). On completion of the reaction, the reaction mixture was evaporated to dryness and 25 mL of water was added. The suspension was stirred for 5 min and filtered, washed with water (10 mL), hexane (10 mL) and dried under vacuum to give 6-chloro-8-fluoro-3,4-dihydronaphthalen-1(2H)-one oxime (3.35 g, 15.68 mmol, 97% yield) as a pale brown solid, as a 1:1 mixture of syn and anti stereoisomers. MS (m/z) 214/216 (M+H$^+$).

To a solution of 6-chloro-8-fluoro-3,4-dihydronaphthalen-1(2H)-one oxime (3.2 g, 14.98 mmol) and TEA (6.26 mL, 44.9 mmol) in DCM (90 mL) stirred under nitrogen at 5° C. was added tosyl-chloride (8.57 g, 44.9 mmol) portionwise during 5 min. The reaction mixture was allowed to stir at rt for 18 hr. After completion of the reaction (monitored by TLC, 20% ethyl acetate in hexane), the reaction mixture was diluted with water, extracted with DCM (2×90 mL). The organic layer was separated and washed with water (2×50 mL), and the combined organic phases were washed with brine, dried over anhydrous sodium sulfate and evaporated under reduced pressure to afford the crude product. The crude product was added to a silica gel column and was eluted with Hexane/EtOAc. Collected product fractions: from 5-6% EtOAc elution were concentrated under reduced pressure to afford 6-chloro-8-fluoro-3,4-dihydronaphthalen-1(2H)-one O-tosyl oxime (3.0 g, 6.61 mmol, 44.1% yield) as a light brown solid, as a 4:1 unassigned mixture of syn and anti stereoisomers. $^1$H NMR (DMSO-d$_6$) δ: 7.95 (m, 2H), 7.35 (m, 2H), 7.0 (m, 2H), 2.85 (m, 2H), 2.65 (m, 2H), 1.8 (m, 2H); MS (m/z) 368/370 (M+H$^+$).

To a solution of 6-chloro-8-fluoro-3,4-dihydronaphthalen-1(2H)-one O-tosyl oxime (3 g, 8.16 mmol) in ethanol (150 mL) and water (80 mL) was added potassium acetate (17.61 g, 179 mmol) and reaction mixture was stirred at 100° C. for 16 h. After the completion of the reaction (monitored the reaction by TLC 30% ethyl acetate in hexane), the reaction mixture was evaporated under reduced pressure to remove the ethanol, remaining aqueous layer was further diluted with water (5 mL) and cooled for 30 min at 5° C. The resulting solid precipitate formed was filtered off, washed with cold water, hexane and dried under vacuum to afford 7-chloro-9-fluoro-4,5-dihydro-1H-benzo[b]azepin-2(3H)-one (1 g, 4.16 mmol, 51.0% yield) as brown solid. $^1$H NMR (DMSO-d$_6$) δ: 9.43 (s, 1H), 7.35 (d, 1H), 7.22 (s, 1H), 2.75 (m, 2H), 2.15 (m, 4H); MS (m/z) 213/215 (M+H$^+$).

Example 1

Method A (R)-5-benzyl-N-(5-methyl-4-oxo-2,3,4,5-tetrahydrobenzo[1,4]thiazepin-3-yl)isoxazole-3-carboxamide

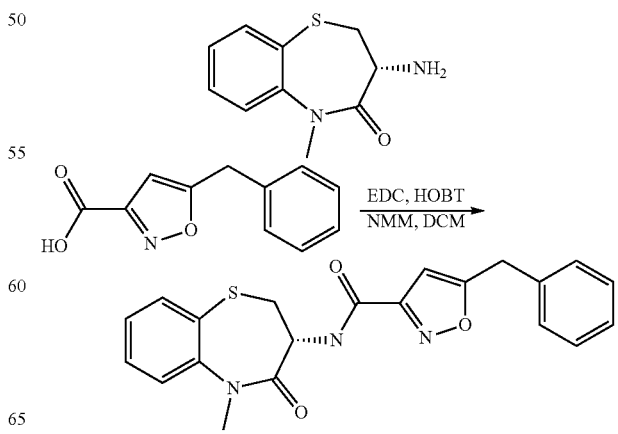

To a solution of 5-benzylisoxazole-3-carboxylic acid (208 mg, 0.919 mmol) in DCM (30 mL) was added N1-((ethylimino)methylene)-N3,N3-dimethylpropane-1,3-diamine hydrochloride (129 mg, 0.674 mmol) and 1H-benzo[d][1,2,3]triazol-1-ol hydrate (103 mg, 0.674 mmol), then 4-methylmorpholine (0.202 mL, 1.839 mmol). Stirred at rt for 5 min, then added (R)-3-amino-5-methyl-2,3-dihydrobenzo[b][1,4]thiazepin-4(5H)-one, hydrochloride (150 mg, 0.613 mmol). The reaction mixture was stirred at 25° C. for 5 h. LCMS showed product and the reaction was completed. Removed all the DCM and added 200 ml of EtOAc and the mixture was washed with water, 0.1N HCl aq, NaHCO$_3$ aq and brine. The organic phase was dried over Na$_2$SO$_4$ and concentrated under reduced pressure to afford crude product. ISCO purification (eluting with 0-50% of EtOAc in hexane) to afford the title compound as (R)-5-benzyl-N-(5-methyl-4-oxo-2,3,4,5-tetrahydrobenzo[b][1,4]thiazepin-3-yl)isoxazole-3-carboxamide. The residue was triturated with ether and hexane. The resulting solid was filtered and rinsed with hexane and collected (200 mg, 83%). 1H NMR (400 MHz, DMSO-d6) δ=8.96 (d, J=7.8 Hz, 1H), 7.67 (d, J=7.3 Hz, 1H), 7.59 (d, J=4.0 Hz, 2H), 7.44-7.19 (m, 6H), 6.52 (s, 1H), 4.62-4.43 (m, 1H), 4.21 (s, 2H), 3.52 (dd, J=6.8, 11.4 Hz, 1H), 3.71-3.44 (m, 1H), 3.30 (s, 3H). MS (m/z) 394 (M+H$^+$).

Example 2

Method B (R)-5-benzyl-N-(5-methyl-1,1-dioxido-4-oxo-2,3,4,5-tetrahydrobenzo[b][1,4]thiazepin-3-yl)isoxazole-3-carboxamide

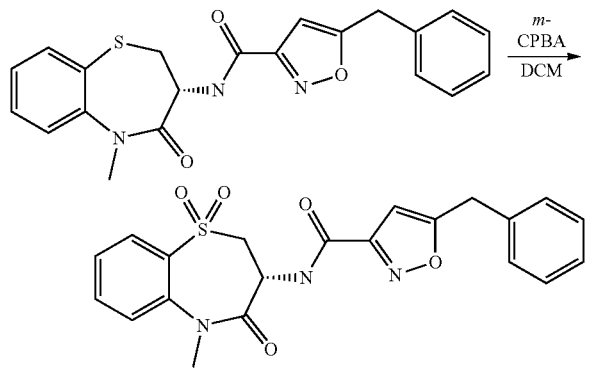

To a solution of (R)-5-benzyl-N-(5-methyl-4-oxo-2,3,4,5-tetrahydrobenzo[b][1,4]thiazepin-3-yl)isoxazole-3-carboxamide (69 mg, 0.175 mmol) in DCM (15 mL) was added 3-chlorobenzoperoxoic acid (101 mg, 0.438 mmol) at 0° C. The reaction mixture was stirred for 1 hr at 0° C. and warmed up to rt, then stirred for 12 hr at rt. The reaction was quenched with cold 1N aq. NaOH solution. After extraction with DCM, the combined organic solution was washed with 2.5% aq. Na$_2$S$_2$O$_3$ solution and brine. After drying over MgSO$_4$, filtration, and concentration, the residue was subjected to the column chromatography (ISCO 40 g, eluent: 5% to 50% EtOAc/Hex) to provide (R)-5-benzyl-N-(5-methyl-1, 1-dioxido-4-oxo-2,3,4, 5-tetrahydrobenzo[b][1,4]thiazepin-3-yl)isoxazole-3-carboxamide (60 mg, 0.141 mmol, 80% yield) as gum. Trituration with DCM and hexane to afford the white solid. 1H NMR (400 MHz, DMSO-d6) δ=9.14 (d, J=7.6 Hz, 1H), 8.06-7.90 (m, 2H), 7.81 (d, J=8.1 Hz, 1H), 7.64 (t, J=7.6 Hz, 1H), 7.49-7.19 (m, 5H), 6.52 (s, 1H), 5.76 (s, 1H), 4.72 (dt, J=7.5, 11.2 Hz, 1H), 4.22 (s, 2H), 4.14-3.95 (m, 2H), 3.29 (s, 3H). MS (m/z) 426 (M+H$^+$).

Examples 3 and 4

Method C 5-benzyl-N-((1 S,3R)-5-methyl-1-oxido-4-oxo-2,3,4,5-tetrahydrobenzo[b][1,4]thiazepin-3-yl)isoxazole-3-carboxamide and 5-benzyl-N-((1R,3R)-5-methyl-1-oxido-4-oxo-2,3,4,5-tetrahydrobenzo[b][1,4]thiazepin-3-yl)isoxazole-3-carboxamide

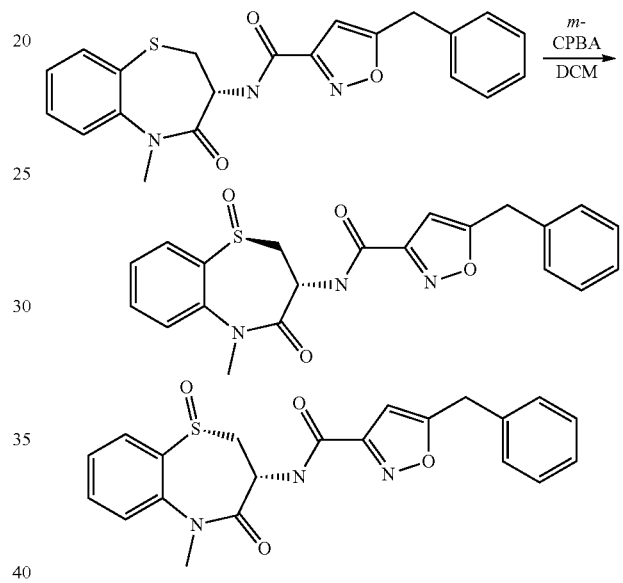

To a solution of (R)-5-benzyl-N-(5-methyl-4-oxo-2,3,4,5-tetrahydrobenzo[b][1,4]thiazepin-3-yl)isoxazole-3-carboxamide (75 mg, 0.191 mmol) in DCM (15 mL) was added 3-chlorobenzoperoxoic acid (54.8 mg, 0.238 mmol) at 0° C. The reaction mixture was stirred for 1 hr at 0° C. and warmed up to rt, then stirred for 12 hr at rt. The reaction was quenched with cold 1N aq. NaOH solution. After extraction with DCM, the combined organic solution was washed with 2.5% aq. Na$_2$S$_2$O$_3$ solution and brine. After drying over MgSO$_4$, filtration, and concentration, the residue was subjected to the column chromatography (ISCO 40 g, eluent: 0% to 40%, then to 60% EtOAc/Hex) to provide 2 isomers as 5-benzyl-N-((1R,3R)-5-methyl-1-oxido-4-oxo-2,3,4,5-tetrahydrobenzo[b][1,4]thiazepin-3-yl)isoxazole-3-carboxamide (64 mg, 0.156 mmol, 82% yield)) and 5-benzyl-N-((1 S,3R)-5-methyl-1-oxido-4-oxo-2,3,4,5-tetrahydrobenzo[b][1,4]thiazepin-3-yl)isoxazole-3-carboxamide (14 mg, 0.034 mmol, 17.94% yield. 5-benzyl-N-((1 S,3R)-5-methyl-1-oxido-4-oxo-2,3,4,5-tetrahydrobenzo[b][1,4]thiazepin-3-yl)isoxazole-3-carboxamide. MS (m/z) 410 (M+H$^+$). $^1$H NMR (400 MHz, DMSO-d6) δ=9.06 (d, J=7.8 Hz, 1H), 7.88-7.75 (m, 1H), 7.73-7.63 (m, 2H), 7.55-7.44 (m, 1H), 7.42-7.20 (m, 4H), 6.54 (s, 1H), 5.76 (s, 1H), 4.73 (dt, J=7.6, 11.1 Hz, 1H), 4.22 (s, 2H), 3.83 (dd, J=7.5, 14.5 Hz, 1H), 3.53 (dd, J=11.1, 14.4 Hz, 1H), 3.25 (s, 3H). 5-benzyl-N-((1R,3R)-5-methyl-1-oxido-4-oxo-2,3,4,5-tetrahydrobenzo[b][1,4]thiazepin-3-yl)isoxazole-3-carboxamide. MS (m/z) 410 (M+H$^+$). $^1$H NMR (DMSO-d$_6$) 8.89-9.19 (m, 1H), 7.56-7.86 (m, 4H), 7.22-7.48 (m, 5H), 6.51 (s, 1H), 4.45-4.65 (m, 2H), 4.13-4.35 (m, 3H), 3.30 (s, 3H).

Example 5

Method D

3-Benzyl-N—((S)-5-methyl-4-oxo-2,3,4,5-tetrahydrobenzo[b][1,4]oxazepin-3-yl)piperidine-1-carboxamide

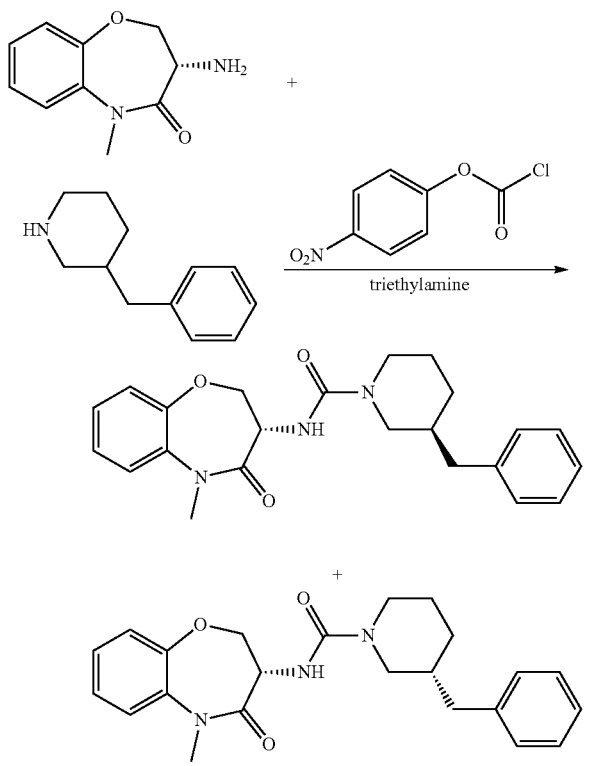

To a suspension of (S)-3-amino-5-methyl-2,3-dihydrobenzo[b][1,4]oxazepin-4(5H)-one, hydrochloride (100 mg, 0.437 mmol) and Et$_3$N (0.152 ml, 1.093 mmol) in THF (4 ml) was added 4-nitrophenyl carbonochloridate (97 mg, 0.481 mmol) at 0° C. After 45 min, 3-benzylpiperidine (0.085 ml, 0.481 mmol) and Et$_3$N (0.091 ml, 0.656 mmol) were added and warmed up to rt. After 2 hr at rt, the reaction mixture was concentrated, then diluted with MeOH-DMSO (2 mL, 1:1). After filtration through Acrodisc CR 25 mm syringe filter with 0.2 uM PTFE membrane, the solution was purified by HPLC (Waters, column: Waters Sunfire 30×150 mm, eluent: Acetonitrile:Water TFA 50-100%, flow rate: 50 ml/min) to give 3-benzyl-N—((S)-5-methyl-4-oxo-2,3,4,5-tetrahydrobenzo[b][1,4]oxazepin-3-yl)piperidine-1-carboxamide (52.2 mg, 0.123 mmol, 28.2% yield, unoptimized) as a mixture of diastereomers. MS (m/z) 393.9 (M+H$^+$). After separation using a chiral column (Chiralpak IA-H, eluent: Co-solvent: IPA, % Co-solvent: 30% Isocratic, Flow rate=4 mL/min), two diastereomers were obtained without assigning the absolute stereochemistry at the C-3 piperidine. Isomer A (9.9 mg): $^1$H NMR (CDCl$_3$) δ: 7.14-7.36 (m, 9H), 5.50 (d, J=6.3 Hz, 1H), 4.86 (dt, J=11.1, 6.8 Hz, 1H), 4.63 (dd, J=9.7, 7.5 Hz, 1H), 4.16 (dd, J=11.2, 9.7 Hz, 1H), 3.87 (dt, J=13.1, 1.6 Hz, 1H), 3.72-3.81 (m, 1H), 3.43 (s, 3H), 2.88 (ddd, J=12.9, 11.4, 3.2 Hz, 1H), 2.52-2.69 (m, 2H), 2.45 (dd, J=13.6, 8.1 Hz, 1H), 1.65-1.81 (m, 3H), 1.36-1.46 (m, 1H), 1.06-1.18 (m, 1H). MS (m/z) 393.9 (M+H$^+$). Isomer B (13.9 mg): $^1$H NMR (CDCl$_3$) δ: 7.09-7.73 (m, 9H), 5.51 (br. s., 1H), 4.79-4.92 (m, 1H), 4.59-4.70 (m, 1H), 4.10-4.20 (m, 1H), 3.89 (m, 1H), 3.77 (m, 1H), 3.42 (s, 3H), 2.77-2.93 (m, 1H), 2.40-2.67 (m, 3H), 1.63-1.81 (m, 3H), 1.38-1.49 (m, 1H), 1.06-1.20 (m, 1H). MS (m/z) 393.9 (M+H$^+$).

Example 6

Method E (S)-5-Benzyl-N-(8-(2-methoxyethoxy)-4-oxo-2,3,4,5-tetrahydrobenzo[b][1,4]oxazepin-3-yl)isoxazole-3-carboxamide

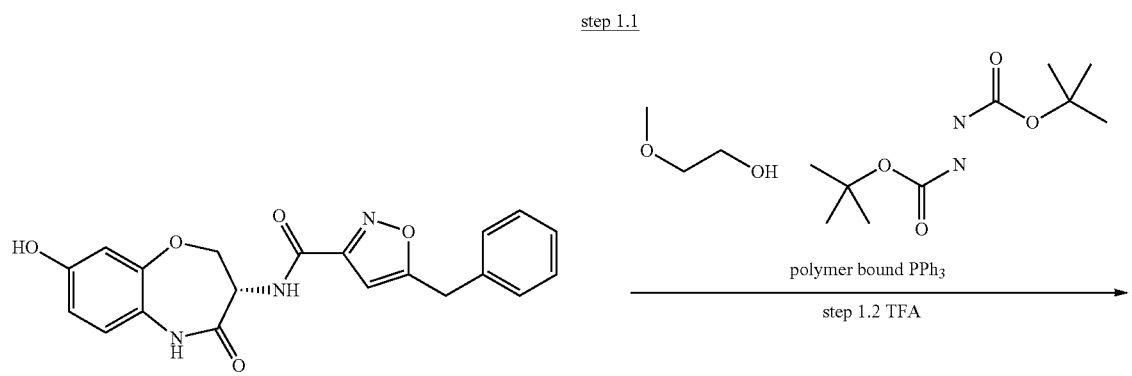

Example 21

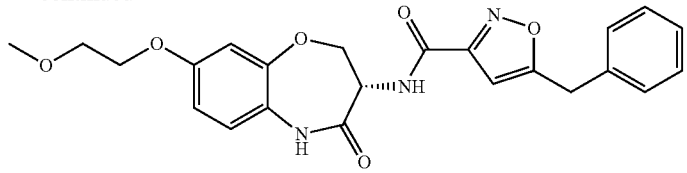

Polymer bound PPh₃ (1.6 mmol/g loading, 2.5 eq, 268 mg), (S)-5-benzyl-N-(8-hydroxy-4-oxo-2,3,4,5-tetrahydrobenzo[b][1,4]oxazepin-3-yl)isoxazole-3-carboxamide (65 mg, 0.171 mmol) and 2-methoxyethanol (0.027 mL, 0.343 mmol) were combined in THF (3 mL). Next added di-tert-butyl azodicarboxylate (79 mg, 0.343 mmol) and stirred mixture at rt for 20 hours. TFA (0.066 mL, 0.857 mmol) was added and mixture was stirred for 1 hour. Reaction was filtered through Celite, rinsing with 10% MeOH/DCM and concentrated. Crude was partitioned between DCM and satd. NaHCO₃ and layers were separated. Organics were concentrated and purified by flash chromatography, Biotage (4 g silica column; 0.5-3% MeOH/DCM (plus NH₄OH), 15 min.) to give 37 mg white foam in 48% yield. ¹H NMR (DMSO-d₆) δ: 9.92 (s, 1H), 8.77 (d, J=8.1 Hz, 1H), 7.25-7.40 (m, 5H), 7.02 (d, J=8.8 Hz, 1H), 6.70-6.79 (m, 2H), 6.57 (s, 1H), 4.80 (dt, J=10.8, 7.4 Hz, 1H), 4.50 (t, J=10.6 Hz, 1H), 4.41 (dd, J=10.5, 6.7 Hz, 1H), 4.23 (s, 2H), 4.01-4.13 (m, 2H), 3.60-3.68 (m, 2H), 3.30 (s, 3H); MS (m/z) 438.3 (M+H⁺).

Example 7

5-Benzyl-N-(1-hydroxy-5-methyl-4-oxo-2,3,4, 5-tetrahydro-1H-benzo[b]azepin-3-yl)isoxazole-3-carboxamide fractions containing the product were combined and concentrated to give benzyl (1-methyl-2,5-dioxo-2,3,4,5-tetrahydro-1H-benzo[b]azepin-3-yl) carbamate as a yellow oil (290 mg, 70% yield). 1H NMR (CDCl₃) d ppm 7.53-7.72 (m, 2H), 7.26-7.44 (m, 6H), 7.21 (d, J=8.1 Hz, 1H), 6.14 (d, J=6.6 Hz, 1H), 5.02-5.18 (m, 2H), 4.95 (ddd, J=12.6, 6.6, 4.0 Hz, 1H), 3.38 (s, 3H), 3.33 (dd, 1H), 2.94 (dd, J=19.3, 12.8 Hz, 1H); MS (m/z): 339 (M+H⁺).

Benzyl (1-methyl-2,5-dioxo-2,3,4,5-tetrahydro-1H-benzo[b]azepin-3-yl) carbamate (290 mg, 0.857 mmol) was dissolved in ethanol (20 mL). Palladium on Carbon (10 wt % loading, 91 mg, 0.857 mmol) was added. The reaction mixture was maintained at room temperature for 3 h under a hydrogen balloon. The reaction mixture was filtered and the filtrate was concentrated to a yellow oil, which was then turned into white solid upon standing under high vacuum for 16 h to yield 3-amino-1-methyl-3,4-dihydro-1H-benzo[b]azepine-2,5-dione (158 mg, 90% yield). 1H NMR (MeOH-d4) d ppm 7.60-7.88 (m, 2H), 7.23-7.59 (m, 2H), 4.50-4.72 (m, 1H), 3.43 (s, 3H), 3.11-3.38 (m, 1H), 2.08-2.31 (m, 1H); MS (m/z): 205 (M+H⁺).

5-Benzylisoxazole-3-carboxylic acid (29.8 mg, 0.147 mmol) was dissolved in DCM (2 mL), and then N-hydroxybenzotriazole (24.75 mg, 0.162 mmol) and EDC (31.0 mg, 0.162 mmol) were added. The mixture was maintained at

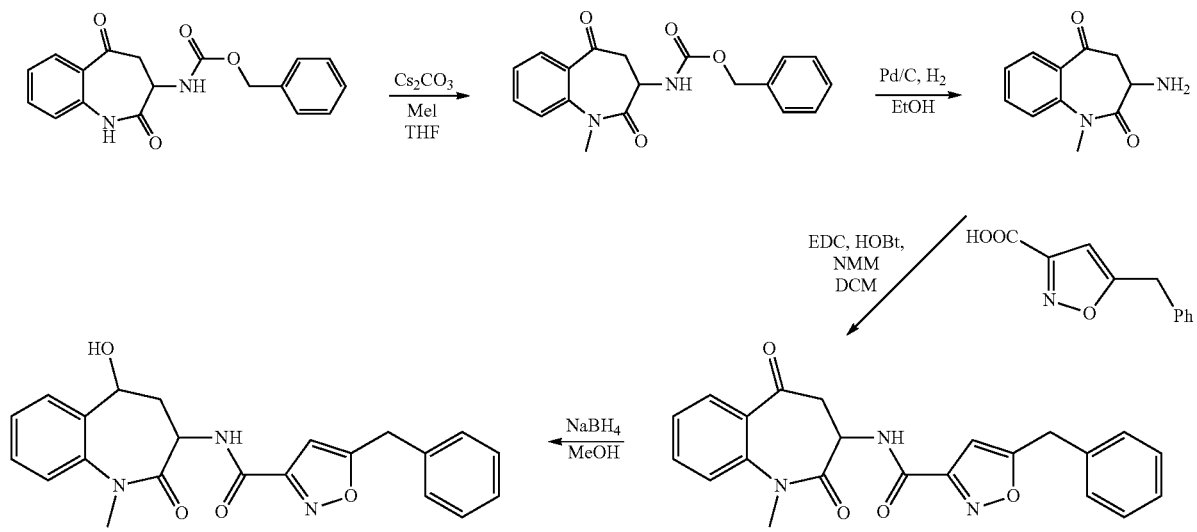

Benzyl (2,5-dioxo-2,3,4,5-tetrahydro-1H-benzo[b]azepin-3-yl)carbamate (400 mg, 1.233 mmol) was dissolved in 10 mL of THF, and then Cs₂CO₃ (1.0 g, 3.08 mmol) was added, followed by methyl iodide (0.116 mL, 1.850 mmol). The reaction mixture was maintained at room temperature for 16 hours. The mixture was then filtered. The filtrate was concentrated, and then purified by Isco Combiflash (15%-80% EtOAc/Hexane; 40 g Isco RediSep column). The room temperature for 10 min. N-methylmorpholine (0.057 mL, 0.514 mmol) and 3-amino-5-methyl-2,3-dihydro-1H-benzo[b]azepine-1,4(5H)-dione (30 mg, 0.147 mmol) were then added. The reaction mixture was maintained at room temperature for 16 h. The mixture was then concentrated and the residue was purified by Isco Combiflash (10%-50% EtOAc/Hexane; 24 g Isco RediSep column). The fractions containing the product were combined and concentrated to give 5-benzyl-N-(5-methyl-1,4-dioxo-2,3,4,5-tetrahydro-1H-benzo[b]azepin-3-yl)isoxazole-3-carboxamid as a clear oil, which turned into a white solid upon standing under high vacuum for 16 h (42 mg, 73% yield). 1H NMR (400 MHz, CDCl$_3$) δ ppm 3.00 (dd, J=19.33, 12.76 Hz, 1H) 3.39-3.48 (m, 4H) 4.13 (s, 2H) 5.26 (ddd, J=12.76, 6.44, 3.79 Hz, 1H) 6.35 (s, 1H) 7.19-7.43 (m, 7H) 7.55-7.72 (m, 2H) 7.99 (d, J=6.57 Hz, 1H); MS (m/z): 390 (M+H$^+$).

5-Benzyl-N-(5-methyl-1,4-dioxo-2,3,4,5-tetrahydro-1H-benzo[b]azepin-3-yl)isoxazole-3-carboxamide (20 mg, 0.051 mmol) was dissolved in 2 mL of MeOH, and then NaBH4 (2.91 mg, 0.077 mmol) was added at rt. The mixture was maintained at rt for 16 h. The mixture was then concentrated and partitioned between sat.NaHCO$_3$ $_{(aq)}$ and DCM. The organic layer was concentrated and the residue was purified by Isco Combiflash (1%-10% MeOH/CH$_2$Cl$_2$, 10% NEt3 in MeOH; 4 g RediSep column). Collected fractions containing the product were combined and concentrated to give 5-benzyl-N-(1-hydroxy-5-methyl-4-oxo-2,3,4,5-tetrahydro-1H-benzo[b]azepin-3-yl)isoxazole-3-carboxamide as a clear oil (14 mg, 70% yield). $^1$H NMR (400 MHz, CDCl$_3$) δ ppm 2.34 (d, J=4.55 Hz, 1H) 2.44 (ddd, J=12.13, 10.86, 7.58 Hz, 1H) 2.67 (td, J=11.68, 8.21 Hz, 1H) 3.43 (s, 3H) 4.12 (s, 2H) 4.51 (dt, J=10.48, 7.89 Hz, 1H) 5.06 (t, J=3.66 Hz, 1H) 6.32 (s, 1H) 7.13-7.45 (m, 8H) 7.67 (dd, J=6.69, 2.15 Hz, 1H) 7.81 (d, J=7.07 Hz, 1H); MS (m/z): 392 (M+H$^+$).

Example 8

(S)-5-benzyl-N-(5-methyl-4-oxo-7-(1H-tetrazol-5-yl)-2,3,4, 5-tetrahydrobenzo[b][1,4]oxazepin-3-yl)isoxazole-3-carboxamide Step 1: (S)-5-benzyl-N-(7-(1-(2-cyanoethyl)-1H-tetrazol-5-yl)-5-methyl-4-oxo-2,3,4,5-tetrahydrobenzo[b][1,4]oxazepin-3-yl)isoxazole-3-carboxamide. To a solution of (S)-3-(5-benzylisoxazole-3-carboxamido)-N-(2-cyanoethyl)-5-methyl-4-oxo-2,3,4,5-tetrahydrobenzo[b][1,4]oxazepine-7-carboxamide (69.0 mg, 0.146 mmol) and pyridine (0.071 mL, 0.874 mmol) in DCM (2.0 mL) was added phosphorus pentachloride (45.5 mg, 0.219 mmol). The reaction mixture was heated to reflux for 3.0 hr then additional 0.25 eq PCl$_5$ was added. The reaction mixture was cooled to rt then TMSN$_3$ (0.110 mL, 0.831 mmol) was added and the reaction mixture was stirred overnight at rt. At 20 h, additional 4.0 eq. of TMS-N$_3$ and 3.0 eq. pyridine were added to the reaction mixture. The reaction mixture was carefully quenched with a few drops of sat. aq. NaHCO$_3$ followed after 5 min with excess NaHCO$_3$. The mixture was stirred for 15 min. The organic phase was separated and washed with 10% aq citric acid and brine. The organic phase was dried over Na$_2$SO$_4$, filtered and concentrated in vacuo. The residue was purified by FCC (EtOAc-Hex: 50-70%). MS (m/z) 499.3 (M+H$^+$).

Step 2: (S)-5-benzyl-N-(5-methyl-4-oxo-7-(1H-tetrazol-5-yl)-2,3,4,5-tetrahydrobenzo[b][1,4]oxazepin-3-yl)isoxazole-3-carboxamide. To a solution of (S)-5-benzyl-N-(7-(1-(2-cyanoethyl)-1H-tetrazol-5-yl)-5-methyl-4-oxo-2,3,4,5-tetrahydrobenzo[b][1,4]oxazepin-3-yl)isoxazole-3-carboxamide (42.0 mg, 0.084 mmol) in THF (2.0 mL) was added 2.0 M NaOH (0.051 mL, 0.101 mmol). The reaction mixture was stirred for 2 h then quenched with cold 1N HCl and extracted with EtOAc. The organic phase was washed with brine, dried over Na$_2$SO$_4$, filtered then concentrated in vacuo. The solid product obtained was used without further purification (36.0 mg, 96%). $^1$H NMR (DMSO-d$_6$) δ: 8.92 (d, J=8.1 Hz, 1H), 8.12 (d, J=2.0 Hz, 1H), 7.94 (dd, J=8.3, 2.3 Hz, 1H), 7.46 (d, J=8.3 Hz, 1H), 7.25-7.39 (m, 6H), 6.55 (s, 1H), 4.87-4.96 (m, 1H), 4.67 (dd, J=11.6, 10.1 Hz, 1H), 4.49 (dd, J=9.9, 7.6 Hz, 1H), 4.22 (s, 2H), 3.39 (s, 3H). MS (m/z) 446.3 (M+H$^+$).

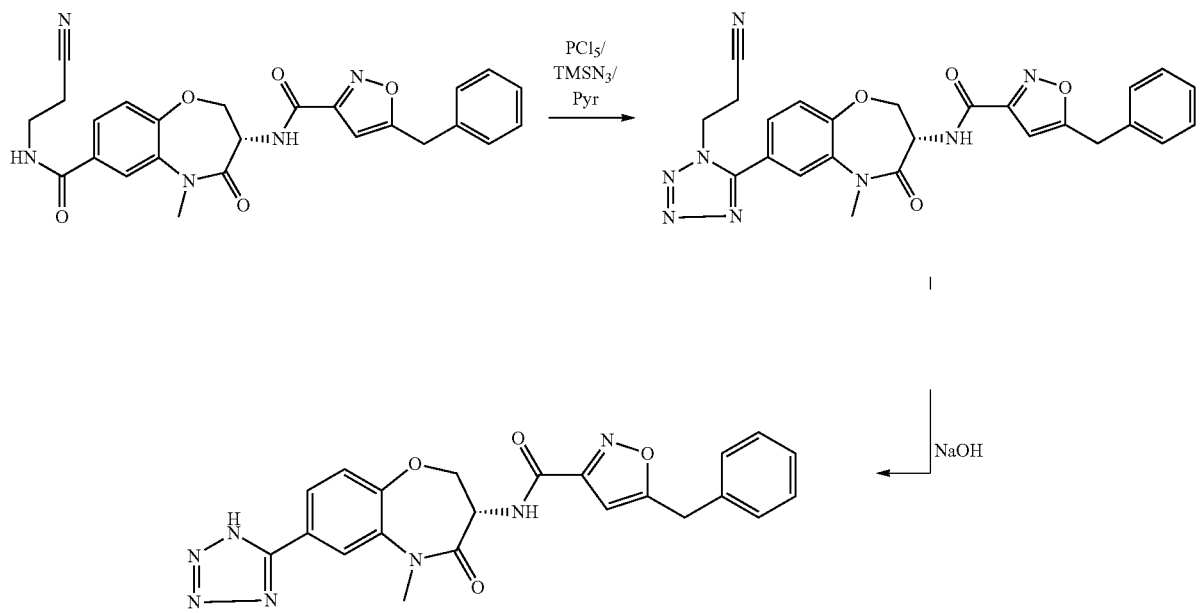

Example 9

(S)-3-(5-benzylisoxazole-3-carboxamido)-5-methyl-N-(methylsulfonyl)-4-oxo-2,3,4,5-tetrahydro benzo[b][1,4]oxazepine-7-carboxamide

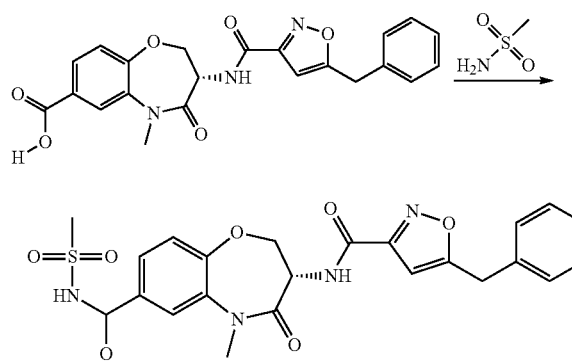

To a suspension of (S)-3-(5-benzylisoxazole-3-carboxamido)-5-methyl-4-oxo-2,3,4,5-tetrahydro benzo[b][1,4]oxazepine-7-carboxylic acid (60.0 mg, 0.142 mmol) in DCM (2.0 mL) was added 1-chloro-N,N,2-trimethylprop-1-en-1-amine (22.83 mg, 0.171 mmol) as a solution in DCM (0.10 ml) dropwise over 1 min. The reaction mixture was stirred at rt for 1 h and became a homogeneous solution. This mixture was added dropwise to a mixture of methanesulfonamide (54.2 mg, 0.570 mmol), TEA (0.079 mL, 0.570 mmol) and DMAP (1.044 mg, 8.54 µmol) in 1.0 mL DCM and stirring was continued over 2 h at rt. The reaction mixture was diluted with EtOAc, then washed with 10% aq citric acid, water and brine. The organic phase was dried over $Na_2SO_4$, filtered then concentrated in vacuo. The residue was purified by FCC[MeOH-DCM: 0-4.0%] to yield the desired product (26.0 mg, 36.6%). $^1$H NMR (DMSO-$d_6$) δ: 8.82 (d, J=8.1 Hz, 1H), 7.95 (d, J=1.8 Hz, 1H), 7.83 (dd, J=8.3, 2.0 Hz, 1H), 7.25-7.38 (m, 6H), 7.20 (d, J=8.1 Hz, 1H), 6.56 (s, 1H), 4.84 (dt, J=11.6, 7.8 Hz, 1H), 4.59 (dd, J=11.7, 10.0 Hz, 1H), 4.42 (dd, J=9.7, 7.7 Hz, 1H), 4.22 (s, 2H), 3.32 (br. s., 3H), 2.95 (s, 3H). MS (m/z) 499.1 (M+H$^+$).

Example 10

Method F (S)-5-benzyl-N-(7-fluoro-4-oxo-2,3,4,5-tetrahydrobenzo[b][1,4]oxazepin-3-yl)isoxazole-3-carboxamide

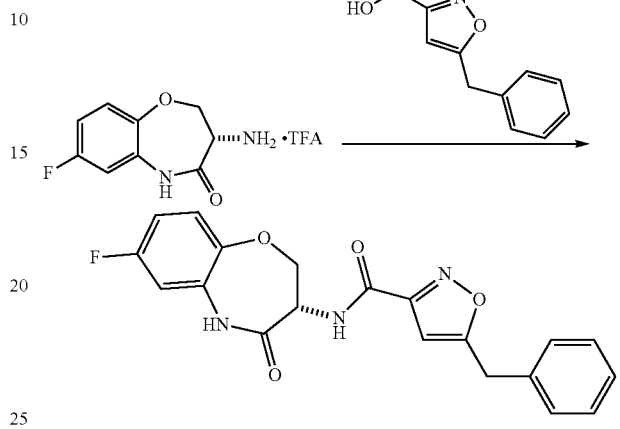

To a solution of 5-benzylisoxazole-3-carboxylic acid (79 mg, 0.390 mmol) and DIEA (0.186 mL, 1.064 mmol) in DMSO (1 mL) was added HATU (135 mg, 0.355 mmol) in one portion. After stirring at rt for 5 min, a solution of (S)-3-amino-7-fluoro-2,3-dihydrobenzo [b][1,4]oxazepin-4(5H)-one, trifluoroacetic acid salt (110.0 mg, 0.355 mmol) in DMSO (1 mL) was added dropwise to the mixture. The reaction was allowed to stir at rt for 2 h. LCMS analysis indicated starting material still remained. An additional amount of DIEA (0.20 mL) and HATU (0.11 g) were added and the reaction allowed to stir for 2 h. The reaction mixture was diluted with EtOAc then washed with water (3×), NH$_4$Cl and brine. After drying the solution over Na$_2$SO$_4$ and concentrating in vacuo, the residue was purified by FCC [EtOAc/Hex: 25-60%] to yield the desired product (50 mg, 37%). $^1$H NMR (DMSO-$d_6$) δ: 10.21 (s, 1H), 8.88 (d, J=8.1 Hz, 1H), 7.25-7.40 (m, 5H), 7.17 (dd, J=8.6, 5.6 Hz, 1H), 6.92-7.00 (m, 2H), 6.55-6.59 (m, 1H), 4.83 (dt, J=10.5, 7.5 Hz, 1H), 4.38-4.53 (m, 2H), 4.23 (s, 2H). MS (m/z) 382.9 (M+H$^+$).

Example 11

Method G (S)-5-benzyl-N-(7-(3-isopropylureido)-5-methyl-4-oxo-2,3,4,5-tetrahydrobenzo[b][1,4]oxazepin-3-yl)isoxazole-3-carboxamide

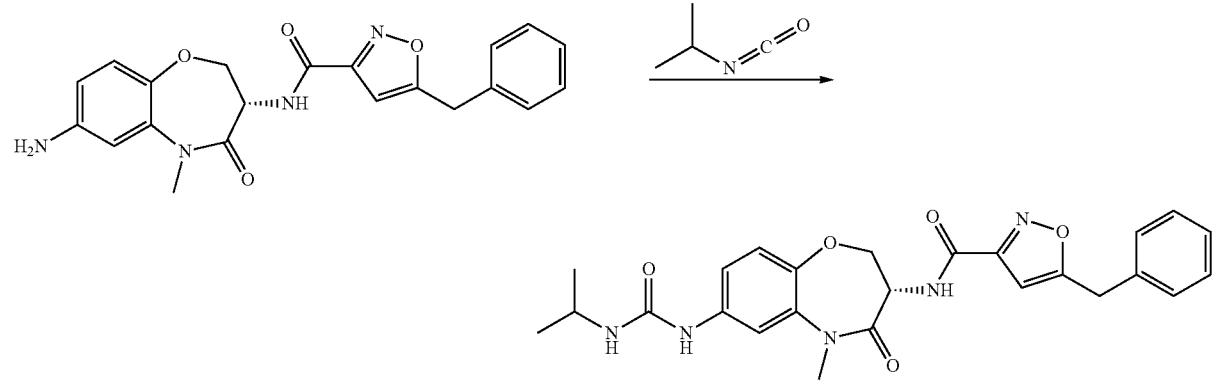

To a solution of (S)—N-(7-amino-5-methyl-4-oxo-2,3,4,5-tetrahydrobenzo[b][1,4]oxazepin-3-yl)-5-benzylisoxazole-3-carboxamide (50.0 mg, 0.112 mmol) in DMF (0.50 mL) at 0° C. was added 2-isocyanatopropane (0.023 mL, 0.235 mmol). After 2 d, additional 2-isocyanatopropane (0.023 mL, 0.235 mmol) was added and the reaction was continued. The reaction mixture was diluted with EtOAc then it was washed in succession with sat.NH$_4$Cl, water, and brine. The organic phase was dried over Na$_2$SO$_4$, filtered then concentrated in vacuo. The residue was purified by FCC [EtOAc/Hex-45-80%]. $^1$H NMR (DMSO-d$_6$) δ: 8.83 (d, J=8.3 Hz, 1H), 8.44 (s, 1H), 7.57 (d, J=2.5 Hz, 1H), 7.25-7.38 (m, 5H), 7.12-7.16 (m, 1H), 7.05-7.09 (m, 1H), 6.55 (s, 1H), 6.06 (d, J=7.6 Hz, 1H), 4.83 (dt, J=11.4, 8.1 Hz, 1H), 4.46-4.53 (m, 1H), 4.33 (dd, J=9.9, 7.8 Hz, 1H), 4.22 (s, 2H), 3.71-3.81 (m, 1H), 3.26 (s, 3H), 1.11 (s, 3H), 1.09 (s, 3H). MS (m/z) 478.2 (M+H$^+$).

Example 12

Method H (S)-5-benzyl-N-(5-methyl-4-oxo-2,3,4,5-tetrahydrobenzo [1,4]oxazepin-3-yl)-4H-1,2,4-triazole-3-carboxamide

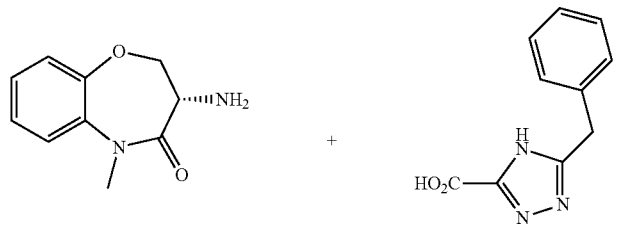

A mixture of (S)-3-amino-5-methyl-2,3-dihydrobenzo[b][1,4]oxazepin-4(5H)-one, hydrochloride (4.00 g, 16.97 mmol), 5-benzyl-4H-1,2,4-triazole-3-carboxylic acid, hydrochloride (4.97 g, 18.66 mmol) and DIEA (10.37 mL, 59.4 mmol) in isopropanol (150 mL) was stirred vigorously for 10 minutes and then 2,4,6-tripropyl-1,3,5,2,4,6-trioxatriphosphinane 2,4,6-trioxide (T3P) (50% by wt. in EtOAc) (15.15 mL, 25.5 mmol) was added. The mixture was stirred at rt for 10 minutes and then quenched with water and concentrated to remove isopropanol. The resulting crude material is dissolved in EtOAc and washed with 1M HCl, satd. NaHCO$_3$ and brine. Organics were concentrated and purified by column chromatography (220 g silica column; 20-90% EtOAc/hexanes, 15 min.; 90%, 15 min.) to give the title compound as a light orange foam (5.37 g, 83%). $^1$H NMR (MeOH-d$_4$) δ: 7.40-7.45 (m, 1H), 7.21-7.35 (m, 8H), 5.01 (dd, J=11.6, 7.6 Hz, 1H), 4.60 (dd, J=9.9, 7.6 Hz, 1H), 4.41 (dd, J=11.4, 9.9 Hz, 1H), 4.17 (s, 2H), 3.41 (s, 3H); MS (m/z) 378.3 (M+H$^+$).

Alternative Preparation:

To a solution of (S)-3-amino-5-methyl-2,3-dihydrobenzo[b][1,4]oxazepin-4(5H)-one hydrochloride (100 g, 437 mmol), 5-benzyl-4H-1,2,4-triazole-3-carboxylic acid hydrochloride (110 g, 459 mmol) in DCM (2.5 L) was added DIPEA (0.267 L, 1531 mmol) at 15° C. The reaction mixture was stirred for 10 min. and 2,4,6-tripropyl-1,3,5,2,4,6-trioxatriphosphinane 2,4,6-trioxide ≥50 wt. % in ethyl acetate (0.390 L, 656 mmol) was slowly added at 15° C. After stirring for 60 mins at RT the LCMS showed the reaction was complete, upon which time it was quenched with water, partitioned between DCM and washed with 0.5N HCl aq (2 L), saturated aqueous NaHCO$_3$ (2 L), brine (2 L) and water (2 L). The organic phase was separated and activated charcoal (100 g) and sodium sulfate (200 g) were added. The dark solution was shaken for 1 h before filtering. The filtrate was then concentrated under reduced pressure to afford the

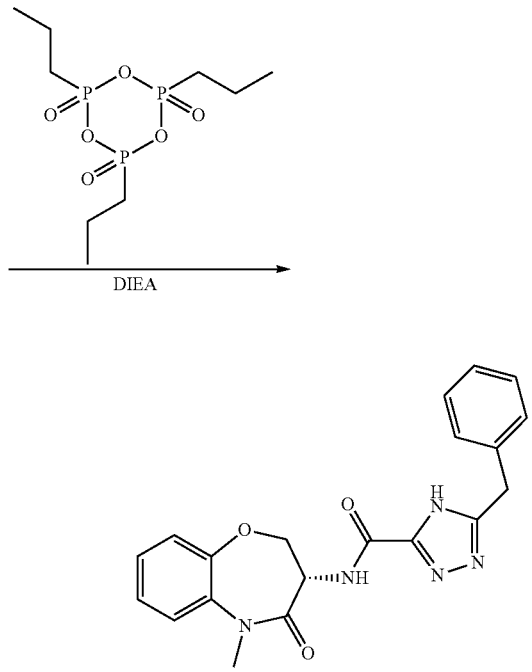

product as a tan foam (120 g). The product was dried under a high vacuum at 50° C. for 16 h. $^1$H NMR showed 4-5% wt of ethyl acetate present. The sample was dissolved in EtOH (650 ml) and stirred for 30 mins, after which the solvent was removed using a rotavapor (water-bath T=45° C.). The product was dried under high vacuum for 16 h at RT (118 g, 72% yield). The product was further dried under high vacuum at 50° C. for 5 h. $^1$H NMR showed <1% of EtOH and no ethyl acetate. $^1$H NMR (400 MHz, DMSO-d$_6$) δ ppm 4.12 (s, 2H), 4.31-4.51 (m, 1H), 4.60 (t, J=10.36 Hz, 1H), 4.83 (dt, J=11.31, 7.86 Hz, 1H), 7.12-7.42 (m, 8H), 7.42-7.65 (m, 1H), 8.45 (br. s., 1H), 14.41 (br. s., 1H). MS (m/z) 378 (M+H$^+$).

Figure 7:
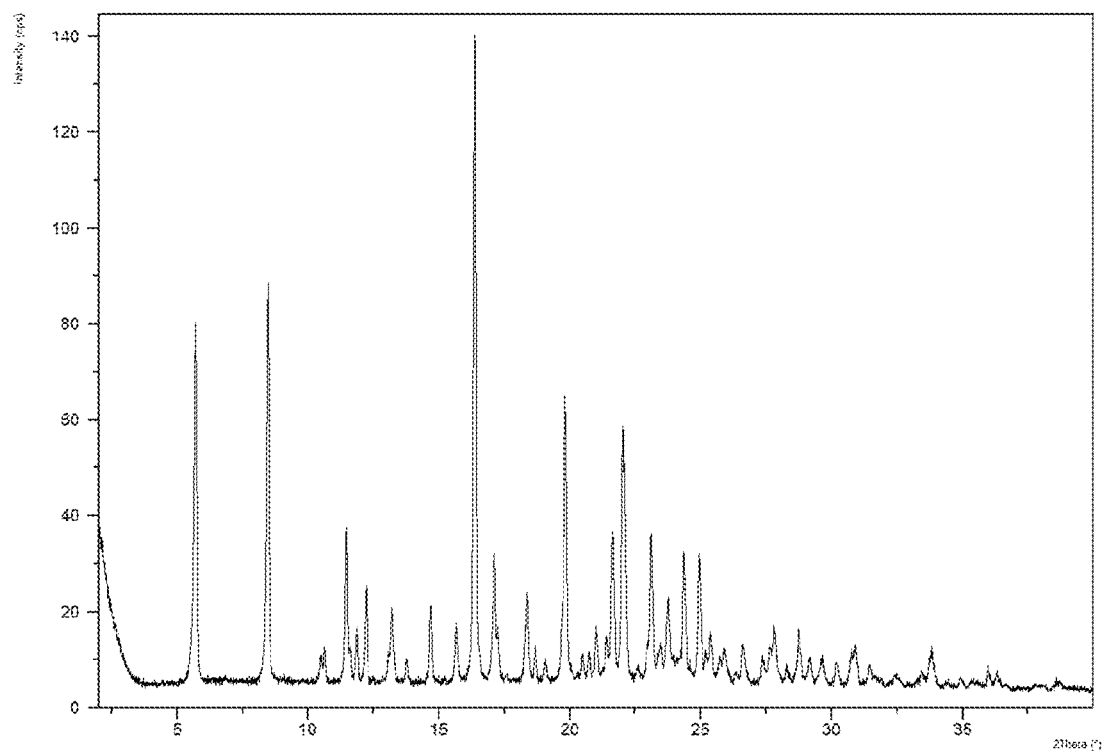
FIG. 7 is a powder x-ray diffraction (PXRD) pattern of a crystalline form of anhydrous (S)-5-benzyl-N-(5-methyl-4-oxo-2,3,4,5-tetrahydrobenzo[b][1,4]oxazepin-3-yl)-4H-1,2, 4-triazole-3-carboxamide (free base).

Crystallization:

(S)-5-Benzyl-N-(5-methyl-4-oxo-2,3,4,5-tetrahydrobenzo[b][1,4]oxazepin-3-yl)-4H-1,2,4-triazole-3-carboxamide (100 mg) was dissolved in 0.9 mL of toluene and 0.1 mL of methylcyclohexane at 60° C., then stirred briskly at room temperature (20° C.) for 4 days. After 4 days, an off-white solid was recovered (76 mg, 76% recovery). The powder X-ray diffraction (PXRD) pattern of this material is shown in FIG. 7 and the corresponding diffraction data is provided in Table 1.

The PXRD analysis was conducted using a PANanalytical X'Pert Pro diffractometer equipped with a copper anode X-ray tube, programmable slits, and X'Celerator detector fitted with a nickel filter. Generator tension and current were set to 45 kV and 40 mA respectively to generate the copper Kα radiation powder diffraction pattern over the range of 2-40° 2θ. The test specimen was lightly triturated using an agate mortar and pestle and the resulting fine powder was mounted onto a silicon zero background plate.

TABLE 1

| Diffraction Angle (°2θ) |
| --- |
| 5.70 |
| 8.46 |
| 11.46 |
| 16.36 |
| 17.10 |
| 19.82 |
| 21.63 |
| 22.03 |
| 23.11 |
| 23.75 |
| 24.35 |
| 24.94 |

Example 13

Method I (S)-5-benzyl-N-(2-oxo-7-(1H-pyrazol-3-yl)-2,3,4,5-tetrahydro-1H-benzo[b]azepin-3-yl)-4H-1,2,4-triazole-3-carboxamide

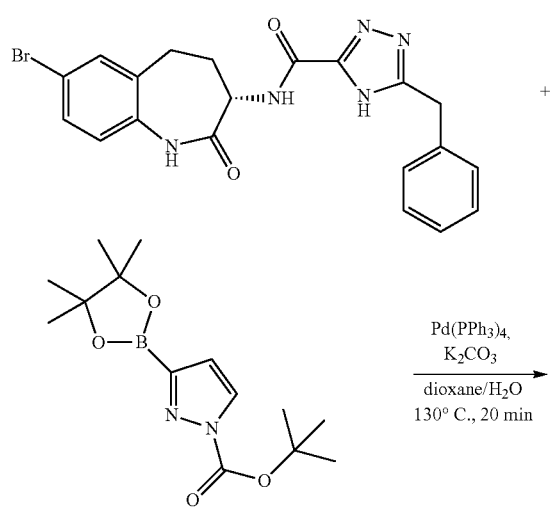

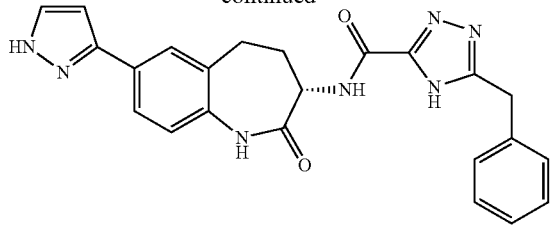

(S)-5-benzyl-N-(7-bromo-2-oxo-2,3,4,5-tetrahydro-1H-benzo[b]azepin-3-yl)-4H-1,2,4-triazole-3-carboxamide (60 mg, 0.136 mmol), tert-butyl 3-(4,4,5,5-tetramethyl-1,3,2-dioxaborolan-2-yl)-1H-pyrazole-1-carboxylate (40.1 mg, 0.136 mmol), Pd(PPh$_3$)$_4$(29.8 mg, 0.026 mmol) and K$_2$CO$_3$ (107 mg, 0.775 mmol) were mixed in 1,4-dioxane (2 mL) and water (1 mL). The reaction mixture was put in an Emrys Optimizer (150 W, absorption normal) and microwaved at 130° C., for 20 min. The reaction mixture was filtered and the filtrate was concentrated. The residue was purified by reverse phase HPLC (Waters Sunfire 30×150 mm, 26-60% CH$_3$CN:H$_2$O (0.1% TFA), 50 mg/mL). Collected fractions containing the product were combined, neutralized by NaHCO$_3$, and then concentrated to give the desired product as a white solid (6 mg, 11% yield). $^1$H NMR (DMSO-d$_6$) δ ppm 10.05 (s, 1H), 8.31 (br. s., 1H), 7.77 (s, 1H), 7.65-7.75 (m, 2H), 7.19-7.42 (m, 5H), 7.07 (d, J=8.0 Hz, 1H), 6.71 (d, J=1.5 Hz, 1H), 4.38 (dt, J=11.2, 7.9 Hz, 1H), 4.12 (s, 2H), 2.66-2.90 (m, 2H), 2.42-2.51 (m, 1H), 2.28 (br. s., 1H); MS (m/z): 428 (M+H$^+$).

Example 14

(S)-3-(5-benzylisoxazole-3-carboxamido)-5-methyl-4-oxo-2,3,4,5-tetrahydrobenzo[b][1,4]oxazepine-7-carboxylic acid

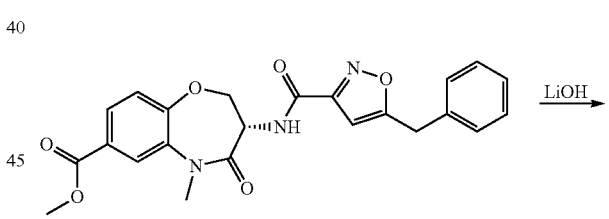

Example 78

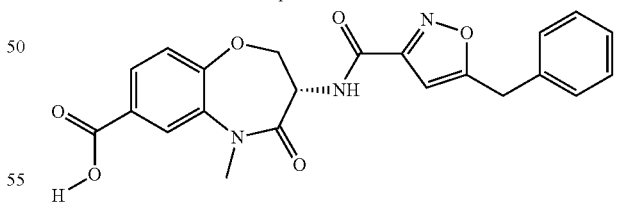

To a solution of (S)-methyl 3-(5-benzylisoxazole-3-carboxamido)-5-methyl-4-oxo-2,3,4,5-tetrahydrobenzo[b][1,4]oxazepine-7-carboxylate (332 mg, 0.762 mmol) in THF (6 mL)/Water (2.0 mL) was added LiOH (1.144 mL, 1.144 mmol) as a solution in water. Reaction was stirred at rt for about 2 h. The reaction mixture was diluted with water then extracted with EtOAc twice. The aqueous phase was acidified to pH-3.0 then it was extracted with EtOAc. The latter organic phase was dried over Na$_2$SO$_4$ then filtered and concentrated in vacuo to yield the desired product as a solid.

The solid was warmed in toluene then decanted to give the final solid product that was used directly in the next step. $^{1}$H NMR (DMSO-d$_{6}$) δ: 13.18 (br. s., 1H), 8.87 (d, J=8.1 Hz, 1H), 7.98 (d, J=2.0 Hz, 1H), 7.85 (dd, J=8.3, 2.0 Hz, 1H), 7.25-7.38 (m, 6H), 6.55 (s, 1H), 4.87 (dt, J=11.8, 7.7 Hz, 1H), 4.64 (dd, J=11.6, 10.1 Hz, 1H), 4.46 (dd, J=9.9, 7.6 Hz, 1H), 4.22 (s, 2H). MS (m/z) 422.3 (M+H$^{+}$).

Example 15

Method J (S)—N-(7-acetamido-5-methyl-4-oxo-2,3,4,5-tetrahydrobenzo[b][1,4]oxazepin-3-yl)-5-benzylisoxazole-3-carboxamide

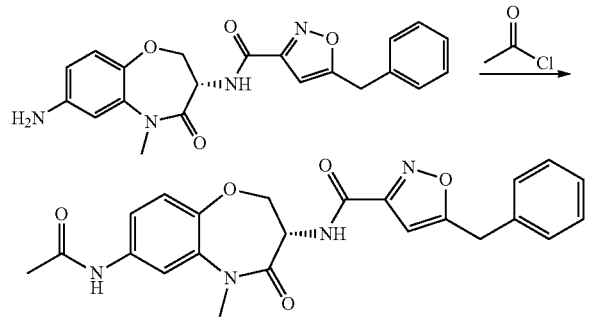

(S)—N-(7-acetamido-5-methyl-4-oxo-2,3,4,5-tetrahydrobenzo[b][1,4]oxazepin-3-yl)-5-benzylisoxazole-3-carboxamide. To a solution of (S)—N-(7-amino-5-methyl-4-oxo-2,3,4,5-tetrahydrobenzo[b][1,4]oxazepin-3-yl)-5-benzylisoxazole-3-carboxamide (60.0 mg, 0.153 mmol) in THF (2.0 mL) at 0° C. was added DIEA (0.061 mL, 0.352 mmol) then AcCl (10.87 μL, 0.153 mmol). The reaction mixture was monitored by LCMS. Reaction showed desired mass after 10 min with all sm consumed. The reaction mixture was concentrated to a solid residue. The solid was suspended in small amount of DCM and 1 mL of 25% EtOAc/Hex. The suspension was lightly warmed then cooled and filtered to collect the solid product. The solid was washed with ethyl ether yield=56 mg solid powder; NMR shows much impurity, so the sample was subjected to FCC [MeOH-DCM:0-3.0%]. yield=18 mg. $^{1}$H NMR (DMSO-d$_{6}$) δ: 10.11 (s, 1H), 8.86 (d, J=8.1 Hz, 1H), 7.71 (d, J=2.3 Hz, 1H), 7.25-7.42 (m, 6H), 7.15 (d, J=8.6 Hz, 1H), 6.55 (s, 1H), 4.84 (dt, J=11.6, 8.0 Hz, 1H), 4.49-4.56 (m, 1H), 4.35 (dd, J=9.9, 7.8 Hz, 1H), 4.22 (s, 2H), 3.27 (s, 3H), 2.06 (s, 3H). MS (m/z) 435.3 (M+H$^{+}$).

Example 16

Method K (S)-(3-(5-benzyl-4H-1,2,4-triazole-3-carboxamido)-2-oxo-2,3,4,5-tetrahydro-1H-benzo[b]azepin-7-yl)boronic acid

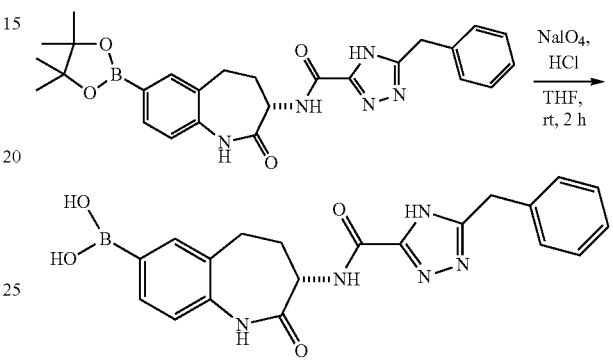

(S)-5-benzyl-N-(2-oxo-7-(4,4,5,5-tetramethyl-1,3,2-dioxaborolan-2-yl)-2,3,4,5-tetrahydro-1H-benzo[b]azepin-3-yl)-4H-1,2,4-triazole-3-carboxamide (65 mg, 0.133 mmol) was dissolved in 2 mL THF, and then sodium periodate (28.5 mg, 0.133 mmol) was added, followed by HCl (1N in H$_{2}$O, 0.041 mL, 1.334 mmol). The mixture was maintained at rt for 2 h. The mixture was then concentrated and the residue was purified by Isco Combiflash (2%-10% MeOH/CH$_{2}$Cl$_{2}$, 10% NEt$_{3}$ in MeOH; 40 g RediSep column). Collected fractions containing the product were combined and concentrated to give the desired product as a colorless oil, which was then lyophilized to a white solid (36 mg, 67% yield). $^{1}$H NMR (400 MHz, MeOD-d4) δ ppm 2.11-2.32 (m, 1H) 2.57-2.74 (m, 1H) 2.74-2.89 (m, 1H) 2.97 (td, J=13.33, 7.96 Hz, 1H) 4.12-4.22 (m, 2H) 4.49-4.65 (m, 1H) 6.98-7.17 (m, 1H) 7.19-7.43 (m, 5H) 7.51-7.66 (m, 1H) 7.71 (br. s., 1H); MS (m/z): 406 (M+H$^{+}$).

Example 17

(S)-(3-(3-benzyl-1H-pyrazole-5-carboxamido)-2-oxo-2, 3,4, 5-tetrahydro-1H-benzo[b]azepin-8-yl)boronic acid

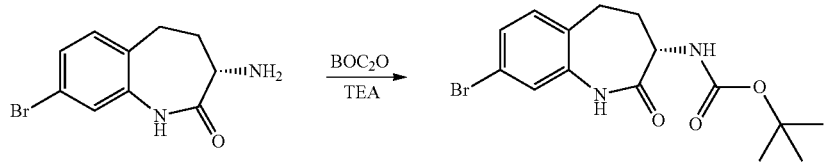

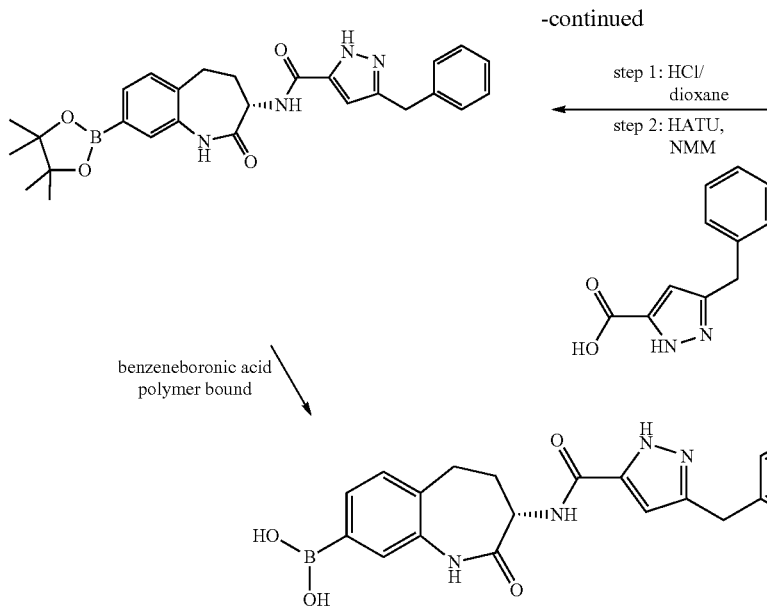
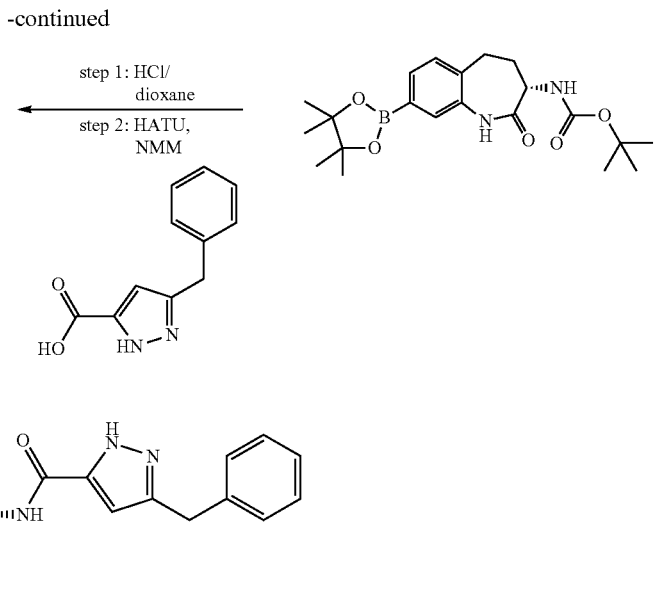

To a mixture of (S)-3-amino-8-bromo-4,5-dihydro-1H-benzo[b]azepin-2(3H)-one (1.0 g, 3.92 mmol) in DCM (30 mL) was added TEA (0.820 mL, 5.88 mmol) and BOC$_2$O (0.956 mL, 4.12 mmol). Mixture was stirred at room temperature for 1.5 hours and a solid precipitated out. Water was added and the mixture was stirred for 5 minutes and solid was filtered and dried to give 869 mg of (S)-tert-butyl (8-bromo-2-oxo-2,3,4,5-tetrahydro-1H-benzo[b]azepin-3-yl)carbamate as a pale yellow solid. Layers of the filtrate were separated and organics were concentrated to a solid. Solid was triturated in diethyl ether, filtered and dried to give 390 mg pale yellow solid. Yield=87%. $^1$H NMR (DMSO-d$_6$) δ: 9.81 (s, 1H), 7.29-7.33 (m, 1H), 7.24 (d, J=8.1 Hz, 1H), 7.18 (d, J=1.8 Hz, 1H), 7.05 (d, J=8.3 Hz, 1H), 3.86 (dt, J=12.0, 8.1 Hz, 1H), 2.56-2.72 (m, 2H), 2.19 (m, 1H), 2.06 (td, J=12.3, 7.3 Hz, 1H), 1.34 (s, 9H); MS (m/z) 355/357 (bromine splitting pattern) (M+H$^+$).

Nitrogen was bubbled through a mixture of (S)-tert-butyl (8-bromo-2-oxo-2,3,4,5-tetrahydro-1H-benzo[b]azepin-3-yl)carbamate (385 mg, 1.084 mmol), potassium acetate (532 mg, 5.42 mmol) and bis(pinacolato)diboron (330 mg, 1.301 mmol) in 1,4-Dioxane (10 mL) for 5 min. Then PdCl$_2$(dppf)-CH$_2$Cl$_2$ adduct (89 mg, 0.108 mmol) was added and mixture was heated at 95° C. for 2 hours. Reaction was cooled to room temperature, diluted with water and ethyl acetate and filtered through a Celite plug. Layers of filtrate were separated. Organics were concentrated and purified by Biotage (10 g silica column, 10-50% E/H, 10 min.; 70%, 5 min.) to give 344 mg of (S)-tert-butyl (2-oxo-8-(4,4,5,5-tetramethyl-1,3,2-dioxaborolan-2-yl)-2,3,4,5-tetrahydro-1H-benzo[b]azepin-3-yl)carbamate as a tan solid in 77% yield. $^1$H NMR (DMSO-d$_6$) δ: 9.70 (s, 1H), 7.41 (d, J=7.3 Hz, 1H), 7.28-7.33 (m, 2H), 7.00 (d, J=8.3 Hz, 1H), 3.83 (dt, J=11.9, 8.3 Hz, 1H), 2.68 (m, 2H), 2.18 (m, 1H), 2.08 (m, 1H), 1.34 (s, 9H), 1.30 (s, 12H); MS (m/z) 403.4 (M+H$^+$).

To a mixture of (S)-tert-butyl (2-oxo-8-(4,4,5,5-tetramethyl-1,3,2-dioxaborolan-2-yl)-2,3,4,5-tetrahydro-1H-benzo[b]azepin-3-yl)carbamate (70 mg, 0.174 mmol) in DCM (3 mL) was added 4.0 M HCl in dioxane (218 μl, 0.870 mmol). Mixture was stirred at room temperature for 2 days, concentrated to remove solvents to yield (S)-3-benzyl-N-(2-oxo-8-(4,4,5,5-tetramethyl-1,3,2-dioxaborolan-2-yl)-2,3,4,5-tetrahydro-1H-benzo[b]azepin-3-yl)-1H-pyrazole-5-carboxamide which was used as-is in the next step. MS (m/z) 303.3 (M+H$^+$).

A solution of 3-benzyl-1H-pyrazole-5-carboxylic acid (38.7 mg, 0.191 mmol) and HATU (79 mg, 0.209 mmol) in CH$_3$CN (1 mL) and DMSO (0.3 mL) was stirred for 40 minutes. Then it was added to a mixture of N-methylmorpholine (0.067 mL, 0.609 mmol) and (S)-3-amino-8-(4,4,5,5-tetramethyl-1,3,2-dioxaborolan-2-yl)-4,5-dihydro-1H-benzo[b]azepin-2(3H)-one (from the prior step) in CH$_3$CN (1 mL). The mixture was stirred at room temperature for 40 minutes. Water (5 mL) was slowly added while stirring vigorously. A solid precipitated out and it was stirred for 5 minutes, filtered and dried to give 60 mg light brown solid in 70% yield. $^1$H NMR (MeOH-d4) δ: 7.58 (d, J=7.3 Hz, 1H), 7.46 (s, 1H), 7.27-7.37 (m, 4H), 7.19-7.26 (m, 4H), 6.49 (br. s., 1H), 4.54 (dd, J=11.6, 8.1 Hz, 1H), 4.02 (s, 2H), 2.98 (td, J=13.2, 8.0 Hz, 1H), 2.75-2.83 (m, 1H), 2.61 (m, 1H), 2.16-2.28 (m, 1H), 1.36 (s, 12H); MS (m/z) 487.5 (M+H$^+$).

To a solution of (S)-3-benzyl-N-(2-oxo-8-(4,4,5,5-tetramethyl-1,3,2-dioxaborolan-2-yl)-2,3,4,5-tetrahydro-1H-benzo[b]azepin-3-yl)-1H-pyrazole-5-carboxamide (45 mg, 0.093 mmol) in THF (2 mL) was added benzeneboronic acid, polymer bound [5 eq, 0.46 mmol, 170 mg (assuming 2.6 mmol/g loading), 2.6-3.2 mmol/g loading] and conc. HCl (0.039 mL, 0.463 mmol). Mixture was stirred at room temperature for 3 days. Reaction was not quite complete, so more benzeneboronic acid, polymer bound (50 mg) was added and mixture was stirred for another 4 hours, then filtered to remove resin and concentrated. Water (3 mL) was added and a solid formed. Solid was filtered and purified by column chromatography (4 g silica column; 50-100% ethyl acetate/hexanes, then 10% methanol/ethyl acetate) to give 9 mg of (S)-(3-(3-benzyl-1H-pyrazole-5-carboxamido)-2-oxo-2,3,4,5-tetrahydro-1H-benzo[b]azepin-8-yl)boronic acid as an off-white solid in 33% yield. $^1$H NMR (MeOH-d4) δ: 7.46 (d, J=7.3 Hz, 1H), 7.28-7.36 (m, 4H), 7.21-7.26 (m, 3H), 6.48 (br. s., 1H), 4.56 (dd, J=11.2, 8.0 Hz, 1H), 4.03 (s, 2H), 2.92-3.03 (m, 1H), 2.73-2.81 (m, 1H), 2.63 (br. s., 1H), 2.20 (m, 1H); MS (m/z) 405.4 (M+H$^+$).

The following compounds were prepared via coupling of the appropriate amine and acid using the method indicated.

| Ex | Name | Structure | 1H NMR | MS (M + H)+ | Method |
|---|---|---|---|---|---|
| 18 | (S)-5-benzyl-N-(7-bromo-5-methyl-4-oxo-2,3,4,5-tetrahydrobenzo[b][1,4]oxazepin-3-yl)isoxazole-3-carboxamide | 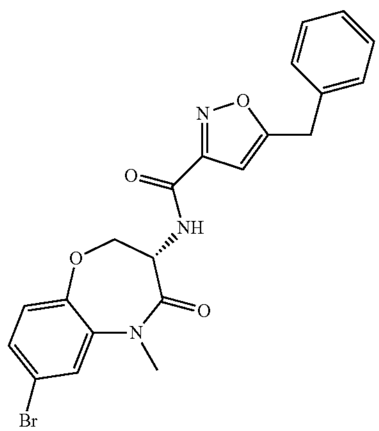 [SMILES: CN1C(=O)[C@@H](NC(=O)c2cc(Cc3ccccc3)on2)COc2ccc(Br)cc21] | ¹H NMR (DMSO-d₆) δ: 8.88 (d, J = 8.1 Hz, 1H), 7.78 (d, J = 2.3 Hz, 1H), 7.46 (dd, J = 8.6, 2.3 Hz, 1H), 7.24-7.40 (m, 5H), 7.19 (d, J = 8.6 Hz, 1H), 6.55 (s, 1H), 4.85 (dt, J = 11.7, 7.9 Hz, 1H), 4.54-4.64 (m, 1H), 4.41 (dd, J = 9.9, 7.8 Hz, 1H), 4.22 (s, 2H), 3.30 (s, 3H) | 456/458 | F |
| 19 | (S)-N-(7-bromo-5-methyl-4-oxo-2,3,4,5-tetrahydrobenzo[b][1,4]oxazepin-3-yl)-3-(4-methylbenzyl)-1H-pyrazole-5-carboxamide | 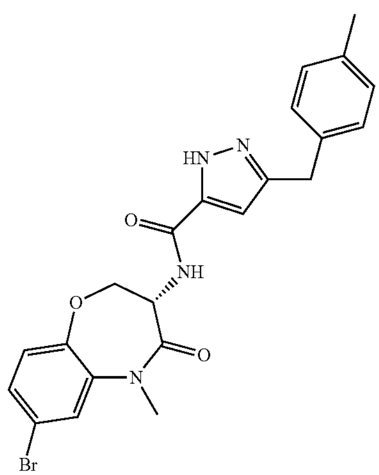 [SMILES: Cc1ccc(Cc2cc(C(=O)N[C@H]3COc4ccc(Br)cc4N(C)C3=O)[nH]n2)cc1] | ¹H NMR (DMSO-d₆) δ: 13.18 (s, 1H), 8.09 (d, J = 8.1 Hz, 1H), 7.76 (d, J = 2.3 Hz, 1H), 7.46 (dd, J = 8.6, 2.5 Hz, 1H), 7.19 (d, J = 8.6 Hz, 1H), 7.11 (s, 4H), 6.32-6.36 (m, 1H), 4.79-4.89 (m, 1H), 4.50-4.59 (m, 1H), 4.39 (dd, J = 9.7, 7.7 Hz, 1H), 3.93 (s, 2H), 3.30 (s, 3H) | 469/471 | F |
| 20 | (S)-3-benzyl-N-(7-bromo-5-methyl-4-oxo-2,3,4,5-tetrahydrobenzo[b][1,4]oxazepin-3-yl)-1H-pyrazole-5-carboxamide | 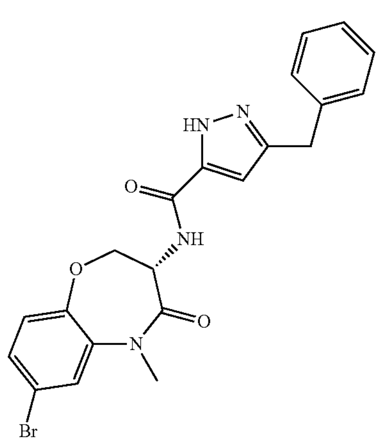 [SMILES: CN1C(=O)[C@@H](NC(=O)c2cc(Cc3ccccc3)n[nH]2)COc2ccc(Br)cc21] | ¹H NMR (CDCl₃) δ: 8.25 (br. s., 1H), 7.24-7.42 (m, 6H), 7.17-7.23 (m, 2H), 7.08 (d, J = 8.6 Hz, 1H), 6.55 (s, 1H), 5.14 (dt, J = 11.6, 7.6 Hz, 1H), 4.61 (dd, J = 9.7, 7.5 Hz, 1H), 4.31 (dd, J = 11.6, 9.9 Hz, 1H), 4.03 (s, 2H), 3.39 (s, 3H) | 455/457 | F |

-continued

| Ex | Name | Structure | 1H NMR | MS (M + H)+ | Method |
|---|---|---|---|---|---|
| 21 | (S)-5-benzyl-N-(8-hydroxy-4-oxo-2,3,4,5-tetrahydrobenzo[b][1,4]oxazepin-3-yl)isoxazole-3-carboxamide | 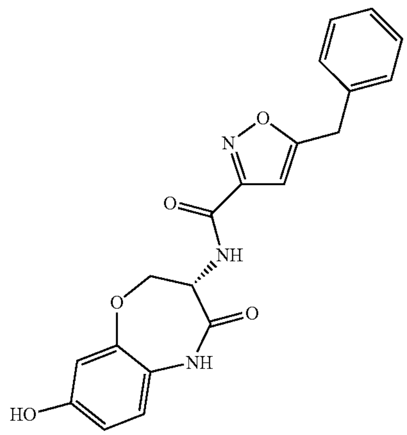 [SMILES: O=C(N[C@H]1COc2cc(O)ccc2NC1=O)c1cc(Cc2ccccc2)on1] | ¹H NMR (DMSO-d₆) δ: 9.79 (s, 1H), 9.56 (s, 1H), 8.73 (d, J = 8.1 Hz, 1H), 7.23-7.41 (m, 5H), 6.91 (d, J = 8.3 Hz, 1H), 6.50-6.61 (m, 3H), 4.79 (dt, J = 11.1, 7.3 Hz, 1H), 4.47 (t, J = 10.6 Hz, 1H), 4.38 (dd, J = 10.4, 7.1 Hz, 1H), 4.22 (s, 2H) | 380 | F |
| 22 | (S)-5-benzyl-N-(5-methyl-4-oxo-7-(1H-pyrazol-3-yl)-2,3,4,5-tetrahydrobenzo[b][1,4]oxazepin-3-yl)isoxazole-3-carboxamide | 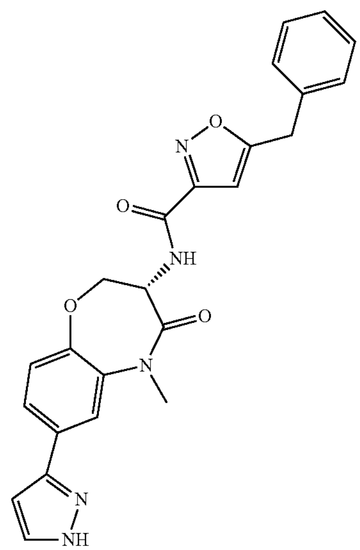 [SMILES: CN1C(=O)[C@@H](NC(=O)c2cc(Cc3ccccc3)on2)COc2ccc(-c3cc[nH]n3)cc21] | ¹H NMR (DMSO-d₆) δ: 12.94 (s, 1H), 8.87 (d, J = 8.3 Hz, 1H), 7.88 (d, J = 2.0 Hz, 1H), 7.81 (d, J = 2.0 Hz, 1H), 7.73 (dd, J = 8.2, 1.9 Hz, 1H), 7.20-7.39 (m, 7H), 6.81 (br. m., 1H), 6.55 (s, 1H), 4.84-4.96 (m, 1H), 4.54-4.66 (m, 1H), 4.36-4.47 (m, 1H), 4.22 (s, 2H), 3.36 (s, 3H) | 444 | F |
| 23 | (S)-5-benzyl-N-(5-methyl-4-oxo-7-(1H-pyrazol-1-yl)-2,3,4,5-tetrahydrobenzo[b][1,4]oxazepin-3-yl)isoxazole-3-carboxamide | 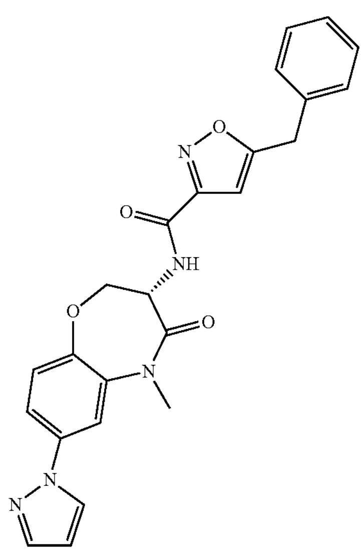 [SMILES: CN1C(=O)[C@@H](NC(=O)c2cc(Cc3ccccc3)on2)COc2ccc(-n3cccn3)cc21] | ¹H NMR (DMSO-d₆) δ: 8.90 (d, J = 8.3 Hz, 1H), 8.58 (d, J = 2.0 Hz, 1H), 7.94 (d, J = 2.5 Hz, 1H), 7.73-7.80 (m, 2H), 7.24-7.39 (m, 6H), 6.56-6.60 (m, 1H), 6.55 (s, 1H), 4.91 (dt, J = 11.6, 8.0 Hz, 1H), 4.61 (dd, J = 11.6, 10.1 Hz, 1H), 4.44 (dd, J = 9.9, 7.8 Hz, 1H), 4.22 (s, 2H), 3.38 (s, 3H) | 444 | F |

| Ex | Name | Structure | 1H NMR | MS (M + H)+ | Method |
|----|------|-----------|--------|-------------|--------|
| 24 | (S)-5-benzyl-N-(8-bromo-2-oxo-2,3,4,5-tetrahydro-1H-benzo[b]azepin-3-yl)isoxazole-3-carboxamide | 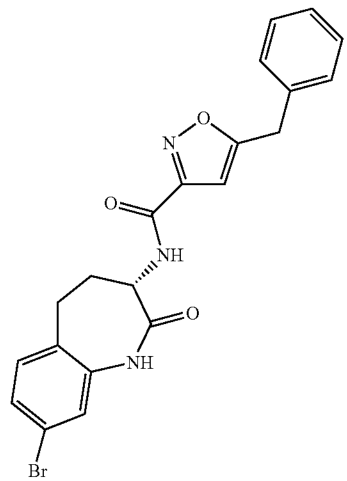 [SMILES: O=C(N[C@H]1CCc2ccc(Br)cc2NC1=O)c1cc(Cc2ccccc2)on1] | ¹H NMR (DMSO-d₆) δ: 10.03 (s, 1H), 8.72 (d, J = 7.8 Hz, 1H), 7.25-7.40 (m, 7H), 7.21 (d, J = 2.0 Hz, 1H), 6.54 (s, 1H), 4.28-4.40 (m, 1H), 4.21 (s, 2H), 2.61-2.78 (m, 2H), 2.25-2.38 (m, 2H) | 440/442 | F |
| 25 | (S)-N-(8-bromo-2-oxo-2,3,4,5-tetrahydro-1H-benzo[b]azepin-3-yl)-3-(4-methylbenzyl)-1H-pyrazole-5-carboxamide | 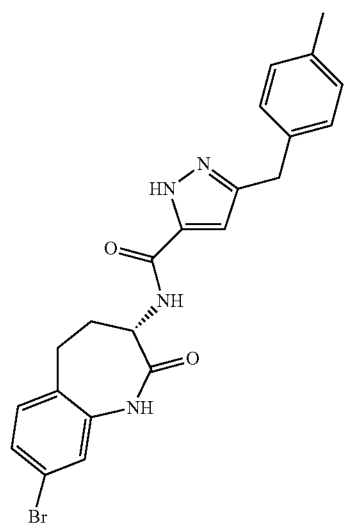 [SMILES: Cc1ccc(Cc2cc(C(=O)N[C@H]3CCc4ccc(Br)cc4NC3=O)[nH]n2)cc1] | ¹H NMR (MeOH-d4) δ: 7.36 (dd, J = 8.0, 1.9 Hz, 1H), 7.23-7.31 (m, 2H), 7.06-7.16 (m, 4H), 6.45 (s, 1H), 4.55 (dd, J = 11.6, 8.1 Hz, 1H), 3.98 (s, 2H), 2.84-2.96 (m, 1H), 2.74-2.83 (m, 1H), 2.57-2.70 (m, 1H), 2.31 (s, 3H), 2.20 (m, 1H) | 453/455 | F |
| 26 | (S)-3-benzyl-N-(8-bromo-2-oxo-2,3,4,5-tetrahydro-1H-benzo[b]azepin-3-yl)-1H-pyrazole-5-carboxamide | 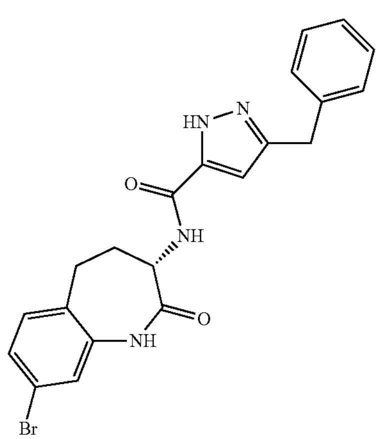 [SMILES: O=C(N[C@H]1CCc2ccc(Br)cc2NC1=O)c1cc(Cc2ccccc2)n[nH]1] | ¹H NMR (DMSO-d₆) δ: 13.15 (s, 1H), 10.06 (s, 1H), 7.93 (d, J = 7.6 Hz, 1H), 7.16-7.39 (m, 8H), 6.36 (s, 1H), 4.28-4.39 (m, 1H), 3.98 (s, 2H), 2.70 (m, 2H), 2.33-2.46 (m, 1H), 2.09-2.31 (m, 1H) | 439/441 | F |

| Ex | Name | Structure | 1H NMR | MS (M + H)+ | Method |
|---|---|---|---|---|---|
| 27 | (S)-3-(2-fluorobenzyl)-N-(2-oxo-2,3,4,5-tetrahydro-1H-benzo[b]azepin-3-yl)-1H-pyrazole-5-carboxamide | 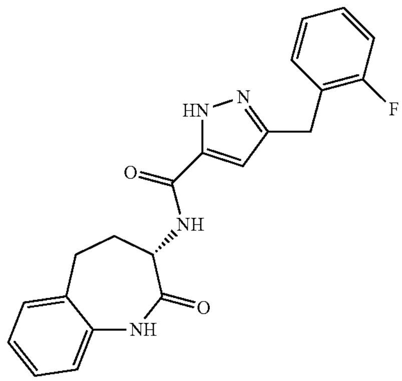 [SMILES: O=C(N[C@H]1CCc2ccccc2NC1=O)c1cc(Cc2ccccc2F)n[nH]1] | ¹H NMR (MeOH-d4) δ: 7.18-7.36 (m, 6H), 7.04-7.16 (m, 3H), 6.45 (s, 1H), 4.56 (dd, J = 11.6, 8.1 Hz, 1H), 4.07 (s, 2H), 2.91-3.03 (m, 1H), 2.73-2.81 (m, 1H), 2.58-2.67 (m, 1H), 2.13-2.25 (m, 1H) | 379 | F |
| 28 | (S)-3-(3-fluorobenzyl)-N-(2-oxo-2,3,4,5-tetrahydro-1H-benzo[b]azepin-3-yl)-1H-pyrazole-5-carboxamide | 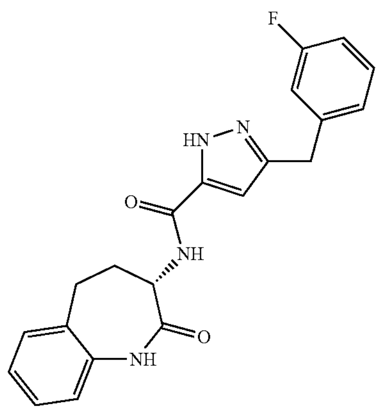 [SMILES: O=C(N[C@H]1CCc2ccccc2NC1=O)c1cc(Cc2cccc(F)c2)n[nH]1] | ¹H NMR (MeOH-d4) δ: 7.28-7.38 (m, 3H), 7.17-7.25 (m, 1H), 7.03-7.14 (m, 2H), 6.98 (d, J = 9.6 Hz, 2H), 6.50 (s, 1H), 4.57 (dd, J = 11.5, 8.0 Hz, 1H), 4.06 (s, 2H), 2.90-3.03 (m, 1H), 2.73-2.81 (m, 1H), 2.60-2.71 (m, 1H), 2.15-2.25 (m, 1H) | 379 | F |
| 29 | (S)-1-benzyl-N-(2-oxo-2,3,4,5-tetrahydro-1H-benzo[b]azepin-3-yl)-1H-1,2,3-triazole-4-carboxamide | 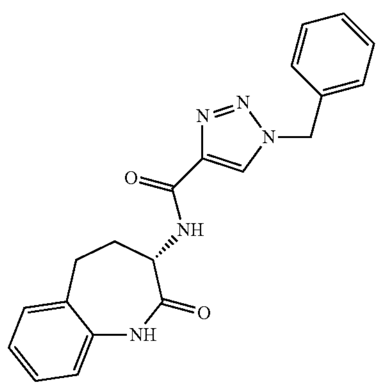 | ¹H NMR (DMSO-d₆) δ: 9.97 (s, 1H), 8.66 (s, 1H), 8.35 (d, J = 7.8 Hz, 1H), 7.23-7.45 (m, 7H), 7.11-7.21 (m, 1H), 7.04 (d, J = 7.8 Hz, 1H), 5.65 (s, 2H), 4.37 (dt, J = 11.6, 8.0 Hz, 1H), 2.65-2.85 (m, 2H), 2.34-2.46 (m, 1H), 2.18-2.32 (m, 1H) | 362 | F |
| 30 | (S)-5-benzyl-N-(2-oxo-2,3,4,5-tetrahydro-1H-benzo[b]azepin-3-yl)thiophene-2-carboxamide | 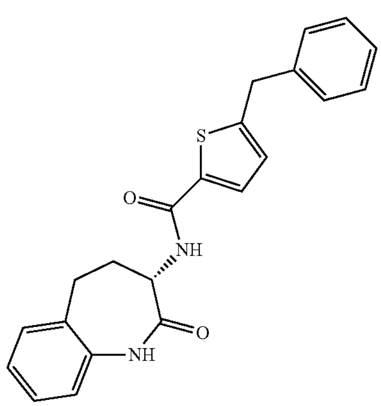 [SMILES: O=C(N[C@H]1CCc2ccccc2NC1=O)c1ccc(Cc2ccccc2)s1] | ¹H NMR (DMSO-d₆) δ: 9.83 (s, 1H), 8.47 (d, J = 8.1 Hz, 1H), 7.72 (d, J = 3.8 Hz, 1H), 7.19-7.36 (m, 7H), 7.10-7.18 (m, 1H), 7.03 (d, J = 7.6 Hz, 1H), 6.92 (d, J = 3.5 Hz, 1H), 4.34 (m, 1H), 4.14 (s, 2H), 2.72 (m, 2H), 2.28 (m, 2H) | 377 | F |

| Ex | Name | Structure | 1H NMR | MS (M + H)+ | Method |
|---|---|---|---|---|---|
| 31 | (S)-5-benzyl-N-(2-oxo-8-(2-(pyrrolidin-1-yl)ethoxy)-2,3,4,5-tetrahydro-1H-benzo[b]azepin-3-yl)isoxazole-3-carboxamide | 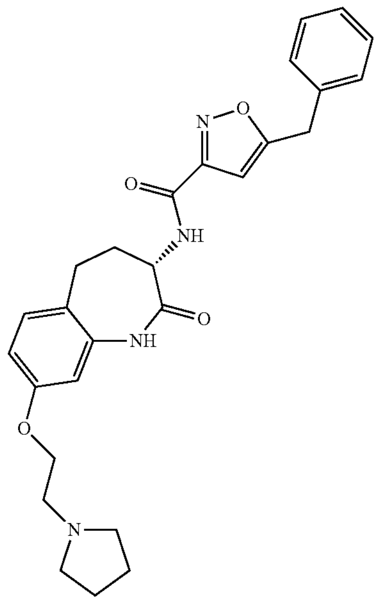 [SMILES: O=C(N[C@H]1CCc2ccc(OCCN3CCCC3)cc2NC1=O)c1cc(Cc2ccccc2)on1] | ¹H NMR (DMSO-d₆) δ: 9.87 (s, 1H), 8.64 (d, J = 7.8 Hz, 1H), 7.26-7.40 (m, 5H), 7.19 (d, J = 8.3 Hz, 1H), 6.73 (dd, J = 8.3, 2.8 Hz, 1H), 6.59 (d, J = 2.5 Hz, 1H), 6.54 (s, 1H), 4.29-4.41 (m, 1H), 4.21 (s, 2H), 3.96-4.12 (m, 2H), 2.78 (t, J = 5.7 Hz, 2H), 2.60-2.71 (m, 2H), 2.52 (m, 4H), 2.21-2.35 (m, 2H), 1.69 (dt, J = 6.7, 3.2 Hz, 4H) | 475 | F |
| 32 | 5-benzyl-N-((3S)-2-oxo-8-((tetrahydrofuran-2-yl)methoxy)-2,3,4,5-tetrahydro-1H-benzo[b]azepin-3-yl)isoxazole-3-carboxamide | 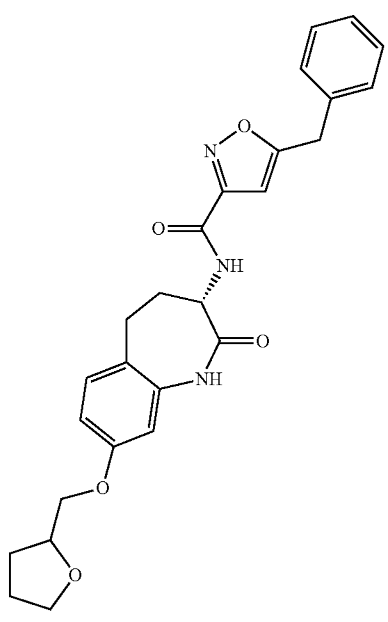 [SMILES: O=C(N[C@H]1CCc2ccc(OCC3CCCO3)cc2NC1=O)c1cc(Cc2ccccc2)on1] | ¹H NMR (DMSO-d₆) δ: 9.87 (s, 1H), 8.64 (d, J = 7.8 Hz, 1H), 7.25-7.40 (m, 5H), 7.19 (d, J = 8.3 Hz, 1H), 6.73 (dd, J = 8.3, 2.5 Hz, 1H), 6.60 (d, J = 2.5 Hz, 1H), 6.54 (s, 1H), 4.35 (dt, J = 11.2, 8.3 Hz, 1H), 4.21 (s, 2H), 4.10-4.18 (m, 1H), 3.83-4.00 (m, 2H), 3.74-3.83 (m, 1H), 3.63-3.72 (m, 1H), 2.65 (dd, J = 9.5, 5.7 Hz, 2H), 2.19-2.36 (m, 2H), 1.94-2.05 (m, 1H), 1.77-1.93 (m, 2H), 1.57-1.73 (m, 1H) | 462 | F |

-continued

| Ex | Name | Structure | 1H NMR | MS (M + H)⁺ | Method |
|---|---|---|---|---|---|
| 33 | (S)-1-(4-methylbenzyl)-N-(2-oxo-2,3,4,5-tetrahydro-1H-benzo[b]azepin-3-yl)-1H-1,2,3-triazole-4-carboxamide | 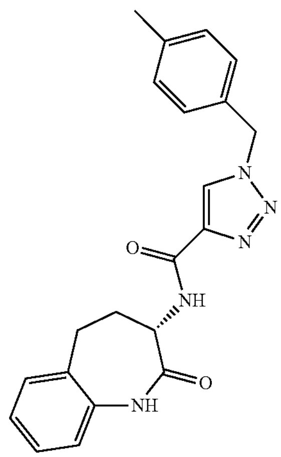 [SMILES: Cc1ccc(Cn2cc(C(=O)N[C@H]3CCc4ccccc4NC3=O)nn2)cc1] | $^1$H NMR (MeOH-d4) δ: 8.41 (d, J = 7.1 Hz, 1H), 8.30 (s, 1H), 7.15-7.39 (m, 8H), 7.09 (d, J = 7.8 Hz, 1H), 5.55-5.64 (m, 2H), 4.53-4.64 (m, 1H), 2.96 (dd, J = 13.4, 8.1 Hz, 1H), 2.73-2.84 (m, 1H), 2.57-2.71 (m, 1H), 2.33 (s, 3H), 2.19-2.29 (m, 1H) | 376 | F |
| 34 | (S)-1-(4-fluorobenzyl)-N-(2-oxo-2,3,4,5-tetrahydro-1H-benzo[b]azepin-3-yl)-1H-1,2,3-triazole-4-carboxamide | 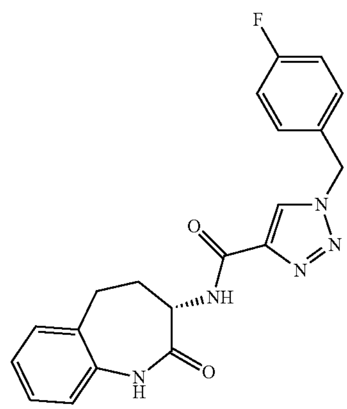 [SMILES: O=C(N[C@H]1CCc2ccccc2NC1=O)c1cn(Cc2ccc(F)cc2)nn1] | $^1$H NMR (MeOH-d4) δ: 8.40-8.46 (m, 1H), 8.36 (s, 1H), 7.38-7.45 (m, 2H), 7.28-7.36 (m, 2H), 7.19-7.24 (m, 1H), 7.07-7.17 (m, 3H), 5.64 (s, 2H), 4.53-4.62 (m, 1H), 2.91-3.04 (m, 1H), 2.75-2.82 (m, 1H), 2.65 (m, 1H), 2.24 (m, 1H) | 380 | F |
| 35 | (S)-3-benzyl-N-(8-chloro-2-oxo-2,3,4,5-tetrahydro-1H-benzo[b]azepin-3-yl)-1H-pyrazole-5-carboxamide | 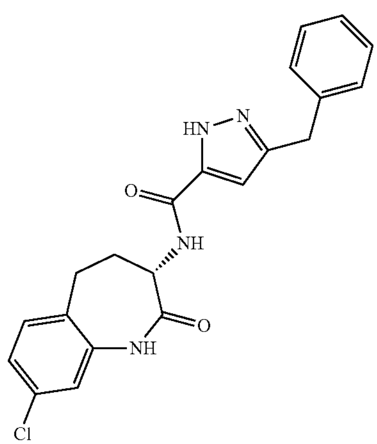 [SMILES: O=C(N[C@H]1CCc2ccc(Cl)cc2NC1=O)c1cc(Cc2ccccc2)n[nH]1] | $^1$H NMR (MeOH-d4) δ: 7.27-7.36 (m, 4H), 7.17-7.27 (m, 4H), 7.13 (d, J = 2.0 Hz, 1H), 6.47 (s, 1H), 4.55 (dd, J = 11.5, 8.0 Hz, 1H), 4.03 (s, 2H), 2.91 (dd, J = 13.8, 8.0 Hz, 1H), 2.73-2.85 (m, 1H), 2.59-2.70 (m, 1H), 2.21 (m, 1H) | 395/397 | F |

-continued

| Ex | Name | Structure | 1H NMR | MS (M + H)+ | Method |
|---|---|---|---|---|---|
| 36 | (S)-1-benzyl-N-(8-chloro-2-oxo-2,3,4,5-tetrahydro-1H-benzo[b]azepin-3-yl)-1H-1,2,3-triazole-4-carboxamide | 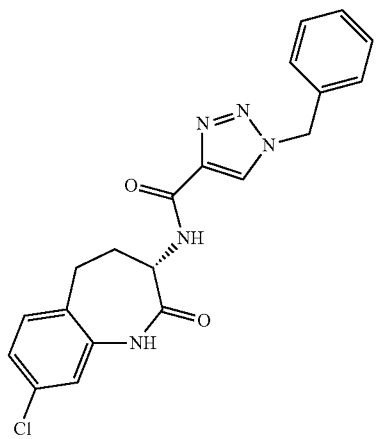 [SMILES: O=C(N[C@H]1CCc2ccc(Cl)cc2NC1=O)c1cn(Cc2ccccc2)nn1] | ¹H NMR (CDCl₃) δ: 7.95 (s, 2H), 7.55 (s, 1H), 7.36-7.46 (m, 3H), 7.26-7.33 (m, 2H), 7.14-7.26 (m, 2H), 7.06 (d, J = 1.8 Hz, 1H), 5.56 (s, 2H), 4.71 (dt, J = 11.2, 7.7 Hz, 1H), 2.91-3.03 (m, 1H), 2.66-2.85 (m, 2H), 2.14 (td, J = 11.8, 7.5 Hz, 1H) | 396/398 | F |
| 37 | (S)-1-benzyl-N-(8-chloro-2-oxo-2,3,4,5-tetrahydro-1H-benzo[b]azepin-3-yl)-1H-imidazole-4-carboxamide | 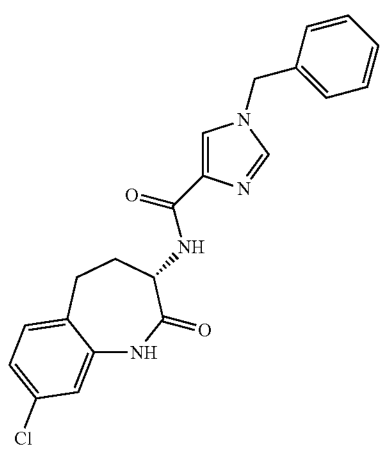 [SMILES: O=C(N[C@H]1CCc2ccc(Cl)cc2NC1=O)c1cn(Cc2ccccc2)cn1] | ¹H NMR (CDCl₃) δ: 7.92 (d, J = 7.3 Hz, 1H), 7.66 (s, 1H), 7.50-7.60 (m, 2H), 7.32-7.46 (m, 3H), 7.19 (m, 4H), 7.05 (s, 1H), 5.14 (s, 2H), 4.70 (dt, J = 11.1, 7.7 Hz, 1H), 2.89-3.04 (m, 1H), 2.59-2.86 (m, 2H), 2.01-2.20 (m, 1H) | 395/397 | F |
| 38 | (S)-3-benzyl-N-(8-fluoro-2-oxo-2,3,4,5-tetrahydro-1H-benzo[b]azepin-3-yl)-1H-pyrazole-5-carboxamide | 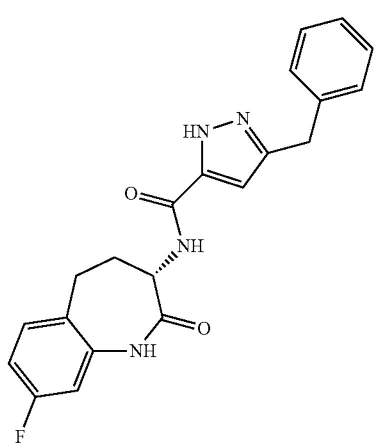 [SMILES: O=C(N[C@H]1CCc2ccc(F)cc2NC1=O)c1cc(Cc2ccccc2)n[nH]1] | ¹H NMR (MeOH-d4) δ: 7.29-7.40 (m, 3H), 7.18-7.27 (m, 3H), 6.95 (td, J = 8.5, 2.7 Hz, 1H), 6.86 (dd, J = 9.5, 2.7 Hz, 1H), 6.49 (br. s., 1H), 4.56 (dd, J = 11.6, 8.1 Hz, 1H), 4.03 (s, 2H), 2.90 (td, J = 13.5, 8.0 Hz, 1H), 2.78 (dd, J = 13.6, 7.1 Hz, 1H), 2.62 (br. s., 1H), 2.12-2.27 (m, 1H) | 379 | F |

-continued

| Ex | Name | Structure | 1H NMR | MS (M + H)⁺ | Method |
|---|---|---|---|---|---|
| 39 | (S)-1-benzyl-N-(8-fluoro-2-oxo-2,3,4,5-tetrahydro-1H-benzo[b]azepin-3-yl)-1H-imidazole-4-carboxamide | 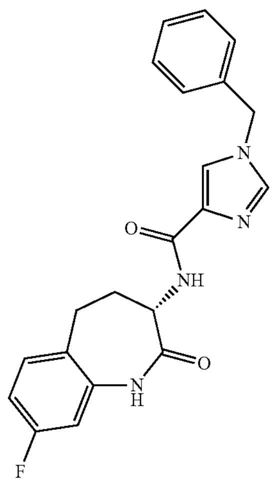 [SMILES: O=C(N[C@H]1CCc2ccc(F)cc2NC1=O)c1cn(Cc2ccccc2)cn1] | $^1$H NMR (MeOH-d4) δ: 7.78 (d, J = 1.3 Hz, 1H), 7.65 (d, J = 1.3 Hz, 1H), 7.26-7.42 (m, 6H), 6.95 (td, J = 8.5, 2.5 Hz, 1H), 6.86 (dd, J = 9.6, 2.5 Hz, 1H), 5.26 (s, 2H), 4.55 (dd, J = 11.6, 8.1 Hz, 1H), 2.86-2.97 (m, 1H), 2.75-2.83 (m, 1H), 2.57-2.69 (m, 1H), 2.18 (td, J = 12.0, 7.3 Hz, 1H) | 379 | F |
| 40 | (S)-5-benzyl-N-(2-oxo-2,3,4,5-tetrahydro-1H-benzo[b]azepin-3-yl)-4H-1,2,4-triazole-3-carboxamide | 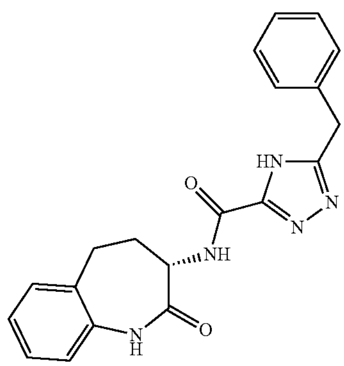 [SMILES: O=C(N[C@H]1CCc2ccccc2NC1=O)c1nnc(Cc2ccccc2)[nH]1] | $^1$H NMR (MeOH-d4) δ: 7.18-7.48 (m, 8H), 7.10 (d, J = 7.6 Hz, 1H), 4.58 (m, 1H), 4.17 (s, 2H), 2.97 (m 1H), 2.77 (m, 1H), 2.67 (m, 1H), 2.23 (m, 1H) | 362 | F |
| 41 | (S)-5-benzyl-N-(8-fluoro-2-oxo-2,3,4,5-tetrahydro-1H-benzo[b]azepin-3-yl)-4H-1,2,4-triazole-3-carboxamide | 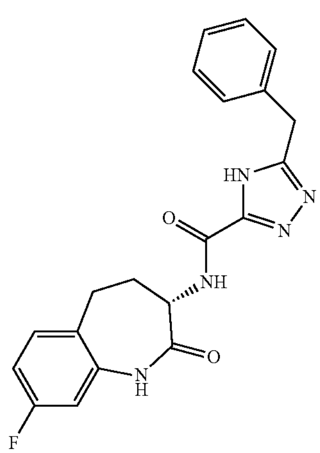 [SMILES: O=C(N[C@H]1CCc2ccc(F)cc2NC1=O)c1nnc(Cc2ccccc2)[nH]1] | $^1$H NMR (MeOH-d4) δ: 7.22-7.40 (m, 6H), 6.96 (td, J = 8.5, 2.7 Hz, 1H), 6.87 (dd, J = 9.6, 2.5 Hz, 1H), 4.58 (dd, J = 11.5, 8.0 Hz, 1H), 4.18 (s, 2H), 2.86-2.98 (m, 1H), 2.75-2.85 (m, 1H), 2.57-2.72 (m, 1H), 2.14-2.27 (m, 1H) | 380 | F |

| Ex | Name | Structure | 1H NMR | MS (M + H)+ | Method |
|---|---|---|---|---|---|
| 42 | (S)-2-benzyl-N-(2-oxo-2,3,4,5-tetrahydro-1H-benzo[b]azepin-3-yl)-2H-tetrazole-5-carboxamide | 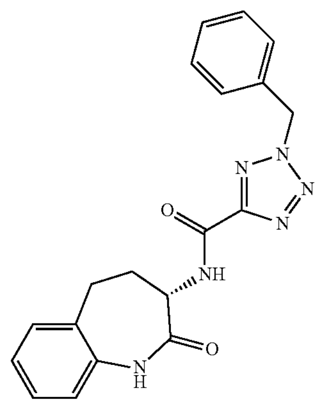 [SMILES: O=C(N[C@H]1CCc2ccccc2NC1=O)c1nnn(Cc2ccccc2)n1] | $^1$H NMR (MeOH-d4) δ: 7.36-7.54 (m, 5H), 7.28-7.36 (m, 2H), 7.17-7.27 (m, 1H), 7.10 (d, J = 7.6 Hz, 1H), 5.95 (s, 2H), 4.60 (dd, J = 11.6, 8.1 Hz, 1H), 2.98 (td, J = 13.4, 8.1 Hz, 1H), 2.79 (dd, J = 13.3, 6.9 Hz, 1H), 2.57-2.72 (m, 1H), 2.24-2.37 (m, 1H) | 363 | F |
| 43 | (S)-2-benzyl-N-(8-fluoro-2-oxo-2,3,4,5-tetrahydro-1H-benzo[b]azepin-3-yl)-2H-tetrazole-5-carboxamide | 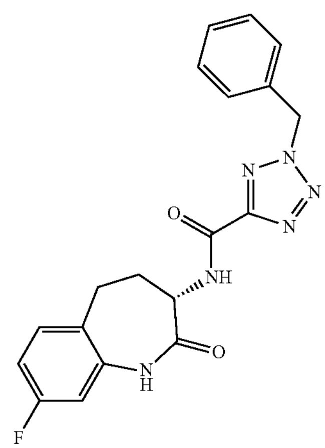 [SMILES: O=C(N[C@H]1CCc2ccc(F)cc2NC1=O)c1nnn(Cc2ccccc2)n1] | $^1$H NMR (MeOH-d4) δ: 7.38-7.47 (m, 5H), 7.34 (dd, J = 8.3, 6.3 Hz, 1H), 6.96 (td, J = 8.5, 2.8 Hz, 1H), 6.87 (dd, J = 9.5, 2.7 Hz, 1H), 5.95 (s, 2H), 4.61 (dd, J = 11.6, 8.1 Hz, 1H), 2.88-2.99 (m, 1H), 2.76-2.85 (m, 1H), 2.56-2.68 (m, 1H), 2.23-2.36 (m, 1H) | 381 | F |
| 44 | (S)-1-benzyl-N-(1-methyl-2-oxo-2,3,4,5-tetrahydro-1H-benzo[b]azepin-3-yl)-1H-imidazole-4-carboxamide | 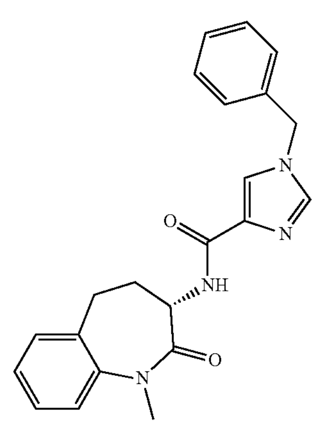 [SMILES: CN1C(=O)[C@@H](NC(=O)c2cn(Cc3ccccc3)cn2)CCc2ccccc21] | $^1$H NMR (MeOH-d4) δ: 7.77 (d, J = 1.3 Hz, 1H), 7.63 (d, J = 1.3 Hz, 1H), 7.23-7.44 (m, 9H), 5.25 (s, 2H), 4.51 (dd, J = 11.4, 7.8 Hz, 1H), 3.41 (s, 3H), 2.89 (td, J = 13.4, 7.8 Hz, 1H), 2.73 (dd, J = 13.5, 6.7 Hz, 1H), 2.54 (tt, J = 13.1, 7.3 Hz, 1H), 2.09-2.20 (m, 1H) | 375 | F |

| Ex | Name | Structure | 1H NMR | MS (M + H)+ | Method |
|---|---|---|---|---|---|
| 45 | (S)-1-benzyl-N-(5-methyl-4-oxo-2,3,4,5-tetrahydrobenzo[b][1,4]oxazepin-3-yl)-1H-1,2,4-triazole-3-carboxamide | 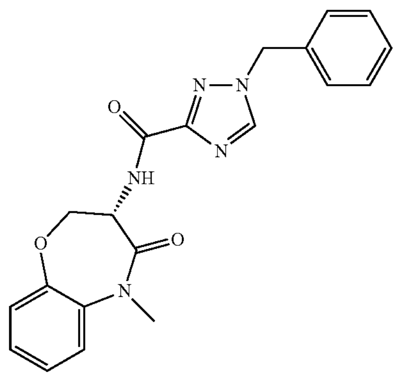 [SMILES: CN1C(=O)[C@@H](NC(=O)c2ncn(Cc3ccccc3)n2)COc2ccccc21] | $^1$H NMR (MeOH-d4) δ: 8.58 (s, 1H), 7.42-7.48 (m, 1H), 7.28-7.42 (m, 7H), 7.20-7.27 (m, 1H), 5.49 (s, 2H), 5.02 (dd, J = 11.4, 7.6 Hz, 1H), 4.61 (dd, J = 9.9, 7.6 Hz, 1H), 4.43 (dd, J = 11.4, 9.9 Hz, 1H), 3.42 (s, 3H) | 378 | H |
| 46 | (S)-5-benzyl-N-(2-oxo-2,3,4,5-tetrahydro-1H-benzo[b]azepin-3-yl)-1,3,4-oxadiazole-2-carboxamide | 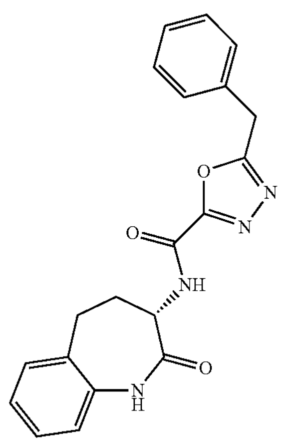 [SMILES: O=C(N[C@H]1CCc2ccccc2NC1=O)c1nnc(Cc2ccccc2)o1] | $^1$H NMR (MeOH-d4) δ: 7.27-7.41 (m, 7H), 7.16-7.24 (m, 1H), 7.10 (d, J = 7.8 Hz, 1H), 4.53 (dd, J = 11.7, 8.2 Hz, 1H), 4.34 (s, 2H), 2.91-3.05 (m, 1H), 2.80 (dt, J = 14.0, 7.1 Hz, 1H), 2.52-2.66 (m, 1H), 2.25-2.38 (m, 1H) | 363 | H |
| 47 | (S)-5-benzyl-N-(8-fluoro-2-oxo-2,3,4,5-tetrahydro-1H-benzo[b]azepin-3-yl)-1,3,4-oxadiazole-2-carboxamide | 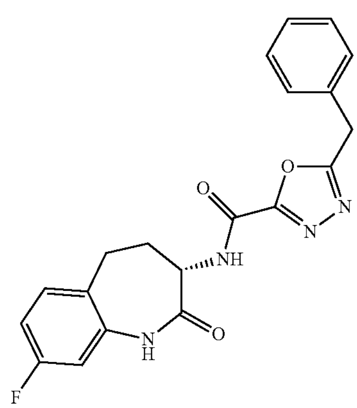 [SMILES: O=C(N[C@H]1CCc2ccc(F)cc2NC1=O)c1nnc(Cc2ccccc2)o1] | $^1$H NMR (MeOH-d4) δ: 7.27-7.40 (m, 6H), 6.96 (td, J = 8.5, 2.7 Hz, 1H), 6.87 (dd, J = 9.6, 2.5 Hz, 1H), 4.54 (dd, J = 11.9, 8.1 Hz, 1H), 4.34 (s, 2H), 2.90 (dd, J = 13.4, 7.8 Hz, 1H), 2.76-2.83 (m, 1H), 2.52-2.64 (m, 1H), 2.26-2.37 (m, 1H) | 381 | H |

| Ex | Name | Structure | 1H NMR | MS (M + H)+ | Method |
|---|---|---|---|---|---|
| 48 | (S)-1-benzyl-N-(8-fluoro-2-oxo-2,3,4,5-tetrahydro-1H-benzo[b]azepin-3-yl)-1H-1,2,3-triazole-4-carboxamide | 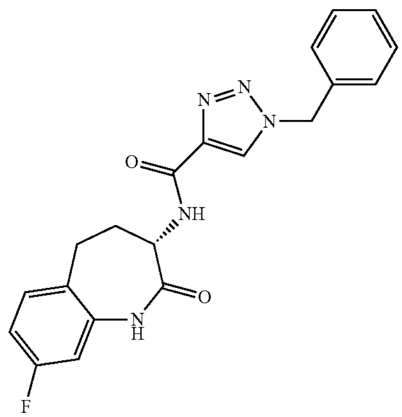 [SMILES: O=C(N[C@H]1CCc2ccc(F)cc2NC1=O)c1cn(Cc2ccccc2)nn1] | ¹H NMR (DMSO-d₆) δ: 10.07 (s, 1H), 8.67 (s, 1H), 8.39 (d, J = 7.8 Hz, 1H), 7.29-7.42 (m, 6H), 7.00 (td, J = 8.5, 2.7 Hz, 1H), 6.86 (dd, J = 9.9, 2.5 Hz, 1H), 5.65 (s, 2H), 4.38 (dt, J = 11.6, 8.0 Hz, 1H), 2.63-2.80 (m, 2H), 2.21-2.47 (m, 2H) | 380 | H |
| 49 | (S)-5-benzyl-N-(1-methyl-2-oxo-2,3,4,5-tetrahydro-1H-benzo[b]azepin-3-yl)-4H-1,2,4-triazole-3-carboxamide | 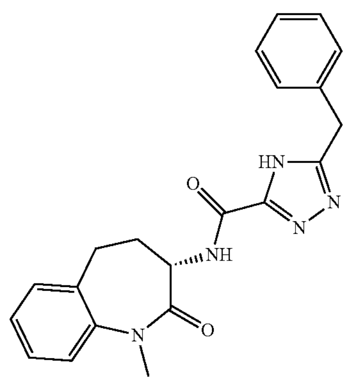 [SMILES: CN1C(=O)[C@@H](NC(=O)c2nnc(Cc3ccccc3)[nH]2)CCc2ccccc21] | ¹H NMR (MeOH-d4) δ: 7.22-7.45 (m, 10H), 4.54 (dd, J = 11.6, 7.8 Hz, 1H), 4.14-4.20 (m, 2H), 3.42 (s, 3H), 2.84-2.96 (m, 1H), 2.70-2.78 (m, 1H), 2.50-2.63 (m, 1H), 2.12-2.24 (m, 1H) | 376 | H |
| 50 | (S)-1-benzyl-N-(8-fluoro-1-methyl-2-oxo-2,3,4,5-tetrahydro-1H-benzo[b]azepin-3-yl)-1H-imidazole-4-carboxamide | 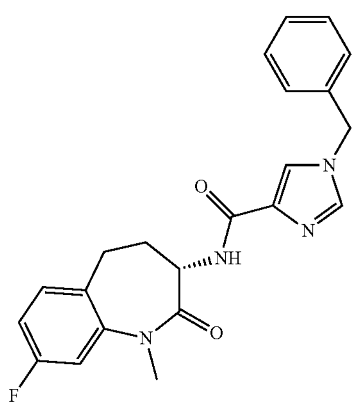 [SMILES: CN1C(=O)[C@@H](NC(=O)c2cn(Cc3ccccc3)cn2)CCc2ccc(F)cc21] | ¹H NMR (MeOH-d4) δ: 7.78 (s, 1H), 7.64 (s, 1H), 7.25-7.44 (m, 6H), 7.19 (dd, J = 9.9, 2.5 Hz, 1H), 6.96-7.08 (m, 1H), 5.25 (s, 2H), 4.51 (dd, J = 11.4, 7.8 Hz, 1H), 3.40 (s, 3H), 2.72-2.91 (m, 2H), 2.45-2.59 (m, 1H), 2.07-2.21 (m, 1H) | 393 | A |

| Ex | Name | Structure | 1H NMR | MS (M + H)+ | Method |
|---|---|---|---|---|---|
| 51 | (S)-1-benzyl-N-(8-fluoro-1-methyl-2-oxo-2,3,4,5-tetrahydro-1H-benzo[b]azepin-3-yl)-1H-1,2,4-triazole-3-carboxamide | 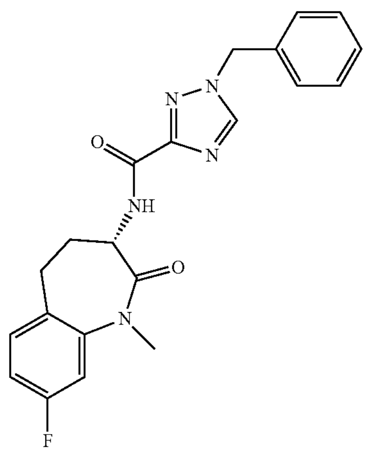 [SMILES: CN1C(=O)[C@@H](NC(=O)c2ncn(Cc3ccccc3)n2)CCc2ccc(F)cc21] | 1H NMR (MeOH-d4) δ: 8.57 (s, 1H), 7.31-7.42 (m, 6H), 7.20 (dd, J = 9.9, 2.8 Hz, 1H), 7.03 (td, J = 8.4, 2.7 Hz, 1H), 5.48 (s, 2H), 4.54 (dd, J = 11.5, 8.0 Hz, 1H), 3.41 (s, 3H), 2.71-2.89 (m, 2H), 2.49-2.62 (m, 1H), 2.13-2.24 (m, 1H) | 394 | A |
| 52 | (S)-5-benzyl-N-(8-fluoro-1-methyl-2-oxo-2,3,4,5-tetrahydro-1H-benzo[b]azepin-3-yl)-4H-1,2,4-triazole-3-carboxamide | 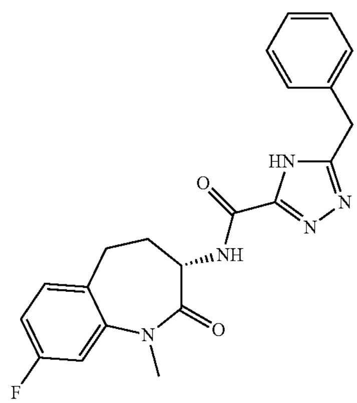 [SMILES: CN1C(=O)[C@@H](NC(=O)c2nnc(Cc3ccccc3)[nH]2)CCc2ccc(F)cc21] | 1H NMR (MeOH-d4) δ: 7.25-7.39 (m, 6H), 7.20 (dd, J = 9.9, 2.5 Hz, 1H), 7.03 (td, J = 8.4, 2.7 Hz, 1H), 4.54 (dd, J = 11.4, 7.8 Hz, 1H), 4.17 (s, 2H), 3.41 (s, 3H), 2.71-2.91 (m, 2H), 2.48-2.62 (m, 1H), 2.12-2.24 (m, 1H) | 394 | A |
| 53 | (S)-1-benzyl-N-(1-methyl-2-oxo-2,3,4,5-tetrahydro-1H-benzo[b]azepin-3-yl)-1H-1,2,4-triazole-3-carboxamide | 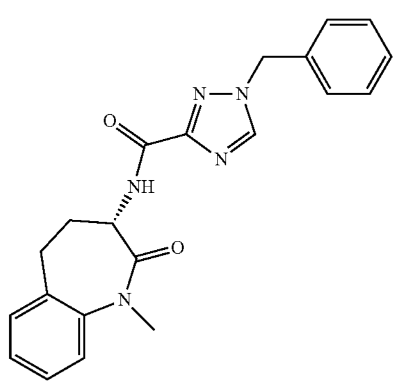 [SMILES: CN1C(=O)[C@@H](NC(=O)c2ncn(Cc3ccccc3)n2)CCc2ccccc21] | 1H NMR (MeOH-d4) δ: 8.57 (s, 1H), 7.32-7.44 (m, 8H), 7.24-7.31 (m, 1H), 5.48 (s, 2H), 4.54 (dd, J = 11.4, 7.8 Hz, 1H), 3.42 (s, 3H), 2.83-2.93 (m, 1H), 2.68-2.79 (m, 1H), 2.49-2.63 (m, 1H), 2.12-2.25 (m, 1H) | 376 | A |

-continued

| Ex | Name | Structure | 1H NMR | MS (M + H)+ | Method |
|---|---|---|---|---|---|
| 54 | (S)-5-benzyl-N-(8-chloro-2-oxo-2,3,4,5-tetrahydro-1H-benzo[b]azepin-3-yl)-4H-1,2,4-triazole-3-carboxamide | 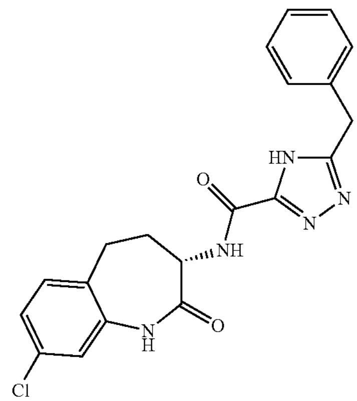 [SMILES: O=C(N[C@H]1CCc2ccc(Cl)cc2NC1=O)c1nnc(Cc2ccccc2)[nH]1] | $^1$H NMR (MeOH-d4) δ: 7.24-7.37 (m, 7H), 7.22 (dd, J = 8.1, 2.0 Hz, 1H), 7.13 (d, J = 2.0 Hz, 1H), 4.57 (dd, J = 11.6, 8.1 Hz, 1H), 4.17 (s, 2H), 2.87-3.00 (m, 1H), 2.75-2.84 (m, 1H), 2.59-2.70 (m, 1H), 2.16-2.29 (m, 1H) | 396/398 | H |
| 55 | (S)-N-(8-chloro-2-oxo-2,3,4,5-tetrahydro-1H-benzo[b]azepin-3-yl)-5-(4-fluorobenzyl)-4H-1,2,4-triazole-3-carboxamide | 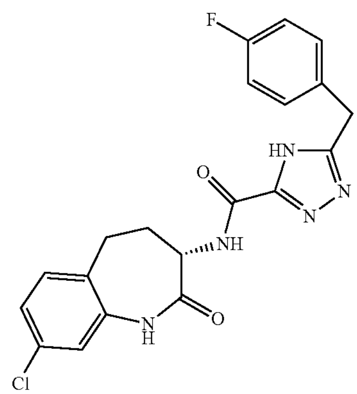 [SMILES: O=C(N[C@H]1CCc2ccc(Cl)cc2NC1=O)c1nnc(Cc2ccc(F)cc2)[nH]1] | $^1$H NMR (MeOH-d4) δ: 7.26-7.40 (m, 4H), 7.19-7.26 (m, 1H), 7.13 (s, 1H), 7.01-7.11 (m, 2H), 4.57 (dd, J = 11.4, 8.1 Hz, 1H), 4.16 (s, 2H), 2.86-3.01 (m, 1H), 2.75-2.85 (m, 1H), 2.58-2.73 (m, 1H), 2.14-2.30 (m, 1H) | 414/416 | H |
| 56 | (S)-N-(8-chloro-2-oxo-2,3,4,5-tetrahydro-1H-benzo[b]azepin-3-yl)-5-(3-fluorobenzyl)-4H-1,2,4-triazole-3-carboxamide | 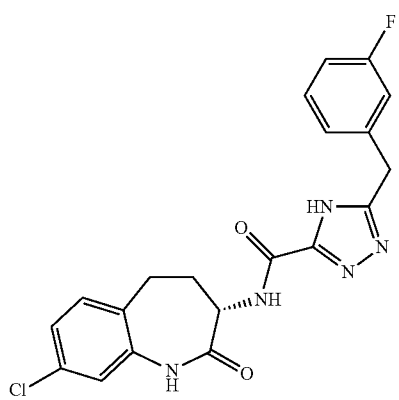 [SMILES: O=C(N[C@H]1CCc2ccc(Cl)cc2NC1=O)c1nnc(Cc2cccc(F)c2)[nH]1] | $^1$H NMR (MeOH-d4) δ: 7.31-7.39 (m, 2H), 7.22 (dd, J = 8.1, 2.3 Hz, 1H), 6.96-7.16 (m, 4H), 4.57 (dd, J = 11.6, 8.1 Hz, 1H), 4.19 (s, 2H), 2.93 (td, J = 13.3, 8.0 Hz, 1H), 2.80 (dd, J = 13.9, 6.8 Hz, 1H), 2.58-2.71 (m, 1H), 2.19-2.29 (m, 1H) | 414/416 | H |
| 57 | (S)-N-(8-chloro-2-oxo-2,3,4,5-tetrahydro-1H-benzo[b]azepin-3-yl)-5-(4-methylbenzyl)-4H-1,2,4-triazole-3-carboxamide | 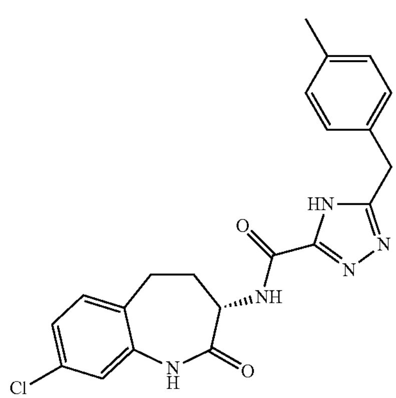 [SMILES: Cc1ccc(Cc2nnc(C(=O)N[C@H]3CCc4ccc(Cl)cc4NC3=O)[nH]2)cc1] | $^1$H NMR (MeOH-d4) δ: 7.33 (d, J = 8.1 Hz, 1H), 7.22 (dd, J = 8.1, 2.0 Hz, 1H), 7.12-7.19 (m, 5H), 4.57 (dd, J = 11.6, 8.1 Hz, 1H), 4.12 (s, 2H), 2.87-2.99 (m, 1H), 2.76-2.84 (m, 1H), 2.57-2.71 (m, 1H), 2.32 (s, 3H), 2.17-2.28 (m, 1H) | 410/412 | H |

| Ex | Name | Structure | 1H NMR | MS (M + H)+ | Method |
|---|---|---|---|---|---|
| 58 | (S)-N-(8-fluoro-2-oxo-2,3,4,5-tetrahydro-1H-benzo[b]azepin-3-yl)-5-(4-fluorobenzyl)-4H-1,2,4-triazole-3-carboxamide | 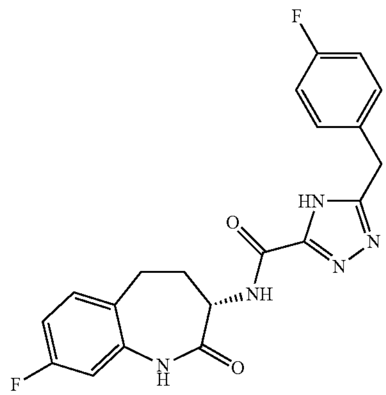 [SMILES: O=C(N[C@H]1CCc2ccc(F)cc2NC1=O)c1nnc(Cc2ccc(F)cc2)[nH]1] | 1H NMR (MeOH-d4) δ: 7.27-7.44 (m, 3H), 7.02-7.15 (m, 2H), 6.96 (td, J = 8.4, 2.4 Hz, 1H), 6.82-6.90 (m, 1H), 4.58 (dd, J = 11.6, 8.1 Hz, 1H), 4.16 (s, 2H), 2.86-2.99 (m, 1H), 2.79 (dd, J = 13.6, 7.1 Hz, 1H), 2.59-2.73 (m, 1H), 2.13-2.27 (m, 1H) | 398 | H |
| 59 | (S)-N-(8-fluoro-2-oxo-2,3,4,5-tetrahydro-1H-benzo[b]azepin-3-yl)-5-(4-methylbenzyl)-4H-1,2,4-triazole-3-carboxamide | 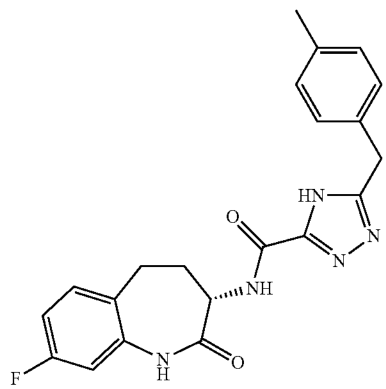 [SMILES: Cc1ccc(Cc2nnc(C(=O)N[C@H]3CCc4ccc(F)cc4NC3=O)[nH]2)cc1] | 1H NMR (MeOH-d4) δ: 7.34 (dd, J = 8.3, 6.3 Hz, 1H), 7.10-7.23 (m, 6H), 6.96 (td, J = 8.5, 2.7 Hz, 1H), 6.87 (dd, J = 9.5, 2.7 Hz, 1H), 4.58 (dd, J = 11.6, 8.1 Hz, 1H), 4.12 (s, 2H), 2.92 (td, J = 13.5, 7.8 Hz, 1H), 2.79 (dd, J = 13.9, 6.8 Hz, 1H), 2.58-2.70 (m, 1H), 2.32 (s, 3H), 2.14-2.26 (m, 1H) | 394 | H |
| 60 | (S)-N-(8-fluoro-2-oxo-2,3,4,5-tetrahydro-1H-benzo[b]azepin-3-yl)-5-(3-fluorobenzyl)-4H-1,2,4-triazole-3-carboxamide | 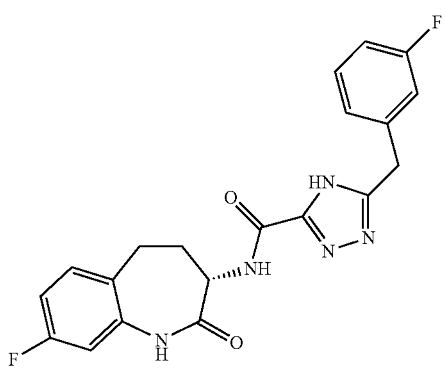 [SMILES: O=C(N[C@H]1CCc2ccc(F)cc2NC1=O)c1nnc(Cc2cccc(F)c2)[nH]1] | 1H NMR (MeOH-d4) δ: 7.28-7.41 (m, 2H), 6.93-7.18 (m, 4H), 6.81-6.92 (m, 1H), 4.58 (dd, J = 11.4, 8.1 Hz, 1H), 4.19 (s, 2H), 2.90 (dd, J = 13.3, 7.7 Hz, 1H), 2.73-2.85 (m, 1H), 2.58-2.72 (m, 1H), 2.15-2.29 (m, 1H) | 398 | H |
| 61 | (S)-5-benzyl-N-(4-oxo-7-(trifluoromethyl)-2,3,4,5-tetrahydrobenzo[b][1,4]oxazepin-3-yl)isoxazole-3-carboxamide | 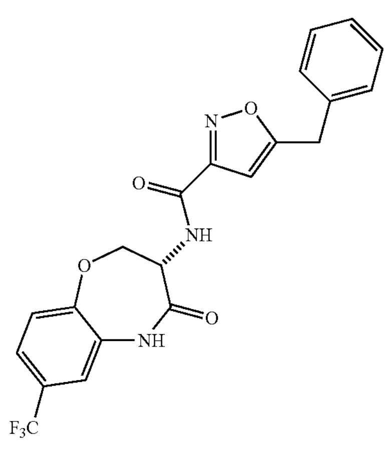 [SMILES: O=C(N[C@H]1COc2ccc(C(F)(F)F)cc2NC1=O)c1cc(Cc2ccccc2)on1] | N22077-36-A1: 1H NMR (DMSO-d6) δ: 10.36 (s, 1H), 8.92 (d, J = 7.8 Hz, 1H), 7.49 (d, J = 2.0 Hz, 1H), 7.44 (dd, J = 8.3, 1.8 Hz, 1H), 7.25-7.38 (m, 6H), 6.59 (s, 1H), 4.86 (ddd, J = 9.5, 8.0, 5.6 Hz, 1H), 4.44-4.57 (m, 2H), 4.23 (s, 2H). | 431.9 | F |

-continued

| Ex | Name | Structure | 1H NMR | MS (M + H)+ | Method |
|---|---|---|---|---|---|
| 62 | S)-5-benzyl-N-(7,9-difluoro-2-oxo-2,3,4,5-tetrahydro-1H-benzo[b]azepin-3-yl)-4H-1,2,4-triazole-3-carboxamide | 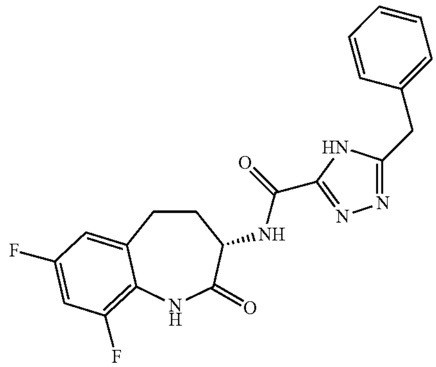 [SMILES: O=C(N[C@H]1CCc2cc(F)cc(F)c2NC1=O)c1nnc(Cc2ccccc2)[nH]1] | 1H NMR (DMSO-d6) δ ppm 13.75-15.37 (m, 1H), 9.97 (s, 1H), 8.06-8.97 (m, 1H), 6.93-7.69 (m, 6H), 4.24-4.59 (m, 1H), 4.14 (br. s., 2H), 2.68-2.95 (m, 2H), 2.32-2.46 (m, 1H), 2.25 (br. s., 1H) | 398 | H |
| 63 | (S)-5-benzyl-N-(8-methyl-4-oxo-2,3,4,5-tetrahydrobenzo[b][1,4]oxazepin-3-yl)isoxazole-3-carboxamide | 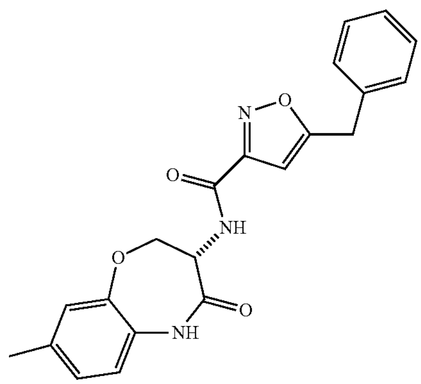 [SMILES: Cc1ccc2c(c1)OC[C@H](NC(=O)c1cc(Cc3ccccc3)on1)C(=O)N2] | $^1$H NMR (DMSO-d$_6$) δ: 10.01 (s, 1H), 8.79 (d, J = 8.1 Hz, 1H), 7.26-7.39 (m, 5H), 6.94-7.02 (m, 3H), 6.57 (s, 1H), 4.75-4.83 (m, 1H), 4.45-4.52 (m, 1H), 4.36-4.42 (m, 1H), 4.23 (s, 2H), 2.27 (s, 3H). | 377.9 | F |
| 64 | (S)-N-(1-methyl-2-oxo-2,3,4,5-tetrahydro-1H-benzo[b][1,4]diazepin-3-yl)-5-(4-methylbenzyl)-1H-pyrazole-3-carboxamide | 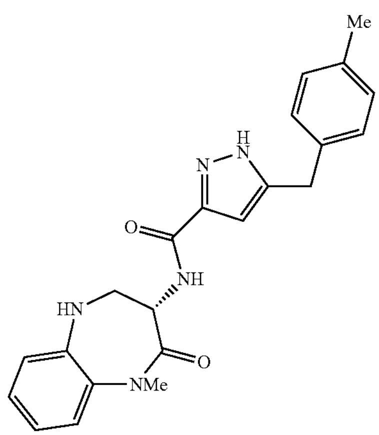 [SMILES: Cc1ccc(Cc2cc(C(=O)N[C@H]3CNc4ccccc4N(C)C3=O)n[nH]2)cc1] | $^1$H NMR (DMSO-d$_6$, 400 MHz): δ = 13.16 (s, 1 H), 7.91 (d, J = 7.6 Hz, 1 H), 7.29 (d, J = 7.6 Hz, 1 H), 6.88-7.20 (m, 8 H), 6.34 (s, 1 H), 5.39 (d, J = 5.3 Hz, 1 H), 4.46-4.87 (m, 1 H), 3.93 (s, 2 H), 3.37-3.49 (m, 1 H), 2.66-2.76 (m, 3 H), 2.26 ppm (s, 3 H) | 390 | F |
| 65 | (S)-5-benzyl-N-(6-methyl-4-oxo-2,3,4,5-tetrahydrobenzo[b][1,4]oxazepin-3-yl)isoxazole-3-carboxamide | 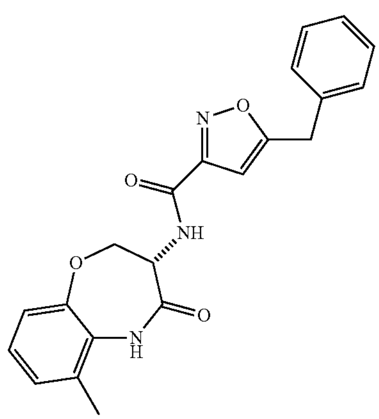 [SMILES: Cc1cccc2c1NC(=O)[C@@H](NC(=O)c1cc(Cc3ccccc3)on1)CO2] | $^1$H NMR (DMSO-d$_6$) δ: 9.70 (s, 1H), 8.73 (d, J = 8.1 Hz, 1H), 7.24-7.39 (m, 5H), 7.01-7.15 (m, 3H), 6.56 (s, 1H), 4.78 (dt, J = 11.4, 8.1 Hz, 1H), 4.54 (t, J = 10.7 Hz, 1H), 4.40 (dd, J = 10.1, 8.1 Hz, 1H), 4.22 (s, 2H), 2.27 (s, 3H). | 377.9 | F |

| Ex | Name | Structure | 1H NMR | MS (M + H)+ | Method |
|---|---|---|---|---|---|
| 66 | (S)-5-benzyl-N-(9-methyl-4-oxo-2,3,4,5-tetrahydrobenzo[b][1,4]oxazepin-3-yl)isoxazole-3-carboxamide | 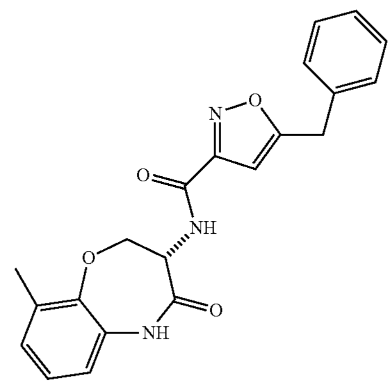 [SMILES: Cc1cccc2c1OC[C@H](NC(=O)c1cc(Cc3ccccc3)on1)C(=O)N2] | $^1$H NMR (DMSO-d$_6$) δ: 10.02 (s, 1H), 8.84 (d, 1H), 7.25-7.39 (m, 5H), 7.02-7.08 (m, 2H), 6.91-6.96 (m, 1H), 6.56 (s, 1H), 4.78 (dt, J = 11.1, 7.9 Hz, 1H), 4.44-4.58 (m, 2H), 4.23 (s, 2H), 2.25 (s, 3H). | 378.2 | F |
| 67 | (S)-3-(5-benzylisoxazole-3-carboxamido)-5-methyl-N-(2-(methylsulfonyl)ethyl)-4-oxo-2,3,4,5-tetrahydrobenzo[b][1,4]oxazepine-7-carboxamide | 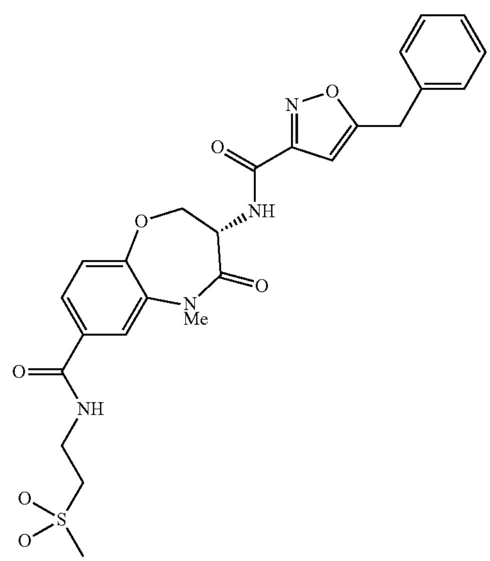 [SMILES: CN1C(=O)[C@@H](NC(=O)c2cc(Cc3ccccc3)on2)COc2ccc(C(=O)NCCS(C)(O)O)cc21] | $^1$H NMR (DMSO-d$_6$) δ: 8.89 (d, J = 8.1 Hz, 1H), 8.84 (t, J = 5.6 Hz, 1H), 7.92 (d, J = 2.0 Hz, 1H), 7.75 (dd, J = 8.3, 2.0 Hz, 1H), 7.26-7.38 (m, 6H), 6.54 (s, 1H), 4.85 (dt, J = 11.9, 7.8 Hz, 1H), 4.60-4.68 (m, 1H), 4.44 (dd, J = 9.7, 7.7 Hz, 1H), 4.22 (s, 2H), 3.65-3.73 (m, 2H), 3.39 (t, J = 6.7 Hz, 2H), 3.34 (s, 3H), 3.05 (s, 3H). | 526.9 | F |
| 68 | (S)-3-(5-benzylisoxazole-3-carboxamido)-5-methyl-4-oxo-N-(2-(pyrrolidin-1-yl)ethyl)-2,3,4,5-tetrahydrobenzo[b][1,4]oxazepine-7-carboxamide | 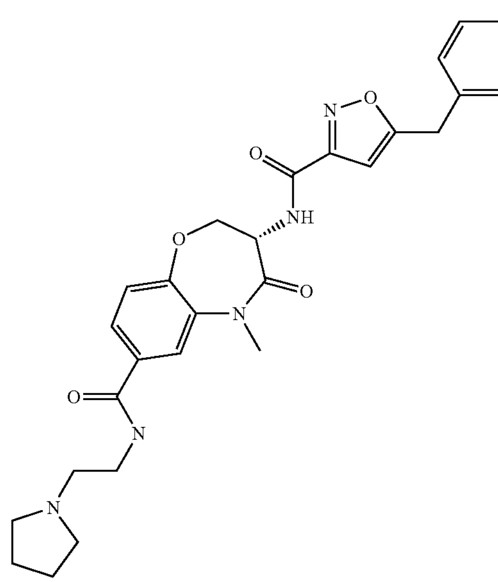 | $^1$H NMR (DMSO-d$_6$) δ: 8.88 (d, 1H), 8.52-8.59 (m, 1H), 7.91-7.95 (m, 1H), 7.75 (dd, J = 8.3, 2.0 Hz, 1H), 7.25-7.40 (m, 6H), 6.55 (s, 1H), 4.85 (dt, J = 11.6, 7.8 Hz, 1H), 4.58-4.67 (m, 1H), 4.43 (dd, J = 9.9, 7.6 Hz, 1H), 4.22 (s, 2H), 3.37-3.46 (m, 2H), 2.56-2.64 (m, 2H), 1.69 (t, J = 3.3 Hz, 4H) | 518.0 | F |

| Ex | Name | Structure | 1H NMR | MS (M + H)+ | Method |
|---|---|---|---|---|---|
| 69 | (S)-5-benzyl-N-(7-methyl-2-oxo-1,2,3,4-tetrahydropyrido[2,3-b][1,4]oxazepin-3-yl)isoxazole-3-carboxamide | 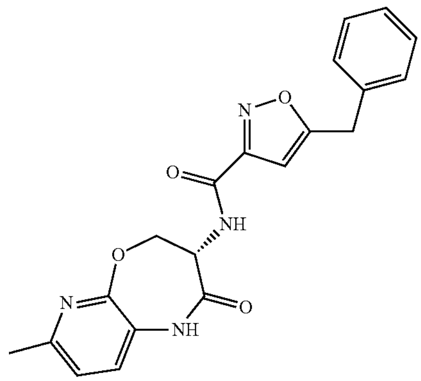 [SMILES: Cc1ccc2c(n1)OC[C@H](NC(=O)c1cc(Cc3ccccc3)on1)C(=O)N2] | $^1$H NMR (DMSO-d$_6$) δ: 10.18 (s, 1H), 8.89 (d, J = 6.8 Hz, 1H), 7.45 (dd, J = 7.7, 1.4 Hz, 1H), 7.26-7.39 (m, 5H), 7.01-7.07 (m, 1H), 6.59 (s, 1H), 4.77-4.86 (m, 1H), 4.43-4.52 (m, 2H), 4.24 (s, 2H), 2.35 (s, 3H). | 379.2 | F |
| 70 | 5-(hydroxy(phenyl)methyl)-N-((S)-4-oxo-2,3,4,5-tetrahydrobenzo[b][1,4]oxazepin-3-yl)thiophene-2-carboxamide | 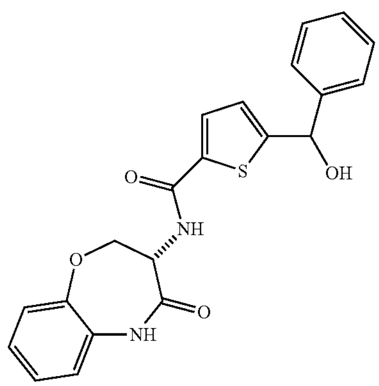 [SMILES: O=C(N[C@H]1COc2ccccc2NC1=O)c1ccc(C(O)c2ccccc2)s1] | $^1$H NMR (600 MHz, DMSO-d$_6$) δ: 10.06 (s, 1 H), 8.62 (d, J = 8.69 Hz, 1 H), 7.31-7.37 (m, 2 H), 7.23-7.29 (m, 1 H), 7.08-7.18 (m, 4 H), 6.87-6.95 (m, 1 H), 6.40 (br. s., 1 H), 5.92 (br. s., 1 H), 4.81 (dt, J = 10.39, 8.03 Hz, 1 H), 4.45 (td, J = 10.67, 4.72 Hz, 1 H), 4.35-4.42 (m, 1 H). | 395.1 | F |
| 71 | (S)-5-benzyl-N-(7-methoxy-4-oxo-2,3,4,5-tetrahydrobenzo[b][1,4]oxazepin-3-yl)isoxazole-3-carboxamide | 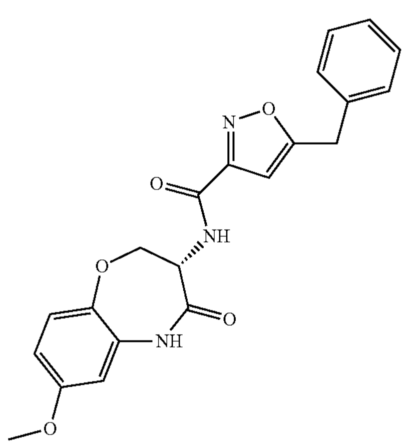 [SMILES: COc1ccc2c(c1)NC(=O)[C@@H](NC(=O)c1cc(Cc3ccccc3)on1)CO2] | H NMR (DMSO-d$_6$) δ: 10.06 (s, 1H), 8.85 (d, J = 8.1 Hz, 1H), 7.26-7.39 (m, 5H), 7.08 (d, J = 8.8 Hz, 1H), 6.71 (dd, J = 8.8, 3.0 Hz, 1H), 6.67 (d, J = 2.8 Hz, 1H), 6.57 (s, 1H), 4.81 (dt, J = 11.2, 7.7 Hz, 1H), 4.35-4.50 (m, 2H), 4.23 (s, 2H), 3.73 (s, 3H). | 394.2 | F |

| Ex | Name | Structure | 1H NMR | MS (M + H)+ | Method |
|---|---|---|---|---|---|
| 72 | (S)-5-benzyl-N-(5-methyl-7-(methylsulfonyl)-4-oxo-2,3,4,5-tetrahydrobenzo[b][1,4]oxazepin-3-yl)isoxazole-3-carboxamide | 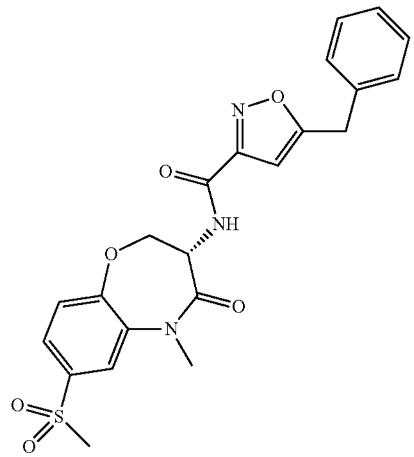 [SMILES: CN1C(=O)[C@@H](NC(=O)c2cc(Cc3ccccc3)on2)COc2ccc(S(C)(=O)=O)cc21] | $^1$H NMR (DMSO-d$_6$) δ: 8.94 (d, J = 8.1 Hz, 1H), 8.04 (d, J = 2.0 Hz, 1H), 7.83 (dd, J = 8.3, 2.3 Hz, 1H), 7.48 (d, J = 8.3 Hz, 1H), 7.26-7.38 (m, 5H), 6.55 (s, 1H), 4.89 (dt, J = 11.6, 7.8 Hz, 1H), 4.66-4.72 (m, 1H), 4.50 (dd, J = 9.9, 7.6 Hz, 1H), 4.22 (s, 2H), 3.37 (s, 3H), 3.31 (s, 3H). [456.1]. | 456.1 | F |
| 73 | (S)-5-benzyl-N-(5-methyl-7-(morpholine-4-carbonyl)-4-oxo-2,3,4,5-tetrahydrobenzo[b][1,4]oxazepin-3-yl)isoxazole-3-carboxamide | 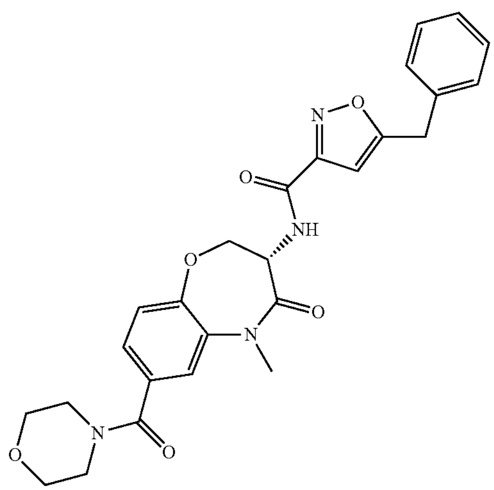 [SMILES: CN1C(=O)[C@@H](NC(=O)c2cc(Cc3ccccc3)on2)COc2ccc(C(=O)N3CCOCC3)cc21] | $^1$H NMR (CDCl$_3$) δ: 7.75 (d, J = 7.1 Hz, 1H), 7.31-7.39 (m, 6H), 7.22-7.25 (m, 2H), 6.32 (s, 1H), 5.06 (dt, J = 11.2, 7.2 Hz, 1H), 4.75 (dd, J = 9.7, 7.2 Hz, 1H), 4.31 (dd, J = 11.1, 10.1 Hz, 1H), 4.13 (s, 2H), 3.75 (br. s., 8H), 3.46 (s, 3H). | 491.2 | F |
| 74 | (S)-5-benzyl-N-(4-oxo-2,3,4,5-tetrahydropyrido[4,3-b][1,4]oxazepin-3-yl)isoxazole-3-carboxamide | 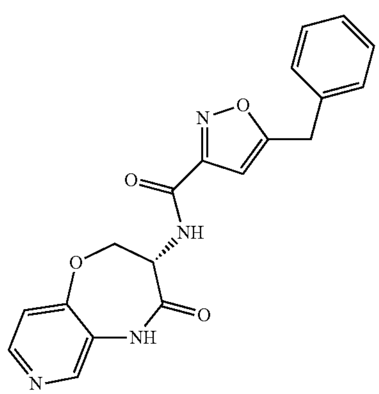 [SMILES: O=C(N[C@H]1COc2ccncc2NC1=O)c1cc(Cc2ccccc2)on1] | $^1$H NMR (DMSO-d$_6$) δ: 10.42 (s, 1H), 8.88 (d, J = 7.6 Hz, 1H), 8.35 (s, 1H), 8.12 (d, J = 5.3 Hz, 1H), 7.24-7.40 (m, 5H), 7.02 (d, J = 5.6 Hz, 1H), 6.61 (s, 1H), 4.82 (td, J = 8.0, 3.3 Hz, 1H), 4.40-4.52 (m, 2H), 4.24 (s, 2H). | 365.2 | F |

| Ex | Name | Structure | 1H NMR | MS (M + H)+ | Method |
|---|---|---|---|---|---|
| 75 | (S)-5-benzyl-N-(5,6-dimethyl-4-oxo-2,3,4,5-tetrahydrobenzo[b][1,4]oxazepin-3-yl)isoxazole-3-carboxamide | 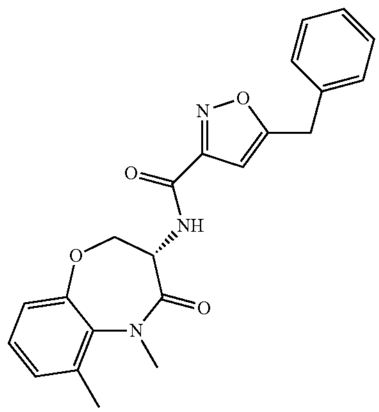 [SMILES: Cc1cccc2c1N(C)C(=O)[C@@H](NC(=O)c1cc(Cc3ccccc3)on1)CO2] | $^1$H NMR (DMSO-d$_6$) δ: 8.77 (d, J = 7.8 Hz, 1H), 7.19-7.38 (m, 7H), 7.08 (d, J = 7.6 Hz, 1H), 6.55 (s, 1H), 4.74-4.82 (m, 1H), 4.47 (dd, J = 11.1, 10.1 Hz, 1H), 4.27 (dd, J = 10.0, 8.0 Hz, 1H), 4.22 (s, 2H), 3.13 (s, 3H), 2.32 (s, 3H) | 392.1 | F |
| 76 | (S)-3-(5-benzylisoxazole-3-carboxamido)-N,N,5-trimethyl-4-oxo-2,3,4,5-tetrahydrobenzo[b][1,4]oxazepine-7-carboxamide | 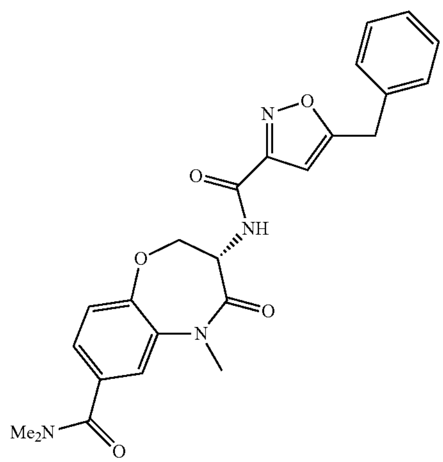 [SMILES: CN(C)C(=O)c1ccc2c(c1)N(C)C(=O)[C@@H](NC(=O)c1cc(Cc3ccccc3)on1)CO2] | $^1$H NMR (DMSO-d$_6$) δ: 8.86 (d, J = 8.1 Hz, 1H), 7.56 (d, J = 2.0 Hz, 1H), 7.24-7.39 (m, 7H), 6.55 (s, 1H), 4.88 (dt, J = 11.4, 7.9 Hz, 1H), 4.57-4.65 (m, 1H), 4.44 (dd, J = 10.0, 7.7 Hz, 1H), 4.22 (s, 2H), 3.32 (s, 3H), 2.98 (d, J = 13.6 Hz, 6H). | 449.2 | F |
| 77 | (S)-5-benzyl-N-(5-methyl-4-oxo-2,3,4,5-tetrahydrobenzo[b][1,4]oxazepin-3-yl)isoxazole-3-carboxamide | 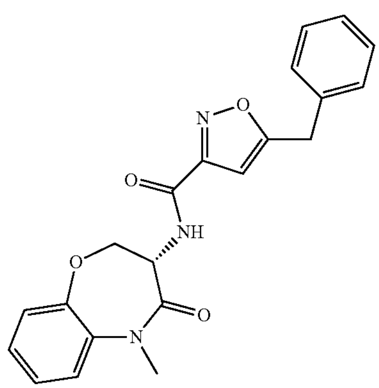 [SMILES: CN1C(=O)[C@@H](NC(=O)c2cc(Cc3ccccc3)on2)COc2ccccc21] | $^1$H NMR (DMSO-d$_6$) δ: 8.85 (d, J = 8.1 Hz, 1H), 7.51 (dd, J = 7.8, 1.8 Hz, 1H), 7.25-7.38 (m, 7H), 7.20-7.25 (m, 1H), 6.54 (s, 1H), 4.83 (dt, J = 11.6, 8.0 Hz, 1H), 4.58 (dd, J = 11.6, 9.9 Hz, 1H), 4.39 (dd, J = 9.9, 7.8 Hz, 1H), 4.22 (s, 2H), 3.30 (s, 3H) | 378.3 | F |

-continued

| Ex | Name | Structure | 1H NMR | MS (M + H)+ | Method |
|---|---|---|---|---|---|
| 78 | (S)-methyl 3-(5-benzylisoxazole-3-carboxamido)-5-methyl-4-oxo-2,3,4,5-tetrahydrobenzo[b][1,4]oxazepine-7-carboxylate | 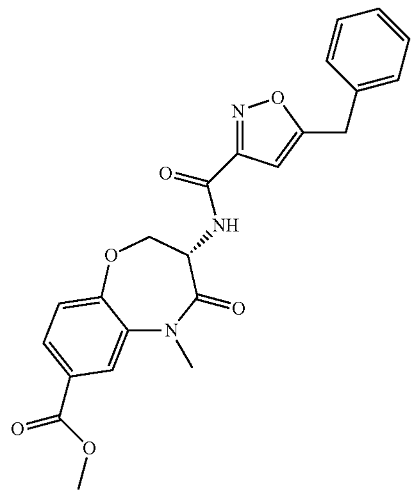 [SMILES: COC(=O)c1ccc2c(c1)N(C)C(=O)[C@@H](NC(=O)c1cc(Cc3ccccc3)on1)CO2] | $^1$H NMR (DMSO-d$_6$) δ: 8.90 (d, J = 7.8 Hz, 1H), 8.01 (d, J = 2.0 Hz, 1H), 7.87 (dd, J = 8.3, 2.0 Hz, 1H), 7.27-7.39 (m, 6H), 6.55 (s, 1H), 4.87 (dt, J = 11.7, 7.8 Hz, 1H), 4.66 (dd, J = 11.6, 9.9 Hz, 1H), 4.47 (dd, J = 9.9, 7.6 Hz, 1H), 4.22 (s, 2H), 3.88 (s, 3H). | 436.4 | F |
| 79 | S)-5-(cyclopentylmethyl)-N-(5-methyl-7-(5-methyl-1,3,4-oxadiazol-2-yl)-4-oxo-2,3,4,5-tetrahydrobenzo[b][1,4]oxazepin-3-yl)-4H-1,2,4-triazole-3-carboxamide | 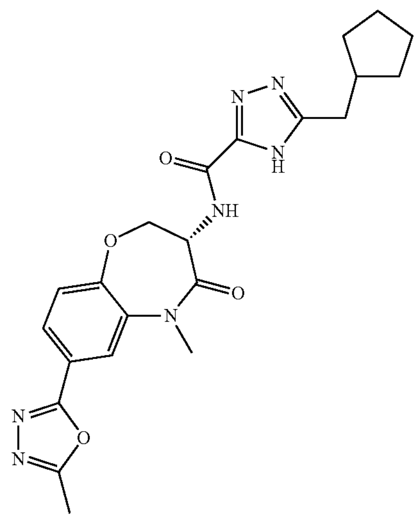 [SMILES: Cc1nnc(-c2ccc3c(c2)N(C)C(=O)[C@@H](NC(=O)c2nnc(CC4CCCC4)[nH]2)CO3)o1] | $^1$H NMR (DMSO-d$_6$, 400 MHz): δ = 8.66 (d, J = 7.8 Hz, 1 H), 7.22-7.44 (m, 6 H), 7.07-7.17 (m, 1 H), 6.96-7.06 (m, 2 H), 6.55 (s, 1 H), 5.32 (d, J = 4.5 Hz, 1 H), 4.65 (dt, J = 11.7, 7.0 Hz, 1 H), 4.22 (s, 2 H), 3.47-3.69 (m, 2 H), 3.33 ppm (s, 3 H) | 452 | H |
| 80 | (S)-5-benzyl-N-(5-methyl-4-oxo-7-(5-oxo-4,5-dihydro-1,3,4-oxadiazol-2-yl)-2,3,4,5-tetrahydrobenzo[b][1,4]oxazepin-3-yl)isoxazole-3-carboxamide | 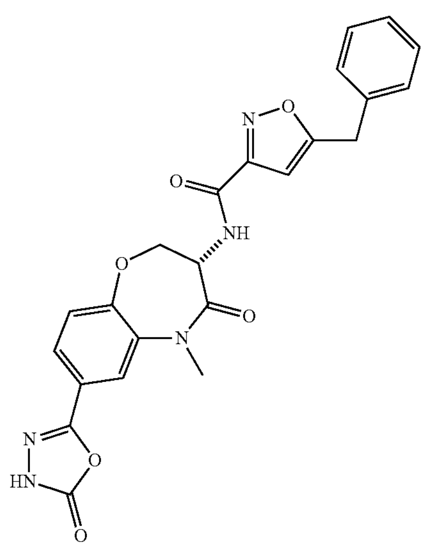 [SMILES: CN1C(=O)[C@@H](NC(=O)c2cc(Cc3ccccc3)on2)COc2ccc(-c3n[nH]c(=O)o3)cc21] | 1H NMR (DMSO-d$_6$) δ 8.33-8.57 (m, 1H), 8.04 (d, J = 2.0 Hz, 1H), 7.89 (dd, J = 8.3, 2.0 Hz, 1H), 7.45 (d, J = 8.3 Hz, 1H), 4.91 (dt, J = 11.6, 7.6 Hz, 1H), 4.69 (s, 1H), 4.51 (dd, J = 9.7, 7.5 Hz, 1H), 3.39 (s, 3H), 2.72 (d, J = 7.3 Hz, 2H), 2.61 (s, 3H), 2.18-2.31 (m, 1H), 1.40-1.80 (m, 5H), 1.07-1.31 (m, 3H) | 462.2 | F |

| Ex | Name | Structure | 1H NMR | MS (M + H)⁺ | Method |
|---|---|---|---|---|---|
| 81 | (S)-5-benzyl-N-(7-fluoro-5-methyl-4-oxo-2,3,4,5-tetrahydrobenzo[b][1,4]oxazepin-3-yl)-1H-pyrazole-3-carboxamide | 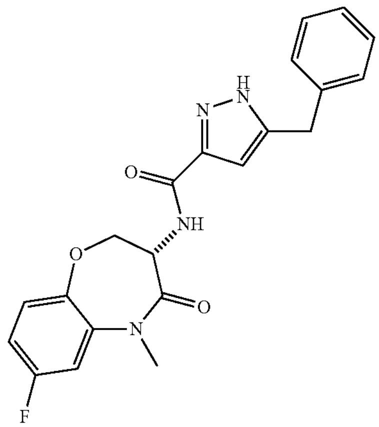 [SMILES: CN1C(=O)[C@@H](NC(=O)c2cc(Cc3ccccc3)[nH]n2)COc2ccc(F)cc21] | $^1$H NMR (DMSO-d$_6$) δ: 13.22 (br. s., 1H), 8.11 (br. s., 1H), 7.47 (dd, J = 9.9, 2.8 Hz, 1H), 7.19-7.34 (m, 6H), 7.09-7.16 (m, 1H), 6.37 (br. s., 1H), 4.84 (dt, J = 11.5, 8.0 Hz, 1H), 4.47-4.56 (m, 1H), 4.35-4.42 (m, 1H), 3.98 (br. s., 2H), 3.30 (s, 3H). | 395.2 | F |
| 82 | (S)-N-(7-fluoro-5-methyl-4-oxo-2,3,4,5-tetrahydrobenzo[b][1,4]oxazepin-3-yl)-5-(4-methylbenzyl)-1H-pyrazole-3-carboxamide | 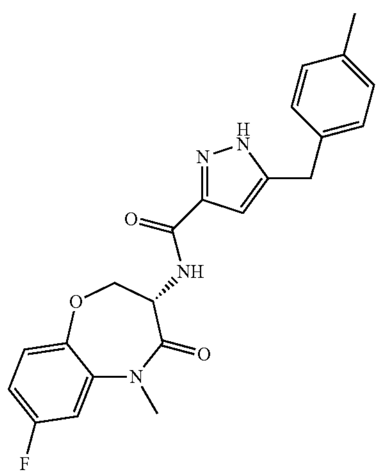 [SMILES: Cc1ccc(Cc2cc(C(=O)N[C@H]3COc4ccc(F)cc4N(C)C3=O)n[nH]2)cc1] | $^1$H NMR (DMSO-d$_6$) δ: 13.18 (br. s., 1H), 8.09 (d, J = 7.8 Hz, 1H), 7.47 (dd, J = 9.9, 3.0 Hz, 1H), 7.27 (dd, J = 9.0, 5.7 Hz, 1H), 7.09-7.15 (m, 5H), 6.34 (br. s., 1H), 4.84 (dt, J = 11.4, 8.1 Hz, 1H), 4.46-4.56 (m, 1H), 4.35-4.42 (m, 1H), 3.93 (br. s., 2H), 3.30 (s, 3H), 2.26 (s, 3H). | 409.3 | F |
| 83 | (S)-1-benzyl-N-(7-fluoro-5-methyl-4-oxo-2,3,4,5-tetrahydrobenzo[b][1,4]oxazepin-3-yl)-1H-1,2,3-triazole-4-carboxamide | 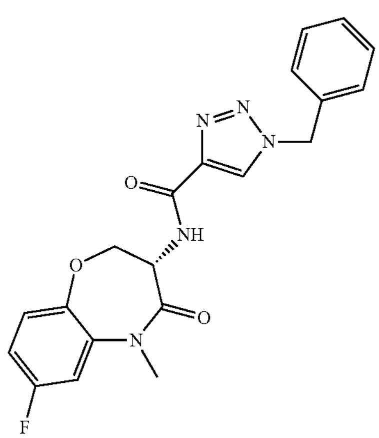 | $^1$H NMR (DMSO-d$_6$) δ: 8.69 (s, 1H), 8.61 (d, J = 8.3 Hz, 1H), 7.48 (dd, J = 9.9, 3.0 Hz, 1H), 7.32-7.41 (m, 5H), 7.27 (dd, J = 9.0, 5.7 Hz, 1H), 7.13 (td, J = 8.5, 3.0 Hz, 1H), 5.66 (s, 2H), 4.88 (dt, J = 11.6, 7.9 Hz, 1H), 4.60 (dd, J = 11.5, 10.0 Hz, 1H), 4.40 (dd, J = 9.9, 7.8 Hz, 1H), 3.31 (s, 3H). | 396.2 | F |

-continued

| Ex | Name | Structure | 1H NMR | MS (M + H)+ | Method |
|---|---|---|---|---|---|
| 84 | (S)-1-benzyl-N-(7-fluoro-5-methyl-4-oxo-2,3,4,5-tetrahydrobenzo[b][1,4]oxazepin-3-yl)-1H-imidazole-4-carboxamide | 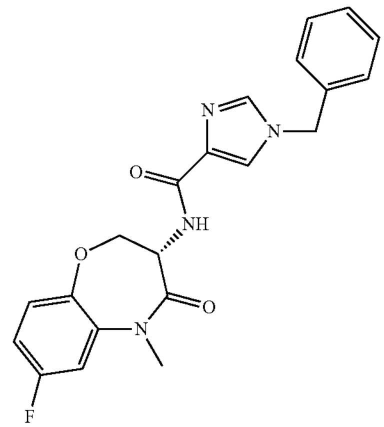 [SMILES: CN1C(=O)[C@@H](NC(=O)c2cn(Cc3ccccc3)cn2)COc2ccc(F)cc21] | ¹H NMR (DMSO-d₆) δ: 8.01 (d, J = 7.8 Hz, 1H), 7.90 (d, J = 1.3 Hz, 1H), 7.75 (d, J = 1.3 Hz, 1H), 7.46 (dd, J = 9.7, 2.9 Hz, 1H), 7.25-7.39 (m, 6H), 7.13 (td, J = 8.5, 2.9 Hz, 1H), 5.23 (s, 2H), 4.83 (dt, J = 11.3, 7.9 Hz, 1H), 4.37-4.50 (m, 2H), 3.31 (s, 3H). | 395.3 | F |
| 85 | (S)-5-benzyl-N-(7-(1-(2-cyanoethyl)-1H-tetrazol-5-yl)-5-methyl-4-oxo-2,3,4,5-tetrahydrobenzo[b][1,4]oxazepin-3-yl)-1H-pyrazole-3-carboxamide | 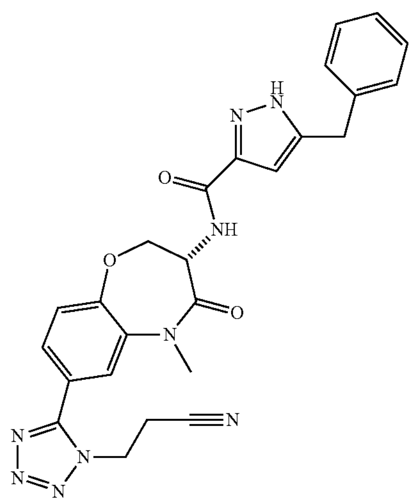 [SMILES: CN1C(=O)[C@@H](NC(=O)c2cc(Cc3ccccc3)[nH]n2)COc2ccc(-c3nnnn3CCC#N)cc21] | ¹H NMR (DMSO-d₆) δ: 13.23 (br. s., 1H), 8.11 (d, J = 7.6 Hz, 1H), 7.89 (d, J = 1.0 Hz, 1H), 7.70 (dd, J = 8.2, 2.1 Hz, 1H), 7.48 (d, J = 8.3 Hz, 1H), 7.28-7.34 (m, 2H), 7.19-7.26 (m, 3H), 6.38 (s, 1H), 4.95 (dt, J = 11.6, 7.6 Hz, 1H), 4.74-4.88 (m, 2H), 4.59-4.67 (m, 1H), 4.48-4.54 (m, 1H), 3.99 (s, 2H), 3.37 (s, 3H), 3.24 (t, J = 6.3 Hz, 2H). | 498.4 | F |
| 86 | (S)-1-benzyl-N-(5-methyl-4-oxo-7-(5-oxo-4,5-dihydro-1,3,4-oxadiazol-2-yl)-2,3,4,5-tetrahydrobenzo[b][1,4]oxazepin-3-yl)-1H-imidazole-4-carboxamide | 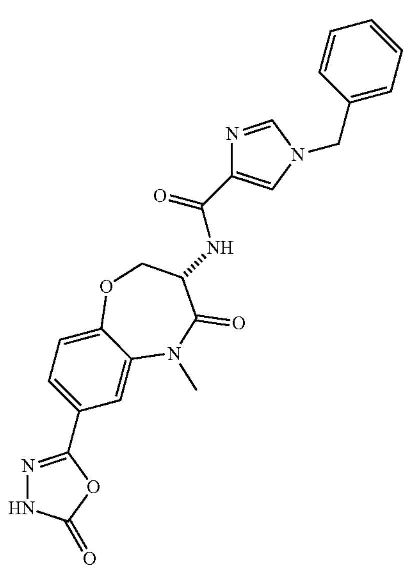 [SMILES: CN1C(=O)[C@@H](NC(=O)c2cn(Cc3ccccc3)cn2)COc2ccc(-c3n[nH]c(=O)o3)cc21] | ¹H NMR (DMSO-d₆) δ: 12.66 (br. s., 1H), 8.02 (d, J = 7.8 Hz, 1H), 7.90 (d, J = 1.3 Hz, 1H), 7.84 (d, J = 2.0 Hz, 1H), 7.76 (d, J = 1.3 Hz, 1H), 7.70 (dd, J = 8.5, 2.1 Hz, 1H), 7.28-7.41 (m, 6H), 5.23 (s, 2H), 4.86 (dt, J = 11.6, 7.7 Hz, 1H), 4.53-4.60 (m, 1H), 4.43-4.49 (m, 1H), 3.36 (s, 3H). | 377.3 | A |

-continued

| Ex | Name | Structure | 1H NMR | MS (M + H)+ | Method |
|---|---|---|---|---|---|
| 87 | (S)-5-benzyl-N-(7-fluoro-5-methyl-4-oxo-2,3,4,5-tetrahydrobenzo[b][1,4]oxazepin-3-yl)-4H-1,2,4-triazole-3-carboxamide | 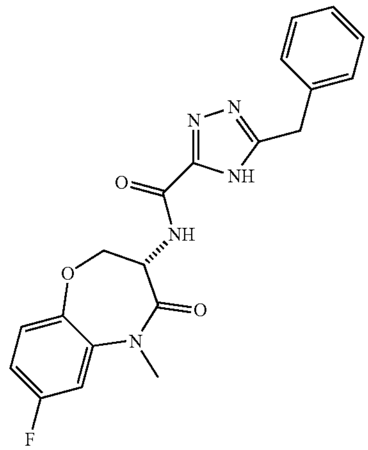 [SMILES: CN1C(=O)[C@@H](NC(=O)c2nnc(Cc3ccccc3)[nH]2)COc2ccc(F)cc21] | ¹H NMR (DMSO-d₆) δ: 14.38 (br. s., 1H), 8.45 (br. s., 1H), 7.48 (dd, J = 9.9, 3.0 Hz, 1H), 7.22-7.36 (m, 6H), 7.14 (td, J = 8.5, 2.9 Hz, 1H), 5.76 (s, 1H), 4.81-4.90 (m, 1H), 4.60 (t, J = 10.5 Hz, 1H), 4.40 (dd, J = 9.7, 7.7 Hz, 1H), 4.13 (br. s., 2H), 3.31 (s, 3H). | 396.2 | A |
| 88 | (S)-5-benzyl-N-(6-fluoro-5-methyl-4-oxo-2,3,4,5-tetrahydrobenzo[b][1,4]oxazepin-3-yl)isoxazole-3-carboxamide | 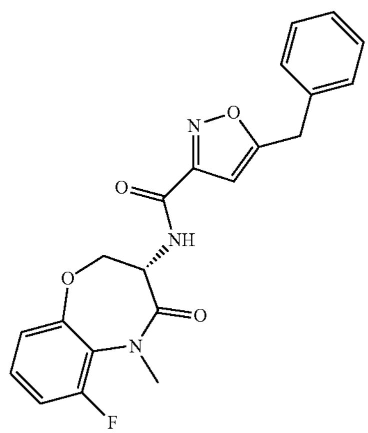 [SMILES: CN1C(=O)[C@@H](NC(=O)c2cc(Cc3ccccc3)on2)COc2cccc(F)c21] | ¹H NMR (DMSO-d₆) δ: 8.91 (d, J = 7.8 Hz, 1H), 7.26-7.43 (m, 7H), 7.13 (d, J = 8.1 Hz, 1H), 6.55 (s, 1H), 4.88 (dt, J = 11.6, 7.9 Hz, 1H), 4.61 (dd, J = 11.4, 10.1 Hz, 1H), 4.41 (dd, J = 10.0, 7.7 Hz, 1H), 4.22 (s, 2H), 3.22 (d, 2H). | 396.3 | F |
| 89 | (S)-1-benzyl-N-(6-fluoro-5-methyl-4-oxo-2,3,4,5-tetrahydrobenzo[b][1,4]oxazepin-3-yl)-1H-imidazole-4-carboxamide | 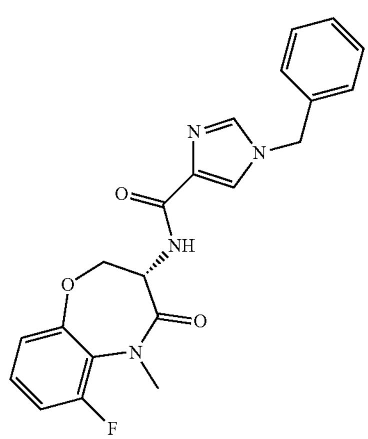 [SMILES: CN1C(=O)[C@@H](NC(=O)c2cn(Cc3ccccc3)cn2)COc2cccc(F)c21] | ¹H NMR (DMSO-d₆) δ: 8.02 (d, J = 8.1 Hz, 1H), 7.90 (d, J = 1.3 Hz, 1H), 7.76 (d, J = 1.3 Hz, 1H), 7.24-7.43 (m, 7H), 7.14 (d, J = 8.3 Hz, 1H), 5.24 (s, 2H), 4.87 (dt, J = 11.4, 7.8 Hz, 1H), 4.49-4.57 (m, 1H), 4.40 (dd, J = 10.0, 7.7 Hz, 1H), 3.23 (d, 3H). | 395.3 | F |

| Ex | Name | Structure | 1H NMR | MS (M + H)+ | Method |
|---|---|---|---|---|---|
| 90 | (S)-5-benzyl-N-(6-fluoro-4-oxo-2,3,4,5-tetrahydrobenzo[b][1,4]oxazepin-3-yl)isoxazole-3-carboxamide | 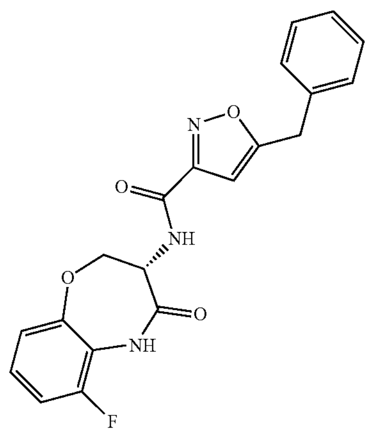 [SMILES: O=C(N[C@H]1COc2cccc(F)c2NC1=O)c1cc(Cc2ccccc2)on1] | ¹H NMR (DMSO-d₆) δ: 10.08 (s, 1H), 8.84 (d, J = 8.1 Hz, 1H), 7.12-7.39 (m, 7H), 7.06 (d, 1H), 6.57 (s, 1H), 4.87 (dt, J = 11.3, 7.7 Hz, 1H), 4.62 (t, J = 10.7 Hz, 1H), 4.48 (dd, J = 10.2, 7.5 Hz, 1H), 4.21-4.26 (m, 2H). | 382.3 | F |
| 91 | (S)-5-benzyl-N-(6-fluoro-5-methyl-4-oxo-2,3,4,5-tetrahydrobenzo[b][1,4]oxazepin-3-yl)-4H-1,2,4-triazole-3-carboxamide | 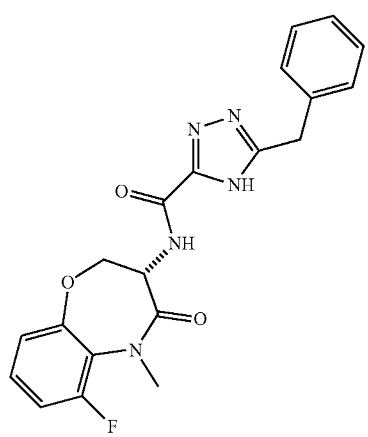 [SMILES: CN1C(=O)[C@@H](NC(=O)c2nnc(Cc3ccccc3)[nH]2)COc2cccc(F)c21] | ¹H NMR (DMSO-d₆) δ: 14.48 (br. s., 1H), 8.52 (br. s., 1H), 7.21-7.45 (m, 7H), 7.14 (d, J = 8.1 Hz, 1H), 4.89 (dt, J = 11.5, 7.8 Hz, 1H), 4.58-4.70 (m, 1H), 4.41 (dd, J = 9.9, 7.8 Hz, 1H), 4.12 (s, 2H), 3.23 (d, J = 2.3 Hz, 3H). | 396.3 | H |
| 92 | (S)-N-(7-fluoro-5-methyl-4-oxo-2,3,4,5-tetrahydrobenzo[b][1,4]oxazepin-3-yl)-5-(4-methylbenzyl)-4H-1,2,4-triazole-3-carboxamide | 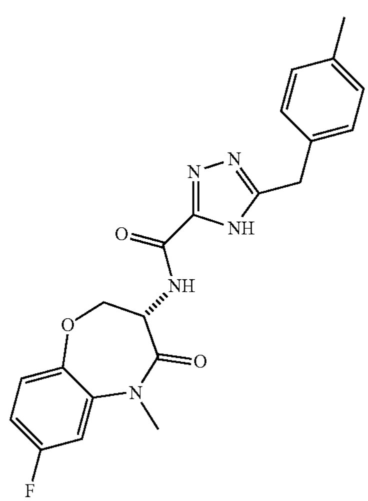 [SMILES: Cc1ccc(Cc2nnc(C(=O)N[C@H]3COc4ccc(F)cc4N(C)C3=O)[nH]2)cc1] | ¹H NMR (DMSO-d₆) δ: 14.31 (s, 1H), 8.41 (d, J = 7.3 Hz, 1H), 7.48 (dd, J = 9.9, 3.0 Hz, 1H), 7.28 (dd, J = 9.0, 5.7 Hz, 1H), 7.07-7.20 (m, 5H), 4.85 (dt, J = 11.3, 7.9 Hz, 1H), 4.54-4.70 (m, 1H), 4.40 (dd, J = 9.9, 7.8 Hz, 1H), 4.09 (s, 2H), 3.31 (s, 3H). | 410.2 | H |

-continued

| Ex | Name | Structure | 1H NMR | MS (M + H)+ | Method |
|---|---|---|---|---|---|
| 93 | (S)-N-(6-fluoro-5-methyl-4-oxo-2,3,4,5-tetrahydrobenzo[b][1,4]oxazepin-3-yl)-5-(3-fluorobenzyl)-4H-1,2,4-triazole-3-carboxamide | 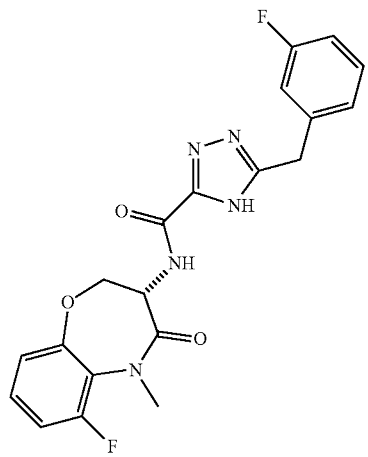 [SMILES: CN1C(=O)[C@@H](NC(=O)c2nnc(Cc3cccc(F)c3)[nH]2)COc2cccc(F)c21] | $^1$H NMR (DMSO-d$_6$) δ: 8.50 (br. s., 1H), 7.25-7.44 (m, 3H), 7.06-7.17 (m, 4H), 4.89 (dt, J = 11.6, 7.8 Hz, 1H), 4.64 (t, J = 10.7 Hz, 1H), 4.42 (dd, J = 9.9, 7.8 Hz, 1H), 4.16 (s, 2H), 3.23 (d, 3H). | 414.2 | H |
| 94 | (S)-5-benzyl-N-(4-oxo-2,3,4,5-tetrahydrobenzo[b][1,4]oxazepin-3-yl)furan-2-carboxamide | 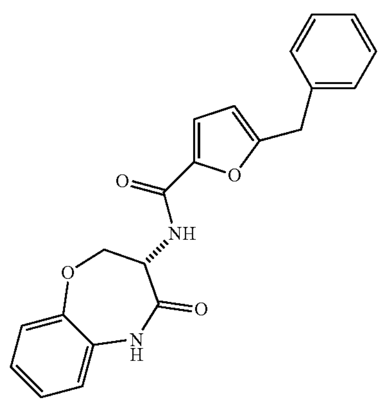 [SMILES: O=C(N[C@H]1COc2ccccc2NC1=O)c1ccc(Cc2ccccc2)o1] | $^1$H NMR (DMSO-d$_6$) δ: 10.10 (s, 1H), 8.39 (d, J = 8.3 Hz, 1H), 7.30-7.38 (m, 2H), 7.22-7.30 (m, 3H), 7.09-7.18 (m, 5H), 6.30 (d, J = 3.3 Hz, 1H), 4.76-4.86 (m, 1H), 4.44-4.53 (m, 1H), 4.35-4.42 (m, 1H), 4.06 (s, 2H) | 363 | F |
| 95 | (S)-3-(methyl(phenyl)amino)-N-(4-oxo-2,3,4,5-tetrahydrobenzo[b][1,4]oxazepin-3-yl)benzamide | 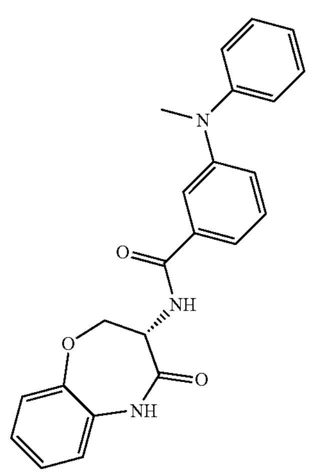 [SMILES: CN(c1ccccc1)c1cccc(C(=O)N[C@H]2COc3ccccc3NC2=O)c1] | $^1$H NMR (DMSO-d$_6$) δ: 10.07 (s, 1H), 8.64 (d, J = 8.5 Hz, 1H), 7.27-7.49 (m, 5H), 7.09-7.21 (m, 5H), 6.97-7.08 (m, 3H), 4.88 (dt, J = 10.7, 7.7 Hz, 1H), 4.47-4.56 (m, 1H), 4.37-4.45 (m, 1H), 3.30 (s, 3H) | 388 | F |

-continued

| Ex | Name | Structure | 1H NMR | MS (M + H)+ | Method |
|---|---|---|---|---|---|
| 96 | (S)-1-(4-fluorobenzyl)-N-(4-oxo-2,3,4,5-tetrahydrobenzo[b][1,4]oxazepin-3-yl)-1H-1,2,3-triazole-4-carboxamide | 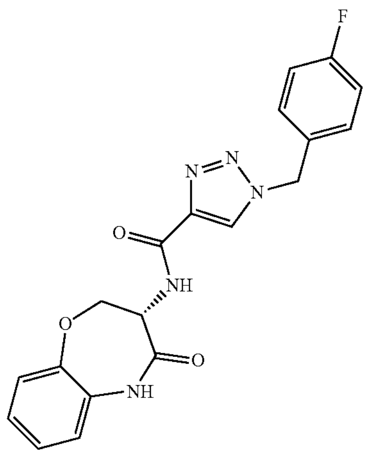 [SMILES: O=C(N[C@H]1COc2ccccc2NC1=O)c1cn(Cc2ccc(F)cc2)nn1] | ¹H NMR (DMSO-d₆) δ: 10.15 (s, 1H), 8.73 (s, 1H), 8.60 (d, J = 7.8 Hz, 1H), 7.43 (dd, J = 8.4, 5.6 Hz, 2H), 7.23 (t, J = 8.9 Hz, 2H), 7.14 (s, 4H), 5.66 (s, 2H), 4.84 (dt, J = 10.5, 7.3 Hz, 1H), 4.49-4.58 (m, 1H), 4.39-4.47 (m, 1H) | 382 | F |
| 97 | (S)-N-(5-methyl-4-oxo-2,3,4,5-tetrahydrobenzo[b][1,4]oxazepin-3-yl)-4-phenoxypicolinamide | 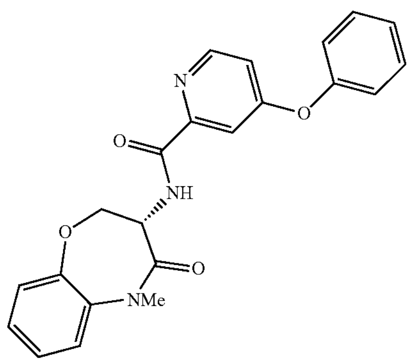 [SMILES: CN1C(=O)[C@@H](NC(=O)c2cc(Oc3ccccc3)ccn2)COc2ccccc21] | ¹H NMR (CDCl₃) δ: 8.89 (d, J = 7.3 Hz, 1H), 8.43 (d, J = 5.6 Hz, 1H), 7.60 (d, J = 2.3 Hz, 1H), 7.34-7.44 (m, 2H), 7.12-7.26 (m, 5H), 7.01-7.10 (m, 2H), 6.93 (dd, J = 5.7, 2.7 Hz, 1H), 5.05 (dt, J = 11.3, 7.4 Hz, 1H), 4.72 (dd, J = 9.7, 7.5 Hz, 1H), 4.29 (dd, J = 11.1, 9.9 Hz, 1H), 3.42 (s, 3H) | 390 | A |
| 98 | (S)-N-(5-methyl-4-oxo-2,3,4,5-tetrahydrobenzo[b][1,4]oxazep'in-3-yl)-3-phenoxy-benzamide | 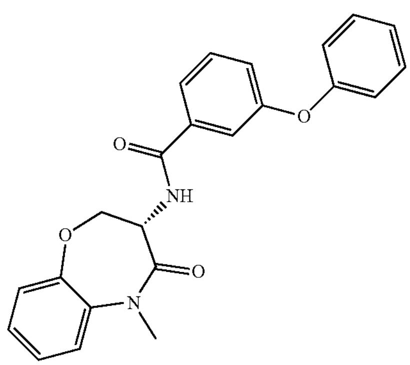 [SMILES: CN1C(=O)[C@@H](NC(=O)c2cccc(Oc3ccccc3)c2)COc2ccccc21] | ¹H NMR (DMSO-d₆) δ: 8.75 (d, J = 8.3 Hz, 1H), 7.66 (d, J = 7.8 Hz, 1H), 7.46-7.56 (m, 3H), 7.38-7.46 (m, 2H), 7.13-7.37 (m, 5H), 7.04 (d, J = 8.0 Hz, 2H), 4.91 (dt, J = 11.7, 8.2 Hz, 1H), 4.51-4.60 (m, 1H), 4.40 (dd, J = 9.8, 7.8 Hz, 1H), 3.31 (s, 3H) | 389 | F |
| 99 | 3-benzyl-N-((S)-4-oxo-2,3,4,5-tetrahydrobenzo[b][1,4]oxazepin-3-yl)piperidine-1-carboxamide | 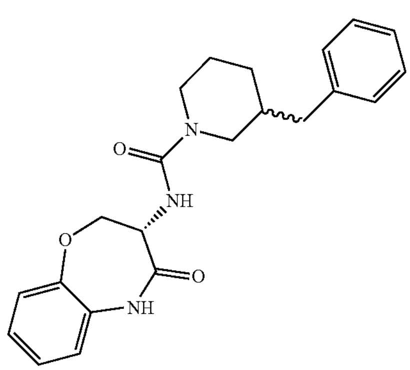 | ¹H NMR (DMSO-d₆) δ: 9.93 (br. s., 1H), 7.02-7.34 (m, 9H), 6.56 (d, J = 8.3 Hz, 1H), 4.54 (dt, J = 10.8, 7.9 Hz, 1H), 4.23-4.44 (m, 2H), 3.69-3.93 (m, 2H), 2.64-2.85 (m, 1H), 2.53-2.60 (m, 1H), 2.34-2.48 (m, 2H), 1.51-1.72 (m, 3H), 1.17-1.40 (m, 1H), 0.99-1.17 (m, 1H) | 380 | D |

(Mixture of diastereomers)

| Ex | Name | Structure | 1H NMR | MS (M + H)+ | Method |
|---|---|---|---|---|---|
| 100 | (S)-5-(4-chlorobenzyl)-N-(5-methyl-4-oxo-2,3,4,5-tetrahydrobenzo[b][1,4]oxazepin-3-yl)isoxazole-3-carboxamide | 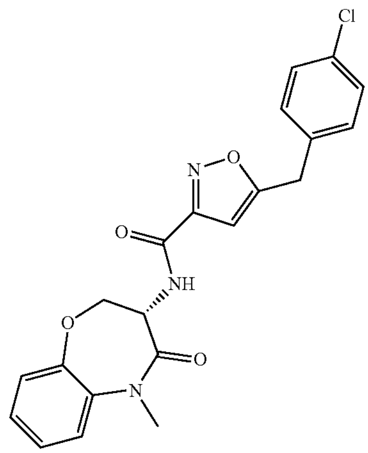 [SMILES: CN1C(=O)[C@@H](NC(=O)c2cc(Cc3ccc(Cl)cc3)on2)COc2ccccc21] | ¹H NMR (DMSO-d₆) δ: 8.88 (d, J = 8.3 Hz, 1H), 7.51 (dd, J = 7.7, 1.6 Hz, 1H), 7.38-7.45 (m, 2H), 7.19-7.38 (m, 5H), 6.56 (s, 1H), 4.84 (dt, J = 11.5, 8.0 Hz, 1H), 4.53-4.63 (m, 1H), 4.40 (dd, J = 9.8, 7.8 Hz, 1H), 4.24 (s, 2H), 3.31 (s, 3H) | 412 | F |
| 101 | (S)-1-benzyl-5-methyl-N-(5-methyl-4-oxo-2,3,4,5-tetrahydrobenzo[b][1,4]oxazepin-3-yl)-1H-pyrazole-3-carboxamide | 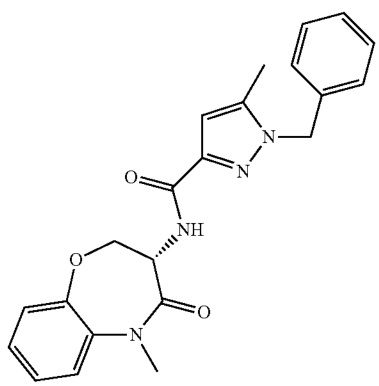 [SMILES: Cc1cc(C(=O)N[C@H]2COc3ccccc3N(C)C2=O)nn1Cc1ccccc1] | ¹H NMR (DMSO-d₆) δ: 8.07 (d, J = 8.0 Hz, 1H), 7.50 (dd, J = 7.7, 1.9 Hz, 1H), 7.26-7.40 (m, 5H), 7.21-7.26 (m, 1H), 7.13 (d, J = 7.0 Hz, 2H), 6.49 (s, 1H), 5.41 (s, 2H), 4.84 (dt, J = 11.5, 7.8 Hz, 1H), 4.50-4.60 (m, 1H), 4.41 (dd, J = 9.7, 7.7 Hz, 1H), 3.32 (s, 3H), 2.22 (s, 3H) | 391 | F |
| 102 | (S)-5-(cyclopentylmethyl)-N-(6-fluoro-8-methyl-4-oxo-2,3,4,5-tetrahydrobenzo[b][1,4]oxazepin-3-yl)-4H-1,2,4-triazole-3-carboxamide | 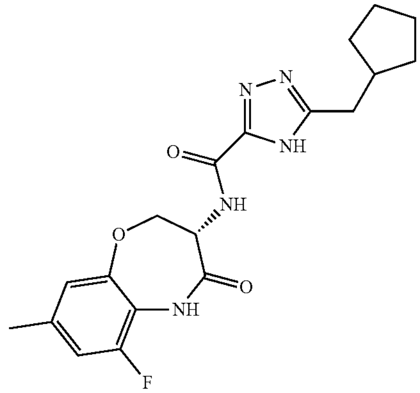 [SMILES: Cc1cc(F)c2c(c1)OC[C@H](NC(=O)c1nnc(CC3CCCC3)[nH]1)C(=O)N2] | ¹H NMR (DMSO-d₆) δ: 14.17 (br. s., 1H), 10.03 (s, 1H), 8.34 (d, J = 7.5 Hz, 1H), 7.00 (d, J = 10.8 Hz, 1H), 6.90 (s, 1H), 4.86 (dt, J = 11.0, 7.6 Hz, 1H), 4.60 (t, J = 10.7 Hz, 1H), 4.47 (dd, J = 9.9, 7.4 Hz, 1H), 2.74 (d, J = 7.3 Hz, 2H), 2.31 (s, 3H), 2.20-2.30 (m, 1H), 1.46-1.76 (m, 6H), 1.14-1.28 (m, 2H) | 388.3 | F |

| Ex | Name | Structure | 1H NMR | MS (M + H)+ | Method |
|---|---|---|---|---|---|
| 103 | 3-benzyl-N-((S)-5-methyl-4-oxo-2,3,4,5-tetrahydrobenzo[b][1,4]oxazepin-3-yl)pyrrolidine-1-carboxamide | Single diastereoisomer. Absolute stereochemistry at the C3 pyrrolidine is unknown. | $^1$H NMR (CDCl$_3$) δ: 7.27-7.34 (m, 4H), 7.15-7.26 (m, 5H), 5.24 (d, J = 6.6 Hz, 1H), 4.88 (dt, J = 11.2, 7.0 Hz, 1H), 4.63 (dd, J = 9.7, 7.5 Hz, 1H), 4.16 (dd, J = 11.2, 9.7 Hz, 1H), 3.44-3.55 (m, 2H), 3.42 (s, 3H), 3.27-3.36 (m, 1H), 3.01-3.09 (m, 1H), 2.71 (d, J = 7.6 Hz, 2H), 2.44-2.54 (m, 1H), 1.96-2.06 (m, 1H), 1.61-1.71 (m, 1H) | 380 | D |
| 104 | 3-benzyl-N-((S)-5-methyl-4-oxo-2,3,4,5-tetrahydrobenzo[b][1,4]oxazepin-3-yl)pyrrolidine-1-carboxamide | Single diastereoisomer. Absolute stereochemistry at the C3 pyrrolidine is unknown. | $^1$H NMR (CDCl$_3$) δ: 7.27-7.34 (m, 4H), 7.15-7.26 (m, 5H), 5.27 (d, J = 6.6 Hz, 1H), 4.87 (dt, J = 11.2, 7.0 Hz, 1H), 4.64 (dd, J = 9.7, 7.5 Hz, 1H), 4.17 (dd, J = 11.2, 9.7 Hz, 1H), 3.46-3.57 (m, 2H), 3.42 (s, 3H), 3.30 (td, J = 9.1, 7.3 Hz, 1H), 3.04 (dd, J = 9.6, 7.8 Hz, 1H), 2.67-2.74 (m, 2H), 2.43-2.56 (m, 1H), 1.94-2.06 (m, 1H), 1.60-1.72 (m, 1H) | 380 | D |
| 105 | N-((S)-5-methyl-4-oxo-2,3,4,5-tetrahydrobenzo[b][1,4]oxazepin-3-yl)-3-phenoxy-pyrrolidine-1-carboxamide | (Mixture of diastereomers) | $^1$H NMR (DMSO-d$_6$) δ: 7.44-7.50 (m, 1H), 7.18-7.33 (m, 5H), 6.90-6.99 (m, 3H), 6.38 (t, J = 8.8 Hz, 1H), 5.03 (br. s., 1H), 4.54-4.66 (m, 1H), 4.36-4.45 (m, 1H), 4.30-4.22 (m, 1H), 3.37-3.62 (m, 4H), 3.30 & 3.28 (two s, 3H), 2.03-2.19 (m, 2H) | 382 | D |

| Ex | Name | Structure | 1H NMR | MS (M + H)+ | Method |
|---|---|---|---|---|---|
| 106 | (S)-1-((1H-pyrazol-1-yl)methyl)-5-methyl-N-(5-methyl-4-oxo-2,3,4,5-tetrahydrobenzo[b][1,4]oxazepin-3-yl)-1H-pyrazole-3-carboxamide | 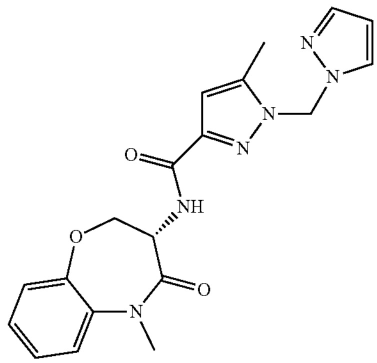 [SMILES: Cc1cc(C(=O)N[C@H]2COc3ccccc3N(C)C2=O)nn1Cn1cccn1] | ¹H NMR (DMSO-d₆) δ: 8.08 (d, J = 8.0 Hz, 1H), 7.98 (d, J = 2.0 Hz, 1H), 7.54 (d, J = 1.3 Hz, 1H), 7.50 (dd, J = 7.5, 1.8 Hz, 1H), 7.26-7.36 (m, J = 14.7, 7.4, 7.4, 1.9 Hz, 2H), 7.22-7.26 (m, 1H), 6.41-6.47 (m, 3H), 6.30-6.35 (m, 1H), 4.83 (dt, J = 11.4, 8.0 Hz, 1H), 4.48-4.57 (m, 1H), 4.41 (dd, J = 9.9, 7.7 Hz, 1H), 3.32 (s, 3H), 2.46 (s, 3H) | 381 | F |
| 107 | (S)-1-benzyl-5-methyl-N-(2-oxo-2,3,4,5-tetrahydro-1H-benzo[b]azepin-3-yl)-1H-pyrazole-3-carboxamide | 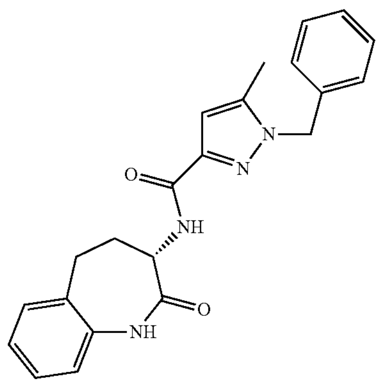 [SMILES: Cc1cc(C(=O)N[C@H]2CCc3ccccc3NC2=O)nn1Cc1ccccc1] | ¹H NMR (DMSO-d₆) δ: 10.00 (s, 1H), 7.88 (d, J = 7.8 Hz, 1H), 7.25-7.41 (m, 5H), 7.09-7.22 (m, 3H), 7.04 (d, J = 7.5 Hz, 1H), 6.47 (s, 1H), 5.40 (s, 2H), 4.34 (dt, J = 11.5, 7.8 Hz, 1H), 2.64-2.85 (m, 2H), 2.37-2.49 (m, 1H), 2.13-2.30 (m, 4H) | 375 | F |
| 108 | (S)-3-benzyl-N-(5-methyl-4-oxo-2,3,4,5-tetrahydrobenzo[b][1,4]oxazepin-3-yl)-1H-pyrazole-5-carboxamide | 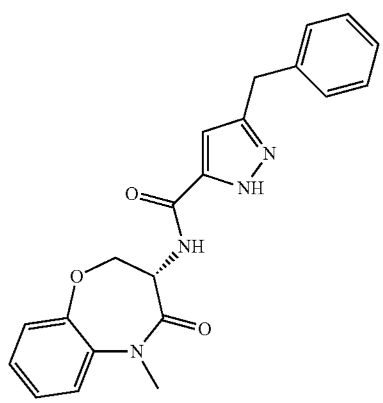 [SMILES: CN1C(=O)[C@@H](NC(=O)c2cc(Cc3ccccc3)n[nH]2)COc2ccccc21] | ¹H NMR (DMSO-d₆) δ: 13.22 (br. s., 1H), 8.11 (br. s., 1H), 7.50 (d, J = 7.5 Hz, 1H), 7.18-7.36 (m, 8H), 6.41 (br. s., 1H), 4.83 (dt, J = 11.4, 7.8 Hz, 1H), 4.51 (t, J = 10.7 Hz, 1H), 4.35-4.42 (m, 1H), 3.98 (s, 2H), 3.31 (s, 3H) | 377 | F |
| 109 | (S)-5-methyl-N-(5-methyl-4-oxo-2,3,4,5-tetrahydrobenzo[b][1,4]oxazepin-3-yl)-1-((2-oxopyridin-1(2H)-yl)methyl)-1H-pyrazole-3-carboxamide | 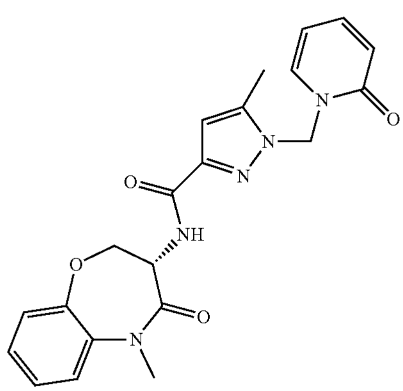 [SMILES: Cc1cc(C(=O)N[C@H]2COc3ccccc3N(C)C2=O)nn1Cn1ccccc1=O] | ¹H NMR (DMSO-d₆) δ: 8.07 (d, J = 8.0 Hz, 1H), 7.87 (dd, J = 6.9, 1.6 Hz, 1H), 7.44-7.53 (m, 2H), 7.21-7.36 (m, 3H), 6.40-6.47 (m, 2H), 6.33 (td, J = 6.8, 1.3 Hz, 1H), 6.14 (s, 2H), 4.83 (dt, J = 11.4, 8.0 Hz, 1H), 4.46-4.56 (m, 1H), 4.41 (dd, J = 9.8, 7.8 Hz, 1H), 3.32 (s, 3H), 2.47 (s, 3H) | 408 | F |

| Ex | Name | Structure | 1H NMR | MS (M + H)+ | Method |
|---|---|---|---|---|---|
| 110 | (S)-5-methyl-N-(5-methyl-4-oxo-2,3,4,5-tetrahydrobenzo[b][1,4]oxazepin-3-yl)-1-(4-methylbenzyl)-1H-pyrazole-3-carboxamide | 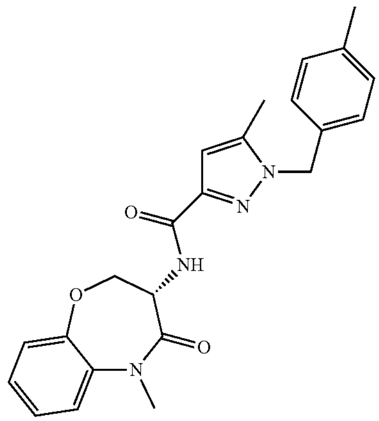 [SMILES: Cc1ccc(Cn2nc(C(=O)N[C@H]3COc4ccccc4N(C)C3=O)cc2C)cc1] | ¹H NMR (DMSO-d₆) δ: 8.06 (d, J = 8.0 Hz, 1H), 7.50 (dd, J = 7.7, 1.6 Hz, 1H), 7.21-7.37 (m, 3H), 7.17 (d, J = 8.0 Hz, 2H), 7.03 (d, J = 8.0 Hz, 2H), 6.47 (s, 1H), 5.35 (s, 2H), 4.84 (dt, J = 11.5, 7.9 Hz, 1H), 4.55 (dd, J = 11.4, 9.9 Hz, 1H), 4.41 (dd, J = 9.8, 7.8 Hz, 1H), 3.32 (s, 3H), 2.28 (s, 3H), 2.21 (s, 3H) | 405 | F |
| 111 | (S)-1-((3,5-dimethyl-1H-pyrazol-1-yl)methyl)-5-methyl-N-(5-methyl-4-oxo-2,3,4,5-tetrahydrobenzo[b][1,4]oxazepin-3-yl)-1H-pyrazole-3-carboxamide | 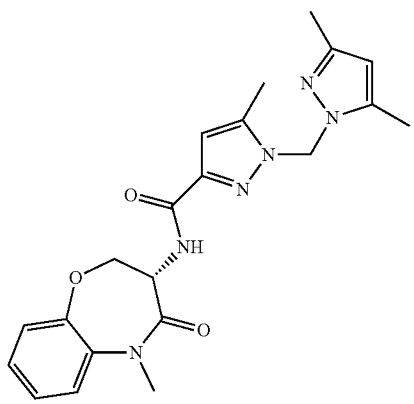 [SMILES: Cc1cc(C)n(Cn2nc(C(=O)N[C@H]3COc4ccccc4N(C)C3=O)cc2C)n1] | ¹H NMR (DMSO-d₆) δ: 8.01 (d, J = 7.8 Hz, 1H), 7.50 (dd, J = 7.7, 1.9 Hz, 1H), 7.22-7.36 (m, 3H), 6.43 (s, 1H), 6.24 (s, 2H), 5.86 (s, 1H), 4.81 (dt, J = 11.3, 7.8 Hz, 1H), 4.37-4.55 (m, 2H), 3.33 (s, 3H), 2.48 (s, 6H), 2.07 (s, 3H) | 409 | F |
| 112 | (S)-3-(4-methylbenzyl)-N-(4-oxo-2,3,4,5-tetrahydrobenzo[b][1,4]oxazepin-3-yl)-1H-pyrazole-5-carboxamide | 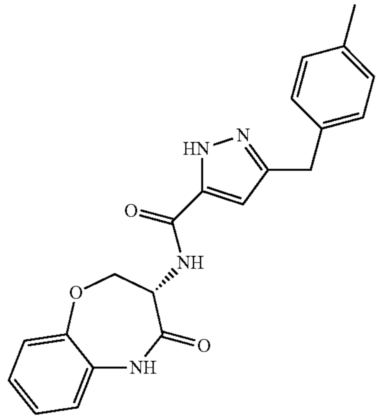 [SMILES: Cc1ccc(Cc2cc(C(=O)N[C@H]3COc4ccccc4NC3=O)[nH]n2)cc1] | ¹H NMR (DMSO-d₆) δ: 13.18 (br. s., 1H), 10.13 (s, 1H), 8.10 (br. s., 1H), 7.02-7.27 (m, 8H), 6.37 (br. s., 1H), 4.72-4.87 (m, 1H), 4.34-4.53 (m, 2H), 3.93 (br. s., 2H), 2.27 (s, 3H) | 377 | F |

| Ex | Name | Structure | 1H NMR | MS (M + H)+ | Method |
|---|---|---|---|---|---|
| 113 | (S)-1-benzyl-5-methyl-N-(4-oxo-2,3,4,5-tetrahydrobenzo[b][1,4]oxazepin-3-yl)-1H-pyrazole-3-carboxamide | 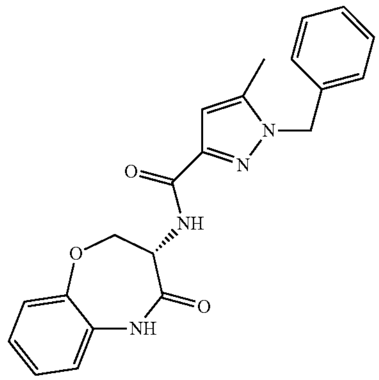 [SMILES: Cc1cc(C(=O)N[C@H]2COc3ccccc3NC2=O)nn1Cc1ccccc1] | $^1$H NMR (DMSO-d$_6$) δ: 10.15 (s, 1H), 8.09 (d, J = 7.8 Hz, 1H), 7.27-7.42 (m, 3H), 7.09-7.19 (m, 6H), 6.52 (s, 1H), 5.41 (s, 2H), 4.81 (dt, J = 10.4, 7.2 Hz, 1H), 4.40-4.53 (m, 2H), 2.23 (s, 3H) | 377 | F |
| 114 | (S)-5-methyl-N-(5-methyl-4-oxo-2,3,4,5-tetrahydrobenzo[b][1,4]oxazepin-3-yl)-1-(2-methylbenzyl)-1H-pyrazole-3-carboxamide | 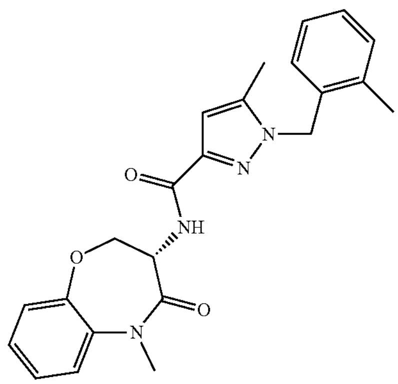 [SMILES: Cc1ccccc1Cn1nc(C(=O)N[C@H]2COc3ccccc3N(C)C2=O)cc1C] | $^1$H NMR (DMSO-d$_6$) δ: 8.02 (d, J = 8.0 Hz, 1H), 7.49 (dd, J = 7.7, 1.6 Hz, 1H), 7.07-7.38 (m, 6H), 6.53 (s, 1H), 6.40 (d, J = 7.5 Hz, 1H), 5.39 (s, 2H), 4.83 (dt, J = 11.5, 7.8 Hz, 1H), 4.46-4.57 (m, 1H), 4.41 (dd, J = 9.9, 7.7 Hz, 1H), 3.31 (s, 3H), 2.35 (s, 3H), 2.19 (s, 3H) | 405 | F |
| 115 | (S)-1-(2,5-difluorobenzyl)-5-methyl-N-(5-methyl-4-oxo-2,3,4,5-tetrahydrobenzo[b][1,4]oxazepin-3-yl)-1H-pyrazole-3-carboxamide | 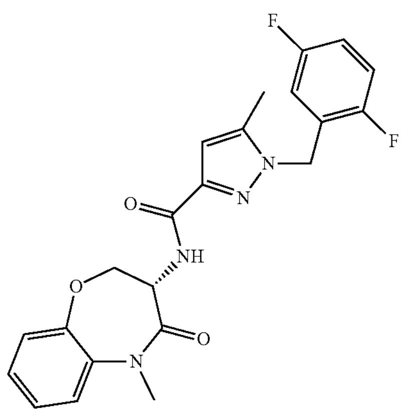 [SMILES: Cc1cc(C(=O)N[C@H]2COc3ccccc3N(C)C2=O)nn1Cc1cc(F)ccc1F] | $^1$H NMR (DMSO-d$_6$) δ: 8.05 (d, J = 8.0 Hz, 1H), 7.50 (dd, J = 7.7, 1.9 Hz, 1H), 7.21-7.38 (m, 5H), 6.76 (ddd, J = 8.8, 5.6, 3.1 Hz, 1H), 6.50 (s, 1H), 5.43 (s, 2H), 4.83 (dt, J = 11.4, 8.0 Hz, 1H), 4.48-4.57 (m, 1H), 4.40 (dd, J = 9.8, 7.8 Hz, 1H), 3.31 (s, 3H), 2.28 (s, 3H) | 427 | F |
| 116 | (S)-1-benzyl-5-methyl-N-(1-methyl-2-oxo-2,3,4,5-tetrahydro-1H-benzo[b]azepin-3-yl)-1H-pyrazole-3-carboxamide | 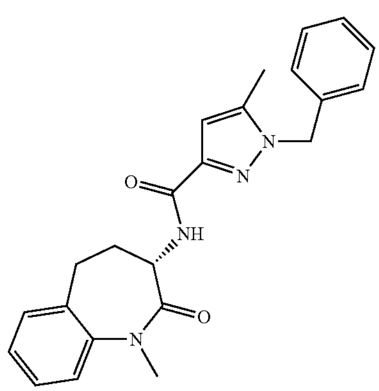 [SMILES: Cc1cc(C(=O)N[C@H]2CCc3ccccc3N(C)C2=O)nn1Cc1ccccc1] | $^1$H NMR (DMSO-d$_6$) δ: 7.89 (d, J = 7.8 Hz, 1H), 7.23-7.42 (m, 7H), 7.12 (d, J = 7.0 Hz, 2H), 6.46 (s, 1H), 5.39 (s, 2H), 4.34 (dt, J = 11.5, 7.8 Hz, 1H), 3.31 (s, 3H), 2.63-2.80 (m, 2H), 2.35 (tt, J = 12.8, 7.4 Hz, 1H), 2.21 (s, 3H), 2.06-2.20 (m, 1H) | 389 | F |

| Ex | Name | Structure | 1H NMR | MS (M + H)+ | Method |
|---|---|---|---|---|---|
| 117 | (S)-5-methyl-N-(5-methyl-4-oxo-2,3,4,5-tetrahydrobenzo[b][1,4]oxazepin-3-yl)-1-((6-methylpyridin-3-yl)methyl)-1H-pyrazole-3-carboxamide | 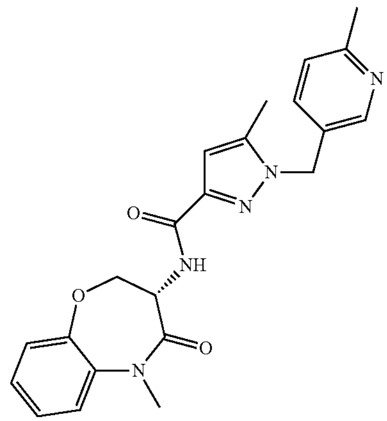 [SMILES: Cc1ccc(Cn2nc(C(=O)N[C@H]3COc4ccccc4N(C)C3=O)cc2C)cn1] | $^1$H NMR (DMSO-$d_6$) δ: 8.47 (d, J = 1.8 Hz, 1H), 8.07 (d, J = 8.3 Hz, 1H), 7.68 (dd, J = 8.3, 2.0 Hz, 1H), 7.44-7.53 (m, 2H), 7.21-7.36 (m, 3H), 6.49 (s, 1H), 5.45 (s, 2H), 4.84 (dt, J = 11.4, 7.8 Hz, 1H), 4.53 (dd, J = 11.5, 10.0 Hz, 1H), 4.40 (dd, J = 9.8, 7.8 Hz, 1H), 3.31 (s, 3H), 2.54 (s, 3H), 2.28 (s, 3H) | 406 | F |
| 118 | (S)-5-methyl-N-(5-methyl-4-oxo-2,3,4,5-tetrahydrobenzo[b][1,4]oxazepin-3-yl)-1-phenethyl-1H-pyrazole-3-carboxamide | 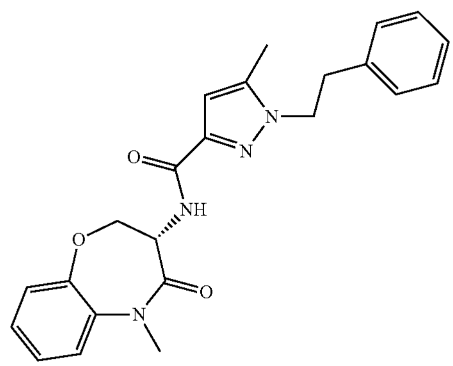 [SMILES: Cc1cc(C(=O)N[C@H]2COc3ccccc3N(C)C2=O)nn1CCc1ccccc1] | $^1$H NMR (DMSO-$d_6$) δ: 8.04 (d, J = 8.0 Hz, 1H), 7.51 (dd, J = 7.7, 1.6 Hz, 1H), 7.20-7.37 (m, 6H), 7.13 (d, J = 7.0 Hz, 2H), 6.34 (s, 1H), 4.85 (dt, J = 11.4, 8.0 Hz, 1H), 4.51-4.60 (m, 1H), 4.43 (dd, J = 9.7, 7.7 Hz, 1H), 4.29 (t, J = 7.2 Hz, 2H), 3.33 (s, 3H), 3.08 (t, J = 7.2 Hz, 2H), 1.97 (s, 3H) | 405 | F |
| 119 | 5-methyl-N-((S)-5-methyl-4-oxo-2,3,4,5-tetrahydrobenzo[b][1,4]oxazepin-3-yl)-1-(1-phenylethyl)-1H-pyrazole-3-carboxamide | (Mixture of diastereomers) | $^1$H NMR (DMSO-$d_6$) δ: 8.07 (dd, J = 7.9, 2.4 Hz, 1H), 7.48-7.54 (m, 1H), 7.23-7.39 (m, 6H), 7.17 (d, J = 8.0 Hz, 2H), 6.46 (s, 1H), 5.68 (q, J = 7.0 Hz, 1H), 4.81-4.91 (m, 1H), 4.57 (ddd, J = 11.4, 9.9, 4.3 Hz, 1H), 4.45 (dd, J = 9.8, 7.8 Hz, 1H), 3.33 (s, 3H), 2.17 (s, 3H), 1.85 (dd, J = 6.8, 3.8 Hz, 3H, actually two doublets from diasteromers) | 405 | F |

| Ex | Name | Structure | 1H NMR | MS (M + H)+ | Method |
|---|---|---|---|---|---|
| 120 | (S)-5-methyl-N-(5-methyl-4-oxo-2,3,4,5-tetrahydrobenzo[b][1,4]oxazepin-3-yl)-1-((2-methylpyrimidin-5-yl)methyl)-1H-pyrazole-3-carboxamide | 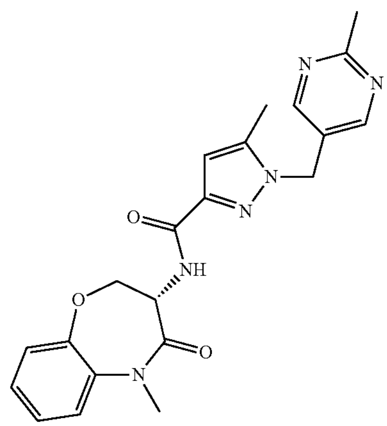 [SMILES: Cc1ncc(Cn2nc(C(=O)N[C@H]3COc4ccccc4N(C)C3=O)cc2C)cn1] | ¹H NMR (DMSO-d₆) δ: 8.60 (s, 2H), 8.08 (d, J = 8.0 Hz, 1H), 7.50 (dd, J = 7.7, 1.9 Hz, 1H), 7.20-7.36 (m, 3H), 6.47 (s, 1H), 5.41 (s, 2H), 4.83 (dt, J = 11.5, 7.9 Hz, 1H), 4.54 (dd, J = 11.4, 9.9 Hz, 1H), 4.40 (dd, J = 9.8, 7.8 Hz, 1H), 3.31 (s, 3H), 2.62 (s, 3H), 2.32 (s, 3H) | 407 | F |
| 121 | (S)-1-(3,5-difluorobenzyl)-5-methyl-N-(5-methyl-4-oxo-2,3,4,5-tetrahydrobenzo[b][1,4]oxazepin-3-yl)-1H-pyrazole-3-carboxamide | 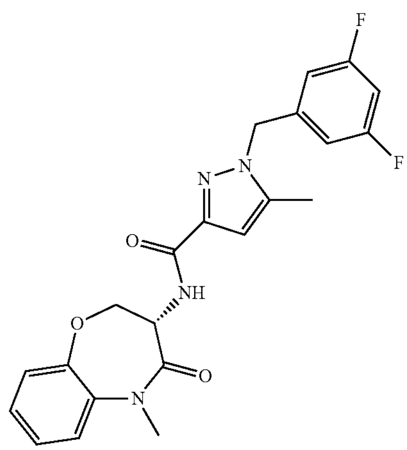 [SMILES: Cc1cc(C(=O)N[C@H]2COc3ccccc3N(C)C2=O)nn1Cc1cc(F)cc(F)c1] | ¹H NMR (DMSO-d₆) δ: 8.11 (d, J = 8.0 Hz, 1H), 7.50 (dd, J = 7.8, 1.8 Hz, 1H), 7.17-7.37 (m, 4H), 6.78-6.88 (m, 2H), 6.51 (s, 1H), 5.44 (s, 2H), 4.84 (dt, J = 11.5, 7.9 Hz, 1H), 4.55 (dd, J = 11.4, 9.9 Hz, 1H), 4.41 (dd, J = 9.8, 7.8 Hz, 1H), 3.32 (s, 3H), 2.24 (s, 3H) | 427 | v |
| 122 | (S)-1-(2-fluorobenzyl)-5-methyl-N-(5-methyl-4-oxo-2,3,4,5-tetrahydrobenzo[b][1,4]oxazepin-3-yl)-1H-pyrazole-3-carboxamide | 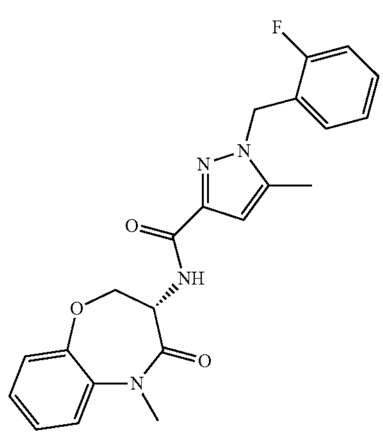 [SMILES: Cc1cc(C(=O)N[C@H]2COc3ccccc3N(C)C2=O)nn1Cc1ccccc1F] | ¹H NMR (DMSO-d₆) δ: 8.03 (d, J = 8.0 Hz, 1H), 7.50 (dd, J = 7.7, 1.9 Hz, 1H), 7.15-7.44 (m, 6H), 6.93 (td, J = 7.7, 1.5 Hz, 1H), 6.50 (s, 1H), 5.44 (s, 2H), 4.83 (dt, J = 11.5, 7.8 Hz, 1H), 4.48-4.58 (m, 1H), 4.40 (dd, J = 9.8, 7.8 Hz, 1H), 3.31 (s, 3H), 2.26 (s, 3H) | 409 | F |

| Ex | Name | Structure | 1H NMR | MS (M + H)+ | Method |
|---|---|---|---|---|---|
| 123 | (S)-1-(3,4-difluorobenzyl)-5-methyl-N-(5-methyl-4-oxo-2,3,4,5-tetrahydrobenzo[b][1,4]oxazepin-3-yl)-1H-pyrazole-3-carboxamide | 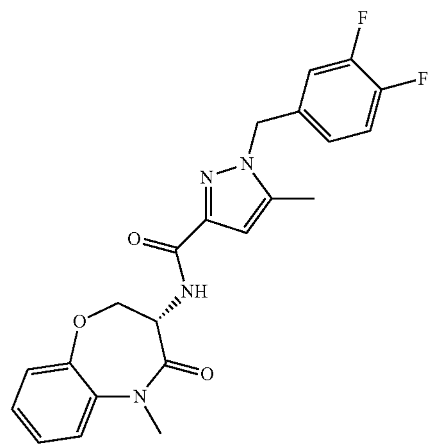 [SMILES: Cc1cc(C(=O)N[C@H]2COc3ccccc3N(C)C2=O)nn1Cc1ccc(F)c(F)c1] | $^1$H NMR (DMSO-d$_6$) δ: 8.09 (d, J = 8.0 Hz, 1H), 7.39-7.52 (m, 2H), 7.20-7.37 (m, 4H), 6.96 (ddd, J = 6.1, 4.0, 2.0 Hz, 1H), 6.49 (s, 1H), 5.40 (s, 2H), 4.84 (dt, J = 11.5, 7.9 Hz, 1H), 4.50-4.59 (m, 1H), 4.41 (dd, J = 9.8, 7.8 Hz, 1H), 3.32 (s, 3H), 2.24 (s, 3H) | 427 | F |
| 124 | (S)-1-benzyl-N-(1-methyl-2-oxo-2,3,4,5-tetrahydro-1H-benzo[b]azepin-3-yl)-1H-pyrazole-4-carboxamide | 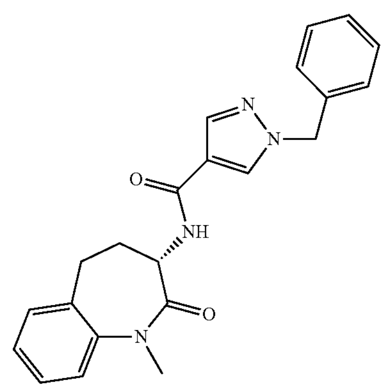 | $^1$H NMR (DMSO-d$_6$) δ: 8.28 (s, 1H), 8.25 (d, J = 8.3 Hz, 1H), 7.90 (s, 1H), 7.20-7.43 (m, 9H), 5.35 (s, 2H), 4.37 (dt, J = 11.2, 8.4 Hz, 1H), 3.29 (s, 3H), 2.66-2.74 (m, 2H), 2.12-2.23 (m, 2H) | 375 | F |
| 125 | (S)-3-(4-fluorobenzyl)-N-(5-methyl-4-oxo-2,3,4,5-tetrahydrobenzo[b][1,4]oxazepin-3-yl)-1H-pyrazole-5-carboxamide | 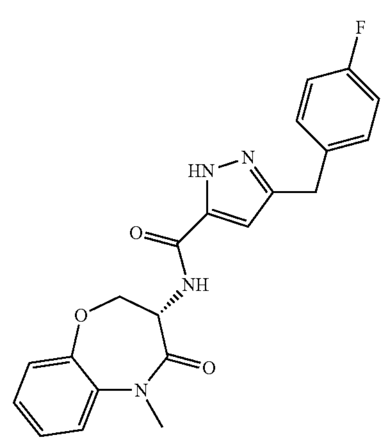 [SMILES: CN1C(=O)[C@@H](NC(=O)c2cc(Cc3ccc(F)cc3)n[nH]2)COc2ccccc21] | $^1$H NMR (DMSO-d$_6$) δ: 13.23 (br. s., 1H), 8.09 (br. s., 1H), 7.50 (dd, J = 7.5, 1.8 Hz, 1H), 7.20-7.37 (m, 5H), 7.10-7.18 (m, 2H), 6.37 (br. s., 1H), 4.83 (dt, J = 11.3, 8.0 Hz, 1H), 4.50 (t, J = 11.0 Hz, 1H), 4.39 (dd, J = 9.7, 7.9 Hz, 1H), 3.98 (br. s., 2H), 3.31 (s, 3H) | 395 | F |

| Ex | Name | Structure | 1H NMR | MS (M + H)+ | Method |
|---|---|---|---|---|---|
| 126 | (S)-1-(2,4-difluorobenzyl)-5-methyl-N-(5-methyl-4-oxo-2,3,4,5-tetrahydrobenzo[b][1,4]oxazepin-3-yl)-1H-pyrazole-3-carboxamide | 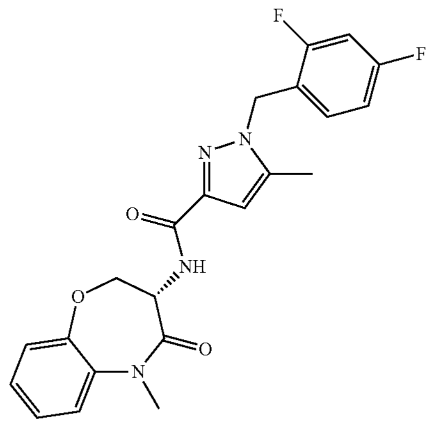 [SMILES: Cc1cc(C(=O)N[C@H]2COc3ccccc3N(C)C2=O)nn1Cc1ccc(F)cc1F] | $^1$H NMR (DMSO-d$_6$) δ: 8.02 (d, J = 8.0 Hz, 1H), 7.50 (dd, J = 7.7, 1.6 Hz, 1H), 7.20-7.37 (m, 4H), 7.00-7.15 (m, 2H), 6.49 (s, 1H), 5.40 (s, 2H), 4.83 (dt, J = 11.5, 7.8 Hz, 1H), 4.48-4.56 (m, 1H), 4.40 (dd, J = 9.8, 7.8 Hz, 1H), 3.31 (s, 3H), 2.27 (s, 3H) | 427 | F |
| 127 | (S)-1-(2-fluorobenzyl)-5-methyl-N-(2-oxo-2,3,4,5-tetrahydro-1H-benzo[b]azepin-3-yl)-1H-pyrazole-3-carboxamide | 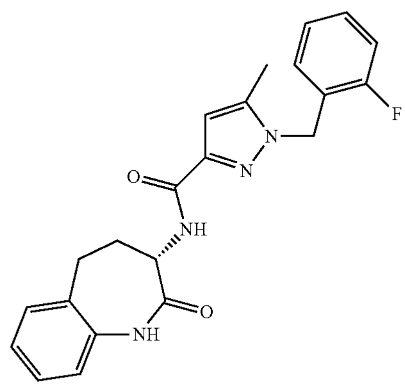 [SMILES: Cc1cc(C(=O)N[C@H]2CCc3ccccc3NC2=O)nn1Cc1ccccc1F] | $^1$H NMR (DMSO-d$_6$) δ: 9.99 (br. s., 1H), 7.78-7.94 (m, 1H), 7.11-7.48 (m, 6H), 6.88-7.10 (m, 2H), 6.50 (br. s., 1H), 5.43 (br. s., 2H), 4.25-4.42 (m, 1H), 2.64-2.85 (m, 2H), 2.38-2.61 (m, 4H), 2.05-2.22 (m, 1H) | 393 | F |
| 128 | (S)-3-(2,4-difluorobenzyl)-N-(5-methyl-4-oxo-2,3,4,5-tetrahydrobenzo[b][1,4]oxazepin-3-yl)-1H-pyrazole-5-carboxamide | 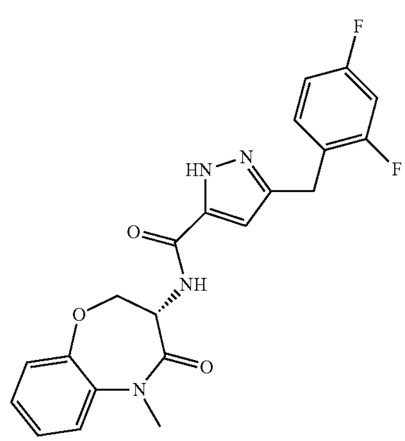 [SMILES: CN1C(=O)[C@@H](NC(=O)c2cc(Cc3ccc(F)cc3F)n[nH]2)COc2ccccc21] | $^1$H NMR (DMSO-d$_6$) δ: 8.22 (br. s., 1H), 7.50 (dd, J = 7.7, 1.6 Hz, 1H), 7.19-7.40 (m, 5H), 7.06 (td, J = 8.5, 1.8 Hz, 1H), 6.41 (br. s., 1H), 4.83 (dt, J = 11.5, 8.0 Hz, 1H), 4.51 (t, J = 10.8 Hz, 1H), 4.38 (dd, J = 9.8, 7.8 Hz, 1H), 3.98 (s, 2H), 3.31 (s, 3H) | 413 | F |

| Ex | Name | Structure | 1H NMR | MS (M + H)+ | Method |
|---|---|---|---|---|---|
| 129 | (S)-1-(2-fluorobenzyl)-N-(5-methyl-4-oxo-2,3,4,5-tetrahydrobenzo[b][1,4]oxazepin-3-yl)-1H-pyrazole-4-carboxamide | 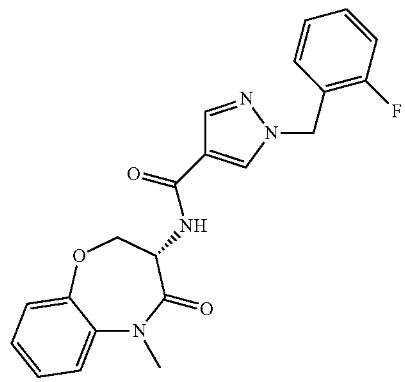 [SMILES: CN1C(=O)[C@@H](NC(=O)c2cnn(Cc3ccccc3F)c2)COc2ccccc21] | ¹H NMR (DMSO-d₆) δ: 8.37 (d, 1H), 8.30 (s, 1H), 7.91 (s, 1H), 7.52 (dd, J = 7.8, 1.8 Hz, 1H), 7.37-7.45 (m, 1H), 7.18-7.36 (m, 6H), 5.42 (s, 2H), 4.89 (dt, J = 11.7, 8.2 Hz, 1H), 4.30-4.48 (m, 2H), 3.30 (s, 3H) | 395 | F |
| 130 | (S)-3-benzyl-N-(4-oxo-2,3,4,5-tetrahydrobenzo[b][1,4]oxazepin-3-yl)-1H-pyrazole-5-carboxamide | 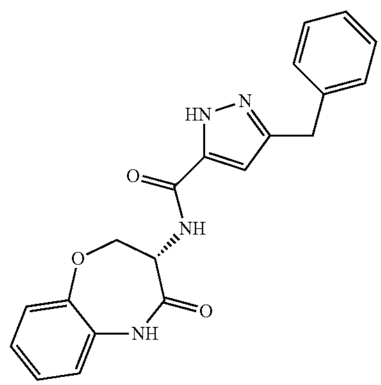 [SMILES: O=C(N[C@H]1COc2ccccc2NC1=O)c1cc(Cc2ccccc2)n[nH]1] | ¹H NMR (DMSO-d₆) δ: 10.13 (s, 1H), 8.19 (br. s., 1H), 7.10-7.36 (m, 10H), 6.44 (br. s., 1H), 4.80 (dt, J = 10.2, 7.4 Hz, 1H), 4.37-4.51 (m, 2H), 3.99 (s, 2H) | 363 | F |
| 131 | (S)-N-(5-methyl-4-oxo-2,3,4,5-tetrahydrobenzo[b][1,4]oxazepin-3-yl)-1-(4-methylbenzyl)-1H-pyrazole-4-carboxamide | 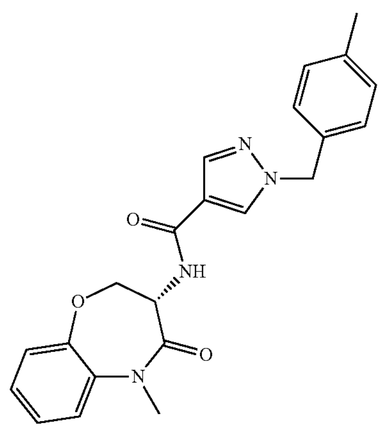 [SMILES: Cc1ccc(Cn2cc(C(=O)N[C@H]3COc4ccccc4N(C)C3=O)cn2)cc1] | ¹H NMR (DMSO-d₆) δ: 8.33 (d, J = 8.8 Hz, 1H), 8.26 (s, 1H), 7.90 (s, 1H), 7.51 (d, J = 7.8 Hz, 1H), 7.10-7.37 (m, 7H), 5.30 (s, 2H), 4.83-4.94 (m, 1H), 4.30-4.49 (m, 2H), 3.30 (s, 3H), 2.29 (s, 3H) | 391 | F |
| 132 | (S)-1-benzyl-N-(5-methyl-4-oxo-2,3,4,5-tetrahydrobenzo[b][1,4]oxazepin-3-yl)-1H-pyrrole-3-carboxamide | 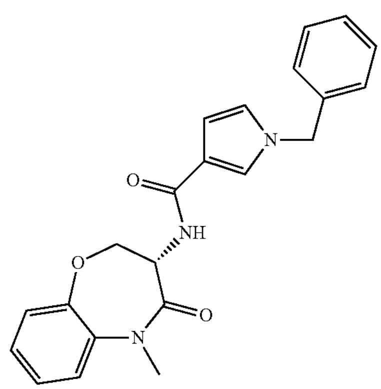 [SMILES: CN1C(=O)[C@@H](NC(=O)c2ccn(Cc3ccccc3)c2)COc2ccccc21] | ¹H NMR (DMSO-d₆) δ: 7.91-7.98 (m, 1H), 7.48-7.53 (m, 1H), 7.42 (t, J = 1.9 Hz, 1H), 7.19-7.39 (m, 8H), 6.86 (t, J = 2.5 Hz, 1H), 6.51 (dd, J = 2.8, 1.8 Hz, 1H), 5.13 (s, 2H), 4.88 (dt, J = 11.9, 8.2 Hz, 1H), 4.46 (dd, J = 11.8, 9.8 Hz, 1H), 4.31 (dd, J = 9.8, 7.8 Hz, 1H), 3.30 (s, 3H) | 773 (2M + Na) | F |

-continued

| Ex | Name | Structure | 1H NMR | MS (M + H)+ | Method |
|---|---|---|---|---|---|
| 133 | (S)-1-(2,5-difluorobenzyl)-5-methyl-N-(2-oxo-2,3,4,5-tetrahydro-1H-benzo[b]azepin-3-yl)-1H-pyrazole-3-carboxamide | 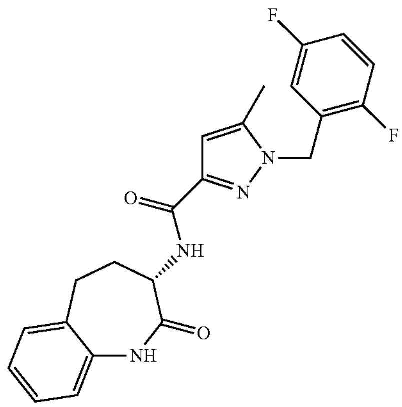 [SMILES: Cc1cc(C(=O)N[C@H]2CCc3ccccc3NC2=O)nn1Cc1cc(F)ccc1F] | $^1$H NMR (DMSO-$d_6$) δ: 9.99 (s, 1H), 7.87 (d, J = 7.5 Hz, 1H), 7.21-7.40 (m, 4H), 7.13-7.20 (m, 1H), 7.03 (d, J = 7.8 Hz, 1H), 6.77 (ddd, J = 8.7, 5.6, 3.3 Hz, 1H), 6.49 (s, 1H), 5.42 (s, 2H), 4.33 (dt, J = 11.5, 7.9 Hz, 1H), 2.64-2.82 (m, 2H), 2.37-2.48 (m, 1H), 2.28 (s, 3H), 2.17 (td, J = 12.0, 7.7 Hz, 1H) | 411 | F |
| 134 | (S)-1-benzyl-N-(2-oxo-2,3,4,5-tetrahydro-1H-benzo[b]azepin-3-yl)-1H-pyrrole-3-carboxamide | 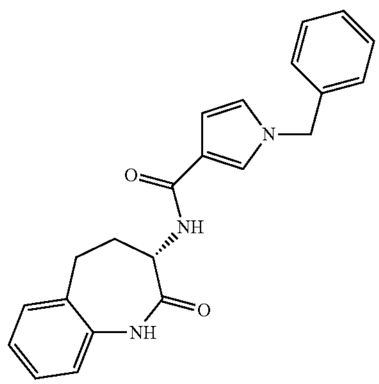 [SMILES: O=C(N[C@H]1CCc2ccccc2NC1=O)c1ccn(Cc2ccccc2)c1] | $^1$H NMR (DMSO-$d_6$) δ: 9.80 (s, 1H), 7.81 (d, J = 8.3 Hz, 1H), 7.20-7.44 (m, 8H), 7.11-7.17 (m, 1H), 7.03 (d, J = 7.5 Hz, 1H), 6.84 (t, J = 2.5 Hz, 1H), 6.48-6.54 (m, 1H), 5.12 (s, 2H), 4.32-4.46 (m, 1H), 2.64-2.80 (m, 2H), 2.24 (td, J = 9.6, 5.6 Hz, 2H) | 360 | F |
| 135 | (S)-3-(4-fluorobenzyl)-N-(4-oxo-2,3,4,5-tetrahydrobenzo[b][1,4]oxazepin-3-yl)-1H-pyrazole-5-carboxamide | 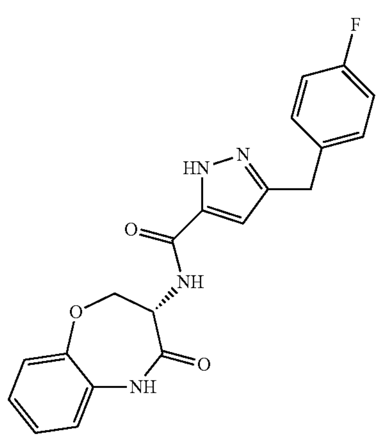 [SMILES: O=C(N[C@H]1COc2ccccc2NC1=O)c1cc(Cc2ccc(F)cc2)n[nH]1] | $^1$H NMR (DMSO-$d_6$) δ: 13.21 (br. s., 1H), 10.13 (br. s., 1H), 8.11 (d, J = 6.3 Hz, 1H), 7.06-7.36 (m, 8H), 6.40 (br. s., 1H), 4.80 (d, J = 8.3 Hz, 1H), 4.35-4.53 (m, 2H), 3.99 (br. s., 2H) | 381 | F |

| Ex | Name | Structure | 1H NMR | MS (M + H)+ | Method |
|---|---|---|---|---|---|
| 136 | (S)-2-(2,5-difluorobenzyl)-N-(5-methyl-4-oxo-2,3,4,5-tetrahydrobenzo[b][1,4]oxazepin-3-yl)-2H-tetrazole-5-carboxamide | 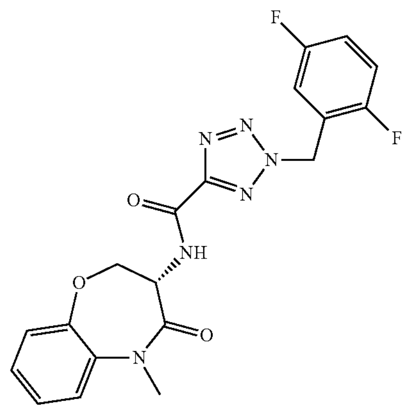 [SMILES: CN1C(=O)[C@@H](NC(=O)c2nnn(Cc3cc(F)ccc3F)n2)COc2ccccc21] | ¹H NMR (DMSO-d₆) δ: 9.15 (d, J = 8.0 Hz, 1H), 7.43-7.56 (m, 2H), 7.22-7.41 (m, 5H), 6.09 (s, 2H), 4.88 (dt, J = 11.5, 7.9 Hz, 1H), 4.66 (t, J = 10.7 Hz, 1H), 4.43 (dd, J = 9.5, 8.0 Hz, 1H), 3.32 (s, 3H) | 415 | F |
| 137 | (S)-4-butoxy-N-(5-methyl-4-oxo-2,3,4,5-tetrahydrobenzo[b][1,4]oxazepin-3-yl)picolinamide | 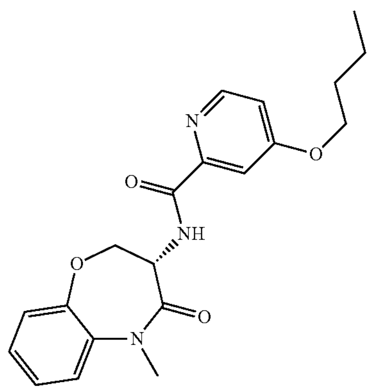 [SMILES: CCCCOc1ccnc(C(=O)N[C@H]2COc3ccccc3N(C)C2=O)c1] | ¹H NMR (DMSO-d₆) δ: 8.88 (d, J = 8.0 Hz, 1H), 8.49 (d, J = 5.5 Hz, 1H), 7.51 (dd, J = 7.5, 1.8 Hz, 1H), 7.45 (d, J = 2.5 Hz, 1H), 7.24-7.38 (m, 3H), 7.20 (dd, J = 5.8, 2.8 Hz, 1H), 4.86 (dt, J = 11.2, 7.8 Hz, 1H), 4.44-4.60 (m, 2H), 4.12 (t, J = 6.5 Hz, 2H), 3.34 (s, 3H), 1.66-1.78 (m, 2H), 1.43 (sxt, J = 7.4 Hz, 2H), 0.93 (t, J = 7.4 Hz, 3H) | 370 | F |
| 138 | (S)-4-(cyclopentyloxy)-N-(5-methyl-4-oxo-2,3,4,5-tetrahydrobenzo[b][1,4]oxazepin-3-yl)picolinamide | 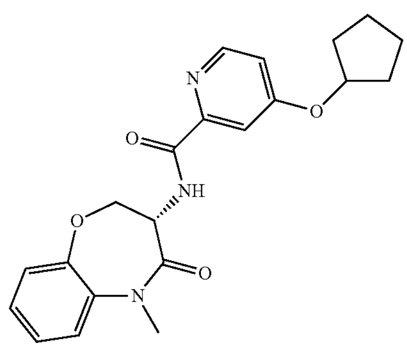 [SMILES: CN1C(=O)[C@@H](NC(=O)c2cc(OC3CCCC3)ccn2)COc2ccccc21] | ¹H NMR (DMSO-d₆) δ: 8.88 (d, J = 8.0 Hz, 1H), 8.48 (d, J = 5.8 Hz, 1H), 7.47-7.56 (m, 1H), 7.42 (d, J = 2.5 Hz, 1H), 7.22-7.39 (m, 3H), 7.16 (dd, J = 5.5, 2.5 Hz, 1H), 5.00 (t, J = 5.6 Hz, 1H), 4.86 (dt, J = 11.1, 8.0 Hz, 1H), 4.39-4.61 (m, 2H), 3.34 (br. s., 3H), 1.86-2.03 (m, 2H), 1.51-1.77 (m, 6H) | 382 | F |
| 139 | (S)-2-benzyl-N-(5-methyl-4-oxo-2,3,4,5-tetrahydrobenzo[b][1,4]oxazepin-3-yl)-2H-tetrazole-5-carboxamide | 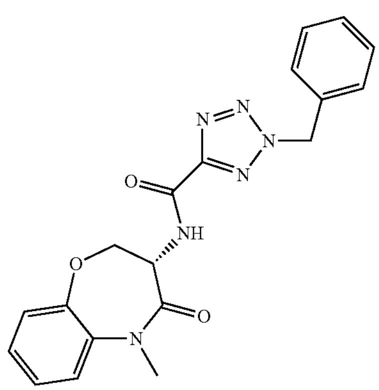 | ¹H NMR (DMSO-d₆) δ: 9.14 (d, J = 8.0 Hz, 1H), 7.52 (d, J = 7.5 Hz, 1H), 7.19-7.45 (m, 8H), 6.03 (s, 2H), 4.87 (dt, J = 11.5, 7.9 Hz, 1H), 4.65 (t, J = 10.8 Hz, 1H), 4.42 (dd, J = 9.8, 8.0 Hz, 1H), 3.31 (s, 3H) | 379 | F |

| Ex | Name | Structure | 1H NMR | MS (M + H)+ | Method |
|---|---|---|---|---|---|
| 140 | (S)-1-benzyl-N-(4-oxo-2,3,4,5-tetrahydrobenzo[b][1,4]oxazepin-3-yl)-1H-imidazole-4-carboxamide | 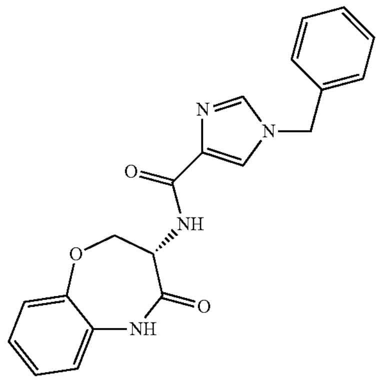 | $^1$H NMR (DMSO-d$_6$) δ: 10.17 (s, 1H), 8.06 (d, J = 7.8 Hz, 1H), 7.95 (s, 1H), 7.80 (s, 1H), 7.25-7.45 (m, 5H), 7.03-7.24 (m, 4H), 5.25 (s, 2H), 4.71-4.84 (m, 1H), 4.38-4.48 (m, 2H) | 363 | F |
| 141 | (S)-1-benzyl-N-(2-oxo-2,3,4,5-tetrahydro-1H-benzo[b]azepin-3-yl)-1H-imidazole-4-carboxamide | 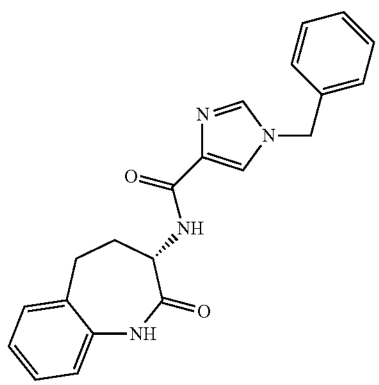 [SMILES: O=C(N[C@H]1CCc2ccccc2NC1=O)c1cn(Cc2ccccc2)cn1] | $^1$H NMR (DMSO-d$_6$) δ: 10.01 (s, 1H), 7.83-7.92 (m, 2H), 7.72 (s, 1H), 7.24-7.43 (m, 7H), 7.12-7.20 (m, 1H), 7.03 (d, J = 7.8 Hz, 1H), 5.23 (s, 2H), 4.32 (dt, J = 11.4, 7.9 Hz, 1H), 2.65-2.84 (m, 2H), 2.40-2.50 (m, 1H), 2.10 (td, 1H) | 361 | F |
| 142 | (S)-N-(5-methyl-4-oxo-2,3,4,5-tetrahydrobenzo[b][1,4]oxazepin-3-yl)-1-(4-methylbenzyl)-1H-1,2,3-triazole-4-carboxamide | 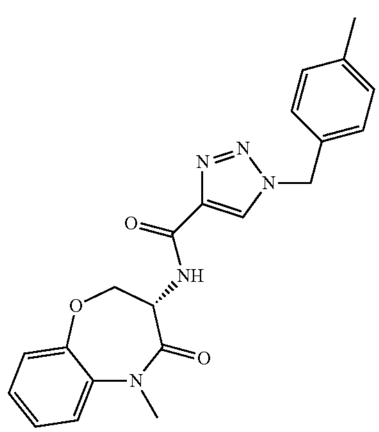 [SMILES: Cc1ccc(Cn2cc(C(=O)N[C@H]3COc4ccccc4N(C)C3=O)nn2)cc1] | $^1$H NMR (DMSO-d$_6$) δ: 8.66 (s, 1H), 8.57 (d, J = 8.0 Hz, 1H), 7.48-7.54 (m, 2H), 7.17-7.36 (m, 6H), 5.60 (s, 2H), 4.86 (dt, J = 11.5, 7.9 Hz, 1H), 4.60 (t, J = 10.8 Hz, 1H), 4.40 (dd, J = 9.7, 7.9 Hz, 1H), 3.31 (s, 3H), 2.28 (s, 3H) | 392 | F |

-continued

| Ex | Name | Structure | 1H NMR | MS (M + H)+ | Method |
|---|---|---|---|---|---|
| 143 | (S)-1-(4-fluorobenzyl)-N-(5-methyl-4-oxo-2,3,4,5-tetrahydrobenzo[b][1,4]oxazepin-3-yl)-1H-1,2,3-triazole-4-carboxamide | 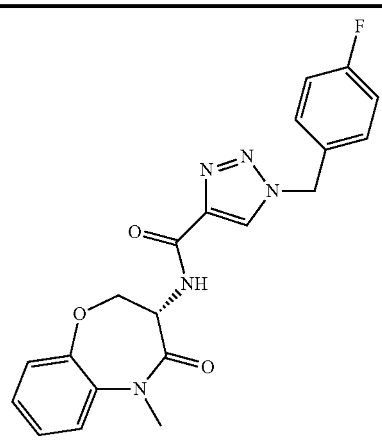 | $^1$H NMR (DMSO-$d_6$) δ: 8.70 (s, 1H), 8.59 (d, J = 8.3 Hz, 1H), 7.51 (dd, J = 7.7, 1.4 Hz, 1H), 7.43 (dd, J = 8.4, 5.6 Hz, 2H), 7.18-7.37 (m, 5H), 5.65 (s, 2H), 4.86 (dt, J = 11.5, 8.0 Hz, 1H), 4.61 (t, J = 10.7 Hz, 1H), 4.40 (dd, J = 9.7, 7.9 Hz, 1H), 3.32 (s, 3H) | 396 | F |
| 144 | (S)-2-(2,5-difluorobenzyl)-N-(4-oxo-2,3,4,5-tetrahydrobenzo[b][1,4]oxazepin-3-yl)-2H-tetrazole-5-carboxamide | 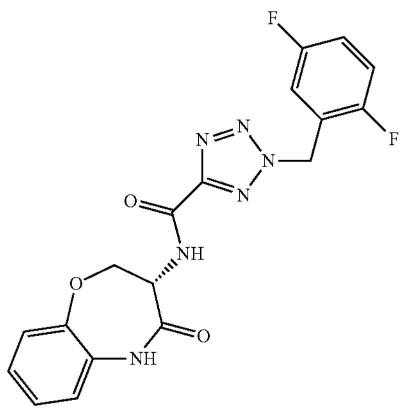 [SMILES: O=C(N[C@H]1COc2ccccc2NC1=O)c1nnn(Cc2cc(F)ccc2F)n1] | $^1$H NMR (DMSO-$d_6$) δ: 10.17 (s, 1H), 9.15 (d, J = 8.0 Hz, 1H), 7.43-7.51 (m, 1H), 7.33-7.41 (m, 2H), 7.09-7.19 (m, 4H), 6.10 (s, 2H), 4.80-4.90 (m, 1H), 4.57 (t, J = 10.7 Hz, 1H), 4.45 (dd, 1H) | 401 | F |
| 145 | (S)-2-benzyl-N-(4-oxo-2,3,4,5-tetrahydrobenzo[b][1,4]oxazepin-3-yl)-2H-tetrazole-5-carboxamide | 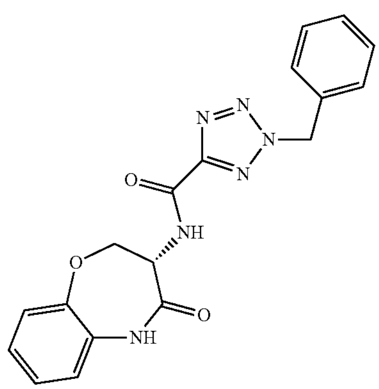 [SMILES: O=C(N[C@H]1COc2ccccc2NC1=O)c1nnn(Cc2ccccc2)n1] | $^1$H NMR (DMSO-$d_6$) δ: 10.17 (s, 1H), 9.14 (d, J = 8.0 Hz, 1H), 7.36-7.46 (m, 5H), 7.10-7.18 (m, 4H), 6.05 (s, 2H), 4.86 (dt, J = 10.5, 7.3 Hz, 1H), 4.57 (t, J = 10.7 Hz, 1H), 4.45 (dd, 1H) | 365 | F |
| 146 | (S)-5-benzyl-N-(5-methyl-4-oxo-2,3,4,5-tetrahydrobenzo[b][1,4]oxazepin-3-yl)-1,3,4-oxadiazole-2-carboxamide | 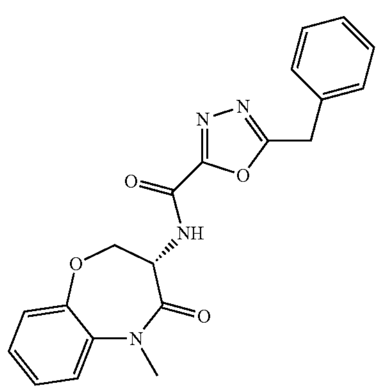 [SMILES: CN1C(=O)[C@@H](NC(=O)c2nnc(Cc3ccccc3)o2)COc2ccccc21] | $^1$H NMR (DMSO-$d_6$) δ: 9.43 (br. s., 1H), 7.52 (dd, J = 7.7, 1.6 Hz, 1H), 7.21-7.41 (m, 8H), 4.80 (br. s., 1H), 4.65 (dd, J = 11.6, 9.9 Hz, 1H), 4.35-4.45 (m, 3H), 3.31 (s, 3H) | 379 | F |

-continued

| Ex | Name | Structure | 1H NMR | MS (M + H)+ | Method |
|---|---|---|---|---|---|
| 147 | (S)-5-benzyl-N-(4-oxo-2,3,4,5-tetrahydrobenzo[b][1,4]oxazepin-3-yl)-1,3,4-oxadiazole-2-carboxamide | 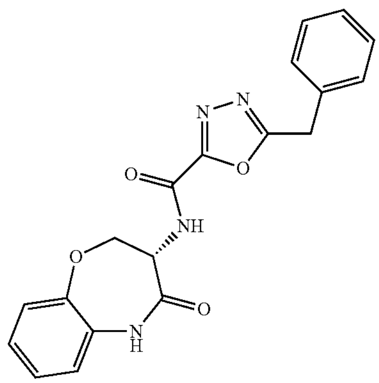 [SMILES: O=C(N[C@H]1COc2ccccc2NC1=O)c1nnc(Cc2ccccc2)o1] | ¹H NMR (DMSO-d₆) δ: 10.17 (s, 1H), 9.43 (d, J = 8.0 Hz, 1H), 7.28-7.42 (m, 5H), 7.11-7.17 (m, 4H), 4.79 (dt, J = 10.5, 7.3 Hz, 1H), 4.56 (t, J = 10.5 Hz, 1H), 4.44 (dd, J = 10.5, 6.5 Hz, 1H), 4.39 (s, 2H) | 365 | F |
| 148 | (S)-3-benzyl-N-(4-chloro-5-methyl-6-oxo-6,7,8,9-tetrahydro-5H-pyrimido[4,5-b][1,4]diazepin-7-yl)-1H-pyrazole-5-carboxamide | 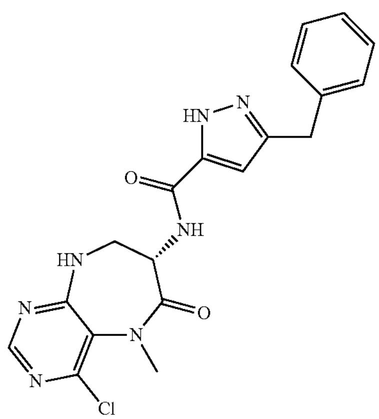 [SMILES: CN1C(=O)[C@@H](NC(=O)c2cc(Cc3ccccc3)n[nH]2)CNc2ncnc(Cl)c21] | ¹H NMR (DMSO-d₆) δ: 13.23 (br. s., 1H), 8.22-8.31 (m, 1H), 8.20 (s, 1H), 8.02 (br. s., 1H), 7.29-7.34 (m, 2H), 7.21-7.27 (m, 3H), 6.41 (br. s., 1H), 4.80-4.92 (m, 1H), 3.99 (br. s., 2H), 3.64 (br. s., 1H), 3.39-3.50 (m, 1H), 3.17 (s, 3H) | 412 | F |
| 149 | (S)-3-benzyl-N-(4-chloro-6-oxo-6,7,8,9-tetrahydro-5H-pyrimido[4,5-b][1,4]diazepin-7-yl)-1H-pyrazole-5-carboxamide | 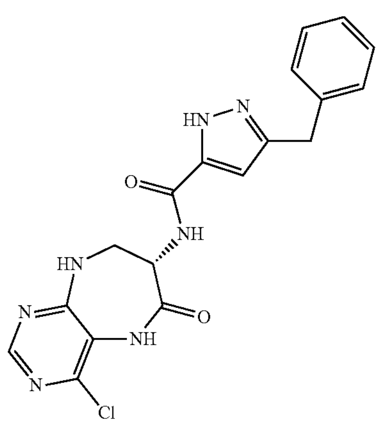 [SMILES: O=C(N[C@H]1CNc2ncnc(Cl)c2NC1=O)c1cc(Cc2ccccc2)n[nH]1] | ¹H NMR (DMSO-d₆) δ: 13.24 (s, 1H), 9.75 (s, 1H), 8.35 (d, J = 7.0 Hz, 1H), 8.10 (s, 1H), 8.05 (d, J = 6.0 Hz, 1H), 7.19-7.37 (m, 5H), 6.43 (s, 1H), 4.73 (t, J = 7.5 Hz, 1H), 4.01 (s, 2H), 3.59-3.69 (m, 1H), 3.42-3.53 (m, 1H) | 398 | F |

-continued

| Ex | Name | Structure | 1H NMR | MS (M + H)+ | Method |
|---|---|---|---|---|---|
| 150 | (S)-1-(3-fluorobenzyl)-N-(4-oxo-2,3,4,5-tetrahydrobenzo[b][1,4]oxazepin-3-yl)-1H-1,2,3-triazole-4-carboxamide | 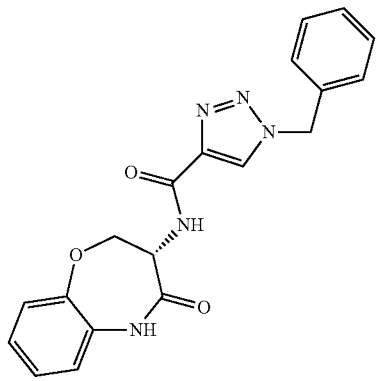 [SMILES: O=C(N[C@H]1COc2ccccc2NC1=O)c1cn(Cc2ccccc2)nn1] | $^1$H NMR (DMSO-d$_6$) δ: 10.14 (s, 1H), 8.76 (s, 1H), 8.60 (d, J = 8.0 Hz, 1H), 7.44 (q, J = 7.1 Hz, 1H), 7.06-7.28 (m, 7H), 5.70 (s, 2H), 4.77-4.92 (m, 1H), 4.48-4.61 (m, 1H), 4.39-4.48 (m, 1H) | 382 | F |
| 151 | (S)-5-benzyl-N-(5-methyl-4-oxo-2,3,4,5-tetrahydrobenzo[b][1,4]oxazepin-3-yl)-1,2,4-oxadiazole-3-carboxamide | 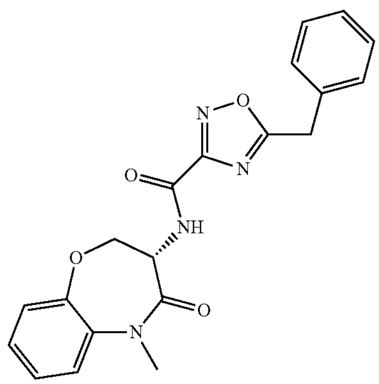 [SMILES: CN1C(=O)[C@@H](NC(=O)c2noc(Cc3ccccc3)n2)COc2ccccc21] | $^1$H NMR (DMSO-d$_6$) δ: 9.10 (d, J = 7.8 Hz, 1H), 7.52 (dd, J = 7.8, 1.8 Hz, 1H), 7.21-7.41 (m, 8H), 4.84 (dt, J = 11.4, 7.9 Hz, 1H), 4.62 (dd, J = 11.5, 10.0 Hz, 1H), 4.46 (s, 2H), 4.42 (dd, J = 9.9, 7.6 Hz, 1H), 3.31 (s, 3H) | 379 | F |
| 152 | (S)-3-benzyl-N-(6-oxo-6,7,8,9-tetrahydro-5H-pyrimido[4,5-b][1,4]diazepin-7-yl)-1H-pyrazole-5-carboxamide | 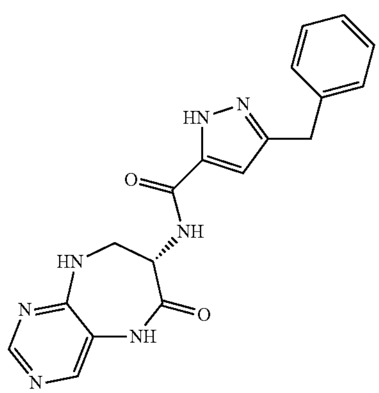 [SMILES: O=C(N[C@H]1CNc2ncncc2NC1=O)c1cc(Cc2ccccc2)n[nH]1] | $^1$H NMR (DMSO-d$_6$) δ: 13.22 (br. s., 1H), 10.25 (s, 1H), 8.20 (s, 1H), 8.09 (br. s., 1H), 7.95-8.04 (m, 2H), 7.29-7.35 (m, 2H), 7.20-7.28 (m, 3H), 6.43 (s, 1H), 4.55-4.65 (m, 1H), 4.01 (s, 2H), 3.54-3.63 (m, 1H), 3.38-3.48 (m, 1H) | 364 | F |
| 153 | (S)-3-benzyl-N-(5-methyl-6-oxo-6,7,8,9-tetrahydro-5H-pyrimido[4,5-b][1,4]diazepin-7-yl)-1H-pyrazole-5-carboxamide | 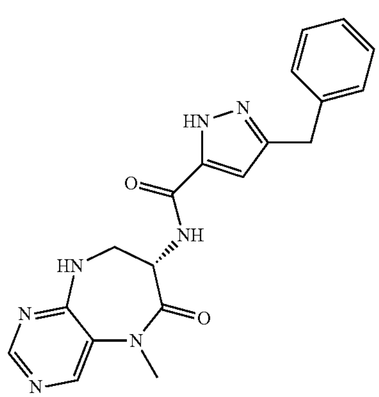 [SMILES: CN1C(=O)[C@@H](NC(=O)c2cc(Cc3ccccc3)n[nH]2)CNc2ncncc21] | $^1$H NMR (DMSO-d$_6$) δ: 9.08 (br. s., 1H), 8.52 (s, 1H), 8.43 (s, 1H), 8.17 (br. s., 1H), 7.19-7.36 (m, 6H), 6.44 (s, 1H), 4.78-4.89 (m, 1H), 4.00 (s, 2H), 3.55-3.70 (m, 2H), 3.33 (s, 3H) | 378 | F |

-continued

| Ex | Name | Structure | 1H NMR | MS (M + H)+ | Method |
|---|---|---|---|---|---|
| 154 | (S)-1-benzyl-N-(5-methyl-6-oxo-6,7,8,9-tetrahydro-5H-pyrimido[4,5-b][1,4]diazepin-7-yl)-1H-1,2,4-triazole-3-carboxamide | 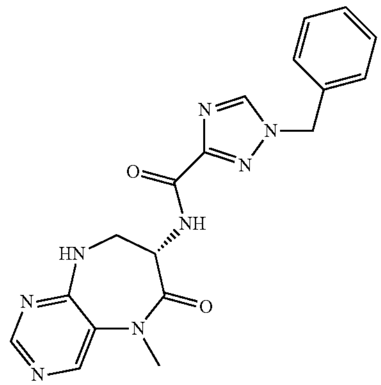 [SMILES: CN1C(=O)[C@@H](NC(=O)c2ncn(Cc3ccccc3)n2)CNc2ncncc21] | ¹H NMR (DMSO-d₆) δ: 9.10 (br. s., 1H), 8.87 (s, 1H), 8.52 (s, 1H), 8.42-8.49 (m, 2H), 7.30-7.43 (m, 5H), 5.51 (s, 2H), 4.82-4.89 (m, 1H), 3.58-3.71 (m, 2H), 3.34 (s, 3H) | 379 | F |
| 155 | (S)-5-benzyl-N-(4-oxo-2,3,4,5-tetrahydrobenzo[b][1,4]oxazepin-3-yl)-1,2,4-oxadiazole-3-carboxamide | 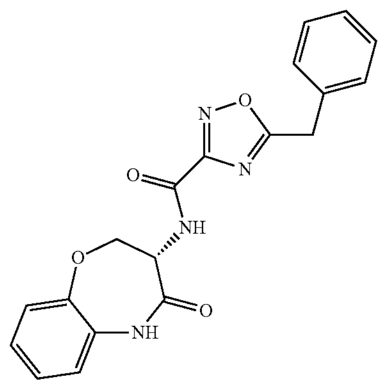 [SMILES: O=C(N[C@H]1COc2ccccc2NC1=O)c1noc(Cc2ccccc2)n1] | ¹H NMR (DMSO-d₆) δ: 10.17 (s, 1H), 9.07 (d, J = 8.0 Hz, 1H), 7.08-7.46 (m, 9H), 4.76-4.89 (m, 1H), 4.37-4.61 (m, 4H) | 365 | F |
| 156 | (S)-5-(difluoro(phenyl)methyl)-N-(4-oxo-2,3,4,5-tetrahydrobenzo[b][1,4]oxazepin-3-yl)isoxazole-3-carboxamide | 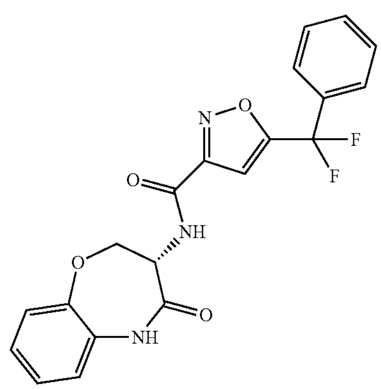 [SMILES: O=C(N[C@H]1COc2ccccc2NC1=O)c1cc(C(F)(F)c2ccccc2)on1] | ¹H NMR (400 MHz, CDCl₃) δ ppm 4.34 (t, 1 H) 4.79 (dd, J = 10.36, 6.57 Hz, 1 H) 5.09 (dt, J = 10.55, 6.60 Hz, 1 H) 6.87 (s, 1 H) 7.05-7.10 (m, 1 H) 7.13-7.23 (m, 3 H) 7.45-7.68 (m, 5 H) 7.83 (d, J = 6.82 Hz, 1 H) 8.26 (s, 1 H) | 400 | A |
| 157 | (S)-5-(difluoro(phenyl)methyl)-N-(5-methyl-4-oxo-2,3,4,5-tetrahydrobenzo[b][1,4]oxazepin-3-yl)isoxazole-3-carboxamide | 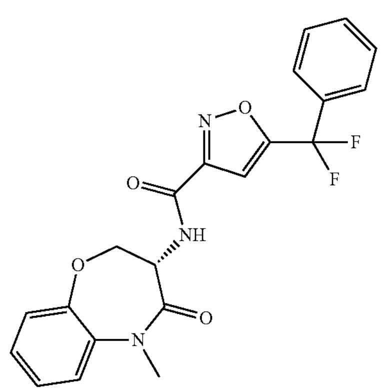 [SMILES: CN1C(=O)[C@@H](NC(=O)c2cc(C(F)(F)c3ccccc3)on2)COc2ccccc21] | ¹H NMR (400 MHz, CDCl₃) δ ppm 3.46 (s, 3 H) 4.28 (dd, J = 11.12, 9.85 Hz, 1 H) 4.76 (dd, J = 9.85, 7.33 Hz, 1 H) 5.04 (dt, J = 11.12, 7.07 Hz, 1 H) 6.83 (s, 1 H) 7.18-7.32 (m, 5 H) 7.45-7.56 (m, 3 H) 7.56-7.64 (m, 2 H) 7.83 (d, J = 6.82 Hz, 1 H) | 414 | A |

| Ex | Name | Structure | 1H NMR | MS (M + H)+ | Method |
|---|---|---|---|---|---|
| 158 | (S)-5-(3-bromobenzyl)-N-(5-methyl-4-oxo-2,3,4,5-tetrahydrobenzo[b][1,4]oxazepin-3-yl)-1H-pyrazole-3-carboxamide | 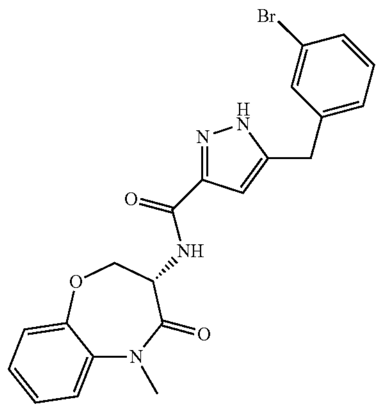 [SMILES: CN1C(=O)[C@@H](NC(=O)c2cc(Cc3cccc(Br)c3)[nH]n2)COc2ccccc21] | 1H NMR (400 MHz, CDCl$_3$) δ ppm 3.34 (s, 3 H) 3.91 (s, 2 H) 4.21 (dd, J = 11.37, 9.85 Hz, 1 H) 4.59 (dd, J = 9.85, 7.58 Hz, 1 H) 5.06 (dt, J = 11.49, 7.64 Hz, 1 H) 6.43 (s, 1 H) 7.00-7.21 (m, 6 H) 7.21-7.32 (m, 2 H) 8.07 (d, J = 7.58 Hz, 1 H) 12.45 (br. s., 1 H) | 455 | A |
| 159 | (S)-5-(4-bromobenzyl)-N-(5-methyl-4-oxo-2,3,4,5-tetrahydrobenzo[b][1,4]oxazepin-3-yl)-1H-pyrazole-3-carboxamide | 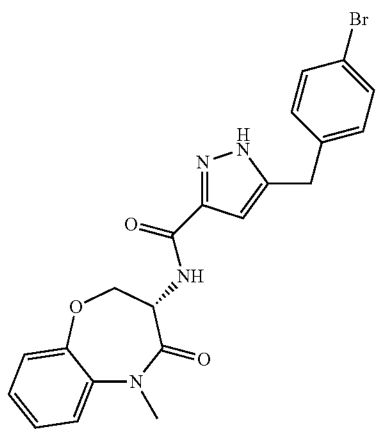 [SMILES: CN1C(=O)[C@@H](NC(=O)c2cc(Cc3ccc(Br)cc3)[nH]n2)COc2ccccc21] | 1H NMR (400 MHz, DMSO-d6) δ ppm 3.31 (s, 3 H) 3.97 (s, 2 H) 4.39 (dd, J = 9.60, 7.83 Hz, 1 H) 4.52 (t, J = 10.74 Hz, 1 H) 4.83 (d, J = 11.62 Hz, 1 H) 6.38 (s, 1 H) 7.09-7.40 (m, 5 H) 7.43-7.62 (m, 3 H) 8.08 (d, J = 8.08 Hz, 1 H) 13.22 (s, 1 H) | 455 | A |
| 160 | 5-benzyl-N-(7-bromo-2-oxo-2,3,4,5-tetrahydro-1H-benzo[b]azepin-3-yl)isoxazole-3-carboxamide | 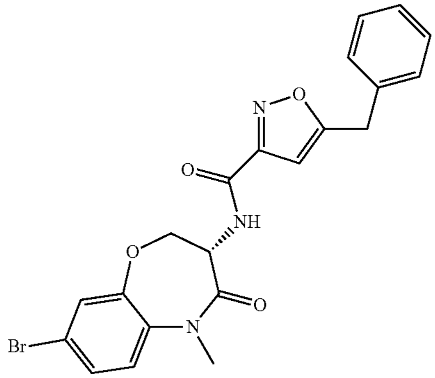 [SMILES: CN1C(=O)[C@@H](NC(=O)c2cc(Cc3ccccc3)on2)COc2cc(Br)ccc21] | 1H NMR (400 MHz, CDCl$_3$) δ ppm 2.02-2.75 (m, 2 H) 2.77-3.09 (m, 2 H) 4.12 (s, 2 H) 4.66 (dt, J = 11.18, 7.67 Hz, 1 H) 6.34 (s, 1 H) 6.91 (d, J = 8.34 Hz, 1 H) 7.23-7.39 (m, 5 H) 7.39-7.49 (m, 3 H) 7.68 (d, J = 6.82 Hz, 1 H) | 442 | F |

Example 161

(S)-5-benzyl-N-(7-chloro-2-oxo-2,3,4,5-tetrahydro-1H-benzo[b]azepin-3-yl)-4H-1,2,4-triazole-3-carboxamide

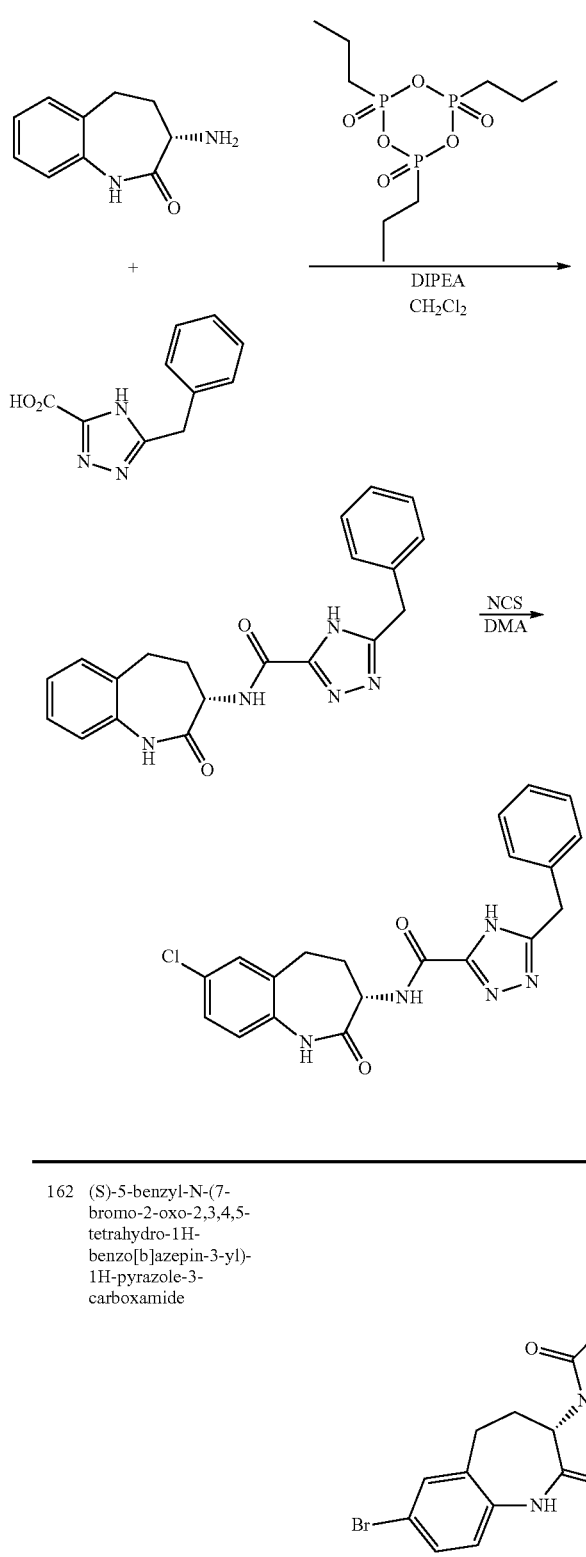

Preparation 1: The title compound was prepared via coupling of the appropriate amine and acid using Method H.

Preparation 2: To a solution of (S)-3-amino-4,5-dihydro-1H-benzo[b]azepin-2(3H)-one (50 g, 284 mmol), 5-benzyl-4H-1,2,4-triazole-3-carboxylic acid (72.1 g, 355 mmol) in dichloromethane (1500 ml) was added DIPEA (173 ml, 993 mmol) at 15° C. The reaction mixture was stirred for 20 minutes and 2,4,6-tripropyl-1,3,5,2,4,6-trioxatriphosphinane 2,4,6-trioxide (236 ml, 397 mmol) was slowly added at 15° C. The reaction was stirred for over night. The resulting solid was filtered and the solid was washed with DCM. The solid was dried under vacuum at 50° C. for over night. For the filtration, it was concentrated under rotary-evaporator and to the sticky residue added plenty of cold water and stirring, the slowly precipitated white solid was collected and washed the solid with water and ethyl ether. The solid was dried under vacuum at 50° C. for 3 days to afford the product (S)-5-benzyl-N-(2-oxo-2,3,4,5-tetrahydro-1H-benzo[b]azepin-3-yl)-4H-1,2,4-triazole-3-carboxamide (Total recovery: 102 g, 282 mmol, 99% yield). $^1$H NMR (MeOH-d4) δ: 7.18-7.48 (m, 8H), 7.10 (d, J=7.6 Hz, 1H), 4.58 (m, 1H), 4.17 (s, 2H), 2.97 (m 1H), 2.77 (m, 1H), 2.67 (m, 1H), 2.23 (m, 1H). MS (m/z) 362 (M+H$^+$).

To a solution of (S)-5-benzyl-N-(2-oxo-2,3,4,5-tetrahydro-1H-benzo[b]azepin-3-yl)-4H-1,2,4-triazole-3-carboxamide (35 g, 97 mmol) in DMA (700 ml) was added NCS (14.87 g, 111 mmol) at 0° C. After 30 mins, the reaction mixture was warmed up to RT and continued stirring for 5 hrs. A second portion of NCS (3.88 g, 29.1 mmol) was added to the reaction mixture and stirring continued for an additional 24 hrs. A third portion of NCS (1.293 g, 9.68 mmol) was then added and the solution was stirred at RT for 16 h further. The reaction was then quenched with cold water. The white solid was collected by filtration and washed with water 3 times to provide (S)-5-benzyl-N-(7-chloro-2-oxo-2,3,4,5-tetrahydro-1H-benzo[b]azepin-3-yl)-4H-1,2,4-triazole-3-carboxamide (36 g, 91 mmol, 94% yield). The product was air dried overnight. Additional purification was achieved by suspending (S)-5-benzyl-N-(7-chloro-2-oxo-2,3,4,5-tetrahydro-1H-benzo[b]azepin-3-yl)-4H-1,2,4-triazole-3-carboxamide (10 g, 25.3 mmol) in hot methanol (500 mL) for 1 h. The solution was then cooled to RT, filtered and the solid was washed with methanol 2 times (75 mL) to give the product (7 g, 70% yield). $^1$H NMR (DMSO-d$_6$) δ: 10.06 (s, 1H), 8.31 (br. s., 1H), 7.44 (d, J=2.5 Hz, 1H), 7.18-7.40 (m, 7H), 7.05 (d, J=8.6 Hz, 1H), 4.32 (dt, J=11.5, 7.9 Hz, 1H), 4.11 (s, 2H), 2.63-2.80 (m, 2H), 2.37-2.49 (m, 1H), 2.25 (br. s., 1H). MS (m/z) 396/398 (M+H$^+$). The following compounds were prepared via coupling of the appropriate amine and acid using the method indicated.

| 162 | (S)-5-benzyl-N-(7-bromo-2-oxo-2,3,4,5-tetrahydro-1H-benzo[b]azepin-3-yl)-1H-pyrazole-3-carboxamide | | 1H NMR (400 MHz, MeOD-d4) δ ppm 2.17 (m, 1 H) 2.65 (m, 1 H) 2.72-2.81 (m, 1 H) 2.86-3.00 (m, 1 H) 4.03 (s, 2 H) 4.55 (dd, J = 11.62, 8.08 Hz, 1 H) 6.47 (s, 1 H) 7.01 (d, J = 8.34 Hz, 1 H) 7.23 (d, J = 7.58 Hz, 3 H) 7.30 (d, J = 6.82 Hz, 2 H) 7.46 (dd, J = 8.46, 2.15 Hz, 1 H) 7.53 (d, J = 2.27 Hz, 1 H) | 440 | F |

| | | | | |
|---|---|---|---|---|
| 163 | (S)-5-benzyl-N-(7-bromo-2-oxo-2,3,4,5-tetrahydro-1H-benzo[b]azepin-3-yl)-4H-1,2,4-triazole-3-carboxamide | 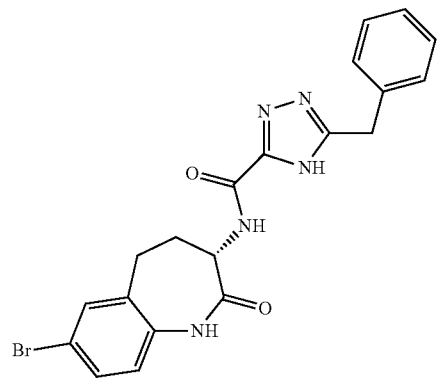 [SMILES: O=C(N[C@H]1CCc2cc(Br)ccc2NC1=O)c1nnc(Cc2ccccc2)[nH]1] | 1H NMR (400 MHz, DMSO-d6) δ ppm 2.66-2.80 (m, 2 H) 3.39 (m, 2 H) 4.12 (br. s., 2 H) 4.24-4.42 (m, 1 H) 6.99 (d, J = 8.34 Hz, 1 H) 7.16-7.41 (m, 5 H) 7.47 (dd, J = 8.34, 2.27 Hz, 1 H) 7.57 (d, J = 2.27 Hz, 1 H) 10.06 (s, 1H) | 442 H |
| 164 | (S)-5-benzyl-N-(6-fluoro-8-methyl-4-oxo-2,3,4,5-tetrahydrobenzo[b][1,4]oxazepin-3-yl)-4H-1,2,4-triazole-3-carboxamide | 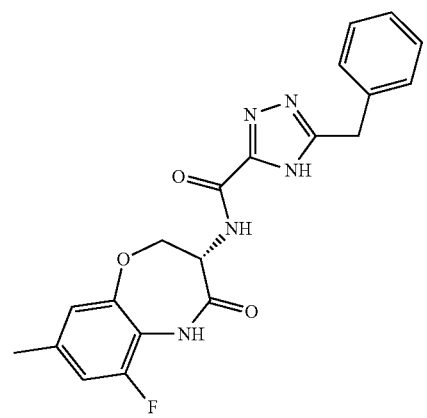 [SMILES: Cc1cc(F)c2c(c1)OC[C@H](NC(=O)c1nnc(Cc3ccccc3)[nH]1)C(=O)N2] | 1H NMR (DMSO-d6) δ: 14.38 (br. s., 1H), 10.02 (s, 1H), 8.42 (br. s., 1H), 7.21-7.38 (m, 5H), 7.00 (d, J = 10.8 Hz, 1H), 6.90 (s, 1H), 4.85 (dt, J = 11.1, 7.6 Hz, 1H), 4.57-4.68 (m, 1H), 4.45 (dd, J = 9.9, 7.4 Hz, 1H), 4.13 (br. s., 2H), 2.30 (s, 3H) | 396.2 F |
| 165 | (S)-5-benzyl-N-(7-cyano-2-oxo-2,3,4,5-tetrahydro-1H-benzo[b]azepin-3-yl)-4H-1,2,4-triazole-3-carboxamide | 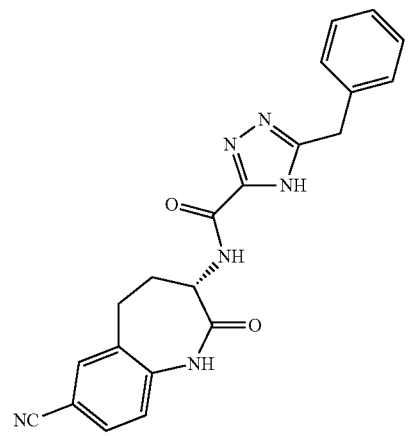 [SMILES: N#Cc1ccc2c(c1)CC[C@H](NC(=O)c1nnc(Cc3ccccc3)[nH]1)C(=O)N2] | 1H NMR (400 MHz, DMSO-d6) δ ppm 2.34 (m, 2 H) 2.62-2.87 (m, 2 H) 4.12 (br. s., 2 H) 4.23-4.48 (m, 1 H) 7.19 (d, J = 8.34 Hz, 1 H) 7.21-7.39 (m, 5 H) 7.75 (dd, J = 8.21, 1.89 Hz, 1 H) 7.83 (d, J = 1.77 Hz, 1 H) 8.30 (br. s., 1 H) 10.38 (s, 1 H) | 387 F |

| | | | | |
|---|---|---|---|---|
| 166 | (S)-5-benzyl-N-(2-oxo-7-(1H-tetrazol-5-yl)-2,3,4,5-tetrahydro-1H-benzo[b]azepin-3-yl)-4H-1,2,4-triazole-3-carboxamide | 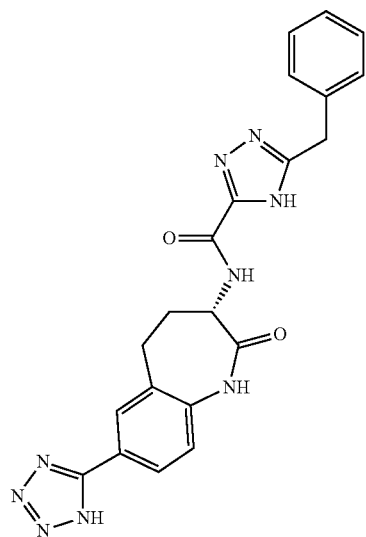 [SMILES: O=C(N[C@H]1CCc2cc(-c3nnn[nH]3)ccc2NC1=O)c1nnc(Cc2ccccc2)[nH]1] | ¹H NMR (400 MHz, DMSO-d6) δ ppm 2.20-2.39 (m, 1 H) 2.44 (m, 1 H) 2.75-2.85 (m, 2 H) 4.11 (s, 2 H) 4.39 (dt, J = 11.37, 7.83 Hz, 1 H) 7.12 (d, J = 8.34 Hz, 1 H) 7.20-7.38 (m, 5 H) 7.91 (dd, J = 8.21, 1.89 Hz, 1 H) 7.97 (d, J = 1.52 Hz, 1 H) 8.32 (br. s., 1 H) 10.12 (s, 1 H) | 430 F 1 |
| 167 | (S)-5-benzyl-N-(2-oxo-7-(1H-pyrazol-4-yl)-2,3,4,5-tetrahydro-1H-benzo[b]azepin-3-yl)-4H-1,2,4-triazole-3-carboxamide | 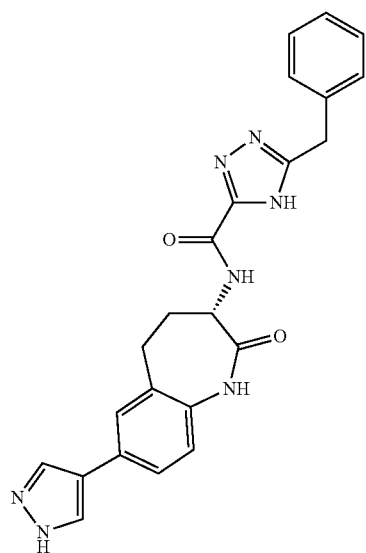 [SMILES: O=C(N[C@H]1CCc2cc(-c3cn[nH]c3)ccc2NC1=O)c1nnc(Cc2ccccc2)[nH]1] | 1H NMR (400 MHz, DMSO-d6) δ ppm 1.42 (d, J = 7.83 Hz, 1 H) 1.80-1.96 (m, 1 H) 1.97-2.11 (m, 1 H) 2.11-2.27 (m, 1 H) 3.35 (s, 2 H) 3.82 (dd, J = 11.49, 7.96 Hz, 1 H) 6.29 (d, J = 8.08 Hz, 1 H) 6.38-6.59 (m, 5 H) 6.65-6.82 (m, 2 H) 7.19 (br. s., 2 H) | 428 F |
| 168 | 5-benzyl-N-(1-methyl-2-oxo-7-(2,2,2-trifluoro-1,1-dihydroxyethyl)-2,3,4,5-tetrahydro-1H-benzo[b]azepin-3-yl)-1H-pyrazole-3-carboxamide | 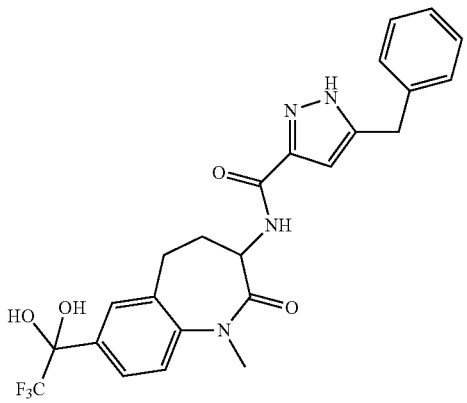 [SMILES: CN1C(=O)C(NC(=O)c2cc(Cc3ccccc3)[nH]n2)CCc2cc(C(O)(O)C(F)(F)F)ccc21] | 1H NMR (400 MHz, CDCl₃) δ ppm 2.11 (m, 2 H) 2.51-2.70 (m, 2 H) 3.44 (s, 3 H) 4.00 (s, 2 H) 4.68 (dt, J = 11.56, 7.86 Hz, 1 H) 6.50 (s, 1 H) 7.14-7.32 (m, 6 H) 7.37 (d, J = 8.34 Hz, 1 H) 7.96 (s, 1 H) 8.05 (d, J = 8.34 Hz, 1 H) 8.22 (d, J = 7.83 Hz, 1 H) | 489 F |

| | | | | |
|---|---|---|---|---|
| 169 | (S)-5-benzyl-N-(5-methyl-7-(5-methyl-1,3,4-oxadiazol-2-yl)-4-oxo-2,3,4,5-tetrahydrobenzo[b][1,4]oxazepin-3-yl)-4H-1,2,4-triazole-3-carboxamide | 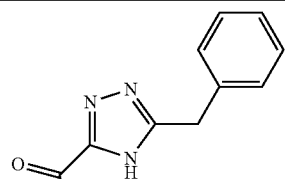 | ¹H NMR (DMSO-d₆) δ: 14.38 (br. s., 1H), 8.45 (br. s., 1H), 8.04 (d, J = 1.5 Hz, 1H), 7.88 (dd, J = 8.3, 1.8 Hz, 1H), 7.45 (d, J = 8.5 Hz, 1H), 7.23-7.37 (m, 5H), 4.91 (dt, J = 11.5, 7.8 Hz, 1H), 4.62-4.81 (m, 1H), 4.49 (dd, J = 9.4, 7.9 Hz, 1H), 4.14 (br. s., 2H), 3.39 (s, 3H), 2.61 (s, 3H) | 460.2 F |
| 170 | (S)-1-benzyl-N-(7-bromo-2-oxo-2,3,4,5-tetrahydro-1H-benzo[b]azepin-3-yl)-1H-1,2,4-triazole-3-carboxamide | 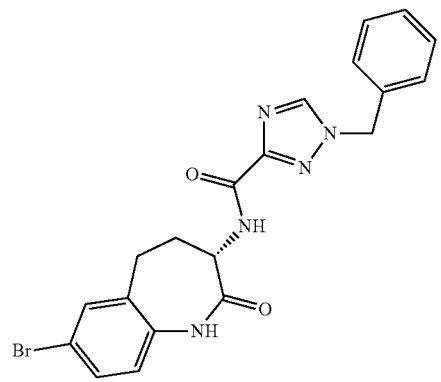 [SMILES: O=C(N[C@H]1CCc2cc(Br)ccc2NC1=O)c1ncn(Cc2ccccc2)n1] | 1H NMR (400 MHz, DMSO-d6) δ ppm 2.22 (t, J = 11.62 Hz, 1 H) 2.37-2.48 (m, 1 H) 2.63-2.79 (m, 2 H) 4.32 (dt, J = 11.43, 7.80 Hz, 1 H) 5.48 (s, 2 H) 6.99 (d, J = 8.34 Hz, 1 H) 7.27-7.42 (m, 5 H) 7.47 (dd, J = 8.46, 2.40 Hz, 1 H) 7.57 (d, J = 2.27 Hz, 1 H) 8.29 (d, J = 7.58 Hz, 1 H) 8.82 (s, 1 H) 10.07 (s, 1 H) | 442 F |
| 171 | N-[(3S)-7-deuterio-1-methyl-2-oxo-2,3,4,5-tetrahydro-1H-1-benzazepin-3-yl]-5-(phenylmethyl)-1H-pyrazole-3-carboxamide | 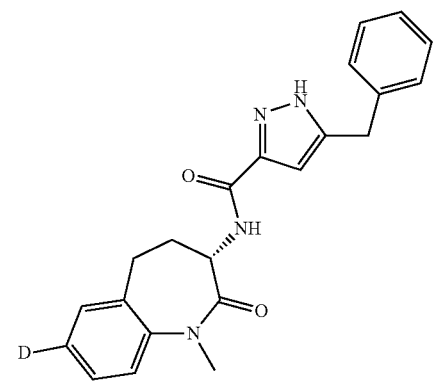 [SMILES: [2H]c1ccc2c(c1)CC[C@H](NC(=O)c1cc(Cc3ccccc3)[nH]n1)C(=O)N2C] | 1H NMR (400 MHz, MeOD-d4) δ ppm 2.10-2.21 (m, 1 H) 2.54 (br. s., 1 H) 2.68-2.81 (m, 1 H) 2.86 (dd, J = 13.26, 7.96 Hz, 1 H) 3.41 (s, 3 H) 4.02 (s, 2 H) 4.52 (dd, J = 11.62, 7.83 Hz, 1 H) 6.45 (br. s., 1 H) 7.23 (d, J = 7.33 Hz, 3 H) 7.26-7.35 (m, 4 H) 7.35-7.44 (m, 2 H) | 376 A |
| 172 | (R)-5-benzyl-N-(4-oxo-2,3,4,5-tetrahydrobenzo[b][1,4]thiazepin-3-yl)isoxazole-3-carboxamide | 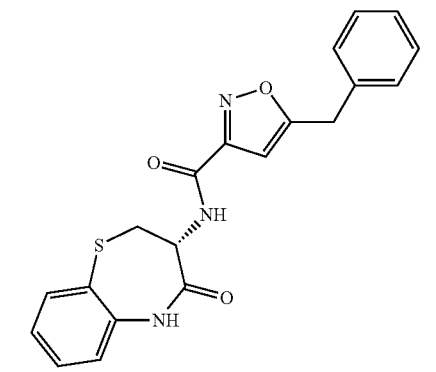 [SMILES: O=C(N[C@H]1CSc2ccccc2NC1=O)c1cc(Cc2ccccc2)on1] | 1H NMR (CDCl₃) δ: 7.80 (br. s., 1H), 7.70 (dd, J = 7.7, 1.4 Hz, 1H), 7.49-7.60 (m, 1H), 7.18-7.48 (m, 5H), 7.14 (dd, J = 7.8, 1.3 Hz, 1H), 6.33 (s, 1H), 4.86 (dt, J = 11.7, 7.0 Hz, 1H), 4.13 (s, 2H), 3.98 (dd, J = 11.1, 6.6 Hz, 1H), 3.04 (t, J = 11.4 Hz, 1H) | 380 A |

| | | | | |
|---|---|---|---|---|
| 173 | (S)-3-butoxy-N-(4-oxo-2,3,4,5-tetrahydrobenzo[b][1,4]oxazepin-3-yl)benzamide | 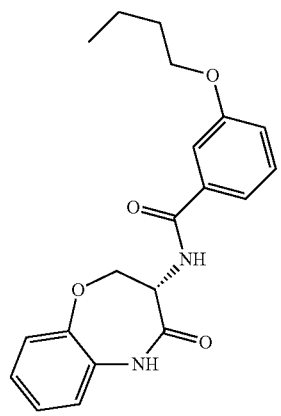 [SMILES: CCCCOc1cccc(C(=O)N[C@H]2COc3ccccc3NC2=O)c1] | 1H NMR (DMSO-d6) δ: 10.08 (br. s., 1H), 8.67 (d, J = 8.0 Hz, 1H), 7.42 (d, J = 4.5 Hz, 4H), 7.16 (br. s., 6H), 4.90 (d, J = 8.0 Hz, 1H), 4.33-4.67 (m, 2H), 4.02 (br. s., 2H), 1.72 (d, J = 5.0 Hz, 2H), 1.30-1.56 (m, 2H), 0.77-1.06 (m, 3H) | 355 F |
| 174 | (S)-5-(4-methoxybenzyl)-N-(4-oxo-2,3,4,5-tetrahydrobenzo[b][1,4]oxazepin-3-yl)thiophene-2-carboxamide | 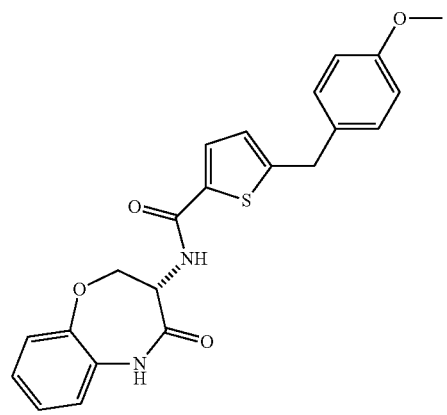 [SMILES: COc1ccc(Cc2ccc(C(=O)N[C@H]3COc4ccccc4NC3=O)s2)cc1] | $^1$H NMR (DMSO-d$_6$) δ: 10.07 (s, 1H), 8.52-8.69 (m, 1H), 7.69 (d, J = 3.8 Hz, 1H), 7.05-7.28 (m, 6H), 6.78-7.01 (m, 3H), 4.67-4.94 (m, 1H), 4.46 (s, 2H), 4.08 (s, 2H), 3.72 (s, 3H) | 409 F |
| 175 | (R)-N-(5-methyl-4-oxo-2,3,4,5-tetrahydrobenzo[b][1,4]thiazepin-3-yl)-3-phenoxybenzamide | 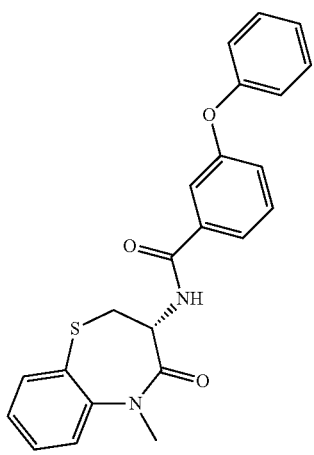 [SMILES: CN1C(=O)[C@@H](NC(=O)c2cccc(Oc3ccccc3)c2)CSc2ccccc21] | $^1$H NMR (DMSO-d$_6$) δ: 8.91 (d, J = 7.8 Hz, 1H), 7.56-7.75 (m, 4H), 6.92-7.55 (m, 8H), 4.58 (dt, J = 12.1, 7.4 Hz, 1H), 3.52 (dd, J = 11.4, 7.1 Hz, 2H), 3.29 (s, 3H) | 405 A |

| | | | | |
|---|---|---|---|---|
| 176 | (S)-N-(5-methyl-4-oxo-2,3,4,5-tetrahydrobenzo[b][1,4]oxazepin-3-yl)-5-(4-methylbenzyl)-1H-pyrazole-3-carboxamide | 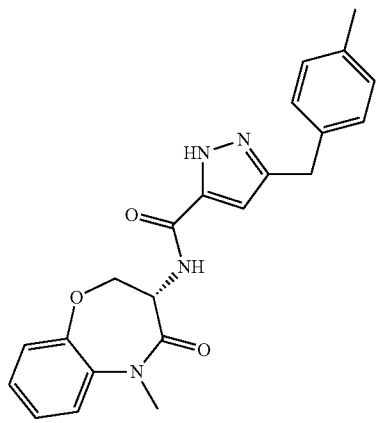 [SMILES: Cc1ccc(Cc2cc(C(=O)N[C@H]3COc4ccccc4N(C)C3=O)[nH]n2)cc1] | ¹H NMR (DMSO-d₆) δ: 13.18 (br. s., 1H), 8.40-8.72 (m, 1H), 8.05 (d, J = 7.8 Hz, 1H), 7.50 (dd, J = 7.6, 1.8 Hz, 1H), 7.01-7.40 (m, 6H), 6.34 (br. s., 1H), 5.76 (s, 1H), 4.72-5.01 (m, 1H), 4.25-4.68 (m, 2H), 3.93 (br. s., 3H), 2.26 (s, 3H) | 391 A |
| 177 | (S)-N-(5-methyl-4-oxo-2,3,4,5-tetrahydrobenzo[b][1,4]oxazepin-3-yl)-5-pentyl-1H-pyrazole-3-carboxamide | 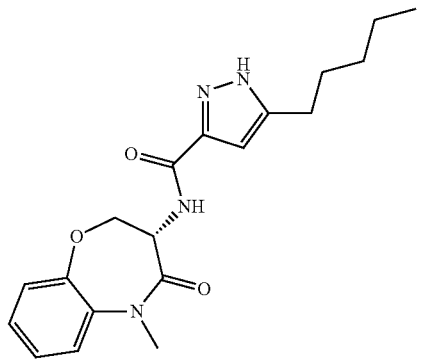 [SMILES: CCCCCc1cc(C(=O)N[C@H]2COc3ccccc3N(C)C2=O)n[nH]1] | ¹H NMR (DMSO-d₆) 13.04 (s, 1H), 8.06 (d, J = 8.0 Hz, 1H), 7.50 (dd, J = 7.7, 1.6 Hz, 1H), 7.08-7.41 (m, 3H), 6.38 (d, J = 1.5 Hz, 1H), 4.71-4.97 (m, 1H), 4.28-4.64 (m, 2H), 2.49-2.56 (m, 3H), 1.46-1.80 (m, 2H), 1.12-1.43 (m, 6H), 0.86 (t, J = 6.9 Hz, 3H) | 357 F |
| 178 | (S)-1-(2-iodobenzyl)-N-(5-methyl-4-oxo-2,3,4,5-tetrahydrobenzo[b][1,4]oxazepin-3-yl)-1H-pyrazole-3-carboxamide | 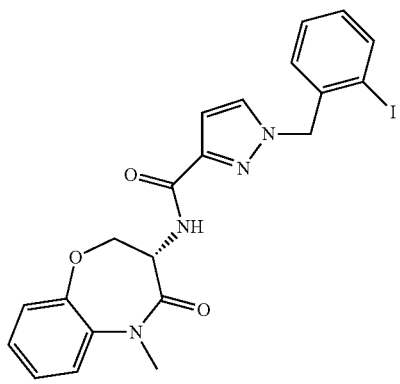 [SMILES: CN1C(=O)[C@@H](NC(=O)c2ccn(Cc3ccccc3I)n2)COc2ccccc21] | ¹H NMR (DMSO-d₆) 8.15 (d, J = 8.0 Hz, 1H), 7.82-8.01 (m, 2H), 7.51 (dd, J = 7.7, 1.6 Hz, 1H), 7.19-7.45 (m, 4H), 7.11 (td, J = 7.7, 1.5 Hz, 1H), 6.65-6.83 (m, 2H), 5.45 (s, 2H), 4.85 (dt, J = 11.5, 7.9 Hz, 1H), 4.55 (dd, J = 11.5, 10.0 Hz, 1H), 4.40 (dd, J = 9.8, 7.8 Hz, 1H), 3.16-3.40 (m, 3H) | 503 F |
| 179 | (S)-3-(4-methoxyphenethyl)-N-(5-methyl-4-oxo-2,3,4,5-tetrahydrobenzo[b][1,4]oxazepin-3-yl)isoxazole-5-carboxamide | 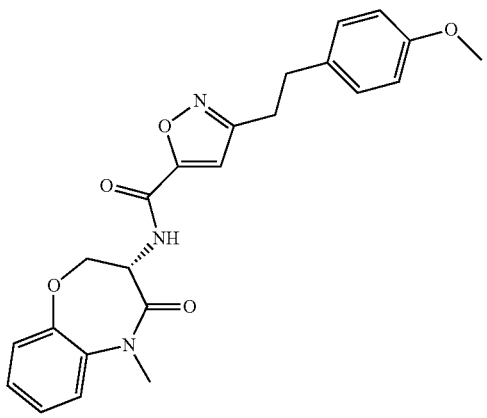 [SMILES: COc1ccc(CCc2cc(C(=O)N[C@H]3COc4ccccc4N(C)C3=O)on2)cc1] | ¹H NMR (DMSO-d₆) δ: 9.14 (d, J = 8.0 Hz, 1H), 7.53 (dd, J = 7.8, 1.8 Hz, 1H), 6.96-7.41 (m, 5H), 6.75-6.97 (m, 3H), 4.83 (dt, J = 11.5, 8.0 Hz, 1H), 4.31-4.68 (m, 2H), 3.64-3.78 (m, 3H), 3.31 (s, 3H), 2.83-3.07 (m, 4H) | 422 F |

| | | | | |
|---|---|---|---|---|
| 180 | (S)-5-isobutyl-N-(5-methyl-4-oxo-2,3,4,5-tetrahydrobenzo[b][1,4]oxazepin-3-yl)isoxazole-3-carboxamide | 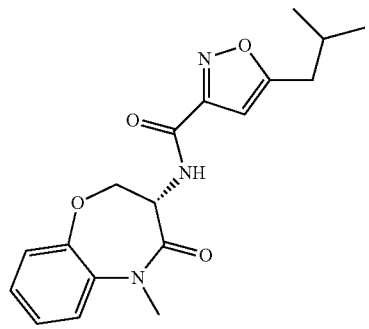 [SMILES: CC(C)Cc1cc(C(=O)N[C@H]2COc3ccccc3N(C)C2=O)no1] | $^1$H NMR (DMSO-d$_6$) δ: 8.86 (d, J = 8.1 Hz, 1H), 7.52 (dd, J = 7.7, 1.6 Hz, 1H), 7.10-7.44 (m, 3H), 6.58 (s, 1H), 4.85 (dt, J = 11.6, 8.0 Hz, 1H), 4.61 (dd, J = 11.6, 9.9 Hz, 1H), 4.41 (dd, J = 9.7, 7.7 Hz, 1H), 3.31 (s, 3H), 2.71 (d, J = 7.1 Hz, 2H), 2.00 (dt, J = 13.5, 6.8 Hz, 1H), 0.91 (d, 6H) | 344 F |
| 181 | (S)-5-isobutyl-N-(5-methyl-4-oxo-2,3,4,5-tetrahydrobenzo[b][1,4]oxazepin-3-yl)-1H-pyrazole-3-carboxamide | 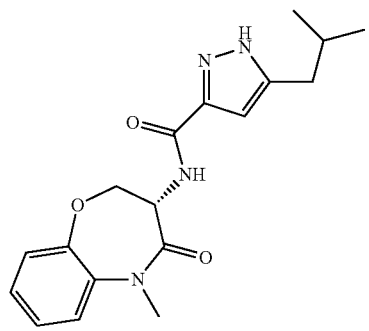 [SMILES: CC(C)Cc1cc(C(=O)N[C@H]2COc3ccccc3N(C)C2=O)n[nH]1] | $^1$H NMR (DMSO-d$_6$) 13.04 (br. s., 1H), 8.09 (br. s., 1H), 7.51 (dd, J = 7.7, 1.9 Hz, 1H), 7.09-7.43 (m, 3H), 6.39 (br. s., 1H), 4.84 (dt, J = 11.5, 7.9 Hz, 1H), 4.27-4.65 (m, 2H), 2.48 (d, J = 7.0 Hz, 3H), 1.88 (dt, J = 13.6, 6.8 Hz, 2H), 1.09-1.41 (m, 1H), 0.67-1.06 (m, 6H) | 343 F |
| 182 | (S)-N-(5-methyl-4-oxo-2,3,4,5-tetrahydrobenzo[b][1,4]oxazepin-3-yl)-5-propyl-1H-pyrazole-3-carboxamide | 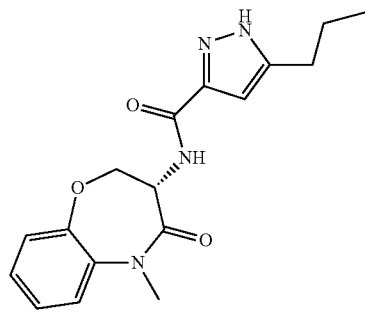 [SMILES: CCCc1cc(C(=O)N[C@H]2COc3ccccc3N(C)C2=O)n[nH]1] | $^1$H NMR (DMSO-d$_6$) 8.11 (d, J = 8.0 Hz, 1H), 7.51 (dd, J = 7.7, 1.9 Hz, 1H), 7.16-7.44 (m, 3H), 6.42 (s, 1H), 4.84 (dt, J = 11.5, 7.9 Hz, 1H), 4.25-4.67 (m, 2H), 3.32 (s, 3H), 2.58 (t, J = 7.4 Hz, 2H), 1.51-1.69 (m, 2H), 1.20-1.30 (m, 0H), 0.88 (t, J = 7.3 Hz, 3H) | 329 F |
| 183 | (S)-1-benzyl-N-(5-methyl-4-oxo-2,3,4,5-tetrahydrobenzo[b][1,4]oxazepin-3-yl)-1H-pyrazole-4-carboxamide | 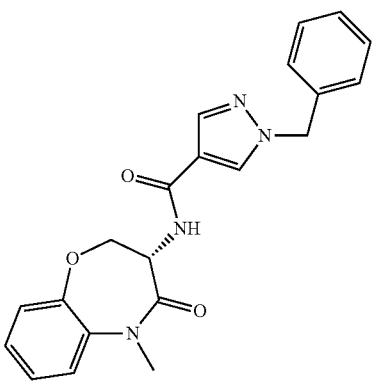 [SMILES: CN1C(=O)[C@@H](NC(=O)c2cnn(Cc3ccccc3)c2)COc2ccccc21] | $^1$H NMR (DMSO-d$_6$) 8.17-8.45 (m, 2H), 7.92 (s, 1H), 7.52 (dd, J = 7.8, 1.8 Hz, 1H), 7.14-7.43 (m, 9H), 5.28-5.47 (m, 2H), 4.89 (dt, J = 11.7, 8.3 Hz, 1H), 4.24-4.57 (m, 2H), 3.40 (br. s., 3H) | 377 F |

| # | Name | Structure | 1H NMR | MS | |
|---|---|---|---|---|---|
| 184 | (S)-3-(allyloxy)-N-(5-methyl-4-oxo-2,3,4,5-tetrahydrobenzo[b][1,4]oxazepin-3-yl)benzamide | 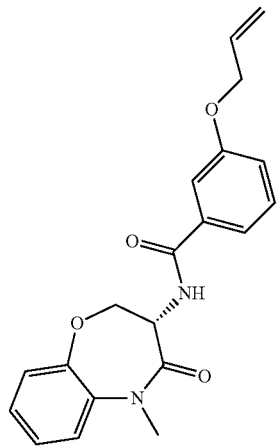 [SMILES: C=CCOc1cccc(C(=O)N[C@H]2COc3ccccc3N(C)C2=O)c1] | $^1$H NMR (DMSO-d$_6$) 8.66 (d, J = 8.3 Hz, 1H), 6.94-7.65 (m, 8H), 5.93-6.21 (m, J = 17.3, 10.5, 5.2, 5.2 Hz, 1H), 5.42 (dd, J = 17.2, 1.6 Hz, 1H), 5.28 (dd, J = 10.5, 1.5 Hz, 1H), 4.93 (dt, J = 11.7, 8.1 Hz, 1H), 4.51-4.73 (m, 3H), 4.41 (dd, J = 9.8, 7.8 Hz, 1H), 3.32 (s, 3H) | 353 | F |
| 185 | (S)-3-butoxy-N-(5-methyl-4-oxo-2,3,4,5-tetrahydrobenzo[b][1,4]oxazepin-3-yl)benzamide | 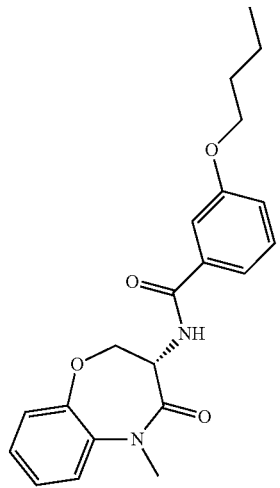 [SMILES: CCCCOc1cccc(C(=O)N[C@H]2COc3ccccc3N(C)C2=O)c1] | $^1$H NMR (DMSO-d$_6$) 8.65 (d, J = 8.5 Hz, 1H), 7.53 (dd, J = 7.8, 1.8 Hz, 1H), 7.19-7.47 (m, 5H), 7.05-7.17 (m, 1H), 6.97 (s, 1H), 4.93 (dt, J = 11.8, 8.2 Hz, 1H), 4.58 (dd, J = 11.8, 10.0 Hz, 1H), 4.41 (dd, J = 9.9, 7.9 Hz, 1H), 4.02 (t, J = 6.4 Hz, 2H), 3.32 (s, 3H), 1.61-1.82 (m, 2H), 1.34-1.60 (m, 2H), 0.95 (t, J = 7.4 Hz, 3H) | 367 | F |
| 186 | (S)-N-(5-methyl-4-oxo-2,3,4,5-tetrahydrobenzo[b][1,4]oxazepin-3-yl)-6-phenoxy picolinamide | 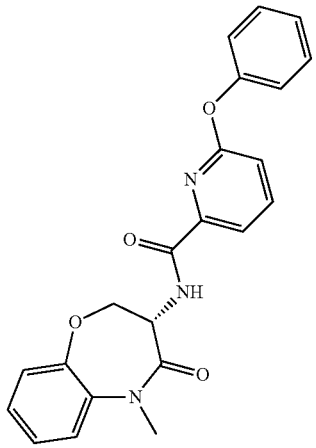 [SMILES: CN1C(=O)[C@@H](NC(=O)c2cccc(Oc3ccccc3)n2)COc2ccccc21] | 1H NMR (DMSO-d6) 8.42 (d, J = 7.6 Hz, 1H), 7.94-8.11 (m, 1H), 7.73 (d, J = 6.8 Hz, 1H), 7.42-7.61 (m, 3H), 7.20-7.39 (m, 5H), 7.13 (d, J = 8.1 Hz, 1H), 4.81 (dt, J = 11.4, 7.6 Hz, 1H), 4.49 (dd, J = 9.9, 7.6 Hz, 1H), 4.37 (dd, J = 11.4, 10.1 Hz, 1H), 3.33-3.39 (m, 3H) | 390 | F |

| | | | | |
|---|---|---|---|---|
| 187 | (S)-N-(5-methyl-4-oxo-2,3,4,5-tetrahydrobenzo[b][1,4]oxazepin-3-yl)-3-phenethyl-1H-pyrazole-5-carboxamide | 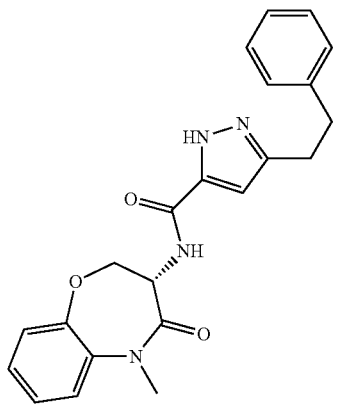 [SMILES: CN1C(=O)[C@@H](NC(=O)c2cc(CCc3ccccc3)n[nH]2)COc2ccccc21] | 1H NMR (DMSO-d6) 13.09 (br. s., 1H), 8.06 (br. s., 1H), 7.50 (dd, J = 7.7, 1.6 Hz, 1H), 7.07-7.39 (m, 8H), 6.38 (br. s., 1H), 4.83 (dt, J = 11.2, 7.9 Hz, 1H), 4.25-4.62 (m, 2H), 3.35 (s, 3H), 2.92 (s, 4H) | 391 A |
| 188 | (S)-N-(2-oxo-2,3,4,5-tetrahydro-1H-benzo[b]azepin-3-yl)-3-phenethyl-1H-pyrazole-5-carboxamide | 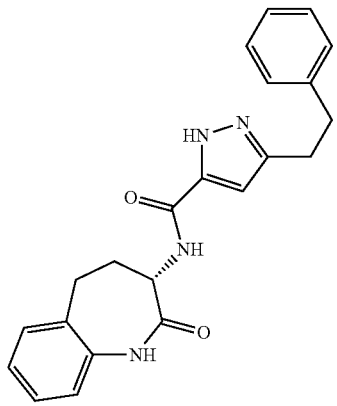 [SMILES: O=C(N[C@H]1CCc2ccccc2NC1=O)c1cc(CCc2ccccc2)n[nH]1] | 1H NMR (DMSO-d6) 13.09 (br. s., 1H), 8.06 (br. s., 1H), 7.50 (dd, J = 7.7, 1.6 Hz, 1H), 7.07-7.39 (m, 8H), 6.38 (br. s., 1H), 4.83 (dt, J = 11.2, 7.9 Hz, 1H), 4.25-4.62 (m, 2H), 2.92 (s, 4H), 2.81-2..91 (m, 2H) | 375 A |
| 189 | (S)-1-methyl-N-(5-methyl-4-oxo-2,3,4,5-tetrahydrobenzo[b][1,4]oxazepin-3-yl)-5-(phenoxymethyl)-1H-pyrazole-3-carboxamide | 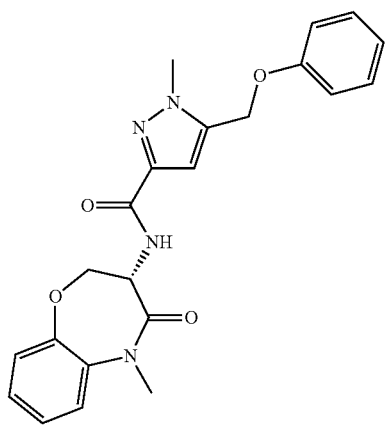 [SMILES: CN1C(=O)[C@@H](NC(=O)c2cc(COc3ccccc3)n(C)n2)COc2ccccc21] | $^1$H NMR (DMSO-d$_6$) 8.11 (d, J = 8.1 Hz, 1H), 6.89-7.61 (m, 9H), 6.76 (s, 1H), 5.21 (s, 2H), 4.84 (dt, J = 11.6, 7.9 Hz, 1H), 4.32-4.66 (m, 2H), 3.93 (s, 3H), 3.32 (d, J = 4.0 Hz, 2H) | 407 F |
| 190 | (S)-5-benzyl-N-(1-methyl-2-oxo-2,3,4,5-tetrahydro-1H-benzo[b][1,4]diazepin-3-yl)-1H-pyrazole-3-carboxamide | 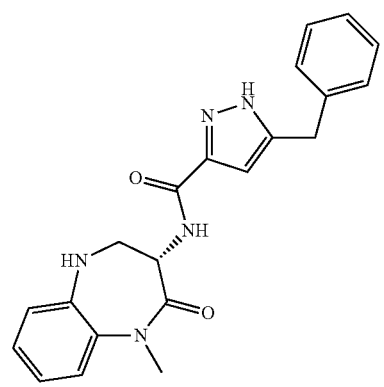 [SMILES: CN1C(=O)[C@@H](NC(=O)c2cc(Cc3ccccc3)[nH]n2)CNc2ccccc21] | $^1$H NMR (DMSO-d$_6$) 13.19 (s, 1H), 7.91 (d, J = 7.3 Hz, 1H), 6.91-7.46 (m, 9H), 6.37 (s, 1H), 5.38 (d, J = 5.6 Hz, 1H), 4.64 (d, J = 6.6 Hz, 1H), 3.85-4.20 (m, 3H), 3.65 (d, J = 1.0 Hz, 1H), 3.36-3.56 (m, 1H), 3.33 (s, 3H) | 376 F |

| | | | | |
|---|---|---|---|---|
| 191 | (S)-5-(2-fluorobenzyl)-N-(1-methyl-2-oxo-2,3,4,5-tetrahydro-1H-benzo[b]azepin-3-yl)-1H-pyrazole-3-carboxamide | 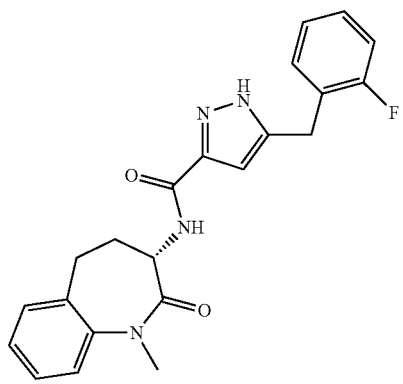 [SMILES: CN1C(=O)[C@@H](NC(=O)c2cc(Cc3ccccc3F)[nH]n2)CCc2ccccc21] | ¹H NMR (DMSO-d₆) 13.19 (br. s., 1H), 7.91 (br. s., 1H), 6.83-7.68 (m, 7H), 6.29 (br. s., 1H), 4.22-4.47 (m, 1H), 3.86-4.20 (m, 2H), 3.33 (s, 3H), 2.57-2.87 (m, 2H), 2.14 (br. s., 2H) | 393 A |
| 192 | (S)-5-(2-fluorobenzyl)-N-(5-methyl-4-oxo-2,3,4,5-tetrahydrobenzo[b][1,4]oxazepin-3-yl)-1H-pyrazole-3-carboxamide | 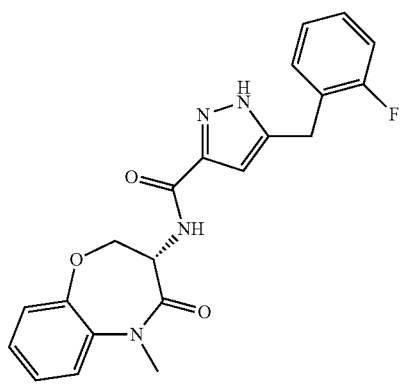 [SMILES: CN1C(=O)[C@@H](NC(=O)c2cc(Cc3ccccc3F)[nH]n2)COc2ccccc21] | ¹H NMR (DMSO-d₆) 13.27 (br. s., 1H), 8.43-8.79 (m, 1H), 8.09 (br. s., 1H), 7.49 (d, J = 7.3 Hz, 1H), 7.01-7.41 (m, 6H), 6.32 (br. s., 1H), 4.75-4.97 (m, 1H), 4.25-4.66 (m, 2H), 4.01 (br. s., 2H), 3.34 (s, 3H) | 395 A |
| 193 | (S)-5-benzyl-N-(5-oxo-3,4,5,6-tetrahydro-2H-benzo[b][1,4]oxazocin-4-yl)isoxazole-3-carboxamide | 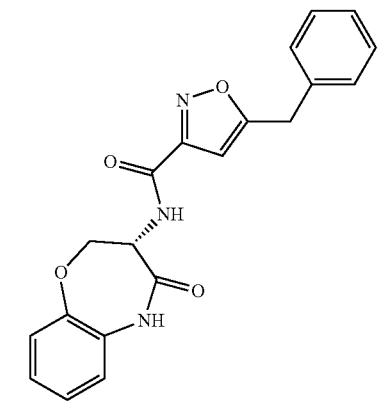 [SMILES: O=C(N[C@H]1COc2ccccc2NC1=O)c1cc(Cc2ccccc2)on1] | ¹H NMR (CDCl₃) 7.90 (d, J = 6.8 Hz, 1H), 7.79 (s, 1H), 7.07-7.47 (m, 7H), 6.32 (s, 1H), 5.32 (s, 1H), 4.56-4.88 (m, 2H), 3.93-4.25 (m, 3H), 2.26-2.48 (m, 1H), 1.98-2.20 (m, 1H) | 378 A |
| 194 | (S)-5-((methyl(phenyl)amino)methyl)-N-(5-methyl-4-oxo-2,3,4,5-tetrahydrobenzo[b][1,4]oxazepin-3-yl)-1H-pyrazole-3-carboxamide | 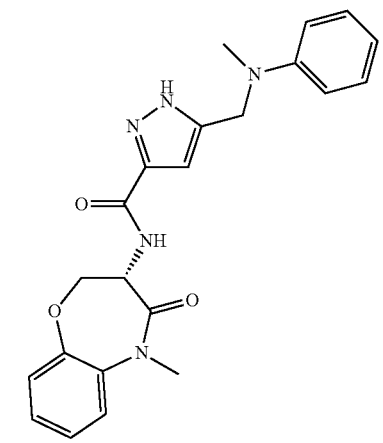 [SMILES: CN(Cc1cc(C(=O)N[C@H]2COc3ccccc3N(C)C2=O)n[nH]1)c1ccccc1] | ¹H NMR (DMSO-d₆) 13.27 (br. s., 1H), 7.85-8.22 (m, 1H), 6.42-7.68 (m, 9H), 6.36 (br. s., 1H), 4.83 (br. s., 1H), 4.28-4.74 (m, 4H), 3.17-3.42 (m, 3H), 2.69 (s, 3H) | 406 A |

| | | | | | |
|---|---|---|---|---|---|
| 195 | (S)-1-benzyl-N-(5-methyl-4-oxo-2,3,4,5-tetrahydrobenzo[b][1,4]oxazepin-3-yl)-1H-1,2,3-triazole-4-carboxamide | 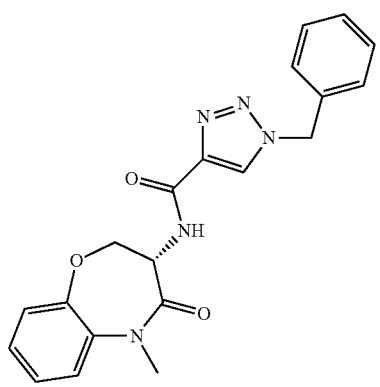 [SMILES: CN1C(=O)[C@@H](NC(=O)c2cn(Cc3ccccc3)nn2)COc2ccccc21] | 1H NMR (DMSO-d6) δ: 8.69 (s, 1H), 8.57 (d, J = 8.1 Hz, 1H), 7.51 (dd, J = 7.7, 1.6 Hz, 1H), 7.17-7.43 (m, 8H), 5.66 (s, 2H), 4.86 (d, J = 11.6 Hz, 1H), 4.60 (dd, J = 11.6, 10.1 Hz, 1H), 4.40 (dd, J = 9.9, 7.6 Hz, 1H), 3.22-3.40 (m, 3H) | 378 | A |
| 196 | (S)-N-(5-methyl-4-oxo-2,3,4,5-tetrahydrobenzo[b][1,4]oxazepin-3-yl)-5-(thiophen-2-ylmethyl)-4H-1,2,4-triazole-3-carboxamide | 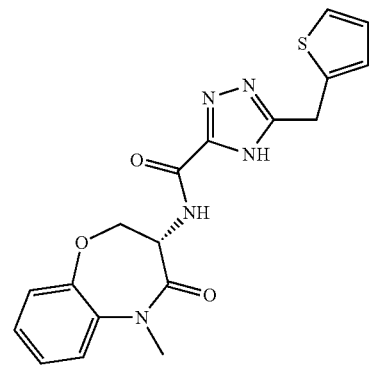 [SMILES: CN1C(=O)[C@@H](NC(=O)c2nnc(Cc3cccs3)[nH]2)COc2ccccc21] | $^1$H NMR (DMSO-d$_6$) δ: 14.42 (br. s., 1H), 8.42 (d, J = 7.8 Hz, 1H), 7.51 (d, J = 7.8 Hz, 1H), 7.22-7.45 (m, 4H), 6.93-7.02 (m, 2H), 4.78-4.88 (m, 1H), 4.59 (t, J = 10.5 Hz, 1H), 4.24-4.47 (m, 3H), 3.32 (s, 3H) | 384.1 | F |
| 197 | (S)-5-(2-fluorobenzyl)-N-(4-oxo-2,3,4,5-tetrahydrobenzo[b][1,4]oxazepin-3-yl)-1H-pyrazole-3-carboxamide | 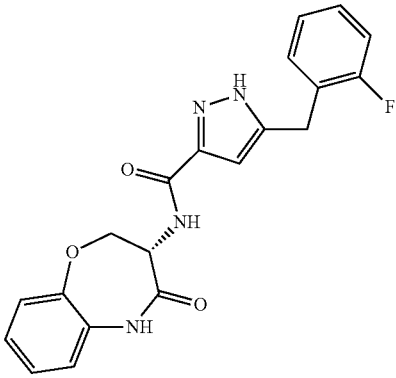 [SMILES: O=C(N[C@H]1COc2ccccc2NC1=O)c1cc(Cc2ccccc2F)[nH]n1] | $^1$H NMR (DMSO-d$_6$) 13.26 (br. s., 1H), 10.12 (br. s., 1H), 8.11 (br. s., 1H), 6.96-7.48 (m, 9H), 6.34 (br. s., 1H), 4.78 (br. s., 1H), 4.29-4.63 (m, 2H), 4.02 (br. s., 2H) | 381 | A |
| 198 | (S)-2-benzyl-N-(5-methyl-4-oxo-2,3,4,5-tetrahydrobenzo[b][1,4]oxazepin-3-yl)oxazole-4-carboxamide | 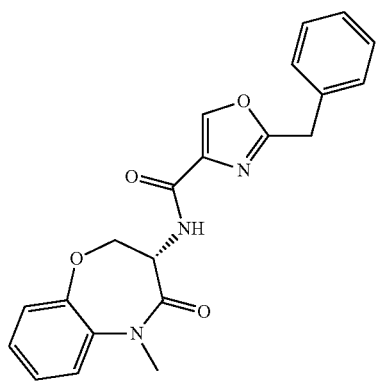 | $^1$H NMR (DMSO-d$_6$) 8.56 (s, 1H), 8.24 (d, J = 8.1 Hz, 1H), 7.50 (dd, J = 7.7, 1.9 Hz, 1H), 7.12-7.43 (m, 8H), 4.83 (dt, J = 11.6, 7.9 Hz, 1H), 4.57 (dd, J = 11.5, 10.0 Hz, 1H), 4.40 (dd, J = 9.9, 7.8 Hz, 1H), 4.22 (s, 2H), 3.20-3.38 (m, 3H) | 378 | A |

-continued

| | | | | |
|---|---|---|---|---|
| 199 | 5-methyl-N-((S)-5-methyl-4-oxo-2,3,4,5-tetrahydrobenzo[b][1,4]oxazepin-3-yl)-1-((tetrahydrofuran-2-yl)methyl)-1H-pyrazole-3-carboxamide | 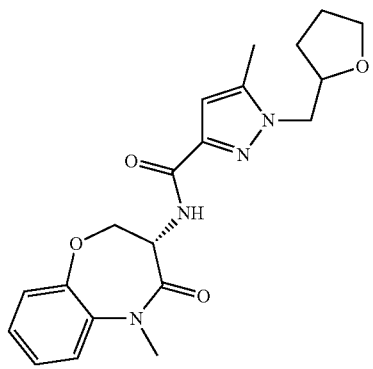 [SMILES: Cc1cc(C(=O)N[C@H]2COc3ccccc3N(C)C2=O)nn1CC1CCCO1] | $^1$H NMR (CDCl$_3$) 8.58 (d, J = 8.1 Hz, 1H), 7.77 (d, J = 7.1 Hz, 1H), 6.98-7.39 (m, 3H), 6.47 (d, J = 8.1 Hz, 1H), 4.97-5.40 (m, 1H), 4.51-4.85 (m, 1H), 3.94-4.47 (m, 3H), 3.64-3.94 (m, 1H), 3.44 (d, J = 1.3 Hz, 3H), 2.21-2.42 (m, 3H), 2.05 (s, 2H), 1.63-1.95 (m, 2H), 1.18-1.41 (m, 2H) | 385 A |
| 200 | (S)-1-benzyl-N-(5-methyl-4-oxo-2,3,4,5-tetrahydrobenzo[b][1,4]oxazepin-3-yl)-1H-imidazole-4-carboxamide | 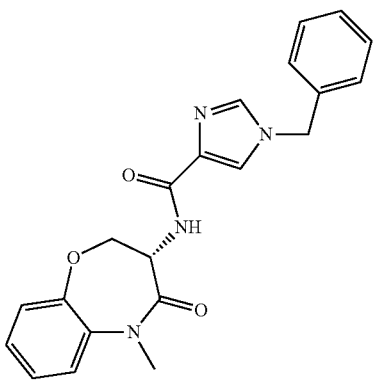 [SMILES: CN1C(=O)[C@@H](NC(=O)c2cn(Cc3ccccc3)cn2)COc2ccccc21] | 1H NMR (DMSO-d6) δ: 7.98 (d, J = 8.1 Hz, 1H), 7.89 (d, J = 1.3 Hz, 1H), 7.75 (d, J = 1.0 Hz, 1H), 7.49 (dd, J = 7.6, 1.8 Hz, 1H), 7.16-7.42 (m, 7H), 5.23 (s, 2H), 4.81 (dt, J = 11.2, 7.9 Hz, 1H), 4.27-4.60 (m, 2H), 3.22-3.43 (m, 3H) | 377 A |
| 201 | (S)-5-(3-fluorobenzyl)-N-(5-methyl-4-oxo-2,3,4,5-tetrahydrobenzo[b][1,4]oxazepin-3-yl)-1H-pyrazole-3-carboxamide | 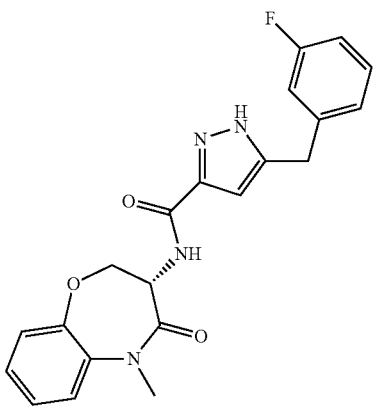 [SMILES: CN1C(=O)[C@@H](NC(=O)c2cc(Cc3cccc(F)c3)[nH]n2)COc2ccccc21] | $^1$H NMR (DMSO-d$_6$) 13.23 (br. s., 1H), 8.08 (d, J = 7.8 Hz, 1H), 7.50 (d, J = 7.6 Hz, 1H), 7.16-7.43 (m, 4H), 6.91-7.16 (m, 3H), 6.41 (s, 1H), 4.72-4.97 (m, 1H), 4.27-4.63 (m, 2H), 4.01 (s, 2H), 3.15-3.43 (m, 3H) | 395 A |
| 202 | (S)-5-(3-fluorobenzyl)-N-(4-oxo-2,3,4,5-tetrahydrobenzo[b][1,4]oxazepin-3-yl)-1H-pyrazole-3-carboxamide | 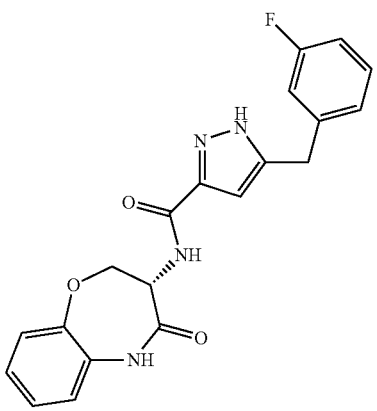 [SMILES: O=C(N[C@H]1COc2ccccc2NC1=O)c1cc(Cc2cccc(F)c2)[nH]n1] | $^1$H NMR (DMSO-d$_6$) 13.22 (s, 1H), 10.13 (s, 1H), 8.10 (d, J = 7.6 Hz, 1H), 7.24-7.58 (m, 2H), 6.94-7.22 (m, 6H), 6.43 (s, 1H), 4.71-4.94 (m, 1H), 4.37-4.54 (m, 2H), 4.02 (s, 2H) | 381 A |

| | | | | |
|---|---|---|---|---|
| 203 | (S)-5-benzyl-N-(5-methyl-4-oxo-2,3,4,5-tetrahydrobenzo[b][1,4]oxazepin-3-yl)thiophene-2-carboxamide | 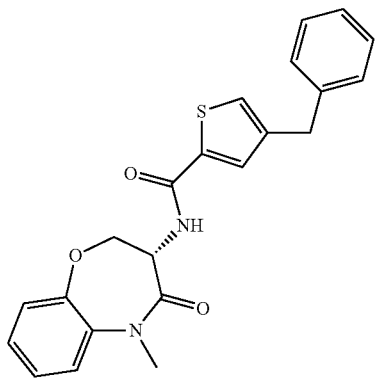 [SMILES: CN1C(=O)[C@@H](NC(=O)c2cc(Cc3ccccc3)cs2)COc2ccccc21] | 1H NMR (DMSO-d6) δ: 8.60 (d, J = 8.3 Hz, 1H), 7.71 (d, J = 3.8 Hz, 1H), 7.50 (dd, J = 7.7, 1.6 Hz, 1H), 7.15-7.38 (m, 8H), 6.95 (d, J = 3.8 Hz, 1H), 4.84 (dt, J = 11.7, 8.1 Hz, 1H), 4.50 (dd, J = 11.7, 10.0 Hz, 1H), 4.37 (dd, J = 9.9, 7.8 Hz, 1H), 4.15 (s, 2H), 3.30 (s, 3H) | 393 A |
| 204 | (S)-1-(3-fluorobenzyl)-N-(5-methyl-4-oxo-2,3,4,5-tetrahydrobenzo[b][1,4]oxazepin-3-yl)-1H-imidazole-4-carboxamide | 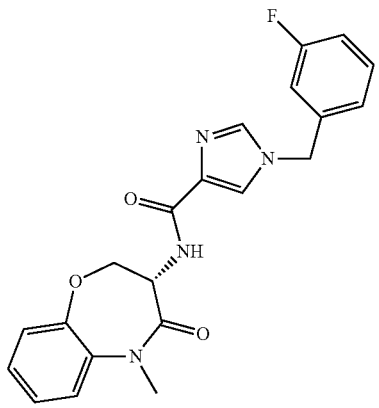 [SMILES: CN1C(=O)[C@@H](NC(=O)c2cn(Cc3cccc(F)c3)cn2)COc2ccccc21] | 1H NMR (400 MHz, DMSO-d6) δ 9.37 (none, 1H), 7.99 (d, J = 7.83 Hz, 1H), 7.91 (d, J = 1.26 Hz, 1H), 7.79 (d, J = 1.01 Hz, 1H), 7.00-7.59 (m, 8H), 5.25 (s, 2H), 4.81 (dt, J = 8.02, 11.24 Hz, 1H), 4.32-4.57 (m, 2H), 3.32 (d, J = 4.29 Hz, 3H) | 395 A |
| 205 | (S)-1-(3-fluorobenzyl)-N-(2-oxo-2,3,4,5-tetrahydro-1H-benzo[b]azepin-3-yl)-1H-imidazole-4-carboxamide | 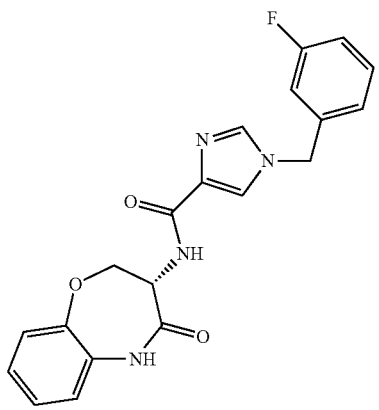 [SMILES: O=C(N[C@H]1COc2ccccc2NC1=O)c1cn(Cc2cccc(F)c2)cn1] | $^1$H NMR (DMSO-$d_6$) 9.83 (s, 1H), 8.44 (d, J = 8.3 Hz, 1H), 7.89-8.13 (m, 1H), 7.77 (s, 1H), 6.69-7.57 (m, 7H), 5.76 (s, 1H), 5.50 (s, 2H), 4.23-4.50 (m, 1H), 2.61-2.84 (m, 2H), 2.13-2.37 (m, 2H) | 379 A |
| 206 | (S)-N-(5-methyl-4-oxo-2,3,4,5-tetrahydrobenzo[b][1,4]oxazepin-3-yl)-1-(4-methylbenzyl)-1H-imidazole-4-carboxamide | 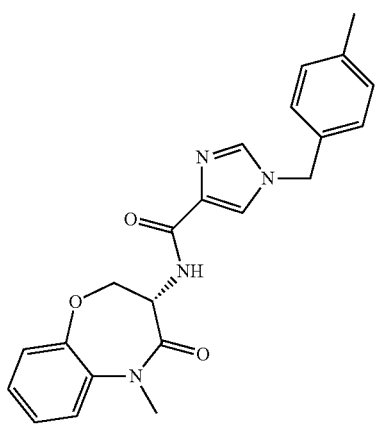 [SMILES: Cc1ccc(Cn2cnc(C(=O)N[C@H]3COc4ccccc4N(C)C3=O)c2)cc1] | $^1$H NMR (DMSO-$d_6$) 7.97 (d, J = 7.8 Hz, 1H), 7.87 (d, J = 1.0 Hz, 1H), 7.72 (d, J = 1.3 Hz, 1H), 7.49 (dd, J = 7.6, 1.8 Hz, 1H), 6.97-7.41 (m, 6H), 5.76 (s, 1H), 5.17 (s, 2H), 4.81 (dt, J = 11.2, 7.9 Hz, 1H), 4.21-4.59 (m, 2H), 3.34 (s, 3H), 2.27 (s, 3H) | 391 A |

-continued

| | | | | |
|---|---|---|---|---|
| 207 | (S)-5-(4-methylbenzyl)-N-(4-oxo-2,3,4,5-tetrahydrobenzo[b][1,4]oxazepin-3-yl)-4H-1,2,4-triazole-3-carboxamide | 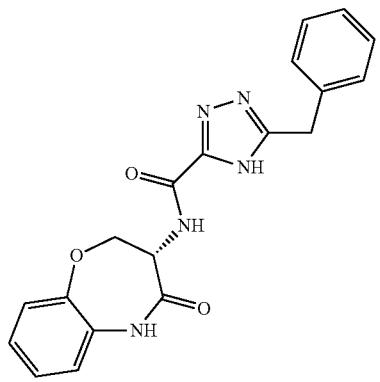 [SMILES: O=C(N[C@H]1COc2ccccc2NC1=O)c1nnc(Cc2ccccc2)[nH]1] | $^1$H NMR (DMSO-d$_6$) 13.95-14.91 (m, 1H), 10.16 (s, 1H), 8.51 (br. s., 1H), 7.08-7.52 (m, 7H), 4.80 (dt, J = 10.5, 7.1 Hz, 1H), 4.35-4.64 (m, 2H), 4.12 (s, 2H), 2.51 (s, 3H) | 364 A |
| 208 | (S)-N-(5-methyl-4-oxo-2,3,4,5-tetrahydrobenzo[b][1,4]oxazepin-3-yl)-5-(4-methylbenzyl)-4H-1,2,4-triazole-3-carboxamide | 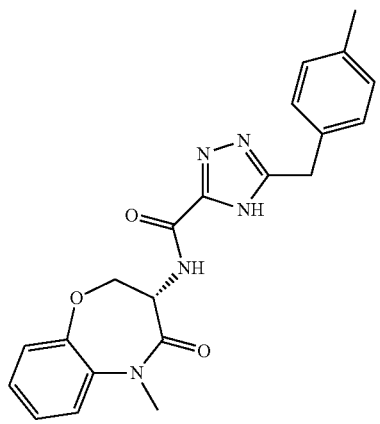 [SMILES: Cc1ccc(Cc2nnc(C(=O)N[C@H]3COc4ccccc4N(C)C3=O)[nH]2)cc1] | $^1$H NMR (DMSO-d$_6$) 14.13-14.72 (m, 1H), 8.31-8.77 (m, 1H), 6.82-7.66 (m, 8H), 4.83 (dt, J = 11.6, 7.9 Hz, 1H), 4.29-4.72 (m, 2H), 4.06 (s, 2H), 3.10-3.45 (m, 3H), 2.27 (s, 3H) | 392 A |
| 209 | (S)-5-(4-fluorobenzyl)-N-(5-methyl-4-oxo-2,3,4,5-tetrahydrobenzo[b][1,4]oxazepin-3-yl)-4H-1,2,4-triazole-3-carboxamide | 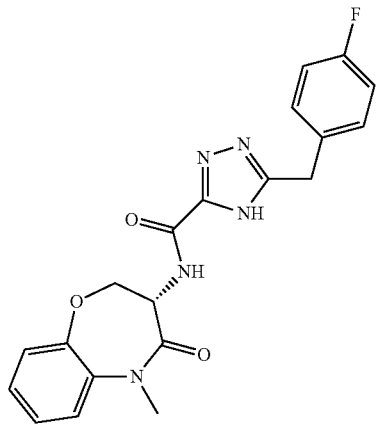 [SMILES: CN1C(=O)[C@@H](NC(=O)c2nnc(Cc3ccc(F)cc3)[nH]2)COc2ccccc21] | $^1$H NMR (DMSO-d$_6$) 14.08-14.88 (m, 1H), 8.48 (br. s., 1H), 6.84-7.75 (m, 8H), 4.83 (dt, J = 11.6, 7.9 Hz, 1H), 4.60 (t, J = 10.7 Hz, 1H), 4.41 (dd, J = 9.9, 7.8 Hz, 1H), 4.12 (s, 2H), 3.00-3.47 (m, 3H) | 396 A |
| 210 | (S)-5-(3-fluorobenzyl)-N-(5-methyl-4-oxo-2,3,4,5-tetrahydrobenzo[b][1,4]oxazepin-3-yl)-4H-1,2,4-triazole-3-carboxamide | 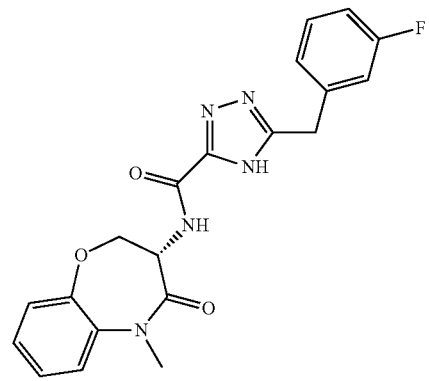 [SMILES: CN1C(=O)[C@@H](NC(=O)c2nnc(Cc3cccc(F)c3)[nH]2)COc2ccccc21] | $^1$H NMR (DMSO-d$_6$) 14.09-14.89 (m, 1H), 8.50 (br. s., 1H), 6.75-7.62 (m, 8H), 4.83 (dt, J = 11.4, 7.8 Hz, 1H), 4.60 (t, J = 10.6 Hz, 1H), 4.41 (dd, J = 9.7, 7.7 Hz, 1H), 4.16 (s, 2H), 3.32 (s, 3H) | 396 A |

| | | | | |
|---|---|---|---|---|
| 211 | (S)-1-(3-fluorobenzyl)-N-(5-methyl-4-oxo-2,3,4,5-tetrahydrobenzo[b][1,4]oxazepin-3-yl)-1H-1,2,3-triazole-4-carboxamide | 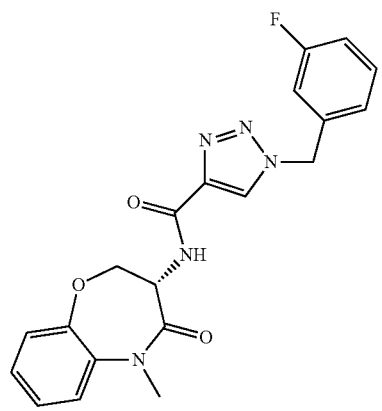 [SMILES: CN1C(=O)[C@@H](NC(=O)c2cn(Cc3cccc(F)c3)nn2)COc2ccccc21] | $^1$H NMR (DMSO-d$_6$) 8.72 (s, 1H), 8.58 (d, J = 8.1 Hz, 1H), 7.07-7.65 (m, 8H), 5.68 (s, 2H), 4.87 (d, J = 11.6 Hz, 1H), 4.60 (dd, J = 11.6, 9.9 Hz, 1H), 4.40 (dd, J = 9.9, 7.8 Hz, 1H), 3.21-3.41 (m, 3H) | 396 A |
| 212 | (S)-5-benzyl-N-(7-chloro-5-methyl-4-oxo-2,3,4,5-tetrahydrobenzo[b][1,4]oxazepin-3-yl)-4H-1,2,4-triazole-3-carboxamide | 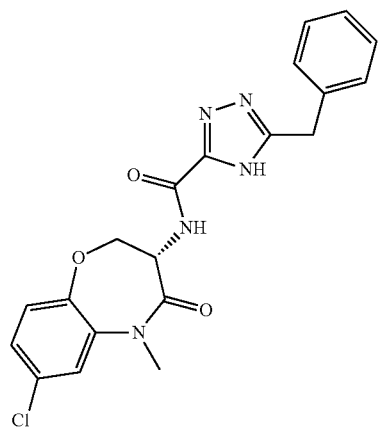 [SMILES: CN1C(=O)[C@@H](NC(=O)c2nnc(Cc3ccccc3)[nH]2)COc2ccc(Cl)cc21] | 1H NMR (400 MHz, DMSO-d6) δ 13.93-15.01 (m, 1H), 8.22-8.73 (m, 1H), 7.66 (d, J = 2.53 Hz, 1H), 7.06-7.45 (m, 6H), 4.74-5.11 (m, 1H), 4.54-4.70 (m, 1H), 4.42 (dd, J = 7.58, 9.85 Hz, 1H), 3.14-3.46 (m, 3H) | 412 A |
| 213 | (S)-1-benzyl-N-(7-chloro-5-methyl-4-oxo-2,3,4,5-tetrahydrobenzo[b][1,4]oxazepin-3-yl)-1H-imidazole-4-carboxamide | 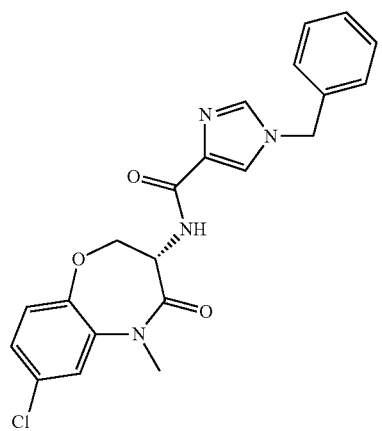 [SMILES: CN1C(=O)[C@@H](NC(=O)c2cn(Cc3ccccc3)cn2)COc2ccc(Cl)cc21] | $^1$H NMR (DMSO-d$_6$) 8.00 (d, J = 8.1 Hz, 1H), 7.90 (d, J = 1.3 Hz, 1H), 7.76 (d, J = 1.3 Hz, 1H), 7.64 (d, J = 2.5 Hz, 1H), 7.14-7.51 (m, 7H), 5.23 (s, 2H), 4.83 (dt, J = 11.4, 7.8 Hz, 1H), 4.28-4.64 (m, 2H), 3.26-3.39 (m, 3H) | 411 A |

| | | | | |
|---|---|---|---|---|
| 214 | (S)-1-benzyl-N-(7-chloro-5-methyl-4-oxo-2,3,4,5-tetrahydrobenzo[b][1,4]oxazepin-3-yl)-1H-1,2,3-triazole-4-carboxamide | 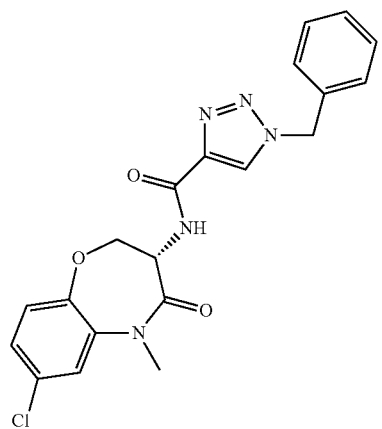 [SMILES: CN1C(=O)[C@@H](NC(=O)c2cn(Cc3ccccc3)nn2)COc2ccc(Cl)cc21] | $^1$H NMR (DMSO-d$_6$) 8.70 (s, 1H), 8.60 (d, J = 8.1 Hz, 1H), 7.66 (d, J = 2.3 Hz, 1H), 7.10-7.52 (m, 6H), 5.66 (s, 2H), 4.88 (dt, J = 11.6, 8.0 Hz, 1H), 4.62 (dd, J = 11.5, 10.0 Hz, 1H), 4.41 (dd, J = 9.7, 7.7 Hz, 1H), 3.22-3.40 (m, 3H) | 412 A |
| 215 | (S)-5-benzyl-N-(7-chloro-5-methyl-4-oxo-2,3,4,5-tetrahydrobenzo[b][1,4]oxazepin-3-yl)-1H-pyrazole-3-carboxamide | 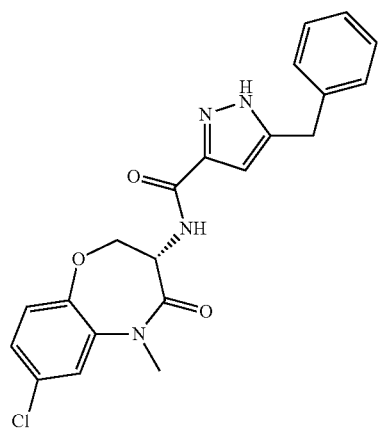 [SMILES: CN1C(=O)[C@@H](NC(=O)c2cc(Cc3ccccc3)[nH]n2)COc2ccc(Cl)cc21] | $^1$H NMR (DMSO-d$_6$) 13.21 (s, 1H), 8.10 (d, J = 8.1 Hz, 1H), 7.65 (d, J = 2.5 Hz, 1H), 7.06-7.51 (m, 5H), 6.37 (d, J = 1.8 Hz, 2H), 4.84 (dt, J = 11.6, 7.9 Hz, 1H), 4.31-4.67 (m, 2H), 3.99 (s, 2H), 3.18-3.41 (m, 3H) | 411 A |
| 216 | (S)-N-(4-oxo-2,3,4,5-tetrahydrobenzo[b][1,4]oxazepin-3-yl)-3-phenoxy benzamide | 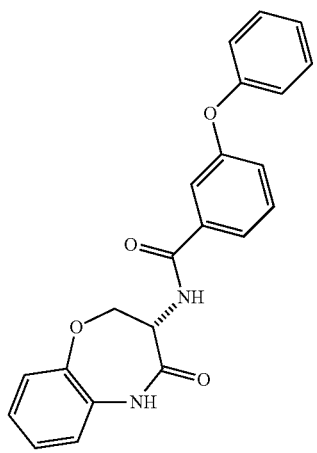 [SMILES: O=C(N[C@H]1COc2ccccc2NC1=O)c1cccc(Oc2ccccc2)c1] | $^1$H NMR (DMSO-d$_6$) δ: 10.06 (s, 1H), 8.75 (d, J = 8.3 Hz, 1H), 7.65-7.70 (m, 1H), 7.48-7.55 (m, 2H), 7.38-7.45 (m, 2H), 7.09-7.24 (m, 6H), 7.01-7.06 (m, 2H), 4.81-4.93 (m, 1H), 4.50 (dd, J = 11.5, 10.6 Hz, 1H), 4.41 (dd, J = 10.6, 7.0 Hz, 1H) | 375 A |

| | | | | |
|---|---|---|---|---|
| 217 | (S)-N-(4-oxo-2,3,4,5-tetrahydrobenzo[b][14]oxazepin-3-yl)-5-pentyl-1H-pyrazole-3-carboxamide | 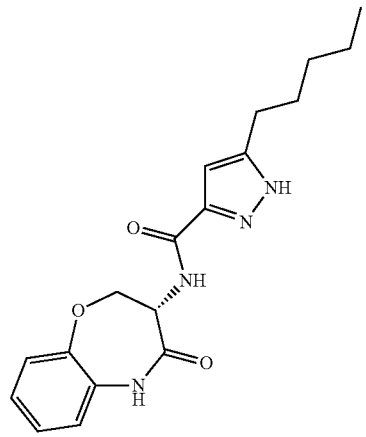 [SMILES: CCCCCc1cc(C(=O)N[C@H]2COc3ccccc3NC2=O)n[nH]1] | ¹H NMR (DMSO-d₆) δ: 13.01 (br s, 1H), 10.13 (s, 1H), 8.06 (d, J = 7.8 Hz, 1H), 7.10-7.18 (m, 4H), 6.39 (d, J = 1.8 Hz, 1H), 4.76-4.83 (m, 1H), 4.39-4.49 (m, 2H), 2.60 (t, J = 7.6 Hz, 2H), 1.59 (quin, J = 7.5 Hz, 2H), 1.19-1.36 (m, 4H), 0.86 (t, J = 6.9 Hz, 3H) | 343 A |
| 218 | (S)-N-(4-oxo-2,3,4,5-tetrahydrobenzo[b][1,4]oxazepin-3-yl)-3-(phenylamino)benzamide | 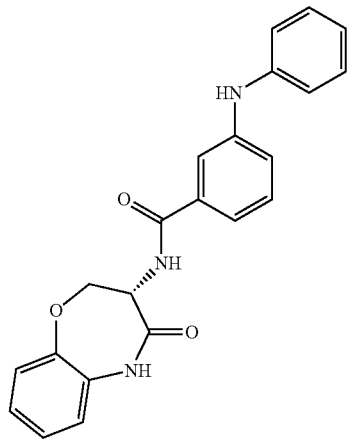 [SMILES: O=C(N[C@H]1COc2ccccc2NC1=O)c1cccc(Nc2ccccc2)c1] | ¹H NMR (400 MHz, DMSO-d₆) δ 10.06 (s, 1H), 8.57 (d, J = 8.34 Hz, 1H), 8.35 (s, 1H), 7.54 (s, 1H), 7.33 (d, J = 5.05 Hz, 2H), 7.20-7.29 (m, 3H), 7.11-7.19 (m, 4H), 7.09 (d, J = 7.58 Hz, 2H), 6.86 (t, J = 7.20 Hz, 1H), 4.84-4.93 (m, 1H), 4.47-4.57 (m, 1H), 4.38-4.46 (m, 1H) | 374 A |
| 219 | (S)-N-(5-methyl-4-oxo-2,3,4,5-tetrahydrobenzo[b][1,4]oxazepin-3-yl)-5-phenoxyfuran-2-carboxamide | 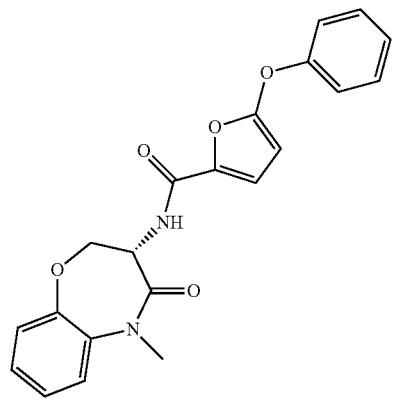 [SMILES: CN1C(=O)[C@@H](NC(=O)c2ccc(Oc3ccccc3)o2)COc2ccccc21] | ¹H NMR (400 MHz, DMSO-d₆) δ 8.44 (d, 1H), 7.51 (dd, J = 1.77, 7.83 Hz, 1H), 7.46 (t, J = 8.08 Hz, 2H), 7.23-7.36 (m, 3H), 7.22 (d, J = 3.54 Hz, 1H), 7.15-7.20 (m, 1H), 5.88 (d, J = 3.54 Hz, 1H), 4.84 (dt, J = 8.08, 11.62 Hz, 1H), 4.54 (dd, J = 9.85, 11.62 Hz, 1H), 4.36 (dd, J = 7.71, 9.98 Hz, 1H), 3.33 (s, 3H) | 379 A |

| | | | | |
|---|---|---|---|---|
| 220 | (S)-N-(5-methyl-4-oxo-2,3,4,5-tetrahydrobenzo[b][1,4]oxazepin-3-yl)-3-(pyridin-2-yloxy)benzamide | 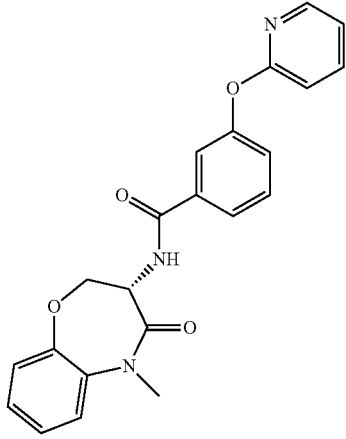 [SMILES: CN1C(=O)[C@@H](NC(=O)c2cccc(Oc3ccccn3)c2)COc2ccccc21] | $^1$H NMR (400 MHz, DMSO-d$_6$) δ 8.73 (d, J = 8.34 Hz, 1H), 8.16 (dd, J = 1.26, 4.80 Hz, 1H), 7.85-7.93 (m, 1H), 7.73 (d, J = 8.08 Hz, 1H), 7.63 (t, J = 1.89 Hz, 1H), 7.50-7.57 (m, 2H), 7.34 (dd, 2H), 7.26-7.32 (m, 1H), 7.21-7.26 (m, 1H), 7.13-7.18 (m, 1H), 7.10 (d, J = 8.34 Hz, 1H), 4.92 (dt, J = 8.12, 11.81 Hz, 1H), 4.56 (dd, J = 9.98, 11.75 Hz, 1H), 4.40 (dd, J = 7.71, 9.98 Hz, 1H), 3.31 (s, 3H) | 390 A |
| 221 | (S)-N-(5-methyl-4-oxo-2,3,4,5-tetrahydrobenzo[b][1,4]oxazepin-3-yl)-3-(morpholinomethyl)benzamide | 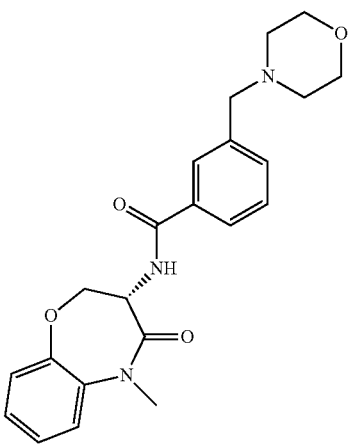 [SMILES: CN1C(=O)[C@@H](NC(=O)c2cccc(CN3CCOCC3)c2)COc2ccccc21] | $^1$H NMR (400 MHz, DMSO-d$_6$) δ 8.77 (d, J = 8.53 Hz, 1H), 7.96 (br. s., 2H), 7.56-7.72 (m, 2H), 7.54 (dd, J = 1.76, 7.78 Hz, 1H), 7.22-7.39 (m, 3H), 4.94 (dt, J = 8.22, 11.67 Hz, 1H), 4.58 (dd, J = 9.91, 11.67 Hz, 1H), 4.43 (dd, J = 7.91, 9.91 Hz, 1H), 4.36 (br. s., 1H), 3.79-4.04 (m, 2H), 3.59-3.77 (m, 3H), 3.32 (br. s, 5H) | 396 A |
| 222 | (S)-N-(5-methyl-4-oxo-2,3,4,5-tetrahydrobenzo[b][1,4]oxazepin-3-yl)-3-(3-(trifluoromethyl)phenoxy)benzamide | 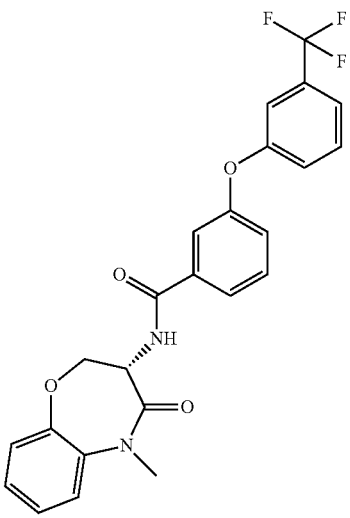 [SMILES: CN1C(=O)[C@@H](NC(=O)c2cccc(Oc3cccc(C(F)(F)F)c3)c2)COc2ccccc21] | $^1$H NMR (400 MHz, DMSO-d$_6$) δ 8.78 (d, J = 8.28 Hz, 1H), 7.73 (d, J = 8.03 Hz, 1H), 7.61-7.69 (m, 1H), 7.56-7.60 (m, 1H), 7.55 (d, J = 5.52 Hz, 1H), 7.53 (d, J = 1.51 Hz, 1H), 7.51 (d, J = 1.76 Hz, 1H), 7.37 (s, 1H), 7.26-7.36 (m, 2H), 7.21-7.26 (m, 1H), 4.91 (dt, J = 8.16, 11.80 Hz, 1H), 4.56 (dd, J = 10.04, 11.80 Hz, 1H), 4.40 (dd, J = 7.78, 9.79 Hz, 1H), 3.31 (s, 3H) | 457 A |

| | | | | |
|---|---|---|---|---|
| 223 | (S)-3-(cyclopentyloxy)-N-(5-methyl-4-oxo-2,3,4,5-tetrahydrobenzo[b][1,4]oxazepin-3-yl)benzamide | 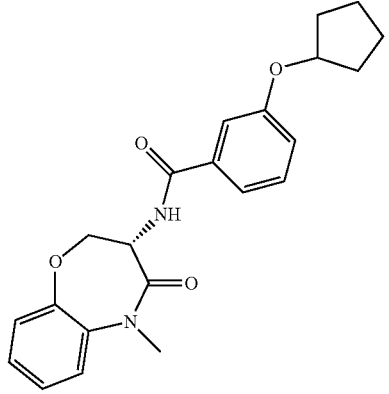 [SMILES: CN1C(=O)[C@@H](NC(=O)c2cccc(OC3CCCC3)c2)COc2ccccc21] | $^1$H NMR (400 MHz, DMSO-d$_6$) δ 8.64 (d, J = 8.53 Hz, 1H), 7.52 (dd, J = 1.76, 7.78 Hz, 1H), 7.33-7.43 (m, 3H), 7.32 (t, J = 2.51 Hz, 1H), 7.26-7.31 (m, 1H), 7.21-7.26 (m, 1H), 7.10 (dt, J = 1.98, 7.59 Hz, 1H), 4.90-4.98 (m, 1H), 4.84-4.90 (m, 1H), 4.58 (dd, J = 9.91, 11.67 Hz, 1H), 4.40 (dd, J = 7.78, 9.79 Hz, 1H), 3.31 (s, 3H), 1.84-1.99 (m, 1H), 1.65-1.77 (m, 3H), 1.53-1.65 (m, 2H) | 381 A |
| 224 | (S)-N-(5-methyl-4-oxo-2,3,4,5-tetrahydrobenzo[b][1,4]oxazepin-3-yl)-2-phenoxy isonicotinamide | 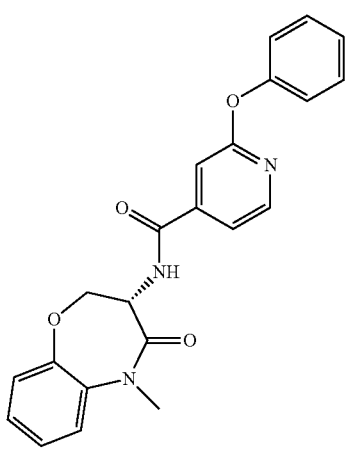 [SMILES: CN1C(=O)[C@@H](NC(=O)c2ccnc(Oc3ccccc3)c2)COc2ccccc21] | $^1$H NMR (400 MHz, DMSO-d$_6$) δ 9.03 (d, J = 8.34 Hz, 1H), 8.30 (d, J = 5.05 Hz, 1H), 7.47-7.55 (m, 2H), 7.41-7.47 (m, 2H), 7.39 (s, 1H), 7.27-7.37 (m, 2H), 7.21-7.27 (m, 2H), 7.13-7.19 (m, 2H), 4.91 (dt, J = 7.99, 11.81 Hz, 1H), 4.56 (dd, J = 10.11, 11.62 Hz, 1H), 4.44 (dd, J = 7.83, 9.85 Hz, 1H), 3.32 (s, 3H) | 390 A |
| 225 | (S)-5-(4-bromophenoxy)-N-(5-methyl-4-oxo-2,3,4,5-tetrahydrobenzo[b][1,4]oxazepin-3-yl)furan-2-carboxamide | 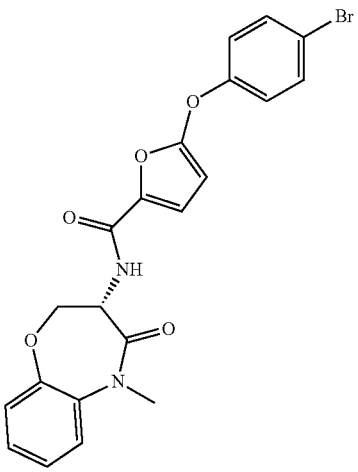 [SMILES: CN1C(=O)[C@@H](NC(=O)c2ccc(Oc3ccc(Br)cc3)o2)COc2ccccc21] | $^1$H NMR (400 MHz, DMSO-d$_6$) δ 8.47 (d, J = 8.28 Hz, 1H), 7.60-7.66 (m, 1H), 7.52 (dd, J = 1.76, 7.78 Hz, 1H), 7.26-7.35 (m, 2H), 7.23 (q, J = 2.76 Hz, 1H), 7.13-7.19 (m, 1H), 5.96 (d, J = 3.76 Hz, 1H), 4.84 (dt, J = 8.16, 11.80 Hz, 1H), 4.54 (dd, J = 10.04, 11.54 Hz, 1H), 4.36 (dd, J = 7.78, 9.79 Hz, 1H), 3.31 (s, 3H), 2.08 (s, 1H) | 459 A |

| | | | | |
|---|---|---|---|---|
| 226 | (S)-5-((4-methyl-1H-pyrazol-1-yl)methyl)-N-(5-methyl-4-oxo-2,3,4,5-tetrahydrobenzo[b][1,4]oxazepin-3-yl)furan-2-carboxamide | 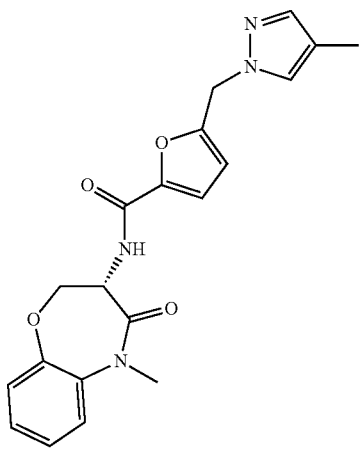 [SMILES: Cc1cnn(Cc2ccc(C(=O)N[C@H]3COc4ccccc4N(C)C3=O)o2)c1] | $^1$H NMR (400 MHz, DMSO-d$_6$) δ 8.48 (d, 1H), 7.54 (s, 1H), 7.52 (dd, J = 1.89, 7.71 Hz, 1H), 7.28-7.36 (m, 2H), 7.21-7.28 (m, 2H), 7.15 (d, J = 3.54 Hz, 1H), 6.51 (d, J = 3.54 Hz, 1H), 5.33 (s, 2H), 4.84 (dt, J = 8.27, 11.75 Hz, 1H), 4.54 (dd, J = 9.85, 11.62 Hz, 1H), 4.37 (dd, J = 7.71, 9.73 Hz, 1H), 3.31 (s, 2H), 2.00 (s, 2H) | 381 A |
| 227 | (S)-5-((3,5-dimethylisoxazol-4-yl)methyl)-N-(5-methyl-4-oxo-2,3,4,5-tetrahydrobenzo[b][1,4]oxazepin-3-yl)thiophene-2-carboxamide | 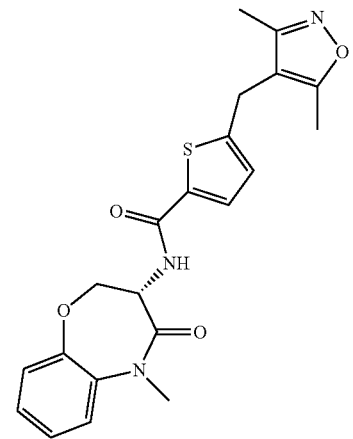 [SMILES: Cc1noc(C)c1Cc1ccc(C(=O)N[C@H]2COc3ccccc3N(C)C2=O)s1] | $^1$H NMR (400 MHz, DMSO-d$_6$) δ 8.59 (d, J = 8.28 Hz, 1H), 8.21 (s, 1H), 7.52 (dd, J = 1.76, 7.78 Hz, 1H), 7.20-7.42 (m, 7H), 5.74 (s, 2H), 4.87 (dt, J = 8.03, 11.54 Hz, 1H), 4.59 (dd, J = 10.04, 11.54 Hz, 1H), 4.40 (dd, J = 7.91, 9.91 Hz, 1H), 3.31 (s, 3H), 1.21 (d, J = 6.27 Hz, 1H) | 412 A |
| 228 | (S)-2-benzyl-N-(5-methyl-4-oxo-2,3,4,5-tetrahydrobenzo[b][1,4]oxazepin-3-yl)thiazole-4-carboxamide | 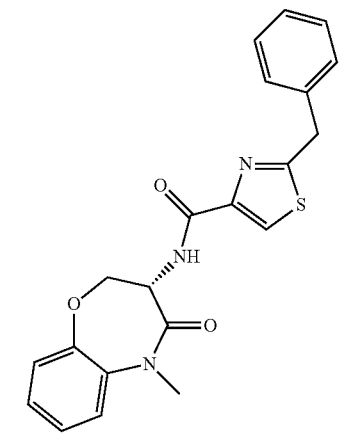 [SMILES: CN1C(=O)[C@@H](NC(=O)c2csc(Cc3ccccc3)n2)COc2ccccc21] | $^1$H NMR (400 MHz, DMSO-d$_6$) δ 8.41 (d, J = 7.78 Hz, 1H), 8.16 (s, 1H), 7.51 (dd, J = 1.88, 7.65 Hz, 1H), 7.38 (d, J = 4.52 Hz, 3H), 7.29-7.37 (m, 4H), 7.27 (td, J = 1.88, 7.84 Hz, 1H), 4.86 (dt, J = 7.87, 11.36 Hz, 1H), 4.54-4.64 (m, 1H), 4.45 (dd, J = 7.78, 9.79 Hz, 1H), 4.42 (s, 2H), 2.08 (s, 1H) | 394 A |

| # | Name | Structure | NMR | MS | Activity |
|---|---|---|---|---|---|
| 229 | (S)-2-(4-bromobenzyl)-N-(5-methyl-4-oxo-2,3,4,5-tetrahydrobenzo[b][1,4]oxazepin-3-yl)thiazole-4-carboxamide | 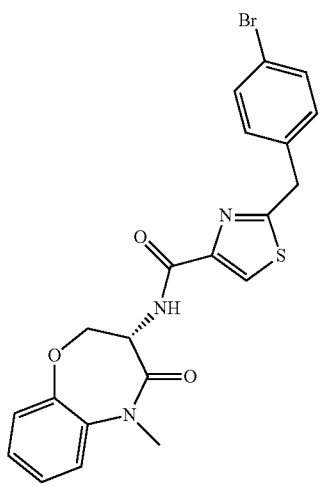 [SMILES: CN1C(=O)[C@@H](NC(=O)c2csc(Cc3ccc(Br)cc3)n2)COc2ccccc21] | ¹H NMR (400 MHz, DMSO-d₆) δ 8.10 (d, 1H), 7.51 (dd, J = 1.76, 7.78 Hz, 1H), 7.20-7.36 (m, 3H), 6.41 (s, 1H), 4.84 (dt, J = 7.91, 11.54 Hz, 1H), 4.47-4.56 (m, 1H), 4.41 (dd, J = 7.91, 9.91 Hz, 1H), 2.60 (t, J = 7.65 Hz, 2H), 1.57 (dt, J = 7.59, 14.93 Hz, 2H), 1.29 (dq, J = 7.34, 14.87 Hz, 2H), 0.89 (t, J = 7.40 Hz, 3H) | 472 474 | A |
| 230 | (S)-N-(5-methyl-4-oxo-2,3,4,5-tetrahydrobenzo[b][1,4]oxazepin-3-yl)-3-(p-tolyloxy)benzamide | 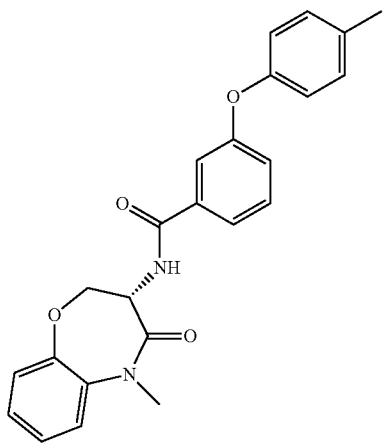 [SMILES: Cc1ccc(Oc2cccc(C(=O)N[C@H]3COc4ccccc4N(C)C3=O)c2)cc1] | ¹H NMR (400 MHz, DMSO-d₆) δ 8.72 (d, J = 8.53 Hz, 1H), 7.62 (d, J = 8.03 Hz, 1H), 7.44-7.53 (m, 2H), 7.41-7.45 (m, 1H), 7.26-7.36 (m, 2H), 7.20-7.25 (m, 3H), 7.17 (dd, J = 1.63, 8.16 Hz, 1H), 6.95 (d, J = 8.53 Hz, 2H), 4.90 (dt, J = 8.06, 11.73 Hz, 1H), 4.56 (dd, J = 10.04, 11.80 Hz, 1H), 4.39 (dd, J = 7.91, 9.91 Hz, 1H), 3.31 (s, 3H), 2.30 (s, 3H) | 403 | A |
| 231 | ((S)-5-(cyclohexylmethyl)-N-(5-methyl-7-(5-methyl-1,3,4-oxadiazol-2-yl)-4-oxo-2,3,4,5-tetrahydrobenzo[b][1,4]oxazepin-3-yl)-4H-1,2,4-triazole-3-carboxamide | 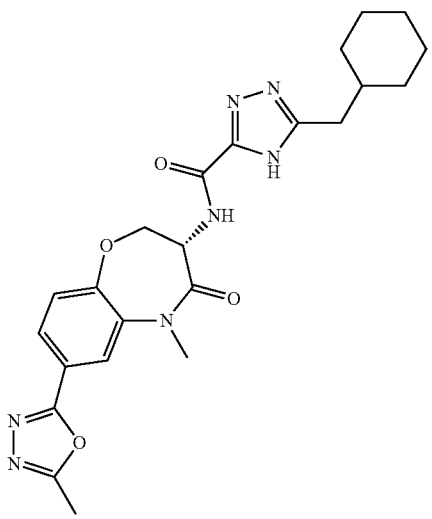 [SMILES: Cc1nnc(-c2ccc3c(c2)N(C)C(=O)[C@@H](NC(=O)c2nnc(CC4CCCCC4)[nH]2)CO3)o1] | ¹H NMR (DMSO-d₆) δ: 14.17 (s, 1H), 8.42 (d, J = 7.8 Hz, 1H), 8.04 (d, J = 2.0 Hz, 1H), 7.89 (dd, J = 8.3, 2.0 Hz, 1H), 7.45 (d, J = 8.3 Hz, 1H), 4.91 (dt, J = 11.6, 7.7 Hz, 1H), 4.65-4.73 (m, 1H), 4.50 (dd, J = 9.9, 7.3 Hz, 1H), 3.39 (s, 3H), 2.61-2.68 (m, 2H), 2.61 (s, 3H), 0.90-1.76 (m, 11H) | 466.3 | F |

| | | | | |
|---|---|---|---|---|
| 232 | (S)-5-benzyl-N-(2-oxo-2,3,4,5-tetrahydro-1H-benzo[b][1,4]diazepin-3-yl)isoxazole-3-carboxamide | 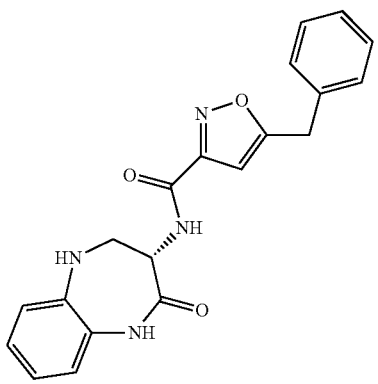 [SMILES: O=C(N[C@H]1CNc2ccccc2NC1=O)c1cc(Cc2ccccc2)on1] | ¹H NMR (DMSO-d₆, 400 MHz): δ = 8.72 (d, J = 7.8 Hz, 1 H), 7.21-7.48 (m, 6 H), 7.07-7.17 (m, 1 H), 6.96-7.06 (m, 2 H), 6.55 (s, 1 H), 5.30 (d, J = 4.5 Hz, 1 H), 4.59 (dt, J = 11.7, 7.2 Hz, 1 H), 4.22 (s, 2 H), 3.47-3.69 (m, 2 H), 3.14 (t, J = 7.2 Hz, 1 H). | 363 F |
| 233 | (S)-5-benzyl-N-(1-methyl-4-oxo-2,3,4,5-tetrahydro-1H-benzo[b][1,4]diazepin-3-yl)isoxazole-3-carboxamide | 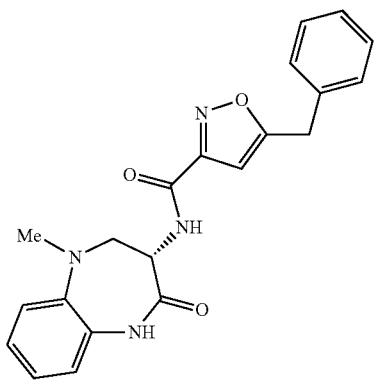 [SMILES: CN1C[C@H](NC(=O)c2cc(Cc3ccccc3)on2)C(=O)Nc2ccccc21] | ¹H NMR (DMSO-d₆, 400 MHz): δ = 9.90 (s, 1 H), 8.71 (d, J = 7.8 Hz, 1 H), 6.92-7.45 (m, 9 H), 6.56 (s, 1 H), 4.51 (dt, J = 12.1, 7.3 Hz, 1 H), 4.22 (s, 2 H), 3.65 (dd, J = 11.9, 10.1 Hz, 1 H), 3.17-3.31 (m, 1 H), 2.74 ppm (s, 3 H) | 377 F |
| 234 | (S)-N-(1,5-dimethyl-2-oxo-2,3,4,5-tetrahydro-1H-benzo[b][1,4]diazepin-3-yl)-5-(4-methylbenzyl)-1H-pyrazole-3-carboxamide | 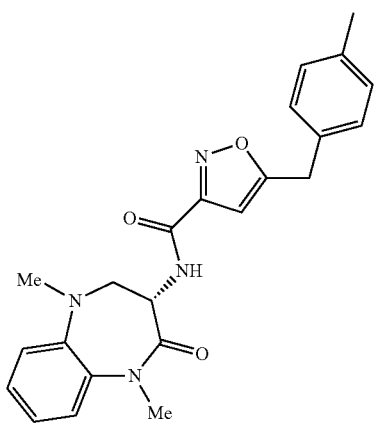 [SMILES: Cc1ccc(Cc2cc(C(=O)N[C@H]3CN(C)c4ccccc4N(C)C3=O)no2)cc1] | ¹H NMR (DMSO-d₆, 400 MHz): δ = 13.17 (br. s., 1 H), 7.93 (d, J = 7.6 Hz, 1 H), 6.89-7.56 (m, 8 H), 6.33 (s, 1 H), 4.35-4.67 (m, 1 H), 3.92 (s, 2 H), 3.49 (t, 1 H), 3.34 (s, 3 H), 2.71 (s, 3 H), 2.69 (s, 1 H), 2.26 ppm (s, 3 H) | 404 F |
| 235 | (S)-5-benzyl-N-(1-methyl-2-oxo-2,3,4,5-tetrahydro-1H-benzo[b][1,4]diazepin-3-yl)isoxazole-3-carboxamide | 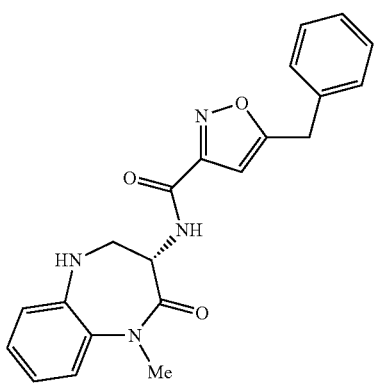 [SMILES: CN1C(=O)[C@@H](NC(=O)c2cc(Cc3ccccc3)on2)CNc2ccccc21] | ¹H NMR (DMSO-d₆, 400 MHz): δ = 8.66 (d, J = 7.8 Hz, 1 H), 7.22-7.44 (m, 6 H), 7.07-7.17 (m, 1 H), 6.96-7.06 (m, 2 H), 6.55 (s, 1 H), 5.32 (d, J = 4.5 Hz, 1 H), 4.65 (dt, J = 11.7, 7.0 Hz, 1 H), 4.22 (s, 2 H), 3.47-3.69 (m, 2 H), 3.33 ppm (s, 3 H) | 377 F |

| | | | | |
|---|---|---|---|---|
| 236 | (S)-5-benzyl-N-(2-oxo-2,3,4,5-tetrahydro-1H-benzo[b]azepin-3-yl)isoxazole-3-carboxamide | 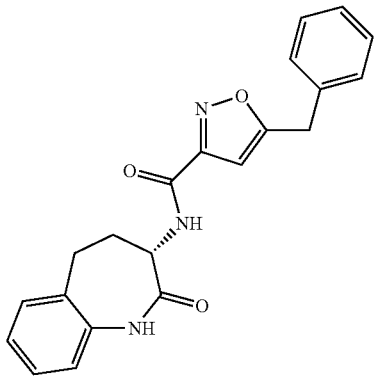 [SMILES: O=C(N[C@H]1CCc2ccccc2NC1=O)c1cc(Cc2ccccc2)on1] | 1H NMR (DMSO-d6) δ: 9.93 (s, 1H), 8.65 (d, J = 7.6 Hz, 1H), 7.23-7.40 (m, 7H), 7.11-7.19 (m, 1H), 7.04 (d, J = 7.6 Hz, 1H), 6.54 (s, 1H), 4.27-4.48 (m, 1H), 4.21 (s, 2H), 2.63-2.83 (m, 2H), 2.17-2.39 (m, 2H) | 362.0 F |
| 237 | (S)-N-(6-fluoro-8-methyl-4-oxo-2,3,4,5-tetrahydrobenzo[b][1,4]oxazepin-3-yl)-5-((5-methyl thiophen-2-yl)methyl)-4H-1,2,4-triazole-3-carboxamide | 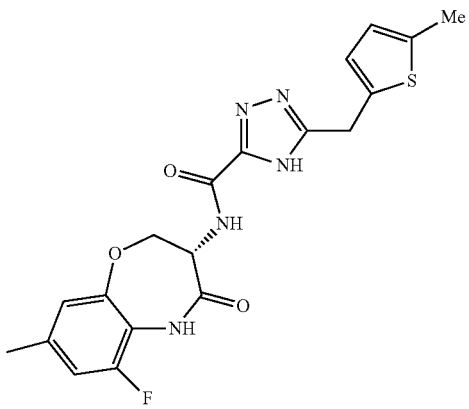 [SMILES: Cc1cc(F)c2c(c1)OC[C@H](NC(=O)c1nnc(Cc3ccc(C)s3)[nH]1)C(=O)N2] | 1H NMR (DMSO-d6) δ: 14.53 (br. s., 1H), 10.02 (s, 1H), 8.49 (br. s., 1H), 6.97-7.03 (m, 1H), 6.90 (s, 1H), 6.73 (d, J = 3.3 Hz, 1H), 6.61-6.65 (m, 1H), 4.85 (dt, J = 11.4, 7.6 Hz, 1H), 4.63 (t, J = 10.7 Hz, 1H), 4.46 (dd, J = 10.1, 7.3 Hz, 1H), 4.23 (s, 2H), 2.38 (s, 3H), 2.30 (s, 3H) | 416.2 F |
| 238 | (S)-5-benzyl-N-(8-methoxy-1-methyl-2-oxo-2,3,4,5-tetrahydro-1H-benzo[b]azepin-3-yl)-4H-1,2,4-triazole-3-carboxamide | 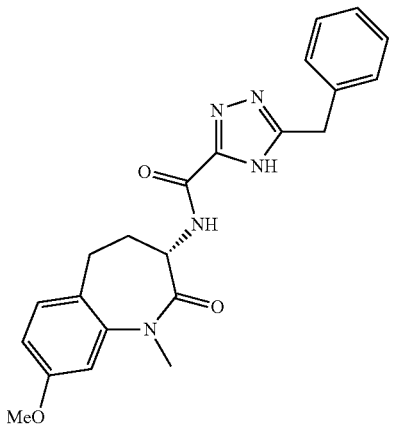 [SMILES: COc1ccc2c(c1)N(C)C(=O)[C@@H](NC(=O)c1nnc(Cc3ccccc3)[nH]1)CC2] | $^1$H NMR (400 MHz, DMSO-d$_6$) δ ppm 14.35 (br. S., 1 H), 8.19 (br. s., 1 H) 7.23-7.33 (m, 6 H) 6.99 (d, J = 8.5 Hz, 1 H), 6.85 (dd, J = 8.28, 2.26 Hz, 1 H) 4.31-4.44 (m, 1 H) 4.12 (br. s., 2 H) 3.79 (s, 3 H) 3.31 (s, 3 H) 2.56-2.68 (m, 2 H) 2.25-2.40 (m, 1 H) 2.14 (s, 1 H) | 406.2 H |
| 239 | (S)-5-(3-fluorobenzyl)-N-(8-methoxy-1-methyl-2-oxo-2,3,4,5-tetrahydro-1H-benzo[b]azepin-3-yl)-4H-1,2,4-triazole-3-carboxamide | 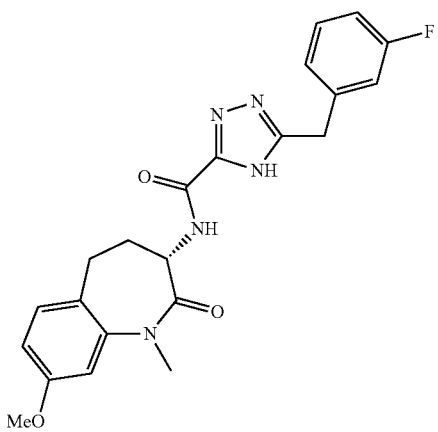 [SMILES: COc1ccc2c(c1)N(C)C(=O)[C@@H](NC(=O)c1nnc(Cc3cccc(F)c3)[nH]1)CC2] | $^1$H NMR (400 MHz, DMSO-d$_6$) δ ppm 14.31 (br. S., 1 H), 8.21 (br. s., 1 H) 7.37 (q, J = 7.4 Hz, 1 H) 7.25 (d, J = 8.5 Hz, 1 H) 7.03-7.19 (m, 3 H) 6.93-7.03 (m, 1 H) 6.84 (dd, J = 8.28, 2.26 Hz, 1 H) 4.27-4.43 (m, 1 H) 4.15 (br. s., 2 H) 3.79 (s, 3 H) 3.31 (s, 3 H) 2.59-2.71 (m, 2 H) 2.32 (d, J = 8.03 Hz, 1 H) 2.08 (s, 1 H) | 424.2 H |

| | | | | |
|---|---|---|---|---|
| 240 | (S)-5-benzyl-N-(6,8-difluoro-4-oxo-2,3,4,5-tetrahydrobenzo[b][1,4]oxazepin-3-yl)-4H-1,2,4-triazole-3-carboxamide | 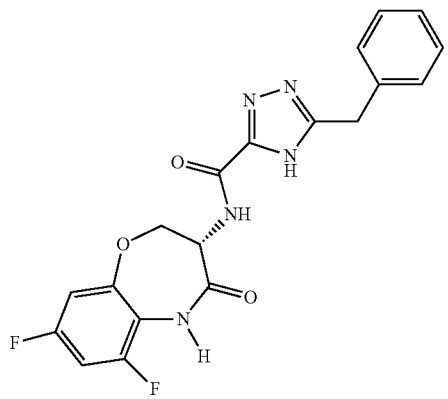 [SMILES: O=C(N[C@H]1COc2cc(F)cc(F)c2NC1=O)c1nnc(Cc2ccccc2)[nH]1] | 1H NMR (DMSO-d6) δ: 14.45 (br. s., 1H), 10.09 (s, 1H), 8.46 (br. s., 1H), 7.20-7.37 (m, 6H), 7.04 (dt, J = 9.3, 2.3 Hz, 1H), 4.90 (dt, J = 11.2, 7.5 Hz, 1H), 4.67 (t, J = 10.7 Hz, 1H), 4.51 (dd, J = 10.1, 7.1 Hz, 1H), 4.13 (s, 2H). | 400.2 H |
| 241 | (S)-5-isopentyl-N-(5-methyl-7-(5-methyl-1,3,4-oxadiazol-2-yl)-4-oxo-2,3,4,5-tetrahydrobenzo[b][1,4]oxazepin-3-yl)-4H-1,2,4-triazole-3-carboxamide | 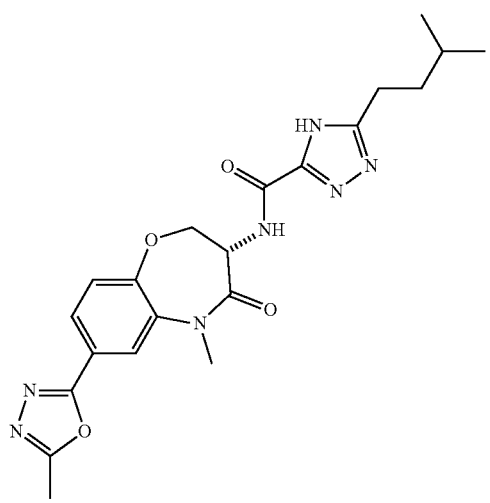 [SMILES: Cc1nnc(-c2ccc3c(c2)N(C)C(=O)[C@@H](NC(=O)c2nnc(CCC(C)C)[nH]2)CO3)o1] | $^1$H NMR (DMSO-d$_6$) δ: 14.16 (br. s., 1H), 8.33-8.45 (m, 1H), 8.04 (d, J = 1.8 Hz, 1H), 7.89 (dd, J = 8.5, 1.9 Hz, 1H), 7.45 (d, J = 8.3 Hz, 1H), 4.91 (dt, J = 11.5, 7.8 Hz, 1H), 4.69 (t, J = 11.7 Hz, 1H), 4.51 (dd, J = 9.6, 7.6 Hz, 1H), 3.39 (s, 3H), 2.73 (d, J = 7.6 Hz, 2H), 2.61 (s, 3H), 1.50-1.63 (m, 3H), 0.91 (d, J = 6.3 Hz, 6H); MS (m/z): | 440.2 H |
| 242 | (S)-5-benzyl-N-(5-methyl-8-(5-methyl-1,3,4-oxadiazol-2-yl)-4-oxo-2,3,4,5-tetrahydrobenzo[b][1,4]oxazepin-3-yl)-4H-1,2,4-triazole-3-carboxamide | 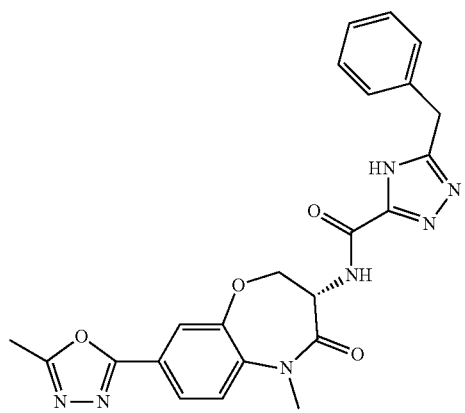 [SMILES: Cc1nnc(-c2ccc3c(c2)OC[C@H](NC(=O)c2nnc(Cc4ccccc4)[nH]2)C(=O)N3C)o1] | 1H NMR (DMSO-d6) δ: 14.41 (br. s., 1H), 8.53 (br. s., 1H), 7.91 (dd, J = 8.3, 2.0 Hz, 1H), 7.78 (d, J = 2.0 Hz, 1H), 7.71 (d, J = 8.3 Hz, 1H), 7.22-7.36 (m, 5H), 4.89 (dt, J = 11.6, 7.9 Hz, 1H), 4.71 (t, J = 10.7 Hz, 1H), 4.52 (dd, J = 9.7, 7.7 Hz, 1H), 4.13 (s, 2H), 3.36 (s, 3H), 2.60 (s, 3H); | 460.2 F |

The following compounds were prepared via the oxidation method indicated.

| 243 | 5-benzyl-N-((3R)-1-oxido-4-oxo-2,3,4,5-tetrahydrobenzo[b][1,4]thiazepin-3-yl)isoxazole-3-carboxamide | 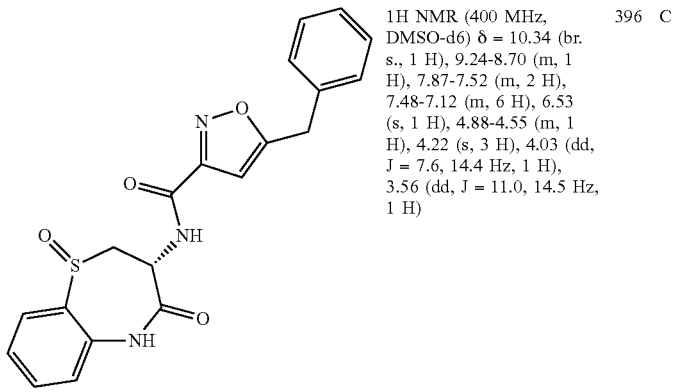 | 1H NMR (400 MHz, DMSO-d6) δ = 10.34 (br. s., 1 H), 9.24-8.70 (m, 1 H), 7.87-7.52 (m, 2 H), 7.48-7.12 (m, 6 H), 6.53 (s, 1 H), 4.88-4.55 (m, 1 H), 4.22 (s, 3 H), 4.03 (dd, J = 7.6, 14.4 Hz, 1 H), 3.56 (dd, J = 11.0, 14.5 Hz, 1 H) | 396 | C |
|---|---|---|---|---|---|
| 244 | (R)-5-benzyl-N-(1,1-dioxido-4-oxo-2,3,4,5-tetrahydrobenzo[b][1,4]thiazepin-3-yl)isoxazole-3-carboxamide | 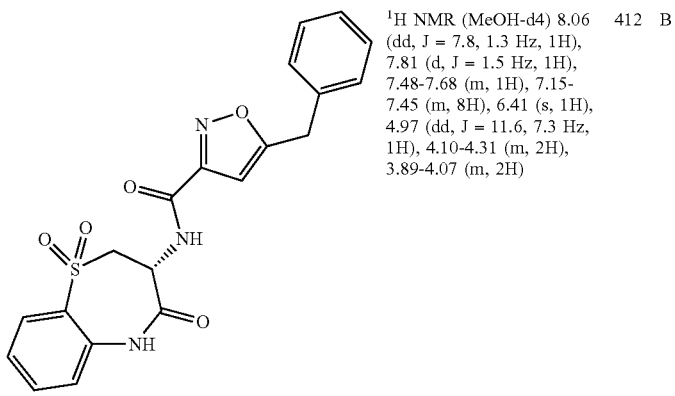 | $^1$H NMR (MeOH-d4) 8.06 (dd, J = 7.8, 1.3 Hz, 1H), 7.81 (d, J = 1.5 Hz, 1H), 7.48-7.68 (m, 1H), 7.15-7.45 (m, 8H), 6.41 (s, 1H), 4.97 (dd, J = 11.6, 7.3 Hz, 1H), 4.10-4.31 (m, 2H), 3.89-4.07 (m, 2H) | 412 | B |

The following compounds were prepared via acylation or isocyante addition of the appropriate amine using the method indicated.

| 245 | (S)-methyl (3-(5-benzylisoxazole-3-carboxamido)-5-methyl-4-oxo-2,3,4,5-tetrahydrobenzo[b][1,4]oxazepin-7-yl)carbamate | 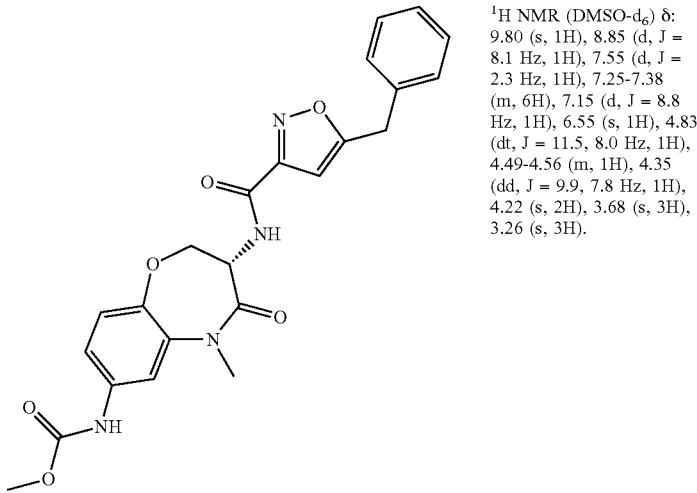 | $^1$H NMR (DMSO-d$_6$) δ: 9.80 (s, 1H), 8.85 (d, J = 8.1 Hz, 1H), 7.55 (d, J = 2.3 Hz, 1H), 7.25-7.38 (m, 6H), 7.15 (d, J = 8.8 Hz, 1H), 6.55 (s, 1H), 4.83 (dt, J = 11.5, 8.0 Hz, 1H), 4.49-4.56 (m, 1H), 4.35 (dd, J = 9.9, 7.8 Hz, 1H), 4.22 (s, 2H), 3.68 (s, 3H), 3.26 (s, 3H). | 451.2 | J |

| | | | | |
|---|---|---|---|---|
| 246 | (S)-5-benzyl-N-(5-methyl-7-(1-methyl-1H-pyrazole-4-carboxamido)-4-oxo-2,3,4,5-tetrahydrobenzo[b][1,4]oxazepin-3-yl)isoxazole-3-carboxamide | 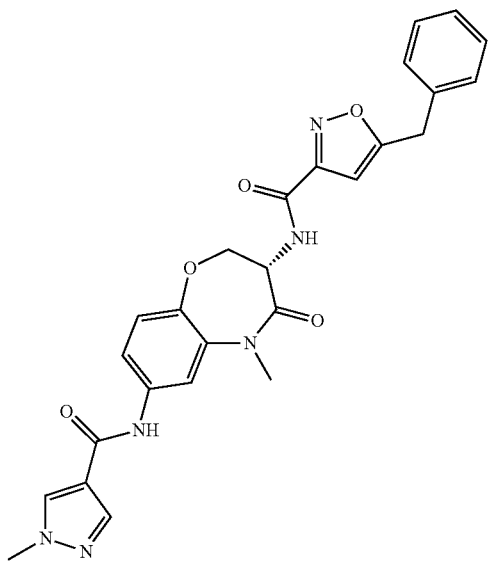 [SMILES: CN1C(=O)[C@@H](NC(=O)c2cc(Cc3ccccc3)on2)COc2ccc(NC(=O)c3cnn(C)c3)cc21] | $^1$H NMR (DMSO-d$_6$) δ: 9.96 (s, 1H), 8.86 (d, J = 8.3 Hz, 1H), 8.31 (s, 1H), 8.02 (s, 1H), 7.83 (d, J = 2.3 Hz, 1H), 7.58 (dd, J = 8.8, 2.5 Hz, 1H), 7.26-7.38 (m, 5H), 7.19 (d, J = 8.8 Hz, 1H), 6.55 (s, 1H), 4.87 (dt, J = 11.6, 8.0 Hz, 1H), 4.51-4.58 (m, 1H), 4.38 (dd, J = 9.9, 7.8 Hz, 1H), 4.22 (s, 2H), 3.91 (s, 3H), 3.30 (s, 3H). | 501.4 J |
| 247 | (S)-5-benzyl-N-(5-methyl-7-(N-methylacetamido)-4-oxo-2,3,4,5-tetrahydrobenzo[b][1,4]oxazepin-3-yl)isoxazole-3-carboxamide | 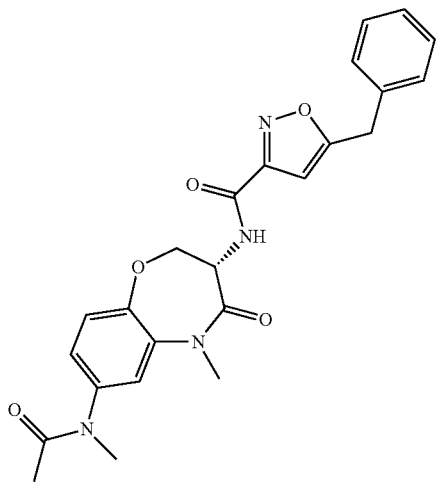 [SMILES: CC(=O)N(C)c1ccc2c(c1)N(C)C(=O)[C@@H](NC(=O)c1cc(Cc3ccccc3)on1)CO2] | $^1$H NMR (DMSO-d$_6$) δ: 8.87 (d, 1H), 7.56-7.61 (m, 1H), 7.24-7.38 (m, 7H), 6.54 (s, 1H), 4.88 (dt, J = 11.5, 8.0 Hz, 1H), 4.60 (t, J = 10.7 Hz, 1H), 4.41-4.47 (m, 1H), 4.22 (s, 2H), 3.31 (s, 3H), 3.18 (br. s., 3H), 1.83 (br. s., 3H) | 449.2 J |
| 248 | (S)-5-benzyl-N-(7-(3-methoxy-propanamido)-5-methyl-4-oxo-2,3,4,5-tetrahydrobenzo[b][1,4]oxazepin-3-yl)isoxazole-3-carboxamide | 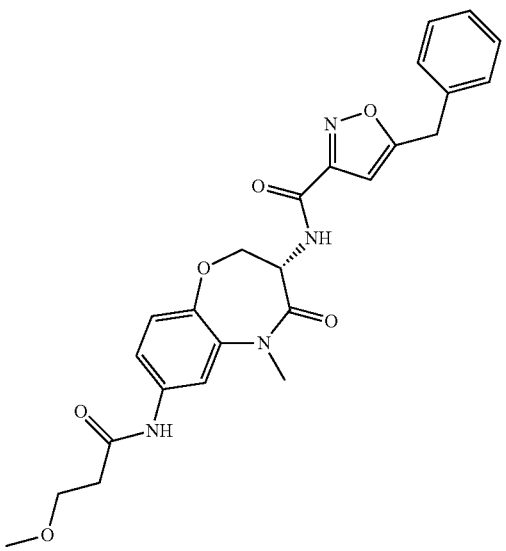 [SMILES: COCCC(=O)Nc1ccc2c(c1)N(C)C(=O)[C@@H](NC(=O)c1cc(Cc3ccccc3)on1)CO2] | $^1$H NMR (DMSO-d$_6$) δ: 10.12 (s, 1H), 8.85 (d, J = 8.1 Hz, 1H), 7.75 (d, J = 2.5 Hz, 1H), 7.26-7.43 (m, 6H), 7.16 (d, J = 8.6 Hz, 1H), 6.55 (s, 1H), 4.84 (dt, J = 11.6, 8.1 Hz, 1H), 4.49-4.57 (m, 1H), 4.33-4.39 (m, 1H), 4.22 (s, 2H), 3.62 (t, J = 6.2 Hz, 2H), 3.27 (s, 3H), 3.25 (s, 3H), 2.55 (t, 2H). | 479.2 J |

| | | | | |
|---|---|---|---|---|
| 249 | (S)-5-benzyl-N-(7-(3-ethylureido)-5-methyl-4-oxo-2,3,4,5-tetrahydrobenzo[b][1,4]oxazepin-3-yl)isoxazole-3-carboxamide | 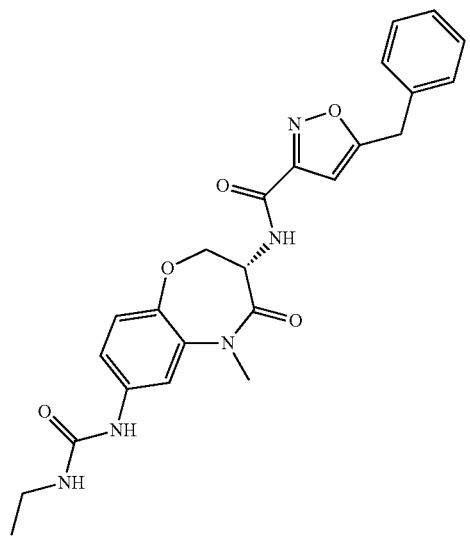 [SMILES: CCNC(=O)Nc1ccc2c(c1)N(C)C(=O)[C@@H](NC(=O)c1cc(Cc3ccccc3)on1)CO2] | $^1$H NMR (DMSO-d$_6$) δ: 8.85 (d, J = 8.1 Hz, 1H), 8.58 (s, 1H), 7.57 (d, J = 2.5 Hz, 1H), 7.26-7.38 (m, 5H), 7.15-7.20 (m, 1H), 7.04-7.09 (m, 1H), 6.55 (s, 1H), 6.17 (t, J = 5.6 Hz, 1H), 4.79-4.87 (m, 1H), 4.46-4.53 (m, 1H), 4.33 (dd, J = 9.9, 7.8 Hz, 1H), 4.22 (s, 2H), 3.26 (s, 3H), 3.07-3.15 (m, 2H), 1.05 (t, 3H). | 464.3 G |
| 250 | (S)-5-benzyl-N-(7-(3-(2-methoxyethyl)ureido)-5-methyl-4-oxo-2,3,4,5-tetrahydrobenzo[b][1,4]oxazepin-3-yl)isoxazole-3-carboxamide | 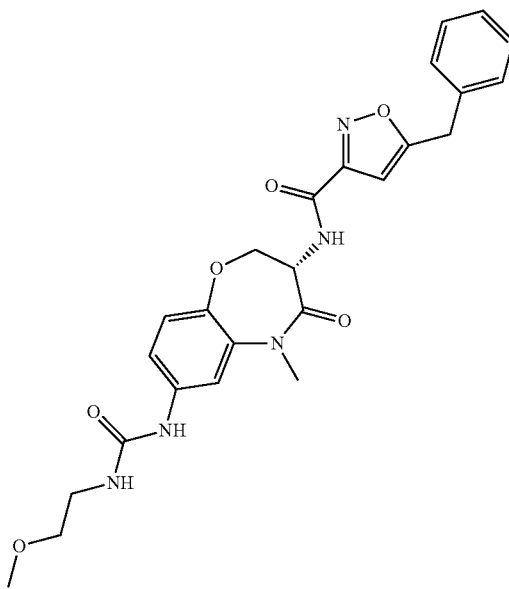 [SMILES: COCCNC(=O)Nc1ccc2c(c1)N(C)C(=O)[C@@H](NC(=O)c1cc(Cc3ccccc3)on1)CO2] | $^1$H NMR (DMSO-d$_6$) δ: 8.83 (d, J = 8.3 Hz, 1H), 8.69 (s, 1H), 7.56 (d, J = 2.3 Hz, 1H), 7.25-7.39 (m, 5H), 7.14-7.17 (m, 1H), 7.06-7.10 (m, 1H), 6.55 (s, 1H), 6.26 (t, J = 5.6 Hz, 1H), 4.84 (dt, J = 11.4, 8.1 Hz, 1H), 4.46-4.53 (m, 1H), 4.33 (dd, J = 9.9, 7.8 Hz, 1H), 4.22 (s, 2H), 3.37-3.40 (m, 2H), 3.24-3.29 (m, 8H). | 494.4 G |

The following compounds were prepared via Suzuki coupling using the method indicated.

| | | | | |
|---|---|---|---|---|
| 251 | (S)-5-benzyl-N-(7-(1-methyl-1H-pyrazol-3-yl)-2-oxo-2,3,4,5-tetrahydro-1H-benzo[b]azepin-3-yl)-4H-1,2,4-triazole-3-carboxamide | 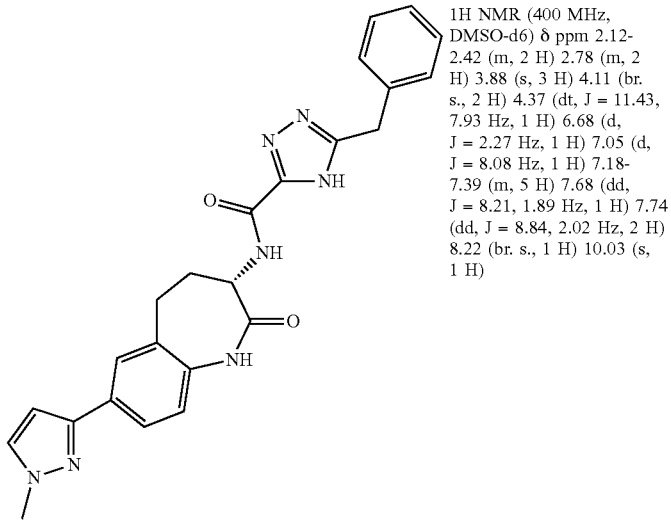 | 1H NMR (400 MHz, DMSO-d6) δ ppm 2.12-2.42 (m, 2 H) 2.78 (m, 2 H) 3.88 (s, 3 H) 4.11 (br. s., 2 H) 4.37 (dt, J = 11.43, 7.93 Hz, 1 H) 6.68 (d, J = 2.27 Hz, 1 H) 7.05 (d, J = 8.08 Hz, 1 H) 7.18-7.39 (m, 5 H) 7.68 (dd, J = 8.21, 1.89 Hz, 1 H) 7.74 (dd, J = 8.84, 2.02 Hz, 2 H) 8.22 (br. s., 1 H) 10.03 (s, 1 H) | 442 I |

The following compounds were prepared via coupling of the appropriate amine and acid using the method indicated.

| | | | | |
|---|---|---|---|---|
| 252 | (S)-5-benzyl-N-(2,5-dimethyl-6-oxo-6,7,8,9-tetrahydro-5H-pyrimido[4,5-b][1,4]diazepin-7-yl)-4H-1,2,4-triazole-3-carboxamide | 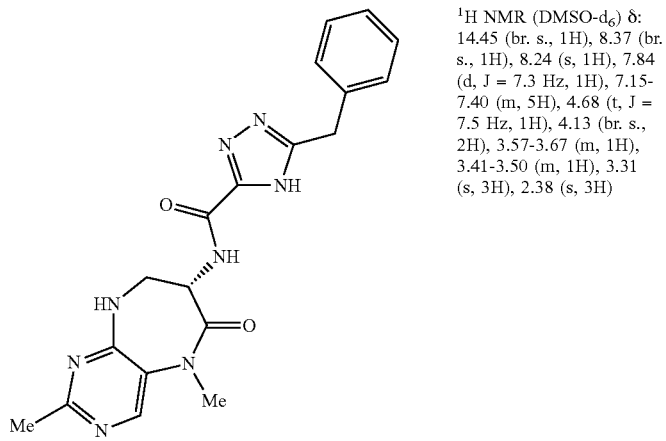 | $^1$H NMR (DMSO-$d_6$) δ: 14.45 (br. s., 1H), 8.37 (br. s., 1H), 8.24 (s, 1H), 7.84 (d, J = 7.3 Hz, 1H), 7.15-7.40 (m, 5H), 4.68 (t, J = 7.5 Hz, 1H), 4.13 (br. s., 2H), 3.57-3.67 (m, 1H), 3.41-3.50 (m, 1H), 3.31 (s, 3H), 2.38 (s, 3H) | 393 F |
| 253 | (S)-5-benzyl-N-(8-fluoro-1-methyl-2-oxo-2,3,4,5-tetrahydro-1H-pyrido[2,3-b][1,4]diazepin-3-yl)-4H-1,2,4-triazole-3-carboxamide | 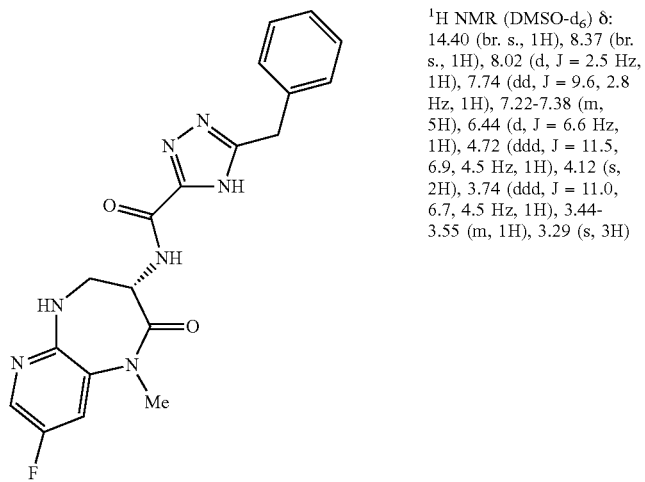 | $^1$H NMR (DMSO-$d_6$) δ: 14.40 (br. s., 1H), 8.37 (br. s., 1H), 8.02 (d, J = 2.5 Hz, 1H), 7.74 (dd, J = 9.6, 2.8 Hz, 1H), 7.22-7.38 (m, 5H), 6.44 (d, J = 6.6 Hz, 1H), 4.72 (ddd, J = 11.5, 6.9, 4.5 Hz, 1H), 4.12 (s, 2H), 3.74 (ddd, J = 11.0, 6.7, 4.5 Hz, 1H), 3.44-3.55 (m, 1H), 3.29 (s, 3H) | 396 F |

-continued

| | | | | |
|---|---|---|---|---|
| 254 (S)-5-benzyl-N-(7-bromo-5-methyl-4-oxo-2,3,4,5-tetrahydrobenzo[b][1,4]oxazepin-3-yl)-4H-1,2,4-triazole-3-carboxamide | 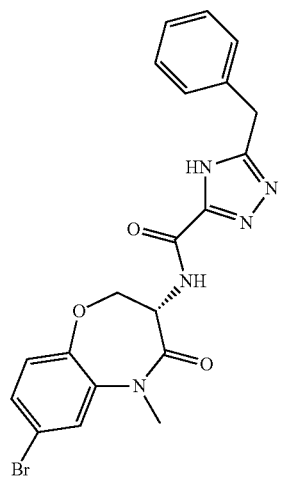 [SMILES: CN1C(=O)[C@@H](NC(=O)c2nnc(Cc3ccccc3)[nH]2)COc2ccc(Br)cc21] | ¹H NMR (DMSO-d₆) δ: 8.38-8.66 (m, 1H), 7.77 (d, J = 2.5 Hz, 1H), 7.02-7.60 (m, 7H), 4.85 (dt, J = 11.6, 7.8 Hz, 1H), 4.62 (t, J = 10.7 Hz, 1H), 4.41 (dd, J = 9.9, 7.6 Hz, 1H), 4.12 (s, 2H), 3.18-3.43 (m, 3H) | 456/458 | H |
| 255 5-benzyl-N-(7-(1H-pyrazol-4-yl)-5-methyl-4-oxo-2,3,4,5-tetrahydrobenzo[b][1,4]oxazepin-3-yl)-4H-1,2,4-triazole-3-carboxamide | 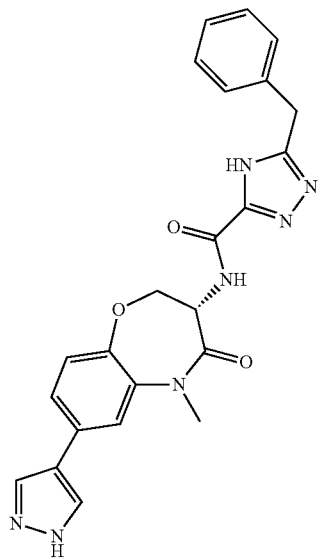 [SMILES: CN1C(=O)[C@@H](NC(=O)c2nnc(Cc3ccccc3)[nH]2)COc2ccc(-c3cn[nH]c3)cc21] | ¹H NMR (CDCl₃) δ: 8.10 (d, J = 7.3 Hz, 1H), 7.85 (s, 2H), 7.12-7.47 (m, 8H), 5.12 (br. s., 1H), 4.63-4.82 (m, 1H), 4.32 (t, J = 10.5 Hz, 1H), 4.21 (s, 2H), 3.48 (s, 3H) | 444 | I |
| 256 ((S)-N-(6-fluoro-8-methyl-4-oxo-2,3,4,5-tetrahydrobenzo[b][1,4]oxazepin-3-yl)-5-(2-fluorobenzyl)-4H-1,2,4-triazole-3-carboxamide | 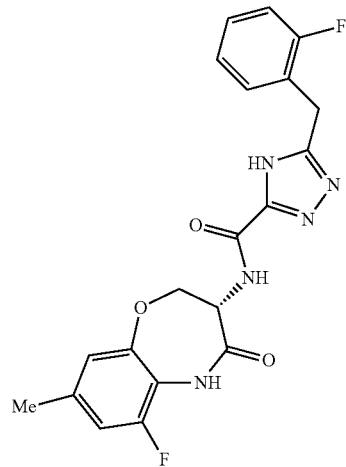 [SMILES: Cc1cc(F)c2c(c1)OC[C@H](NC(=O)c1nnc(Cc3ccccc3F)[nH]1)C(=O)N2] | ¹H NMR (DMSO-d₆) δ: 14.49 (none, 1H), 10.00 (s, 1H), 8.28-8.68 (m, 1H), 6.73-7.53 (m, 6H), 4.84 (dt, J = 11.1, 7.6 Hz, 1H), 4.61 (t, J = 10.6 Hz, 1H), 4.45 (dd, J = 10.1, 7.3 Hz, 1H), 4.15 (s, 2H), 2.30 (s, 3H) | 414 | H |

| | | | | |
|---|---|---|---|---|
| 257 (S)-5-benzyl-N-(8-(difluoromethoxy)-5-methyl-4-oxo-2,3,4,5-tetrahydrobenzo[b][1,4]oxazepin-3-yl)-4H-1,2,4-triazole-3-carboxamide | 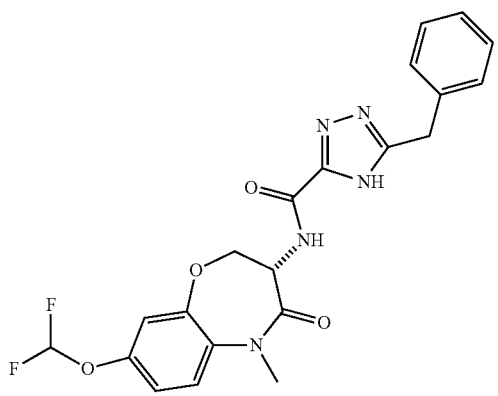 [SMILES: CN1C(=O)[C@@H](NC(=O)c2nnc(Cc3ccccc3)[nH]2)COc2cc(OC(F)F)ccc21] | ¹H NMR (DMSO-d₆) δ: 14.37 (br. s., 1H), 8.42 (d, J = 8.1 Hz, 1H), 7.57 (d, J = 8.8 Hz, 1H), 7.09-7.38 (m, 8H), 4.85 (dt, J = 11.6, 7.8 Hz, 1H), 4.62 (t, J = 10.9 Hz, 1H), 4.44 (dd, J = 9.9, 7.6 Hz, 1H), 4.15 (s, 2H), 3.30 (s, 3H) | 444 | F |
| 258 (S)-N-(5-methyl-7-(5-methyl-1,3,4-oxadiazol-2-yl)-4-oxo-2,3,4,5-tetrahydrobenzo[b][1,4]oxazepin-3-yl)-5-(thiophen-2-ylmethyl)-4H-1,2,4-triazole-3-carboxamide | 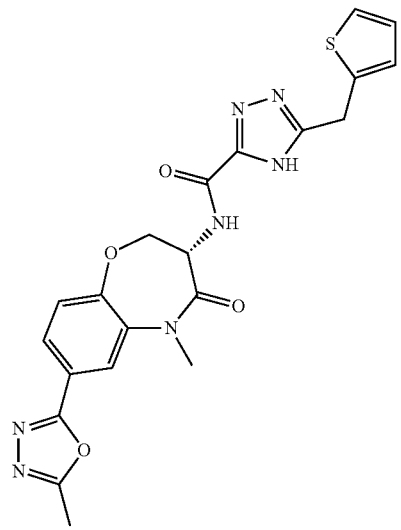 [SMILES: Cc1nnc(-c2ccc3c(c2)N(C)C(=O)[C@@H](NC(=O)c2nnc(Cc4cccs4)[nH]2)CO3)o1] | NA | 466 | F |
| 259 (S)-1-benzyl-N-(5-methyl-7-(5-methyl-1,3,4-oxadiazol-2-yl)-4-oxo-2,3,4,5-tetrahydrobenzo[b][1,4]oxazepin-3-yl)-1H-1,2,4-triazole-3-carboxamide | 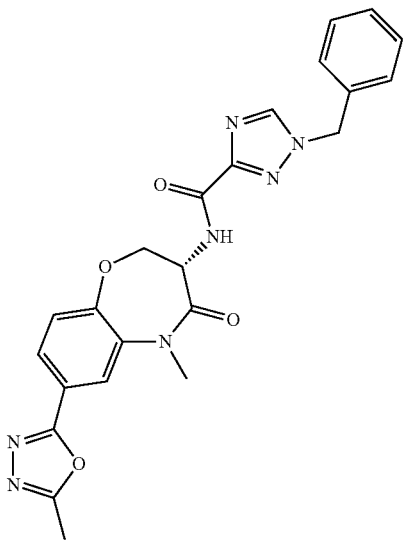 [SMILES: Cc1nnc(-c2ccc3c(c2)N(C)C(=O)[C@@H](NC(=O)c2ncn(Cc4ccccc4)n2)CO3)o1] | Very broad signals observed in ¹H NMR run in DMSO-d₆. | 460 | F |

| | | | | |
|---|---|---|---|---|
| 260 | (S)-5-benzyl-N-(8-cyclopropyl-5-methyl-4-oxo-2,3,4,5-tetrahydrobenzo[b][1,4]oxazepin-3-yl)-4H-1,2,4-triazole-3-carboxamide | 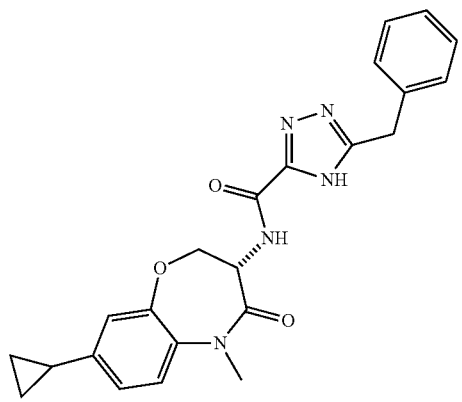 [SMILES: CN1C(=O)[C@@H](NC(=O)c2nnc(Cc3ccccc3)[nH]2)COc2cc(C3CC3)ccc21] | ¹H NMR (DMSO-d₆) δ: 14.34 (br. s., 1H), 8.33 (d, J = 7.6 Hz, 1H), 7.22-7.61 (m, 7H), 6.84-7.03 (m, 1H), 4.08-5.08 (m, 3H), 4.01 (s, 2H), 3.27 (s, 3H), 0.58-1.46 (m, 5H) | 418 H |
| 261 | (S)-N-(7-cyano-5,8-dimethyl-4-oxo-2,3,4,5-tetrahydrobenzo[b][1,4]oxazepin-3-yl)-5-(4-methylbenzyl)-4H-1,2,4-triazole-3-carboxamide | 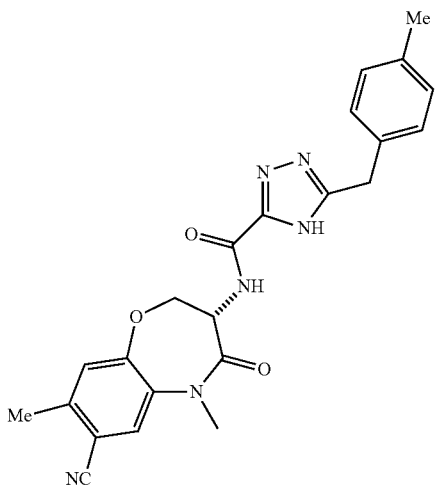 [SMILES: Cc1ccc(Cc2nnc(C(=O)N[C@H]3COc4cc(C)c(C#N)cc4N(C)C3=O)[nH]2)cc1] | ¹H NMR (DMSO-d₆) δ: 14.31 (br. s., 1H), 8.39 (d, J = 7.1 Hz, 1H), 8.02 (s, 1H), 7.34 (s, 1H), 7.14 (m, 4H), 4.86 (m, 1H), 4.68 (m, 1H), 4.45 (m, 1H), 4.09 (s, 2H), 3.33 (s, 3H), 3.31 (s, 3H), 2.27 (s, 3H) | 431 H |
| 262 | (S)-N-(6-fluoro-8-methyl-4-oxo-2,3,4,5-tetrahydrobenzo[b][1,4]oxazepin-3-yl)-5-(thiophen-2-ylmethyl)-4H-1,2,4-triazole-3-carboxamide | 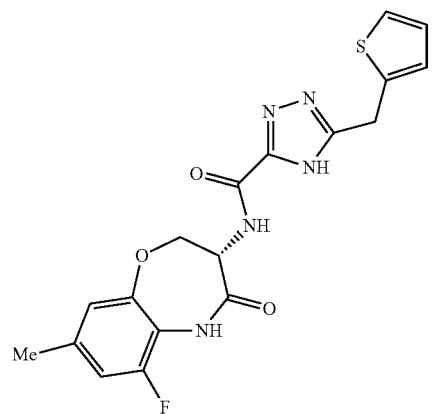 [SMILES: Cc1cc(F)c2c(c1)OC[C@H](NC(=O)c1nnc(Cc3cccs3)[nH]1)C(=O)N2] | 1H NMR (DMSO-d6) δ: 14.56 (br. s., 1H), 10.02 (s, 1H), 8.53 (br. s., 1H), 7.37-7.43 (m, 1H), 6.87-7.03 (m, 3H), 6.48-6.59 (m, 1H), 4.85 (dt, J = 11.4, 7.6 Hz, 1H), 4.63 (t, J = 10.7 Hz, 1H), 4.46 (dd, J = 10.1, 7.3 Hz, 1H), 4.33 (s, 2H), 2.30 (s, 3H) | 402 F |

-continued

| | | | | |
|---|---|---|---|---|
| 263 | (S)-5-benzyl-N-(6-chloro-4-oxo-2,3,4,5-tetrahydrobenzo[b][1,4]oxazepin-3-yl)-4H-1,2,4-triazole-3-carboxamide | 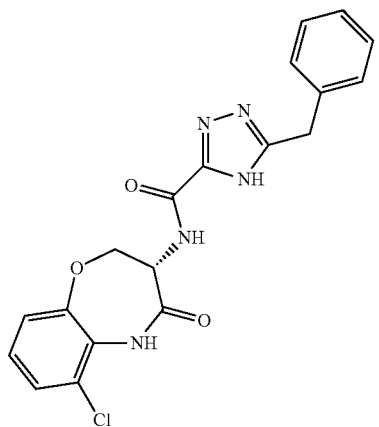 [SMILES: O=C(N[C@H]1COc2cccc(Cl)c2NC1=O)c1nnc(Cc2ccccc2)[nH]1] | ¹H NMR (DMSO-d₆) δ: 10.01 (br. s., 1H), 8.51 (br. s., 1H), 7.17-7.48 (m, 9H), 4.81 (dt, J = 11.3, 7.9 Hz, 1H), 4.66 (t, J = 10.7 Hz, 1H), 4.47 (dd, J = 9.9, 7.8 Hz, 1H), 4.12 (s, 2H) | 399 H |
| 264 | (S)-N-(5-methyl-4-oxo-2,3,4,5-tetrahydrobenzo[b][1,4]oxazepin-3-yl)-5-phenethyl-4H-1,2,4-triazole-3-carboxamide | 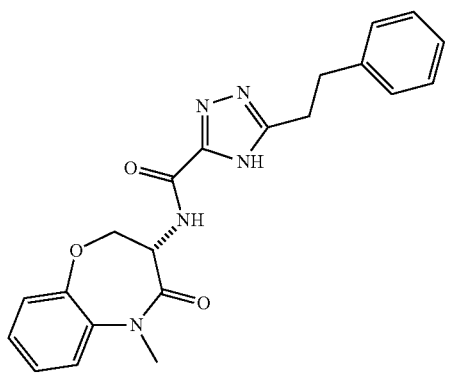 [SMILES: CN1C(=O)[C@@H](NC(=O)c2nnc(CCc3ccccc3)[nH]2)COc2ccccc21] | 1H NMR (DMSO-d6) δ: 14.18 (br. s., 1H), 8.37 (br. s., 1H), 7.52 (d, J = 7.5 Hz, 1H), 7.11-7.40 (m, 8H), 4.79-4.90 (m, 1H), 4.54-4.63 (m, 1H), 4.39-4.48 (m, 1H), 3.33 (s, 3H), 3.05 (br. s., 4H) | 392 F |
| 265 | (S)-5-benzyl-N-(7-(difluoromethoxy)-5-methyl-4-oxo-2,3,4,5-tetrahydrobenzo[b][1,4]oxazepin-3-yl)-4H-1,2,4-triazole-3-carboxamide | 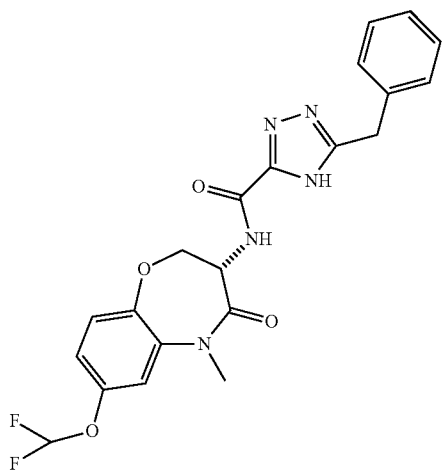 [SMILES: CN1C(=O)[C@@H](NC(=O)c2nnc(Cc3ccccc3)[nH]2)COc2ccc(OC(F)F)cc21] | ¹H NMR (DMSO-d₆) δ: 14.35 (br. s., 1H), 8.43 (br. s., 1H), 7.06-7.49 (m, 9H), 4.86 (dt, J = 11.3, 8.0 Hz, 1H), 4.55-4.68 (m, 1H), 4.35-4.47 (m, 1H), 4.13 (br. s., 2H), 3.32 (s, 3H) | 444 F |

| | | | | |
|---|---|---|---|---|
| 266 | (S)-5-(2-cyclopentylethyl)-N-(6-fluoro-8-methyl-4-oxo-2,3,4,5-tetrahydrobenzo[b][1,4]oxazepin-3-yl)-4H-1,2,4-triazole-3-carboxamide | 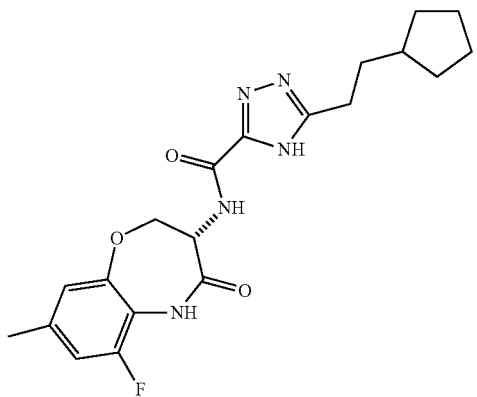 [SMILES: Cc1cc(F)c2c(c1)OC[C@H](NC(=O)c1nnc(CCC3CCCC3)[nH]1)C(=O)N2] | ¹H NMR (DMSO-d₆) δ: 14.24 (br. s., 1H), 10.01 (br. s., 1H), 8.38 (br. s., 1H), 6.99 (dd, J = 10.7, 1.1 Hz, 1H), 6.90 (s, 1H), 4.85 (dt, J = 11.1, 7.6 Hz, 1H), 4.61 (t, J = 10.6 Hz, 1H), 4.46 (dd, J = 10.1, 7.3 Hz, 1H), 2.74 (t, J = 7.3 Hz, 2H), 2.31 (s, 3H), 1.66-1.79 (m, 6H), 1.44-1.62 (m, 5H) | 402 F |
| 267 | (S)-N-(7-chloro-2-oxo-2,3,4,5-tetrahydro-1H-benzo[b]azepin-3-yl)-5-(cyclopentylmethyl)-4H-1,2,4-triazole-3-carboxamide | 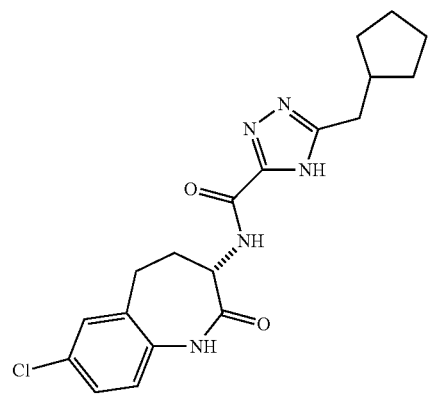 | ¹H NMR (DMSO-d₆) δ: 10.09 (s, 1H), 8.25 (br. s., 1H), 7.45 (d, J = 2.3 Hz, 1H), 7.35 (dd, J = 8.3, 2.5 Hz, 1H), 7.05 (d, J = 8.3 Hz, 1H), 4.33 (dt, J = 11.6, 7.8 Hz, 1H), 3.09-3.56 (m, 2H), 2.24 (dt, J = 15.1, 7.5 Hz, 2H), 1.37-1.86 (m, 5H), 1.01-1.34 (m, 3H) | 388 H |
| 268 | (S)-5-benzyl-N-(5,8-dimethyl-7-(5-methyl-1,3,4-oxadiazol-2-yl)-4-oxo-2,3,4,5-tetrahydrobenzo[b][1,4]oxazepin-3-yl)-4H-1,2,4-triazole-3-carboxamide | 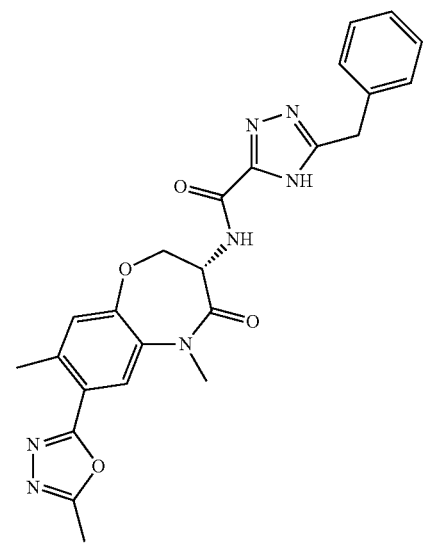 [SMILES: Cc1nnc(-c2cc3c(cc2C)OC[C@H](NC(=O)c2nnc(Cc4ccccc4)[nH]2)C(=O)N3C)o1] | ¹H NMR (DMSO-d₆) δ: 8.29-8.63 (m, 1H), 7.91 (s, 1H), 7.09-7.52 (m, 7H), 4.90 (dt, J = 11.6, 7.7 Hz, 1H), 4.67 (br. s., 1H), 4.46 (dd, J = 9.9, 7.3 Hz, 1H), 4.12 (br. s., 2H), 3.32 (s, 3H), 2.54-2.68 (m, 6H) | 474 F |

| | | | | |
|---|---|---|---|---|
| 269 | N-((S)-6-fluoro-8-methyl-4-oxo-2,3,4,5-tetrahydrobenzo[b][1,4]oxazepin-3-yl)-5-((tetrahydro-2H-pyran-3-yl)methyl)-4H-1,2,4-triazole-3-carboxamide | 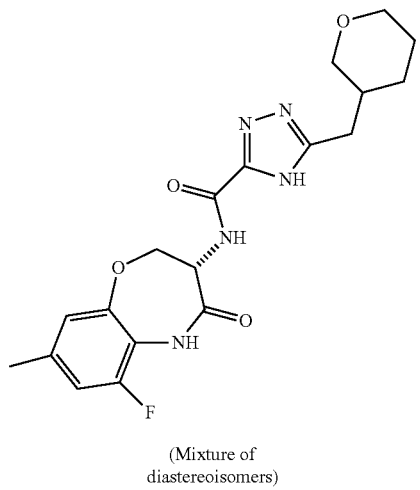<br>(Mixture of diastereoisomers) | Complex ¹H NMR due to diastereoisomer mixture | 404 | F |
| 270 | (S)-5-(cyclopentylmethyl)-N-(5,8-dimethyl-7-(5-methyl-1,3,4-oxadiazol-2-yl)-4-oxo-2,3,4,5-tetrahydrobenzo[b][1,4]oxazepin-3-yl)-4H-1,2,4-triazole-3-carboxamide | 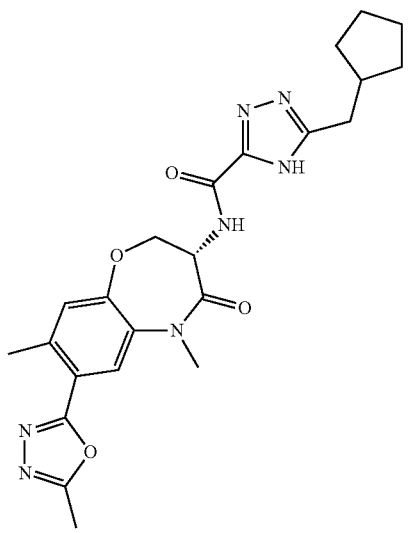 [SMILES: Cc1nnc(-c2cc3c(cc2C)OC[C@H](NC(=O)c2nnc(CC4CCCC4)[nH]2)C(=O)N3C)o1] | ¹H NMR (DMSO-$d_6$) δ: 8.26-8.44 (m, 1H), 7.91 (s, 1H), 7.34 (s, 1H), 4.90 (dt, J = 11.6, 7.6 Hz, 1H), 4.66 (br. s., 1H), 4.48 (dd, J = 9.7, 7.5 Hz, 1H), 3.36 (s, 3H), 2.72 (d, J = 7.3 Hz, 2H), 2.58-2.65 (m, 6H), 2.19-2.30 (m, 1H), 1.43-1.80 (m, 8H) | 466 | A |
| 271 | (S)-5-benzyl-N-(9-fluoro-7-methyl-2-oxo-2,3,4,5-tetrahydro-1H-benzo[b][1,4]diazepin-3-yl)-4H-1,2,4-triazole-3-carboxamide | 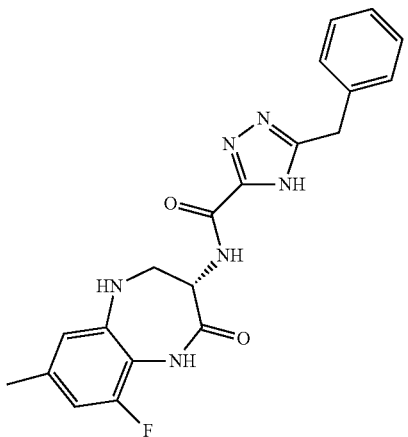 [SMILES: Cc1cc(F)c2c(c1)NC[C@H](NC(=O)c1nnc(Cc3ccccc3)[nH]1)C(=O)N2] | ¹H NMR (DMSO-$d_6$) δ: 14.38 (br. s., 1H), 9.69 (s, 1H), 8.29 (br. s., 1H), 7.20-7.40 (m, 5H), 6.41-6.55 (m, 2H), 6.12 (br. s., 1H), 4.62 (ddd, J = 10.4, 6.5, 4.1 Hz, 1H), 4.13 (s, 2H), 3.65-3.71 (m, 2H), 2.19 (s, 3H) | 395 | F |

| | | | | |
|---|---|---|---|---|
| 272 | (S)-5-(cyclopentylmethyl)-N-(7,9-difluoro-2-oxo-2,3,4,5-tetrahydro-1H-benzo[b]azepin-3-yl)-4H-1,2,4-triazole-3-carboxamide | 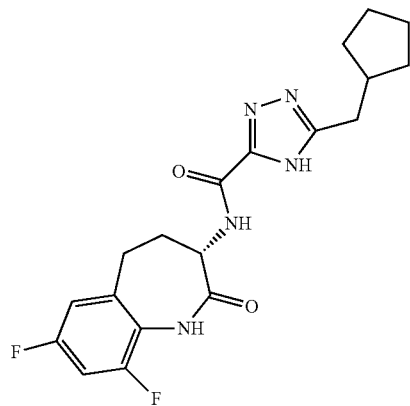 [SMILES: O=C(N[C@H]1CCc2cc(F)cc(F)c2NC1=O)c1nnc(CC2CCCC2)[nH]1] | $^1$H NMR (DMSO-$d_6$) δ: 14.10 (br. s., 1H), 9.97 (s, 1H), 8.25 (br. s., 1H), 7.23-7.37 (m, 1H), 7.16 (d, J = 8.8 Hz, 1H), 4.36 (dt, J = 11.2, 7.9 Hz, 1H), 2.76-2.85 (m, 2H), 2.72 (d, J = 7.3 Hz, 2H), 2.40-2.49 (m, 1H), 2.20-2.34 (m, 2H), 1.49-1.75 (m, 6H), 1.15-1.27 (m, 2H) | 390 F |
| 273 | (S)-5-(cyclopentylmethyl)-N-(9-fluoro-7-methyl-2-oxo-2,3,4,5-tetrahydro-1H-benzo[b][1,4]diazepin-3-yl)-4H-1,2,4-triazole-3-carboxamide | 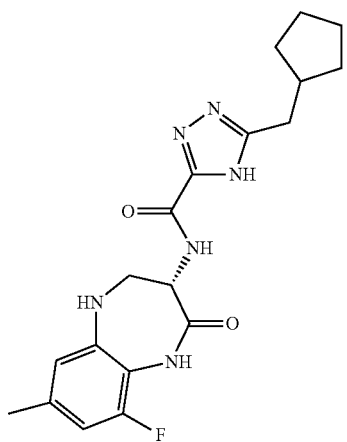 [SMILES: Cc1cc(F)c2c(c1)NC[C@H](NC(=O)c1nnc(CC3CCCC3)[nH]1)C(=O)N2] | $^1$H NMR (DMSO-$d_6$) δ: 13.94 (br. s., 1H), 9.71 (s, 1H), 8.26 (d, J = 5.8 Hz, 1H), 6.51 (s, 1H), 6.46 (d, J = 10.8 Hz, 1H), 6.15 (br. s., 1H), 4.64 (ddd, J = 10.5, 6.5, 4.0 Hz, 1H), 3.71 (dd, J = 11.0, 3.8 Hz, 1H), 3.42-3.50 (m, 1H), 2.75 (d, J = 7.5 Hz, 2H), 2.23-2.36 (m, 1H), 2.21 (s, 3H), 1.48-1.77 (m, 6H), 1.16-1.30 (m, 2H) | 387 F |
| 274 | (S)-5-(2,6-difluorobenzyl)-N-(6-fluoro-8-methyl-4-oxo-2,3,4,5-tetrahydrobenzo[b][1,4]oxazepin-3-yl)-4H-1,2,4-triazole-3-carboxamide | 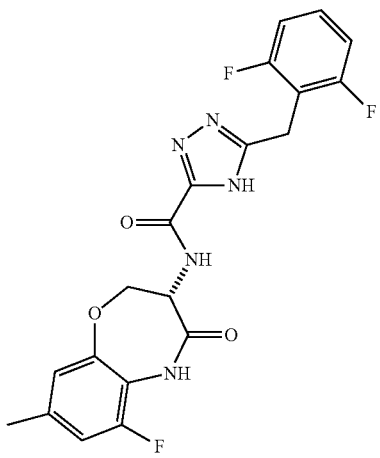 | $^1$H NMR (DMSO-$d_6$) δ: 14.46 (br. s., 1H), 10.01 (s, 1H), 8.39 (br. s., 1H), 7.41 (quin, J = 7.5 Hz, 1H), 7.07-7.18 (m, 2H), 6.99 (d, J = 10.5 Hz, 1H), 6.89 (s, 1H), 4.84 (dt, J = 11.2, 7.6 Hz, 1H), 4.57-4.68 (m, 1H), 4.44 (dd, J = 10.0, 7.3 Hz, 1H), 4.15 (br. s., 2H), 2.30 (s, 3H) | 432 F |

| | | | | |
|---|---|---|---|---|
| 275 | (S)-5-benzyl-N-(5-methyl-7-(5-methyl-1,2,4-oxadiazol-3-yl)-4-oxo-2,3,4,5-tetrahydrobenzo[b][1,4]oxazepin-3-yl)-4H-1,2,4-triazole-3-carboxamide | 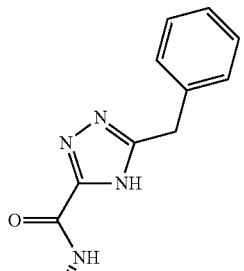 | ¹H NMR (DMSO-d₆) δ: 14.45 (br. s., 1H), 8.50 (br. s., 1H), 8.02 (d, J = 2.0 Hz, 1H), 7.90 (dd, J = 8.3, 2.0 Hz, 1H), 7.42 (d, J = 8.3 Hz, 1H), 7.30-7.36 (m, 2H), 7.22-7.29 (m, 3H), 4.90 (dt, J = 11.6, 7.7 Hz, 1H), 4.68 (t, J = 10.7 Hz, 1H), 4.49 (dd, J = 10.0, 7.5 Hz, 1H), 4.12 (s, 2H), 3.38 (s, 3H), 2.69 (s, 3H) | 460 F |
| 276 | (S)-5-(2,3-difluorobenzyl)-N-(6-fluoro-8-methyl-4-oxo-2,3,4,5-tetrahydrobenzo[b][1,4]oxazepin-3-yl)-4H-1,2,4-triazole-3-carboxamide | 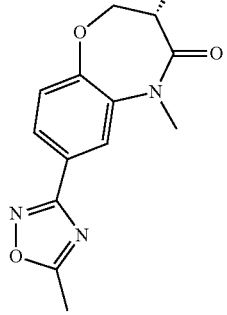 | ¹H NMR (DMSO-d₆) δ: 14.40 (br. s., 1H), 10.00 (s, 1H), 8.34 (br. s., 1H), 7.13-7.33 (m, 3H), 6.99 (d, J = 10.8 Hz, 1H), 6.89 (s, 1H), 4.85 (dt, J = 11.3, 7.5 Hz, 1H), 4.55-4.69 (m, 1H), 4.45 (dd, J = 10.0, 7.3 Hz, 1H), 4.18 (br. s., 2H), 2.30 (s, 3H) | 432 F |
| 277 | (S)-5-benzyl-N-(9-fluoro-8-methyl-2-oxo-2,3,4,5-tetrahydro-1H-benzo[b]azepin-3-yl)-4H-1,2,4-triazole-3-carboxamide | 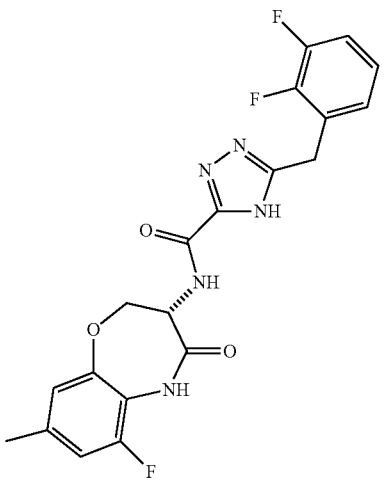 | ¹H NMR (DMSO-d₆) δ: 9.95 (s, 1H), 6.96-7.41 (m, 8H), 4.26-4.50 (m, 1H), 4.10 (s, 2H), 2.67-2.98 (m, 3H), 2.15-2.35 (m, 4H) | 394 H |

| | | | | |
|---|---|---|---|---|
| 278 (S)-5-(cyclopentylmethyl)-N-(5-methyl-7-(5-methyl-1,2,4-oxadiazol-3-yl)-4-oxo-2,3,4,5-tetrahydrobenzo[b][1,4]oxazepin-3-yl)-4H-1,2,4-triazole-3-carboxamide | 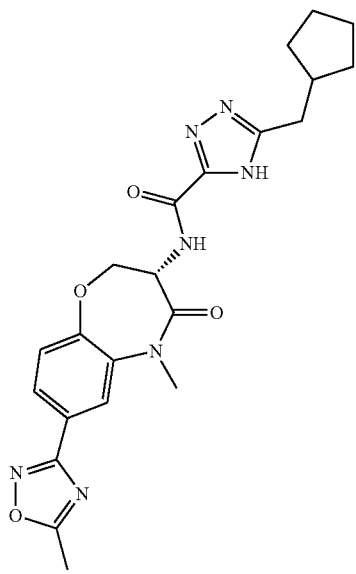 [SMILES: Cc1nc(-c2ccc3c(c2)N(C)C(=O)[C@@H](NC(=O)c2nnc(CC4CCCC4)[nH]2)CO3)no1] | ¹H NMR (DMSO-d₆) δ: 14.20 (br. s., 1H), 8.42 (br. s., 1H), 8.02 (d, J = 2.0 Hz, 1H), 7.91 (dd, J = 8.3, 2.0 Hz, 1H), 7.43 (d, J = 8.3 Hz, 1H), 4.91 (dt, J = 11.6 7.6 Hz, 1H), 4.67 (t, J = 10.7 Hz, 1H), 4.51 (dd, J = 9.9, 7.6 Hz, 1H), 3.38 (s, 3H), 2.72 (d, J = 7.6 Hz, 2H), 2.69 (s, 3H), 2.25 (dt, J = 15.0, 7.6 Hz, 1H), 1.47-1.75 (m, 6H), 1.14-1.29 (m, 2H) | 452 | H |
| 279 (S)-N-(5-methyl-7-(5-methyl-1,2,4-oxadiazol-3-yl)-4-oxo-2,3,4,5-tetrahydrobenzo[b][1,4]oxazepin-3-yl)-4-phenoxy picolinamide | 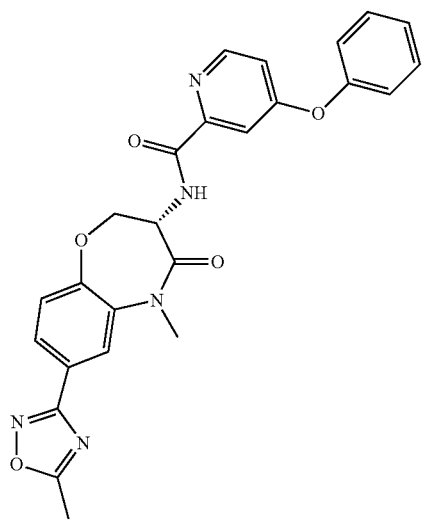 [SMILES: Cc1nc(-c2ccc3c(c2)N(C)C(=O)[C@@H](NC(=O)c2cc(Oc4ccccc4)ccn2)CO3)no1] | ¹H NMR (DMSO-d₆) δ: 8.67 (m, 1H), 8.45 (m, 1H), 7.29-7.07 (m, 10H), 5.04 (m, 1H), 4.29-4.49 (m, 2H), 2.62-2.93 (m, 3H), 2.25 (s, 3H) | 472 | H |
| 280 (S)-5-benzyl-N-(8-methoxy-5-methyl-7-(5-methyl-1,3,4-oxadiazol-2-yl)-4-oxo-2,3,4,5-tetrahydrobenzo[b][1,4]oxazepin-3-yl)-4H-1,2,4-triazole-3-carboxamide | 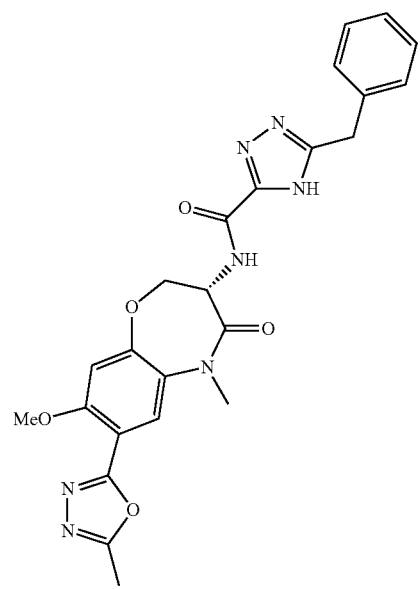 [SMILES: COc1cc2c(cc1-c1nnc(C)o1)N(C)C(=O)[C@@H](NC(=O)c1nnc(Cc3ccccc3)[nH]1)CO2] | ¹H NMR (DMSO-d₆) δ: 7.88 (s, 1H), 7.12-7.43 (m, 6H), 4.91 (s, 1H), 4.61-4.73 (m, 1H), 4.46-4.57 (m, 1H), 4.13 (s, 2H), 3.92 (s, 3H), 3.31 (s, 3H), 2.58 (s, 3H) | 490 | A |

| | | | | |
|---|---|---|---|---|
| 281 | (S)-5-benzyl-N-(5-methyl-7-(3-methyl-1,2,4-oxadiazol-5-yl)-4-oxo-2,3,4,5-tetrahydrobenzo[b][1,4]oxazepin-3-yl)-4H-1,2,4-triazole-3-carboxamide | 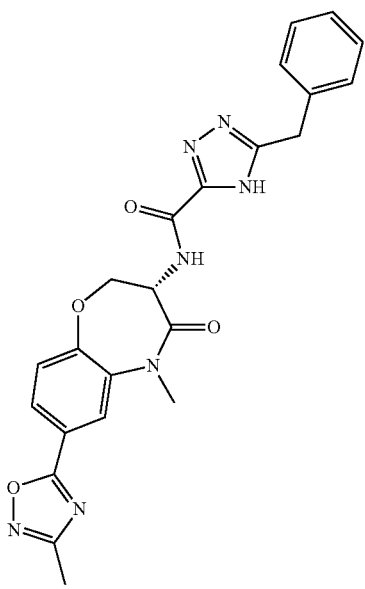 [SMILES: Cc1noc(-c2ccc3c(c2)N(C)C(=O)[C@@H](NC(=O)c2nnc(Cc4ccccc4)[nH]2)CO3)n1] | ¹H NMR (DMSO-d₆) δ: 8.53 (d, J = 7.3 Hz, 1H), 8.16 (d, J = 2.0 Hz, 1H), 8.00 (dd, J = 8.3, 2.0 Hz, 1H), 7.47 (d, J = 8.5 Hz, 1H), 7.21-7.36 (m, 6H), 4.91 (dt, J = 11.6, 7.7 Hz, 1H), 4.68-4.75 (m, 1H), 4.51 (dd, J = 9.8, 7.3 Hz, 1H), 4.12 (s, 2H), 3.39 (s, 3H), 2.44 (s, 3H) | 460 F |
| 282 | ((S)-5-(cyclopentylmethyl)-N-(5-methyl-7-(3-methyl-1,2,4-oxadiazol-5-yl)-4-oxo-2,3,4,5-tetrahydrobenzo[b][1,4]oxazepin-3-yl)-4H-1,2,4-triazole-3-carboxamide | 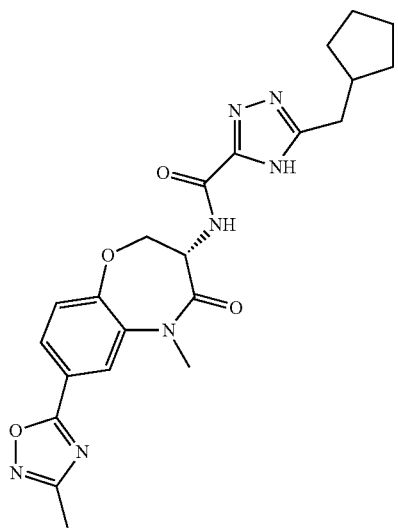 [SMILES: Cc1noc(-c2ccc3c(c2)N(C)C(=O)[C@@H](NC(=O)c2nnc(CC4CCCC4)[nH]2)CO3)n1] | ¹H NMR (DMSO-d₆) δ: 8.46 (d, J = 7.8 Hz, 1H), 8.16 (d, J = 2.0 Hz, 1H), 8.01 (dd, J = 8.3, 2.0 Hz, 1H), 7.48 (d, J = 8.3 Hz, 1H), 4.92 (dt, J = 11.5, 7.7 Hz, 1H), 4.67-4.76 (m, 1H), 4.52 (dd, J = 9.8, 7.5 Hz, 1H), 3.40 (s, 3H), 2.72 (d, J = 7.5 Hz, 2H), 2.44 (s, 3H), 2.24 (dt, J = 15.2, 7.6 Hz, 1H), 1.45-1.73 (m, 6H), 1.14-1.25 (m, 2H) | 452 F |
| 283 | (S)-5-benzyl-N-(5-methyl-4-oxo-7-(pyridin-2-yl)-2,3,4,5-tetrahydrobenzo[b][1,4]oxazepin-3-yl)-4H-1,2,4-triazole-3-carboxamide | 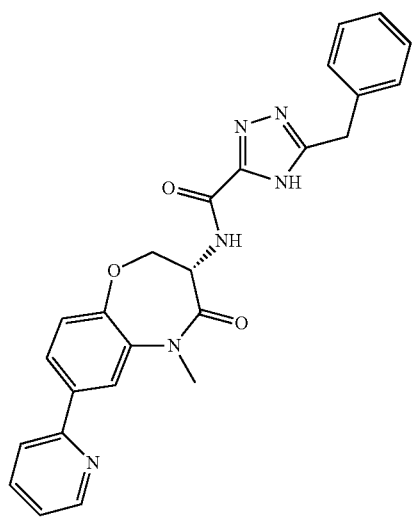 [SMILES: CN1C(=O)[C@@H](NC(=O)c2nnc(Cc3ccccc3)[nH]2)COc2ccc(-c3ccccn3)cc21] | ¹H NMR (DMSO-d₆) δ: 14.43 (br. s., 1H), 8.67-8.71 (m, 1H), 8.49 (br. s., 1H), 8.17 (d, J = 2.3 Hz, 1H), 8.00-8.09 (m, 2H), 7.92 (td, J = 7.7, 1.8 Hz, 1H), 7.21-7.41 (m, 7H), 4.91 (dt, J = 11.6, 7.7 Hz, 1H), 4.60-4.69 (m, 1H), 4.46 (dd, J = 9.9, 7.6 Hz, 1H), 4.12 (s, 2H), 3.40 (s, 3H) | 455 F |

| | | | |
|---|---|---|---|
| 284 | (S)-5-benzyl-N-(6,8-difluoro-7-methyl-4-oxo-2,3,4,5-tetrahydro-benzo[b][1,4]oxazepin-3-yl)-4H-1,2,4-triazole-3-carboxamide | 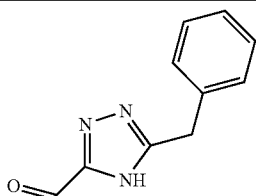 | $^1$H NMR (DMSO-d$_6$) δ: 10.09 (br. s., 1H), 8.49 (d, J = 7.0 Hz, 1H), 7.19-7.38 (m, 5H), 7.02 (dd, J = 9.8, 1.5 Hz, 1H), 4.87 (dt, J = 11.3, 7.5 Hz, 1H), 4.64 (t, J = 10.7 Hz, 1H), 4.48 (dd, J = 10.0, 7.3 Hz, 1H), 4.12 (s, 2H), 2.15 (s, 3H) | 414 F |
| 285 | (S)-N-(7-chloro-9-fluoro-2-oxo-2,3,4,5-tetrahydro-1H-benzo[b]azepin-3-yl)-5-(cyclopentylmethyl)-4H-1,2,4-triazole-3-carboxamide | 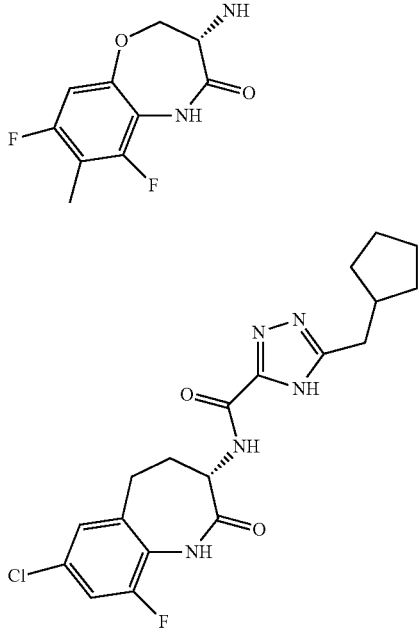 | $^1$H NMR (DMSO-d$_6$) δ: 14.14 (s, 1H), 10.08 (s, 1H), 8.22 (d, J = 7.5 Hz, 1H), 7.43-7.54 (m, 1H), 7.35 (s, 1H), 4.36 (dt, J = 11.3, 7.9 Hz, 1H), 2.62-2.88 (m, 4H), 2.34-2.48 (m, 1H), 2.19-2.32 (m, 2H), 1.44-1.78 (m, 6H), 1.10-1.29 (m, 2H) | 406/408 F |

Example 286

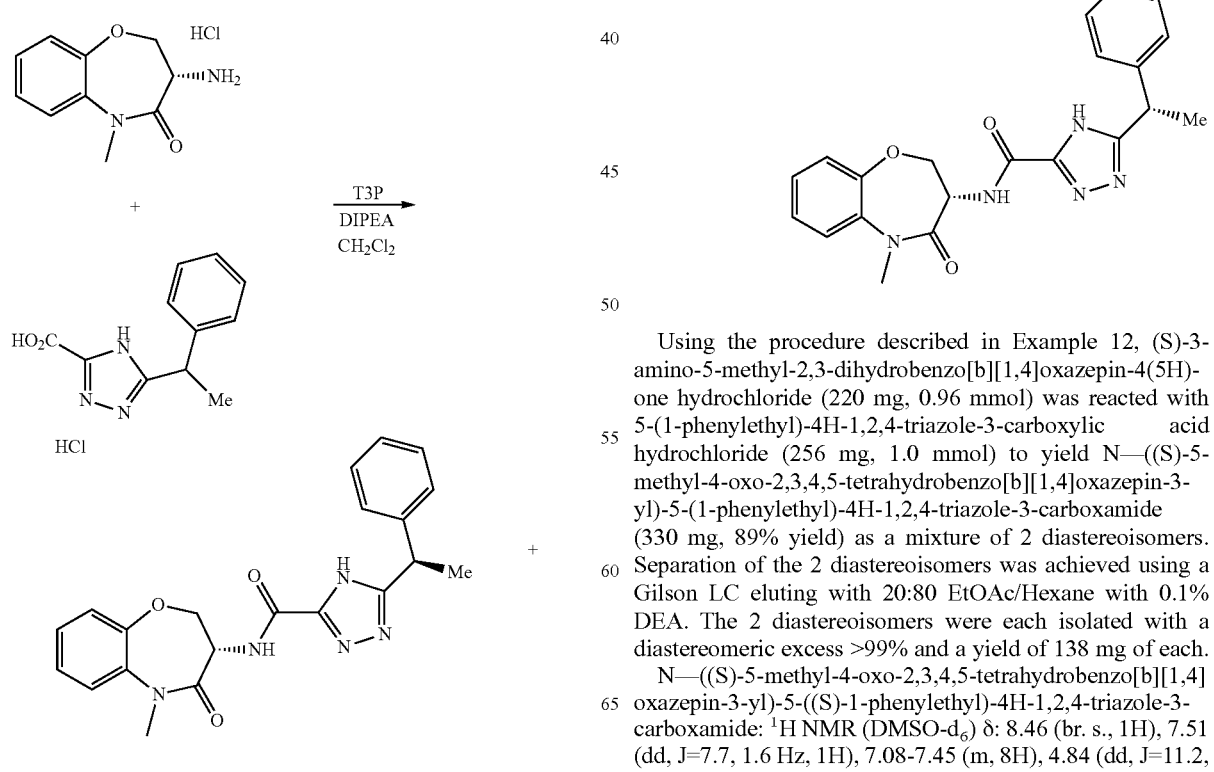

Using the procedure described in Example 12, (S)-3-amino-5-methyl-2,3-dihydrobenzo[b][1,4]oxazepin-4(5H)-one hydrochloride (220 mg, 0.96 mmol) was reacted with 5-(1-phenylethyl)-4H-1,2,4-triazole-3-carboxylic acid hydrochloride (256 mg, 1.0 mmol) to yield N—((S)-5-methyl-4-oxo-2,3,4,5-tetrahydrobenzo[b][1,4]oxazepin-3-yl)-5-(1-phenylethyl)-4H-1,2,4-triazole-3-carboxamide (330 mg, 89% yield) as a mixture of 2 diastereoisomers. Separation of the 2 diastereoisomers was achieved using a Gilson LC eluting with 20:80 EtOAc/Hexane with 0.1% DEA. The 2 diastereoisomers were each isolated with a diastereomeric excess >99% and a yield of 138 mg of each.

N—((S)-5-methyl-4-oxo-2,3,4,5-tetrahydrobenzo[b][1,4]oxazepin-3-yl)-5-((S)-1-phenylethyl)-4H-1,2,4-triazole-3-carboxamide: $^1$H NMR (DMSO-d$_6$) δ: 8.46 (br. s., 1H), 7.51 (dd, J=7.7, 1.6 Hz, 1H), 7.08-7.45 (m, 8H), 4.84 (dd, J=11.2, 8.0 Hz, 1H), 4.52-4.72 (m, 1H), 4.25-4.49 (m, 2H), 3.32 (s, 3H), 1.63 (d, J=7.3 Hz, 3H). MS (m/z) 392 (M+H$^+$).

N—((S)-5-methyl-4-oxo-2,3,4,5-tetrahydrobenzo[b][1,4]oxazepin-3-yl)-5-((R)-1-phenylethyl)-4H-1,2,4-triazole-3-carboxamide: $^1$H NMR (DMSO-d$_6$) δ: 8.45 (br. s., 1H), 7.51 (dd, J=7.7, 1.9 Hz, 1H), 7.12-7.42 (m, 9H), 4.76-4.94 (m, 1H), 4.53-4.70 (m, 1H), 4.28-4.49 (m, 2H), 3.26-3.42 (m, 3H), 1.63 (d, J=7.3 Hz, 3H). MS (m/z) 392 (M+H$^+$).

Pharmaceutical Compositions

Example A

Tablets are prepared using conventional methods and are formulated as follows:

| Ingredient | Amount per tablet |
| --- | --- |
| Compound | 5 mg |
| Microcrystalline cellulose | 100 mg |
| Lactose | 100 mg |
| Sodium starch glycollate | 30 mg |
| Magnesium stearate | 2 mg |
| Total | 237 mg |

Example B

Capsules are prepared using conventional methods and are formulated as follows:

| Ingredient | Amount per tablet |
| --- | --- |
| Compound | 15 mg |
| Dried starch | 178 mg |
| Magnesium stearate | 2 mg |
| Total | 195 mg |

Biological Assays:
Biological In Vitro Assay

A fluorescent polarization based binding assay was developed to quantitate interaction of novel test compounds at the ATP binding pocket of RIP1, by competition with a fluorescently labeled ATP competitive ligand. GST-RipK1(1-375) was purified from a Baculovirus expression system and was used at a final assay concentration of 10 nM. A fluorescent labeled ligand (14-(2-{[3-({2-{[4-(cyanomethyl)phenyl]amino}-6-[(5-cyclopropyl-1H-pyrazol-3-yl)amino]-4-pyrimidinyl}amino)propyl]amino}-2-oxoethyl)-16,16,18,18-tetramethyl-6,7,7a,8a,9,10,16,18-octahydrobenzo[2",3"]indolizino[8",7":5',6']pyrano[3',2':3,4]pyrido[1,2-a]indol-5-ium-2-sulfonate (prepared as described below) was used at a final assay concentration of 5 nM. Both the enzyme and ligand were prepared in solutions in 50 mM HEPES pH7.5, 10 mM NaCl, 50 mM MgCl2, 0.5 mM DTT, and 0.02% CHAPS. Test compounds were prepared in neat DMSO and 100 nL was dispensed to individual wells of a multiwell plate. Next, 5 ul GST-RipK1(1-375) was added to the test compounds at twice the final assay concentration, and incubated at room temperature for 10 minutes. Following the incubation, 5 ul of the fluorescent labeled ligand solution, was added to each reaction, at twice the final assay concentration, and incubated at room temperature for at least 15 minutes. Finally, samples were read on an instrument capable of measuring fluorescent polarization. Test compound inhibition was expressed as percent (%) inhibition of internal assay controls. For concentration response experiments, normalized data were fit and pIC$_{50}$s determined using conventional techniques. The pIC$_{50}$s are averaged to determine a mean value, for a minimum of 2 experiments.

As determined using the above method, the compounds of Examples 1-286 exhibited a pIC$_{50}$ between approximately 5.0 and 9.0. For instance, the compounds of Examples 12, 91, 102, 161, 163 and 169 inhibited RIP1 kinase in the above method with a mean pIC$_{50}$ of approximately 7.6, 7.6, 7.8, 7.9, 7.9 and 7.2 respectively. Continued testing resulted in a slight change in the reported average pIC$_{50}$ for these compounds (Example 161 (7.7) and Example 169 (7.3)).

Preparation of (14-(2-{[3-({2-{[4-(cyanomethyl)phenyl]amino}-6-[(5-cyclopropyl-1H-pyrazol-3-yl)amino]-4-pyrimidinyl}amino)propyl]amino}-2-oxoethyl)-16,16,18,18-tetramethyl-6,7,7a,8a,9,10,16,18-octahydrobenzo[2",3"]indolizino[8",7":5',6']pyrano[3',2':3,4]pyrido[1,2-a]indol-5-ium-2-sulfonate

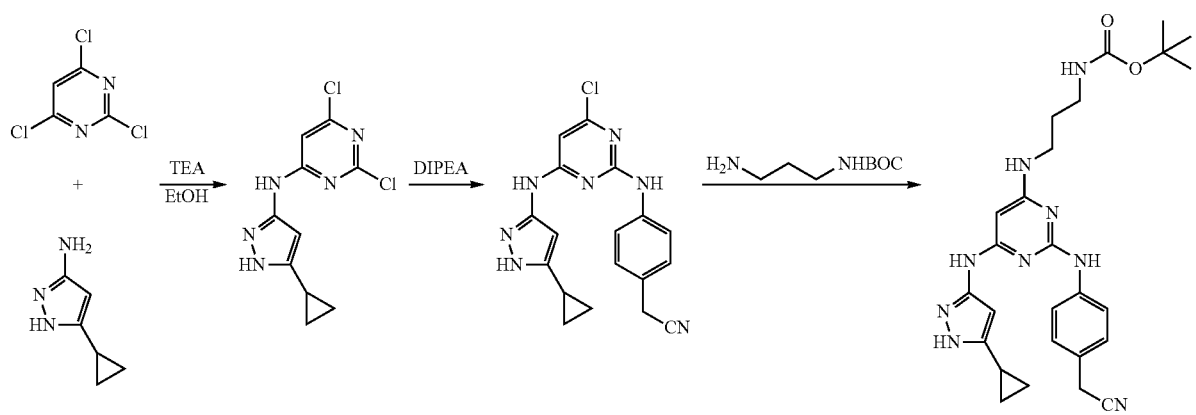

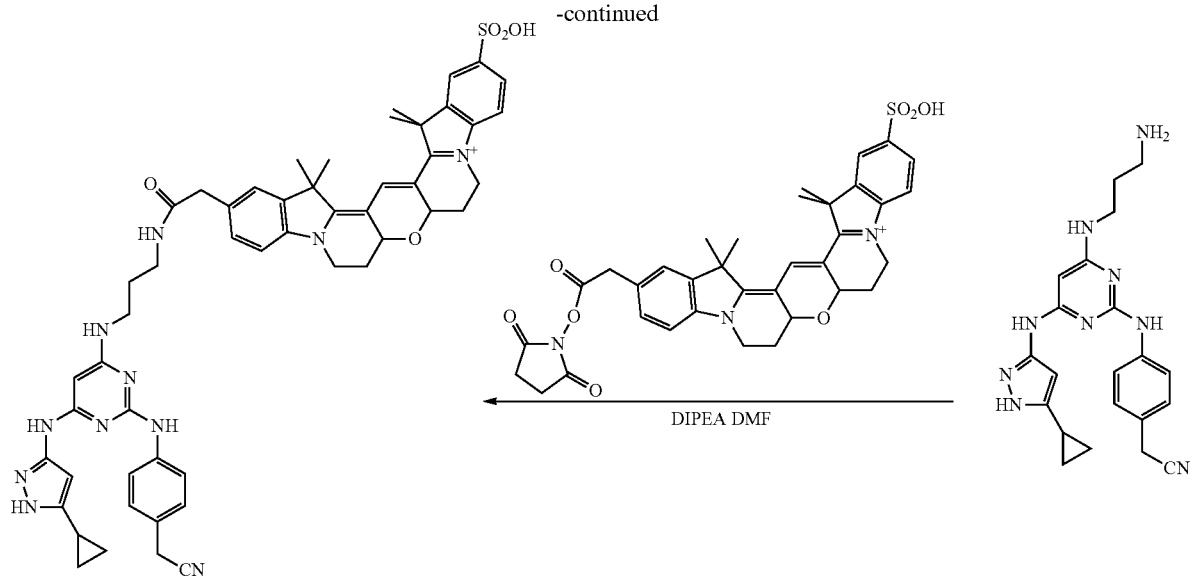

A solution of 2,4,6-trichloropyrimidine (Alfa, 12.25 g, 66.8 mmol), 3-amino-5-cyclopropyl-1H-pyrazole (Fluorochem 8.23 g, 66.8 mmol) and triethylamine (11.2 mL, 80.4 mmol) in ethanol (100 mL) was stirred at room temperature for 16 hours under Ar (balloon). The solvent was removed in vacuo and the crude material was dissolved in ethyl acetate. The solution was washed with water and dried ($Na_2SO_4$), filtered and evaporated to give a beige solid. Pure product was obtained as a white crystalline solid after recrystallisation from acetonitrile. It was possible to obtain a second crop. From two runs performed under the same conditions, 29.0 g (88%) of 2,6-dichloro-N-(5-cyclopropyl-1H-pyrazol-3-yl)pyrimidin-4-amine. The product contained ~10% acetonitrile but was carried through to the next step regardless.

A suspension of (5-cyclopropyl-1H-pyrazol-3-yl)-(2,6-dichloro-pyrimidin-4-yl)-amine (25.8 g, 0.1 mol) and 4-aminophenylacetonitrile (Alfa, 13.91 g, 0.11 mol) in diisopropylethylamine (Alfa, 342 mL) was stirred at 110° C. for 16 hours under Ar (balloon). The resultant gummy suspension was dissolved in DCM, washed with water and dried ($Na_2SO_4$), filtered and concentrated. When the DCM was reduced to a small volume the material was left to stand and the product dropped out of solution. After filtration and washing with DCM, formation of 2-(4-((4-chloro-6-((5-cyclopropyl-1H-pyrazol-3-yl)amino)pyrimidin-2-yl)amino)phenyl)acetonitrile was obtained as a beige powder (10.6 g, 30.3%).

A mixture of {4-[4-chloro-6-(5-cyclopropyl-1H-pyrazol-3-ylamino)-pyrimidin-2-ylamino]-phenyl}-acetonitrile (1.54 g, 4.2 mmol) and tert-butyl N-(2-aminopropyl)carbamate (Aldrich, 2.20 g, 12.6 mmol, 3.0 eq) were heated at 115° C. for 16 hours under Ar (balloon). The resultant glassy solid was purified by column chromatography (at least 25 cm depth of silica, eluent=DCM→5% MeOH in DCM). Recovered starting material is the first yellow band to elute from the column (eluent ~2% MeOH in DCM) and the product elutes when the second yellow band has moved through the column (eluent ~4% MeOH in DCM). A purple band elutes once almost all the product has eluted. A good eluent for TLC analysis of the fractions is 1:1 EtOAc/Pet. Ether. The initial fractions of the product are contaminated with a trace of higher $R_f$ material whereas the final fractions of product contain traces of a lower $R_f$ material. Therefore only the middle product fractions were combined. tert-Butyl (3-((2-((4-(cyanomethyl)phenyl)amino)-6-((5-cyclopropyl-1H-pyrazol-3-yl)amino)pyrimidin-4-yl)amino)propyl)carbamate was obtained as a yellow foam (0.7 g, 33.0%).

tert-Butyl (3-((2-((4-(cyanomethyl)phenyl)amino)-6-((5-cyclopropyl-1H-pyrazol-3-yl)amino)pyrimidin-4-yl)amino)propyl)carbamate (20 mg, 0.040 mmol) was dissolved in an ice-cold solution of water (0.1 mL) in trifluoroacetic acid (TFA) (1.9 mL). The reaction mixture was allowed to warm to room temperature and left for a total of 2 hours. Excess acid was removed under reduced pressure and the oily residue triturated with several portions of dry ether. The residual solid was dried under reduced pressure. MS (m/z) 403 (M+H$^+$). Analytical C18 HPLC showed only one major component. Yield of 2-(4-((4-((3-aminopropyl)amino)-6-((5-cyclopropyl-1H-pyrazol-3-yl)amino)pyrimidin-2-yl)amino)phenyl)acetonitrile estimated at approximately 98%.

2-(4-((4-((3-Aminopropyl)amino)-6-((5-cyclopropyl-1H-pyrazol-3-yl)amino)pyrimidin-2-yl)amino)phenyl)acetonitrile trifluoroacetic acid salt (3.2 mg, 6.18 mol) and 14-{2-[(2, 5-dioxo-1-pyrrolidinyl)oxy]-2-oxoethyl}-16,16,18,18-tetramethyl-6,7,7a,8a,9,10,16,18-octahydrobenzo[2″,3″]indolizino[8″,7″:5′,6′]pyrano[3′,2′:3,4]pyrido[1,2-a]indol-5-ium-2-sulfonate trifluoroacetic acid salt (2.6 mg, 3.37 μmol) were placed in a 2 ml Eppendorf tube and DMF (200 μl) added. The mixture was stirred till all solid had dissolved and then the mixture was basified by the addition of DIPEA (2 μl, 0.011 mmol). The reaction was stirred overnight at room temperature. The reaction mixture was evaporated to dryness and redissolved in DMSO/MeOH (<1 ml), filtered (0.2 μm) and applied to a Phenomenex Jupiter C18 preparative column and eluted with the following gradient (A=0.1% trifluoroacetic acid in water, B=0.1% TFA/90% acetonitrile/10% water): Flow rate=10 ml/min., AU=20/10 (214 nm). The target component was eluted in two fractions. Both fractions were combined and evaporated to dryness to yield 1.4 mg of 14-(2-{[3-({2-{[4-(cyanomethyl)phenyl]amino}-6-[(5-cyclopropyl-1H-pyrazol-3-yl)amino]-4-pyrimidinyl}amino)propyl]amino}-2-oxoethyl)-16,16,18, 18-tetramethyl-6,7,7a,8a,9,10,16,18-octahydrobenzo[2",3"]indolizino[8",7":5',6']pyrano[3',2':3,4]pyrido[1,2-a]indol-5-ium-2-sulfonate.

GST-RipK1 Preparation: His.GST.TEV.RIPK1 1-375

The RIPK1 gene [receptor (TNFRSF)-interacting serine-threonine kinase 1] was cloned from human adrenal gland cDNA. Primers were designed from the reference sequence NM_003804.3 with an added CACC Kozak directional tag for cloning into pENTR/TEV/D-TOPO. Gateway® LR cloning was used to site-specifically recombine RIPK1 downstream to an N-terminal HisGST contained within the destination vector pDEST8-His.GST according to the protocol described by Invitrogen. A stop codon was inserted after amino acid 375 using Quikchange Stratagene mutagenesis kit according to manufacturer's protocol and resulted in pDEST8.His.GST.TEV.human RIPK1 1-375. His.GST.Tev.human RIPK1 1-375 baculovirus was generated using the bac to bac system (Invitrogen) according to manufacturer's specifications. Transfection of *Spodoptera frugiperda*(Sf9) insect cells was performed using Fugene 6 (Roche), according to the manufacturer's protocol. His.GST.TEV.human RIPK1 1-375 baculovirus infected insect cells (BIICs) were prepared during the baculovirus generation according to David Wasilko and S Edward Lee, TIPS: Titerless Infected Cells Preservation and Scale up, BioProcessing Journal Fall 2006 p29-32. 20 L Sf9 cells were grown in serum free Hyclone, SFX media (HyClone Laboratories, 925 West 1800 South Logan, Utah 84321) at 27° C. in wave bags seeded at a density of 8×10^6cell/ml with a rock rate of 25 rpm, airflow of 0.18 to 0.22. in wave reactor (WAVE Bioreactor, System 20/50EH). Cells were grown ON at 27 C. His.GST.TEV.human RIPK1 1-375 baculovirus infected insect cells (BIICs) were used to infect Sf9s at a cell density of 1.7 to 2.4×10^6. 2 ml of BIIC (1×10^7cells/mL) were added to 20 L cells. Rock rate is increased to 25 rom at infection. Harvest 72 hrs post infection using the Viafuge. Weigh pellets, seal wave bags and freeze at −80.

A 50 g cell pellet was re-suspended in 250 ml lysis buffer (50 mM Tris pH 7.5, 250 mM NaCl, 1 mM DTT and Complete Protease Inhibitor tablets (1/50 ml, from Roche Diagnostics). The cells were lysed by sonication on ice, 3×30" at power level 4 using the large probe on a Branson Sonicator. The suspension was then clarified by centrifugation at 15,000 g for 30 minutes, at 4° C. The lysate was decanted from the insoluble pellet and batch bound to 10 ml of Glutathione Agarose (Pierce) for 2 h at 4 C with gentle end over end rotation. The beads were then packed into a column and washed to baseline with lysis buffer (no protease inhibitors) and then eluted with 20 mM reduced glutathione in 50 mM Tris, pH8.

Fractions identified by SDS-PAGE as containing protein of interest were pooled (10 ml total volume), concentrated to about 5 ml and loaded onto a 300 ml SDX200 SEC column (GE Healthcare) which had been equilibrated in 50 mM Tris, pH7.5, 150 mM NaCl, 1 mM DTT and 10% Glycerol. The Rip1 protein eluted as a dimer off the SEC column.

The protein concentration was determined by Bradford assay using BSA as a standard. The yield was 12.5 mg at 0.63 mg/ml. The purity was >95% as determined by scanning a Coomassie stained SDS-PAGE gel.

LCMS analysis showed that the major species had lost the N-terminal methionine, was acetylated and had one phosphorylated site. The protein was aliquoted and frozen at −80° C. for use as needed.

Biological In Vivo Assay

The efficacy of RIP1 inhibitors can be tested in mice in vivo using a TNF-driven systemic inflammatory response syndrome model (Duprez, L., et al. 2011. Immunity 35(6): 908-918). The model can be run in a long modality (using TNF alone i.v.) which results in the termination of the study in ~7 hrs (under IACUC guidelines for temperature loss) or a short modality (using TNF plus the caspase inhibitor zVAD i.v.) which needs to be terminated at ~3 hrs (under IACUC guidelines for temperature loss). TNF (or TNF/zVAD) induced manifestations include temperature loss, the production of numerous cytokines (including IL-6, IL-1b, MIP1β and MIP2) in the periphery, liver and intestinal inflammation and an increase of markers of cellular (LDH and CK) and liver damage (AST and ALT) in the serum. Inhibition of these TNF (or TNF/zVAD) induced manifestations can be shown by orally or IP pre-dosing with selected compounds of this invention.

Each test compound is run through the TNF/zVAD and TNF (alone) versions of the model. For example, mice (7 mice per group) were orally pre-dosed with vehicle or test compound at 50 mg/kg 15 minutes before i.v. administration of mouse TNF (30 μg/mouse) and zVAD (0.4 mg/mouse) simultaneously. Temperature loss in the mice was measured by rectal probe. The study was terminated when the control group lost 7 degrees, per our IACUC protocol. Representative data expressed over time or at the 2.5 hour time point is provided in FIGS. 1A, 1B, 4A and 4B, respectively. All data are shown as means±standard error of the mean. Data for compounds tested in this model are provided in Table 2.

TABLE 2

| Example No. | Dose (mg/kg) | % Inhibition |
|---|---|---|
| 12 | 30 | 93 |
| 20 | 30 | 52 |
| 45 | 10 | 91 |
| 64 | 30 | 62 |
| 125 | 30 | 25 |
| 108 | 30 | 56 |
| 161 | 50 | 85 |
| 163 | 10 | 73 |
| 176 | 30 | 34 |
| 190 | 30 | 85 |
| 97 | 30 | 70 |
| 235 | 30 | 58 |
| 236 | 30 | 23 |

In addition to the TNF/zVAD model, each compound is also tested in a TNF alone model. For the TNF (alone) version of the model, mice (7 mice per group) were orally pre-dosed with vehicle or test compound at 50 mg/kg 15 minutes before i.v. administration of mouse TNF (30 μg/mouse). An example of the TNF (alone) model over time and at the 6 hour time point can be seen in FIGS. 2A, 2B, 5A and 5B, respectively. All data are shown as means±standard error of the mean. Data for compounds tested in this model are provided in Table 3.

TABLE 3

| Example No. | Dose (mg/kg) | % Inhibition |
|---|---|---|
| 12 | 50 | 87 |
| 20 | 50 | 51 |
| 161 | 50 | 82 |
| 190 | 50 | 56 |
| 235 | 50 | 73 |

Biological In Vitro Cell Assay

The efficacy of RIP1 inhibitors can be tested in mice in vitro using a human monocytic leukemia U937 or mouse L929 fibrosarcoma cells in a necroptosis assay (He, S. et al.

Figure 3A:
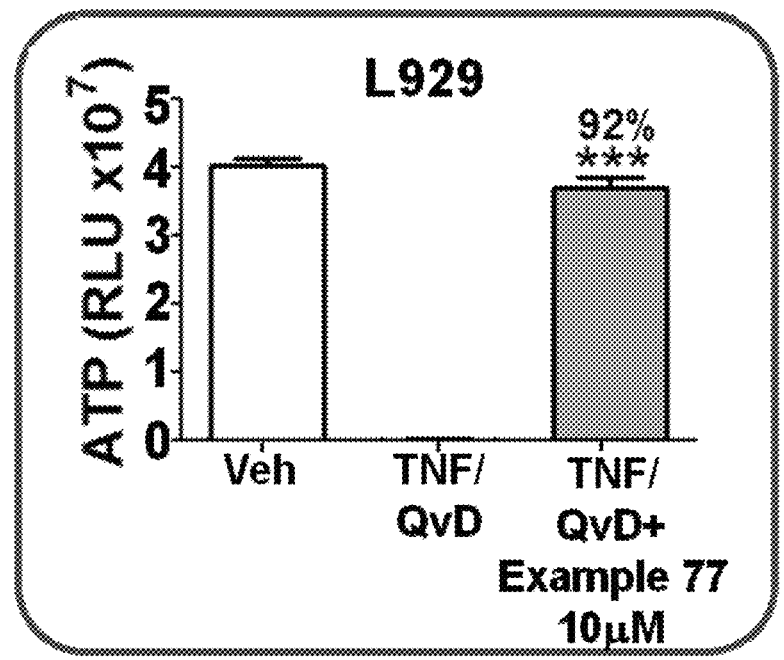
FIG. 3A shows the cellular levels of ATP in mouse L929 fibrosarcoma cells pre-treated with the compound of Example 77 followed by treatment with TNFα+QvD.
Figure 3B:
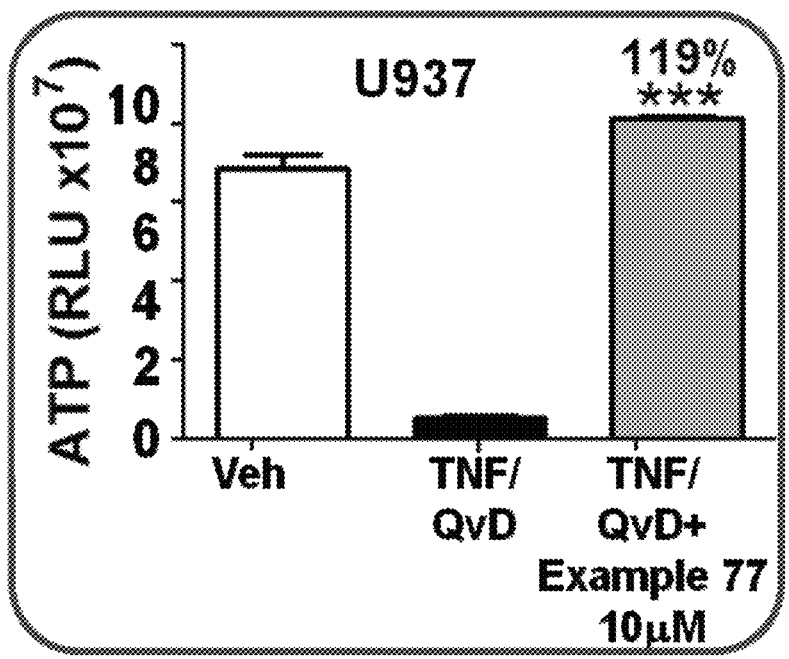
FIG. 3B shows the cellular levels of ATP in human monocytic leukemia U937 fibrosarcoma cells pre-treated with the compound of Example 77 followed by treatment with TNFα+QvD.
Figure 4A:
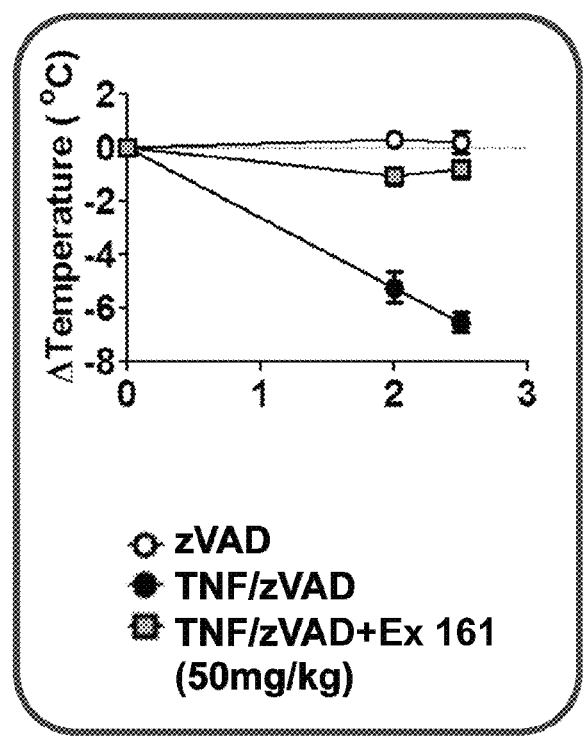
FIG. 4A shows the temperature loss over time in mice after oral pre-dosing with the compound of Example 161 or vehicle followed by simultaneous i.v. administration of mouse TNF and zVAD.
Figure 4B:
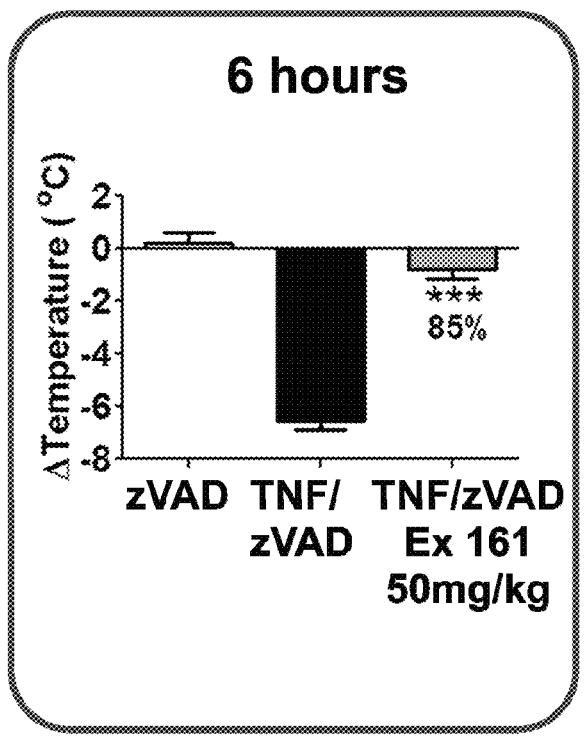
FIG. 4B shows the temperature loss in mice 6 hours after oral pre-dosing with the compound of Example 161 or vehicle followed by simultaneous i.v. administration of mouse TNF and zVAD.
Figure 5A:
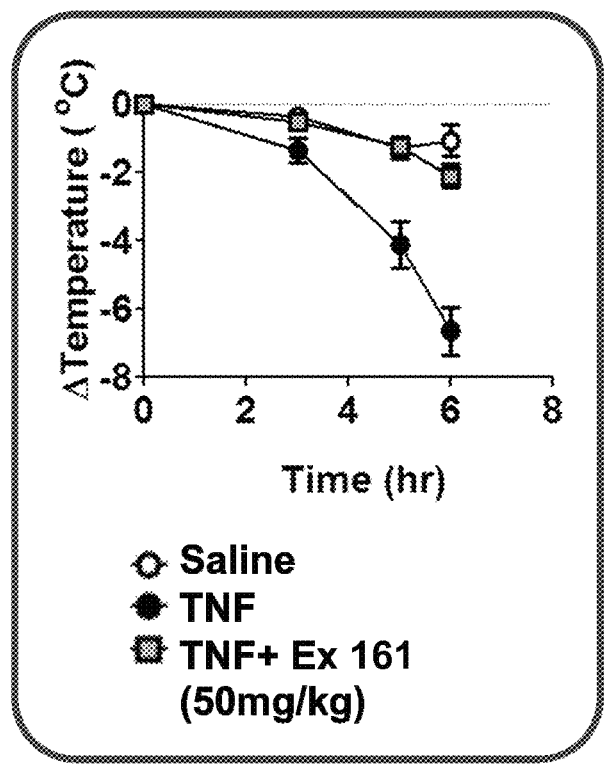
FIG. 5A shows the temperature loss over time in mice after oral pre-dosing with the compound of Example 161 or vehicle followed by i.v. administration of mouse TNF.
Figure 5B:
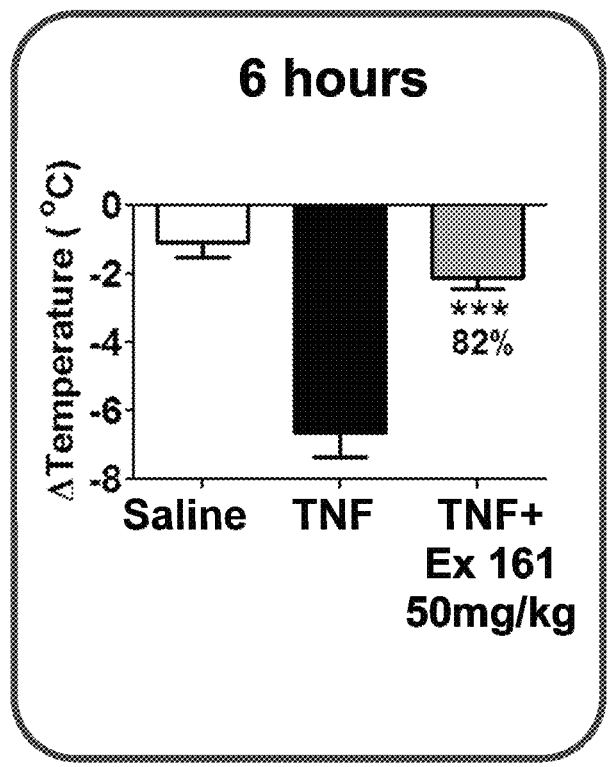
FIG. 5B shows the temperature loss in mice 6 hours after oral pre-dosing with the compound of Example 161 or vehicle followed by i.v. administration of mouse TNF.
Figure 6A:
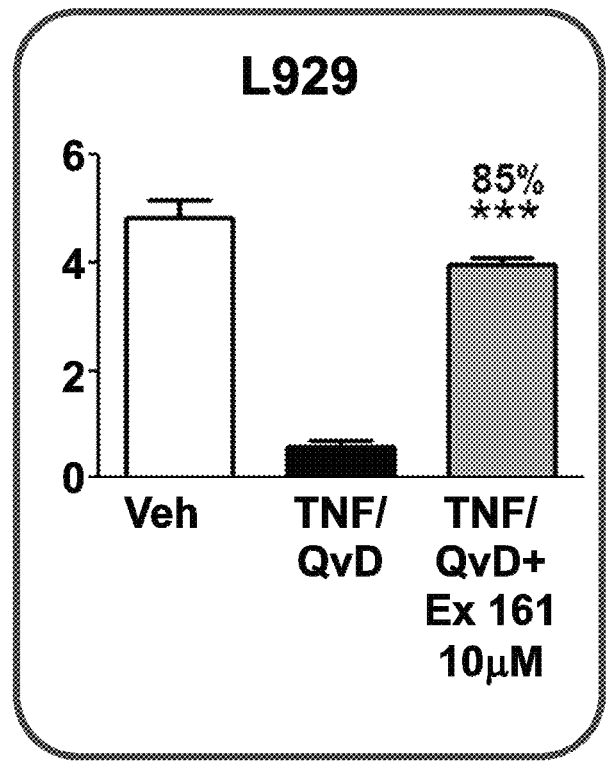
FIG. 6A shows the cellular levels of ATP in mouse L929 fibrosarcoma cells pre-treated with the compound of Example 161 followed by treatment with TNFα+QvD.
Figure 6B:
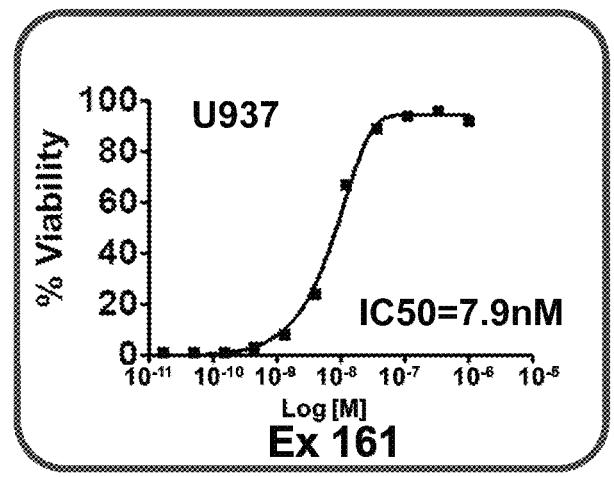
FIG. 6B shows an IC$_{50}$ curve of ATP in human monocytic leukemia U937 fibrosarcoma cells pre-treated with the compound of Example 161 followed by treatment with TNFα+ QvD. Data are normalized to 10 mM Nec-1 which was set at 100% survival.

2009. Cell 137(6):1100-1111). Cells were maintained in RPMI supplemented with 10% fetal bovine serum 100 U/ml penicillin, 100 ug/ml streptomycin. For the assay, cells were suspended at 5e5 cells/ml in phenol red free RPMI supplemented with 1% fetal bovine serum, 100 U/ml penicillin, 100 ug/ml streptomycin. Thirty-five (35) ul of the cell suspension was aliquotted into a white, half area assay plate. Five (5) ul each of QVD (final concentration 50 uM) or compound was added to the cells and incubated at 37° C. for 30 min to 1 h. Following the incubation, 5 ul TNFα (final concentration 100 ng/ml) was added to the cells and the samples were incubated overnight. The next day, cellular levels of ATP was determined using the Cell Titer-Glo Luminescent Cell Viability kit (available from Promega Corporation, Madison, Wis., USA). For example, L929 (FIG. 3A) or U937 (FIG. 3B) cells were treated with vehicle or 10 µM of Example 77. For example, L929 (FIG. 6A) or U937 (FIG. 6B) cells were treated with vehicle or indicated concentrations of the compound of Example 161. Viability was measured by quantitating cellular levels of ATP using the Cell Titer-Glo kit. All data are shown as means±standard deviation of the mean.

What is claimed is:

1. A compound which is:

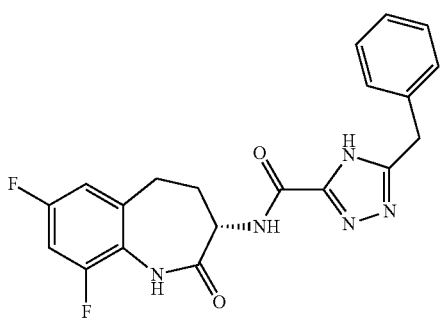 [SMILES: O=C(N[C@H]1CCc2cc(F)cc(F)c2NC1=O)c1nnc(Cc2ccccc2)[nH]1]

or a tautomer thereof, or a pharmaceutically acceptable salt thereof.

2. A pharmaceutical composition comprising the compound, or a tautomer thereof, or pharmaceutically acceptable salt thereof, according to claim 1 and one or more pharmaceutically acceptable excipients.

3. A method of treating ulcerative colitis comprising administering a therapeutically effective amount of the compound, or a tautomer thereof, or pharmaceutically acceptable salt thereof, according to claim 1 to a human in need thereof.

4. A method of treating Crohn's disease comprising administering a therapeutically effective amount of the compound, or a tautomer thereof, or pharmaceutically acceptable salt thereof, according to claim 1 to a human in need thereof.

5. A method of treating rheumatoid arthritis comprising administering a therapeutically effective amount of the compound, or a tautomer thereof, or pharmaceutically acceptable salt thereof, according to claim 1 to a human in need thereof.

6. A method of treating psoriasis comprising administering a therapeutically effective amount of the compound, or a tautomer thereof, or pharmaceutically acceptable salt thereof, according to claim 1 to a human in need thereof.

7. A method of treating spondyloarthritis comprising administering a therapeutically effective amount of the compound, or a tautomer thereof, or pharmaceutically acceptable salt thereof, according to claim 1 to a human in need thereof.

8. A method of treating SoJIA comprising administering a therapeutically effective amount of the compound, or a tautomer thereof, or pharmaceutically acceptable salt thereof, according to claim 1 to a human in need thereof.

9. A method of treating osteoarthritis comprising administering a therapeutically effective amount of the compound, or a tautomer thereof, or pharmaceutically acceptable salt thereof, according to claim 1 to a human in need thereof.

10. A method of treating multiple sclerosis comprising administering a therapeutically effective amount of the compound, or a tautomer thereof, or pharmaceutically acceptable salt thereof, according to claim 1 to a human in need thereof.

11. A method of treating sepsis comprising administering a therapeutically effective amount of the compound, or a tautomer thereof, or pharmaceutically acceptable salt thereof, according to claim 1 to a human in need thereof.

12. A method of treating ischemia reperfusion injury of solid organs comprising administering a therapeutically effective amount of the compound, or a tautomer thereof, or pharmaceutically acceptable salt thereof, according to claim 1 to a human in need thereof.

13. A method of treating systemic inflammatory response syndrome comprising administering a therapeutically effective amount of the compound, or a tautomer thereof, or pharmaceutically acceptable salt thereof, according to claim 1 to a human in need thereof.

14. A compound which is:

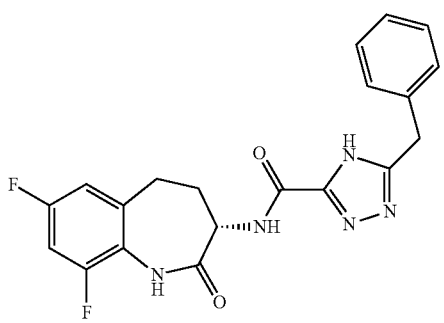 [SMILES: O=C(N[C@H]1CCc2cc(F)cc(F)c2NC1=O)c1nnc(Cc2ccccc2)[nH]1]

or a tautomer thereof.

15. A pharmaceutical composition comprising the compound, or a tautomer thereof, according to claim 14 and one or more pharmaceutically acceptable excipients.

16. A method of treating ulcerative colitis comprising administering a therapeutically effective amount of the compound, or a tautomer thereof, according to claim 14 to a human in need thereof.

17. A method of treating Crohn's disease comprising administering a therapeutically effective amount of the compound, or a tautomer thereof, according to claim 14 to a human in need thereof.

18. A method of treating rheumatoid arthritis comprising administering a therapeutically effective amount of the compound, or a tautomer thereof, according to claim 14 to a human in need thereof.

19. A method of treating psoriasis comprising administering a therapeutically effective amount of the compound, or a tautomer thereof, according to claim 14 to a human in need thereof.

20. A method of treating spondyloarthritis comprising administering a therapeutically effective amount of the compound, or a tautomer thereof, according to claim 14 to a human in need thereof.

21. A method of treating SoJIA comprising administering a therapeutically effective amount of the compound, or a tautomer thereof, according to claim 14 to a human in need thereof.

22. A method of treating osteoarthritis comprising administering a therapeutically effective amount of the compound, or a tautomer thereof, according to claim 14 to a human in need thereof.

23. A method of treating multiple sclerosis comprising administering a therapeutically effective amount of the compound, or a tautomer thereof, according to claim 14 to a human in need thereof.

24. A method of treating sepsis comprising administering a therapeutically effective amount of the compound, or a tautomer thereof, according to claim 14 to a human in need thereof.

25. A method of treating ischemia reperfusion injury of solid organs comprising administering a therapeutically effective amount of the compound, or a tautomer thereof, according to claim 14 to a human in need thereof.

26. A method of treating systemic inflammatory response syndrome comprising administering a therapeutically effective amount of the compound, or a tautomer thereof, according to claim 14 to a human in need thereof.

* * * * *